US009616048B2

(12) United States Patent
McKnight et al.

(10) Patent No.: US 9,616,048 B2
(45) Date of Patent: *Apr. 11, 2017

(54) ANTI-DEPRESSION COMPOUNDS

(71) Applicant: Board of Regents of The University of Texas System, Austin, TX (US)

(72) Inventors: Steven L. McKnight, Dallas, TX (US); Andew A. Pieper, Iowa City, IA (US); Joseph M. Ready, Carrollton, TX (US); Jef K. De Brabander, Flower Mound, TX (US); Jeffrey M. Zigman, Dallas, TX (US)

(73) Assignee: Board of Regents of The University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/886,332

(22) Filed: Oct. 19, 2015

(65) Prior Publication Data

US 2016/0206596 A1 Jul. 21, 2016

Related U.S. Application Data

(63) Continuation of application No. 14/339,772, filed on Jul. 24, 2014, now Pat. No. 9,162,980, and a (Continued)

(51) Int. Cl.
| | | |
|---|---|---|
| *A61K 31/44* | (2006.01) | |
| *A61K 31/403* | (2006.01) | |
| *A61K 31/4439* | (2006.01) | |
| *A61K 31/4045* | (2006.01) | |
| *C07D 209/04* | (2006.01) | |
| *C07D 209/82* | (2006.01) | |
| *C07D 401/06* | (2006.01) | |
| *C07D 413/06* | (2006.01) | |
| *C07D 471/04* | (2006.01) | |
| *C07D 403/12* | (2006.01) | |
| *C07D 403/06* | (2006.01) | |
| *C07F 5/02* | (2006.01) | |

(Continued)

(52) U.S. Cl.
CPC ........ *A61K 31/4045* (2013.01); *A61K 31/403* (2013.01); *A61K 31/404* (2013.01); *A61K 31/4155* (2013.01); *A61K 31/4188* (2013.01); *A61K 31/4192* (2013.01); *A61K 31/422* (2013.01); *A61K 31/437* (2013.01); *A61K 31/44* (2013.01); *A61K 31/4425* (2013.01); *A61K 31/4439* (2013.01); *A61K 31/506* (2013.01); *C07D 209/04* (2013.01); *C07D 209/08* (2013.01); *C07D 209/82* (2013.01); *C07D 209/86* (2013.01); *C07D 209/88* (2013.01); *C07D 401/06* (2013.01); *C07D 401/12* (2013.01); *C07D 403/06* (2013.01); *C07D 403/12* (2013.01); *C07D 403/14* (2013.01); *C07D 405/12* (2013.01); *C07D 407/06* (2013.01); *C07D 413/06* (2013.01); *C07D 413/14* (2013.01); *C07D 471/04* (2013.01); *C07D 487/04* (2013.01); *C07D 495/04* (2013.01); *C07F 5/022* (2013.01); *C07F 7/0812* (2013.01)

(58) Field of Classification Search
CPC ... A61K 31/403; A61K 31/44; A61K 31/4439
See application file for complete search history.

(56) References Cited

U.S. PATENT DOCUMENTS

| | | |
|---|---|---|
| 3,409,628 A | 11/1968 | Berger et al. |
| 3,518,250 A | 6/1970 | Schumaker |

(Continued)

FOREIGN PATENT DOCUMENTS

| | | |
|---|---|---|
| CN | 101139347 A | 3/2008 |
| CN | 101429198 A | 5/2009 |

(Continued)

OTHER PUBLICATIONS

Abad, J. et al., "Internal Oxidosqualenes: Determination of Absolute Configuration and Activity as Inhibitors of Purified Pig Liver Squalene Epoxidase," *J. Org. Chem.*, 60(12), pp. 3648-3656 (Jun. 1995).
Abrous, D. et al., "Adult Neurogenesis: From Precursors to Network and Physiology," *Physiol Rev*, vol. 85, pp. 523-569 (2005).
Alexander, M. et al., "A Central Strategy for Converting Natural Products into Fluorescent Probes," *ChemBioChem*, 7(3), pp. 409-416 (Mar. 2006).
Altman, J., "Are New Neurons Formed in the Brains of Adult Mammals?" *Science*, 135, pp. 1127-1128 (Mar. 1962).
Altman, J., "Autoradiographic Investigation of Cell Proliferation in the Brains of Rats and Cats,"*Anat. Rec.*, 145, pp. 573-591 (Apr. 1963).

(Continued)

*Primary Examiner* — Robert Halvin
(74) *Attorney, Agent, or Firm* — Greenberg Traurig, LLP; David J. Dykeman; Fang Xie

(57) ABSTRACT

This technology relates generally to compounds and methods for stimulating neurogenesis (e.g., post-natal neurogenesis, including post-natal hippocampal and hypothalamic neurogenesis) and/or protecting neuronal cell from cell death. Various compounds are disclosed herein. In vivo activity tests suggest that these compounds may have therapeutic benefits in neuropsychiatric and/or neurodegenerative diseases such as schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of a neuroactive drug, retinal degeneration, spinal cord injury, peripheral nerve injury, physiological weight loss associated with various conditions, as well as cognitive decline associated with normal aging, chemotherapy, and the like.

25 Claims, 72 Drawing Sheets

Related U.S. Application Data continuation-in-part of application No. 13/594,223, filed on Aug. 24, 2012, which is a continuation-in-part of application No. 13/177,981, filed on Jul. 7, 2011, now Pat. No. 9,095,572, which is a continuation-in-part of application No. 12/832,056, filed on Jul. 7, 2010, now Pat. No. 8,362,277, which is a continuation-in-part of application No. 12/685,652, filed on Jan. 11, 2010, now Pat. No. 8,604,074.

(60) Provisional application No. 61/958,282, filed on Jul. 24, 2013, provisional application No. 61/143,755, filed on Jan. 9, 2009.

(51) Int. Cl.

| | | |
|---|---|---|
| *C07D 487/04* | (2006.01) | |
| *A61K 31/404* | (2006.01) | |
| *A61K 31/4155* | (2006.01) | |
| *A61K 31/4192* | (2006.01) | |
| *A61K 31/422* | (2006.01) | |
| *A61K 31/437* | (2006.01) | |
| *A61K 31/4425* | (2006.01) | |
| *A61K 31/506* | (2006.01) | |
| *C07D 413/14* | (2006.01) | |
| *C07D 401/12* | (2006.01) | |
| *C07D 403/14* | (2006.01) | |
| *C07D 407/06* | (2006.01) | |
| *C07D 209/88* | (2006.01) | |
| *C07D 405/12* | (2006.01) | |
| *C07D 495/04* | (2006.01) | |
| *C07D 209/08* | (2006.01) | |
| *C07D 209/86* | (2006.01) | |
| *C07F 7/08* | (2006.01) | |
| *A61K 31/4188* | (2006.01) | |

(56) References Cited

U.S. PATENT DOCUMENTS

| 4,495,281 A | 1/1985 | Buckler et al. |
|---|---|---|
| 5,234,923 A | 8/1993 | Poss et al. |
| 5,306,609 A | 4/1994 | Mihayashi et al. |
| 6,187,785 B1 | 2/2001 | Zefirov et al. |
| 6,468,996 B1 | 10/2002 | Jeppesen et al. |
| 6,514,968 B1 | 2/2003 | TenBrink |
| 6,569,849 B1 | 5/2003 | Jorgensen et al. |
| 6,770,656 B2 | 8/2004 | Halazy et al. |
| 6,835,513 B2 | 12/2004 | Jubran et al. |
| 6,849,640 B2 | 2/2005 | Ennis et al. |
| 6,864,025 B2 | 3/2005 | Law et al. |
| 7,018,988 B2 | 3/2006 | Halazy et al. |
| 7,071,206 B2 | 7/2006 | Zefirov et al. |
| 7,148,259 B1 | 12/2006 | Li et al. |
| 7,438,916 B2 | 10/2008 | Rathore et al. |
| 7,445,877 B2 | 11/2008 | Jubran et al. |
| 7,449,478 B2 | 11/2008 | Hsieh et al. |
| 7,807,704 B2 | 10/2010 | Thomas et al. |
| 7,834,063 B2 | 11/2010 | Turnbull et al. |
| 7,989,127 B2 | 8/2011 | Wu et al. |
| 8,268,575 B2 | 9/2012 | Imai et al. |
| 8,362,277 B2 | 1/2013 | McKnight et al. |
| 8,604,074 B2 | 12/2013 | McKnight et al. |
| 8,735,440 B2 | 5/2014 | McKnight et al. |
| 8,748,473 B2 | 6/2014 | McKnight et al. |
| 8,791,149 B2 | 7/2014 | McKnight et al. |
| 8,877,797 B2 | 11/2014 | McKnight et al. |
| 9,095,571 B2 | 8/2015 | McKnight et al. |
| 9,095,572 B2 | 8/2015 | McKnight et al. |
| 9,156,787 B2 | 10/2015 | McKnight et al. |
| 9,162,980 B2 | 10/2015 | McKnight et al. |
| 9,243,281 B2 | 1/2016 | McKnight et al. |
| 9,278,923 B2 | 3/2016 | McKnight et al. |
| 2003/0171309 A1 | 9/2003 | Halazy et al. |
| 2003/0203296 A1 | 10/2003 | Law et al. |
| 2003/0207188 A1 | 11/2003 | Jubran et al. |
| 2003/0216427 A1 | 11/2003 | Halazy et al. |
| 2005/0124675 A1 | 6/2005 | Hsieh et al. |
| 2005/0277038 A1 | 12/2005 | Jubran et al. |
| 2006/0038170 A1 | 2/2006 | Brunschwiler et al. |
| 2007/0185152 A1 | 8/2007 | Yamashita et al. |
| 2007/0196395 A1 | 8/2007 | Mackerell et al. |
| 2007/0197524 A1 | 8/2007 | Brauer et al. |
| 2007/0203236 A1* | 8/2007 | Smith .................. C07D 239/62 514/560 |
| 2007/0275965 A1 | 11/2007 | Thomas et al. |
| 2007/0293558 A1 | 12/2007 | Gao et al. |
| 2008/0039629 A1 | 2/2008 | Ramesh et al. |
| 2008/0058383 A1 | 3/2008 | Jernstedt et al. |
| 2008/0255124 A1 | 10/2008 | Turnbull et al. |
| 2009/0137420 A1 | 5/2009 | VonHoff et al. |
| 2009/0143376 A1 | 6/2009 | Milburn et al. |
| 2009/0163545 A1 | 6/2009 | Goldfarb |
| 2009/0236229 A1 | 9/2009 | Advincula |
| 2009/0246803 A1 | 10/2009 | Imai et al. |
| 2010/0022580 A1 | 1/2010 | Hung et al. |
| 2010/0305121 A1 | 12/2010 | Smith et al. |
| 2011/0003836 A1 | 1/2011 | McKnight et al. |
| 2011/0015217 A1 | 1/2011 | McKnight et al. |
| 2012/0022013 A1 | 1/2012 | Sinclair et al. |
| 2012/0022096 A1 | 1/2012 | McKnight et al. |
| 2012/0122924 A1 | 5/2012 | Curtin et al. |
| 2012/0172584 A1 | 7/2012 | Sauve et al. |
| 2013/0040977 A1 | 2/2013 | McKnight et al. |
| 2013/0096181 A1 | 4/2013 | Ashkenazi et al. |
| 2013/0184271 A1 | 7/2013 | McKnight et al. |
| 2013/0184300 A1 | 7/2013 | McKnight et al. |
| 2013/0184301 A1 | 7/2013 | McKnight et al. |
| 2013/0190273 A1 | 7/2013 | McKnight et al. |
| 2013/0190339 A1 | 7/2013 | McKnight et al. |
| 2014/0057900 A1 | 2/2014 | McKnight et al. |
| 2014/0094480 A1 | 4/2014 | McKnight et al. |
| 2014/0343018 A1 | 11/2014 | McKnight et al. |
| 2015/0057301 A1 | 2/2015 | McKnight et al. |
| 2015/0132783 A1 | 5/2015 | McKnight et al. |
| 2015/0290195 A1 | 10/2015 | McKnight et al. |
| 2016/0074361 A1 | 3/2016 | McKnight et al. |
| 2016/0200695 A1 | 7/2016 | Ready et al. |
| 2016/0206594 A1 | 7/2016 | McKnight et al. |

FOREIGN PATENT DOCUMENTS

| EP | 1 094 063 | 4/2001 |
|---|---|---|
| EP | 1 591 511 | 11/2005 |
| FR | 1167510 | 11/1958 |
| GB | 2 355 659 | 5/2001 |
| JP | H04-217657 A | 8/1992 |
| JP | 2007/223916 | 9/2007 |
| WO | WO 92/21660 | 12/1992 |
| WO | WO 96/34863 | 11/1996 |
| WO | WO 00/23425 | 4/2000 |
| WO | WO 00/78795 | 12/2000 |
| WO | WO 01/29028 | 4/2001 |
| WO | WO 01/71430 | 9/2001 |
| WO | WO 02/038142 | 5/2002 |
| WO | WO 02/060867 | 8/2002 |
| WO | WO 03/007069 | 1/2003 |
| WO | WO 03/007070 | 1/2003 |
| WO | WO 03/007071 | 1/2003 |
| WO | WO 03/032072 | 1/2003 |
| WO | WO 03/091247 | 11/2003 |
| WO | WO 2004/052885 | 6/2004 |
| WO | WO 2004/106335 | 9/2004 |
| WO | WO 2005/055951 | 6/2005 |
| WO | WO 2005/056522 | 6/2005 |
| WO | WO 2005/074971 | 8/2005 |
| WO | WO 2007/008541 | 1/2007 |
| WO | WO 2007/041697 | 4/2007 |
| WO | WO 2007/062399 | 5/2007 |
| WO | WO 2007/079239 | 7/2007 |
| WO | WO 2007/081091 | 7/2007 |
| WO | WO 2007/087425 | 8/2007 |

(56) References Cited

FOREIGN PATENT DOCUMENTS

| | | |
|---|---|---|
| WO | WO 2007/137227 | 11/2007 |
| WO | WO 2008/021745 | 2/2008 |
| WO | WO 2008/060190 | 5/2008 |
| WO | WO 2008/115098 | 9/2008 |
| WO | WO 2008/123796 | 10/2008 |
| WO | WO 2008/123800 | 10/2008 |
| WO | WO 2008/156105 | 12/2008 |
| WO | WO 2009/040517 | 4/2009 |
| WO | WO 2009/055828 | 4/2009 |
| WO | WO 2009/094668 | 7/2009 |
| WO | WO 2009/120717 | 10/2009 |
| WO | WO 2010/048446 | 4/2010 |
| WO | WO 2010/051503 | 5/2010 |
| WO | WO 2010/081115 | 7/2010 |
| WO | WO 2011/019417 | 2/2011 |
| WO | WO 2011/038162 | 3/2011 |
| WO | WO 2011/117668 | 9/2011 |
| WO | WO 2012/006419 | 1/2012 |
| WO | WO 2014/031125 | 2/2014 |
| WO | WO 2014/031986 | 2/2014 |
| WO | WO 2015/035051 | 3/2015 |

OTHER PUBLICATIONS

Altman, J., "Autoradiographic and Histological Evidence of Postnatal Hippocampal Neurogenesis in Rats," *J. Comp. Neur.*, 124(3), pp. 319-335 (Jun. 1965).

Altman, J., "Autoradiographic and Histological Studies of Postnatal Neurogenesis: I. A Longitudinal Investigation of the Kinetics, Migration and Transformation of Cells Incorporating Tritiated Thymidine in Neonate Rats, with Special Reference to Postnatal Neurogenesis in Some Brain Regions," *J. Comp. Neur.*, 126(3), pp. 337-389 (Mar. 1966).

Altman, J., "Autoradiographic and Histological Studies of Postnatal Neurogenesis: II. A Longitudinal Investigation of the Kinetics, Migration and Transformation of Cells Incorporating Tritiated Thymidine in Infant Rats, with Special Reference to Postnatal Neurogenesis in Some Brain Regions," *J. Comp. Neur.*, 128(4), pp. 431-473 (Dec. 1966).

Altman, J., "Autoradiographic and Histological Studies of Postnatal Neurogenesis: IV. Cell Proliferation and Migration in the Anterior Forebrain, with Special Reference to Persisting Neurogenesis in the Olfactory Bulb," *J. Comp. Neur.*, 137(4), pp. 433-457 (Dec. 1969).

Araki et al., "Increased Nuclear NAD Biosynthesis and SIRT1 Activation Prevent Axonal Degeneration" *Science* 305:1010-1013, Aug. 13, 2004.

AsInEx Chemical Library, Compound "9H-Carbazole-9-Ethanol, 3,6-dibromo-a-[[(3-chlorophenyl) amino]methyl]" (2001).

Asso, V. et al., "α-Naphthylaminopropan-2-ol Derivatives as BACE1 Inhibitors," *ChemMedChem*, 3(10), pp. 1530-1534 (Oct. 2008).

Awasthi, S. et al., "Modulation of Doxorubicin Cytotoxicity by Ethacrynic Acid", *Int. J. Cancer*, vol. 69, pp. 333-339 (1996).

Bachurin, S. et al., "Antihistamine Agent Dimebon as a Novel Neuroprotector and a Cognition Enhancer," *Ann. N.Y. Acad. Sci.*, 939, pp. 425-435 (Jun. 2001).

Bachurin, S. et al., "Mitochondria as a Target for Neurotoxins and Neuroprotective Agents," *Ann. N.Y. Acad. Sci.*, 993, pp. 334-344 (May 2003).

Bachurin, S. et al., "Questions and Answers: Session VII: Oxidative Stress, Mitochondria, and Approaches to Neuroprotection," *Ann. N.Y. Acad. Sci.*, 993, pp. 345-349 (May 2003).

Berg et al., "New Neuronal Growth Factors" *Ann. Rev. Neurosci.*, 7: 149-170 (Jul. 1984).

Beyer, M. et al., "Synthesis of Novel Aromatic Nitroxides as Potential DNA Intercalators. An EPR Spectroscopical and DFT Computational Study," *J. Org. Chem.*, 68(6), pp. 2209-2215 (Mar. 2003).

Boekelheide, V. et al., "Curariform Activity and Chemical Structure. VII. Some 1-Skatylisoquinoline Derivatives and a Novel Method for their Synthesis," *J. Am. Chem. Soc.*, 72(5), pp. 2134-2137 (May 1950).

Boldrini, M. et al., "Antidepressants Increase Neural Progenitor Cells in the Human Hippocampus," *Neuropsychopharmacology*, 34(11), pp. 2376-2389 (Oct. 2009).

Bombrun, A. et al., "3,6-Dibromocarbazole Piperazine Derivatives of 2-Propanol as First Inhibitors of Cytochrome c Release via Bax Channel Modulation," *J. Med. Chem.*, 46(21), pp. 4365-4368 (Oct. 2003).

Borrell-Pages, M. et al., "Huntington's Disease: From Huntington Function and Dysfunction to Therapeutic Strategies," *Cell. Mol. Life Sci.*, 63(22), pp. 2462-2660 (Nov. 2006).

Bradshaw et al., The Development of the Antitumour Benzothiazole Prodrug, Phortress, as a Clinical Candidate, Current Medicinal Chemistry 11, pp. 1-13 (pp. 1241-1253) 2004; (retrieved from the Internet) http://www.pharminox.com/pdf/Phortess_rev.pdf.

Brown, J. et al., "Transient Expression of Doublecortin during Adult Neurogenesis," *The Journal of Comparative Neurology*, 467(1), pp. 1-10 (Dec. 2003).

Browne, S. et al., "The Energetics of Huntington's Disease," *Neurochemical Research*, 29(3), pp. 531-546 (Mar. 2004).

Burd, G. et al., "Ultrastructural Characterization of Synaptic Terminals Formed on Newly Generated Neurons in a Song Control Nucleus of the Adult Canary Forebrain," *The Journal of Comparative Neurology*, 240(2), pp. 143-152 (Oct. 1985).

Burns, A. et al., "Dimebon in Alzheimer's Disease: Old Drug for New Indication," *The Lancet*, 372, pp. 179-180 (Jul. 2008).

Cao, R. et al., "Synthesis, Acute Toxicities, and Antitumor Effects of Novel 9-Substituted β-Carboline Derivatives," *Bioorganic & Medicinal Chemistry*, 12(17), pp. 4613-4623 (Sep. 2004).

Cao, R. et al., "Design, Synthesis and In Vitro and In Vivo Antitumor Activities of Novel β-Carboline Derivatives," *European Journal of Medicinal Chemistry*, 40(10), pp. 991-1001 (Oct. 2005).

Cao, R. et al., "DNA Binding Properties of 9-Substituted Harmine Derivatives," *Biochemical and Biophysical Research Communications*, 338(3), pp. 1557-1563 Dec. 2005.

Cao, R. et al., "Synthesis and Cytotoxic Activities of 1-Benzylidine Substituted β-Carboline Derivatives," *Bioorganic & Medicinal Chemistry Letters*, 18(24), pp. 6558-6561 (Dec. 2008).

Cattaneo, E. et al., "Normal Huntington Function: An Alternative Approach to Huntington's Disease," *Nature Reviews: Neuroscience*, 6, pp. 919-930 (Dec. 2005).

Carter, R. et al., "Characterization of Progressive Motor Deficits in Mice Transgenic for the Human Huntington's Disease Mutation," *The Journal of Neuroscience*, 19(8), pp. 3248-3257 (Apr. 1999).

Cha, J. et al., "Altered Brain Neurotransmitter Receptors in Transgenic Mice Expressing a Portion of an Abnormal Human Huntington Disease Gene," *Proc. Natl. Acad. Sci. USA*, 95, pp. 6480-6485 (May 1998).

Cha, J., "Transcriptional Dysregulation in Huntington's Disease," *TINS*, 23(9), pp. 387-392 (Sep. 2000).

Chakraborti, A. et al., "Lithium Bromide, an Inexpensive and Efficient Catalyst for Opening of Epoxide Rings by Amines at Room Temperature under Solvent-Free Condition," *Eur. J. Org. Chem.*, 2004(17), pp. 3597-3600 (Sep. 2004).

Cimini et al., "Expression of Peroxisome Proliferator-Activated Receptors (PPARs) and Retinoic Acid Receptors (RXRs) in Rat Cortical Neurons.", Neuroscience, vol. 130, pp. 325-337, 2005.

Davies, S. et al., "Formation of Neuronal Intranuclear Inclusions Underlies the Neurological Dysfunction in Mice Transgenic for the HD Mutation," *Cell*, 90, pp. 537-548 (Aug. 1997).

DeJesus-Cortes, H. et al., "Neuroprotective Efficacy of Aminopropyl Carbazoles in a Mouse Model of Parkinson Disease" *PNAS*, vol. 109, No. 42, pp. 17010-17015 (Oct. 16, 2012).

Distelmaier, F. et al., "Life Cell Quantification of Mitochondrial Membrane Potential at the Single Organelle Level," *Cytometry A*, 73(2), pp. 129-138 (Feb. 2008).

Di Santo, R. et al., "Design, Synthesis and QSAR Studies on N-Aryl Heteroarylisopropanolamines, a New Class of Non-Peptidic HIV-1 Protease Inhibitors," *Bioorganic & Medicinal Chemistry*, 10(8), pp. 2511-2526 (Aug. 2002).

(56) References Cited

OTHER PUBLICATIONS

Doody, R. et al., "Effect of Dimebon on Cognition, Activities of Daily Living, Behaviour, and Global Function in Patients with Mild-to-Moderate Alzheimer's Disease: A Randomised, Double-Blind, Placebo-Controlled Study," The Lancet, 372, pp. 207-215 (Jul. 2008).
Doody, R. et al., "Intermittent Preventive Antimalarial Treatment in Infancy," The Lancet, 372, pp. 1383-1384 (Oct. 2008).
Dow, R. et al., "Identification of Tricyclic Analogs Related to Ellagic Acid as Potent/Selective Tyrosine Protein Kinase Inhibitors," J. Med. Chem., 37(14), pp. 2224-2231 (Jul. 1994).
Driscoll, I. et al., "The Aging Hippocampus: A Multi-Level Analysis in the Rat," Neuroscience, 139(4), pp. 1173-1185 (Mar. 2006).
Enyedy et al., "Discovery of Small-Molecule Inhibitors of Bcl-2 through Structure-Based Computer Screening," J. Med. Chem., 44(25), pp. 4313-4324 (Dec. 6, 2001).
Eriksson, P. et al., "Neurogenesis in the Adult Human Hippocampus," Nature Medicine, 4(11), pp. 1313-1317 (Nov. 1998).
Fedele, V. et al., "Neurogenesis in the R6/2 Mouse Model of Huntington's Disease is Impaired at the Level of Neurod1," Neuroscience, 173, pp. 76-81 (Jan. 2011).
Fernandes, H. et al., "Mitochondrial Sensitivity and Altered Calcium Handling Underlie Enhanced NMDA-Induced Apoptosis in YAC128 Model of Huntington's Diase," The Journal of Neuroscience, 27(50), pp. 13614-13623 (Dec. 2007).
Ferris, R.M. et al., "Rimcazole (BW 234U), a Novel Antipsychotic Agent Whose Mechanism of Action Cannot be Explained by a Direct Blockade of Postsynaptic Dopaminergic Receptors in Brain," Drug Development Research, 9(3), pp. 171-188 (Nov. 1986).
Freireich, E. et al., "Quantitative Comparison of Toxicity of Anticancer Agents in Mouse, Rat, Hamster, Dog, Monkey, and Man," Cancer Chemotherapy Reports, 50(4), pp. 219-244 (May 1966).
Gennaro, A. et al., "Remington's Pharmaceutical Sciences," Mack Publishing Company, 17$^{th}$ Edition, pp. 1418-1419 (1985).
Getautis, V. et al., "Study of the Products from Reaction of 1(2)-Aminoanthraquinones with 1-Chloro-2,3-Epoxypropane," Chemistry of Heterocyclic Compounds, 41(4), pp. 426-436 (Apr. 2005).
Giancaspro et al., "Synthesis of Disubstituted Tetrahydrocarbazoles with Potential Antidepressive Activity," IL Farmaco, 44(5), 483-493, 1989.
Giancaspro et al., "Trypanocidal Activity of 1,2,3,4-Tetrahydrocathazoles," Rev. Microbiol., Sao Paulo, 25(3):201-205, 1994.
Gil, J. et al., "Asialoerythropoetin is not Effective in the R6/2 Line of Huntington's Disease Mice," BMC Neuroscience, 5(17), pp. 1-10 (May 2004).
Gil, J. et al., "Reduced Hippocampal Neurogenesis in R6/2 Transgenic Huntington's Disease Mice," Neurobiology of Disease, 20, pp. 744-751 (Jun. 2005).
Gil, J. et al., "The R6 Lines of Transgenic Mice: A Model for Screening New Therapies for Huntington's Disease," Brain Research Reviews, 59(2), pp. 410-431 (Mar. 2009).
Godin, J. et al., "Huntingtin is Required for Mitotic Spindle Orientation and Mammalian Neurogenesis," Neuron, 67, pp. 392-406 (Aug. 2010).
Goehler, H. et al., "A Protein Interaction Network links GIT1, an Enhancer of Huntingtin Aggregation, to Huntington's Disease," Molecular Cell, 15, pp. 853-865 (Sep. 2004).
Goldberg, Y.P. et al., "Cleavage of Huntingtin by Apopain, a Proapoptotic Cysteine Protease, is Modulated by the Poyglutamine Tract," Nature Genetics, 13, pp. 442-449 (Aug. 1996).
Goldman, S. et al., "Neuronal Production, Migration, and Differentiation in a Vocal Control Nucleus of the Adult Female Canary Brain," Proc. Natl. Acad. Sci. USA, 80, pp. 2390-2394 (Apr. 1983).
Gross, C. "Neurogenesis in the Adult Brain: Death of a Dogma," Nature Reviews, 1, pp. 67-73 (Oct. 2000).

Haggquist, G. et al., "Intramolecular Triplet Energy Transfer. 3. A Carbazole-Naphthalene System Having Short Chain Length Methylene Spacer Units," J. Phys. Chem., 97, pp. 9270-9273 (Sep. 1993).
Harbert, C. et al., "Neuroleptic Activity in 5-Aryltetrahydro-γ-carbolines," J. Med. Chem., 23(6), pp. 635-643 (Jun. 1980).
Hisada, K. et al., "Intramolecular Triplet Energy Transfer. 4. A Carbazole-Naphthalene System Having a Flexible Alkyl Spacer Doped in Poly(methyl methacrylate) Matrixes," J. Phys. Chem. B, 102, pp. 2640-2645 (Mar. 1998).
Jackson-Lewis, V. et al., "Protocol for the MPTP Mouse Model of Parkinson's Disease," Nature Protocols, 2, pp. 141-151 (Feb. 2007).
Jantas, D. et al., "Protective Effect of Memantine Against Doxorubicin Toxicity in Primary Neuronal Cell Cultures: Influence a Development Stage", Neurotox Res., vol. 15, pp. 24-37 (2009).
Jin, K. et al., "Heparin-Binding Epidermal Growth Factor-Like Growth Factor: Hypoxia-Inducible Expresstion In Vitro and Stimulation of Neurogenesis In Vitro and In Vivo," The Journal of Neuroscience, vol. 22, Chapter 13, pp. 5365-5373 (Jul. 1, 2002).
Jorapur, Y. et al., "Potassium Carbonate as a Base for the N-alkylation of Indole and Pyrrole in Ionic Liquids," Tetrahedron Letters, 47(14), pp. 2435-2438 (Apr. 2006).
Jun, W. et al., "Inorganic-Organic Hybrid Photorefractive Materials Bearing the Bifunctional Chromophore," Journal of Nonlinear Optical Physics & Materials, 14(4), pp. 497-504 (Dec. 2005).
Kaewtong, C. et al., "Self-Assembly and Electrochemical Oxidation of Pollyamidoamine—Carbazole Dendron Surfmer Complexes: Nanoring Formation," ACS Nano, 2(8), pp. 1533-1542 (Aug. 2008).
Kamal et al., "Carbazole-pyrrolo [2,1-c] [1, 4] benzodiazepine conjugates: design, synthesis, and biological evaluation", MedChemComm, vol. 2, No. 8, pp. 780-788 (2001).
Kamnasaran, D. et al., "Disruption of the Neuronal PAS3 Gene in a Family Affected with Schizophrenia," J. Med. Genet., 40(5), pp. 325-332 (May 2003).
Kamogawa, H. et al., "Syntheses of N-Substituted Carbazoles Involving Polymerizable Terminal Vinyl Groups," Journal of Polymer Science, 17(1), pp. 9-18 (Jan. 1979).
Kemp et al., "Pharmacologic Rescue of Motor and Sensory Function by the Neuroprotective Compound P7C3 Following Neonatal Nerve Injury," Neuroscience (2015), 284, 202-216.
Kempermann, G. et al., "More Hippocampal Neurons in Adult Mice Living in an Enriched Environment," Nature, 386, pp. 493-495 (Apr. 1997).
Kim, J et al., "Mitochondrial Loss, Dysfunction and Altered Dynamics in Huntington's Disease," Human Molecular Genetics, 19(20), pp. 3919-3935 (Jul. 2010).
Kim, S. et al., "Treadmill Exercise Prevents Aging-Induced Failure of Memory through an Increase in Neurogenesis and Suppression of Apoptosis in Rat Hippocampus," Experimental Gerontology, 45(5), pp. 357-365 (May 2010).
Kim, T. et al., "Molecular Tripods Showing Fluorescence Enhancement upon Binding to Streptavidin," Organic Letters, 7(1), pp. 111-114 (Jan. 2005).
Kim, T. et al., "Self-Quenching Mechanism: the Influence of Quencher and Spacer on Quencher-fluorescein Probes," Bull. Korean. Chem. Soc., 28(7), pp. 1221-1223 (2007).
Kohl, Z. et al., "Impaired Adult Olfactory Bulb Neurogenesis in the R6/2 Mouse Model of Huntington's Disease," BMC Neuroscience, 11, pp. 1-11 (Sep. 2010).
Kondratov et al., "Small molecules that dramatically alter multidrug resistance phenotype by modulating the substrate specificity of P-glycoprotein," Proceedings of the National Academy of Sciences of the United States of America (2001), 98(24), 14078-14083.
Krishnan, V. et al., "The Molecular Neurobiology of Depression," Nature, 455, pp. 894-902 (Oct. 2008).
Kuhn, G. et al., "Neurogenesis in the Dentate Gyrus of the Adult Rat: Age-Related Decrease of Neuronal Progenitor Proliferation," The Journal of Neuroscience, 16(6), pp. 2027-2033 (Mar. 1996).
Landree et al., "C75, a Fatty Acid Synthase Inhibitor, Modulates AMP-activated Protein Kinase to Alter Neuronal Energy Metabolism" J. Biol. Chem., 2004, v. 279, p. 3817-3827 (Jan. 30, 2004).

(56) References Cited

OTHER PUBLICATIONS

Lavedan, C. et al., "Effect of a Ciliary Neurotrophic Factor Polymorphism on Schizophrenia Symptom Improvement in an Iloperidone Clinical Trial," *Pharmacogenomics*, 9(3), pp. 289-301 (Mar. 2008).
Lavedan, C. et al., "Association of the *NPAS3* Gene and Five Other Loci with Response to the Antipsychotic Iloperidone Identified in a Whole Genome Association Study," *Molecular Psychiatry*, 14(8), pp. 804-819 (Aug. 2009).
Lee, H. et al., "Structure-Activity Relationship Studies of the Chromosome Segregation Inhibitor, Incentrom A," *Bioorganic & Medicinal Chemistry Letters*, 18(6), pp. 4670-4674 (Aug. 2008).
Li, Z. et al., "Two Types of Nonlinear Optical Polyurethanes Containing the Same Isolation Groups: Syntheses, Optical Properties, and Influence of Binding Mode," *J. Phys. Chem. B*, 113, pp. 14943-14949 (Oct. 2009).
Lione, L. et al., "Selective Discrimination Learning Impairments in Mice Expressing the Human Huntington's Disease Mutation," *The Journal of Neuroscience*, 19(23), pp. 10428-10437 (Dec. 1999).
Liu, X. et al., "Induction of Apoptotic Program in Cell-Free Extracts: Requirement for dATP and Cytochrome c," *Cell*, 86, pp. 147-157 (Jul. 1996).
Liu et al., "Synthesis and Spectroscopic and Electrochemical Properties of TTF-Derivatized Polycarbazole", *Macromolecules*, vol. 41, No. 6, pp. 2045-2048 (2011).
Loo, D. et al., "Apoptosis is Inducted by β-Amyloid in Cultured Central Nervous System Neurons," *Proc. Natl. Acad. Sci. USA*, 90, pp. 7951-7955 (Sep. 1993).
Lygaitis, R. et al., "Synthesis and Photophysical Properties of Bipolar Low-Molar-Mass Amorphous Materials," *Journal of Photochemistry and Photobiology A: Chemistry*, 167(2-3), pp. 163-168 (Oct. 2004).
MacMillan, et al., "Development of Proneurogenic, Neuroprotective Small Molecules", Journal of the American Chemical Society, vol. 133, No. 5, pp. 1428-1437 (2011).
Maegawa, Y. et al., "A Useful Procedure for Diiodination of Carbazoles and Subsequent Efficient Transformation to Novel 3,6-bis(triethoxysilyl) Carbazoles Giving Mesoporous Materials," *Tetrahedron Letters*, 47(39), pp. 6957-6960 (Sep. 2006).
Mahapatra, et al., "A Small Molecule Which Protects Newborn Neurons", ACS Chemical Neuroscience, vol. 1, No. 9, pp. 589 (2010).
Mangialasche, F. et al., "Alzheimer's Disease: Clinical Trials and Drug Development," *The Lancet*, 9, pp. 702-716 (Jul. 2010).
Mangiarini, L. et al., "Exon 1 of the *HD* Gene with an Expanded CAG Repeat is Sufficient to Cause a Progressive Neurological Phenotype in Transgenic Mice," *Cell*, 87, pp. 493-506 (Nov. 1996).
Martin, D. et al., "Apoptotic Changes in the Aged Brain are Triggered by Interleukin-1β-Induced Activation of p. 38 and Reversed by Treatment with Eicosapentaeonic Acid," *The Journal of Biological Chemistry*, 277(37), pp. 34239-34246 (Sep. 2002).
Mattos et al., "Multiple Binding Modes," in *3D QSAR in Drug Design: Theory, Methods and Applications*, ed. H. Kubinyi, Springer, pp. 243-244 (Dec. 31, 1993).
McGrath, J. et al., "Novel Carbazole Phenoxy-Based Methacrylates to Produce High-Refractive Index Polymers," *Polymer*, 47, pp. 4042-4057 (Mar. 2006).
Menalled, L. et al., "Mouse Models of Huntington's Disease," *TRENDS in Pharmacological Sciences*, 23(1), pp. 32-39 (Jan. 2002).
Morcuende, A. et al., "Microwave-Promoted Transformations: Fast and Chemoselective N-Acylation of Amino Alcohols Using Catalytic Amounts of Dibutyltin Oxide. Influence of the Power Output and the Nature of the Acylating Agent on the Selectivity," *J. Org. Chem.*, 61(16), pp. 5264-5270 (Aug. 1996).
Murphy, K. et al., "Abnormal Synaptic Plasticity and Impaired Spatial Cognition in Mice Transgenic for Exon 1 of the Human Huntington's Disease Mutation," *The Journal of Neuroscience*, 20(13), pp. 5115-5123 (Jul. 2000).

Muruganantham et al., "Synthesis, anticonvulsant and antihypertensive activities of 8-substituted quinoline derivatives," Vel's College of Pharmacy, Biological & Pharmaceutical Bulletin. 27(10):1683-7 (2004).
Naidoo, J. et al., "Development of a Scalable Synthesis of P7C3-A20, a Potent Neuroprotective Agent" *Tetrahedron Letters*, vol. 54, pp. 4429-4431 (2013).
Naumova et al., CAPLUS Abstract of: Vestsi Akademii Navuk BSSR, Seryya Khimichnykh Navuk (1988), (4), 110-111)).
Negrin, C.M. et al., "In Vivo-In Vitro Study of Biodegradable Methadone Delivery Systems," *Biomaterials*, 22(6), pp. 563-570 (Mar. 2001).
Neitzert, H.C. et al., "Monitoring of the Initial Degradation of Oxadiazole Based Blue OLED's," *Journal of Non-Crystalline Solids*, 352, pp. 1695-1699 (Mar. 2006).
Newman, Robert A. et al., "Amelioration of Adriamycin and Daunorubicin Myocardial Toxicity by Adenosine", *Cancer Research*, vol. 41, pp. 3483-3488, Sep. 1981.
Nucifora, Jr., F. et al., "Interference by Huntingtin and Atrophin-1 with CBP-Mediated Transcription Leading to Cellular Toxicity," *Science*, 291, pp. 2423-2428 (Mar. 2001).
O'Brien, J. "A Promising New Treatment for Alzheimer's Disease?" *The Lancet*, 7, pp. 768-769 (Sep. 2008).
Okumura, H. et al., "Phenothiazine and Carbazole-Related Compounds Inhibit Mitotic Kinesin Eg5 and Trigger Apoptosis in Transformed Culture Cells," *Toxicology Letters*, 166(1), pp. 44-52 (Sep. 2006).
Olla, S. et al., "Indolyl-Pyrrolone as a New Scaffold for Pim1 Inhibitors," *Bioorganic & Medical Chemistry Letters*, 19(5), pp. 1512-1516 (Mar. 2009).
Pan, J. et al., "Synthesis of Carrier-Transporting Dendrimers with Perylenebis(dicarboximide)s as a Luminescent Core," *Eur. J. Org. Chem.*, 2006(4) pp. 986-1001 (Feb. 2006).
Panov, A. et al., "Early Mitochondrial Calcium Defects in Huntington's Disease are a Direct Effect of Polyglutamines," *Nature Neuroscience*, 5(8), pp. 731-736 (Aug. 2002).
Park, K. et al., "Promoting Axon Regeneration in the Adult CNS by Modulation of the PTEN/mTOR Pathway," *Science*, 322, pp. 963-966 (Nov. 2008).
Paton, J. et al., "Neurons Generated in the Adult Brain are Recruited into Functional Circuits," *Science*, 225(4666), pp. 1046-1048 (Sep. 1984).
Pattison, L. et al., "Apoptotic Cascades as Possible Targets for Inhibiting Cell Death in Huntington's Disease," *J Neurol*, 253(9), pp. 1137-1142 (Sep. 2006).
Pereira, Olivia M., et al., "Photosensitization of Human Diploid Cell, Cultures by Intracellular Flavins and Protection by Antioxidants", *Photochemistry and Photobiology*, vol. 24, Issue 3, pp. 237-242 (Sep. 1976).
Perutz, M., "Glutamine Repeats and Neurodegenerative Diseases: Molecular Aspects," *TIBS*, 24, pp. 58-63 (Feb. 1999).
Petit, S. et al., "Structure-Activity Relationship Analysis of the Peptide Deformylase Inhibitor 5-Bromo-1*H*-indole-3-acetohydroxamic Acid," *ChemMedChem*, 4(2), pp. 261-275 (Feb. 2009).
Petruska, J. et al., "Analysis of Strand Slippage in DNA Polymerase Expansions of CAG/CTG Triplet Repeats Associated with Neurodegenerative Disease," *The Journal of Biological Chemistry*, 273(9), pp. 5204-5210 (Feb. 1998).
Phillips, W. et al., "Abnormalities of Neurogenesis in the R6/2 Mouse Model of Huntington's Disease are Attributable to the In Vivo Microenvironment," *The Journal of Neuroscience*, 25(50), pp. 11564-11576 (Dec. 2005).
Pickard, B. et al., "Disruption of a Brain Transcription Factor, NPAS3, is Associated with Schizophrenia and Learning Disability," *American Journal of Medical Genetics Part B*, 136B(1), pp. 26-32 (Jul. 2005).
Pickard, B. et al., "The NPAS3 Gene—Emerging Evidence for a Role in Psychiatric Illness," *Annals of Medicine*, 38(6), pp. 439-448 (2006).
Pickard, B. et al., "Interacting Haplotypes at the *NPAS3* Locus Alter Risk of Schizophrenia and Bipolar Disorder," *Molecular Psychiatry*, 14(9), pp. 874-884 (Sep. 2009).

(56) References Cited

OTHER PUBLICATIONS

Pieper, A. et al., "The Neuronal PAS Domain Protein 3 Transcription Factor Controls FGF-Mediated Adult Hippocampal Neurogenesis in Mice," *PNAS*, 102(39), pp. 14052-14057 (Sep. 2005).
Pieper, A. et al., "Discovery of a Proneurogenic, Neuroprotective Chemical," *Cell*, 142, pp. 39-51 (Jul. 2010).
Pieper et al., "P7C3 and an unbiased Approach to Drug Discovery for Neurodegenerative Diseases," Chem. Soc. Rev.(2014), 19: 51-59.
Poesen, K. et al., "Novel Role for Vascular Endothelial Growth Factor (VEGF) Receptor-1 and its Ligand VEGF-B in Motor Neuron Degeneration," *The Journal of Neuroscience*, 28(42), pp. 10451-10459 (Oct. 2008).
Ponce, M. et al., "Synthesis and Isolation of Bromo-β-Carbolines Obtained by Bromination of β-Carboline Alkaloids," *J. Heterocyclic Chem.*, 38, pp. 1087-1095 (Sep.-Oct. 2001).
Pubchem SID 3976298 (deposit date Aug. 9, 2005).
Pubchem SID 7706058 (deposit date Sep. 26, 2005).
PubChem Compound, 1-[(3-chlorophenyl)amino]-3-(3,6-dibromo-9H-carbazol-9-yl)propan-2-ol, create date Jul. 28, 2005.
PubChem compound N-{4-[3-(3,6-dibromo-9H-carbazol-9-yl)-2-hydroxypropoxy]phenyl}acetamide, create date Sep. 15, 2005.
Racke et al., PPARs in Neuroinflammation, Hindawi Publishing (Special Issue), 107 pgs., 2008.
Ramamoorthy, "Synthesis of small molecular inhibitors targeting signal transduction pathways," *University of South Florida Thesis*, pp. 1-70 (Jun. 10, 2009).
Raoul, C et al., "Motoneuron Death Triggered by a Specific Pathway Downstream of Fas: Potentiation by ALS-Linked SOD1 Mutations" *Neuron*, vol. 35, pp. 1067-1083 (Sep. 12, 2002).
Ravlee et al., "Pharmacological evaluation of some new 6-amino/methyl pyridine derivatives," Chem. Pharm. Bull. 51(2): 162-170 (2003).
Rische, T. et al., "One-Pot Synthesis of Pharmacologically Active Diamines via Rhodium-Catalysed Carbonylative Hydroaminomethylation of Heterocyclic Allylic Amines," *Tetrahedron*, 55(32), pp. 9801-9816 (Aug. 1999).
Rubinsztein, D., "Lessons from Animal Models of Huntington's Disease," *TRENDS in Genetics*, 18(4), pp. 202-209 (Apr. 2002).
Rubinsztein, D. et al., "Huntington's Disease: Molecular Basis of Neurodegeneration," *Expert Reviews in Molecular Medicine*, 5(22), pp. 1-21 (Aug. 2003).
Sadri-Vakili, G. et al., "Mechanisms of Disease: Histone Modifications in Huntington's Disease," *Nature Clinical Practice: Neurology*, 2(6), pp. 330-338 (Jun. 2006).
Schmidt, H. et al., "The Role of Neurotrophic Factors in Adult Hippocampal Neurogenesis, Antidepressant Treatments and Animal Models of Depressive-Like Behavior," *Behavioural Pharmacology*, 18(5-6), pp. 391-418 (Sep. 2007).
Schwarcz, G. et al., "Open Label Evaluation of the Novel Antipsychotic Compound BW234U in Chronic Schizophrenics," *Drug Development Research*, vol. 5, pp. 387-393 (1985).
Stanfield, B. et al., "The Development of the Hippocampal Region," *Cerebral Cortex* (ed. Alan Peters and Edward G. Gones), vol. 7, pp. 91-131 (1988).
STN compounds registry Nos. 305862-95-7, 304893-66-1, 304880-74-8, 304878-30-6, 304868-62-0, 301353-98-0, 301353-96-8, 301160-69-0, 300805-47-7, 300588-31-2, 253448-99-6, 119091-28-0, 119091-27-9, 331416-70-7, 331235-98-4, 331235-97-3, 328076-93-3, 327026-16-4, 317842-35-6, 314052-83-0, 313268-34-7, 313268-19-8, 313268-17-6, and 313268-16-5, entry date ranging from Nov. 6, 2000 to May 19, 2009.
STN Registry Entry 312599-43-2 entered Jan. 3, 2001.
STN Registry Entry 448231-97-8 entered Sep. 9, 2002.
Sun, W. et al., "Programmed Cell Death of Adult-Generated Hippocampal Neurons is Mediated by the Proapoptotic Gene Bax," *The Journal of Neuroscience*, 24(49), pp. 11205-11213 (Dec. 2004).
Sundararajan, C. et al., "Photolytic Release of Carboxylic Acids Using Linked Donor-Acceptor Molecules: Direct versus Mediated Photoinduced Electron Transfer to N-Alkyl-4-picolinium Esters," *Organic Letters*, 7(13), pp. 2631-2634 (Jun. 2005).
Suzdalev, K.F. et al., "Synthesis of Indole 2,3-Epoxypropyl Derivatives and their Reactions with Amines," *Russian Journal of Organic Chemistry*, 41(2), pp. 233-237 (Feb. 2005).
Tang, T-S et al., "Disturbed $Ca^{2+}$Signaling and Apoptosis of Medium Spiny Neurons in Huntington's Disease," PNAS, 102(7), pp. 2602-2607 (Feb. 2005).
Tatton, N.A. et al., "In Situ Detection of Apoptotic Nuclei in the Substantia Nigra Compacta of 1-methyl-4-phenyl-1,2,3,6-tetrahydropyridine-treated Mice Using Terminal Deoxynucleotidyl Transferase Labelling and Acridine Orange Staining," *Neuroscience*, 77(4), pp. 1037-1048 (Apr. 1997).
Teles, A.V.F.F. et al., "Increase in *Bax* Expression and Apoptosis are Associated in Huntington's Disease Progression," *Neuroscience Letters*, 438(1), pp. 59-63 (Jun. 2008).
Terfloth et al., "Electronic Screening: Lead Finding from Database Mining," in *The Practice of Medicinal Chemistry*, ed. C. Wermuth, Academic Press, pp. 131-157 (Mar. 7, 1996).
Tesla, R. et al., "Neuroprotective Efficacy of Aminopropyl Carbazoles in a Mouse Model of Amyotrophic Lateral Sclerosis" *PNAS*, vol. 109, No. 42, pp. 17016-17021 (Oct. 16, 2012).
Thiel, M. et al., "Contributions to the Development of Psychotropic Substances, 3 Mitt: Diphenylamine Derivatives with Pyridyl-substituted Side Chains and Guanidyl," *Chemical Monthly*, 93(5), pp. 1080-1089 (1962).
Van Waarde, A. et al., "The Cholinergic System, sigma-1 Receptors and Cognition," *Behavioral Brain Research*, 221 (2), pp. 543-554 (Dec. 26, 2009).
van Praag, H. et al., "Running Increases Cell Proliferation and Neurogenesis in the Adult Mouse Dentate Gyrus," *Nature Neuroscience*, 2(3), pp. 266-270 (Mar. 1999).
Wang et al., "P7C3 Neuroprotective Chemicals Function by Activating the Rate-Limiting Enzyme in NAD Salvage," Cell 158, 11324-1334 (2014).
Wanker, E. et al., "HIP-I: A Huntingtin Interacting Protein Isolated by the Yeast Two-Hybrid System," *Human Molecular Genetics*, 6(3), pp. 487-495 (Mar. 1997).
Watanabe, T. et al., "Palladium-Catalyzed Direct Synthesis of Carbazoles via One-Pot N-Arylation and Oxidative Biaryl Coupling: Synthesis and Mechanistic Study," *J. Org. Chem.*, 74, pp. 4720-4726 (Jul. 2009).
Weissman, S. et al., "Ligand-Free Palladium-Catalyzed Cyanation of Aryl Halids," *J. Org. Chem.*, 70(4), pp. 1508-1510 (Jan. 2005).
Wermuth, C., "Molecular Variations Based on Isosteric Replacements," *The Practice of Medicinal Chemistry* (ed. Camille G. Wermuth), pp. 203-237 (1996).
Wilde, R. et al., "Acyl CoA:Cholesterol Acyltransferase (ACAT) Inhibitors: Heterocyclic Bioisosteres for the Urea Group in DuP 128," *Bioorganic & Medicinal Chemistry Letters*, 5(2), pp. 177-180 (Jan. 1995).
Wilen, S., *Tables of Resolving Agents and Optical Resolutions* (Ed. Ernest L. Eliel) pp. 268-298 (1972).
Wilen, S. et al, "Strategies in Optical Resolutions," *Tetrahedron*, 33, pp. 2725-2736 (1977).
Xuan, A.G. et al., "BDNF Improves the Effects of Neural Stem Cells on the Rat Model of Alzheimer's Disease with Unilateral Lesion of Fimbria-Fornix," *Neuroscience Letters*, 400(3), pp. 331-335 (Aug. 2008).
Xue, Y. et al., "Novel Hypoglycemic Compounds-synthesis of Glycine Derivatives and Research on the Role of PPARS," *Jiefangjun Yaoxue Xueao*, 25(1), pp. 5-10 (2009).
Yang, J. et al., "Prevention of Apoptosis by Bcl-2: Release of Cytochrome c from Mitochondria Blocked," *Science*, 275, pp. 1129-1132 (Feb. 1997).
Yin et al., "P7C3 Neuroprotective Chemicals Block Axonal Degeneration and Preserve Function after Traumatic Brain Injury" Cell Reports, 8, 1-10 (2014).
Yonemura, H. et al., "Spectroscopic Studies on Exchange Properties in Through-Ring Cyclodextrin Complexes of Carbazole-Viologen Linked Compounds: Effects of Spacer Chain Length," *J. Phys. Chem.*, 96, pp. 5765-5770 (Jul. 1992).

(56) References Cited

OTHER PUBLICATIONS

Yonemura, H. et al., "Effect of π-System on Long-Rang Photoinduced Electron Transfer in Through-Ring α-Cyclodextrin Complexes of Carbazole-Viologen Linked Compounds," *Tetrahedron Letters*, 39(38), pp. 6915-6918 (Sep. 1998).

Zeron, M. et al., "Mutant Huntingtin Enhances Excitotoxic Cell Death," *Molecular and Cellular Neuroscience*, 17(1), pp. 41-53 (Jan. 2001).

Zhang, H. et al., "Implantation of Neural Stem Cells Embedded in Hyaluronic Acid and Collagen Composite Conduit Promotes Regeneration in a Rabbit Facial Nerve Injury Model," *Journal of Translational Medicine*, 6(67), pp. 1-11 (Nov. 2008).

Zherebtsov et al., CAPLUS Abstract of: SU 474533, From: Otkrytiya, Izobret., Prom. Obraztsy, Tovarnye Znaki 1975, 52(23), 51-2.

Zoidis, G. et al., "Design and Synthesis of 1,2-annulated Adamantane Piperidines with Anti-Influenza Virus Activity," *Bioorganic & Medicinal Chemistry*, 17(4), pp. 1534-1541 (Feb. 2009).

Zuccato, C. et al., "Huntingtin Interacts with REST/NRSF to Modulate the Transcription of NRSE-controlled Neuronal Genes," *Nature Genetics*, 35(1), pp. 76-83 (Sep. 2003).

PCT International Search Report based on PCT/US2010/020681 dated Jun. 17, 2010.

USPTO Office Action in U.S. Appl. No. 12/832,056 mailed Feb. 9, 2012.

PCT International Search Report based on PCT/2011/043185 dated Apr. 10, 2012.

USPTO Office Action in U.S. Appl. No. 12/832,056 mailed Jul. 11, 2012.

USPTO Office Action in U.S. Appl. No. 12/685,652 mailed Jul. 19, 2012.

PCT International Search Report based on PCT/2012/052283 dated Oct. 24, 2012.

USPTO Notice of Allowance in U.S. Appl. No. 12/832,056 mailed Nov. 20, 2012.

USPTO Office Action in U.S. Appl. No. 12/685,652 mailed Mar. 20, 2013.

USPTO Office Action in U.S. Appl. No. 13/177,981 mailed Apr. 16, 2013.

USPTO Office Action in U.S. Appl. No. 12/685,652 mailed Apr. 26, 2013.

PCT International Preliminary Report on Patentability based on PCT/2011/043185 dated Jun. 25, 2013.

USPTO Office Action in U.S. Appl. No. 13/740,876 mailed Jul. 12, 2013.

USPTO Office Action in U.S. Appl. No. 13/709,531 mailed Jul. 17, 2013.

USPTO Office Action in U.S. Appl. No. 13/770,676 mailed Sep. 6, 2013.

USPTO Office Action in U.S. Appl. No. 13/177,981 mailed Nov. 18, 2013.

USPTO Office Action in U.S. Appl. No. 13/740,807 mailed Dec. 5, 2013.

USPTO Office Action in U.S. Appl. No. 13/594,223 mailed Jan. 13, 2014.

PCT International Search Report based on PCT/US13/56440 dated Jan. 22, 2014.

USPTO Office Action in U.S. Appl. No. 13/770,706 mailed Jan. 27, 2014.

USPTO Office Action in U.S. Appl. No. 13/177,981 mailed Mar. 21, 2014.

USPTO Office Action in U.S. Appl. No. 13/709,531 mailed Apr. 4, 2014.

Extended European Search Report issued in European Application No. EP 11804335 mailed on Apr. 17, 2014.

USPTO Office Action in U.S. Appl. No. 13/177,981 mailed Jun. 26, 2014.

USPTO Office Action in U.S. Appl. No. 13/594,223 mailed Jun. 26, 2014.

USPTO Office Action in U.S. Appl. No. 13/709,531 mailed Jul. 10, 2014.

PCT International Search Report based on PCT/US14/65058 dated Jan. 26, 2015.

PCT International Search Report based on PCT/US14/54099 dated Jan. 29, 2015.

USPTO Office Action in U.S. Appl. No. 14/100,515 mailed Feb. 12, 2015.

USPTO Office Action in U.S. Appl. No. 13/594,223 mailed Feb. 13, 2015.

USPTO Office Action in U.S. Appl. No. 13/594,223 mailed Apr. 19, 2016.

Supplementary European Search Report issued in European Application No. EP 12883358 mailed on May 6, 2016.

Supplementary European Search Report issued in European Application No. EP 13830535 mailed on Jun. 24, 2016.

\* cited by examiner

Pro-Neurogenic or Neuroprotective Molecules

Pool 7 $\longrightarrow$ $C_{21}H_{18}Br_2N_2O$ (MW=474.19)

Pool 14 $\longrightarrow$ None Found

Pool 18 $\longrightarrow$ $C_{21}H_{18}F_3N_3OS$ (MW=417.45)

Pool 19 $\longrightarrow$ $C_{16}H_{19}N_5O_2S_2$ (MW=377.40)

Pool 41 $\longrightarrow$ $C_{15}H_{18}N_4O_4S$ (MW=350.40)

Pool 53 $\longrightarrow$ $C_{14}H_{18}IN_5O_2$ (MW=415.23)

Pool 54 $\longrightarrow$ $C_{11}H_{14}BrN_3O_2S_2$ (MW=364.29)

Pool 61 $\longrightarrow$ $C_{21}H_{22}N_4O_5$ (MW=410.43)

Pool 69 $\longrightarrow$ None Found

Pool 70 $\longrightarrow$ $C_{20}H_{18}ClFN_6O$ (MW=412.85)

FIG. 6B

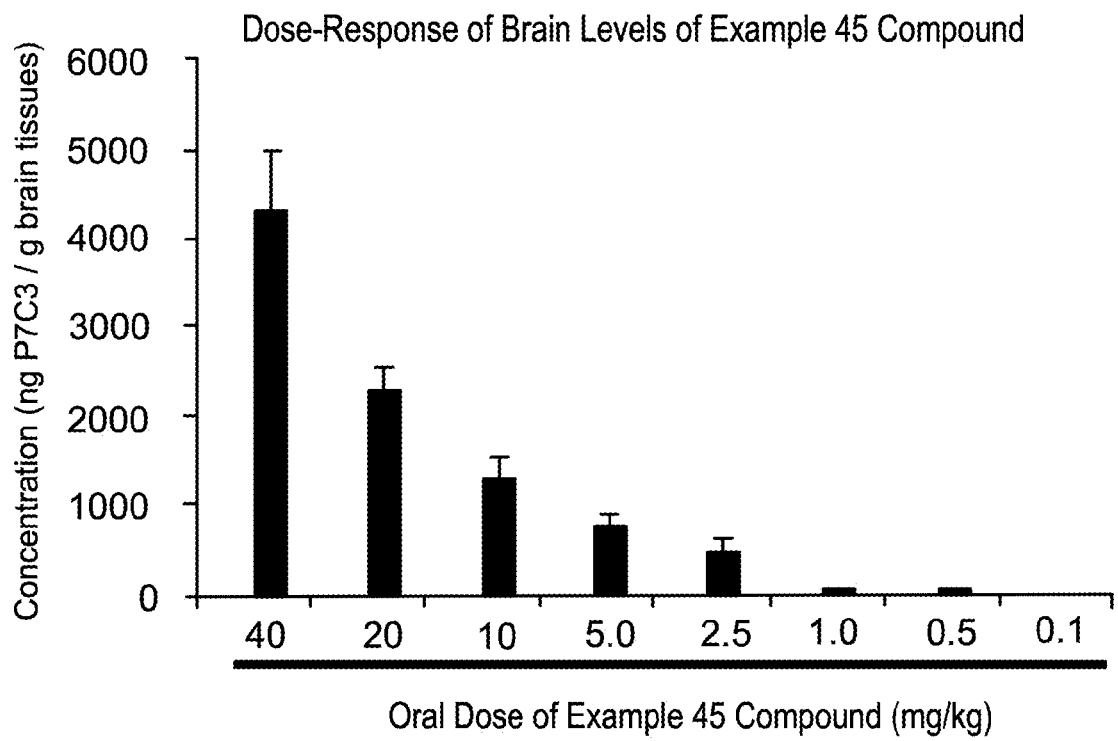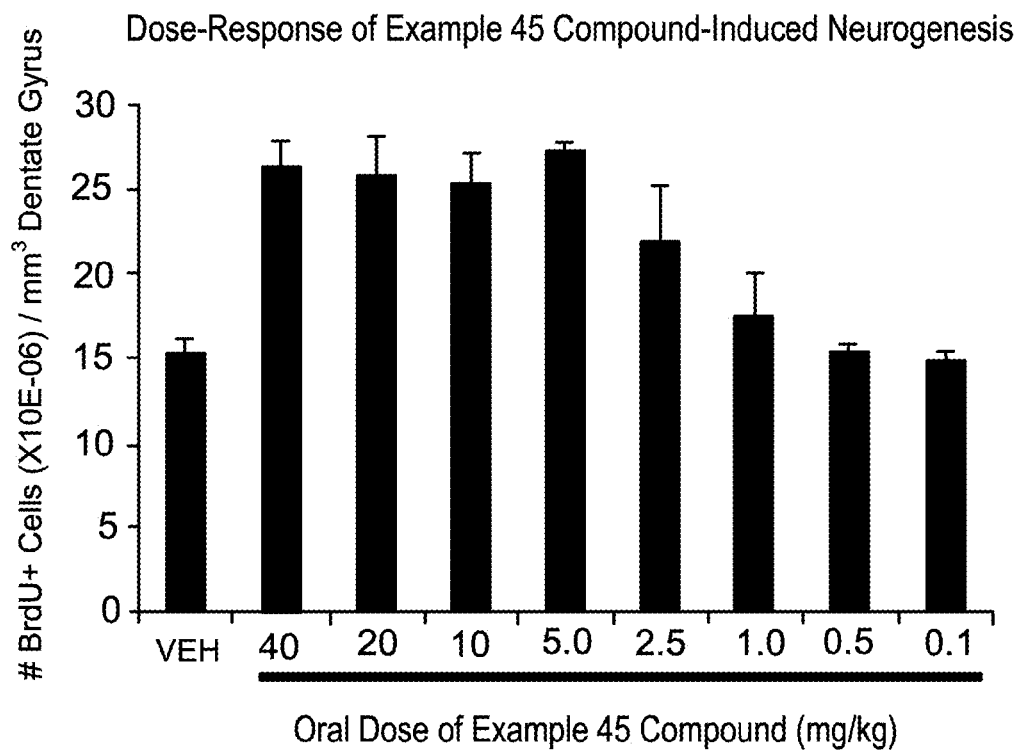
FIG. 7

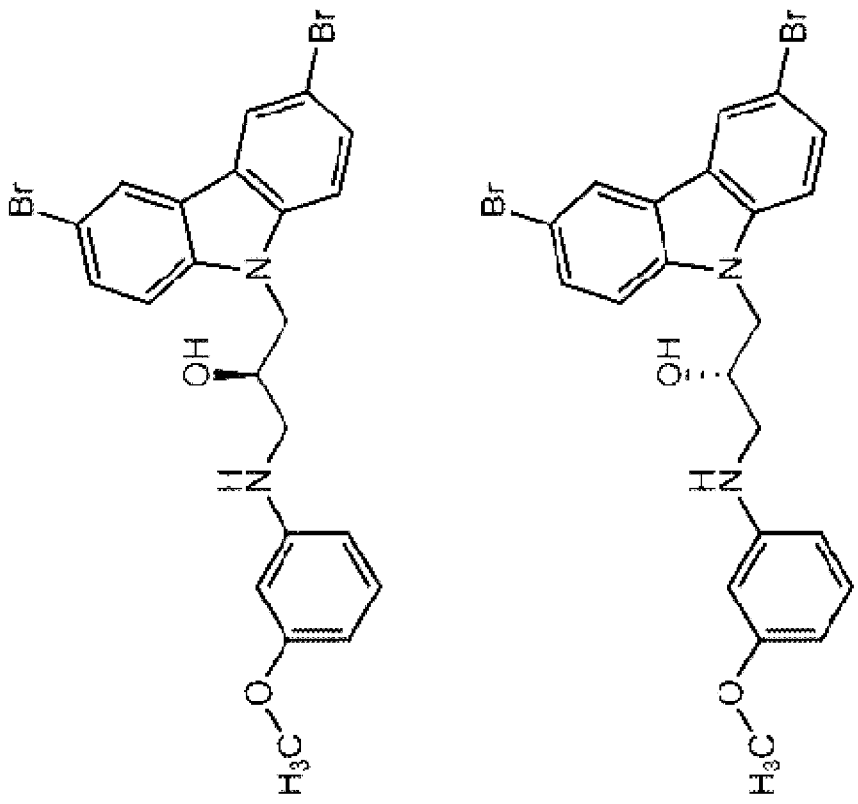
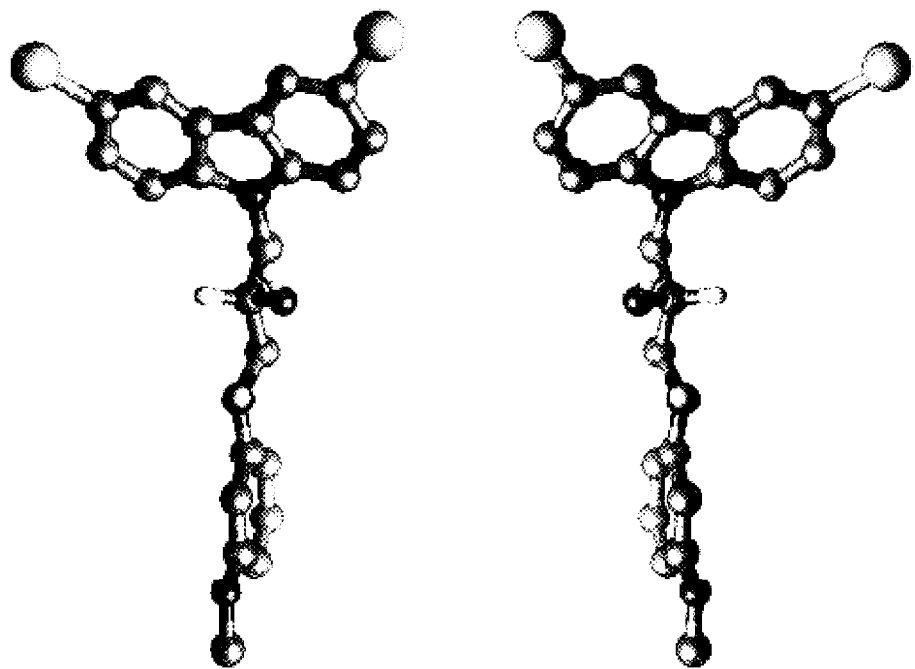
Example 62 Compound Enantiomers
FIG. 9A

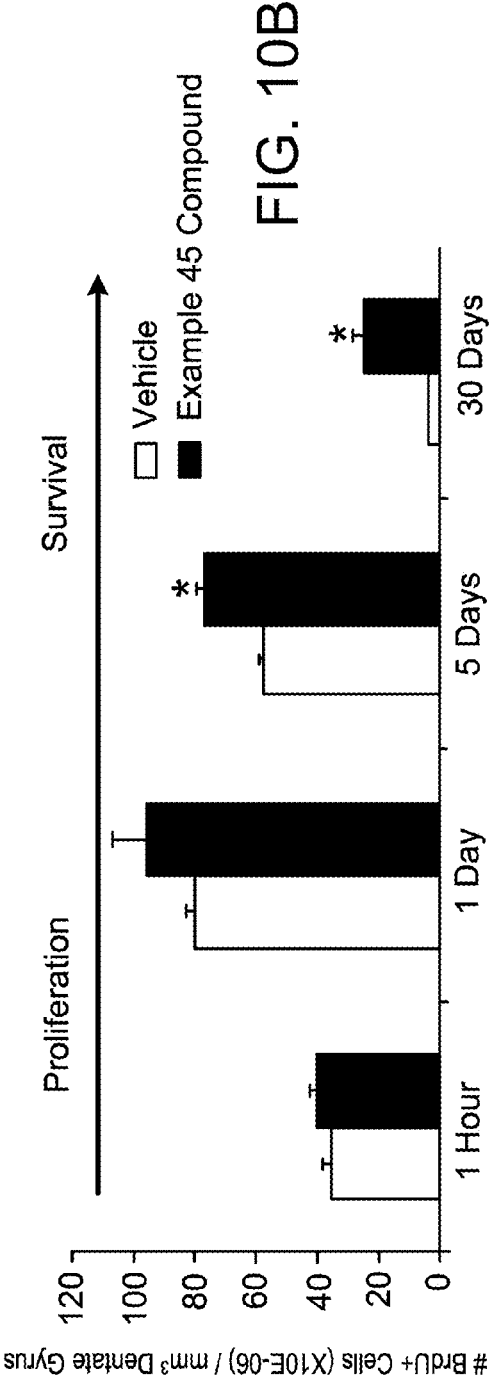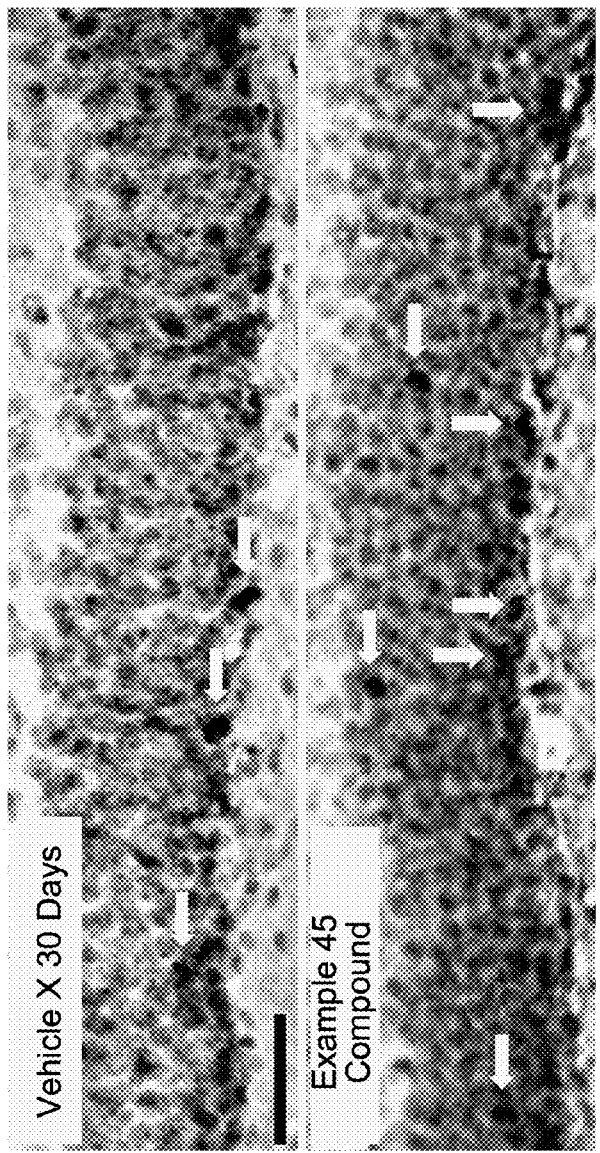
FIG. 10B

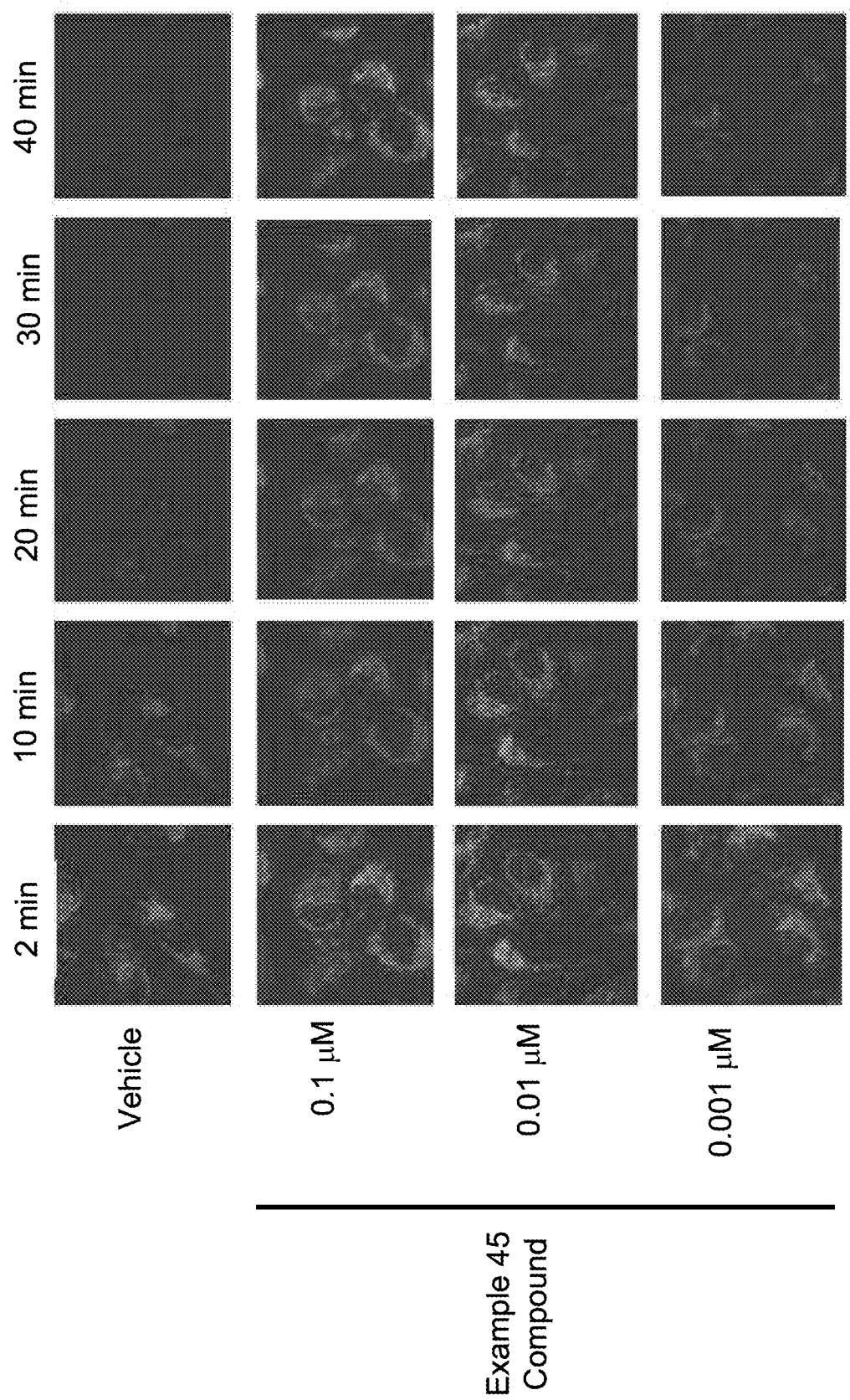

Example 45 Compound 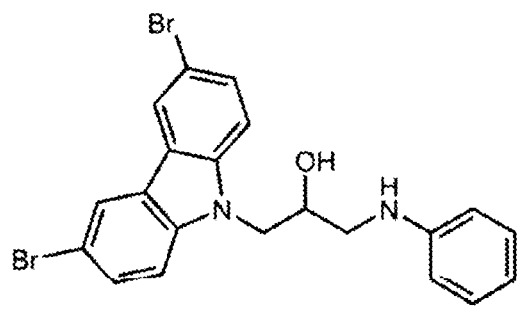  Dimebon 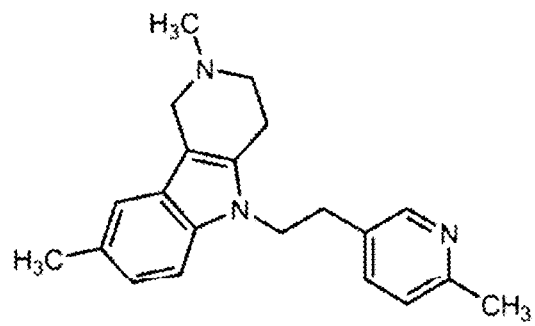
FIG. 19 A

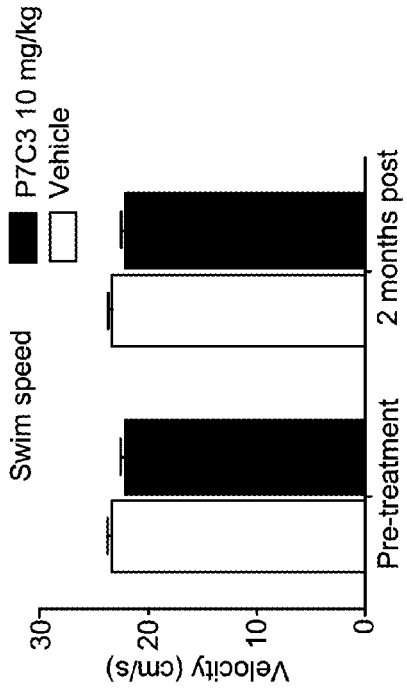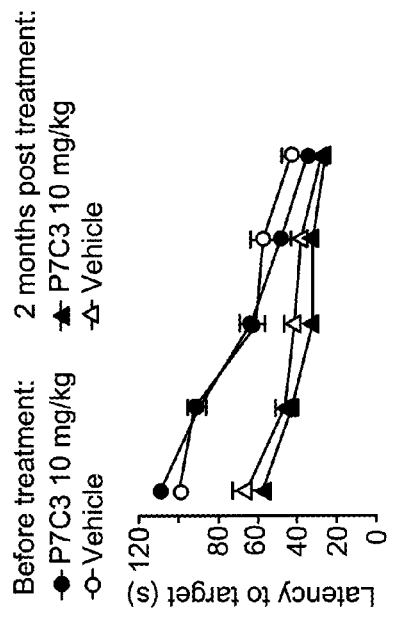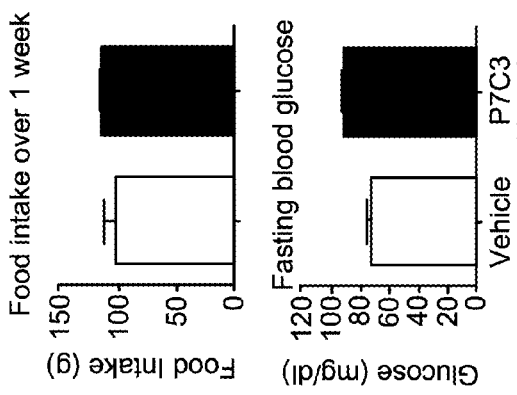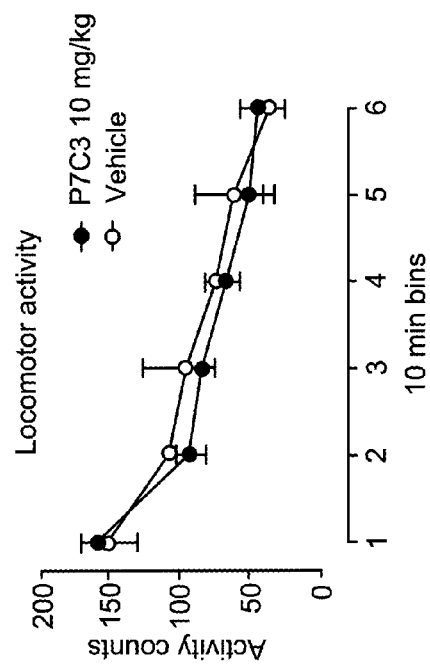
FIG. 20A–E

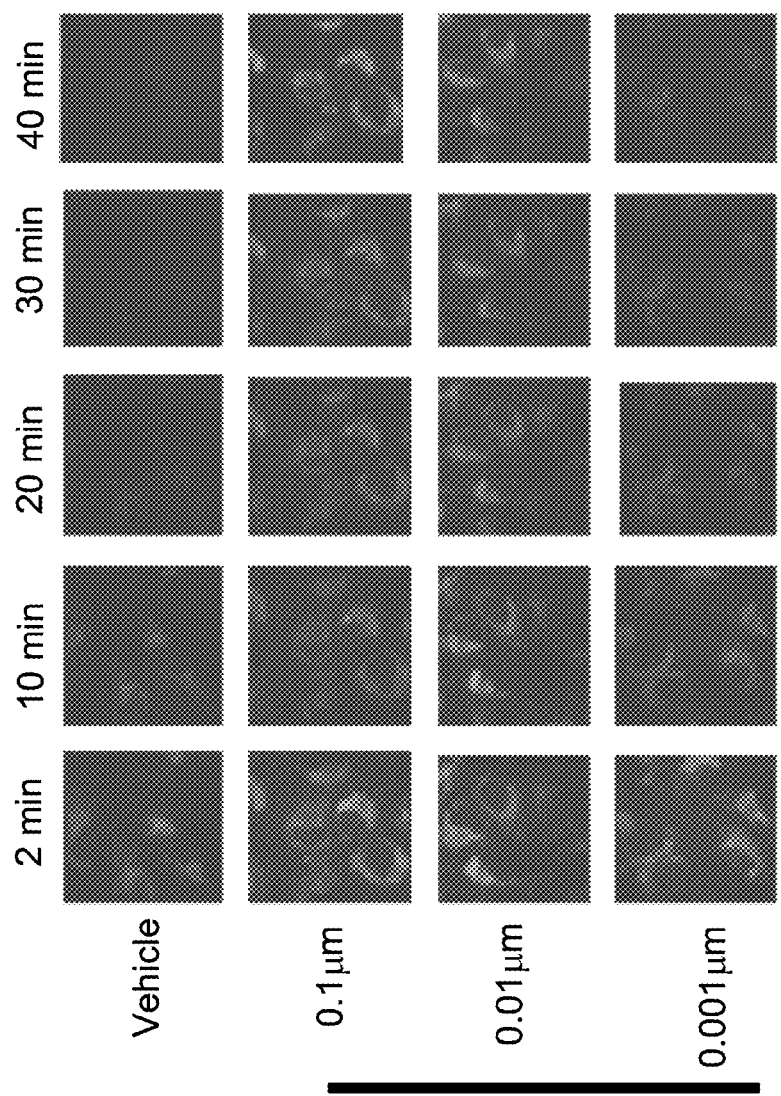
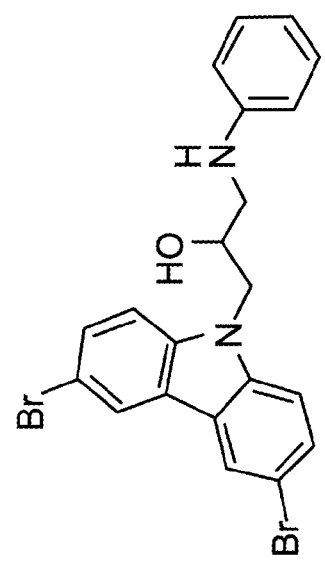
FIG. 22A

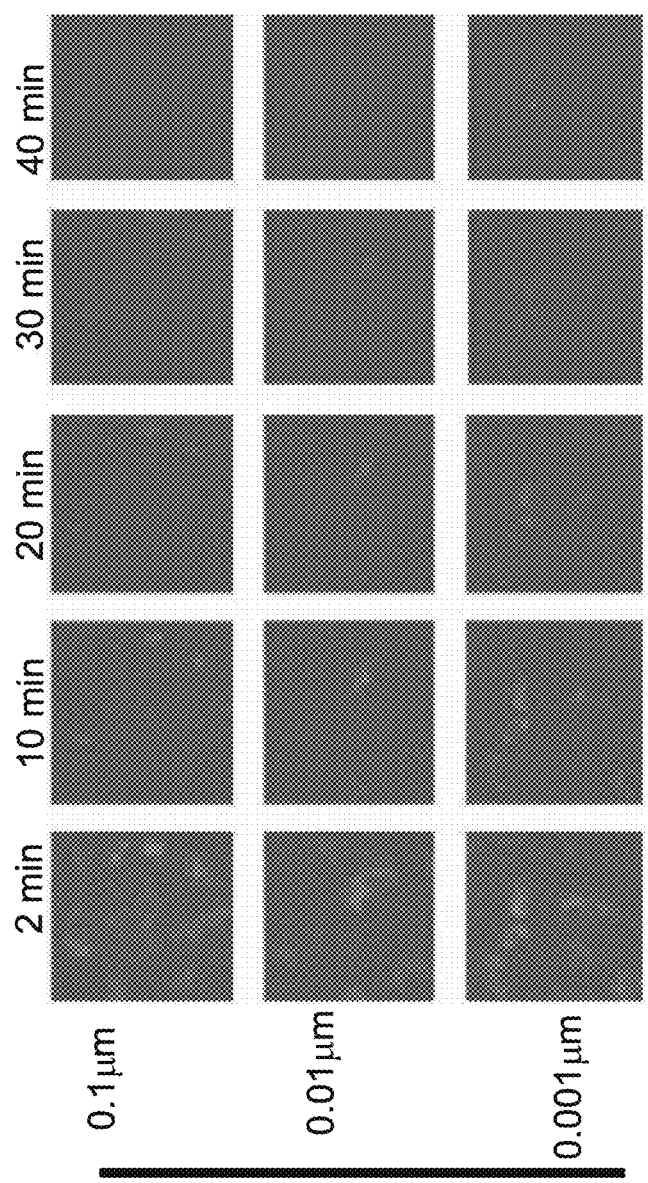
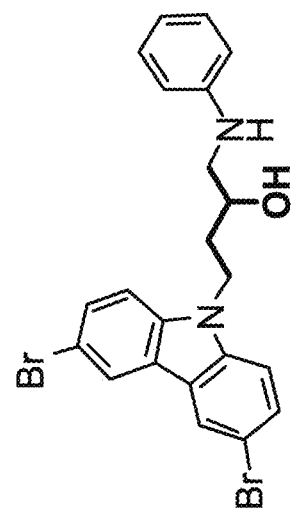
FIG. 22F

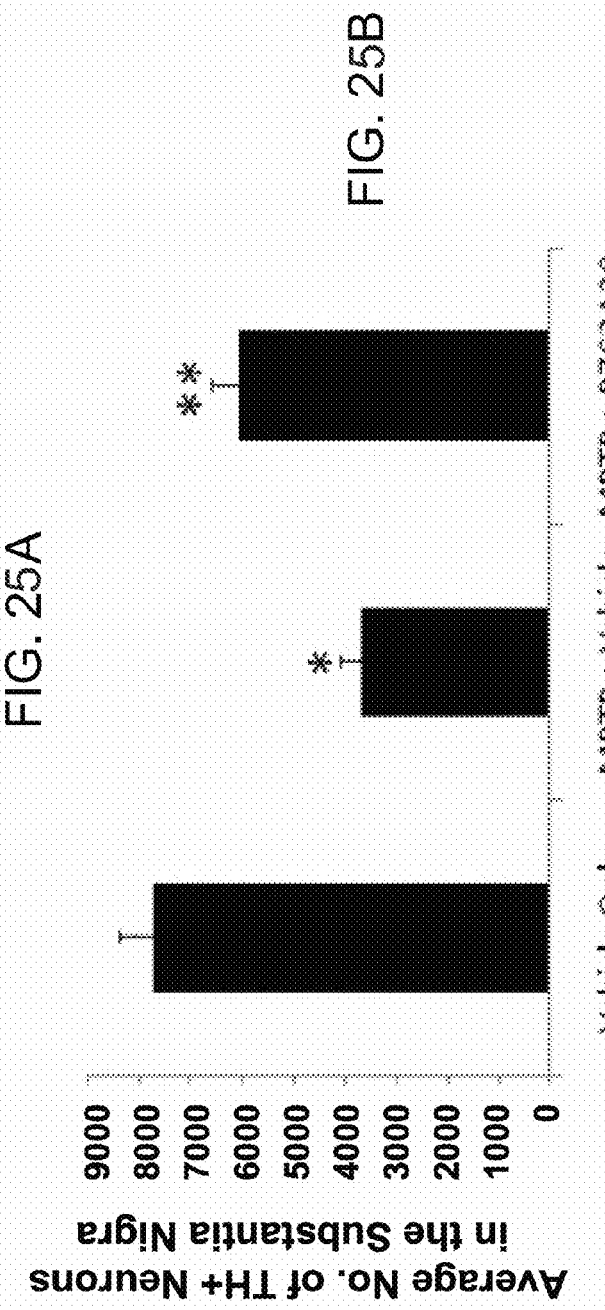

ARC: arcuate nucleus
DNH: dorso medial hypothalamus
VMH: ventral medial hypothalamus

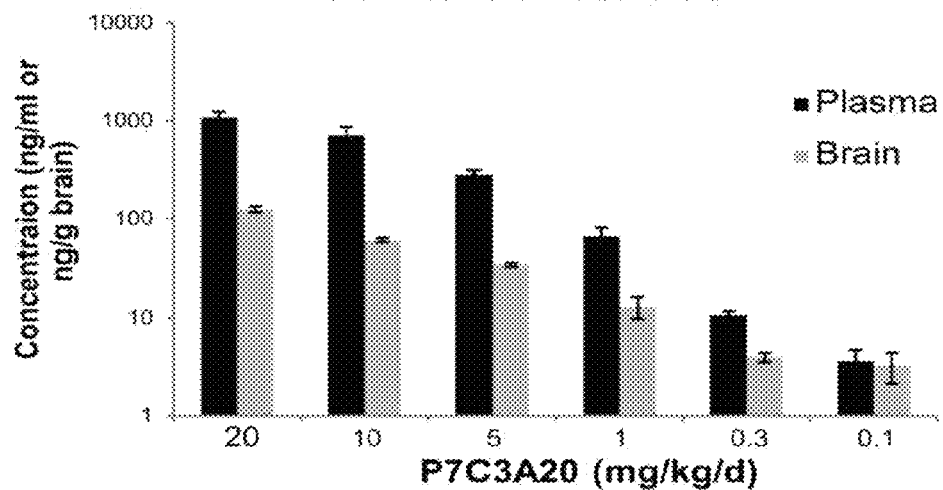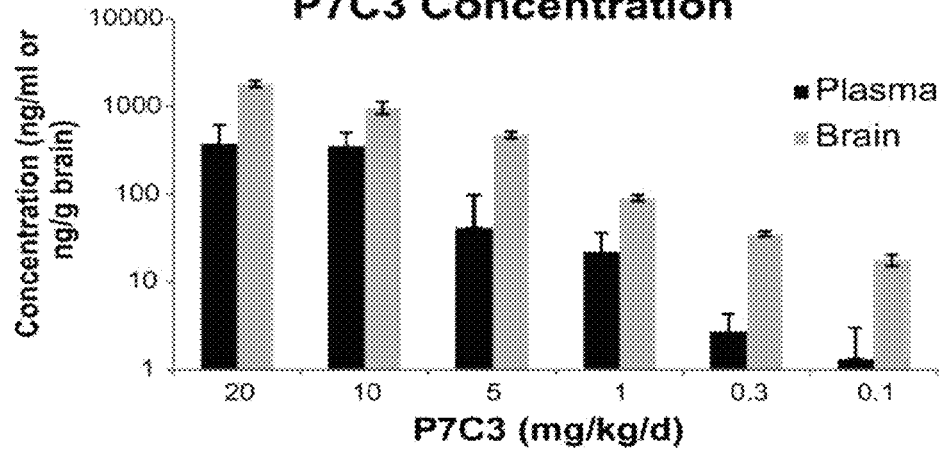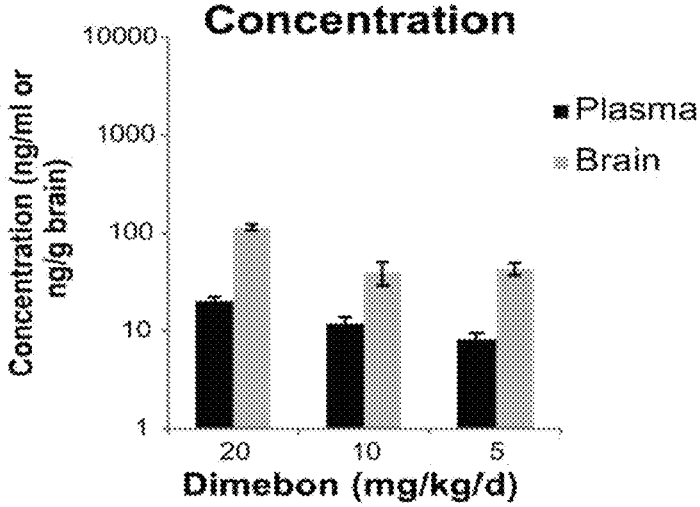
FIG. 30

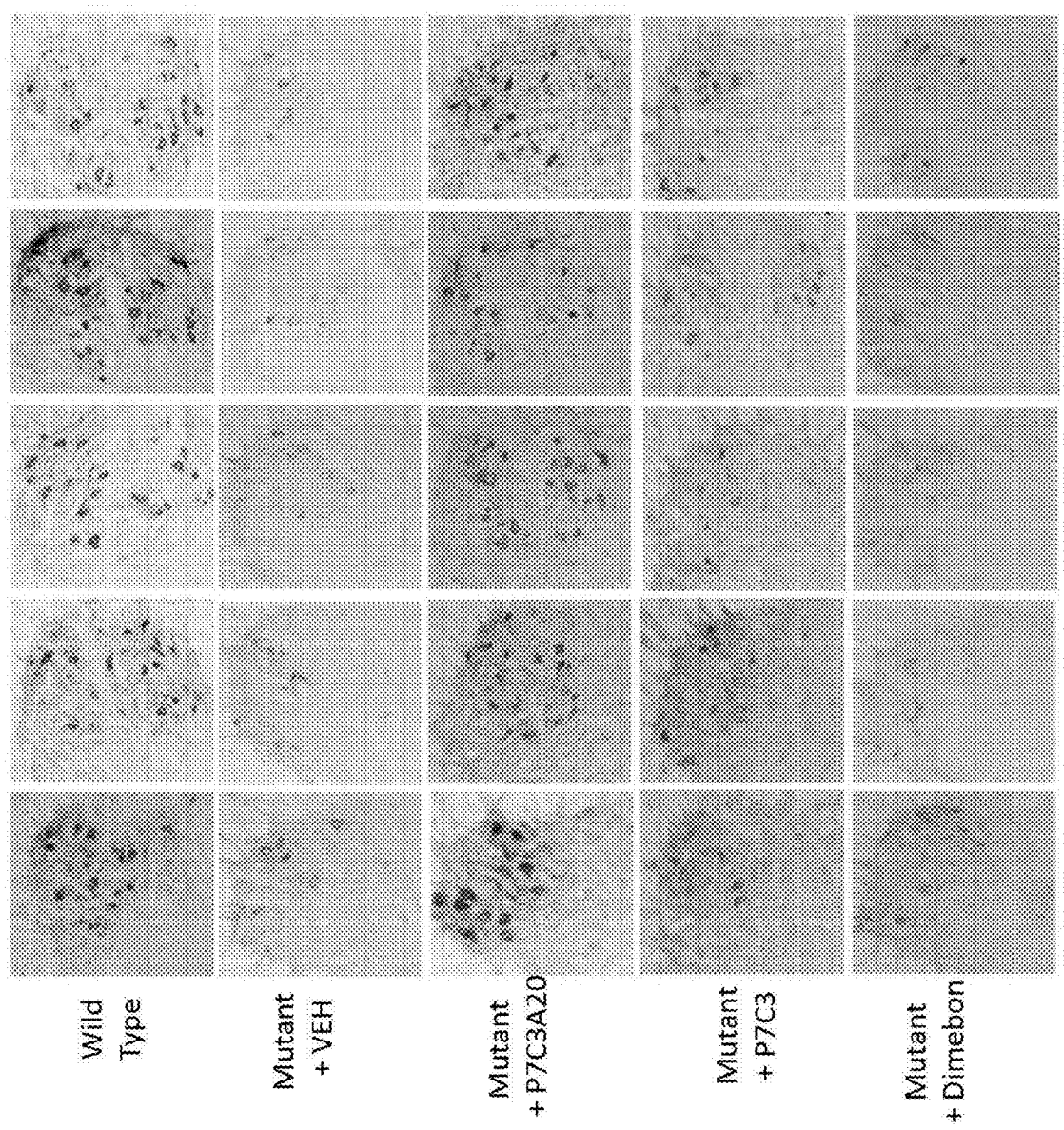

ANTI-DEPRESSION COMPOUNDS

CROSS REFERENCE TO RELATED APPLICATIONS

This application is a continuation application of U.S. application Ser. No. 14/339,772, filed Jul. 24, 2014, which claims the benefit of and priority to U.S. Provisional Application No. 61/958,282, filed Jul. 24, 2013, and which is a continuation-in-part application of U.S. application Ser. No. 13/594,223, filed Aug. 24, 2012, which is a continuation-in-part application of U.S. application Ser. No. 13/177,981 filed Jul. 7, 2011, now U.S. Pat. No. 9,095,572, which is a continuation-in-part of U.S. application Ser. No. 12/832,056 filed Jul. 7, 2010, now U.S. Pat. No. 8,362,277, which is a continuation-in-part of U.S. application Ser. No. 12/685,652 filed Jan. 11, 2010, now U.S. Pat. No. 8,604,074, which claims the benefit of and priority to U.S. Provisional Application No. 61/143,755, filed Jan. 9, 2009. Each of these prior applications is incorporated herein by reference in its entirety.

STATEMENT REGARDING FEDERALLY SPONSORED RESEARCH

This invention was made with government support under Grant Numbers 5DP1OD00027605, 5R37MH05938809, 1R01MH087986, 1R01MH085298 and 1R01DA024680, which were awarded by the National Institute of Health; the Government has certain rights in the invention.

TECHNICAL FIELD

This invention relates generally to the discovery of pro-neurogenic compounds capable of promoting neurogenesis and/or reducing neuronal cell death, more particularly use of such compounds as antidepressant agents.

BACKGROUND

It is now accepted that the adult vertebrate brain fosters the birth and functional incorporation of newly formed neurons (Goldman and Nottebohm, Proc Natl Acad Sci USA 1983, 80: 2390-2394; Paton and Nottebohm, Science 1984, 225, 1046-1048; Burd and Nottebohm, J Comp Neurol 1985, 240:143-152). However, it was long thought that no new neurons could be added to the adult mammalian brain. This dogma was challenged in the 1960's when autoradiographic evidence of new neuron formation in the hippocampal dentate gyms, olfactory bulb, and cerebral cortex of the adult rat was presented (Altman, J. Science 1962, 135, 1127-1128; Altman, J. J Comp Neurol 1966, 128:431-474; Altman, Anat Rec 1963, 145:573-591; Altman and Das, J. Comp. Neurol. 1965, 124, 319-335; Altman and Das, J Comp Neurol 1966, 126:337-390). It is now accepted that within all mammalian species, including humans (Eriksson et al., Nat. Med. 1998, 4(11), 1313-1317), there are two major reservoirs of neuronal stem cells, one located in the subgranular zone (SGZ) of the hippocampal dentate gyms and another in the subventricular zone (SVZ) (Gross, Natl. Rev. 2000, 1, 67-72). Neural stem cells in the SVZ facilitate formation of new neurons that migrate rostrally to populate the olfactory bulb, while neural stem cells in the SGZ produce neurons that integrate locally in the granular layer of the dentate gyms, a region of the hippocampus that exhibits lifelong structural and functional plasticity.

The process of new neuron formation in the adult mouse brain can be influenced by environmental, chemical and genetic variables. As demonstrated by Gage and colleagues, neurogenesis in the adult mouse brain is enhanced when animals are exposed to an enriched environment (Kempermann et al., Nature 1997, 386, 493-495) or able to exercise voluntarily (van Praag et al., Nat. Neuro-sci. 1999, 2, 266-270). More recently, anti-depressant drugs have been shown to enhance levels of adult neurogenesis in animals, including humans (Schmidt et al., Behav Pharmacol. 2007 September; 18(5-6):391-418; Boldrini et al., Neuropsychopharmacology 2009, 34, 2376-2389). Among many genes reported to impact adult neurogenesis is the gene encoding neuronal PAS domain protein 3 (NPAS3), a central nervous system (CNS)-specific transcription factor that has been associated with schizophrenia and bipolar disorder (Kamnasaran et al., J. Med. Genet. 2003, 40, 325-332; Pickard et al., Am. J. Med. Genet. B. Neuropsychiatr. Genet. 2005, 136B, 26-32; Pickard et al., Ann. Med. 2006, 38, 439-448; Pickard et al., Mol. Psychiatry 2009, 14, 874-884; Lavedan et al., Pharmacogenomics 2008, 9: 289-301). Animals missing both copies of the NPAS3 gene suffer a profound loss of adult hippocampal neurogenesis coupled with significant behavioral deficits (Pieper et al., Proc. Natl. Acad. Sci. USA 2005, 102, 14052-14057). Knowing that impaired post-natal neurogenesis elicits unfavorable phenotypic deficits, it is predicted that pro-neurogenic chemical compounds should exhibit favorable therapeutic benefits for a variety of neuropsychiatric and neurodegenerative diseases.

Depression is one of the most prevalent and pervasive forms of mental illness that affects individuals across age and gender lines. The lifetime risk of major depression is about 12% in men and about 25% in women, generally. In addition, about 5 to 10% of all patients in the primary care environment are present with major depression, whereas about 3 to 5% of patients are diagnosed with dysthymia. In an in-patient setting, however, between 10 and 14% of all patients are diagnosed with major depression. Major depression is a particularly disabling and pernicious, in part, because it is recurring. The rate of relapse for patients with major depression is about 40% over a two-year period after a first episode. The occurrence of relapse increases to about 75% within a five year period after the diagnosis of a second episode of major depression.

Depressive disorders are most commonly treated with three main classes of compounds: 1) monamine oxidase inhibitors; 2) heterocyclic antidepressants; and 3) selective serotonin reuptake inhibitors (SSRIs). The known and currently prescribed antidepressants are by numerous side effects. Monoamine oxidase inhibitors were the first class of antidepressants used clinically. Monoamine oxidase inhibitors, including isocarboxazid, phenelzine, and tranylcypromine, inhibit the metabolism of phenylethylamine and catabolism of dopamine, serotonin and norepinephrine. As a consequence of numerous dietary restrictions associated with the use of monoamine oxidase inhibitors, extensive side effects, including hypertension, headache, myoclonic jerk, sleep disruption, and gastrointestinal complications, monoamine oxidase inhibitors are currently not used as a first-line antidepressant. The tricyclic antidepressants, including, imipramine, desipramine, nortrypline, amitrypline, doxepin and protrypline, produce a variety of anticholinergic side effects, drowsiness, orthostatic hypotension, cardiac arrhythmias and weight gain. Although generally milder than the monoamine oxidase inhibitors and the tricyclic antidepressants, SSRIs also produce numerous side effects. For example, SSRIs, including fluoxetine, paroxetine, fluvoxamine, sertraline, and citalopram, are associated with gastrointestinal distress, jitteriness, agitation and sleep disruption.

In addition to the numerous side effects associated with traditional antidepressant medications, these therapeutics are also characterized by marginal efficacy. Several studies on the efficacy of antidepressant therapy for major depression have concluded that the treatment of acute disease or maintenance therapy is associated with a 50-60% response rate. The average absolute response rate between antidepressants and placebo is about 20-25%. Consequently, there is a current need for new antidepressant therapies.

In view of the sometimes severe adverse side effects and marginal efficacy of numerous antidepressant therapies, there is a great need for improved pharmaceuticals that effectively treat depressive disorders without producing the side effects associated with treatments of depression. The present invention identifies those compounds that enhance or improve learning and memory as a new class of therapeutics for the treatment of depressive disorders.

SUMMARY

This invention relates generally to compounds that promote the generation or the survival of existing neurons in the mammalian brain. For the purpose of simplicity these compounds are referred to as being pro-neurogenic. In certain embodiments, the compounds promote the generation or survival of neurons in the post-natal mammalian brain. In certain embodiments, the compounds promote the survival, growth, development and/or function of neurons, particularly CNS, brain, cerebral, and hippocampal neurons. In certain embodiments, the compounds stimulate post-natal hippocampal neurogenesis, which while not wishing to be bound by theory, is believed to represent a therapeutic target for a variety of neuropsychiatric and neurodegenerative diseases, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, abuse of neuro-active drugs (such as alcohol, opiates, methamphetamine, phencyclidine, and cocaine), retinal degeneration, spinal cord injury, and peripheral nerve injury. In certain embodiments, the compounds stimulate post-natal hypothalamic neurogenesis, which can provide therapeutic benefits in weight management, such as physiological weight loss associated with various conditions, including but not limited to, normal aging, chemotherapy, radiation therapy, stress, drug abuse, anorexia, as well as other diseases discussed herein.

The presently disclosed embodiments also feature compositions (e.g., pharmaceutical compositions) that include such compounds as well as methods of making, identifying, and using such compounds. Other features and advantages are described in, or will be apparent from, the present specification and accompanying drawings.

Accordingly, in one aspect, methods for promoting post-natal mammalian neurogenesis and/or reducing neuronal cell death in a subject in need thereof are described, the method comprising administering an effective amount of a compound having formula (I) or a pharmaceutically acceptable salt thereof:

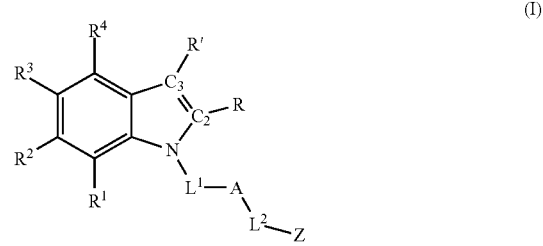

wherein:
each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —$NHC(O)(C_1$-$C_6$ alkyl), and nitro;
R and R' are defined according to (1), (2), (3), (4), or (5) below:
(1) R and R' together with $C_2$ and $C_3$, respectively, form a fused phenyl ring having formula (II):

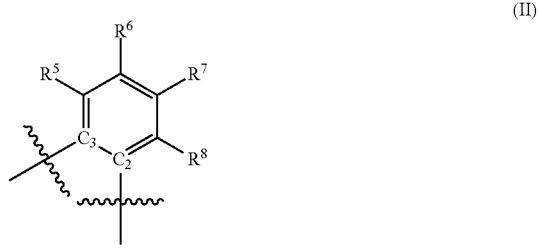

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —$NH(C_1$-$C_6$ alkyl), —$N(C_1$-$C_6$ alkyl)$_2$, —$NHC(O)(C_1$-$C_6$ alkyl), and nitro; OR
(2) each of R and R' is, independently, hydrogen, $C_1$-$C_6$ alkyl, or $C_1$-$C_6$ haloalkyl; OR
(3) R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$; OR
(4) R and R' together with $C_2$ and $C_3$, respectively, form a fused $C_5$-$C_6$ cycloalkyl ring that is optionally substituted with from 1-4 independently selected $R^a$; OR
(5) R and R' together with $C_2$ and $C_3$, respectively, form a fused heteroaryl ring containing from 5-6 ring atoms, wherein from 1-2 of the ring atoms is independently selected from N, NH, N($C_1$-$C_3$ alkyl), O, and S; and wherein said heteroaryl ring is optionally substituted with from 1-3 independently selected $R^b$;
$L^1$ is:
(i) $C_1$-$C_3$ straight chain alkylene, which is optionally substituted with from 1-2 independently selected $R^c$; or
(ii) a bond that directly connects N in the 5-membered ring of formula (I) to A in formula (I);
$L^2$ is:
(i) $C_1$-$C_3$ straight chain alkylene, which is optionally substituted with from 1-2 independently selected $R^c$; or (ii) a bond that directly connects A in formula (I) to Z in formula (I);

A is:
(i) $CR^{A1}R^{A2}$, wherein each of $R^{A1}$ and $R^{A2}$ is independently selected from hydrogen, halo, $C_1$-$C_3$ alkyl, or $OR^9$; or
(ii) C=O; or
(iii) $C_3$-$C_5$ cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;

Z is:
(i) —$NR^{10}R^{11}$; or
(ii) —$C(O)NR^{10}R^{11}$; or
(iii) —$OR^{12}$; or
(iv) —$S(O)_nR^{13}$, wherein n is 0, 1, or 2 or
(v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$;
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
 (1) the aryl portion is optionally substituted with from 1-4 independently selected $R^b$, and
 (2) the cycloalkyl portion is optionally substituted with from 1-4 independently selected $R^a$;
or
(ix) arylheterocyclyl containing from 8-14 ring atoms, wherein:
 (1) the aryl portion from is optionally substituted with from 1-4 independently selected $R^b$, and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(x) heteroarylheterocyclyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(xi) heteroarylcycloalkyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) the cycloalkyl portion is optionally substituted with from 1-4 independently selected $R^a$;

$R^9$ is hydrogen; or $C_1$-$C_3$ alkyl that is optionally substituted with hydroxyl or $C_1$-$C_3$ alkoxy; each of $R^{10}$ and $R^{11}$ is independently selected from the substituents delineated collectively in (a) through (l) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl;
(g) $C_8$-$C_{14}$ arylcycloalkyl, wherein:
 (1) the aryl portion is optionally substituted with from 1-4 independently selected $R^b$, and
 (2) the cycloalkyl portion is optionally substituted with from 1-4 independently selected $R^a$;
(h) arylheterocyclyl containing from 8-14 ring atoms, wherein:
 (1) the aryl portion from is optionally substituted with from 1-4 independently selected $R^b$, and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(i) heteroarylheterocyclyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(j) heteroarylcycloalkyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally the aryl portion from is optionally substituted with from 1-4 independently selected $R^b$, $R^{12}$ is:
(i) $C_6$-$C_{10}$ aryl that is optionally substituted with from 1-4 $R^b$; or (ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or (iii) $C_1$-$C_6$ alkyl or $C_1$-$C_6$ haloalkyl, each of which is optionally substituted with from 1-3 $R^d$; or (iv) $C_8$-$C_{14}$ arylcycloalkyl, wherein:
   (1) the aryl portion is optionally substituted with from 1-4 independently selected $R^b$, and
   (2) the cycloalkyl portion is optionally substituted with from 1-4 independently selected $R^a$;
or (v) arylheterocyclyl containing from 8-14 ring atoms, wherein:
   (1) the aryl portion from is optionally substituted with from 1-4 independently selected $R^b$, and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or (vi) heteroarylheterocyclyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or (vii) heteroarylcycloalkyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) the cycloalkyl portion is optionally substituted with from 1-4 independently selected $R^a$;

$R^{13}$ is:

(i) $C_6$-$C_{10}$ aryl that is optionally substituted with from 1-4 $R^b$; or (ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

(iii) $C_8$-$C_{14}$ arylcycloalkyl, wherein:
   (1) the aryl portion is optionally substituted with from 1-4 independently selected $R^b$, and
   (2) the cycloalkyl portion is optionally substituted with from 1-4 independently selected $R^a$;
or (iv) arylheterocyclyl containing from 8-14 ring atoms, wherein:
   (1) the aryl portion from is optionally substituted with from 1-4 independently selected $R^b$, and
   (2) from 1-2 of the ring atoms of the heterocyclyl portion is independently selected from N, N($C_1$-$C_6$ alkyl), NC(O)($C_1$-$C_6$ alkyl), O, and S; and wherein said heterocyclyl portion is optionally substituted with from 1-3 independently selected $R^a$;
or (v) heteroarylheterocyclyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or (vi) heteroarylcycloalkyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:

(aa) $C_1$-$C_6$ alkoxy; $C_1$-$C_6$ haloalkoxy; $C_1$-$C_6$ thioalkoxy; $C_1$-$C_6$ thiohaloalkoxy; —O—($CH_2$)$_{1-3}$—[O($CH_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;

(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;

(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —$NH(C_1$-$C_6$ alkyl), $N(C_1$-$C_6$ alkyl$)_2$, —$NHC(O)(C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —$NH(C_1$-$C_6$ alkyl), $N(C_1$-$C_6$ alkyl$)_2$, —$NHC(O)(C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —$NH(C_1$-$C_6$ alkyl); $N(C_1$-$C_6$ alkyl$)_2$; —$NHC(O)(C_1$-$C_6$ alkyl); cyano; —$C(O)H$; —$C(O)(C_1$-$C_6$ alkyl); —$C(O)(C_1$-$C_6$ haloalkyl); $C(O)OH$; —$C(O)O(C_1$-$C_6$ alkyl); —$C(O)NH_2$; —$C(O)NH(C_1$-$C_6$ alkyl); $C(O)N(C_1$-$C_6$ alkyl$)_2$; —$SO_2(C_1$-$C_6$ alkyl); —$SO_2NH_2$; —$SO_2NH(C_1$-$C_6$ alkyl); —$SO_2N(C_1$-$C_6$ alkyl$)_2$; and $L^3$-$(C_1$-$C_6$ alkylene)-Cy, where in $L^3$ is a —O—, —NH—, —$NCH_3$—, —$C(O)$—, —$C(O)NH$—, —$C(O)NCH_3$—, —$NHC(O)$—, or —$NCH_3C(O)$—, and Cy is a saturated, partially unsaturated or aromatic carbocyclic or heterocyclic ring system;

or a pharmaceutically acceptable salt thereof.

In some embodiments, one or more of (A), (B), or (C) apply.

(A) Provided that when R and R' are defined according to definition (3), then:

(i) each of $L^1$ and $L^2$ must be $C_1$-$C_3$ alkylene, which is optionally substituted with from 1-2 independently selected $R^c$ when A is $CH_2$; or (ii) Z must be other than heteroaryl containing from 5-14 (e.g., 5-6 or 6) ring atoms, wherein from 1-6 of the ring atoms is independently selected from N, NH, $N(C_1$-$C_3$ alkyl), O, and S; and wherein said heteroaryl is optionally substituted with from 1-4 independently selected $R^b$; e.g., other than substituted pyridyl, e.g., other than pyridyl substituted with $C_1$-$C_3$ alkyl (e.g., $CH_3$), e.g., other than 2 or 6-methylpyridyl.

(B) Each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

(C) $R^{12}$ and/or $R^{13}$ cannot be substituted phenyl. In embodiments, $R^{12}$ and/or $R^{13}$ cannot be substituted phenyl when R and R' are defined according to definition (1); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

In some embodiments, (A), (B), or (C) applies. In other embodiments, (A) and (B); or (A) and (C); or (B) and (C) applies. In still other embodiments, (A), (B), and (C) apply.

In another aspect, methods for promoting post-natal mammalian neurogenesis in a subject in need thereof are featured. The method includes administering to the subject an effective amount of a compound having formula (I) or a pharmaceutically acceptable salt thereof.

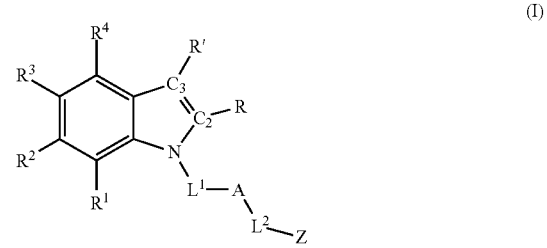

wherein:
each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —$NH(C_1$-$C_6$ alkyl), —$N(C_1$-$C_6$ alkyl$)_2$, —$NHC(O)(C_1$-$C_6$ alkyl), and nitro;

R and R' are defined according to (1), (2), (3), (4), or (5) below:

(1) R and R' together with $C_2$ and $C_3$, respectively, form a fused phenyl ring having formula (II):

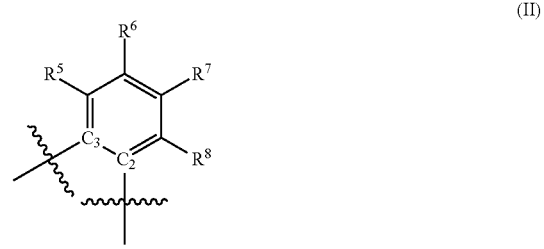

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ halothioalkoxy, $C_1$-$C_6$ alkyl, $C_1$-$C_6$ haloalkyl, cyano, —$NH_2$, —$NH(C_1$-$C_6$ alkyl), $N(C_1$-$C_6$ alkyl$)_2$, —$NHC(O)(C_1$-$C_6$ alkyl), and nitro; OR (2) each of R and R' is, independently, hydrogen, $C_1$-$C_6$ alkyl, or $C_1$-$C_6$ haloalkyl; OR (3) R and R' together with $C_2$ and $C_3$, respectively, form a fused heterocyclic ring containing from 5-6 ring atoms, wherein from 1-2 of the ring atoms is independently selected from N, NH, $N(C_1$-$C_6$ alkyl), $NC(O)(C_1$-$C_6$ alkyl), O, and S; and wherein said heterocyclic ring is optionally substituted with from 1-3 independently selected $R^a$; OR (4) R and R' together with $C_2$ and $C_3$, respectively, form a fused $C_5$-$C_6$ cycloalkyl ring that is optionally substituted with from 1-4 independently selected $R^a$; OR (5) R and R' together with $C_2$ and $C_3$, respectively, form a fused heteroaryl ring containing from 5-6 ring atoms, wherein from 1-2 of the ring atoms is independently selected from N, NH, $N(C_1$-$C_3$ alkyl), O, and S; and wherein said heteroaryl ring is optionally substituted with from 1-3 independently selected $R^b$;

$L^1$ is:
(i) $C_1$-$C_3$ straight chain alkylene, which is optionally substituted with from 1-2 independently selected $R^c$; or
(ii) a bond that directly connects N in the 5-membered ring of formula (I) to A in formula (I);

$L^2$ is:
(i) $C_1$-$C_3$ straight chain alkylene, which is optionally substituted with from 1-2 independently selected $R^c$; or (ii) a bond that directly connects A in formula (I) to Z in formula (I);

A is:
(i) $CR^{A1}R^{A2}$, wherein each of $R^{A1}$ and $R^{A2}$ is independently selected from hydrogen, halo, $C_1$-$C_3$ alkyl, or $OR^9$; or
(ii) C=O; or
(iii) $C_3$-$C_5$ cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;

Z is:
(i) —$NR^{10}R^{11}$; or
(ii) —$C(O)NR^{10}R^{11}$; or
(iii) —$OR^{12}$; or
(iv) —$S(O)_nR^{13}$, wherein n is 0, 1, or 2 or
(v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$;
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
 (1) the aryl portion is optionally substituted with from 1-4 independently selected $R^b$, and
 (2) the cycloalkyl portion is optionally substituted with from 1-4 independently selected $R^a$;
or
(ix) arylheterocyclyl containing from 8-14 ring atoms, wherein:
 (1) the aryl portion from is optionally substituted with from 1-4 independently selected $R^b$, and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(x) heteroarylheterocyclyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(xi) heteroarylcycloalkyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) the cycloalkyl portion is optionally substituted with from 1-4 independently selected $R^a$;

$R^9$ is hydrogen; or $C_1$-$C_3$ alkyl that is optionally substituted with hydroxyl or $C_1$-$C_3$ alkoxy; each of $R^{10}$ and $R^{11}$ is independently selected from the substituents delineated collectively in (a) through (l) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl;
(g) $C_8$-$C_{14}$ arylcycloalkyl, wherein:
 (1) the aryl portion is optionally substituted with from 1-4 independently selected $R^b$, and
 (2) the cycloalkyl portion is optionally substituted with from 1-4 independently selected $R^a$;
(h) arylheterocyclyl containing from 8-14 ring atoms, wherein:
 (1) the aryl portion from is optionally substituted with from 1-4 independently selected $R^b$, and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(i) heteroarylheterocyclyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(j) heteroarylcycloalkyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally the aryl portion from is optionally substituted with from 1-4 independently selected $R^b$, $R^{12}$ is:
(i) $C_6$-$C_{10}$ aryl that is optionally substituted with from 1-4 $R^b$; or (ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is optionally substituted with from 1-3 $R^d$; or
(iv) $C_8$-$C_{14}$ arylcycloalkyl, wherein:
   (1) the aryl portion is optionally substituted with from 1-4 independently selected $R^b$, and
   (2) the cycloalkyl portion is optionally substituted with from 1-4 independently selected $R^a$;
or
(v) arylheterocyclyl containing from 8-14 ring atoms, wherein:
   (1) the aryl portion from is optionally substituted with from 1-4 independently selected $R^b$, and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylheterocyclyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vii) heteroarylcycloalkyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) the cycloalkyl portion is optionally substituted with from 1-4 independently selected $R^a$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_8$-$C_{14}$ arylcycloalkyl, wherein:
   (1) the aryl portion is optionally substituted with from 1-4 independently selected $R^b$, and
   (2) the cycloalkyl portion is optionally substituted with from 1-4 independently selected $R^a$;
or
(iv) arylheterocyclyl containing from 8-14 ring atoms, wherein:
   (1) the aryl portion from is optionally substituted with from 1-4 independently selected $R^b$, and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(v) heteroarylheterocyclyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylcycloalkyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, —NHC(O)($C_1$-$C_6$ alkyl), wherein the alkyl portion of each is optionally substituted with from 1-3 independently selected $R^e$;
(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and
(dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —$NH(C_1$-$C_6$ alkyl), $N(C_1$-$C_6$ alkyl$)_2$, —$NHC(O)(C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —$NH(C_1$-$C_6$ alkyl), $N(C_1$-$C_6$ alkyl$)_2$, —$NHC(O)(C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —$NH(C_1$-$C_6$ alkyl); $N(C_1$-$C_6$ alkyl$)_2$; —$NHC(O)(C_1$-$C_6$ alkyl); cyano; —C(O)H; —$C(O)(C_1$-$C_6$ alkyl); —$C(O)(C_1$-$C_6$ haloalkyl); C(O)OH; —$C(O)O(C_1$-$C_6$ alkyl); —$C(O)NH_2$; —C(O)NH ($C_1$-$C_6$ alkyl); $C(O)N(C_1$-$C_6$ alkyl$)_2$; —$SO_2(C_1$-$C_6$ alkyl); —$SO_2NH_2$; —$SO_2NH(C_1$-$C_6$ alkyl); —$SO_2N(C_1$-$C_6$ alkyl$)_2$; and $L^3$-($C_1$-$C_6$ alkylene)-Cy, where in $L^3$ is a —O—, —NH—, —$NCH_3$—, —C(O)—, —C(O)NH—, —C(O)$NCH_3$—, —NHC(O)—, or —$NCH_3C(O)$—, and Cy is a saturated, partially unsaturated or aromatic carbocyclic or heterocyclic ring system;

or a salt (e.g., pharmaceutically acceptable salt) thereof.

In some embodiments, one or more of (A), (B), or (C) apply.

(A) Provided that when R and R' are defined according to definition (3), then:

(i) each of $L^1$ and $L^2$ must be $C_1$-$C_3$ alkylene, which is optionally substituted with from 1-2 independently selected $R^c$ when A is $CH_2$; or (ii) Z must be other than heteroaryl containing from 5-14 (e.g., 5-6 or 6) ring atoms, wherein from 1-6 of the ring atoms is independently selected from N, NH, $N(C_1$-$C_3$ alkyl), O, and S; and wherein said heteroaryl is optionally substituted with from 1-4 independently selected $R^b$; e.g., other than substituted pyridyl, e.g., other than pyridyl substituted with $C_1$-$C_3$ alkyl (e.g., $CH_3$), e.g., other than 2 or 6-methylpyridyl.

(B) Each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

(C) $R^{12}$ and/or $R^{13}$ cannot be substituted phenyl. In embodiments, $R^{12}$ and/or $R^{13}$ cannot be substituted phenyl when R and R' are defined according to definition (1); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

In embodiments, (A), (B), or (C) applies. In other embodiments, (A) and (B); or (A) and (C); or (B) and (C) applies. In still other embodiments, (A), (B), and (C) apply.

In another aspect, methods for promoting post-natal mammalian neurogenesis in a subject in need thereof are featured. The methods include administering to the subject an effective amount of a compound having formula (I) or a pharmaceutically acceptable salt thereof, in which R and R' together with $C_2$ and $C_3$, respectively, form a fused phenyl ring having formula (II):

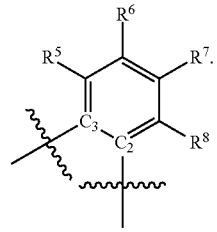

For purposes of clarification, it is understood that compounds in which R and R' together with $C_2$ and $C_3$, respectively, form a fused phenyl ring having formula (II) correspond to compounds having the following general formula:

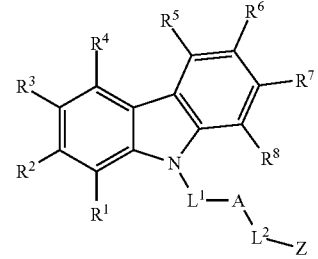

in which $R^1$, $R^2$, $R^3$, $R^4$, $L^1$, $L^2$, A, and Z can be as defined anywhere herein.

In embodiments, (A), (B), or (C) applies. In other embodiments, (A) and (B); or (A) and (C); or (B) and (C) applies. In still other embodiments, (A), (B), or (C) apply.

In another aspect, methods for promoting post-natal mammalian neurogenesis in a subject in need thereof are featured. The method includes administering to the subject an effective amount of a compound having formula (I) or a pharmaceutically acceptable salt thereof, in which:

each of $L^1$ and $L^2$ is $CH_2$;

A is $CR^{41}R^{42}$, wherein one of $R^{41}$ and $R^{42}$ is $OR^9$, and the other is hydrogen;

Z is —$NR^{10}R^{11}$; and each of $R^{10}$ and $R^{11}$ is independently selected from (a) hydrogen;

(b) $C_6$-$C_{10}$ aryl that is optionally substituted with from 1-4 $R^b$;

(d) $C_1$-$C_6$ alkyl or $C_1$-$C_6$ haloalkyl, each of which is optionally substituted with from 1-3 $R^d$;

(f) $C_2$-$C_6$ alkenyl or $C_2$-$C_6$ alkynyl.

In embodiments, (A), (B), or (C) applies. In other embodiments, (A) and (B); or (A) and (C); or (B) and (C) applies. In still other embodiments, (A), (B), and (C) apply.

In one aspect, compositions (e.g., a pharmaceutical composition) are featured, which includes a compound of formula (I) (and/or a compound of any of the other formulae described herein) or a salt (e.g., a pharmaceutically acceptable salt) thereof as defined anywhere herein and a pharmaceutically acceptable carrier. In some embodiments, the compositions can include an effective amount of the compound or salt. In some embodiments, the compositions can further include one or more additional therapeutic agents. These may include, but are not limited to, antidepressant medications (including selective serotonin reuptake inhibitors, tricyclic antidepressants, monoamine oxidase inhibitors, and other antidepressant medications including but not limited to venlafaxine, nefazadone, bupropion, mirtazapine, lithium and trazodone) and acetylcholinesterase inhibitors (including but not limited to Aricept, Reminyl, and Exelon).

In another aspect, dosage forms are featured, which includes from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of formula (I) (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

In one aspect, the compounds of formula (I) themselves (and/or a compound of any of the other formulae described herein) or a salt (e.g., a pharmaceutically acceptable salt) thereof as defined anywhere herein are featured. In another aspect, any of the formula (I) compounds specifically described herein are featured.

In one aspect, compounds having formula (I) are featured.

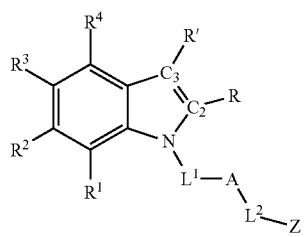

(I)

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano,
—$NH_2$, —$NH(C_1$-$C_6$ alkyl), —$N(C_1$-$C_6$ alkyl)$_2$, —NHC(O) ($C_1$-$C_6$ alkyl), and nitro;

R and R' are defined according to (1) or (2) below:

(1) R and R' together with $C_2$ and $C_3$, respectively, form a fused phenyl ring having formula (II):

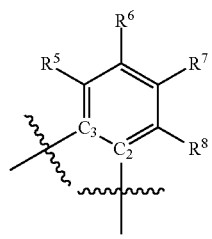

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano,
—$NH_2$, —$NH(C_1$-$C_6$ alkyl), —$N(C_1$-$C_6$ alkyl)$_2$, —NHC(O) ($C_1$-$C_6$ alkyl), and nitro; OR (2) R and R' together with $C_2$ and $C_3$, respectively, form a fused R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$;

each of $L^1$ and $L^2$ is, independently, $C_1$-$C_3$ alkylene, which is optionally substituted with from 1-2 independently selected $R^c$;

A is:
(i) $CR^{A1}R^{A2}$, wherein each of $R^{A1}$ and $R^{A2}$ is independently selected from hydrogen, halo, $C_1$-$C_3$ alkyl, and $OR^9$, wherein $R^9$ is hydrogen or $C_1$-$C_3$ alkyl that is optionally substituted with hydroxyl or $C_1$-$C_3$ alkoxy; or
(ii) C=O; or
(iii) $C_3$-$C_5$ cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;

Z is:
(i) —$NR^{10}R^{11}$; or
(ii) —$C(O)NR^{10}R^{11}$; or
(iii) —$OR^{12}$; or
(iv) —$S(O)R^3$, wherein n is 0, 1, or 2 or
(v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$;
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(ix) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(x) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (xi) heteroarylcycloalkyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) the cycloalkyl portion is optionally substituted with from 1-4 independently selected $R^a$;

each of $R^{10}$ and $R^{11}$ is independently selected from the substituents delineated collectively in (a) through (l) below:

(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl;
(g) $C_8$-$C_{14}$ arylcycloalkyl, wherein:
   (1) the aryl portion is optionally substituted with from 1-4 independently selected $R^b$, and
   (2) the cycloalkyl portion is optionally substituted with from 1-4 independently selected $R^a$;
(h) arylheterocyclyl containing from 8-14 ring atoms, wherein:
   (1) the aryl portion from is optionally substituted with from 1-4 independently selected $R^b$, and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(i) heteroarylheterocyclyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
(j) heteroarylcycloalkyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) the cycloalkyl portion is optionally substituted with from 1-4 independently selected $R^a$;
(k) $C_3$-$C_8$ cycloalkyl or $C_3$-$C_8$ cycloalkenyl, each of which is optionally substituted with from 1-4 independently selected $R^a$; and
(l) $C_7$-$C_{12}$ aralkyl, wherein the aryl portion is optionally the aryl portion from is optionally substituted with from 1-4 independently selected $R^b$, provided that one of $R^{10}$ and $R^{11}$ must be selected from (b), (c), (g), (h), (i), (j), and (k);

$R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is substituted with from 1-3 $R^d$;
(iv) $C_8$-$C_{14}$ arylcycloalkyl, wherein:
   (1) the aryl portion is optionally substituted with from 1-4 independently selected $R^b$, and
   (2) the cycloalkyl portion is optionally substituted with from 1-4 independently selected $R^a$;

or (v) arylheterocyclyl containing from 8-14 ring atoms, wherein:
   (1) the aryl portion from is optionally substituted with from 1-4 independently selected $R^b$, and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (vi) heteroarylheterocyclyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (vii) heteroarylcycloalkyl containing from 8-14 ring atoms, wherein:
   (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
   (2) the cycloalkyl portion is optionally substituted with from 1-4 independently selected $R^a$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_8$-$C_{14}$ arylcycloalkyl, wherein:
   (1) the aryl portion is optionally substituted with from 1-4 independently selected $R^b$, and (2) the cycloalkyl portion is optionally substituted with from 1-4 independently selected $R^a$;

or (iv) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (v) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

or (vi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
  (aa) $C_1$-$C_6$ alkoxy; $C_1$-$C_6$ haloalkoxy; $C_1$-$C_6$ thioalkoxy; $C_1$-$C_6$ thiohaloalkoxy; —O—($CH_2$)$_{1-3}$—[O($CH_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;
  (bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
  (cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and
  (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—; or a pharmaceutically acceptable salt thereof.

In embodiments, 1, 2, 3, 4, 5, or 6 of the following can apply
  provided that $R^3$ and $R^6$ cannot both be hydrogen when A is $CH_2$, and R and R' are defined according to definition (1);
  provided that $R^3$ cannot be hydrogen when A is $CH_2$, and R and R' are defined according to definition (2);
  provided that $R^3$ and $R^6$ cannot both be chloro when A is $CH_2$, R and R' are defined according to definition (1), Z is —$OR^{12}$, and $R^{12}$ is unsubstituted phenyl;
  provided that $R^3$ and $R^6$ cannot both be bromo when A is $CH_2$, R and R' are defined according to definition (1), Z is —$OR^{12}$, and $R^{12}$ is phenyl that is substituted with pyridyl or alkyl that is substituted with from 1-3 $R^e$;
  provided that $R^3$ and $R^6$ cannot both be hydrogen when A is CH($CH_3$), R and R' are defined according to definition (1), Z is $NR^{10}R^{11}$, $R^{10}$ is $CH_3$, and $R^{11}$ is unsubstituted phenyl;
  provided that when A is $CR^{41}R^{42}$, and one of $R^{41}$ and $R^{42}$ is OH (i.e., $R^9$ is H), then the other of $R^{41}$ and $R^{42}$ is $C_1$-$C_3$ alkyl.

In another aspect, pharmaceutical compositions are featured that include the above-described compounds (or salts thereof as described herein) and a pharmaceutically acceptable carrier. In embodiments, 1, 2, 3, 4, 5, or 6 of the above described provisions can apply.

In one aspect, compounds having formula (I) are featured.

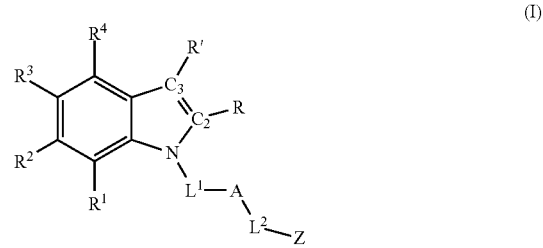

(I)

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro;

R and R' are defined according to (1) or (2) below:

(1) R and R' together with $C_2$ and $C_3$, respectively, form a fused phenyl ring having formula (II):

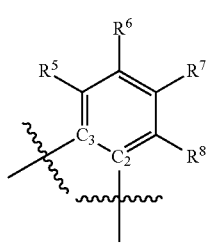

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro; OR (2) R and R' together with $C_2$ and $C_3$, respectively, form a fused R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$;

each of $L^1$ and $L^2$ is, independently, $C_1$-$C_3$ alkylene, which is optionally substituted with from 1-2 independently selected $R^c$;

A is:
(i) $CR^{A1}R^{A2}$, wherein each of $R^{A1}$ and $R^{A2}$ is independently selected from hydrogen, halo, $C_1$-$C_3$ alkyl, and $OR^9$, wherein $R^9$ is $C_1$-$C_3$ alkyl that is optionally substituted with hydroxyl or $C_1$-$C_3$ alkoxy; or
(ii) C=O; or
(iii) $C_3$-$C_5$ cycloalkylene that is (a) substituted with 1 oxo; and (b) optionally further substituted with from 1-4 independently selected $R^a$; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$;

Z is:
(i) —$NR^{10}R^{11}$; or
(ii) —C(O)$NR^{10}R^{11}$; or
(iii) —$OR^{12}$; or
(iv) —S(O)$R^{13}$, wherein n is 0, 1, or 2 or
(v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$;
(vi) $C_6$-$C_{10}$ aryl that is optionally substituted with from 1-4 independently selected $R^b$; or (vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or
(viii) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$;
or
(ix) arylheterocyclyl containing from 8-14 ring atoms, wherein:
(1) the aryl portion from is optionally substituted with from 1-4 independently selected $R^b$, and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(x) heteroarylheterocyclyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(xi) heteroarylcycloalkyl containing from 8-14 ring atoms, wherein:
(1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
(2) the cycloalkyl portion is optionally substituted with from 1-4 independently selected $R^a$;

each of $R^{10}$ and $R^{11}$ is independently selected from the substituents delineated collectively in (a) through (l) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl;
(g) $C_8$-$C_{14}$ arylcycloalkyl, wherein:
(1) the aryl portion is optionally substituted with from 1-4 independently selected $R^b$, and
(2) the cycloalkyl portion is optionally substituted with from 1-4 independently selected $R^a$;
(h) arylheterocyclyl containing from 8-14 ring atoms, wherein:
(1) the aryl portion from is optionally substituted with from 1-4 independently selected $R^b$, and (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(i) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(j) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

(k) $C_3$-$C_8$ cycloalkyl or $C_3$-$C_8$ cycloalkenyl, each of which is optionally substituted with from 1-4 independently selected $R^a$; and (l) $C_7$-$C_{12}$ aralkyl, wherein the aryl portion is optionally the aryl portion from is optionally substituted with from 1-4 independently selected $R^b$, provided that one of $R^{10}$ and $R^{11}$ must be selected from (b), (c), (g), (h), (i), (j), and (k);

$R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; or
(iii) $C_1$-$C_6$ alkyl or $C_1$-$C_6$ haloalkyl, each of which is substituted with from 1-3 $R^d$;
(iv) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(v) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vii) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(iii) $C_8$-$C_{14}$ arylcycloalkyl, wherein:
  (1) the aryl portion is optionally substituted with from 1-4 independently selected $R^b$, and
  (2) the cycloalkyl portion is optionally substituted with from 1-4 independently selected $R^a$;
or
(iv) arylheterocyclyl containing from 8-14 ring atoms, wherein:
  (1) the aryl portion from is optionally substituted with from 1-4 independently selected $R^b$, and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(v) heteroarylheterocyclyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;
or
(vi) heteroarylcycloalkyl containing from 8-14 ring atoms, wherein:
  (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
  (2) the cycloalkyl portion is optionally substituted with from 1-4 independently selected $R^a$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:

(aa) $C_1$-$C_6$ alkoxy; $C_1$-$C_6$ haloalkoxy; $C_1$-$C_6$ thioalkoxy; $C_1$-$C_6$ thiohaloalkoxy; —O—$(CH_2)_{1-3}$—[O$(CH_2)_{1-3}]_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;

(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;

(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—;

or a pharmaceutically acceptable salt thereof.

In embodiments, 1, 2, 3, 4, or 5 of the following can apply
provided that $R^3$ and $R^6$ cannot both be hydrogen when A is $CH_2$, and R and R' are defined according to definition (1);
provided that $R^3$ cannot be hydrogen when A is $CH_2$, and R and R' are defined according to definition (2);
provided that $R^3$ and $R^6$ cannot both be chloro when A is $CH_2$, R and R' are defined according to definition (1), Z is —$OR^{12}$, and $R^{12}$ is unsubstituted phenyl;
provided that $R^3$ and $R^6$ cannot both be bromo when A is $CH_2$, R and R' are defined according to definition (1), Z is —$OR^{12}$, and $R^{12}$ is phenyl that is substituted with pyridyl or alkyl that is substituted with from 1-3 $R^e$; and provided that $R^3$ and $R^6$ cannot both be hydrogen when A is $CH(CH_3)$, R and R' are defined according to definition (1), Z is $NR^{10}R^{11}$, $R^{10}$ is $CH_3$, and $R^{11}$ is unsubstituted phenyl.

In another aspect, pharmaceutical compositions are featured that include the above-described compounds (or salts thereof as described herein) and a pharmaceutically acceptable carrier. In embodiments, 1, 2, 3, 4, or 5 of the above described provisions can apply.

In another aspect, compounds having formula (I) are featured

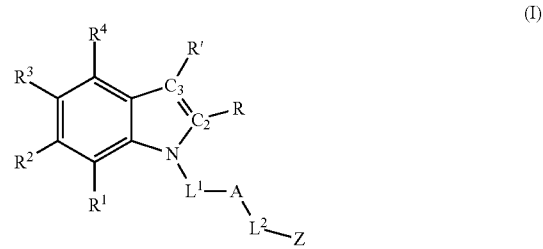

(I)

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro;

R and R' are defined according to (1) or (2) below:

(1) R and R' together with $C_2$ and $C_3$, respectively, form a fused phenyl ring having formula (II):

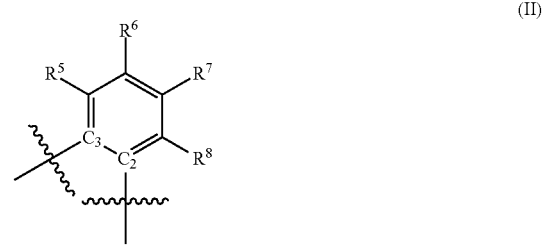

(II)

wherein each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro; OR (2) R and R' together with $C_2$ and $C_3$, respectively, form a fused R and R' together with $C_2$ and $C_3$, respectively, form a fused heteroaryl ring containing 6 ring atoms, wherein from 1-2 independently selected ring atoms is N; and wherein said heteroaryl ring is optionally substituted with from 1-2 independently selected $R^b$;

each of $L^1$ and $L^2$ is, independently, $C_1$-$C_3$ alkylene, which is optionally substituted with from 1-2 independently selected $R^c$;

A is $CR^{41}R^{42}$, wherein one of $R^{41}$ and $R^{42}$ is —OH, and the other of $R^{41}$ and $R^{42}$ is hydrogen or $C_1$-$C_3$ alkyl;

Z is —OR$^{12}$ or —S(O)$_n$R$^{13}$, wherein n is 0, 1, or 2;
each of R$^{12}$ and R$^{13}$ is:
(i) C$_6$-C$_{10}$ aryl that is optionally substituted with from 1-4 R$^b$; or
(ii) heteroaryl containing from 5-14 ring atoms, wherein from 1-6 of the ring atoms is independently selected from N, NH, N(C$_1$-C$_3$ alkyl), O, and S; and wherein said heteroaryl is optionally substituted with from 1-4 R$^b$;
(iii) C$_1$-C$_6$ alkyl or C$_1$-C$_6$ haloalkyl (e.g., C$_1$-C$_6$ alkyl), each of which is substituted with from 1-3 R$^d$; or
(iv) C$_8$-C$_{14}$ arylcycloalkyl, wherein:
  (1) the aryl portion is optionally substituted with from 1-4 independently selected R$^b$, and
  (2) the cycloalkyl portion is optionally substituted with from 1-4 independently selected R$^a$;
or
(v) arylheterocyclyl containing from 8-14 ring atoms, wherein:
  (1) the aryl portion from is optionally substituted with from 1-4 independently selected R$^b$, and
  (2) from 1-2 of the ring atoms of the heterocyclyl portion is independently selected from N, NH, N(C$_1$-C$_6$ alkyl), NC(O)(C$_1$-C$_6$ alkyl), O, and S; and wherein said heterocyclyl portion is optionally substituted with from 1-3 independently selected R$^a$;
or
(vi) heteroarylheterocyclyl containing from 8-14 ring atoms, wherein:
  (1) from 1-2 of the ring atoms of the heteroaryl portion is independently selected from N, NH, N(C$_1$-C$_3$ alkyl), O, and S; and wherein said heteroaryl portion is optionally substituted with from 1-3 independently selected R$^b$; and
  (2) from 1-2 of the ring atoms of the heterocyclyl portion is independently selected from N, NH, N(C$_1$-C$_6$ alkyl), NC(O)(C$_1$-C$_6$ alkyl), O, and S; and wherein said heterocyclyl portion is optionally substituted with from 1-3 independently selected R$^a$;
or
(vii) heteroarylcycloalkyl containing from 8-14 ring atoms, wherein:
  (1) from 1-2 of the ring atoms of the heteroaryl portion is independently selected from N, NH, N(C$_1$-C$_3$ alkyl), O, and S; and wherein said heteroaryl portion is optionally substituted with from 1-3 independently selected R$^b$; and
  (2) the cycloalkyl portion is optionally substituted with from 1-4 independently selected R$^a$;

R$^a$ at each occurrence is, independently selected from halo, hydroxyl, C$_1$-C$_6$ alkoxy, C$_1$-C$_6$ thioalkoxy, C$_1$-C$_6$ haloalkoxy, C$_1$-C$_6$ thiohaloalkoxy, oxo, thioxo, =NH, =N(C$_1$-C$_6$ alkyl), C$_1$-C$_6$ alkyl, C$_1$-C$_6$ haloalkyl, —NH$_2$, —NH(C$_1$-C$_6$ alkyl), N(C$_1$-C$_6$ alkyl)$_2$, —NHC(O)(C$_1$-C$_6$ alkyl), and cyano;

R$^b$ at each occurrence is independently selected from the substituents delineated in (aa) through (dd) below:
(aa) C$_1$-C$_6$ alkoxy; C$_1$-C$_6$ haloalkoxy; C$_1$-C$_6$ thioalkoxy; C$_1$-C$_6$ thiohaloalkoxy; —O—(CH$_2$)$_{1-3}$—[O(CH$_2$)$_{1-3}$]$_{1-3}$—H; —C$_1$-C$_6$ alkyl, C$_1$-C$_6$ haloalkyl, —NH(C$_1$-C$_6$ alkyl), —N(C$_1$-C$_6$ alkyl)$_2$, —NHC(O)(C$_1$-C$_6$ alkyl), wherein the alkyl portion of each is optionally substituted with from 1-3 independently selected R$^e$;
(bb) halo; hydroxyl; cyano; nitro; —NH$_2$; azido; sulfhydryl; C$_2$-C$_6$ alkenyl; C$_2$-C$_6$ alkynyl; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$;
(cc) C$_3$-C$_6$ cycloalkyl or heterocyclyl containing from 5-6 ring atoms, wherein from 1-2 of the ring atoms of the heterocyclyl is independently selected from N, NH, N(C$_1$-C$_6$ alkyl), NC(O)(C$_1$-C$_6$ alkyl), O, and S; and wherein each of said phenyl and heterocyclyl is optionally substituted with from 1-3 independently selected R$^a$; and
(dd) phenyl or heteroaryl containing from 5-6 ring atoms, wherein from 1-2 of the ring atoms of the heteroaryl is independently selected from N, NH, N(C$_1$-C$_3$ alkyl), O, and S; wherein each of said phenyl and heteroaryl is optionally substituted with from 1-3 substituents independently selected from halo; hydroxyl; cyano; nitro; —NH$_2$; —NH(C$_1$-C$_6$ alkyl), N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl;

R$^c$ at each occurrence is, independently selected from halo, C$_1$-C$_6$ alkoxy, C$_1$-C$_6$ thioalkoxy, C$_1$-C$_6$ haloalkoxy, C$_1$-C$_6$ thiohaloalkoxy, C$_1$-C$_6$ alkyl, C$_1$-C$_6$ haloalkyl, —NH$_2$, —NH(C$_1$-C$_6$ alkyl), N(C$_1$-C$_6$ alkyl)$_2$, —NHC(O)(C$_1$-C$_6$ alkyl), and cyano;

R$^d$ at each occurrence is, independently selected from hydroxyl, C$_1$-C$_6$ alkoxy, C$_1$-C$_6$ thioalkoxy, C$_1$-C$_6$ haloalkoxy, C$_1$-C$_6$ thiohaloalkoxy, C$_1$-C$_6$ alkyl, C$_1$-C$_6$ haloalkyl, —NH$_2$, —NH(C$_1$-C$_6$ alkyl), N(C$_1$-C$_6$ alkyl)$_2$, —NHC(O)(C$_1$-C$_6$ alkyl), and cyano; and R$^e$ at each occurrence is, independently selected from hydroxyl, C$_1$-C$_6$ alkoxy; C$_1$-C$_6$ thioalkoxy; C$_1$-C$_6$ haloalkoxy; C$_1$-C$_6$ thiohaloalkoxy; —NH$_2$; —NH(C$_1$-C$_6$ alkyl); N(C$_1$-C$_6$ alkyl)$_2$; —NHC(O)(C$_1$-C$_6$ alkyl); cyano; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$; and L$^3$-(C$_1$-C$_6$ alkylene)-biotin, where in L$^3$ is a —O—, —NH—, —NCH$_3$—, —C(O)—, —C(O)NH—, —C(O)NCH$_3$—, —NHC(O)—, or —NCH$_3$C(O)—;

or a pharmaceutically acceptable salt thereof.

In embodiments, 1, 2, 3, or 4 of the following can apply:
provided that R$^3$ and R$^6$ cannot both be hydrogen when R and R' are defined according to definition (1);

provided that R$^3$ and R$^6$ cannot both be chloro when R and R' are defined according to definition (1), Z is —OR$^{12}$, and R$^{12}$ is phenyl substituted with chloro, formyl, or —NHC(O)CH$_3$;

provided that R$^3$ and R$^6$ cannot both be bromo when R and R' are defined according to definition (1), Z is —OR$^{12}$, and R$^{12}$ is phenyl substituted with —NHC(O)CH$_3$; and provided that R$^3$ and R$^6$ cannot both be bromo when R and R' are defined according to definition (1), Z is —SR$^{13}$, and R$^{13}$ is phenyl substituted with —OH.

In another aspect, pharmaceutical compositions are featured that include the above-described compounds (or salts thereof as described herein) and a pharmaceutically acceptable carrier. In embodiments, 1, 2, 3, 4, or 5 of the above described provisions can apply.

In another aspect, compounds having formula (I) are featured:

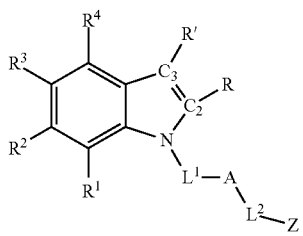

(I)

wherein:

each of $R^1$, $R^2$, $R^3$, and $R^4$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano,
—$NH_2$, —NH($C_1$-$C_6$ alkyl), —N($C_1$-$C_6$ alkyl)$_2$, —NHC(O)($C_1$-$C_6$ alkyl), and nitro;

R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$;

each of $L^1$ and $L^2$ is, independently, $C_1$-$C_3$ alkylene, which is optionally substituted with from 1-2 independently selected $R^c$;

A is:
(i) $CR^{A1}R^{A2}$, wherein one of $R^{A1}$ and $R^{A2}$ is independently selected from hydrogen, halo, $C_1$-$C_3$ alkyl, and $OR^9$; and the other of $R^{A1}$ and $R^{A2}$ is independently selected from halo, $C_1$-$C_3$ alkyl, and $OR^9$; wherein $R^9$ is hydrogen or $C_1$-$C_3$ alkyl that is optionally substituted with hydroxyl or $C_1$-$C_3$ alkoxy; or
(ii) C=O;

Z is:
(i) —$NR^{10}R^{11}$; or
(ii) —C(O)$NR^{10}R^{11}$; or
(iii) —$OR^{12}$; or
(iv) —S(O)$_n R^{13}$, wherein n is 0, 1, or 2 or
(vi) $C_6$-$C_{10}$ aryl that is optionally substituted with from 1-4 independently selected $R^b$; or
(vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$; or each of $R^{10}$ and $R^{11}$ is independently selected from the substituents delineated collectively in (a) through (g) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
(d) $C_1$-$C_6$ alkyl or $C_1$-$C_6$ haloalkyl, each of which is optionally substituted with from 1-3 $R^d$;
(e) —C(O)($C_1$-$C_6$ alkyl), —C(O)($C_1$-$C_6$ haloalkyl), or —C(O)O($C_1$-$C_6$ alkyl);
(f) $C_2$-$C_6$ alkenyl or $C_2$-$C_6$ alkynyl; and
(g) $C_7$-$C_{12}$ aralkyl, wherein the aryl portion is optionally the aryl portion from is optionally substituted with from 1-4 independently selected $R^b$,
provided that one of $R^{10}$ and $R^{11}$ must be selected from (b) and (c);

$R^{12}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

$R^{13}$ is:
(i) $C_6$-$C_{10}$ aryl that is optionally substituted with from 1-4 $R^b$; or
(ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; —O—($CH_2$)$_{1-3}$—[O($CH_2$)$_{1-3}$]$_{1-3}$—H; —$C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;
(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;
(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and
(dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —NH$_2$, —NH(C$_1$-C$_6$ alkyl), N(C$_1$-C$_6$ alkyl)$_2$, —NHC(O)(C$_1$-C$_6$ alkyl), and cyano; and R$^e$ at each occurrence is, independently selected from hydroxyl, C$_1$-C$_6$ alkoxy; C$_1$-C$_6$ thioalkoxy; C$_1$-C$_6$ haloalkoxy; C$_1$-C$_6$ thiohaloalkoxy; —NH$_2$; —NH(C$_1$-C$_6$ alkyl); N(C$_1$-C$_6$ alkyl)$_2$; —NHC(O)(C$_1$-C$_6$ alkyl); cyano; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH (C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$; and L$^3$-(C$_1$-C$_6$ alkylene)-biotin, where in L$^3$ is a —O—, —NH—, —NCH$_3$—, —C(O)—, —C(O)NH—, —C(O)NCH$_3$—, —NHC(O)—, or —NCH$_3$C(O)—;

or a pharmaceutically acceptable salt thereof.

In embodiments, provision (A) described herein can apply.

In another aspect, compounds having formula (I) are featured:

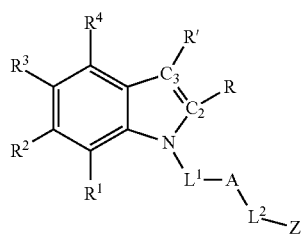

wherein:

each of R$^1$, R$^2$, R$^3$, and R$^4$ is independently selected from hydrogen, halo, hydroxyl, sulfhydryl, C$_1$-C$_6$ alkoxy, C$_1$-C$_6$ thioalkoxy, C$_1$-C$_6$ haloalkoxy, C$_1$-C$_6$ thiohaloalkoxy, C$_1$-C$_6$ alkyl, C$_1$-C$_6$ haloalkyl, C$_2$-C$_6$ alkynyl, cyclopropyl, —N$_3$, cyano, —NH$_2$, —NH(C$_1$-C$_6$ alkyl), —N(C$_1$-C$_6$ alkyl)$_2$, —NHC(O)(C$_1$-C$_6$ alkyl), and nitro;

each of R and R' is, independently, hydrogen, C$_1$-C$_6$ alkyl, or C$_1$-C$_6$ haloalkyl;

each of L$^1$ and L$^2$ is, independently, C$_1$-C$_3$ alkylene, which is optionally substituted with from 1-2 independently selected R$^c$;

A is:
(i) CR$^{A1}$R$^{A2}$, wherein one of R$^{A1}$ and R$^{A2}$ is independently selected from hydrogen, fluoro, chloro, C$_1$-C$_3$ alkyl, and OR$^9$; and the other of R$^{A1}$ and R$^{A2}$ is independently selected from fluoro, chloro, C$_1$-C$_3$ alkyl, and OR$^9$; wherein R$^9$ is hydrogen or C$_1$-C$_3$ alkyl that is optionally substituted with hydroxyl or C$_1$-C$_3$ alkoxy; or
(ii) C=O;

Z is:
(i) —NR$^{10}$R$^{11}$; or
(ii) —C(O)NR$^{10}$R$^{11}$; or
(iii) —OR$^{12}$; or
(iv) —S(O)$_n$R$^{13}$, wherein n is 0, 1, or 2 or
(vi) C$_6$-C$_{10}$ aryl that is optionally substituted with from 1-4 independently selected R$^b$; or
(vii) heteroaryl containing from 5-14 ring atoms, wherein from 1-6 of the ring atoms is independently selected from N, NH, N(C$_1$-C$_3$ alkyl), O, and S; and wherein said heteroaryl is optionally substituted with from 1-4 independently selected R$^b$; or each of R$^{10}$ and R$^{11}$ is independently selected from the substituents delineated collectively in (a) through (g) below:

(a) hydrogen;
(b) C$_6$-C$_{10}$ aryl that is optionally substituted with from 1-4 R$^b$;
(c) heteroaryl containing from 5-14 ring atoms, wherein from 1-6 of the ring atoms is independently selected from N, NH, N(C$_1$-C$_3$ alkyl), O, and S; and wherein said heteroaryl is optionally substituted with from 1-4 R$^b$;
(d) C$_1$-C$_6$ alkyl or C$_1$-C$_6$ haloalkyl, each of which is optionally substituted with from 1-3 R$^d$;
(e) —C(O)(C$_1$-C$_6$ alkyl), —C(O)(C$_1$-C$_6$ haloalkyl), or —C(O)O(C$_1$-C$_6$ alkyl);
(f) C$_2$-C$_6$ alkenyl or C$_2$-C$_6$ alkynyl;
and
(g) C$_7$-C$_{12}$ aralkyl, wherein the aryl portion is optionally the aryl portion from is optionally substituted with from 1-4 independently selected R$^b$, provided that one of R$^{10}$ and R$^{11}$ must be selected from (b) and (c);

each of R$^{12}$ and R$^{13}$ is:
(i) C$_6$-C$_{10}$ aryl that is optionally substituted with from 1-4 R$^b$; or
(ii) heteroaryl containing from 5-14 ring atoms, wherein from 1-6 of the ring atoms is independently selected from N, NH, N(C$_1$-C$_3$ alkyl), O, and S; and wherein said heteroaryl is optionally substituted with from 1-4 R$^b$;

R$^a$ at each occurrence is, independently selected from halo, hydroxyl, C$_1$-C$_6$ alkoxy, C$_1$-C$_6$ thioalkoxy, C$_1$-C$_6$ haloalkoxy, C$_1$-C$_6$ thiohaloalkoxy, oxo, thioxo, =NH, =N(C$_1$-C$_6$ alkyl), C$_1$-C$_6$ alkyl, C$_1$-C$_6$ haloalkyl, —NH$_2$, —NH(C$_1$-C$_6$ alkyl), N(C$_1$-C$_6$ alkyl)$_2$, —NHC(O)(C$_1$-C$_6$ alkyl), and cyano;

R$^b$ at each occurrence is independently selected from the substituents delineated in (aa) through (dd) below:

(aa) C$_1$-C$_6$ alkoxy; C$_1$-C$_6$ haloalkoxy; C$_1$-C$_6$ thioalkoxy; C$_1$-C$_6$ thiohaloalkoxy; —O—(CH$_2$)$_{1-3}$—[O (CH$_2$)$_{1-3}$]$_{1-3}$—H; —C$_1$-C$_6$ alkyl, C$_1$-C$_6$ haloalkyl, —NH(C$_1$-C$_6$ alkyl), —N(C$_1$-C$_6$ alkyl)$_2$, —NHC(O) (C$_1$-C$_6$ alkyl), wherein the alkyl portion of each is optionally substituted with from 1-3 independently selected R$^e$;
(bb) halo; hydroxyl; cyano; nitro; —NH$_2$; azido; sulfhydryl; C$_2$-C$_6$ alkenyl; C$_2$-C$_6$ alkynyl; —C(O)H; —C(O) (C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$;
(cc) C$_3$-C$_6$ cycloalkyl or heterocyclyl containing from 5-6 ring atoms, wherein from 1-2 of the ring atoms of the heterocyclyl is independently selected from N, NH, N(C$_1$-C$_6$ alkyl), NC(O)(C$_1$-C$_6$ alkyl), O, and S; and wherein each of said phenyl and heterocyclyl is optionally substituted with from 1-3 independently selected R$^a$; and
(dd) phenyl or heteroaryl containing from 5-6 ring atoms, wherein from 1-2 of the ring atoms of the heteroaryl is independently selected from N, NH, N(C$_1$-C$_3$ alkyl), O, and S; wherein each of said phenyl and heteroaryl is optionally substituted with from 1-3 substituents independently selected from halo; hydroxyl; cyano; nitro; —NH$_2$; —NH(C$_1$-C$_6$ alkyl), N(C$_1$-C$_6$ alkyl)$_2$, —NHC (O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl;

R$^c$ at each occurrence is, independently selected from halo, C$_1$-C$_6$ alkoxy, C$_1$-C$_6$ thioalkoxy, C$_1$-C$_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH ($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—;

or a pharmaceutically acceptable salt thereof.

In one aspect, compounds of formula (III) are featured in which:

A is $CR^{A1}R^{A2}$, in which each of $R^{A1}$ and $R^{A2}$ is, independently, hydrogen, halo, or $C_1$-$C_3$ alkyl; or A is $CR^{A1}R^{A2}$, in which one of $R^{A1}$ and $R^{A2}$ is halo (e.g., fluoro), and the other of $R^{A1}$ and $R^{A2}$ is, independently, hydrogen, halo, or $C_1$-$C_3$ alkyl (e.g., hydrogen); or A is $CR^{A1}R^{A2}$, in which one of $R^{A1}$ and $R^{A2}$ is halo (e.g., fluoro), and the other of $R^{A1}$ and $R^{A2}$ is hydrogen; and $R^1$, $R^2$, $R^3$, $R^4$, $L^1$, $L^2$, and Z can be as defined anywhere herein; or a salt (e.g., pharmaceutically acceptable salt) thereof.

In embodiments, (B) and/or (C) applies.

In one aspect, compounds of formula (III) are featured in which:

one of $R^{A1}$ and $R^{A2}$ can be $OR^9$. In embodiments, the other of $R^{A1}$ and $R^{A2}$ can be as defined anywhere herein; e.g., the other of $R^{A1}$ and $R^{A2}$ can be hydrogen or $C_1$-$C_3$ alkyl. For example, one of $R^{A1}$ and $R^{A2}$ can be $OR^9$, and the other of $R^{A1}$ and $R^{A2}$ is hydrogen or $C_1$-$C_3$ alkyl. In embodiments, $R^9$ can be hydrogen or $C_1$-$C_3$ alkyl; and $R^1$, $R^2$, $R^3$, $R^4$, $L^1$, $L^2$, and Z can be as defined anywhere herein; or a salt (e.g., pharmaceutically acceptable salt) thereof.

In embodiments, one or more of the following apply, e.g., when A is CHOH and Z is $NR^{10}R^{11}$:

each of $R^3$ and $R^6$ is $CH_3$; and/or each of $R^3$ and $R^6$ is bromo; and/or each of $R^3$ and $R^6$ is chloro; and/or one of $R^3$ and $R^6$ is $CH_3$ (e.g., $R^6$), and the other is bromo (e.g., $R^3$);

each of $R^{10}$ and $R^{11}$ is other than hydrogen;
each of $R^{10}$ and $R^{11}$ is hydrogen;
one of $R^{10}$ and $R^{11}$ is heteroaryl as defined anywhere herein;
$L^1$ and/or $L^2$ is $C_2$-$C_3$ alkylene (optionally substituted);
(B) and/or (C) applies.

In one aspect, compounds of formula (III) are featured in which Z is other than $NR^{10}R^{11}$; and $R^1$, $R^2$, $R^3$, $R^4$, $L^1$, $L^2$, Z, and A can be as defined anywhere herein; or a salt (e.g., pharmaceutically acceptable salt) thereof. In embodiments, (B) and/or (C) applies.

In one aspect, compounds of formula (III) are featured in which Z is —$OR^{12}$ and/or —S(O)$_n R^{13}$; and $R^1$, $R^2$, $R^3$, $R^4$, $L^1$, $L^2$, and A can be as defined anywhere herein; or a salt (e.g., pharmaceutically acceptable salt) thereof. In embodiments, (B) and/or (C) applies.

In one aspect, compounds of formula (III) are featured in which A is (ii) C=O; and/or (iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$; and $R^1$, $R^2$, $R^3$, $R^4$, $L^1$, $L^2$, and Z can be as defined anywhere herein; or a salt (e.g., pharmaceutically acceptable salt) thereof.

In some embodiments, $R^{10}$ is unsubstituted phenyl or phenyl substituted with 1 $R^b$ when:

(i) R and R' are defined according to definition (1),
(ii) $R^3$ and $R^6$ are both halo, and each of $R^1$, $R^2$, $R^4$, $R^5$, $R^7$, and $R^8$ is hydrogen,
(iii) each of $L^1$ and $L^2$ is $CH_2$,
(iv) A is $CR^{A1}R^{A2}$, and one of $R^{A1}$ and $R^{A2}$ is OH and the other is hydrogen, and
(v) Z is —$NHR^{10}$ and $R^{10}$ is $C_6$-$C_{10}$ aryl that is optionally substituted with 1 to 4 $R^b$.

In yet another aspect, compounds of formula (VI) are featured:

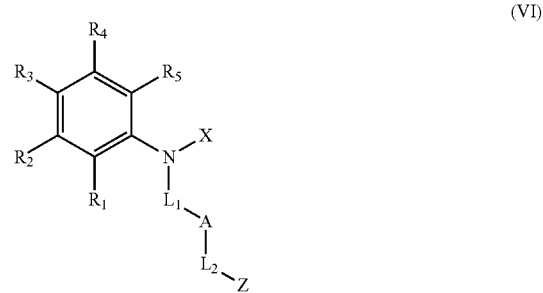

(VI)

wherein:

$R_1$-$R_5$ are each independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro;

X is $C_6$-$C_{10}$ aryl that is optionally substituted with 1-4 $R^b$; or heteroaryl containing 5-14 ring atoms, wherein from 1-6 of the ring atoms is independently selected from N, NH, N($C_1$-$C_3$ alkyl), O, and S, and wherein said heteroaryl is optionally substituted with 1-4 $R^b$;

each of $L^1$ and $L^2$ is, independently, $C_1$-$C_3$ alkylene, which is optionally substituted with from 1-2 independently selected $R^c$;

A is $CR^{A1}R^{A2}$, wherein one of $R^{A1}$ and $R^{A2}$ is independently selected from hydrogen, fluoro, chloro, $C_1$-$C_3$ alkyl, and $OR^9$; and the other of $R^{A1}$ and $R^{A2}$ is independently selected from fluoro, chloro, $C_1$-$C_3$ alkyl, and $OR^9$; wherein $R^9$ is hydrogen or $C_1$-$C_3$ alkyl that is optionally substituted with hydroxyl or $C_1$-$C_3$ alkoxy;

Z is —$NR^{10}R^{11}$ or —$OR^{12}$;

each of $R^{10}$ and $R^{11}$ is independently selected from the substituents delineated collectively in (a) through (g) below:
(a) hydrogen;
(b) $C_6$-$C_{10}$ aryl that is optionally substituted with from 1-4 $R^b$;
(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

(d) $C_1$-$C_6$ alkyl or $C_1$-$C_6$ haloalkyl, each of which is optionally substituted with from 1-3 $R^d$;

(e) —C(O)($C_1$-$C_6$ alkyl), —C(O)($C_1$-$C_6$ haloalkyl), or —C(O)O($C_1$-$C_6$ alkyl);

(f) $C_2$-$C_6$ alkenyl or $C_2$-$C_6$ alkynyl; and (g) $C_7$-$C_{12}$ aralkyl, wherein the aryl portion is optionally the aryl portion from is optionally substituted with from 1-4 independently selected $R^b$, provided that one of $R^{10}$ and $R^{11}$ must be selected from (b) and (c);

$R^{12}$ is:

(i) $C_6$-$C_{10}$ aryl that is optionally substituted with from 1-4 $R^b$; or (ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

$R^a$ at each occurrence is, independently selected from halo, hydroxyl, $C_1$-$C_6$ alkoxy, $C_1$-$C_6$ thioalkoxy, $C_1$-$C_6$ haloalkoxy, $C_1$-$C_6$ thiohaloalkoxy, oxo, thioxo, =NH, =N($C_1$-$C_6$ alkyl), $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano;

$R^b$ at each occurrence is independently selected from the substituents delineated in (aa) through (dd) below:

(aa) $C_1$-$C_6$ alkoxy; $C_1$-$C_6$ haloalkoxy; $C_1$-$C_6$ thioalkoxy; $C_1$-$C_6$ thiohaloalkoxy; —O($CH_2$)$_{1-3}$[O($CH_2$)$_{1-3}$]$_{1-3}$H; $C_1$-$C_6$ alkyl, $C_1$-$C_6$ haloalkyl, —NH($C_1$-$C_6$ alkyl), —N($C_1$-$C_6$ alkyl)$_2$, —NHC(O)($C_1$-$C_6$ alkyl), wherein the alkyl portion of each is optionally substituted with from 1-3 independently selected $R^e$;

(bb) halo; hydroxyl; cyano; nitro; —$NH_2$; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); —C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$;

(cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said phenyl and heterocyclyl is optionally substituted with from 1-3 independently selected $R^a$; and (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —NH($C_1$-$C_6$ alkyl), —N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl;

$R^c$ at each occurrence is, independently selected from halo, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano;

$R^d$ at each occurrence is, independently selected from hydroxyl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —NHC(O)($C_1$-$C_6$ alkyl), and cyano; and $R^e$ at each occurrence is, independently selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); —N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); —C(O)OH; —C(O)O($C_1$-$C_6$ alkyl); —C(O)$NH_2$; —C(O)NH($C_1$-$C_6$ alkyl); —C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; and $L^3$-($C_1$-$C_6$ alkylene)-biotin, where in $L^3$ is a —O—, —NH—, —$NCH_3$—, —C(O)—, —C(O)NH—, —C(O)$NCH_3$—, —NHC(O)—, or —$NCH_3$C(O)—;

or a pharmaceutically acceptable salt thereof.

In certain embodiments, compound of formula (VI) can have a $R_3$ that is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro. In some embodiments, $R_3$ is halo such as bromo. In certain embodiments, each of $R_1$, $R_2$, $R_4$ and $R_5$ is hydrogen.

In certain embodiments, compound of formula (VI) can have X that is $C_6$-$C_{10}$ aryl substituted with one or more halo such as bromo. For example, X can be 4-bromophenyl. X can also be heteroaryl containing 5-14 ring atoms, wherein from 1-6 of the ring atoms is independently selected from N, NH, N($C_1$-$C_3$ alkyl), O, and S, and wherein said heteroaryl is optionally substituted with 1-4 $R^b$. For example, X can be pyridine optionally substituted with 1-4 $R^b$.

In certain embodiments, compound of formula (VI) can have A that is $CR^{A1}R^{A2}$, wherein each of $R^{A1}$ and $R^{A2}$ is, independently, hydrogen, $C_1$-$C_3$ alkyl, or $OR^9$. In some embodiments, one of $R^{A1}$ and $R^{A2}$ is $OR^9$; and the other of $R^{A1}$ and $R^{A2}$ is hydrogen or $C_1$-$C_3$ alkyl. For example, one of $R^{A1}$ and $R^{A2}$ can be OH; and the other of $R^{A1}$ and $R^{A2}$ can be hydrogen.

In some embodiments, A is $CR^{A1}R^{A2}$ and wherein the carbon attached to $R^{A1}$ and $R^{A2}$ is substituted with four different substituents. The carbon attached to $R^{A1}$ and $R^{A2}$ can be (R) or (S) configured. In an embodiment, the (R) configured formula (VI) compound can be substantially free of a formula (VI) compound that is S configured at the carbon atom attached to $R^{A1}$ and $R^{A2}$. In some embodiments, the (S) configured formula (VI) compound can be substantially free of a formula (VI) compound that is (R) configured at the carbon atom attached to $R^{A1}$ and $R^{A2}$.

The compound of formula (VI), in some embodiments, can be (+) or (−) (dextrorotatory). In some embodiments, the (+) (dextrorotatory) compound can be substantially free of a formula (I) compound that is (levorotatory). In some embodiments, the (−) (levorotatory) compound can be substantially free of a formula (I) compound that is (+) (dextrorotatory).

Any of the aforementioned compounds can be used in any of the methods or compositions described anywhere herein.

The presently disclosed embodiments relate generally to stimulating neurogenesis (e.g., post-natal neurogenesis, e.g., post-natal hippocampal and/or hypothalamic neurogenesis) and protecting neurons from death with a compound of formula (I) (and/or a compound of any of the other formulae described herein) or a salt (e.g., a pharmaceutically acceptable salt) thereof as defined anywhere herein.

For example, methods of promoting the generation of neurons are featured. As another example, methods of promoting the survival, growth, development and/or function of neurons, particularly CNS, brain, cerebral, hippocampal and hypothalamic neurons are featured. As a further example, methods of stimulating post-natal hippocampal and/or hypothalamic neurogenesis are featured.

In some embodiments, such methods can include in vitro methods, e.g., contacting a sample (e.g., a cell or tissue) with a compound of formula (I) (and/or a compound of any of the other formulae described herein) or a salt (e.g., a pharmaceutically acceptable salt) thereof as defined anywhere herein. In other embodiments, the methods can include administering a compound of formula (I) (and/or a compound of any of the other formulae described herein) or a salt (e.g., a pharmaceutically acceptable salt) thereof as defined anywhere herein to a subject (e.g., a mammal, such as a human).

Accordingly, in yet another aspect, the presently disclosed embodiments include and feature methods of screening for (thereby identifying) compounds that stimulate neurogenesis (e.g., post-natal neurogenesis, e.g., post-natal hippocampal and/or hypothalamic neurogenesis) or protect newborn neurons from cell death. E.g., such as those described in the Examples section.

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with insufficient (e.g., aberrant) neurogenesis or unwanted neuronal cell death in a subject in need thereof are featured. The methods include administering to the subject an effective amount of a compound of formula (I) (and/or a compound of any of the other formulae described herein) or a salt (e.g., a pharmaceutically acceptable salt) thereof as defined anywhere herein to the subject.

In another aspect, the use of a compound of formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, insufficient (e.g., aberrant) neurogenesis or unwanted neuronal cell death is featured.

In embodiments, the one or more diseases, disorders, or conditions can include neuropathies, nerve trauma, and neurodegenerative diseases. In embodiments, the one or more diseases, disorders, or conditions can be diseases, disorders, or conditions caused by, or associated with insufficient neurogenesis (e.g., aberrant hippocampal and/or hypothalamic neurogenesis) as is believed to occur in neuropsychiatric diseases, or aberrant neuronal cell death as is believed to occur in neurodegenerative diseases. Examples of the one or more diseases, disorders, or conditions include, but are not limited to, schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuroactive drugs (such as alcohol, opiates, methamphetamine, phencyclidine, and cocaine), retinal degeneration, spinal cord injury, peripheral nerve injury, physiological weight loss associated with various conditions, and cognitive decline associated with normal aging, radiation therapy, and chemotherapy.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

In another aspect, methods of making the compounds described herein are featured. In embodiments, the methods include taking any one of the intermediate compounds described herein and reacting it with one or more chemical reagents in one or more steps to produce a compound of formula (I) (and/or a compound of any of the other formulae described herein) or a salt (e.g., a pharmaceutically acceptable salt) thereof as defined anywhere herein.

In some embodiments, compounds in which A is CHOH, and each of $L^1$ and $L^2$ is $C_1$-$C_3$ alkylene (e.g., each of $L^1$ and $L^2$ is $CH_2$) can be converted to compounds in which A is C(O), and each of $L^1$ and $L^2$ is $C_1$-$C_3$ alkylene (e.g., each of $L^1$ and $L^2$ is $CH_2$) that is substituted with $C_1$-$C_6$ thioalkoxy (e.g., —$SCH_3$). The methods include contacting the starting material with an oxidizing agent sulfur trioxide pyridine complex (see, e.g., Example 7a and 7b).

In one aspect, methods of making the pharmaceutical compositions described herein are featured. In embodiments, the methods include taking any one or more of the compounds of formula (I) (and/or compounds of any of the other formulae described herein) or a salt (e.g., a pharmaceutically acceptable salt) thereof as defined anywhere herein, and mixing said compound(s) with one or more pharmaceutically acceptable carriers.

In one aspect, kits for the treatment (e.g., controlling, relieving, ameliorating, alleviating, or slowing the progression of) or prevention (e.g., delaying the onset of or reducing the risk of developing) of one or more diseases, disorders, or conditions caused by, or associated with insufficient (e.g., aberrant) neurogenesis or unwanted neuronal cell death are featured. The kits include (i) a compound of formula (I) (and/or compounds of any of the other formulae described herein) or a salt (e.g., a pharmaceutically acceptable salt) thereof as defined anywhere herein; and (ii) instructions that include a direction to administer said compound to a subject (e.g., a patient).

Embodiments can include, for example, any one or more of the following features.

$R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro. In embodiments, $R^3$ is halo (e.g., bromo). In embodiments, each of $R^1$, $R^2$, and $R^4$ is hydrogen.

R and R' together with $C_2$ and $C_3$, respectively, form a fused phenyl ring having formula (II):

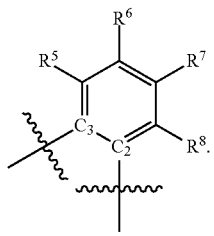
(II)

$R^6$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro. In embodiments, $R^6$ is halo (e.g., bromo) or $C_1$-$C_6$ alkyl (e.g., $CH_3$). In embodiments, $R^6$ is halo (e.g., bromo). In embodiments, each of $R^5$, $R^7$, and $R^8$ is hydrogen.

In embodiments, each of $R^3$ and $R^6$ is an independently selected substituent that is other than hydrogen. In certain embodiments, each of $R^3$ and $R^6$ is independently selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyclopropyl, —$N_3$, cyano, —$NH_2$, —NH($C_1$-$C_6$ alkyl), —N($C_1$-$C_6$ alkyl)$_2$, —NHC(O)($C_1$-$C_6$ alkyl), and nitro. For example, $R^3$ can be halo (e.g., bromo); and $R^6$ can be halo (e.g., bromo) or $C_1$-$C_6$ alkyl (e.g., $CH_3$); e.g., halo (e.g., bromo). In embodiments, each of $R^1$, $R^2$, and $R^4$ is hydrogen; and each of $R^5$, $R^7$, and $R^8$ is hydrogen.

In embodiments, R and R' together with $C_2$ and $C_3$, respectively, form a fused heteroaryl ring containing from 5-6 ring atoms, wherein from 1-2 of the ring atoms is independently selected from N, NH, N($C_1$-$C_3$ alkyl), O, and S; and wherein said heteroaryl ring is optionally substituted with from 1-3 independently selected $R^b$.

For example, R and R' together with $C_2$ and $C_3$, respectively, form a fused heteroaryl ring containing –6 ring atoms, wherein from 1-2 independently selected ring atoms is N; and wherein said heteroaryl ring is optionally substituted with from 1-2 independently selected $R^b$.

In embodiments, R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$.

For example, R and R' together with $C_2$ and $C_3$, respectively, form a fused heterocyclic ring containing 6 ring atoms, wherein from 1-2 of the ring atoms is independently selected from N, NH, N($C_1$-$C_6$ alkyl), and NC(O)($C_1$-$C_6$ alkyl); and wherein said heterocyclic ring is optionally substituted with from 1-3 independently selected $R^a$.

In embodiments, R and R' is, independently, hydrogen, $C_1$-$C_6$ alkyl, or $C_1$-$C_6$ haloalkyl (e.g., $C_1$-$C_6$ alkyl, or $C_1$-$C_6$ haloalkyl; e.g., $C_1$-$C_6$ alkyl).

Each of $L^1$ and $L^2$ is, independently, $C_1$-$C_3$ straight chain alkylene, which is optionally substituted with from 1-2 independently selected $R^c$. For example, each of $L^1$ and $L^2$ is $CH_2$.

A is $CR^{41}R^{42}$, in which each of $R^{41}$ and $R^{42}$ is, independently, hydrogen, halo, $C_1$-$C_3$ alkyl, or $OR^9$.

In some embodiments, A is other than $CH_2$.

In embodiments, one of $R^{41}$ and $R^{42}$ can be independently selected from hydrogen, halo, $C_1$-$C_3$ alkyl, and $OR^9$; and the other of $R^{41}$ and $R^{42}$ can be independently selected from halo, $C_1$-$C_3$ alkyl, and $OR^9$. For example, one of $R^{41}$ and $R^{42}$ is halo, $C_1$-$C_3$ alkyl, or $OR^9$ (e.g., halo or $OR^9$); and the other is hydrogen or $C_1$-$C_3$ alkyl.

In embodiments, one of $R^{41}$ and $R^{42}$ is halo, and the other of $R^{41}$ and $R^{42}$ is hydrogen or halo. For example, one of $R^{41}$ and $R^{42}$ is fluoro, and the other of $R^{41}$ and $R^{42}$ is hydrogen or fluoro. In either embodiments, one of $R^{41}$ and $R^{42}$ is $OR^9$; and the other of $R^{41}$ and $R^{42}$ is $C_1$-$C_3$ alkyl. For example, one of $R^{41}$ and $R^{42}$ is OH; and the other of $R^{41}$ and $R^{42}$ is $CH_3$.

In embodiments, the carbon attached to $R^{41}$ and $R^{42}$ is substituted with four different substituents (for purposes of clarification, these four substituents include $R^{41}$ and $R^{42}$) and is therefore a stereogenic center.

In certain embodiments, the carbon attached to $R^{41}$ and $R^{42}$ is (R) configured, meaning that the carbon attached to $R^{41}$ and $R^{42}$ has the (R) configuration (Cahn Ingold Prelog sequence rules notation). Such compounds are sometimes referred to herein as an "(R)-configured compound" (this term also includes compounds that further contain one or more stereogenic centers in addition to the (R)-$CR^{41}R^{42}$ stereogenic center).

In other embodiments, the carbon attached to $R^{41}$ and $R^{42}$ is (S) configured, meaning that the carbon attached to $R^{41}$ and $R^{42}$ has the (S) configuration (Cahn Ingold Prelog sequence rules notation). Such compounds are sometimes referred to herein as an "(S)-configured compound" (this term also includes compounds that further contain one or more stereogenic centers in addition to the (S)-$CR^{41}R^{42}$ stereogenic center).

In embodiments, the (R) configured compound (or salt, e.g., a pharmaceutically acceptable salt, thereof) is substantially free of (e.g., contains less than about 5% of, less than about 2% of, less than about 1%, less than about 0.5% of) a formula (I) compound (or salt thereof as described herein) that is (S) configured at the carbon attached to $R^{41}$ and $R^{42}$ (i.e., a formula (I) compound in which the carbon attached to $R^{41}$ and R has the (S) configuration). For example, the (R) configured compound can be an (R)-enantiomer that is substantially free of its opposing (S) enantiomer. As another example, an (R) configured compound can be substantially free of a diastereomer in which the carbon attached to $R^{41}$ and $R^{42}$ has the (S) configuration. In certain embodiments, the (R) configured compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

In embodiments, the (S) configured compound (or salt, e.g., a pharmaceutically acceptable salt, thereof) is substantially free of (e.g., contains less than about 5% of, less than about 2% of, less than about 1%, less than about 0.5% of) a formula (I) compound (or salt thereof as described herein) that is (R) configured at the carbon attached to $R^{41}$ and $R^{42}$ (i.e., a formula (I) compound in which the carbon attached to $R^{41}$ and $R^{42}$ has the (R) configuration). For example, the (S) configured compound can be an (S)-enantiomer that is substantially free of its opposing (R) enantiomer. As another example, the (S) configured compound can be substantially free of a diastereomer in which the carbon attached to $R^{41}$ and $R^{42}$ has the (R) configuration. In certain embodiments, the (S) configured compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

In certain embodiments, a formula (I) compound is (+) (dextrorotatory) when in the presence of plane polarized light.

In certain embodiments, a formula (I) compound is (−) (levorotatory) when in the presence of plane polarized light.

In embodiments, the (+) (dextrorotatory) compound is substantially free of (e.g., contains less than about 5% of, less than about 2% of, less than about 1%, less than about 0.5%) a formula (I) compound (or salt thereof as described herein) that is (−) (levorotatory). In certain embodiments, the (+) (dextrorotatory) compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

In embodiments, the (−) (levorotatory) compound is substantially free of (e.g., contains less than about 5% of, less than about 2% of, less than about 1%, less than about 0.5%) a formula (I) compound (or salt thereof as described herein) that is (+) (dextrorotatory). In certain embodiments, the (−) (levorotatory) compound can be additionally in substantially pure form (e.g., contains less than about 5% of, less than about 2% of, less than about 1%, less than about 0.5% of other substances, including, for example, one or more of other formula (I) compounds, non-formula (I) compounds, or biological media).

A is: (i) $CR^{A1}R^{A2}$, wherein each of $R^{A1}$ and $R^{A2}$ is independently selected from hydrogen, halo, $C_1$-$C_3$ alkyl, and $OR^9$, wherein $R^9$ is $C_1$-$C_3$ alkyl that is optionally substituted with hydroxyl or $C_1$-$C_3$ alkoxy; or (ii) C=O.

A is $CR^{A1}R^{A2}$, wherein each of $R^{A1}$ and $R^{A2}$ is, independently, hydrogen, halo, $C_1$-$C_3$ alkyl, or $OR^9$.

In embodiments, one of $R^{A1}$ and $R^{A2}$ is independently selected from hydrogen, halo, $C_1$-$C_3$ alkyl, and $OR^9$; and the other of $R^{A1}$ and $R^{A2}$ is independently selected from halo, $C_1$-$C_3$ alkyl, and $OR^9$.

In certain embodiments, one of $R^{A1}$ and $R^{A2}$ is halo, and the other of $R^{A1}$ and $R^{A2}$ is hydrogen, halo, or $C_1$-$C_3$ alkyl. In embodiments, one of $R^{A1}$ and $R^{A2}$ is halo, and the other of $R^{A1}$ and $R^{A2}$ is hydrogen. For example, one of $R^{A1}$ and $R^{A2}$ is fluoro, and the other of $R^{A1}$ and $R^{A2}$ is hydrogen.

In other embodiments, each of $R^{A1}$ and $R^{A2}$ is, independently, halo; e.g., each of $R^{A1}$ and $R^{A2}$ is fluoro.

In embodiments, one of $R^{A1}$ and $R^{A2}$ is —OH, and the other of $R^{A1}$ and $R^{A2}$ is hydrogen.

In embodiments, A is $CR^{A1}R^{A2}$, wherein one of $R^{A1}$ and $R^{A2}$ is independently selected from hydrogen, halo, $C_1$-$C_3$ alkyl, and $OR^9$; and the other of $R^{A1}$ and $R^{A2}$ is independently selected from halo, $C_1$-$C_3$ alkyl, and $OR^9$; wherein $R^9$ is hydrogen or $C_1$-$C_3$ alkyl that is optionally substituted with hydroxyl or $C_1$-$C_3$ alkoxy.

In certain embodiments, one of $R^{A1}$ and $R^{A2}$ is $OR^9$, and the other is hydrogen, wherein $R^9$ is hydrogen.

In embodiments, one of $R^{A1}$ and $R^{A2}$ is halo, and the other of $R^{A1}$ and $R^{A2}$ is hydrogen or halo. For example, one of $R^{A1}$ and $R^{A2}$ is fluoro, and the other of $R^{A1}$ and $R^{A2}$ is hydrogen or fluoro.

In other embodiments, one of $R^{A1}$ and $R^{A2}$ is $OR^9$; and the other of $R^{A1}$ and $R^{A2}$ is $C_1$-$C_3$ alkyl. For example, one of $R^{A1}$ and $R^{A2}$ is OH; and the other of $R^{A1}$ and $R^{A2}$ is $CH_3$.

Z is: (i) —$NR^{10}R^{11}$; or (ii) —$C(O)NR^{10}R^{11}$; or (iii) —$OR^{12}$; or (iv) —$S(O)_nR^{13}$, wherein n is 0, 1, or 2.

Z is —$NR^{10}R^{11}$. In embodiments, one of $R^{10}$ and $R^{11}$ is: (b) $C_6$-$C_{10}$ aryl that is optionally substituted with from 1-4 $R^b$; or (c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$; and the other of $R^{10}$ and $R^{11}$ is hydrogen or $C_1$-$C_6$ alkyl.

Z is —$OR^{12}$ or —$S(O)_nR^{13}$.

In embodiments, Z is —$OR^{12}$. In certain embodiments, $R^{12}$ is $C_6$-$C_{10}$ aryl that is optionally substituted with from 1-4 $R^b$.

In embodiments, $R^{12}$ is $C_1$-$C_6$ alkyl or $C_1$-$C_6$ haloalkyl (e.g., $C_1$-$C_6$ alkyl), each of which is substituted with from 1-3 $R^d$. In other embodiments, $R^{12}$ is other than $C_1$-$C_6$ alkyl or $C_1$-$C_6$ haloalkyl (e.g., $C_1$-$C_6$ alkyl), each of which is unsubstituted or substituted with from 1-3 $R^d$.

$R^3$ can be selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —$NH(C_1$-$C_6$ alkyl), $N(C_1$-$C_6$ alkyl)$_2$, —$NHC(O)(C_1$-$C_6$ alkyl), and nitro. E.g., $R^3$ can be halo (e.g., bromo). In embodiments, each of $R^1$, $R^2$, and $R^4$ can be hydrogen.

$L^1$ can be $C_1$-$C_3$ straight chain alkylene, which is optionally substituted with from 1-2 independently selected $R^c$. E.g., $L^1$ can be $CH_2$.

$L^2$ can be $C_1$-$C_3$ straight chain alkylene, which is optionally substituted with from 1-2 independently selected $R^c$. E.g., $L^2$ can be $CH_2$.

Each of $L^1$ and $L^2$ can be, independently, $C_1$-$C_3$ straight chain alkylene, which is optionally substituted with from 1-2 independently selected $R^c$. E.g., each of $L^1$ and $L^2$ can be $CH_2$.

A can be $CR^{A1}R^{A2}$, in which each of $R^{A1}$ and $R^{A2}$ is, independently, hydrogen, halo, $C_1$-$C_3$ alkyl, or $OR^9$.

A can be $CR^{A1}R^{A2}$, in which each of $R^{A1}$ and $R^{A2}$ is, independently, hydrogen, halo, or $C_1$-$C_3$ alkyl.

A can be $CR^{A1}R^{A2}$, in which one of $R^{A1}$ and $R^{A2}$ is halo (e.g., fluoro), and the other of $R^{A1}$ and $R^{A2}$ is, independently, hydrogen, halo, or $C_1$-$C_3$ alkyl (e.g., hydrogen).

A can be $CR^{A1}R^{A2}$, in which one of $R^{A1}$ and $R^{A2}$ is halo (e.g., fluoro), and the other of $R^{A1}$ and $R^{A2}$ is hydrogen.

One of $R^{A1}$ and $R^{A2}$ can be halo or $OR^9$, and the other is hydrogen.

One of $R^{A1}$ and $R^{A2}$ can be $OR^9$. In embodiments, the other of $R^{A1}$ and $R^{A2}$ can be as defined anywhere herein; e.g., the other of $R^{A1}$ and $R^{A2}$ can be hydrogen or $C_1$-$C_3$ alkyl. For example, one of $R^{A1}$ and $R^{A2}$ can be $OR^9$, and the other of $R^{A1}$ and $R^{A2}$ is hydrogen. In embodiments, $R^9$ can be hydrogen.

One of $R^{A1}$ and $R^{A2}$ can be halo. In embodiments, the other of $R^{A1}$ and $R^{A2}$ can be as defined anywhere herein; e.g., the other of $R^{A1}$ and $R^{A2}$ can be hydrogen, $C_1$-$C_3$ alkyl, or halo. For example, one of $R^{A1}$ and $R^{A2}$ can be halo (e.g., fluoro), and the other of $R^{A1}$ and $R^{A2}$ is hydrogen.

The carbon attached to $R^{A1}$ and $R^{A2}$ can have the R configuration.

The carbon attached to $R^{A1}$ and $R^{A2}$ can have the S configuration.

Each of $L^1$ and $L^2$ is, independently, $C_1$-$C_3$ alkylene, which is optionally substituted with from 1-2 independently selected $R^c$. E.g., each of $L^1$ and $L^2$ can be $CH_2$.

Z can be —$NR^{10}R^{11}$.

One of $R^{10}$ and $R^{11}$ can be $C_6$-$C_{10}$ aryl that is optionally substituted with from 1-4 $R^b$.

One of $R^{10}$ and $R^{11}$ can be $C_6$-$C_{10}$ aryl that is optionally substituted with from 1-4 $R^b$, and the other is hydrogen or $C_1$-$C_6$ alkyl.

One of $R^{10}$ and $R^{11}$ can be $C_6$-$C_{10}$ aryl that is optionally substituted with from 1-4 $R^b$, and the other is hydrogen. For example, one of $R^{10}$ and $R^{11}$ can be unsubstituted phenyl, and the other is hydrogen. As another example, one of $R^{10}$ and $R^{11}$ can be phenyl that is substituted with 1 $R^b$, and the other is hydrogen. In embodiments, $R^b$ can be $C_1$-$C_6$ alkoxy (e.g., $OCH_3$). For example, one of $R^{10}$ and $R^{11}$ can be 3-methoxyphenyl, and the other is hydrogen.

Z can be $-OR^{12}$. In embodiments, $R^{12}$ can be $C_1$-$C_6$ alkyl or $C_1$-$C_6$ haloalkyl, each of which is optionally substituted with from 1-3 $R^c$. In other embodiments, $R^{12}$ can be $C_6$-$C_{10}$ aryl that is optionally substituted with from 1-4 $R^b$. For example, $R^{12}$ can be unsubstituted phenyl.

Z can be $-S(O)_nR^{13}$, in which n can be 0, 1, or 2. In other embodiments, $R^{13}$ can be $C_6$-$C_{10}$ aryl that is optionally substituted with from 1-4 $R^b$. For example, $R^{13}$ can be unsubstituted phenyl.

Z can be heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$.

R and R' together with $C_2$ and $C_3$, respectively, form a fused phenyl ring having formula (II):

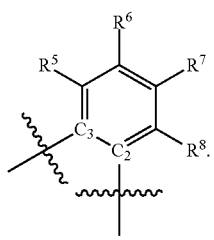

(II)

$R^6$ can be selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, $-NH_2$, $-NH(C_1$-$C_6$ alkyl), N($C_1$-$C_6$ alkyl)$_2$, $-NHC(O)(C_1$-$C_6$ alkyl), and nitro. E.g., $R^6$ can be halo (e.g., bromo). In embodiments, each of $R^5$, $R^7$, and $R^8$ can be hydrogen. Any one or more of the $R^1$, $R^2$, $R^3$, $R^4$, $L^1$, $L^2$, A, and Z embodiments described herein can be combined with any one or more of the $R^5$, $R^6$, $R^7$, and $R^8$ embodiments described herein.

Each of $L^1$ and $L^2$ can be $CH_2$; A can be $CR^{41}R^{42}$, wherein one of $R^{41}$ and $R^{42}$ is $OR^9$, and the other is hydrogen; Z is $-NR^{10}R^{11}$; and each of $R^{10}$ and $R^{11}$ can be independently selected from: (a) hydrogen; (b) $C_6$-$C_{10}$ aryl that is optionally substituted with from 1-4 $R^b$; (d) $C_1$-$C_6$ alkyl or $C_1$-$C_6$ haloalkyl, each of which is optionally substituted with from 1-3 $R^d$; and (f) $C_2$-$C_6$ alkenyl or $C_2$-$C_6$ alkynyl.

Each of $R^3$ and $R^6$ can be halo (e.g., bromo); and each of $R^1$, $R^2$, $R^4$, $R^5$, $R^7$, and $R^8$ can be hydrogen. $R^9$ can be hydrogen. One of $R^{10}$ and $R^{11}$ can be $C_6$-$C_{10}$ aryl that is optionally substituted with from 1-4 $R^b$, and the other is hydrogen. One of $R^{10}$ and $R^{11}$ can be unsubstituted phenyl, and the other is hydrogen. One of $R^{10}$ and $R^{11}$ can be phenyl that is substituted with 1 $R^b$, and the other is hydrogen. $R^b$ can be $C_1$-$C_6$ alkoxy (e.g., $OCH_3$). One of $R^{10}$ and $R^{11}$ can be 3-methoxyphenyl, and the other is hydrogen.

Each of $L^1$ and $L^2$ is $CH_2$; A is $CR^{41}R^{42}$, wherein one of $R^{41}$ and $R^{42}$ is $OR^9$, and the other is hydrogen; Z is $-NR^{10}R^{11}$; and each of $R^{10}$ and $R^{11}$ is independently selected from: (a) hydrogen; (b) $C_6$-$C_{10}$ aryl that is optionally substituted with from 1-4 $R^b$; (d) $C_1$-$C_6$ alkyl or $C_1$-$C_6$ haloalkyl, each of which is optionally substituted with from 1-3 $R^d$; and (f) $C_2$-$C_6$ alkenyl or $C_2$-$C_6$ alkynyl. Embodiment can include one or more of the following features.

Each of $R^3$ and $R^6$ is halo (e.g., bromo); and each of $R^1$, $R^2$, $R^4$, $R^5$, $R^7$, and $R^8$ is hydrogen. $R^9$ can be hydrogen. One of $R^{10}$ and $R^{11}$ can be $C_6$-$C_{10}$ aryl that is optionally substituted with from 1-4 $R^b$, and the other is hydrogen. One of $R^{10}$ and $R^{11}$ can be unsubstituted phenyl, and the other is hydrogen. One of $R^{10}$ and $R^{11}$ can be phenyl that is substituted with 1 $R^b$, and the other is hydrogen. $R^b$ can be $C_1$-$C_6$ alkoxy (e.g., $OCH_3$). One of $R^{10}$ and $R^{11}$ can be 3-methoxyphenyl, and the other is hydrogen.

In embodiments, (A), (B), or (C) applies. In other embodiments, (A) and (B); or (A) and (C); or (B) and (C) applies. In still other embodiments, (A), (B), or (C) apply.

Each of R and R' can be, independently, hydrogen, $C_1$-$C_6$ alkyl, or $C_1$-$C_6$ haloalkyl. Each of R and R' can be, independently, $C_1$-$C_6$ alkyl (e.g., each of R and R' can be $CH_3$). Each of R and R' can be hydrogen.

The compound of the present invention can include any one or more compounds selected from:

R-1-(3,6-Dibromo-9H-carbazol-9-yl)-3-(3-methoxyphenylamino)-propan-2-ol;

S-1-(3,6-Dibromo-9H-carbazol-9-yl)-3-(3-methoxyphenylamino)-propan-2-ol;

1-(3,6-dibromo-9H-carbazol-9-yl)-3-(2-iminopyridin-1 (2H)-yl)propan-2-ol;

1-(3,6-dibromo-9H-carbazol-9-yl)-3-(phenylthio)propan-2-ol;

N-(3-(3,6-dibromo-9H-carbazol-9-yl)-2-hydroxypropyl)-N-(3-methoxyphenyl)acetamide;

5-((3,6-dibromo-9H-carbazol-9-yl)methyl)-3-(3-methoxyphenyl)-oxazolidin-2-one;

N-(3-(3,6-dibromo-9H-carbazol-9-yl)-2-fluoropropyl)-3-methoxyaniline;

1-(3,6-dibromo-9H-carbazol-9-yl)-3-(3-methoxyphenylamino)-propan-2-one;

N-(3-(3,6-dibromo-9H-carbazol-9-yl)-2-methoxypropyl)-3-methoxyaniline;

1-(3,6-Dimethyl-9H-carbazol-9-yl)-3-(3-methoxyphenylamino)propan-2-ol;

1-(3-Bromo-6-methyl-9H-carbazol-9-yl)-3-(3-methoxyphenylamino)-propan-2-ol;

1-(3,6-Dichloro-9H-carbazol-9-yl)-3-(3-methoxyphenylamino)propan-2-ol;

1-(5-bromo-2,3-dimethyl-1H-indol-1-yl)-3-(phenylamino) propan-2-ol;

1-(3,6-Dibromo-9H-pyrido[3,4-b]indol-9-yl)-3-(phenylamino)propan-2-ol;

1-(3-Azidophenylamino)-3-(3,6-dibromo-9H-carbazol-9-yl)propan-2-ol;

1,3-Bis(3,6-dibromo-9H-carbazol-9-yl)propan-2-ol;

1-(9H-Carbazol-9-yl)-3-(3,6-dibromo-9H-carbazol-9-yl) propan-2-ol;

3-(3,6-Dibromo-9H-carbazol-9-yl)-2-hydroxy-N-(3-methoxyphenyl)-propanamide;

Ethyl 5-(2-Hydroxy-3-(3-methoxyphenylamino)propyl)-8-methyl-3,4-dihydro-1H-pyrido[4,3-b]indole-2(5H)-carboxylate;

4-(3,6-dibromo-9H-carbazol-9-yl)-1-(phenylamino)butan-2-ol;

N-(3-(3,6-dibromo-9H-carbazol-9-yl)propyl)aniline;

1-(3,6-dibromo-9H-carbazol-9-yl)-4-(phenylamino)butan-2-ol;
1-(3,6-dibromo-9H-carbazol-9-yl)-3-(pyridin-2-ylamino)propan-2-ol;
1-(3,6-dibromo-9H-carbazol-9-yl)-3-((3-methoxyphenyl)(methyl)-amino)propan-2-ol;
3-(3,6-dibromo-9H-carbazol-9-yl)-1-(3-methoxyphenylamino)-1-(methylthio)propan-2-one;
3-amino-1-(3-(3,6-dibromo-9H-carbazol-9-yl)-2-hydroxypropyl)pyridinium;
1-(3,6-dibromo-9H-carbazol-9-yl)-3-(pyrimidin-2-ylamino)propan-2-ol;
N-(3-(3,6-dibromo-9H-carbazol-9-yl)-2-fluoropropyl)-3-methoxy-N-methylaniline;
1-(3,6-dibromo-9H-carbazol-9-yl)-3-methoxypropan-2-ol;
1-(3,6-dibromo-9H-carbazol-9-yl)-4-phenylbutan-2-ol;
1-(3,6-dibromo-9H-carbazol-9-yl)-3-(1H-indol-1-yl)propan-2-ol;
3-(1-(3-(3,6-dibromo-9H-carbazol-9-yl)-2-hydroxypropyl)-1H-1,2,3-triazol-4-yl)propan-1-ol;
1-(3,6-dibromo-9H-carbazol-9-yl)-3-(3-ethoxyphenylamino)propan-2-ol;
1-(3,6-dibromo-9H-carbazol-9-yl)-3-(3,5-dimethyl-1H-pyrazol-1-yl)propan-2-ol;
1-(3,6-dibromo-9H-carbazol-9-yl)-3-(phenylsulfinyl)propan-2-ol;
1-(3,6-dibromo-9H-carbazol-9-yl)-3-(phenylsulfonyl)propan-2-ol;
1-(3-bromo-9H-carbazol-9-yl)-3-(3-methoxyphenylamino)propan-2-ol;
N-(5-(3-(3-(3,6-dibromo-9H-carbazol-9-yl)-2-hydroxypropylamino)phenoxy)pentyl)-2-(7-(dimethylamino)-2-oxo-2H-chromen-4-yl)acetamide;
1-(3,6-dibromo-9H-carbazol-9-yl)-3-phenoxypropan-2-ol;
N-(2-(3-(3,6-dibromo-9H-carbazol-9-yl)-2-hydroxypropoxy)ethyl)-acetamide;
1-(3,6-dibromo-9H-carbazol-9-yl)-3-(pyridin-3-ylamino)propan-2-ol;
1-(3,6-dibromo-9H-carbazol-9-yl)-3-(pyridin-4-ylamino)propan-2-ol;
1-(2, 8-dimethyl-3,4-dihydro-1H-pyrido[4, 3-b]indol-5(2H)-yl)-3-(phenylamino)propan-2-ol;
N-(3-(3,6-dibromo-9H-carbazol-9-yl)-2,2-difluoropropyl)-3-methoxyaniline;
1-(3,6-dibromo-9H-carbazol-9-yl)-3-phenoxypropan-2-ol;
1-(3,6-dibromo-9H-carbazol-9-yl)-3-(phenylamino)propan-2-ol;
1-(3,6-dibromo-9H-carbazol-9-yl)-3-(o-tolylamino)propan-2-ol;
1-(3,6-dibromo-9H-carbazol-9-yl)-3-(m-tolylamino)propan-2-ol;
1-(3,6-dibromo-9H-carbazol-9-yl)-3-(2-methoxyphenylamino)propan-2-ol;
1-(3,6-dibromo-9H-carbazol-9-yl)-3-(naphthalen-1-ylamino)propan-2-ol;
1-(4-bromophenylamino)-3-(3,6-dichloro-9H-carbazol-9-yl)propan-2-ol;
1-(4-bromophenylamino)-3-(3,6-dibromo-9H-carbazol-9-yl)propan-2-ol;
1-(3,6-dibromo-9H-carbazol-9-yl)-3-(4-ethoxyphenylamino)propan-2-ol;
1-(4-chlorophenylamino)-3-(3,6-dibromo-9H-carbazol-9-yl)propan-2-ol;
1-(3,6-dibromo-9H-carbazol-9-yl)-3-(phenethylamino)propan-2-ol;
1-(3,6-dibromo-9H-carbazol-9-yl)-3-(2-hydroxyethylamino)propan-2-ol;
1-(3,6-dibromo-9H-carbazol-9-yl)-3-(2, 4-dimethoxyphenylamino)propan-2-ol;
1-(3,6-dibromo-9H-carbazol-9-yl)-3-(2, 3-dimethylphenylamino)propan-2-ol;
1-(2-chlorophenylamino)-3-(3,6-dibromo-9H-carbazol-9-yl)propan-2-ol;
1-(tert-butylamino)-3-(3,6-dibromo-9H-carbazol-9-yl)propan-2-ol;
1-(3,6-dibromo-9H-carbazol-9-yl)-3-(isopropylamino)propan-2-ol;
1-(3,6-dibromo-9H-carbazol-9-yl)-3-(4-methoxyphenylamino)propan-2-ol;
1-(3,6-dibromo-9H-carbazol-9-yl)-3-(3-methoxyphenylamino)propan-2-ol;
1-(3,6-dibromo-9H-carbazol-9-yl)-3-(m-tolylamino)propan-2-ol;
1-(3,6-dibromo-9H-carbazol-9-yl)-3-(3,5-dimethylphenylamino)propan-2-ol;
1-(3,6-dibromo-9H-carbazol-9-yl)-3-(3,4-dimethylphenylamino)propan-2-ol;
1-(3,6-dibromo-9H-carbazol-9-yl)-3-(3,4-dimethylphenylamino)propan-2-ol;
1-(3,6-dibromo-9H-carbazol-9-yl)-3-(2,5-dimethylphenylamino)propan-2-ol;
1-(4-bromophenylamino)-3-(2,3-dimethyl-1H-indol-1-yl)propan-2-ol;
1-(2,3-dimethyl-1H-indol-1-yl)-3-(4-methoxyphenylamino)propan-2-ol;
1-(2, 3-dimethyl-1H-indol-1-yl)-3-(4-ethoxyphenylamino)propan-2-ol;
1-(2,3-dimethyl-1H-indol-1-yl)-3-(p-tolylamino)propan-2-ol;
1-(2,3-dimethyl-1H-indol-1-yl)-3-(phenylamino)propan-2-ol oxalate;
1-(1H-indol-1-yl)-3-(4-methoxyphenylamino)propan-2-ol hydrochloride;
1-(1H-indol-1-yl)-3-(phenylamino)propan-2-ol oxalate;
1-(3,4-dihydro-1H-carbazol-9(2H)-yl)-3-(m-tolylamino)propan-2-ol;
1-(9H-carbazol-9-yl)-3-(phenylamino)propan-2-ol;
1-(3,6-dichloro-9H-carbazol-9-yl)-3-(phenylamino)propan-2-ol;
1-(9H-carbazol-9-yl)-3-(p-tolylamino)propan-2-ol;
1-(3,6-dichloro-9H-carbazol-9-yl)-3-(p-tolylamino)propan-2-ol;
1-(3,6-dibromo-9H-carbazol-9-yl)-3-(p-tolylamino)propan-2-ol;
N-(4-(3-(9H-carbazol-9-yl)-2-hydroxypropoxy)phenyl)acetamide;
1-(9H-carbazol-9-yl)-3-phenoxypropan-2-ol;
1-(9H-carbazol-9-yl)-3-(4-methoxyphenylamino)propan-2-ol;
1-(benzylamino)-3-(9H-carbazol-9-yl)propan-2-ol;
methyl 4-(3-(9H-carbazol-9-yl)-2-hydroxypropoxy)benzoate;
1-(9H-carbazol-9-yl)-3-(4-methoxyphenoxy)propan-2-ol;
1-amino-3-(3,6-dibromo-9H-carbazol-9-yl)propan-2-ol;
(S)-1-(3,6-dibromo-9H-carbazol-9-yl)-3-phenoxypropan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;
1-(2,8-dimethyl-3,4-dihydro-1H-pyrido[4,3-b]indol-5(2H)-yl)-3-(3-methoxyphenylamino)propan-2-ol;

1-(4-azidophenylamino)-3-(3,6-dibromo-9H-carbazol-9-yl)propan-2-ol;
1-(3-azido-6-bromo-9H-carbazol-9-yl)-3-(3-methoxyphenylamino)propan-2-ol;
1-(3,6-dibromo-9H-carbazol-9-yl)-3-(4-methoxyphenoxy)propan-2-ol;
1-(3,6-dichloro-9H-carbazol-9-yl)-3-(phenylsulfonyl)propan-2-ol;
3,6-dibromo-9-(2-fluoro-3-(phenylsulfonyl)propyl)-9H-carbazole;
S)-1-(3,6-dibromo-9H-carbazol-9-yl)-3-(phenylsulfonyl)propan-2-ol;
(R)-1-(3,6-dibromo-9H-carbazol-9-yl)-3-(phenylsulfonyl)propan-2-ol;
1-(3,6-dicyclopropyl-9H-carbazol-9-yl)-3-(phenylamino)propan-2-ol;
1-(3,6-diiodo-9H-carbazol-9-yl)-3-(phenylamino)propan-2-ol;
1-(3,6-diethynyl-9H-carbazol-9-yl)-3-(3-methoxyphenylamino) propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline;
3,6-dibromo-9-(2,2-difluoro-3-phenoxypropyl)-9H-carbazole;
N-(3-(3,6-dibromo-9H-carbazol-9-yl)-2-fluoropropyl)-4-methoxyaniline;
N-(2-bromo-3-(3,6-dibromo-9H-carbazol-9-yl)propyl)-N-(4-methoxyphenyl)-4-nitrobenzenesulfonamide;
Ethyl 2-(4-(3-(3,6-dibromo-9H-carbazol-9-yl)-2-fluoropropylamino)phenoxy)acetate; and
N-(3-(3,6-dibromo-9H-carbazol-9-yl)-2-fluoropropyl)-4-(2-(2-methoxyethoxy)ethoxy)aniline;
N-(2-(2-(4-(3-(3,6-dibromo-9H-carbazol-9-yl)-2-fluoropropylamino)phenoxy)acetamido)ethyl)-5-(2-oxohexahydro-1H-thieno[3,4-d]imidazol-4-yl)pentanamide;
2-(4-(3-(3,6-dibromo-9H-carbazol-9-yl)-2-fluoropropylamino)phenoxy)-N,N-dimethylacetamide;
2-(4-(3-(3,6-dibromo-9H-carbazol-9-yl)-2-fluoropropylamino)phenoxy)-N-(2-hydroxyethyl)acetamide;
1-(bis(4-bromophenyl)amino)-3-(phenylamino)propan-2-ol;
(E)-3,6-dibromo-9-(3-phenoxyallyl)-9H-carbazole;
(E)-3,6-dibromo-9-(3-phenoxyprop-1-en-1-yl)-9H-carbazole;
1-(3,6-bis(trifluoromethyl)-9H-carbazol-9-yl)-3-(phenylamino)propan-2-ol;
1-(2, 8-Dibromo-10,11-dihydro-5H-dibenzo[b,f]azepin-5-yl)-3-(3-methoxyphenylamino)propan-2-ol;
1-(3,6-Dibromo-9H-carbazol-9-yl)-3-(3-methoxyphenylthio)propan-2-ol;
1-(3,6-Dibromo-9H-carbazol-9-yl)-3-(4-methoxyphenylthio)propan-2-ol;
3,6-Dibromo-9-(2-fluoro-3-(3-methoxyphenylthio)propyl)-9H-carbazole;
3,6-Dibromo-9-(2-fluoro-3-(4-methoxyphenylthio)propyl)-9H-carbazole;
3,6-Dibromo-9-(2-fluoro-3-(3-methoxyphenylsulfonyl)propyl)-9H-carbazole;
1-(3,6-Dibromo-9H-carbazol-9-yl)-3-(3-methoxyphenylsulfonyl)propan-2-ol;
3,6-Dibromo-9-(2-fluoro-3-(4-methoxyphenylsulfonyl)propyl)-9H-carbazole;
1-(3,6-Dibromo-9H-carbazol-9-yl)-3-(4-methoxyphenylsulfonyl)propan-2-ol;
3-(3-(3,6-Dibromo-9H-carbazol-9-yl)-2-hydroxypropylthio)phenol;
4-(3-(3,6-Dibromo-9H-carbazol-9-yl)-2-hydroxypropylthio)phenol;
3-(3-(3,6-Dibromo-9H-carbazol-9-yl)-2-hydroxypropylsulfonyl)phenol;
4-(3-(3,6-Dibromo-9H-carbazol-9-yl)-2-hydroxypropylsulfonyl)phenol;
1-(3-Aminophenylthio)-3-(3,6-dibromo-9H-carbazol-9-yl)propan-2-ol;
1-(4-Aminophenylthio)-3-(3,6-dibromo-9H-carbazol-9-yl)propan-2-ol;
1-(3,6-dibromo-9H-carbazol-9-yl)-3-phenoxypropan-2-amine;
N-Benzyl-2-(3-(3-(3,6-dibromo-9H-carbazol-9-yl)-2-hydroxypropylthio)-phenoxy)acetamide;
N-Benzyl-2-(4-(3-(3,6-dibromo-9H-carbazol-9-yl)-2-hydroxypropylthio)-phenoxy)acetamide;
3-(3-(3,6-Dibromo-9H-carbazol-9-yl)-2-fluoropropylsulfonyl)phenol; N-Benzyl-2-(3-(3-(3,6-dibromo-9H-carbazol-9-yl)-2-hydroxypropylsulfonyl)-phenoxy)acetamide;
4-(3-(3,6-Dibromo-9H-carbazol-9-yl)-2-fluoropropylsulfonyl)phenol;
5-(5-(3-(3-(3,6-dibromo-9H-carbazol-9-yl)-2-hydroxypropylamino)phenoxy)pentylcarbamoyl)-2-(6-hydroxy-3-oxo-3H-xanthen-9-yl)benzoic acid;
1-(8-bromo-3,4-dihydro-1H-pyrido[4,3-b]indol-5 (2H)-yl)-3-phenoxypropan-2-ol;
1-(8-bromo-2-cyclopropyl-3,4-dihydro-1H-pyrido[4,3-b]indol-5 (2H)-yl)-3-phenoxypropan-2-ol;
8-bromo-5-(2-hydroxy-3-phenoxypropyl)-3,4-dihydro-1H-pyrido[4,3-b]indole-2(5H)-carbonitrile;
8-bromo-5-(2-fluoro-3-phenoxypropyl)-2,3,4,5-tetrahydro-1H-pyrido[4,3-b]indole;
1-(cyclohexylamino)-3-(3,6-dibromo-9H-carbazol-9-yl)propan-2-ol;
(9-(2-hydroxy-3-(phenylthio)propyl)-9H-carbazole-3,6-dicarbonitrile;
9-(2-hydroxy-3-phenoxypropyl)-9H-carbazole-3,6-dicarbonitrile;
R—N-(3-(3,6-dibromo-9H-carbazol-9-yl)-2-fluoropropyl)-3-methoxyaniline
S—N-(3-(3,6-dibromo-9H-carbazol-9-yl)-2-fluoropropyl)-3-methoxyaniline
N-(2-(3,6-dibromo-9H-carbazol-9-yl)ethyl)aniline;
2-(6-Amino-3-imino-3H-xanthen-9-yl)-4-(6-(5-(3-(3,6-dibromo-9H-carbazol-9-yl)-2-hydroxypropylamino)phenoxy)pentylamino)-6-oxohexylcarbamoyl)benzoic acid AND 2-(6-amino-3-imino-3H-xanthen-9-yl)-5-(6-(5-(3-(3-(3,6-dibromo-9H-carbazol-9-yl)-2-hydroxypropylamino)phenoxy)pentylamino)-6-oxohexylcarbamoyl) benzoic acid;
1-(8-bromo-2-methyl-3,4-dihydro-1H-pyrido[4,3-b]indol-5 (2H)-yl)-3-phenoxypropan-2-ol;
6-((4-bromophenyl)(2-hydroxy-3-phenoxypropyl)amino) nicotinonitrile;
1-(3-(3,6-dibromo-9H-carbazol-9-yl)-2-hydroxypropyl) pyridin-2(1H)-one;
9-(2-hydroxy-3-phenoxypropyl)-9H-carbazole-3-carbonitrile;
tert-butyl (5-(4-(((3-(3,6-dibromo-9H-carbazol-9-yl)-2-hydroxypropyl)sulfonyl) phenoxy)pentyl)carbamate;
6-bromo-9-(2-hydroxy-3-phenoxypropyl)-9H-carbazole-3-carbonitrile;
6-bromo-9-(2-hydroxy-3-phenoxypropyl)-9H-carbazole-3-carboxamide;

1-(3,6-dibromo-9H-carbazol-9-yl)-3-(pyridin-2-yloxy)propan-2-ol;
methyl 6-bromo-9-(2-hydroxy-3-phenoxypropyl)-9H-carbazole-3-carboxylate;
6-bromo-9-(2-hydroxy-3-phenoxypropyl)-9H-carbazole-3-carboxylic acid;
6-bromo-9-(2-hydroxy-3-phenoxypropyl)-9H-pyrido[2,3-b]indole-3-carbonitrile;
9-(2-hydroxy-3-phenoxypropyl)-9H-pyrido[2,3-b]indole-3-carbonitrile;
tert-butyl 3-(2-(2-(2-(3-((3-(3,6-dibromo-9H-carbazol-9-yl)-2-hydroxypropyl)amino)phenoxy)ethoxy)ethoxy)ethoxy)propanoate;
1-(3,6-dibromo-1,4-dimethoxy-9H-carbazol-9-yl)-3-(phenylamino)propan-2-ol;
1-(3,6-dibromo-1, 8-dimethyl-9H-carbazol-9-yl)-3-(phenylamino)propan-2-ol;
2-(3,6-dibromo-9H-carbazol-9-yl)acetic acid;
1-(6-bromo-3-methoxy-1-methyl-9H-carbazol-9-yl)-3-(phenylamino)propan-2-ol;
1-(4,6-dibromo-3-methoxy-1-methyl-9H-carbazol-9-yl)-3-(phenylamino)propan-2-ol;
1-(3,6-dibromo-4-methoxy-9H-carbazol-9-yl)-3-(phenylamino)propan-2-ol;
9-(2-hydroxy-3-phenoxypropyl)-9H-pyrido[3,4-b]indole-3-carboxylic acid;
6-bromo-9-(2-hydroxy-3-phenoxypropyl)-9H-pyrido[3,4-b]indole-3-carboxylic acid;
ethyl 6-bromo-9-(2-hydroxy-3-phenoxypropyl)-9H-pyrido[3,4-b]indole-3-carboxylate;
9-(2-fluoro-3-phenoxypropyl)-9H-carbazole-3,6-dicarbonitrile;
9-(2-hydroxy-2-methyl-3-phenoxypropyl)-9H-carbazole-3,6-dicarbonitrile;
1-(cyclohexyloxy)-3-(3,6-dibromo-9H-carbazol-9-yl)propan-2-ol;
(E)-N-(3-(3,6-dibromo-9H-carbazol-9-yl)prop-1-en-1-yl)-1,1,1-trifluoro-N-(3-methoxyphenyl)methanesulfonamide;
1-(3,6-dibromo-9H-pyrido[2,3-b]indol-9-yl)-3-phenoxypropan-2-ol;
1-(3,6-dibromo-9H-carbazol-9-yl)-3-((6-methoxypyridin-2-yl)amino)propan-2-ol;
1-(8-bromo-5H-pyrido[4,3-b]indol-5-yl)-3-phenoxypropan-2-ol;
6-bromo-9-(2-hydroxy-3-phenoxypropyl)-9H-pyrido[3,4-b]indole-3-carboxamide;
8-bromo-5-(2-hydroxy-3-phenoxypropyl)-5H-pyrido[4,3-b]indole 2-oxide;
8-bromo-5-(2-hydroxy-3-phenoxypropyl)-5H-pyrido[3,2-b]indole 1-oxide;
(6-bromo-9H-pyrido[3,4-b]indol-3-yl)methanol;
ethyl 6-bromo-9H-pyrido[3,4-b]indole-3-carboxylate;
tert-butyl (3-(3,6-dibromo-9H-carbazol-9-yl)-2-fluoropropyl)carbamate;
2-(3,6-dibromo-9H-carbazol-9-yl)-N-methylacetamide;
3-(3,6-dibromo-9H-carbazol-9-yl)-2-fluoropropan-1-amine hydrochloride;
N-(3-(3,6-dibromo-9H-carbazol-9-yl)-2-fluoropropyl)acetamide;
2-(3,6-dibromo-9H-carbazol-9-yl)propanamide;
6-bromo-9H-pyrido[3,4-b]indole-3-carbonitrile;
6-bromo-3-methyl-9H-pyrido[3,4-b]indole;
methyl (2-(3,6-dibromo-9H-carbazol-9-yl)acetyl)carbamate;
N-(3-(3,6-dibromo-9H-carbazol-9-yl)-2-fluoropropyl)-1,1,1-trifluoro-N-(3-methoxyphenyl)methanesulfonamide;
N-(3-(3,6-dibromo-9H-carbazol-9-yl)-2-fluoropropyl)-6-methoxypyridin-2-amine;
N-(3-(3,6-dibromo-9H-carbazol-9-yl)-2-hydroxypropyl)-1,1,1-trifluoro-N-(3-methoxyphenyl)methane sulfonamide;
1-(3,6-dibromo-9H-carbazol-9-yl)-3-((4-methoxybenzyl)(3-methoxyphenyl)amino)propan-2-ol;
N-(3-(3,6-dibromo-9H-carbazol-9-yl)-2-hydroxypropyl)-2,2,2-trifluoroacetamide;
tert-butyl (3-(3,6-dibromo-9H-carbazol-9-yl)-2-hydroxypropyl)carbamate;
5-(2-hydroxy-3-phenoxypropyl)-5H-pyrimido[5,4-b]indole-2-carboxylic acid;
N-(3-(3,6-dibromo-9H-carbazol-9-yl)-2-hydroxypropyl)acetamide;
ethyl (3-(3,6-dibromo-9H-carbazol-9-yl)-2-hydroxypropyl)carbamate;
6-bromo-9-(3-(4-bromophenoxy)-2-hydroxypropyl)-9H-carbazole-3-carbonitrile;
methyl 9-(2-hydroxy-3-phenoxypropyl)-9H-pyrido[3,4-b]indole-3-carboxylate;
N-(3-(3-bromo-6-methyl-9H-carbazol-9-yl)-2-fluoropropyl)-6-methoxypyridin-2-amine;
or a salt (e.g., a pharmaceutically acceptable salt) thereof (or any one or a subset thereof, e.g., as delineated in the claims).

In certain embodiments, the compound having formula (I) can be 1-(3,6-dibromo-9H-carbazol-9-yl)-3-(phenylamino)propan-2-ol; or a salt (e.g., a pharmaceutically acceptable salt) thereof.

In certain embodiments, the compound having formula (I) can be R-1-(3,6-Dibromo-9H-carbazol-9-yl)-3-(3-methoxyphenylamino)-propan-2-ol; or a salt (e.g., a pharmaceutically acceptable salt) thereof. In embodiments, R-1-(3,6-Dibromo-9H-carbazol-9-yl)-3-(3-methoxyphenylamino)-propan-2-ol or a salt (e.g., a pharmaceutically acceptable salt) thereof can be substantially free of (e.g., contains less than about 5% of, less than about 2% of, less than about 1%, less than about 0.5% of) S-1-(3,6-Dibromo-9H-carbazol-9-yl)-3-(3-methoxyphenylamino)-propan-2-ol or a salt (e.g., a pharmaceutically acceptable salt) thereof.

In certain embodiments, the compound having formula (I) can be S-1-(3,6-Dibromo-9H-carbazol-9-yl)-3-(3-methoxyphenylamino)-propan-2-ol; or a salt (e.g., a pharmaceutically acceptable salt) thereof. In embodiments, S-1-(3,6-Dibromo-9H-carbazol-9-yl)-3-(3-methoxyphenylamino)-propan-2-ol or a salt (e.g., a pharmaceutically acceptable salt) thereof can be substantially free of (e.g., contains less than about 5% of, less than about 2% of, less than about 1%, less than about 0.5% of) R-1-(3,6-Dibromo-9H-carbazol-9-yl)-3-(3-methoxyphenylamino)-propan-2-ol or a salt (e.g., a pharmaceutically acceptable salt) thereof.

In certain embodiments, the compound having formula (I) can be the (+) (dextrorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof. See, e.g., Example 1a and 1b. In embodiments, the (+) (dextrorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof can be substantially free of (e.g., contains less than about 5% of, less than about 2% of, less than about 1%, less than about 0.5% of) the (−) (levorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof.

In certain embodiments, the compound having formula (I) can be the (−) (levorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof. See, e.g., Example 1a and 1b. In embodiments, the (−) (levorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof can be substantially free of (e.g., contains less than about 5% of, less than about 2% of, less than about 1%, less than about 0.5% of) the (+) (dextrorotatory) enantiomer of 1-(3,6-Dibromo-9H-carbazol-9-yl)-3-(3-methoxyphenylamino)-propan-2-ol as described herein or a salt (e.g., a pharmaceutically acceptable salt) thereof.

In certain embodiments, the compound can be (+) (dextrorotatory)-N-(3-(3,6-dibromo-9H-carbazol-9-yl)-2-fluoropropyl)-3-methoxyaniline as described herein or a salt (e.g., a pharmaceutically acceptable salt) thereof. See, e.g., Example 144a and 144b. In embodiments, the (+) (levorotatory) enantiomer of N-(3-(3,6-dibromo-9H-carbazol-9-yl)-2-fluoropropyl)-3-methoxyaniline as described herein or a salt (e.g., a pharmaceutically acceptable salt) thereof can be substantially free of (e.g., contains less than about 5% of, less than about 2% of, less than about 1%, less than about 0.5% of) the (−) (dextrorotatory) enantiomer of N-(3-(3,6-dibromo-9H-carbazol-9-yl)-2-fluoropropyl)-3-methoxyaniline as described herein or a salt (e.g., a pharmaceutically acceptable salt) thereof.

In certain embodiments, the compound can be (−) (dextrorotatory)-N-(3-(3,6-dibromo-9H-carbazol-9-yl)-2-fluoropropyl)-3-methoxyaniline as described herein or a salt (e.g., a pharmaceutically acceptable salt) thereof. See, e.g., Example 144a and 144b. In embodiments, the (−) (levorotatory) enantiomer of N-(3-(3,6-dibromo-9H-carbazol-9-yl)-2-fluoropropyl)-3-methoxyaniline as described herein or a salt (e.g., a pharmaceutically acceptable salt) thereof can be substantially free of (e.g., contains less than about 5% of, less than about 2% of, less than about 1%, less than about 0.5% of) the (+) (dextrorotatory) enantiomer of N-(3-(3,6-dibromo-9H-carbazol-9-yl)-2-fluoropropyl)-3-methoxyaniline as described herein or a salt (e.g., a pharmaceutically acceptable salt) thereof.

Compounds of formula (I), (II), (III), and (IV) are featured, including title compounds of Examples 1a, 1b, 3a, 3b, 3d, 6a, 10, 13, 21, 22, 88b, 90, 92, 96, 97a, 97b, 102, 116, 117, 118, 119, 120, 121, 122, 132, 143, and 144a; or a pharmaceutically acceptable salt thereof.

In various embodiments, compounds of formula (I), (II), (III), and (IV) can be used in a method for the treatment of a disease, disorder, or condition caused by unwanted neuronal cell death or associated with insufficient neurogenesis in a subject in need thereof. The method can include administering to the subject an effective amount of a compound having formula (I), (II), (III), or (VI), or a pharmaceutically acceptable salt thereof, as defined herein.

The methods can further include detecting a resultant neurotrophism (e.g., neurogenesis; and/or determining that the patient has aberrant neurotrophism, particularly aberrant neurogenesis, particularly aberrant hippocampal and/or hypothalamic neurogenesis, or a disease or disorder associated therewith, particularly by detecting and/or diagnosing the same.

The methods can further include detecting determining that the subject has aberrant neurogenesis or death of neurons or a disease or disorder associated therewith, by detecting the same in said subject.

The methods can further include detecting a resultant hippocampal and/or hypothalamic neurogenesis. The compounds of the present invention may be used to block neuron cell death in a manner that not only protects mature neurons, but also augments hippocampal neurogenesis by promoting survival of newborn neurons. In some embodiments, the compounds of the present invention may have a pro-neurogenic activity that is attributable to their ability to impede the death of newborn hippocampal neurons. Instead of stimulating the birth of neuronal stem cells, the compounds may favor their post-birth survival along the differentiation pathway required for them to evolve into properly wired, granular neurons. In the absence of compound administration, upwards of 80% of newborn neurons die. Administration of the compounds of the present invention can significantly enhance the survival of newborn hippocampal neurons in the adult brain.

The disease, disorder, or condition can be a neuropsychiatric and neurodegenerative disease, including (but not limited to) schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs (such as alcohol, opiates, methamphetamine, phencyclidine, and cocaine), retinal degeneration, spinal cord injury, peripheral nerve injury, physiological weight loss associated with various conditions, and cognitive decline associated with normal aging, and chemotherapy.

In certain embodiments, the compounds of the present invention can be used to treat a depressive disorder. For example, the compounds may augment ghrelin-induced hippocampal neurogenesis, thereby treating the depressice disorder. The depressive disorder can be associated with insufficient ghrelin response. In an embodiment, the insufficient ghrelin response may result in impaired or reduced hippocampal neurogenesis.

In some embodiments, the compounds having formula (I) or a salt (e.g., a pharmaceutically acceptable salt) thereof provide at least about 27 ($\times 10^{-06}$) BrdU+ cells/mm$^3$ dentate gyms when evaluated in the assay described in conjunction with Table 1 (i.e., evaluated for pro-neurogenic efficacy/neuroprotection in our standard in vivo assay at 10 μM concentration in four 12 week old adult male C57/B16 mice.

In some embodiments, the compounds having formula (I) or a salt (e.g., a pharmaceutically acceptable salt) thereof provide at least about 19 ($\times 10^{-6}$) BrdU+ cells/mm$^3$ dentate gyms when evaluated in the assay described in conjunction with Table 1.

In some embodiments, the compounds having formula (I) or a salt (e.g., a pharmaceutically acceptable salt) thereof provide from about 18 to about 30 (e.g., 18-27, 19-26, 20-25, 27-30, 27-29) ($\times 10^{-6}$) BrdU+ cells/mm$^3$ dentate gyms when evaluated in the assay described in conjunction with Table 1.

In some embodiments, the compounds having formula (I) or a salt (e.g., a pharmaceutically acceptable salt) thereof provide from about 18 to about 26 (e.g., 19-26, 20-25) ($\times 10^{-6}$) BrdU+ cells/mm$^3$ dentate gyms when evaluated in the assay described in conjunction with Table 1.

In some embodiments, the compounds having formula (I) or a salt (e.g., a pharmaceutically acceptable salt) thereof provide from about 27 to about 30 (e.g., 27-29) ($\times 10^{-6}$) BrdU+ cells/mm$^3$ dentate gyms when evaluated in the assay described in conjunction with Table 1.

In embodiments, a composition (e.g., a pharmaceutical composition) can include an amount effective to achieve the levels described above.

In embodiments, any compound, composition, or method described herein can also include any one or more of the other features delineated in the detailed description and/or in the claims.

DEFINITIONS

The term "mammal" includes organisms, which include mice, rats, cows, sheep, pigs, rabbits, goats, horses, monkeys, dogs, cats, and humans.

"An effective amount" refers to an amount of a compound that confers a therapeutic effect (e.g., treats, e.g., controls, relieves, ameliorates, alleviates, or slows the progression of; or prevents, e.g., delays the onset of or reduces the risk of developing, a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

As used herein, "depressive disorder" means one or more of major depression, dysthymia, atypical depression, melancholic depression, postpartum depression, seasonal affective disorder, recurrent brief depression, minor depressive disorder, bipolar disorder, substance-induced (e.g., alcohol, benzodiazepine) mood disorder, mood disorder due to a general medical condition, anxiety, or depression not otherwise specified.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

The following definitions are used, unless otherwise described. Specific and general values listed below for radicals, substituents, and ranges, are for illustration only; they do not exclude other defined values or other values within defined ranges for the radicals and substituents. Unless otherwise indicated, alkyl, alkoxy, alkenyl, and the like denote both straight and branched groups.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more substituents. Examples of alkyl groups include without limitation methyl, ethyl, n-propyl, isopropyl, and tert-butyl.

As used herein, the term "straight chain $C_{n-m}$ alkylene," employed alone or in combination with other terms, refers to a non-branched divalent alkyl linking group having n to m carbon atoms. Any atom can be optionally substituted, e.g., by one or more substituents. Examples include methylene (i.e., —$CH_2$—).

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—$OCH_3$), ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). Finally, the terms "haloalkoxy" and "thioalkoxy" refer to —O(haloalkyl) and —S(haloalkyl), respectively. The term "sulfhydryl" refers to —SH. As used herein, the term "hydroxyl," employed alone or in combination with other terms, refers to a group of formula —OH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein from 1-2 of the ring atoms is independently selected from N, NH, N($C_1$-$C_6$ alkyl), NC(O) ($C_1$-$C_6$ alkyl), O, and S; and wherein said heterocyclic ring is optionally substituted with from 1-3 independently selected R$^a$" would include (but not be limited to) tetrahydrofuryl, tetrahydropyranyl, piperidyl (piperidino), piperazinyl, morpholinyl (morpholino), pyrrolinyl, and pyrrolidinyl.

The term "heterocycloalkenyl" refers to partially unsaturated monocyclic, bicyclic, tricyclic, or other polycyclic hydrocarbon groups having one or more (e.g., 1-4) heteroatom ring atoms independently selected from O, N (it is understood that one or two additional groups may be present to complete the nitrogen valence and/or form a salt), or S. A ring carbon (e.g., saturated or unsaturated) or heteroatom can be the point of attachment of the heterocycloalkenyl substituent. Any atom can be optionally substituted, e.g., by one or more substituents. Heterocycloalkenyl groups can include, e.g., dihydropyridyl, tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclohexenyl, cyclohexadienyl, or norbornenyl.

As used herein, the term "cycloalkylene" refers to a divalent monocyclic cycloalkyl group having the indicated number of ring atoms.

As used herein, the term "heterocycloalkylene" refers to a divalent monocyclic heterocyclyl group having the indicated number of ring atoms.

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The terms "arylcycloalkyl" and "arylheterocyclyl" refer to bicyclic, tricyclic, or other polycyclic ring systems that include an aryl ring fused to a cycloalkyl and heterocyclyl, respectively. Similarly, the terms "heteroarylheterocyclyl," and "heteroarylcycloalkyl" refer to bicyclic, tricyclic, or other polycyclic ring systems that include a heteroaryl ring fused to a heterocyclyl and cycloalkyl, respectively. Any atom can be substituted, e.g., by one or more substituents. For example, arylcycloalkyl can include indanyl; arylheterocyclyl can include 2,3-dihydrobenzofuryl, 1,2,3,4-tetrahydroisoquinolyl, and 2,2-dimethylchromanyl.

The descriptors "C=O" or "C(O)" refers to a carbon atom that is doubly bonded to an oxygen atom.

The term "oxo" refers to double bonded oxygen when a substituent on carbon. When oxo is a substituent on nitrogen or sulfur, it is understood that the resultant groups has the structures N→O— and S(O) and SO$_2$, respectively.

As used herein, the term "cyano," employed alone or in combination with other terms, refers to a group of formula —CN, wherein the carbon and nitrogen atoms are bound together by a triple bond.

In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents.

Further, as used herein, the phrase "optionally substituted" means unsubstituted (e.g., substituted with a H) or substituted. As used herein, the term "substituted" means that a hydrogen atom is removed and replaced by a substituent. It is understood that substitution at a given atom is limited by valency.

Descriptors such as "$C_6$-$C_{10}$ aryl that is optionally substituted with from 1-4 independently selected R$^b$" (and the like) is intended to include both an unsubstituted $C_6$-$C_{10}$ aryl group and a $C_6$-$C_{10}$ aryl group that is substituted with from 1-4 independently selected R$^b$. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

In some embodiments, R$^b$ can be as defined in any one, two, three, or all of (aa) through (dd). For example, R$^b$ can be as defined in (aa) and (bb) or combinations thereof.

The phrase "Cy is a saturated, partially unsaturated or aromatic carbocyclic or heterocyclic ring system" in the definition of R$^e$ is understood to include each of the rings systems defined above (e.g., Cy can be coumarinyl or the ring component of biotin optionally substituted as defined anywhere herein).

The details of one or more embodiments are set forth in the description below. Other features and advantages of the presently disclosed embodiments will be apparent from the description and from the claims.

BRIEF DESCRIPTION OF THE DRAWINGS

FIG. 6A, FIG. 6B and FIG. 6C: Pro-neurogenic pools were broken down to identify individual pro-neurogenic compounds. FIG. 6A—In vivo evaluation of the ten individual compounds that composed pool #7 revealed that compound #3 stimulated either the proliferation or survival of neural precursor cells in the SGZ, whereas the remaining individual components of pool #7 did not. In this document this molecule is interchangeably referred to as "P7C3" or "Example 45 Compound." Each compound was infused at two different concentrations (100 µM (A and B) and 10 µM (C and D)) in two mice each. Example 45 Compound showed either pro-neurogenic or neuroprotective activity at both concentrations. Below the graphs are typical results of BrdU incorporation in the SGZ, which is notably greater in animals infused with either Pool #7 or Example 45 Compound. FIG. 6B—Molecular formulas and weights of individual pro-neurogenic compounds identified through the in vivo screen. FIG. 6C—Re-supplied compounds were evaluated in three mice per compound at 10 µM concentration to verify that the pro-neurogenic or neuroprotective effect on neural stem cells was not an artifact of storage conditions in the UTSWMC chemical compound library. Re-supplied compounds were verified to be 99% pure by mass spectrometry and shown to retain either pro-proliferative or neuroprotective properties in vivo in neural stem cells. All compounds significantly (*, P<0.001, Student's t test) stimulated neural precursor cell proliferation in the hippocampal dentate gyms SGZ relative to vehicle control.

FIG. 7: Neurogenic efficacy of orally administered Example 45 Compound was dose-related. The graph on the top shows that the concentration of Example 45 Compound in brain tissue of mice that were administered compound by daily oral gavage for 7 consecutive days correlated with the dose of Example 45 Compound administered. The graph on the bottom shows that pro-neurogenic or neuroprotective efficacy of Example 45 Compound was roughly double that of vehicle control at doses ranging from 5 to 40 mg/kg. At decreasing dosage of Example 45 Compound the amount of neurogenesis decreased accordingly, until it reached levels no greater than vehicle control at compound doses below 1.0 mg/kg. Results shown are the average obtained from analysis of 5 adult wild type male mice at each dose.

FIG. 9A and FIG. 9B: Activity of Example 62 Compound is enantiomer-specific. FIG. 9A—(+) and (−) enantiomers of Example 62 Compound were prepared. FIG. 9B—Evaluation of Example 62 Compound enantiomers showed that in vivo pro-neurogenic or neuroprotective efficacy was fully retained by the (+) enantiomer in a dose-dependent manner, while the (−) enantiomer showed diminished activity. Each enantiomer was evaluated at each dose in between 3 and 5 three month old adult wild type male C57/B6 mice.

FIG. 10A and FIG. 10B: Example 45 Compound enhances the survival of newborn neurons in the dentate gyrus. FIG. 10A—Immunohistochemical staining for doublecortin (DCX), an antigen specifically and transiently expressed in proliferating hippocampal neural precursor cells when they become irreversibly committed to neuronal differentiation, was substantially increased in newborn neurons in mice that were administered Example 45 Compound (20 mg/kg) daily for 30 days by oral gavage, relative to that seen in mice that received vehicle only. These results are representative of 10 sections each from 5 mice in each group, and demonstrate that Example 45 Compound specifically promoted hippocampal neurogenesis. (FIG. 10B) Example 45 Compound enhances hippocampal neurogenesis by promoting survival of newborn neurons. Three month old wild type C57/B6 male mice were exposed to orally-delivered Example 45 Compound or vehicle for 30 days (n=5 animals/group), administered a single pulse of BrdU via IP injection (150 mg/kg), and then sacrificed 1 hour, 1 day, 5 days or 30 days later for immunohistochemical detection of BrdU incorporation into cells localized in the subgranular layer of the dentate gyrus. No significant differences were observed between groups at the 1 hour or 1 day time points, though at one day there was a trend towards increased BrdU+ cells in the Example 45 Compound-treated group. At the 5 day time point, by which time 40% of newborn neurons normally die, animals that received Example 45 Compound showed a statistically significant (*, P<0.001, Student's t test) 25% increase in BrdU+ cells compared to the vehicle-only control group. This difference between groups progressed with time such that mice that received a daily oral dose of Example 45 Compound for 30 days, starting 24 hours after the pulse administration of BrdU, exhibited a 5-fold increase in the abundance of BrdU+ cells in the dentate gyrus relative to vehicle-only controls. In this longer-term trial, BrdU+ cells were observed both in the SGZ and the granular layer of the dentate gyrus.

(FIG. 12A) Golgi-Cox staining of the dentate gyrus illustrates that dendritic arborization of dentate gyrus granule cell neurons in npas3$^{-/-}$ mice is substantially less developed than in wild type littermates. Results shown are representative of 15 sections from five 12-14 week old adult male mice of each genotype. (FIG. 12B) In addition to obviously reduced dendritic length and branching, granular neurons in the dentate gyrus of npas3$^{-/-}$ mice also exhibited significantly reduced spine density relative to wild type littermates (*, P<0.00001, Student's t test). These genotype-specific differences were not exhibited by neurons in the CA1 region of the hippocampus.

(FIG. 18A) Example 45 Compound preserved mitochondrial membrane potential following exposure to the calcium ionophore A23187 in a dose dependent manner as judged by fluorescent imaging of TMRM dye, a cell-permeant, cationic red-orange fluorescent dye that is readily sequestered by intact mitochondria. (FIG. 18B) The protective effect of Example 62 Compound was enantiomeric specific, with the (+) enantiomer retaining activity more so than the (−) enantiomer.

(FIG. 19A) Both Example 45 Compound and the Dimebon anti-histamine enhanced hippocampal neurogenesis (FIG. 19B), and protected mitochondria from dissolution following toxic exposure to the calcium ionophore A23187 (FIG. 19C). In the in vivo assay of neurogenesis the Example 45 Compound exhibited a higher ceiling of efficacy than the Dimebon anti-histamine. In all three assays, the Example 45 Compound performed with greater relative potency than the Dimebon anti-histamine.

FIG. 20A, FIG. 20B, FIG. 20C, FIG. 20D and FIG. 20E: Effect of Example 45 Compound in aged rats. (FIG. 20A) Example 45 Compound (20 mg/kg/d, i.p.) and BrdU (50 mg/kg, i.p.) were administered daily for 7 days to 12-18 month old Fisher 344 rats (n=4 in each group). P7C3 promoted neural precursor cell proliferation by roughly 5 fold compared to vehicle. (*p<0.001, Students t test). DCX staining demonstrates that P7C3 specifically promoted neuronal differentiation and dendritic branching. These micrographs were taken at the same magnification. Scale bar=50 mm. Data are expressed as mean+/−SEM. (FIG. 20B) Latency to find the hidden platform in the Morris water maze task, as well as (FIG. 20C) swim speed and locomotor activity (FIG. 20D) in aged rats treated with P7C3 or vehicle both before and after 2 months of treatment did not differ between groups. Data are expressed as mean+/−SEM. (FIG. 20E) Quantification of food intake (upper panel) and fasting blood glucose levels in aged rats did not differ with respect to whether rats received P7C3 or vehicle. Data are expressed as mean+/−SEM.

(FIG. 21B) Example 45 Compound-treated rats displayed significantly enhanced hippocampal neurogenesis, as assessed by BrdU incorporation, relative to vehicle treated rats. Many more of the BrdU-labeled cells were noted to have migrated into the granular layer in Example 45 Compound-treated rats in comparison to vehicle treated animals, consistent with their functional incorporation into the dentate gyms as properly wired neurons. The scale bar represents 50 mM. (FIG. 21C) Relative to vehicle-treated animals, Example 45 Compound-treated rats displayed significantly lower number of cleaved caspase 3-positive cells in the dentate gyrus, indicating that P7C3 was capable of inhibiting apoptosis in the aged rat brain. The scale bar represents 50 mM. (FIG. 21D) Relative to vehicle-treated animals, Example 45 Compound-treated rats were observed to maintain stable body weight as a function of terminal aging. In all graphs data are expressed as mean+SEM.

FIG. 22A, FIG. 22B, FIG. 22C, FIG. 22D, FIG. 22E and FIG. 22F: Example 45 Compound Preserves Mitochondrial Membrane Potential in Parallel to Proneurogenic Activity U2OS cells were loaded with tetramethylrhodamine methyl ester (TMRM) dye and then exposed to the calcium ionophore A23187 either in the presence or absence of test compounds. Example 45 Compound (FIG. 22A) preserved mitochondrial membrane potential following exposure to the calcium ionophore A23187 in a dose-dependent manner. The protective effect of P7C3 was enantiomeric specific. The (R)-enantiomer of another compound (FIG. 22B) blocked dye release at levels as low as 1 nM, whereas the (S)-enantiomer (FIG. 22C) failed to block dye release even at the highest drug dose tested (100 nM). A proneurogenic compound, P7C3A20 (FIG. 22D) exhibited dye release protection at all doses tested, yet compounds having less proneurogenic activity (FIG. 22E and FIG. 22F) were less effective in preserving mitochondrial membrane potential at any test dose. Each compound was evaluated in triplicate with similar results.

FIG. 24D shows footprint data from two sisters (VEH and P7C3) on day 92 (before disease onset) and day 118 (after disease onset). Front paws are dipped in red ink, and back paws are dipped in black ink. The VEH-treated mouse shows the expected decline in gait after disease onset on day 188, while her P7C3-treated sister showed preservation of normal gait on day 118. All analysis was conducted blind to treatment group.

FIG. 25A and FIG. 25B. Example 6a Compound (P7C3A20) Provides Therapeutic Benefit in Animal Model of Parkinson's Disease. Mice were treated with MPTP (30 mg/kg i.p.) or Vehicle only for 5 days and then immunohistochemically analyzed for tyrosine hydroxylase staining (TH) 21 days later (FIG. 25A). Treatment with MPTP and Vehicle (n=6) reduced the number of TH+ neurons in the substantia nigra (FIG. 25B) by approximately 50% (*, p=0.0002, Student's t test) relative to mice that received Vehicle only (n=8). MPTP-mediated cell death in the substantia nigra was significantly attenuated (**, p=0.005) in mice that additionally received P7C3A20 (10 mg/kg i.p. twice daily) (n=5). TH+ neurons in the substantia nigra of every mouse were counted blind to treatment group by two investigators using Image J software, and results were averaged.

(FIG. 26A) Treatment with P7C3 statistically significantly extends survival of R6/2 mice (p<0.001, Gehan-Breslow-Wilcoxon test). (FIG. 26B) At 14 weeks of age, P7C3-treated R6/2 mice also show statistically improved objective measures of general condition (lower score corresponds to better general better condition, * p<0.0001, Student's t Test). All measurements were conducted blind to genotype and treatment group.

FIG. 29A—Test compounds were evaluated by dose response assay for their ability to block MPTP-neurotoxicity in the SNc. P7C3A20 showed greater potency and CoE than P7C3, and Dimebon showed no protective efficacy. 15 animals were tested per group. VEH group contained 30 animals: animals that received the P7C3A20/P7C3 vehicle, and 15 animals that received Dimebon vehicle (saline). These 2 control groups did not differ in number of surviving TH+ neurons, and were thus combined. Representative immunohistochemical pictures of TH-staining in the SNc are shown below the graph. Dosing is expressed as total mg/day, and was administered intraperitoneally in divided doses twice daily. Data are expressed as mean+ SEM. FIG. 29B—Representative images of TH-staining from the striata of individual animals demonstrate that three weeks after a five day course of daily MPTP administration both P7C3 and P7C3A20 block the loss of dopaminergic axon terminals. P7C3A20 does so with greater effect, and Dimebon offers no protection. Striatal sections were obtained from the same mice used in FIG. 2, and compound treatment groups are from mice that received a dose of 20 mg/kg/d.

FIG. 30. Brain and blood levels of P7C3, P7C3A20 and Dimebon three weeks after MPTP administration. Relative neuroprotective activity within a test compound correlated with brain levels of that compound, and brain levels correlated with blood levels of the test compounds. Only about one-tenth the amount of P7C3A20 accumulated in the brain compared to P7C3. Brain accumulation of Dimebon was equivalent to P7C3. Data are expressed as mean+SEM. Three animals were tested per group.

FIG. 33A—P7C3-S7 differs from P7C3 by replacing the aniline NH with sulfide linker. P7C3-S8 differs from P7C3 by replacing the aniline phenyl ring with a pyrimidine. P7C3-S25 differs from P7C3 by replacing the aniline moiety with a dimethyl pyrazole. P7C3-S40 and S41 differ from P7C3 by replacing the aniline NH with and oxygen linker, and they are R and S single enantiomers, respectively. P7C3-S54 differs from P7C3 mainly by the addition of a methyl group to the central carbon of the propyl linker and an OMe group on the aniline. P7C3-S165 differs from P7C3 by replacing the aniline and carbinol fragments with a carboxylic acid. P7C3-S184 differs from P7C3 by replacing the bromines on the carbazole with chlorines and replacing the aniline with a naphthyl amine.

FIG. 33B—New analogs of P7C3 were subjected to in vivo testing in the hippocampal neurogenesis (4 mice each) and MPTP-protection (10 mice each) assays. Results show that activity in these two assays correlates, such that the in vivo neurogenesis screen is useful for predicting neuroprotective efficacy of P7C3 analogs for dopaminergic neurons in the substantia nigra. LC/MS/MS assay of blood and brain levels of all compounds administered a single time to C57BL/6 mice at 10 mg/kg (i.p.) indicates that they cross the blood brain barrier following intraperitoneal administration.

FIG. 34A and FIG. 34B. P7C3A20 and P7C3 block motor neuron cell death in the spinal cord when administered at the time of disease onset to G93A-SOD1 mutant mice. Treatment of G93A-SOD1 mutant mice with 20 mg/kg/d of P7C3A20, P7C3 or Dimebon, or the appropriate vehicle, was initiated on day 80. Five mice from each group were sacrificed on days 90, 100, 110 and 120. The number of spinal cord motor neurons per cubic millimeter of lumbar spinal cord was determined through immunohistochemical staining for ChAT and quantification with NIH Image J software. All images were analyzed blind to treatment group. Spinal cord motor neurons in G93A-SOD1 mutant mice died over time as expected. Spinal cord motor neuron cell death was blocked by administration of P7C3A20. P7C3 was intermediately protective, while Dimebon had no neuroprotective efficacy. (FIG. 34A) Representative staining of ChAT of one ventral horn from each of the 5 mice in each treatment group at 110 days. (FIG. 34B) Graph representation.

FIG. 36A—The schematic diagram shows parameters used to measure gait. Front and back stride were collected as a straight line from back paw print to the following paw print. Back-front distance was collected as a straight line from back paw print to the corresponding front paw print. 20 measurements (10 on each side) for each parameter were measured per mouse, and 20 mice per group were evaluated at 90 and 118 day time points. All measurements were conducted blind to treatment group, and the student's t test was used for statistical comparison of a treatment group to its matched vehicle group. FIG. 36B—At 90 days, there were no differences between any groups in back stride, front stride and back-front distance. By day 118, all vehicle groups, and P7C3- and Dimebon-treated mice, showed a significant difference in these measures, reflecting disease progression. Back stride and front stride were preserved to near-normal levels in P7C3A20 treated mice on day 118. By day 132, P7C3 and Dimebon treated mice were too sick to participate in the task. At this time point, P7C3A20 treated mice continued to show normalized back stride and front stride levels.

DETAILED DESCRIPTION

Figure 1:
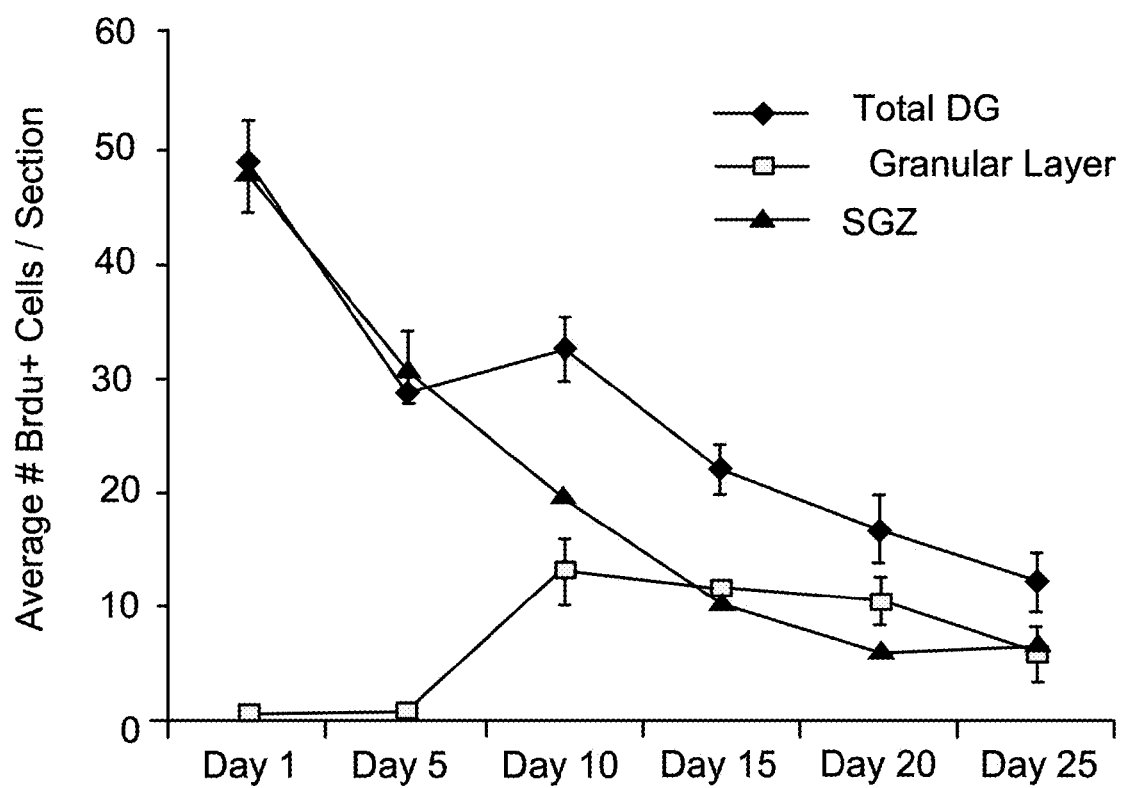
FIG. 1: Pulse-chase analysis of BrdU-labeling identified magnitude and timing of cell death following birth of new neurons in the dentate gyrus. 12 week old wild type male C57/B6 mice were individually housed without access to running wheels and injected on day 0 with BrdU (50 mg/kg, i.p.). Neural precursor cell proliferation in the dentate gyms (DG) subgranular zone (SGZ) and granular layer (GL) was subsequently monitored through immunohistochemistry for BrdU on days 1, 5, 10, 15, 20, and 25 days post-injection. Four mice were evaluated at each time point, and 25-30 adjacent coronal sections through the hippocampus (progressing posteriorly from the point where the suprapyramidal and infrapyramidal blades are joined at the crest region and the dentate gyrus is oriented horizontally beneath the corpus callosum) from each mouse were examined. On days 1 and 5, almost 100% of BrdU-positive cells within the DG were localized in the SGZ. The total number of cells decreased approximately 40% between days 1 and 5, in accordance with the appearance of apoptotic cell bodies in the SGZ. By day 10, some BrdU positive cells had migrated into the GL, with no significant change in total number of BrdU-positive cells in the DG. By day 15, BrdU-positive cells in the SGZ declined as the number of BrdU-positive cells in the GL stayed constant, suggesting that some of the cells migrating out of the SGZ and into the GL between days 10 and 15 underwent apoptosis. This trend continued through days 20-25. These results indicated that daily injection of BrdU over a one week period of continuous molecule infusion, a time period during which 40% of newborn cells in the SGZ normally die, would allow detection of compounds that enhance either proliferation or survival of newborn cells in the dentate gyms.

The presently disclosed embodiments relate generally to stimulating neurogenesis (e.g., post-natal neurogenesis, e.g., post-natal hippocampal and/or hypothalamic neurogenesis) and/or promoting the survival of existing neurons by reducing neuronal cell death.

Compounds

In one aspect, the presently disclosed embodiments feature compounds having general formula (I):

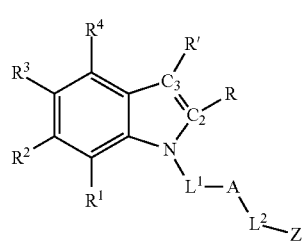

(I)

Here and throughout this specification, $R^1$, $R^2$, $R^3$, $R^4$, R, R', $L^1$, $L^2$, A, and Z can be as defined anywhere herein.

It is appreciated that certain features of the presently disclosed embodiments, which are, for clarity, described in the context of separate embodiments, can also be provided in combination in a single embodiment. Conversely, various features of the presently disclosed embodiments which are, for brevity, described in the context of a single embodiment, can also be provided separately or in any suitable sub-combination.

Thus, for ease of exposition, it is also understood that where in this specification, a variable (e.g., $R^1$) is defined by "as defined anywhere herein" (or the like), the definitions for that particular variable include the first occurring and broadest generic definition as well as any sub-generic and specific definitions delineated anywhere in this specification.

Variables $R^1$, $R^2$, $R^3$, $R^4$

In some embodiments, one or two of $R^1$, $R^2$, $R^3$, and $R^4$ (e.g., one of, e.g., $R^3$) is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —$NH(C_1$-$C_6$ alkyl), $N(C_1$-$C_6$ alkyl)$_2$, —$NHC(O)(C_1$-$C_6$ alkyl), and nitro; and the others are hydrogen.

In certain embodiments, one or two of $R^1$, $R^2$, $R^3$, and $R^4$ (e.g., one of, e.g., $R^3$) is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and the others are hydrogen.

In certain embodiments, one or two of $R^1$, $R^2$, $R^3$, and $R^4$ (e.g., one of, e.g., $R^3$) is selected from halo, $C_1$-$C_6$ alkyl, and $C_1$-$C_6$ haloalkyl; and the others are hydrogen.

In certain embodiments, one or two of $R^1$, $R^2$, $R^3$, and $R^4$ (e.g., one of, e.g., $R^3$) is selected from halo and $C_1$-$C_6$ alkyl; and the others are hydrogen.

In certain embodiments, one or two of $R^1$, $R^2$, $R^3$, and $R^4$ (e.g., one of, e.g., $R^3$) is halo (e.g., bromo or chloro) and $C_1$-$C_6$ alkyl; and the others are hydrogen.

In certain embodiments, one or two of $R^1$, $R^2$, $R^3$, and $R^4$ (e.g., one of, e.g., $R^3$) is bromo; and the others are hydrogen.

In some embodiments, $R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —$NH(C_1$-$C_6$ alkyl), $N(C_1$-$C_6$ alkyl)$_2$, —$NHC(O)(C_1$-$C_6$ alkyl), and nitro; and each of $R^1$, $R^2$, and $R^4$ can be as defined anywhere herein.

In certain embodiments, $R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —$NH(C_1$-$C_6$ alkyl), $N(C_1$-$C_6$ alkyl)$_2$, —$NHC(O)(C_1$-$C_6$ alkyl), and nitro; and each of $R^1$, $R^2$, and $R^4$ is hydrogen.

In some embodiments, $R^3$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^1$, $R^2$, and $R^4$ can be as defined anywhere herein.

In certain embodiments, $R^3$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^1$, $R^2$, and $R^4$ is hydrogen.

In some embodiments, $R^3$ is selected from halo, $C_1$-$C_6$ alkyl, and $C_1$-$C_6$ haloalkyl; and each of $R^1$, $R^2$, and $R^4$ can be as defined anywhere herein.

In certain embodiments, $R^3$ is selected from halo, $C_1$-$C_6$ alkyl, and $C_1$-$C_6$ haloalkyl; and each of $R^1$, $R^2$, and $R^4$ is hydrogen.

In some embodiments, $R^3$ is selected from halo and $C_1$-$C_6$ alkyl; and each of $R^1$, $R^2$, and $R^4$ can be as defined anywhere herein.

In certain embodiments, $R^3$ is selected from halo and $C_1$-$C_6$ alkyl; and each of $R^1$, $R^2$, and $R^4$ is hydrogen.

In some embodiments, $R^3$ is halo (e.g., bromo or chloro); and each of $R^1$, $R^2$, and $R^4$ can be as defined anywhere herein.

In certain embodiments, $R^3$ is halo (e.g., bromo or chloro); and each of $R^1$, $R^2$, and $R^4$ is hydrogen.

In some embodiments, $R^3$ is bromo; and each of $R^1$, $R^2$, and $R^4$ can be as defined anywhere herein.

In certain embodiments, $R^3$ is bromo; and each of $R^1$, $R^2$, and $R^4$ is hydrogen.

In some embodiments, each of $R^1$, $R^2$, $R^3$, and $R^4$ is independently selected from hydrogen, halo, and $C_1$-$C_6$ alkyl.

In certain embodiments, each of $R^1$, $R^2$, $R^3$, and $R^4$ is independently selected from hydrogen and halo (e.g., bromo or chloro).

In some embodiments, each of $R^1$, $R^2$, $R^3$, and $R^4$ is hydrogen.

In some embodiments, when any one or more of $R^1$, $R^2$, $R^3$, and $R^4$ can be a substituent other than hydrogen, said substituent, or each of said substituents, is other than $C_1$-$C_6$ alkyl (e.g., other than $C_1$-$C_3$ alkyl, e.g., other than $CH_3$).

Variable $L^1$

In some embodiments, $L^1$ is $C_1$-$C_3$ (e.g., $C_1$-$C_2$) straight chain alkylene, which is optionally substituted with from 1-2 independently selected $R^c$.

In certain embodiments, $L^1$ is methylene (i.e., —$CH_2$—). In other embodiments, $L^1$ is methylene that is substituted with 1 or 2 (e.g., 1) independently selected $R^c$. In embodiments, $R^c$ is $C_1$-$C_6$ alkyl (e.g., $C_1$-$C_3$ alkyl, e.g., $CH_3$).

In certain embodiments, $L^1$ is ethylene (i.e., —$CH_2CH_2$—). In other embodiments, $L^1$ is ethylene that is substituted with 1 or 2 (e.g., 1) independently selected $R^c$. In embodiments, $R^c$ is $C_1$-$C_6$ alkyl (e.g., $C_1$-$C_3$ alkyl, e.g., $CH_3$).

Variable $L^2$

In some embodiments, $L^2$ is $C_1$-$C_3$ (e.g., $C_1$-$C_2$) straight chain alkylene, which is optionally substituted with from 1-2 independently selected $R^c$.

In certain embodiments, $L^2$ is methylene (i.e., —$CH_2$—). In other embodiments, $L^1$ is methylene that is substituted with 1 or 2 (e.g., 1) independently selected $R^c$. In embodiments, $R^c$ is $C_1$-$C_6$ alkyl (e.g., $C_1$-$C_3$ alkyl, e.g., $CH_3$). In embodiments, $R^c$ is $C_1$-$C_6$ alkoxy, $C_1$-$C_6$ thioalkoxy, $C_1$-$C_6$ haloalkoxy, or $C_1$-$C_6$ thiohaloalkoxy. For example, $R^c$ can be $C_1$-$C_6$ (e.g., $C_1$-$C_3$) thioalkoxy, such as —$SCH_3$.

In certain embodiments, $L^2$ is ethylene (i.e., —$CH_2CH_2$—). In other embodiments, $L^2$ is ethylene that is substituted with 1 or 2 (e.g., 1) independently selected $R^c$. For example, the ethylene carbon more proximal to Z in formula (I) can be substituted as described in the preceding paragraph.

In certain embodiments, $L^2$ is a bond that directly connects A in formula (I) to Z in formula (I).

Non-Limiting Combinations of Variables $L^1$ and $L^2$

In some embodiments, each of $L^1$ and $L^2$ is, independently, $C_1$-$C_3$ alkylene, which is optionally substituted with from 1-2 independently selected $R^c$.

In certain embodiments, each of $L^1$ and $L^2$ is $CH_2$.

In certain embodiments, one of $L^1$ and $L^2$ is $CH_2$ (e.g., $L^1$), and the other (e.g., $L^2$) is methylene that is substituted with 1 or 2 (e.g., 1) independently selected $R^c$, in which $R^c$ can be as defined anywhere herein.

In certain embodiments, each of $L^1$ and $L^2$ is methylene that is substituted with 1 or 2 (e.g., 1) independently selected $R^c$, in which $R^c$ can be as defined anywhere herein.

In some embodiments, $L^1$ is $C_1$-$C_3$ (e.g., $C_1$-$C_2$) straight chain alkylene, which is optionally substituted with from 1-2 independently selected $R^c$, and $L^2$ is a bond that directly connects A in formula (I) to Z in formula (I). In embodiments, $L^1$ can be, for example, methylene (i.e., —$CH_2$—) or methylene that is substituted with 1 or 2 (e.g., 1) independently selected $R^c$ (e.g., $C_1$-$C_6$ alkyl, e.g., $C_1$-$C_3$ alkyl, e.g., $CH_3$).

Variable A

[I] In some embodiments, A is:
(i) $CR^{41}R^{42}$, wherein each of $R^{41}$ and $R^{42}$ is independently selected from hydrogen, halo, $C_1$-$C_3$ alkyl, or $OR^9$; or
(ii) C=O; or
(iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$.

In some embodiments, A is $CR^{41}R^{42}$, in which each of $R^{41}$ and $R^{42}$ is, independently, hydrogen, halo, $C_1$-$C_3$ alkyl, or $OR^9$ (e.g., hydrogen, halo, or $OR^9$).

In certain embodiments, A can be $CR^{41}R^{42}$, in which each of $R^{41}$ and $R^{42}$ is, independently, hydrogen, halo, or $C_1$-$C_3$ alkyl.

In certain embodiments, A can be $CR^{41}R^{42}$, in which one of $R^{41}$ and $R^{42}$ is halo (e.g., fluoro), and the other of $R^{41}$ and $R^{42}$ is, independently, hydrogen, halo, or $C_1$-$C_3$ alkyl (e.g., hydrogen).

In certain embodiments, one of $R^{41}$ and $R^{42}$ is hydrogen. In embodiments, one of $R^{41}$ and $R^{42}$ is halo or $OR^9$, and the other is hydrogen.

In certain embodiments, one of $R^{41}$ and $R^{42}$ can be $OR^9$. In embodiments, the other of $R^{41}$ and $R^{42}$ can be as defined anywhere herein; e.g., the other of $R^{41}$ and $R^{42}$ can be hydrogen or $C_1$-$C_3$ alkyl. For example, one of $R^{41}$ and $R^{42}$ can be $OR^9$, and the other of $R^{41}$ and $R^{42}$ is hydrogen. In embodiments, $R^9$ can be hydrogen or $R^9$ can be $C_1$-$C_3$ alkyl (e.g., $CH_3$).

In certain embodiments, one of $R^{41}$ and $R^{42}$ can be halo. In embodiments, the other of $R^{41}$ and $R^{42}$ can be as defined anywhere herein; e.g., the other of $R^{41}$ and $R^{42}$ can be hydrogen, $C_1$-$C_3$ alkyl, or halo. For example, one of $R^{41}$ and $R^{42}$ can be halo (e.g., fluoro), and the other of $R^{41}$ and $R^{42}$ is hydrogen.

In embodiments, one of $R^{41}$ and $R^{42}$ is halo or $OR^9$, and the other is hydrogen.

For example, one of $R^{41}$ and $R^{42}$ can be $OR^9$, and the other is hydrogen. In embodiments, $R^9$ can be hydrogen. $R^9$ can be $C_1$-$C_3$ alkyl (e.g., $CH_3$).

As another example, one of $R^{41}$ and $R^{42}$ can be halo (e.g., fluoro), and the other is hydrogen.

In other embodiments, each of $R^{41}$ and $R^{42}$ is a substituent other than hydrogen.

For example, each of $R^{41}$ and $R^{42}$ can be halo (e.g., fluoro).

As another example, one of $R^{41}$ and $R^{42}$ can be $OR^9$ (e.g., in which $R^9$ is hydrogen), and the other is $C_1$-$C_3$ alkyl (e.g., $CH_3$).

As a further example, each of $R^{41}$ and $R^{42}$ can be $C_1$-$C_3$ alkyl (e.g., $CH_3$).

In still other embodiments, each of $R^{41}$ and $R^{42}$ is hydrogen.

Embodiments can further include any one or more of the following features.

When the carbon attached to $R^{41}$ and $R^{42}$ is substituted with four different substituents, the carbon attached to $R^{41}$ and $R^{42}$ can have the R configuration.

When the carbon attached to $R^{41}$ and $R^{42}$ is substituted with four different substituents, the carbon attached to $R^{41}$ and $R^{42}$ can have the S configuration.

[II] In some embodiments, A is C=O.

[III] In some embodiments, A is heterocycloalkylene containing from 3-5 ring atoms, in which from 1-2 of the ring atoms is independently selected from N, NH, N($C_1$-$C_3$ alkyl), O, and S; and wherein said heterocycloalkylene is (a) substituted with 1 oxo (e.g., 1 oxo on a ring carbon); and (b) is optionally further substituted with from 1-4 independently selected $R^a$.

In certain embodiments, A is heterocycloalkylene containing 5 ring atoms, in which from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$. For example, A can be:

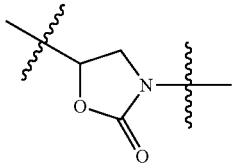 [SMILES: *C1CN(*)C(=O)O1]

Non-Limiting Combinations of Variables $L^1$, $L^2$, and A

In some embodiments:

A is (i) $CR^{41}R^{42}$, wherein each of $R^{41}$ and $R^{42}$ is independently selected from hydrogen, halo, $C_1$-$C_3$ alkyl, or $OR^9$; or (ii) C=O; and each of $L^1$ and $L^2$ is, independently, $C_1$-$C_3$ alkylene, which is optionally substituted with from 1-2 independently selected $R^c$.

In some embodiments:

A is $CR^{41}R^{42}$, wherein each of $R^{41}$ and $R^{42}$ is independently selected from hydrogen, halo, $C_1$-$C_3$ alkyl, or $OR^9$; and each of $L^1$ and $L^2$ is, independently, $C_1$-$C_3$ alkylene, which is optionally substituted with from 1-2 independently selected $R^c$.

Embodiments can include one or more of the following features

Each of $R^{41}$ and $R^{42}$ can be as defined anywhere herein.

Each of $L^1$ and $L^2$ is $CH_2$.

One of $L^1$ and $L^2$ is $CH_2$ (e.g., $L^1$), and the other (e.g., $L^2$) is methylene that is substituted with 1 or 2 (e.g., 1) independently selected $R^c$, in which $R^c$ can be as defined anywhere herein. For example:

$L^1$ can be $CH_2$; and

One of $R^{41}$ and $R^{42}$ is hydrogen; and $L^2$ can be methylene that is substituted with 1 or 2 (e.g., 1) independently selected $R^c$ (e.g., $C_1$-$C_6$ (e.g., $C_1$-$C_3$) alkyl, such as $CH_3$; or $C_1$-$C_6$ (e.g., $C_1$-$C_3$) thioalkoxy, such as —$SCH_3$);

Each of $L^1$ and $L^2$ is methylene that is substituted with 1 or 2 (e.g., 1) independently selected $R^c$, in which $R^c$ can be as defined anywhere herein. For example:

each of $R^{41}$ and $R^{42}$ can be a substituent other than hydrogen (e.g., one of which is $CH_3$), and each of $L^1$ and $L^2$ is methylene that is substituted with $C_1$-$C_3$ alkyl, such as $CH_3$).

In some embodiments:

A is heterocycloalkylene containing from 3-5 (e.g., 5) ring atoms, in which from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$; and $L^1$ is $C_1$-$C_3$ (e.g., $C_1$-$C_2$) straight chain alkylene, which is optionally substituted with from 1-2 independently selected $R^c$, and $L^2$ is a bond that directly connects A in formula (I) to Z in formula (I).

Variable Z

[I] In some embodiments, Z is:

(i) —$NR^{10}R^{11}$; or (ii) —C(O)$NR^{10}R^{11}$; or (iii) —$OR^{12}$; or (iv) —S(O)$_n R^{13}$, wherein n is 0, 1, or 2; or (v) heterocycloalkenyl containing from 5-6 ring atoms, wherein from 1-3 of the ring atoms is independently selected from N, NH, N($C_1$-$C_6$ alkyl), NHC(O)($C_1$-$C_6$ alkyl), O, and S; and wherein said heterocycloalkenyl is optionally substituted with from 1-4 independently selected $R^a$;

(vi) $C_6$-$C_{10}$ aryl that is optionally substituted with from 1-4 independently selected $R^b$; or (vii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$.

In certain embodiments, Z is as defined in (i), (iii), (iv), (v), (vi), or (vii) in the preceding paragraph.

In certain embodiments, Z is as defined in (i), (iii), (iv), (v), or (vii) in the preceding paragraph.

In certain embodiments, Z is as defined in (i), (iii), (v), or (vii) in the preceding paragraph.

In certain embodiments, Z is as defined in (i), (iii), or (iv) in the preceding paragraph.

In certain embodiments, Z is:

(i) —$NR^{10}R^{11}$; or (iii) —$OR^{12}$; or (v) heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$.

In certain embodiments, Z is: (i) —$NR^{10}R^{11}$; or (iii) —$OR^{12}$.

In certain embodiments, Z is: (i) —$NR^{10}R^{11}$; or (iv) —S(O)$_n R^{13}$, wherein n is 0, 1, or 2.

In certain embodiments, Z is: (iii) —$OR^{12}$; or (iv) —S(O)$_n R^{13}$, wherein n is 0, 1, or 2.

In certain embodiments, Z does not include heterocyclyl (e.g., a nitrogenous heterocyclyl, e.g., piperazinyl or piperidinyl) as part of its structure (e.g., as a fused ring or attached to another ring by a bond).

In certain embodiments, Z is other than heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$.

In certain embodiments, Z is other than heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 independently selected $R^b$ (e.g., other than pyridyl).

[II] In some embodiments, Z is $-NR^{10}R^{11}$.

[A] In some embodiments, one of $R^{10}$ and $R^{11}$ is hydrogen, and the other of $R^{10}$ and $R^{11}$ is a substituent other than hydrogen.

In some embodiments, one of $R^{10}$ and $R^{11}$ is hydrogen or a substituent other than hydrogen, and the other of $R^{10}$ and $R^{11}$ is a substituent other than hydrogen.

In some embodiments, each of $R^{10}$ and $R^{11}$ is a substituent other than hydrogen.

In some embodiments, each of $R^{10}$ and $R^{11}$ is hydrogen.

[B] In some embodiments, one of $R^{10}$ and $R^{11}$ is independently selected from the substituents delineated collectively in (b), (c), (g) through (k), and (1) below:

(b) $C_6$-$C_{10}$ aryl that is optionally substituted with from 1-4 $R^b$;

(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

(g) $C_8$-$C_{14}$ arylcycloalkyl, wherein:
 (1) the aryl portion is optionally substituted with from 1-4 independently selected $R^b$, and
 (2) the cycloalkyl portion is optionally substituted with from 1-4 independently selected $R^a$;

(h) arylheterocyclyl containing from 8-14 ring atoms, wherein:
 (1) the aryl portion from is optionally substituted with from 1-4 independently selected $R^b$, and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(i) heteroarylheterocyclyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) from 1-2 of the ring atoms of the heterocyclyl portion is independently selected from N, NH, N($C_1$-$C_6$ alkyl), NC(O)($C_1$-$C_6$ alkyl), O, and S; and wherein said heterocyclyl portion is optionally substituted with from 1-3 independently selected $R^a$;

(j) heteroarylcycloalkyl containing from 8-14 ring atoms, wherein:
 (1) from 1-2 of the ring atoms of the heteroaryl portion is independently selected from N, NH, N($C_1$-$C_3$ alkyl), O, and S; and wherein said heteroaryl portion is optionally substituted with from 1-3 independently selected $R^b$; and
 (2) the cycloalkyl portion is optionally substituted with from 1-4 independently selected $R^a$;

(k) $C_3$-$C_8$ cycloalkyl or $C_3$-$C_8$ cycloalkenyl, each of which is optionally substituted with from 1-4 independently selected $R^a$; and (l) $C_7$-$C_{12}$ aralkyl, wherein the aryl portion is optionally the aryl portion from is optionally substituted with from 1-4 independently selected $R^b$, and the other of $R^{10}$ and $R^{11}$ can be as defined anywhere herein.

In some embodiments, $R^{10}$ and $R^{11}$ cannot be $C_3$-$C_8$ cycloalkyl or $C_3$-$C_8$ cycloalkenyl, each of which is optionally substituted with from 1-4 independently selected $R^a$.

In some embodiments, one of $R^{10}$ and $R^{11}$ is independently selected from the substituents delineated collectively in (b), (c), (g) through (j), and (1) above; and the other of $R^{10}$ and $R^{11}$ can be as defined anywhere herein.

In some embodiments, one of $R^{10}$ and $R^{11}$ is independently selected from the substituents delineated collectively in (b), (c), and (g) through (j); and the other of $R^{10}$ and $R^{11}$ can be as defined anywhere herein.

In some embodiments, one of $R^{10}$ and $R^{11}$ is independently selected from:

(b) $C_6$-$C_{10}$ aryl that is optionally substituted with from 1-4 $R^b$;

(c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;

and the other of $R^{10}$ and $R^{11}$ can be as defined anywhere herein.

In some embodiments, one of $R^{10}$ and $R^{11}$ is $C_6$-$C_{10}$ aryl (e.g., $C_6$) that is optionally substituted with from 1-4 (e.g., 1-3, 1-2, or 1) $R^b$; and the other of $R^{10}$ and $R^{11}$ can be as defined anywhere herein.

In certain embodiments, $R^b$ at each occurrence is independently selected from halo; or $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, $-NH(C_1$-$C_6$ alkyl), N($C_1$-$C_6$ alkyl)$_2$, and $-NHC(O)(C_1$-$C_6$ alkyl), each of which is optionally substituted with from 1-3 independently selected $R^e$.

In certain embodiments, $R^b$ at each occurrence is independently selected from $C_1$-$C_6$ alkoxy; $C_1$-$C_6$ haloalkoxy; $C_1$-$C_6$ thioalkoxy; and $C_1$-$C_6$ thiohaloalkoxy, each of which is optionally substituted with from 1-3 independently selected $R^e$. In embodiments, $R^b$ can further include halo.

In certain embodiments, $R^b$ at each occurrence is independently selected from $C_1$-$C_6$ alkoxy and $C_1$-$C_6$ haloalkoxy, each of which is optionally substituted with from 1-3 independently selected $R^e$. In embodiments, $R^b$ can further include halo.

In certain embodiments, $R^b$ at each occurrence is independently selected from $C_1$-$C_6$ alkoxy, each of which is optionally substituted with from 1-3 independently selected Re. In embodiments, $R^b$ is $C_1$-$C_6$ alkoxy (e.g., $OCH_3$). In embodiments, $R^b$ can further include halo.

In certain embodiments, one of $R^{10}$ and $R^{11}$ is unsubstituted phenyl, and the other of $R^{10}$ and $R^{11}$ can be as defined anywhere herein.

In certain embodiments, one of $R^{10}$ and $R^{11}$ is phenyl that is substituted with 1 $R^b$, and the other of $R^{1'}$ and $R^{11}$ can be as defined anywhere herein. $R^b$ can be as defined anywhere herein (e.g., $R^b$ can be $C_1$-$C_6$ alkoxy, e.g., $OCH_3$). For example, one of $R^{10}$ and $R^{11}$ can be 3-methoxyphenyl. In embodiments, $R^b$ can further include halo.

[C] In some embodiments, when one of $R^{10}$ and $R^{11}$ is independently selected from the substituents delineated collectively in (b), (c), (g) through (k), and (1) above, the other of $R^{10}$ and $R^{11}$ can be:

(a) hydrogen; or (d) $C_1$-$C_6$ alkyl or $C_1$-$C_6$ haloalkyl (e.g., $C_1$-$C_6$ alkyl), each of which is optionally substituted with from 1-3 $R^d$; or (e) $-C(O)(C_1$-$C_6$ alkyl), $-C(O)(C_1$-$C_6$ haloalkyl), or $-C(O)O(C_1$-$C_6$ alkyl); or (f) $C_2$-$C_6$ alkenyl or $C_2$-$C_6$ alkynyl.

In certain embodiments, the other of $R^{10}$ and $R^{11}$ is:
(a) hydrogen; or
(d) $C_1$-$C_6$ alkyl or $C_1$-$C_6$ haloalkyl (e.g., $C_1$-$C_6$ alkyl), each of which is optionally substituted with from 1-3 $R^d$; or
(e) —C(O)($C_1$-$C_6$ alkyl), —C(O)($C_1$-$C_6$ haloalkyl), or —C(O)O($C_1$-$C_6$ alkyl).

In certain embodiments, the other of $R^{10}$ and $R^{11}$ is:
(a) hydrogen; or
(d) $C_1$-$C_6$ alkyl or $C_1$-$C_6$ haloalkyl (e.g., $C_1$-$C_6$ alkyl), each of which is optionally substituted with from 1-3 $R^d$; or
(e) —C(O)($C_1$-$C_6$ alkyl), or —C(O)($C_1$-$C_6$ haloalkyl).

In certain embodiments, the other of $R^{10}$ and $R^{11}$ can be:
(a) hydrogen; or
(d) $C_1$-$C_6$ alkyl (e.g., $C_1$-$C_3$ alkyl, e.g., $CH_3$), which is optionally substituted with from 1-3 $R^d$; or
(e) —C(O)($C_1$-$C_6$ alkyl), e.g., $C_1$-$C_3$ alkyl, e.g., $CH_3$.

In certain embodiments, the other of $R^{10}$ and $R^{11}$ can be:
(a) hydrogen; or
(d) $C_1$-$C_6$ alkyl (e.g., $C_1$-$C_3$ alkyl, e.g., $CH_3$), which is optionally substituted with from 1-3 $R^d$.

In certain embodiments, the other of $R^{10}$ and $R^{11}$ can be hydrogen.

In certain embodiments, the other of $R^{10}$ and $R^{11}$ can be (d) or (e) or any subset thereof.

[E] In some embodiments, one of $R^{10}$ and $R^{11}$ is $C_6$-$C_{10}$ (e.g., $C_6$) aryl that is optionally substituted with from 1-4 $R^b$, and the other is hydrogen or $C_1$-$C_6$ alkyl (e.g., $C_1$-$C_3$ alkyl, e.g., $CH_3$).

In some embodiments, one of $R^{10}$ and $R^{11}$ is $C_6$-$C_{10}$ (e.g., $C_6$) aryl that is optionally substituted with from 1-4 $R^b$, and the other is hydrogen.

In certain embodiments, one of $R^{10}$ and $R^{11}$ is unsubstituted phenyl, and the other is hydrogen.

In certain embodiments, one of $R^{10}$ and $R^{11}$ is phenyl that is substituted with 1 $R^b$, and the other is hydrogen. In embodiments, $R^b$ is $C_1$-$C_6$ alkoxy (e.g., $C_1$-$C_3$ alkoxy, e.g., $OCH_3$). For example, one of $R^{10}$ and $R^{11}$ is 3-methoxyphenyl, and the other is hydrogen.

[F] In some embodiments, each of $R^{10}$ and $R^{11}$ cannot be optionally substituted naphthyl (e.g., each of $R^{10}$ and $R^{11}$ cannot be unsubstituted naphthyl). In embodiments, each of $R^{10}$ and $R^{11}$ is other than optionally substituted naphthyl (e.g., unsubstituted naphthyl) when R and R' are defined according to definitions (1), (2), and (4); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

[G] In some embodiments, one of $R^{10}$ and $R^{11}$ is hydrogen, and the other is heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$.

In certain embodiments, one of $R^{10}$ and $R^{11}$ is hydrogen, and the other is heteroaryl containing from 5-6 ring atoms, wherein from 1-2 of the ring atoms is independently selected from N, NH, N($C_1$-$C_3$ alkyl), O, and S; and wherein said heteroaryl is optionally substituted with from 1-2 $R^b$.

[III] In some embodiments, Z is —$OR^{12}$.

In some embodiments, $R^{12}$ is $C_1$-$C_6$ alkyl or $C_1$-$C_6$ haloalkyl, each of which is optionally substituted with from 1-3 $R^c$.

In some embodiments, $R^{12}$ is $C_1$-$C_6$ alkyl, which is optionally substituted with from 1-3 $R^c$.

In certain embodiments, $R^{12}$ is $C_1$-$C_6$ alkyl (e.g., $C_1$-$C_3$ alkyl, e.g., $CH_3$).

In certain embodiments, $R^{12}$ is $C_1$-$C_6$ alkyl (e.g., $C_1$-$C_3$ alkyl, e.g., $CH_3$), which is optionally substituted with from 1-3 (e.g., 1 or 2, e.g., 1) $R^c$. In embodiments, each occurrence of $R^c$ can be independently selected from —$NH_2$, —NH($C_1$-$C_6$ alkyl), N($C_1$-$C_6$ alkyl)$_2$, and —NHC(O)($C_1$-$C_6$ alkyl).

In some embodiments, $R^{12}$ is $C_6$-$C_{10}$ aryl that is optionally substituted with from 1-4 (e.g., 1-3, 1-2, or 1) $R^b$.

In certain embodiments, $R^b$ at each occurrence is independently selected from halo; or $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, and —NHC(O)($C_1$-$C_6$ alkyl), each of which is optionally substituted with from 1-3 independently selected R.

In certain embodiments, $R^b$ at each occurrence is independently selected from $C_1$-$C_6$ alkoxy; $C_1$-$C_6$ haloalkoxy; $C_1$-$C_6$ thioalkoxy; and $C_1$-$C_6$ thiohaloalkoxy, each of which is optionally substituted with from 1-3 independently selected $R^e$.

In certain embodiments, $R^b$ at each occurrence is independently selected from $C_1$-$C_6$ alkoxy and $C_1$-$C_6$ haloalkoxy, each of which is optionally substituted with from 1-3 independently selected Re.

In certain embodiments, $R^b$ at each occurrence is independently selected from $C_1$-$C_6$ alkoxy, each of which is optionally substituted with from 1-3 independently selected $R^e$. In embodiments, $R^b$ is $C_1$-$C_6$ alkoxy (e.g., $OCH_3$).

In embodiments, $R^b$ can further include halo.

In certain embodiments, $R^{12}$ is unsubstituted phenyl.

In certain embodiments, $R^{12}$ is phenyl that is substituted with 1 $R^b$. $R^b$ can be as defined anywhere herein (e.g., $R^b$ can be $C_1$-$C_6$ alkoxy, e.g., $OCH_3$). For example, $R^{12}$ can be 3-methoxyphenyl.

[IV] In some embodiments, Z is —$S(O)_n R^{13}$, in which n can be 0, 1, or 2.

In some embodiments, $R^{13}$ is $C_6$-$C_{10}$ aryl that is optionally substituted with from 1-4 (e.g., 1-3, 1-2, or 1) $R^b$.

In certain embodiments, $R^b$ at each occurrence is independently selected from halo; or $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, and —NHC(O)($C_1$-$C_6$ alkyl), each of which is optionally substituted with from 1-3 independently selected R.

In certain embodiments, $R^b$ at each occurrence is independently selected from $C_1$-$C_6$ alkoxy; $C_1$-$C_6$ haloalkoxy; $C_1$-$C_6$ thioalkoxy; and $C_1$-$C_6$ thiohaloalkoxy, each of which is optionally substituted with from 1-3 independently selected R.

In certain embodiments, $R^b$ at each occurrence is independently selected from $C_1$-$C_6$ alkoxy and $C_1$-$C_6$ haloalkoxy, each of which is optionally substituted with from 1-3 independently selected R.

In certain embodiments, $R^b$ at each occurrence is independently selected from $C_1$-$C_6$ alkoxy, each of which is optionally substituted with from 1-3 independently selected R. In embodiments, $R^b$ is $C_1$-$C_6$ alkoxy (e.g., $OCH_3$).

In embodiments, $R^b$ can further include halo.

In certain embodiments, $R^{13}$ is unsubstituted phenyl.

In certain embodiments, $R^{13}$ is phenyl that is substituted with 1 $R^b$. $R^b$ can be as defined anywhere herein (e.g., $R^b$ can be $C_1$-$C_6$ alkoxy, e.g., $OCH_3$). For example, $R^{13}$ can be 3-methoxyphenyl.

In embodiments, $R^{12}$ and/or $R^{13}$ cannot be substituted phenyl. In embodiments, $R^{12}$ and/or $R^{13}$ cannot be substituted phenyl when R and R' are defined according to definition (1); and A is $CR^{41}R^{42}$ (e.g., $CHOR^9$, e.g., CHOH), and each of $L^1$ and $L^2$ is $C_1$-$C_3$ alkylene (e.g., each of $L^1$ and $L^2$ is $CH_2$).

[V] In some embodiments, Z is heterocycloalkenyl containing from 5-6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$.

In certain embodiments, Z is heterocycloalkenyl containing 6 ring atoms, wherein from 1-3 of the ring atoms is independently selected from N, NH, N($C_1$-$C_6$ alkyl), NC(O)($C_1$-$C_6$ alkyl), O, and S; and wherein said heterocycloalkenyl is optionally substituted with from 1-4 independently selected $R^a$.

In certain embodiments, from 1-3 of the ring atoms is independently selected from N, NH, N($C_1$-$C_6$ alkyl), and NC(O)($C_1$-$C_6$ alkyl).

In certain embodiments, Ra at each occurrence is, independently selected from oxo, thioxo, =NH, and =N($C_1$-$C_6$ alkyl), e.g., =NH.

For example, Z can be:

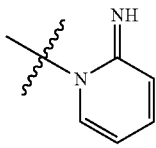

[V]

In some embodiments, Z is heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$.

In certain embodiments, Z is heteroaryl containing from 5-10 ring atoms, wherein from 1-4 of the ring atoms is independently selected from N, NH, and N($C_1$-$C_3$ alkyl); and wherein said heteroaryl is optionally substituted with from 1-2 $R^b$.

Variables R and R'

[I] In some embodiments, R and R' together with $C_2$ and $C_3$, respectively, form a fused phenyl ring having formula (II):

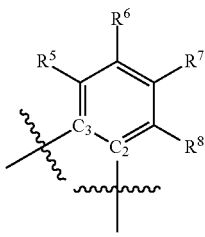

(II)

in which each of $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ halothioalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro.

For purposes of clarification, it is understood that compounds in which R and R' together with $C_2$ and $C_3$, respectively, form a fused phenyl ring having formula (II) correspond to compounds having the following general formula:

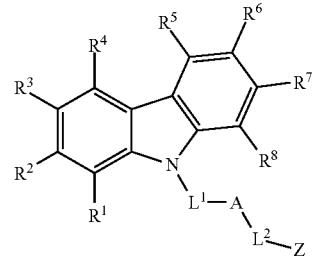

(III)

in which $R^1$, $R^2$, $R^3$, $R^4$, $L^1$, $L^2$, A, and Z can be as defined anywhere herein.

In some embodiments, one or two of $R^5$, $R^6$, $R^7$, and $R^8$ (e.g., one of, e.g., $R^6$) is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and the others are hydrogen.

In certain embodiments, one or two of $R^5$, $R^6$, $R^7$, and $R^8$ (e.g., one of, e.g., $R^6$) is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and the others are hydrogen.

In certain embodiments, one or two of $R^5$, $R^6$, $R^7$, and $R^8$ (e.g., one of, e.g., $R^6$) is selected from halo, $C_1$-$C_6$ alkyl, and $C_1$-$C_6$ haloalkyl; and the others are hydrogen.

In certain embodiments, one or two of $R^5$, $R^6$, $R^7$, and $R^8$ (e.g., one of, e.g., $R^6$) is selected from halo and $C_1$-$C_6$ alkyl; and the others are hydrogen.

In certain embodiments, one or two of $R^5$, $R^6$, $R^7$, and $R^8$ (e.g., one of, e.g., $R^6$) is halo (e.g., bromo or chloro) and $C_1$-$C_6$ alkyl; and the others are hydrogen.

In certain embodiments, one or two of $R^5$, $R^6$, $R^7$, and $R^8$ (e.g., one of, e.g., $R^6$) is bromo; and the others are hydrogen.

In some embodiments, $R^6$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and each of $R^5$, $R^7$, and $R^8$ can be as defined anywhere herein.

In certain embodiments, $R^6$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and each of $R^5$, $R^7$, and $R^8$ is hydrogen.

In some embodiments, $R^6$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^1$, $R^2$, and $R^4$ can be as defined anywhere herein.

In certain embodiments, $R^6$ is selected from halo, $C_1$-$C_6$ alkoxy, $C_1$-$C_6$ haloalkoxy, $C_1$-$C_6$ alkyl, $C_1$-$C_6$ haloalkyl, cyano, and nitro; and each of $R^5$, $R^7$, and $R^8$ is hydrogen.

In some embodiments, $R^6$ is selected from halo, $C_1$-$C_6$ alkyl, and $C_1$-$C_6$ haloalkyl; and each of $R^5$, $R^7$, and $R^8$ can be as defined anywhere herein.

In certain embodiments, $R^6$ is selected from halo, $C_1$-$C_6$ alkyl, and $C_1$-$C_6$ haloalkyl; and each of $R^5$, $R^7$, and $R^8$ is hydrogen.

In some embodiments, $R^6$ is selected from halo and $C_1$-$C_6$ alkyl; and each of $R^5$, $R^7$, and $R^8$ can be as defined anywhere herein.

In certain embodiments, $R^6$ is selected from halo and $C_1$-$C_6$ alkyl; and each of $R^5$, $R^7$, and $R^8$ is hydrogen.

In some embodiments, $R^6$ is halo (e.g., bromo or chloro); and each of $R^5$, $R^7$, and $R^8$ can be as defined anywhere herein.

In certain embodiments, $R^6$ is halo (e.g., bromo or chloro); and each of $R^5$, $R^7$, and $R^8$ is hydrogen.

In some embodiments, $R^6$ is bromo; and each of $R^5$, $R^7$, and $R^8$ can be as defined anywhere herein.

In certain embodiments, $R^6$ is bromo; and each of $R^5$, $R^7$, and $R^8$ is hydrogen.

In some embodiments, each of $R^5$, $R^6$, $R^7$, and $R^8$ is independently selected from hydrogen, halo, and $C_1$-$C_6$ alkyl.

In certain embodiments, each of $R^5$, $R^6$, $R^7$, and $R^8$ is independently selected from hydrogen and halo(e.g., bromo or chloro).

In some embodiments, each of $R^5$, $R^6$, $R^7$, and $R^8$ is hydrogen.

In some embodiments, when any one or more of $R^5$, R6, $R^7$, and $R^8$ can be a substituent other than hydrogen, said substituent, or each of said substituents, is other than $C_1$-$C_6$ alkyl (e.g., $C_1$-$C_3$ alkyl, e.g., $CH_3$).

Embodiments can include any one or more of the features described anywhere herein, including (but not limited to) those described below.

{A}

Each of $R^1$, $R^2$, $R^3$, and $R^4$ can be as defined anywhere herein.

$R^3$ is selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, cyano, —$NH_2$, —NH($C_1$-$C_6$ alkyl), N($C_1$-$C_6$ alkyl)$_2$, —NHC(O)($C_1$-$C_6$ alkyl), and nitro; and each of $R^1$, $R^2$, and $R^4$ can be as defined anywhere herein (e.g., each of $R^1$, $R^2$, and $R^4$ is hydrogen).

$R^3$ is selected from halo and $C_1$-$C_6$ alkyl; and each of $R^1$, $R^2$, and $R^4$ can be as defined anywhere herein (e.g., each of $R^1$, $R^2$, and $R^4$ is hydrogen).

$R^3$ is halo (e.g., bromo or chloro); and each of $R^1$, $R^2$, and $R^4$ can be as defined anywhere herein (e.g., each of $R^1$, $R^2$, and $R^4$ is hydrogen).

$R^3$ is bromo; and each of $R^1$, $R^2$, and $R^4$ can be as defined anywhere herein (e.g., each of $R^1$, $R^2$, and $R^4$ is hydrogen).

Each of $R^1$, $R^2$, $R^3$, and $R^4$ is independently selected from hydrogen and halo(e.g., bromo or chloro).

Each of $R^1$, $R^2$, $R^3$, and $R^4$ is hydrogen.

{B}

Each of $L^1$ and $L^2$ is, independently, $C_1$-$C_3$ alkylene, which is optionally substituted with from 1-2 independently selected $R^c$.

Each of $L^1$ and $L^2$ is $CH_2$.

One of $L^1$ and $L^2$ is $CH_2$ (e.g., L), and the other (e.g., $L^2$) is methylene that is substituted with 1 or 2 (e.g., 1) independently selected $R^c$, in which $R^c$ can be as defined anywhere herein.

Each of $L^1$ and $L^2$ is methylene that is substituted with 1 or 2 (e.g., 1) independently selected $R^c$, in which $R^c$ can be as defined anywhere herein.

$L^1$ is $C_1$-$C_3$ (e.g., $C_1$-$C_2$) straight chain alkylene, which is optionally substituted with from 1-2 independently selected $R^c$, and $L^2$ is a bond that directly connects A in formula (I) to Z in formula (I).

{C}

One of $R^{41}$ and $R^{42}$ is $OR^9$, and the other is hydrogen. In embodiments, $R^9$ can be hydrogen. $R^9$ can be $C_1$-$C_3$ alkyl (e.g., $CH_3$).

One of $R^{41}$ and $R^{42}$ can be halo (e.g., fluoro), and the other is hydrogen.

Each of $R^{41}$ and $R^{42}$ can be a substituent other than hydrogen. For example, each of $R^{41}$ and $R^{42}$ can be halo (e.g., fluoro). As another example, one of $R^{41}$ and $R^{42}$ can be $OR^9$ (e.g., in which $R^9$ is hydrogen), and the other is $C_1$-$C_3$ alkyl (e.g., $CH_3$).

Each of $R^{41}$ and $R^{42}$ is hydrogen.

A is $CR^{41}R^{42}$, wherein each of $R^{41}$ and $R^{42}$ is independently selected from hydrogen, halo, $C_1$-$C_3$ alkyl, or $OR^9$; and each of $L^1$ and $L^2$ is, independently, $C_1$-$C_3$ alkylene, which is optionally substituted with from 1-2 independently selected $R^c$.

{D}

Z is —$NR^{10}R^{11}$, in which $R^{10}$ and $R^{11}$ can be as defined anywhere herein.

One of $R^{10}$ and $R^{11}$ is $C_6$-$C_{10}$ aryl that is optionally substituted with from 1-4 $R^b$. In embodiments, the other of $R^{10}$ and $R^{11}$ is hydrogen or $C_1$-$C_3$ alkyl (e.g., $CH_3$). In embodiments, the other of $R^{10}$ and $R^{11}$ is hydrogen.

In certain embodiments, one of $R^{10}$ and $R^{11}$ is unsubstituted phenyl, and the other is hydrogen.

In certain embodiments, one of $R^{10}$ and $R^{11}$ is phenyl that is substituted with 1 $R^b$, and the other is hydrogen. In embodiments, $R^b$ is $C_1$-$C_6$ alkoxy (e.g., $C_1$-$C_3$ alkoxy, e.g., $OCH_3$). For example, one of $R^{10}$ and $R^{11}$ is 3-methoxyphenyl, and the other is hydrogen.

Z is —$OR^{12}$ or —$S(O)_nR^{13}$, in which $R^{12}$ and $R^{13}$ can be as defined anywhere herein.

Embodiments can include features from any one, two, three, or four of {A}, {B}, {C}, and {D}; or any combinations thereof.

In some embodiments:

$R^3$ is a substituent other than hydrogen (e.g., halo and $C_1$-$C_6$ alkyl; e.g., halo, e.g., bromo); and each of $R^1$, $R^2$, and $R^4$ can be as defined anywhere herein (e.g., each of $R^1$, $R^2$, and $R^4$ is hydrogen); and $R^6$ is a substituent other than hydrogen (e.g., halo and $C_1$-$C_6$ alkyl; e.g., halo, e.g., bromo); and each of $R^5$, $R^7$, and $R^8$ can be as defined anywhere herein (e.g., each of $R^5$, $R^7$, and $R^8$ is hydrogen).

In some embodiments:

$R^3$ is a substituent other than hydrogen (e.g., halo and $C_1$-$C_6$ alkyl; e.g., halo, e.g., bromo); and each of $R^1$, $R^2$, and $R^4$ can be as defined anywhere herein (e.g., each of $R^1$, $R^2$, and $R^4$ is hydrogen); and $R^6$ is a substituent other than hydrogen (e.g., halo and $C_1$-$C_6$ alkyl; e.g., halo, e.g., bromo); and each of $R^5$, $R^7$, and $R^8$ can be as defined anywhere herein (e.g., each of $R^5$, $R^7$, and $R^8$ is hydrogen); and A is $CR^{41}R^{42}$, wherein each of $R^{41}$ and $R^{42}$ is independently selected from hydrogen, halo, $C_1$-$C_3$ alkyl, or $OR^9$; and each of $L^1$ and $L^2$ is, independently, $C_1$-$C_3$ alkylene, which is optionally substituted with from 1-2 independently selected $R^c$.

Embodiments can include any one or more features described herein (e.g., as described under {B} and {C} above).

In some embodiments:

$R^3$ is a substituent other than hydrogen (e.g., halo and $C_1$-$C_6$ alkyl; e.g., halo, e.g., bromo); and each of $R^1$, $R^2$, and $R^4$ can be as defined anywhere herein (e.g., each of $R^1$, $R^2$, and $R^4$ is hydrogen); and $R^6$ is a substituent other than hydrogen (e.g., halo and $C_1$-$C_6$ alkyl; e.g., halo, e.g., bromo); and each of $R^5$, $R^7$, and $R^8$ can be as defined anywhere herein (e.g., each of $R^5$, $R^7$, and $R^8$ is hydrogen); and A is $CR^{A1}R^{A2}$, wherein each of $R^{A1}$ and $R^{A2}$ is independently selected from hydrogen, halo, $C_1$-$C_3$ alkyl, or $OR^9$; and each of $L^1$ and $L^2$ is, independently, $C_1$-$C_3$ alkylene, which is optionally substituted with from 1-2 independently selected $R^c$; and Z is $-NR^{10}R^{11}$, in which $R^{10}$ and $R^{11}$ can be as defined anywhere herein.

Embodiments can include any one or more features described herein (e.g., as described under {B}, {C}, and {D} above).

In some embodiments:
each of $L^1$ and $L^2$ is $CH_2$;
A is $CR^{A1}R^{A2}$, wherein one of $R^{A1}$ and $R^{A2}$ is $OR^9$, and the other is hydrogen;
Z is $-NR^{10}R^{11}$; and
each of $R^{10}$ and $R^{11}$ is independently selected from
(a) hydrogen;
(b) $C_6$-$C_{10}$ aryl that is optionally substituted with from 1-4 $R^b$;
(d) $C_1$-$C_6$ alkyl or $C_1$-$C_6$ haloalkyl, each of which is optionally substituted with from 1-3 $R^d$;
(f) $C_2$-$C_6$ alkenyl or $C_2$-$C_6$ alkynyl.

Embodiments can include any one or more features described herein (e.g., as described under {A}, {C}, and {D} above).

In some embodiments:
A is $CR^{A1}R^{A2}$, in which each of $R^{A1}$ and $R^{A2}$ is, independently, hydrogen, halo, or $C_1$-$C_3$ alkyl; or
A is $CR^{A1}R^{A2}$, in which one of $R^{A1}$ and $R^{A2}$ is halo (e.g., fluoro), and the other of $R^{A1}$ and $R^{A2}$ is, independently, hydrogen, halo, or $C_1$-$C_3$ alkyl (e.g., hydrogen); or
A is $CR^{A1}R^{A2}$, in which one of $R^{A1}$ and $R^{A2}$ is halo (e.g., fluoro), and the other of $R^{A1}$ and $R^{A2}$ is hydrogen; and
$R^1$, $R^2$, $R^3$, $R^4$, $L^1$, $L^2$, and Z can be as defined anywhere herein; or a salt (e.g., pharmaceutically acceptable salt) thereof.

Embodiments can include features from any one, two, three, or four of {A}, {B}, {C}, and {D}; or any combinations thereof.

In some embodiments:
one of $R^{A1}$ and $R^{A2}$ can be $OR^9$. In embodiments, the other of $R^{A1}$ and $R^{A2}$ can be as defined anywhere herein; e.g., the other of $R^{A1}$ and $R^{A2}$ can be hydrogen or $C_1$-$C_3$ alkyl. For example, one of $R^{A1}$ and $R^{A2}$ can be $OR^9$, and the other of $R^{A1}$ and $R^{A2}$ is hydrogen. In embodiments, $R^9$ can be hydrogen; and $R^1$, $R^2$, $R^3$, $R^4$, $L^1$, $L^2$, and Z can be as defined anywhere herein; or a salt (e.g., pharmaceutically acceptable salt) thereof.

In embodiments, one or more of the following apply, e.g., when A is CHOH and Z is $NR^{10}R^{11}$:
each of $R^3$ and $R^6$ is $CH_3$; and/or each of $R^3$ and $R^6$ is bromo; and/or each of $R^3$ and $R^6$ is chloro; and/or one of $R^3$ and $R^6$ is $CH_3$ (e.g., $R^6$), and the other is bromo (e.g., $R^3$);
each of $R^{10}$ and $R^{11}$ is other than hydrogen;
each of $R^{10}$ and $R^{11}$ is hydrogen;
one of $R^{10}$ and $R^{11}$ is heteroaryl as defined anywhere herein;
$L^1$ and/or $L^2$ is $C_2$-$C_3$ alkylene (optionally substituted);
(B) and/or (C) applies.

Embodiments can include features from any one, two, three, or four of {A}, {B}, {C}, and {D}; or any combinations thereof.

In some embodiments, Z is other than $NR^{10}R^{11}$; and $R^1$, $R^2$, $R^3$, $R^4$, $L^1$, $L^2$, Z, and A can be as defined anywhere herein; or a salt (e.g., pharmaceutically acceptable salt) thereof. In embodiments, (B) and/or (C) applies. Embodiments can include features from any one, two, three, or four of {A}, {B}, {C}, and {D}; or any combinations thereof.

In some embodiments, Z is $-OR^{12}$ and/or $-S(O)_nR^{13}$; and $R^1$, $R^2$, $R^3$, $R^4$, $L^1$, $L^2$, and A can be as defined anywhere herein; or a salt (e.g., pharmaceutically acceptable salt) thereof. In embodiments, (B) and/or (C) applies. Embodiments can include features from any one, two, three, or four of {A}, {B}, {C}, and {D}; or any combinations thereof.

In some embodiments, A is (ii) C=O; and/or (iv) heterocycloalkylene containing from 3-5 ring atoms, wherein from 1-2 of the ring atoms is independently selected from N, NH, N($C_1$-$C_3$ alkyl), O, and S; and wherein said heterocycloalkylene is (a) substituted with 1 oxo; and (b) is optionally further substituted with from 1-4 independently selected $R^a$; and $R^1$, $R^2$, $R^3$, $R^4$, $L^1$, $L^2$, and Z can be as defined anywhere herein; or a salt (e.g., pharmaceutically acceptable salt) thereof. Embodiments can include features from any one, two, three, or four of {A}, {B}, {C}, and {D}; or any combinations thereof.

[II] In some embodiments, each of R and R' is, independently, hydrogen, $C_1$-$C_6$ alkyl, or $C_1$-$C_6$ haloalkyl.

In embodiments, R and R' can each be the same or different.

In certain embodiments, each of R and R' is, independently, $C_1$-$C_6$ alkyl, e.g., each of R and R' is $CH_3$.

In other embodiments, each of R and R' is hydrogen.

Embodiments can include any one or more of the features described anywhere herein, including (but not limited to) those described in conjunction with Formula (III).

[III] In some embodiments, R and R' together with $C_2$ and $C_3$, respectively, form a fused heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected $R^a$. For purposes of clarification and illustration, a non-limiting example of these compounds is provided below (formula (IV)):

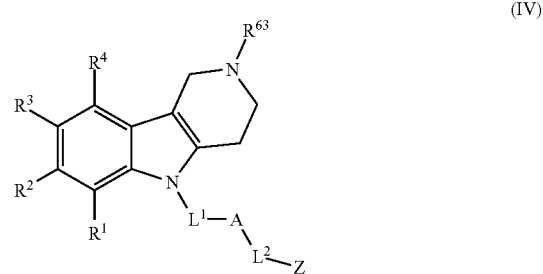

(IV)

in which $R^1$, $R^2$, $R^3$, $R^4$, $L^1$, $L^2$, A, and Z can be as defined anywhere herein. Here, R and R' together with $C_2$ and $C_3$, respectively, form a fused heterocyclic ring containing 5-6 ring atoms.

Embodiments can include any one or more of the features described anywhere herein, including (but not limited to) those described in conjunction with Formula (III). In certain embodiments, $R^{63}$ can be hydrogen or $C_1$-$C_3$ alkyl (e.g., $CH_3$).

In some embodiments, it is provided:
(i) each of $L^1$ and $L^2$ must be $C_1$-$C_3$ alkylene, which is optionally substituted with from 1-2 independently selected $R^c$ when A is $CH_2$; or (ii) Z must be other than heteroaryl containing from 5-14 (e.g., 5-6 or 6) ring atoms, wherein from 1-6 of the ring atoms is independently selected from N, NH, N(C$_1$-C$_3$ alkyl), O, and S; and wherein said heteroaryl is optionally substituted with from 1-4 independently selected R$^b$; e.g., other than substituted pyridyl, e.g., other than pyridyl substituted with C$_1$-C$_3$ alkyl (e.g., CH$_3$), e.g., other than 2 or 6-methylpyridyl.

[IV] In some embodiments, R and R' together with C$_2$ and C$_3$, respectively, form a fused C$_5$-C$_6$ cycloalkyl ring that is optionally substituted with from 1-4 independently selected R$^a$. For purposes of clarification and illustration, a non-limiting example of such compounds is provided below (formula (V)):

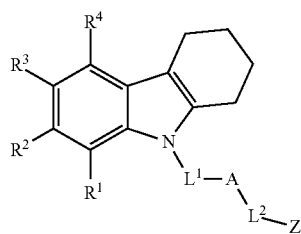

(V)

in which R$^1$, R$^2$, R$^3$, R$^4$, L$^1$, L$^2$, A, and Z can be as defined anywhere herein. Here, R and R' together with C$_2$ and C$_3$, respectively, form a fused C$_6$ cycloalkyl ring. Embodiments can include any one or more of the features described anywhere herein, including (but not limited to) those described in conjunction with Formula (III).

[V] In some embodiments, R and R' together with C$_2$ and C$_3$, respectively, form a fused heteroaryl ring containing from 5-6 ring atoms, wherein from 1-2 of the ring atoms is independently selected from N, NH, N(C$_1$-C$_3$ alkyl), O, and S; and wherein said heteroaryl ring is optionally substituted with from 1-3 independently selected R$^b$. See, e.g., the title compound of Example 13. Embodiments can include any one or more of the features described anywhere herein, including (but not limited to) those described in conjunction with Formula (III).

Any genus, subgenus, or specific compound described herein can include one or more of the stereochemistry features described herein (e.g., as delineated in the Summary).

Compound Forms and Salts

The compounds of the presently disclosed embodiments may contain one or more asymmetric centers and thus occur as racemates and racemic mixtures, enantiomerically enriched mixtures, single enantiomers, individual diastereomers and diastereomeric mixtures. All such isomeric forms of these compounds are expressly included in the presently disclosed embodiments. The compounds of the presently disclosed embodiments may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the presently disclosed embodiments. The compounds of the presently disclosed embodiments may also be represented in multiple tautomeric forms, in such instances, the presently disclosed embodiments expressly includes all tautomeric forms of the compounds described herein, even though only a single tautomeric form may be represented. All such isomeric forms of such compounds are expressly included in the presently disclosed embodiments.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the presently disclosed embodiments encompass all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of the presently disclosed embodiments include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include C$_{1-6}$ alkyl esters of carboxylic acid groups, which, upon administration to a subject, are capable of providing active compounds.

Pharmaceutically acceptable salts of the compounds of the presently disclosed embodiments include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the presently disclosed embodiments and their pharmaceutically acceptable acid addition salts. Salts derived from appropriate bases include alkali metal (e.g., sodium), alkaline earth metal (e.g., magnesium), ammonium and N-(alkyl)$_4$$^+$ salts. The presently disclosed embodiments also envision the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the presently disclosed embodiments.

In addition to salt forms, the presently disclosed embodiments provide compounds which are in a prodrug form. Prodrugs of the compounds described herein are those compounds that undergo chemical changes under physiological conditions to provide the compounds of the presently disclosed embodiments. Additionally, prodrugs can be converted to the compounds of the presently disclosed embodiments by chemical or biochemical methods in an ex vivo environment. For example, prodrugs can be slowly converted to the compounds of the presently disclosed embodiments when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the presently disclosed embodiments which is administered as an ester (the "prodrug"), but then is metabolically hydrolyzed to the carboxylic acid, the active entity. Additional examples include peptidyl derivatives of a compound of the presently disclosed embodiments.

The presently disclosed embodiments also include various hydrate and solvate forms of the compounds.

The compounds of the presently disclosed embodiments may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the presently disclosed embodiments, whether radioactive or not, are intended to be encompassed within the scope of the presently disclosed embodiments.

Synthesis

The compounds of the presently disclosed embodiments can be conveniently prepared in accordance with the procedures outlined in the Examples section, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvents. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}$F NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

The compounds of the presently disclosed embodiments can be prepared, for example, using the reaction pathways and techniques as described below.

A series of carbazole 1,2-aminoalcohol compounds of formula 3 may be prepared by the method outlined in Scheme 1. The 9-oxiranylmethyl-9H-carbazole of formula 2 may be prepared from an appropriately substituted carbazole of formula 1 and epichlorohydrin in the presence of a strong base such as sodium hydride.

$H_2NR^{10}$, to produce the secondary aminoalcohol of formula 4 and then protected with an amine protecting group (P) such as tert-butoxycarbonyl (Boc) to afford the protected aminoalochol of formula 5. Next, the hydroxyl group of formula 5 may be alkylated with a strong base such as sodium hydride and an alkylating agent (RX) such as an alkyl halide, tosylate, triflate or mesylate to produce the ether of formula 6. Removal of the amine protecting group in the presence of a suitable acid can provide the desired OR ether compounds of formula 7. Finally, reductive alkylation of the secondary amine of formula 7 may be achieved in the presence of an aldehyde and a reducing agent such as sodium cyano borohydride ($NaCNBH_3$) to provide the tertiary 1,2-aminoalcohol of formula 8.

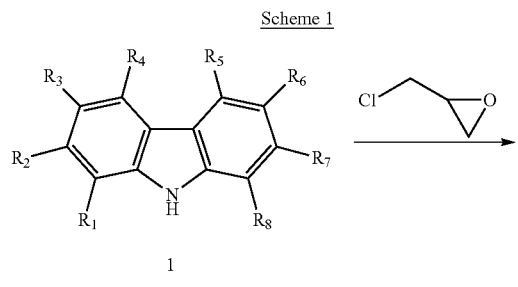

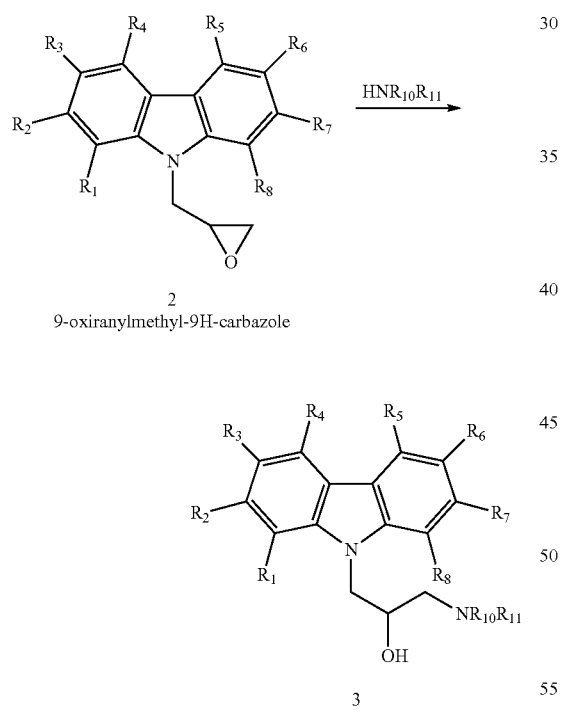

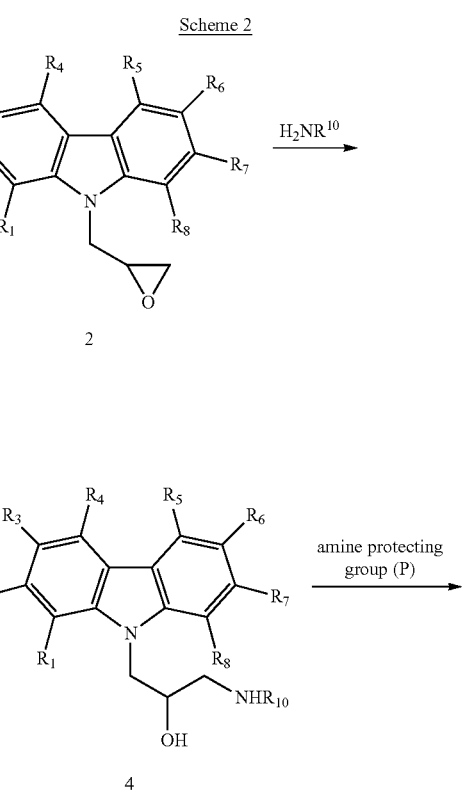

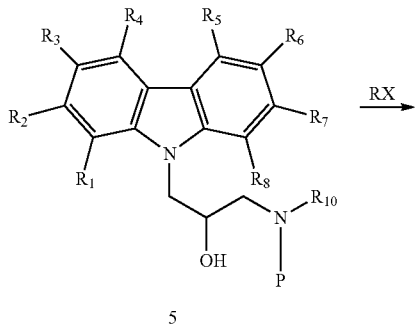

The oxiranyl ring of formula 2 may be opened in the presence of a primary or secondary amine to produce the 1,2-amino alcohol of formula 3. Such reactive primary or secondary amines can be, but are not limited to, phenethylamine, 3-phenylallyl amine, and N-substituted piperazines and the like.

Alternatively, a variety of carbazole 1,2-aminoalcohol compounds of formula 8 may be prepared by the method outlined in Scheme 2. The epoxide of 9-oxiranylmethyl-9H-carbazole of formula 2 may be opened with a primary amine,

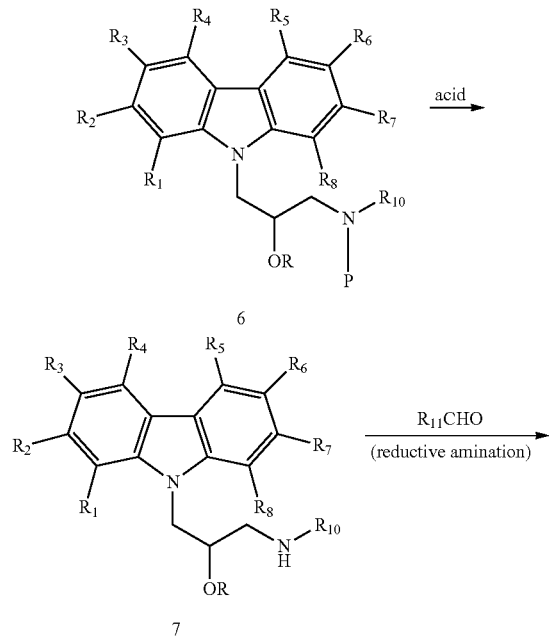

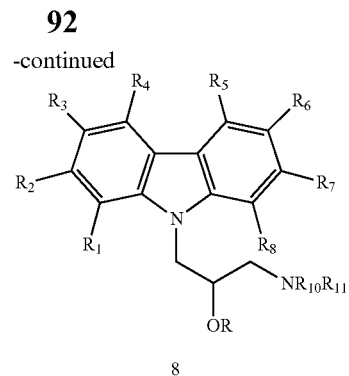

A series of substituted indole compounds of formula 11 and 12 may be prepared by the method outlined below in Scheme 3. Compounds of formula 11 may be prepared by the alkylation of an indole of formula 9 with an epoxide A, for example with epichlorohydrin or epibromohydrin, in the presence of a strong base such as potassium hydroxide (KOH) or n-butyllithium (n-BuLi) to produce the oxiranyl indole of formula 10. Next, opening of the epoxide of compounds of formula 10 with a primary amine, substituted alcohol or thiol in the presence of a strong base or a mild Lewis acid such as lithium bromide (LiBr) or bismuth chloride (BiCl$_3$) can provide the alcohol of formula 11. Additionally, compounds of formula 12 may be prepared by opening an epoxide B at the less hindered position with the indole nitrogen of formula 9.

Scheme 3

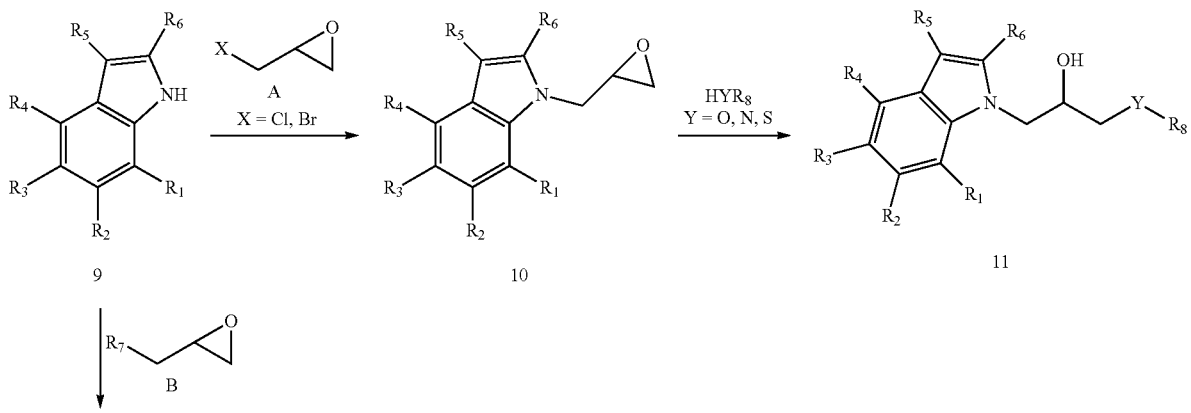

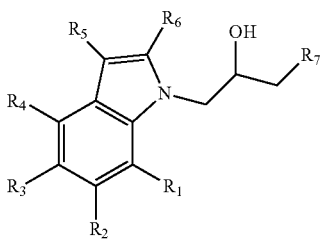

In addition, a variety of epoxide derivatives may be prepared by following the methods outlined in Scheme 4. The secondary alcohol of compounds of formula 11 may be oxidized using an oxidizing agent or under Swern-like oxidation conditions to provide the ketone of formula 13 which can further undergo reductive amination to provide the amine of compound 14. Alternatively, the secondary alcohol may be converted into an ester using a carboxylic acid anhydride (where Z=R"C(O)) or an ether (where Z=alklyl) using standard alkylation conditions to produce compounds of formula 15. Fluorine compounds of formula 16 may be prepared by reaction of the alcohol of formula 11 with a fluorinating agent such as diethylaminosulfur trifluoride (DAST). Nitrogen-heteroarylated compounds of formula 17 may be prepared in the presence of a catalytic amount of copper iodide and a heteroaryl iodide starting from compounds of formula 11 (where Y=N). Finally, sulfoxides and sulfones of formula 18 may be prepared under oxidative conditions, for example in the presence of m-chloroperoxybenzoic acid (m-CPBA), starting from sulfides of formula 11 (where Y=S).

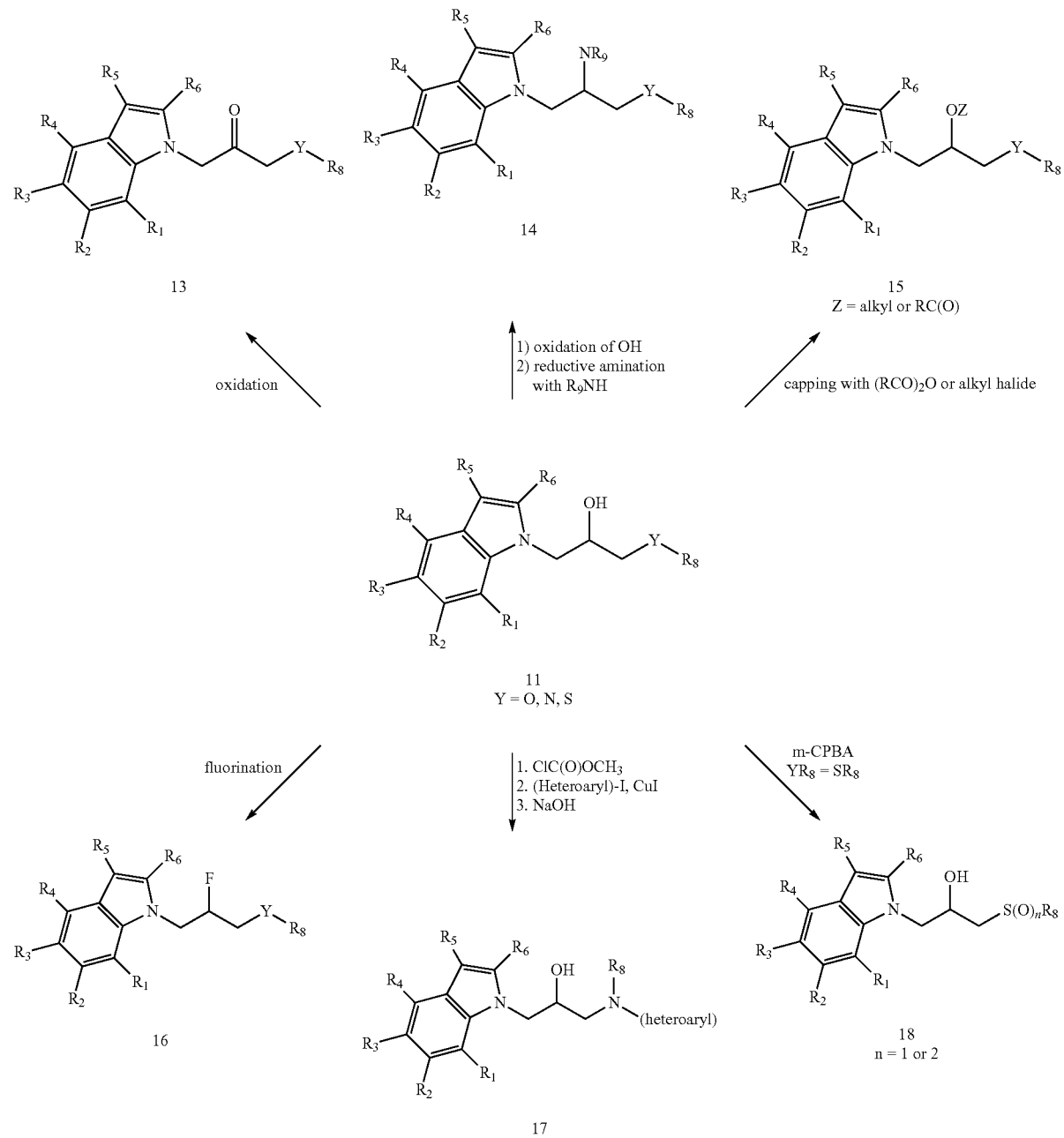

Pharmaceutical Compositions

The term "pharmaceutically acceptable carrier" refers to a carrier or adjuvant that may be administered to a subject (e.g., a patient), together with a compound of the presently disclosed embodiments, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of the presently disclosed embodiments include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Formulations 1-4) of capsule formulations.

| Capsule Formulation | Formulation 1 mg/capsule | Formulation 2 mg/capsule | Formulation 3 mg/capsule | Formulation 4 mg/capsule |
|---|---|---|---|---|
| Carbazole (solid solution) | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline carbazole (80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

Use

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with, aberrant (e.g., insufficient) neurogenesis or accelerated neuron cell death in a subject in need thereof are featured. The methods include administering to the subject an effective amount of a compound of formula (I) (and/or a compound of any of the other formulae described herein) or a salt (e.g., a pharmaceutically acceptable salt) thereof as defined anywhere herein to the subject.

In another aspect, the use of a compound of formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, aberrant (e.g., insufficient) neurogenesis or exacerbated neuronal cell death is featured.

In embodiments, the one or more diseases, disorders, or conditions can include neuropathies, nerve trauma, and neurodegenerative diseases. In embodiments, the one or more diseases, disorders, or conditions can be diseases, disorders, or conditions caused by, or associated with aberrant (e.g., insufficient) neurogenesis (e.g., aberrant hippocampal neurogenesis as is believed to occur in neuropsychiatric diseases) or accelerated death of existing neurons. Examples of the one or more neuropsychiatric and neurodegenerative diseases include, but are not limited to, schizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs (such as alcohol, opiates, methamphetamine, phencyclidine, and cocaine), retinal degeneration, spinal cord injury, peripheral nerve injury, physiological weight loss associated with various conditions, and cognitive decline associated with normal aging, radiation therapy, and chemotherapy. The resultant promotion of neurogenesis or survival of existing neurons (i.e. a resultant promotion of survival, growth, development, function and/or generation of neurons) may be detected directly, indirectly or inferentially from an improvement in, or an amelioration of one or more symptoms of the disease or disorder caused by or associated with aberrant neurogenesis or survival of existing neurons. Suitable assays which directly or indirectly detect neural survival, growth, development, function and/or generation are known in the art, including axon regeneration in rat models (e.g. Park et al., Science. 2008 Nov. 7; 322:963-6), nerve regeneration in a rabbit facial nerve injury models (e.g. Zhang et al., J Transl Med. 2008 Nov. 5; 6(1):67); sciatic nerve regeneration in rat models (e.g. Sun et al., Cell Mol Neurobiol. 2008 Nov. 6); protection against motor neuron degeneration in mice (e.g. Poesen et al., J. Neurosci. 2008 Oct. 15; 28(42):10451-9); rat model of Alzheimer's disease, (e.g. Xuan et al., Neurosci Lett. 2008 Aug. 8; 440(3):331-5); animal models of depression (e.g. Schmidt et al., Behav Pharmacol. 2007 September; 18(5-6):391-418; Krishnan et al., Nature 2008, 455, 894-902); and/or those exemplified herein.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of the presently disclosed embodiments will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of the presently disclosed embodiments may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, the compounds described herein can be coadministered with one or more other therapeutic agents. In certain embodiments, the additional agents may be administered separately, as part of a multiple dose regimen, from the compounds of the presently disclosed embodiments (e.g., sequentially, e.g., on different overlapping schedules with the administration of one or more compounds of formula (I) (including any subgenera or specific compounds thereof)). In other embodiments, these agents may be part of a single dosage form, mixed together with the compounds of the presently disclosed embodiments in a single composition. In still another embodiment, these agents can be given as a separate dose that is administered at about the same time that one or more compounds of formula (I) (including any subgenera or specific compounds thereof) are administered (e.g., simultaneously with the administration of one or more compounds of formula (I) (including any subgenera or specific compounds thereof)). When the compositions of the presently disclosed embodiments include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of the presently disclosed embodiments may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of the presently disclosed embodiments may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of the presently disclosed embodiments may also be administered in the form of suppositories for rectal administration. These compositions can be prepared by mixing a compound of the presently disclosed embodiments with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of the presently disclosed embodiments is useful when the desired treatment involves areas or organs readily accessible by topical application. For application topically to the skin, the composition should be formulated with a suitable ointment containing the active components suspended or dissolved in a carrier. Carriers for topical administration of the compounds of the presently disclosed embodiments include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of the presently disclosed embodiments may also be topically applied to the lower intestinal tract by rectal suppository formulation or in a suitable enema formulation.

In some embodiments, topical administration of the compounds and compositions described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in the presently disclosed embodiments. Also within the presently disclosed embodiments is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The compositions of the presently disclosed embodiments may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in the presently disclosed embodiments. For example, timed-release formulations based on polymer technologies, sustained-release techniques and encapsulation techniques (e.g., polymeric, liposomal) can also be used for delivery of the compounds and compositions delineated herein.

The presently disclosed embodiments will be further described in the following examples. It should be understood that these examples are for illustrative purposes only and are not to be construed as limiting the presently disclosed embodiments in any manner.

EXAMPLES

Example 1a and 1b

P7C3-S16 and P7C3-S17: S- and R-1-(3,6-Dibromo-9H-carbazol-9-yl)-3-(3-methoxyphenylamino)-propan-2-ol 1a and 1b

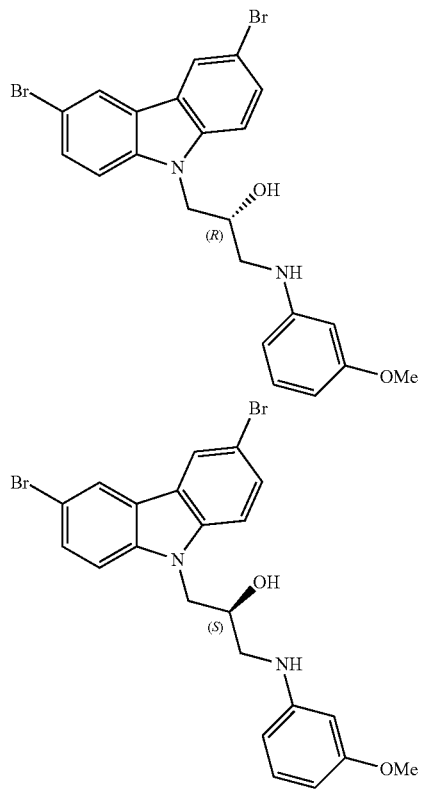

Representative Procedure 1

Step 1. Synthesis of 3,6-Dibromo-9-(oxiran-2-ylmethyl)-9H-carbazole (Epoxide 2-A)

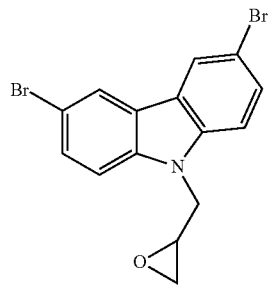 [SMILES: Brc1ccc2c(c1)c1cc(Br)ccc1n2CC1CO1]

Following a literature procedure (Asso, V.; Ghilardi, E.; Bertini, S.; Digiacomo, M.; Granchi, C.; Minutolo, F.; Rapposelli, S.; Bortolato, A.; Moro, S. Macchia, M. ChemMedChem, 2008, 3, 1530-1534) powdered KOH (0.103 g, 1.85 mmol) was added to a solution of 3,6-dibromocarbazole (0.500 g, 1.54 mmol) in DMF (1.5 mL) at ambient temperature and stirred for 30 min until dissolved. Epibromohydrin (0.32 mL, 3.8 mmol) was added via syringe and the reaction was stirred at room temperature overnight. Upon completion, the solution was partitioned between EtOAc and $H_2O$. The aqueous layer was washed 3× with EtOAc, and the combined organics were washed with saturated aqueous NaCl, dried over $Na_2SO_4$, filtered, and concentrated in vacuo. The crude residue was recrystallized from EtOAc/Hexane to afford the desired product (389 mg, 66%).

$^1$H NMR (CDCl$_3$, 500 MHz) δ 8.10 (d, 2H, J=2.0 Hz), 7.54 (dd, 2H, J=2.0, 8.5 Hz), 7.31 (d, 2H, J=8.5 Hz), 4.62 (dd, 1H, J=2.5, 16.0 Hz), 4.25 (dd, 1H, J=5.5, 16.0 Hz), 3.29 (m, 1H), 2.79 (dd, 1H, J=4.0, 4.5 Hz), 2.46 (dd, 1H, J=2.5, 5.0 Hz).

ESI m/z 381.0 ([M+H]$^+$, $C_{15}H_{12}Br_2NO$ requires 379.9)

Representative Procedure 2

Step 2. Synthesis of 1-(3,6-dibromo-9H-carbazol-9-yl)-3-(3-methoxyphenylamino)propan-2-ol

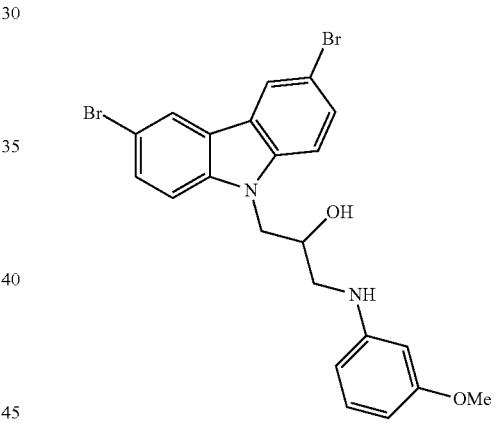

Following a literature procedure (Asso, V.; Ghilardi, E.; Bertini, S.; Digiacomo, M.; Granchi, C.; Minutolo, F.; Rapposelli, S.; Bortolato, A.; Moro, S. Macchia, M. ChemMedChem, 2008, 3, 1530-1534) m-Anisidine (1.0 mL, 8.95 mmol) was added to a suspension of epoxide 2-A (3.02 g, 7.92 mmol) in cyclohexane (73 mL). BiCl$_3$ (0.657 g, 2.08 mmol) was added and the mixture was heated to reflux overnight. Upon completion, the reaction was partitioned between EtOAc and $H_2O$. The aqueous layer was washed 3× with EtOAc, and the combined organics were washed with saturated aqueous NaCl, dried over $Na_2SO_4$, filtered, and concentrated in vacuo. The crude residue was purified by chromatography (SiO$_2$, 0-50% EtOAc/Hexane) to afford the desired alcohol as an opaque yellow solid (998 mg, 25%).

$^1$H NMR (CDCl$_3$, 400 MHz) δ 8.12 (d, 2H, J=1.6 Hz), 7.52 (dd, 2H, J=2.0, 8.8 Hz), 7.32 (d, 2H, J=8.8 Hz), 7.07 (dd, 1H, J=8.0 Hz), 6.31 (dd, 1H, J=2.4, 8.0 Hz), 6.21 (dd, 1H, J=2.0, 8.0 Hz), 6.12 (dd, 1H, J=2.0, 2.4 Hz), 4.34-4.39 (m, 3H), 4.00 (br s, 1H), 3.71 (s, 3H), 3.30 (dd, 1H, J=3.6, 13.2 Hz), 3.16 (dd, 1H, J=6.4, 13.2 Hz), 2.16 (br s, 1H).

$^{13}$C NMR (CDCl$_3$, 100 MHz) δ 161.0, 149.2, 139.9 (2C), 130.4 (2C), 129.5 (2C), 123.8 (2C), 123.5 (2C), 112.8, 111.0 (2C), 106.7, 103.8, 99.8, 69.5, 55.3, 48.0, 47.4

ESI m/z 502.9 ([M+H]$^+$, C$_{22}$H$_{21}$Br$_2$N$_2$O$_2$ requires 503.0)

Step 3. Synthesis of 1-(3,6-Dibromo-9H-carbazol-9-yl)-3-(3-methoxyphenylamino)propan-2-yl 3,3,3-trifluoro-2-methoxy-2-phenylpropanoate

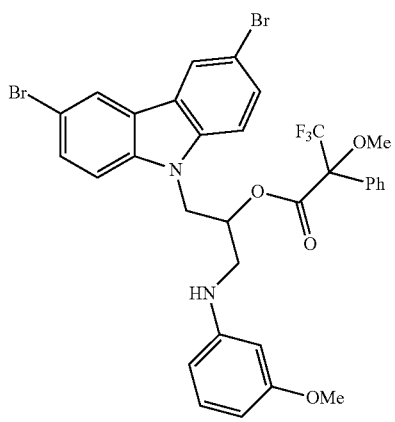 [SMILES: COc1cccc(NCC(Cn2c3ccc(Br)cc3c3cc(Br)ccc32)OC(=O)C(OC)(c2ccccc2)C(F)(F)F)c1]

1-(3,6-dibromo-9H-carbazol-9-yl)-3-(3-methoxyphenylamino)propan-2-ol (0.150 g, 0.298 mmol) was dissolved in anhydrous dichloromethane (6 mL) and cooled to 0° C. Pyridine (0.053 mL, 0.655 mmol) was added, followed by S-(+)-α-methoxy-α-trifluoromethylphenylacetyl chloride (S-Mosher's acid chloride, 0.083 mL, 0.446 mmol) and dimethylaminopyridine (0.004 g, 0.030 mmol). The reaction was allowed to warm to room temperature over 4 hours, after which it was quenched by addition of saturated aqueous NaHCO$_3$. The mixture was extracted 3× with EtOAc, and the combined organics were washed with saturated aqueous NaCl, dried over Na$_2$SO$_4$, filtered, and concentrated in vacuo. The crude residue was purified by chromatography (SiO$_2$, 0-50% EtOAc/Hexane) to afford a mixture of both possible esters and both possible amides (~5:1 ester:amide ratio by $^1$H NMR, 132 mg, 64%). Separation of the mixture was achieved using HPLC (Phenomenex SiO$_2$ Luna, 21×250 mm, 15% EtOAc/Hexane, 16 mL/min; HPLC Retention time: 25.6 min (ester 1) and 41.2 min (ester 2).

Ester 1: $^1$H NMR (CDCl$_3$, 500 MHz) δ 8.11 (d, 2H, J=2.0 Hz), 7.45 (dd, 2H, J=8.5 Hz), 7.24 (m, 2H), 7.22 (m, 4H), 7.05 (t, 1H, J=8.0 Hz), 6.32 (dd, 1H, J=2.0, 8.0 Hz), 6.12 (dd, 1H, J=2.0, 8.0 Hz), 6.05 (dd, 1H, J=2.0, 2.5 Hz), 5.59 (m, 1H), 4.54 (d, 2H, J=6.5 Hz), 3.71 (br s, 1H), 3.69 (s, 3H), 3.43 (m, 1H), 3.29 (ddd, 1H, J=5.5, 13.5 Hz), 3.19 (s, 3H).

Ester 2: $^1$H NMR (CDCl$_3$, 500 MHz) δ 8.08 (d, 2H, J=2.0 Hz), 7.42 (dd, 2H, J=2.0, 9.0 Hz), 7.28 (m, 2H), 7.24 (m, 4H), 7.04 (t, 1H, J=8.0 Hz), 6.31 (dd, 1H, J=2.0, 8.5 Hz), 6.11 (dd, 1H, J=2.0, 8.0 Hz), 6.01 (dd, 1H, J=2.0, 2.5 Hz), 5.63 (m, 1H), 4.49 (d, 2H, J=6.5 Hz), 3.82 (dd, 1H, J=5.5, 6.0 Hz), 3.66 (s, 3H), 3.42 (s, 3H), 3.39 (m, 1H), 3.28 (dd, 1H, J=5.0, 13.5 Hz)

Step 4. Synthesis of S- and R-1-(3,6-Dibromo-9H-carbazol-9-yl)-3-(3-methoxyphenylamino)-propan-2-ol

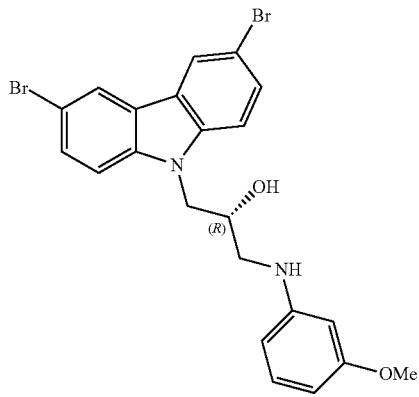

and

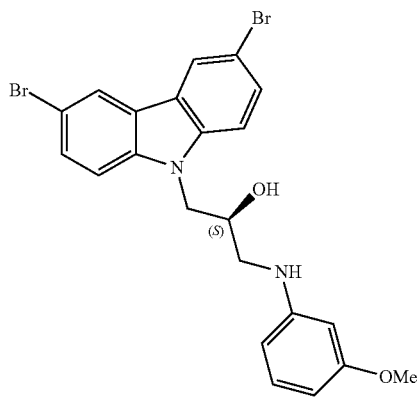

Following a literature procedure (Abad, J-L.; Casas, J.; Sanchez-Baeza, F.; Messeguer, A. *J. Org. Chem.* 1995, 60, 3648-3656) ester 1 from example 3 (0.011 g, 0.015 mmol) was dissolved in degassed Et$_2$O (0.150 mL) and cooled to 0° C. Lithium aluminum hydride (1M in THF, 0.018 mL, 0.018 mmol) was added via syringe and the reaction was stirred for 20 min. Upon completion by TLC the reaction was quenched by the addition of MeOH and stirred for 45 min. The mixture was partitioned between EtOAc and H$_2$O. The aqueous layer was extracted 3× with EtOAc, and the combined organics were washed with saturated aqueous NaCl, dried over Na$_2$SO$_4$, filtered, and concentrated in vacuo. The crude residue was purified by chromatography (SiO$_2$, 0-30% EtOAc/Hexane) to afford the desired alcohol (4.7 mg, 64%).

(From Ester 1): [α]$_D$=+10° (c=0.1, CH$_2$Cl$_2$); Example 1a (From Ester 2): [α]$_D$=−14° (c=0.1, CH$_2$Cl$_2$); Example 1b

Example 2

P7C3-S5: 1-(3,6-dibromo-9H-carbazol-9-yl)-3-(2-iminopyridin-1(2H)-yl)propan-2-ol

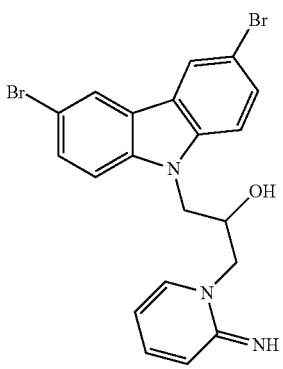 [SMILES: N=c1ccccn1CC(O)Cn1c2ccc(Br)cc2c2cc(Br)ccc21]

Example 2 was prepared following Representative Procedure 2, except with a reaction time of 2 days at 80° C. The crude product was used without further purification.

$^1$H NMR (CDCl$_3$, 400 MHz) d=8.14 (2H, J=1.9 Hz), 7.55 (dd, 2H, J=1.9, 8.8 Hz), 7.35 (d, 2H, J=8.7 Hz), 6.83 (t, 1H, J=7.6 Hz), 6.37 (d, 1H, J=6.8), 6.32 (d, 1H, J=9.1 Hz), 5.65 (t, 1H, J=6.7 Hz), 4.39 (dm, 5H), 3.54 (d, 1H, J=13.9 Hz). MS (ESI), m/z: found 473.9 (M+1)$^+$ ([M+1]+ for C$_{20}$H$_{18}$Br$_2$N$_3$O requires 474.0).

Example 3a

P7C3-S7: 1-(3,6-dibromo-9H-carbazol-9-yl)-3-(phenylthio)propan-2-ol

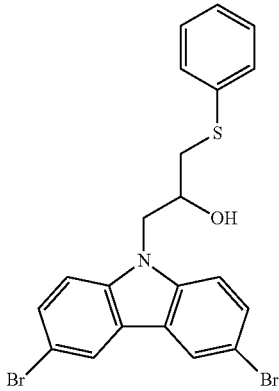 [SMILES: OC(CSc1ccccc1)Cn1c2ccc(Br)cc2c2cc(Br)ccc21]

Benzenethiol (30 TI, 0.29 mmol) was added to a solution of 3,6-dibromo-9-(oxiran-2-ylmethyl)-9H-carbazole (epoxide 2-A, 101.6 mg, 0.27 mmol) in 5.0 ml MeOH at r.t. The reaction mixture was heated to 80° C. and stirred overnight at the same temperature. The reaction was monitored by lc/ms for the consumption of SM. The reaction was cooled, diluted with ethyl acetate and washed with water and brine. The organic layer was dried over Na$_2$SO$_4$, filtered and condensed.

$^1$H NMR (CDCl$_3$, 400 MHz) Λ 8.03 (d, 2H, J=2.1 Hz), 7.48 (dd, 2H, J=2.0, 8.7 Hz), 7.33-7.20 (m, 7H), 4.33 (dd, 1H, J=4.3, 14.9 Hz), 4.20 (dd, 1H, J=6.9, 14.9 Hz), 4.00- 4.12 (m, 1H), 3.05 (dd, 1H, J=5.3, 13.9 Hz), 2.93 (dd, 1H, J=7.2, 13.9 Hz), 2.51 (bs, 1H); $^{13}$C NMR (CDCl$_3$, 126 MHz) δ 139.9, 134.5, 130.4, 129.6, 129.4, 127.4, 123.8, 123.4, 112.7, 111.1, 69.3, 48.1, 39.4; MS (ESI), m/z: found: 505.9 [M+O−1]([M+O−1]− for C$_{21}$H$_{17}$Br$_2$NOS requires 504.9; (oxidation occurred under MS conditions; NMR not consistent with sulfoxide).

Example 3b

P7C3-S39: 1-(3,6-dibromo-9H-carbazol-9-yl)-3-phenoxypropan-2-ol

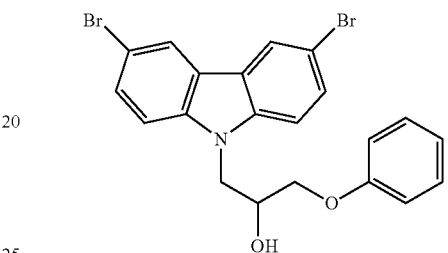

Following Representative Procedure 1, the title compound of Example 3b was prepared from dibromocarbazole and phenoxymethyloxirane in 61% yield.

$^1$H NMR (CDCl$_3$, 400 MHz) δ 8.14 (d, 2H, J=1.9 Hz), 7.51 (dd, 2H, J=1.9, 8.7 Hz), 7.36 (d, 2H, J=8.8 Hz), 7.127-7.32 (m, 2H), 7.00 (t, 1H, J=7.3 Hz), 6.87 (dd, 2H, J=0.8, 8.9 Hz), 4.58 (dd, 1H, J=7.9, 16.7 Hz), 4.41-4.49 (m, 2H), 4.00 (dd, 1H, J=4.4, 9.6 Hz), 3.89 (dd, 1H, J=4.5, 9.5 Hz), 2.38 (d=1H, J=5.7 Hz). MS (ESI), m/z: 517.9 [M+HCOO]$^-$ ([M+HCOO]$^-$ for C21H17Br2NO2 requires 518.0

Example 3c

P7C3-S27: 1-(3,6-dibromo-9H-carbazol-9-yl)-3-(phenylsulfinyl)propan-2-ol

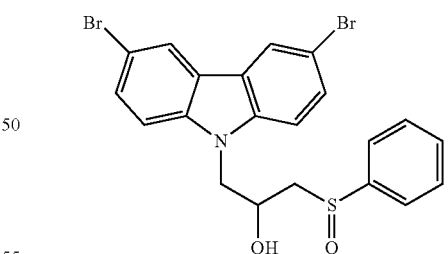

An aqueous solution of NaIO$_4$ (5.14 g) was added to silica gel (20 g) and shaken until a free-flowing solid was obtained. Thio-ether (1-(3,6-dibromo-9H-carbazol-9-yl)-3-(phenylthio)propan-2-ol, (0.0120 g, 0.0244 mmol) and NaIO$_4$/silica gel (0.1018 g NaIO4, 0.122 mmol) were suspended in CH$_2$Cl$_2$ (1 mL). The white suspension was heated to 50° C. in a sealed vial for 4 hours until TLC showed complete disappearance of starting material. The reaction mixture was subjected to silica gel chromatography using Hexanes/EtOAc (1:9) to afford 0.0081 g white solid as product, yield 65.4% as a 1:1 mixture of diastereomers.

¹H NMR (CDCl₃, 400 MHz) δppm=2.39 (dd, J=13.7, 1.7 Hz, 1 H diastereomer A) 2.83 (dd, J=13.2, 2.9 Hz, 1 Dias. B) 2.97 (dd, J=13.2, 8.6 Hz, 1 H Diast. B) 3.15 (dd, J=13.7, 9.3 Hz, 1 H Diast. A) 3.90 (d, J=1.7 Hz, 1 H Dias. B) 3.96 (d, J=2.6 Hz, 1 H Diast. A), 4.24 (dd, J=15.0, 6.3 Hz, 1H Dias A), 4.30 (dd, J=15.2, 6.7, 1H Diast. B), 4.35 (dd, J=15.2, 6.0 Hz, 1 H Diast. B), 4.45 (dd, J=15.1, 6.4 Hz, 1H Diast. B), 4.65-4.55 (m, 1 H Diast. A) 4.87-4.76 (m, 1 H Diast. B) 7.16 (d, J=8.7 Hz, 2 H Diast. A) 7.34 (d, J=8.8 Hz, 2H Diast B) 7.60-7.30 (m, 7 H Diast A+7 H Dast. B) 8.08 (d, J=1.9 Hz, 2 H Diast. A) 8.13 (d, J=1.9 Hz, 2 H Diast B). MS (ESI) m/z: 549.9 [M+HCOO]⁻ ([M+CHOO]⁻ for $C_{21}H_{17}Br_2NO_2S$ requires 549.9).

Example 3d

P7C3-S28: 1-(3,6-dibromo-9H-carbazol-9-yl)-3-(phenylsulfonyl)propan-2-ol

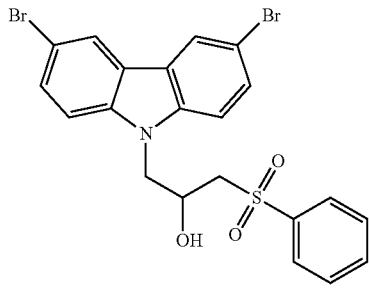 [SMILES: O=S(=O)(CC(O)Cn1c2ccc(Br)cc2c2cc(Br)ccc21)c1ccccc1]

To a solution of thio-ether (1-(3,6-dibromo-9H-carbazol-9-yl)-3-(phenylthio)propan-2-ol, (0.0113 g, 0.0230 mmol) in 0.5 mL CH₂Cl₂, a solution of mCPBA (ca. 77% pure, 0.0129 g, 0.0575 mmol) in 0.5 mL CH₂Cl₂ was added dropwise. The mixture was stirred at room temperature overnight. The crude reaction mixture was neutralized by 9 mL Et₃N and stirred for 30 min then diluted with 30 mL EtOAc and washed with saturated NaHCO₃ 3×30 mL and brine 1×30 mL. The organic layer was dried over anhydrous Na₂SO₄ and evaporated to afford the crude product, which was subjected to silica gel chromatography using Hexanes/EtOAc (3:7) to afford white solid as product (0.0120 g, yield 99.7%).

¹H NMR (CDCl₃, 400 MHz) δppm 3.15 (dd, J=14.2, 3.0 Hz, 1 H) 3.21-3.31 (m, 2 H) 4.38 (d, J=6.3 Hz, 2 H) 4.60-4.76 (m, 1 H) 7.25-7.31 (m, 2 H) 7.47-7.56 (m, 4 H) 7.60-7.70 (m, 1H) 7.79 (dd, J=8.4, 1.2 Hz, 2 H) 8.11 (d, J=1.9 Hz, 2 H); MS (ESI) m/z: 565.9 [M+HCOO]; 543.7 [M+Na]⁺ ([M+HCOO]⁻ for C21H17Br2NO3S requires 595.9; [M+Na]+ requires 543.9).

Example 4

P7C3-S9: N-(3-(3,6-dibromo-9H-carbazol-9-yl)-2-hydroxypropyl)-N-(3-methoxyphenyl)acetamide

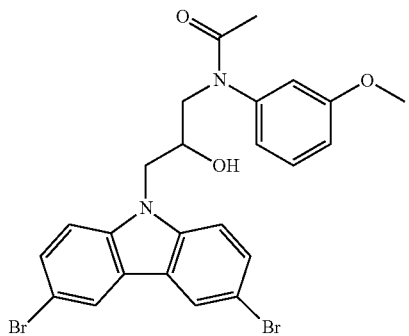 [SMILES: COc1cccc(N(CC(O)Cn2c3ccc(Br)cc3c3cc(Br)ccc32)C(C)=O)c1]

Following a literature procedure (Morcuende et al., J. Org. Chem. 1996, 5264-5270) triethylamine (14 Tl, 0.10 mmol) and acetyl chloride (8 Tl, 0.11 mmol) were added to a heterogeneous mixture of 1-(3,6-dibromo-9H-carbazol-9-yl)-3-(3-methoxyphenylamino)propan-2-ol (53 mg, 0.11 mmol) and dibutyltin oxide (5.5 mg, 0.022 mmol) in anhydrous toluene (1.5 ml). The reaction vessel was purged with nitrogen, sealed and heated under microwave radiation to 150° C. for 9 minutes. The reaction was monitored by lc/ms and all SM had been consumed. The heterogeneous solution was filtered under vacuum to yield a white solid. The crude product was used without purification.

¹H NMR (CDCl₃, 500 MHz) Λ 8.09 (2H, J=1.6 Hz), 7.52 (dd, 2H, J=1.8, 8.7 Hz), 7.29 (d, 2H, J=8.8 Hz), 7.26 (t, 1H, J=8.2 Hz), 6.86 (dd, 1H, J=2.5, 8.4 Hz), 6.68 (dd, 1H, J=1.3, 7.7 Hz), 6.62 (s, 1H,), 4.33-4.40 (m, 1H), 4.29 (dd, 2H, J=2.6, 6.0 Hz), 3.94 (d, 1H, J=4.1 Hz), 3.76 (s, 3H), 3.51 (dd, 1H, J=2.3, 14.0 Hz), 1.9 (s, 3H);

¹³C NMR (CDCl₃, 126 MHz) δ☐ 173.6, 160.9, 144.5, 139.9, 131.0, 129.4, 123.8, 123.4, 119.7, 113.9, 113.5, 112.6, 111.1, 70.9, 55.7, 55.2, 46.0, 22.8.

MS (ESI), m/z: 544.9 (M+1)⁺ ([M+1]⁺ for $C_{24}H_{22}Br_2N_2O_3$ requires 545.0)

Example 5

P7C3-S12: 5-((3,6-dibromo-9H-carbazol-9-yl)methyl)-3-(3-methoxyphenyl)-oxazolidin-2-one

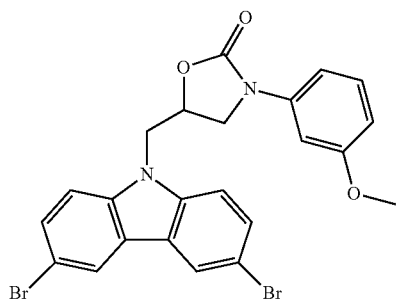 [SMILES: COc1cccc(N2CC(Cn3c4ccc(Br)cc4c4cc(Br)ccc43)OC2=O)c1]

Methyl chloroformate (10 Tl, 0.13 mmol) was added to a stirring solution of jn-128-186 (55.0 mg, 0.11 mmol) and indium powder (3.5 mg, 0.030 mmol) in acetonitrile (3.0 ml), and the reaction mixture was stirred overnight at r.t. An additional 3.1 mg (0.027 mmol) of indium and 20 Tl (2.6 eq.) of methyl chloroformate were added. After several hours, the reaction was diluted with ethyl actetate, and washed with water and then brine. The organic layer was dried over Na₂SO₄, filtered and concentrated. The methyl carbonate was purified via flash chromatography in 20-40% ethyl acetate/hexanes. Sodium methoxide (3.0 ml) was added to a solution of carbonate (21.3 mg, 0.038 mmol) and methanol (1.0 ml). After an hour at ambient temperature the solution was diluted with water and extracted with ethyl acetate. The organic layer was washed with water and brine and condensed.

¹H NMR (CD₃COCD₃, 500 MHz) Λ 8.40 (s, 2H), 7.78 (d, 2H, J=8.5 Hz), 7.64 (d, 2H, J=8.9 Hz), 7.23-7.28 (m, 2H), 7.05 (d, 1H, J=8.3 Hz), 6.70 (d, 1H, J=8.3 Hz), 5.24-5.31 (m, 1H), 5.00 (dd, 1H, J=7.9, 15.7 Hz), 4.91 (dd, 1H, J=3.2, 15.8 Hz), 4.38 (t, 1H, J=9.3 Hz), 4.05 (m, 1H), 3.78 (s, 3H);

¹³C NMR (CDCl₃, 126 MHz) δ ☐160.4, 153.9, 140.3, 140.2, 129.8, 129.4, 124.0, 123.5, 112.4, 112.1, 110.3, 109.0, 104.4, 71.9, 54.9, 47.9, 46.6.

MS (ESI), m/z: 528.9 (M+1)+•. ([M+1]+ for C23H19Br2N2O3 calculated 529.0)

Example 6a

P7C3-S10: N-(3-(3,6-dibromo-9H-carbazol-9-yl)-2-fluoropropyl)-3-methoxyaniline (also designated as "P7C3A20")

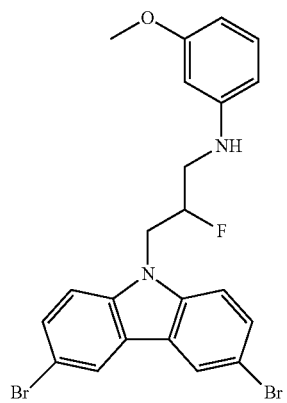 [SMILES: COc1cccc(NCC(F)Cn2c3ccc(Br)cc3c3cc(Br)ccc32)c1]

Representative Procedure 3: Epoxide Opening with Ns-Protected Anilines

N-(3-(3,6-dibromo-9H-carbazol-9-yl)-2-hydroxypropyl)-N-(3-methoxyphenyl)-4-nitrobenzenesulfonamide

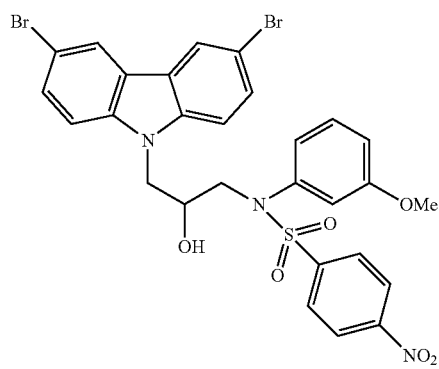 [SMILES: COc1cccc(N(CC(O)Cn2c3ccc(Br)cc3c3cc(Br)ccc32)S(=O)(=O)c2ccc([N+](=O)[O-])cc2)c1]

A heterogeneous mixture of N-(4-methoxyphenyl)-4-nitrobenzenesulfonamide (100.2 mg, 0.32 mmol) in toluene (2.5 ml, 0.13 M) under a N$_2$ atmosphere was cooled in a dry ice/acetone bath before dropwise addition of n-butyllithium (200 ul of 1.78 M in hexanes, 0.36 mmol). The reaction was stirred at −78° C. for 10 minutes before addition of carbazole epoxide 2-A. The heterogeneous mixture was stirred at room temperature for 5 minutes before heating at 100° C. for 48 hours. The cooled reaction was diluted with EtOAc and washed three times with 5% acetic acid solution, followed by a brine wash. The organic layer was dried over Na$_2$SO$_4$, filtered and condensed. The crude mixture was purified in 100% dichloromethane. Yield=88%.

$^1$H NMR (CDCl$_3$, 400 MHz) δ 8.23 (d, 2H, J=8.5 Hz), 8.06 (d, 2H, J=1.9 Hz), 7.65 (d, 2H, J=8.5 Hz), 7.46, (dd, 2H, J=8.6, 1.9 Hz), 7.22 (d, 2H, J=8.8 Hz), 6.94 (d, 2H, 8.8 Hz), 6.83 (d, 2H, 9.1 Hz), 4.44 (dd, 1H, J=14.9, 3.6 Hz), 4.26-4.34 (m, 1H), 4.17-4.24 (bs, 1H), 3.81 (s, 3H), 3.62-3.75 (m, 2H). MS (ESI), m/z: 732.0 [(M+HCOO$^-$); C28H23Br2N3O6S (M) requires 687]

Representative Procedure 4: Fluorination of Secondary Alcohol

N-(3-(3,6-dibromo-9H-carbazol-9-yl)-2-fluoropropyl)-N-(3-methoxyphenyl)-4-nitrobenzenesulfonamide

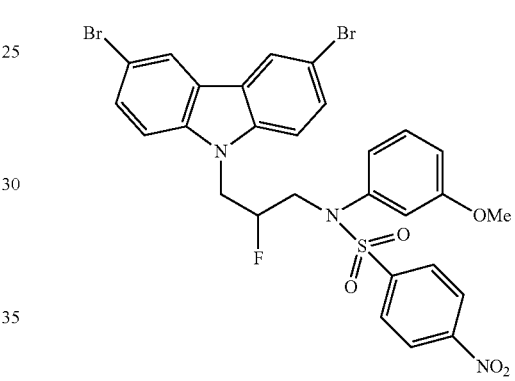

An oven dried 20 ml scintillation vial containing N-(3-(3,6-dibromo-9H-carbazol-9-yl)-2-hydroxypropyl)-N-(3-methoxyphenyl)-4-nitrobenzenesulfonamide (18.3 mg, 0.027 mmol; see representative procedure 3 above) was purged with N$_2$ and charged with anhydrous dichloromethane (1.5 ml, 0.018 M). The sealed vial was cooled in a dry ice acetone bath before the dropwise addition of diethylaminosulfur trifluoride (DAST, 7 ul, 0.053 mmol). The reaction temperature was maintained at −78° C. for an hour and then slowly warmed to room temperature and stirred overnight. The reaction was quenched with 2.0 ml of saturated NaHCO$_3$ solution and diluted with 6 ml CH$_2$Cl$_2$ and extracted three times. The combined organics were dried over Na$_2$SO$_4$, filtered and condensed. Crude product carried forward. Quantitative yield.

Alternatively, morpholinosulfur trifluoride (MORPHO-DAST) can be used at rt.

$^1$H NMR (CDCl$_3$, 400 MHz) δ 8.28 (d, 2H, J=8.0 Hz), 8.13 (s, 2H), 7.72 (d, 2H, J=8.7 Hz), 7.54, (d, 2H, J=8.0 Hz), 7.21 (d, 3H, J=8.1 Hz), 6.89 (dd, 1H, 8.3, 2.4 Hz), 6.67 (t, 1H, J=2.0 Hz), 6.55 (d, 1H, J=8.0 Hz) 4.93 (m, 1H), 4.43-4.68 (m, 2H), 4.20 (t, 1H, J=6.2 Hz), 3.81-3.99 (m, 2H), 3.75 (s, 3H).

MS (ESI), m/z: calculated 688.96, found 733.9 (M+HCOO$^-$).

Representative Procedure 5: Nosyl Group Deprotection (see Fukuyama, T.; Jow, C.-K.; Cheung, M. *Tetrahedron Lett.* 1995, 36, 6373-6374)

N-(3-(3,6-dibromo-9H-carbazol-9-yl)-2-fluoropropyl)-3-methoxyaniline

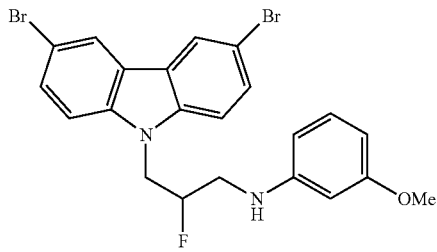

To a vial containing N-(3-(3,6-dibromo-9H-carbazol-9-yl)-2-fluoropropyl)-N-(3-methoxyphenyl)-4-nitrobenzenesulfonamide (21.0 mg, 0.030 mmol; see representative procedure 4) was added lithium hydroxide (3.2 mg, 0.134 mmol), dimethylformamide (0.5 ml, 0.06 M) and mercaptoacetic acid (4.2 ul 0.060 mmol). After stirring at rt for 1 h the reaction mixture was diluted with EtOAc and washed sequentially with water, saturated sodium bicarbonate solution, water (3×) and brine. The organic layer was dried over $Na_2SO_4$, filtered and condensed. The crude reaction mixture was purified in 30% EtOAc/hexanes (+0.2% TEA), with 13.6 mg isolated. Yield=88%

Additional Representative Procedure

DAST [$(Et_2NSF_3)$ 0.12 ml, 0.916 mmol] was added dropwise to a solution of 1-(3,6-dibromo-9H-carbazol-9-yl)-3-(3-methoxyphenylamino)propan-2-ol (0.102 g, 0.203 mmol) in 6.0 ml of anhydrous DCM at −78° C. The reaction was stirred at −78° C. for one hour before being slowly warmed to 0° C. over 5 hours. The reaction was quenched by addition of phosphate buffer (pH=8) and extracted with DCM. The aqueous phase was extracted twice with 10 ml DCM. The combined organics were dried over $Na_2SO4$, filtered and concentrated. The crude reaction material was purified by flash chromatography on $SiO2$ (20% EtOAc/hexanes/0.2% TEA). Fractions containing the desired fluorinated product were further purified with 40% EtOAc/hexanes (+0.1% TEA). Isolated 5.7 mg desired product.

Analytical Data for the title compound of Example 6a
$^1$H NMR ($CDCl_3$, 500 MHz) Λ 8.16 (2H, J=2.0 Hz), 7.56 (dd, 2H, J=1.9, 8.7 Hz), 7.31 (d, 2H, J=8.6 Hz), 7.11 (t, 1H, J=8.1 Hz), 6.36 (dd, 1H, J=2.2, 8.1 Hz), 6.23 (dd, 1H, J=2.0, 8.0 Hz), 6.15 (t, 1H, J=2.3 Hz), 5.11 (dddd, 1H, J=4.6, 5.8, 10.4, 47.7 Hz), 4.60 (m, 2H), 4.39 (dm, 2H), 3.95 (t, 1H, J=6.3 Hz), 3.75 (s, 3H)

MS (ESI), m/z: 504.9 (M+1)$^+$. ([M+1]+ for $C_{22}H_{19}Br_2FN_2O$ calculated 505.0)

Gram-Scale Synthesis of P7C3-S10, Also Known as P7C3A20

3,6-dibromo-9-(oxiran-2-ylmethyl)-9H-carbazole

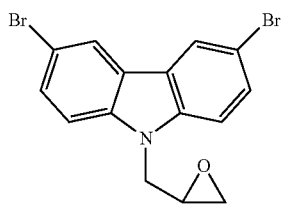 [SMILES: Brc1ccc2c(c1)c1cc(Br)ccc1n2CC1CO1]

A duplicate set of reactions were set up. Solutions of 3,6-dibromocarbazole (49.61 and 51.98 g, 152.6 and 159.9 mmol respectively) and crushed potassium hydroxide pellets (11.1 and 10.6 g, 197.8 and 188.9 mmol, respectively) in dimethylformamide (1 L each) were stirred for an hour before the addition of epibromohydrin (32 and 35 ml, 386.6 and 422.9 mmol respectively). The reactions were stirred overnight. Each reaction was worked up portionwise by dilution with EtOAc, and washed several times with water and then brine. The organic layer was dried over $MgSO_4$, filtered and condensed. The off-white solid was washed with minimal EtOAc to give 95.2 g of epoxide in 80% yield.

$^1$H NMR ($CDCl_3$, 400 MHz) δ 8.15 (d, J=1.9 Hz, 2H), 7.58 (dd, J=8.6, 2.0 Hz, 2H), 7.35 (d, J=8.7 Hz, 2H), 4.66 (dd, J=16.0, 2.7 Hz, 1H), 4.29 (dd, J=15.9, 5.1 Hz, 1H), 3.33 (ddd, J=6.7, 5.2, 2.8 Hz, 1H), 2.82 (t, J=4.3 Hz, 1H), 2.50 (dd, J=4.7, 2.6 Hz, 1H).

1,1,1-trifluoro-N-(3-methoxyphenyl)methanesulfonamide

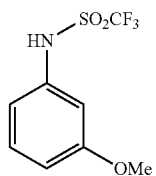

A solution of trifluoromethanesulfonic anhydride (45 ml, 26.7 mmol) in methylene chloride (250 ml) were added dropwise to an ice chilled solution of m-anisidine (25 ml, 22.3 mmol) and triethylamine (39 ml, 28.0 mmol) in methylene chloride (1.25 L). The reaction was stirred overnight at rt. Workup was performed portionwise. Each of the two portions was basified by addition of 250 ml of 2.5 N NaOH solution and 625 ml MeOH. The aqueous was extracted thrice (100 ml each) with methylene chloride to remove any unreacted aniline or doubly triflated product. The aqueous phases were combined, acidified to pH 2 with 18% HCl, and again extracted with methylene chloride three times. The organic layer is dried over $MgSO_4$, filtered and condensed to give 17.69 g of brown solid in 77% yield.

$^1$H NMR ($CDCl_3$, 400 MHz) δ7.48-7.13 (m, 1H), 6.97-6.61 (m, 3H), 3.82 (s, 3H).

MS (ESI), m/z: calculated 255.21, found 255.9 (M+1)$^+$.

N-(3-(3,6-dibromo-9H-carbazol-9-yl)-2-hydroxypropyl)-1,1,1-trifluoro-N-(3-methoxyphenyl)methanesulfonamide (P7C3-S244)

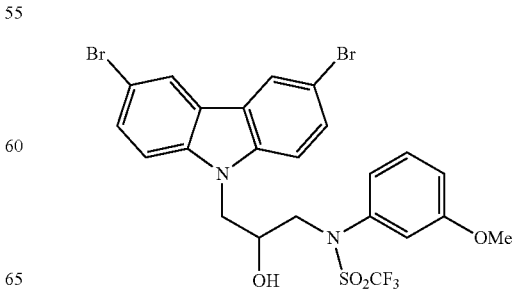

N-butyllithium (2.5 M in hexanes, 48 ml) was added dropwise to an ice-cooled solution of 1,1,1-trifluoro-N-(3-methoxyphenyl)methanesulfonamide (22.07 g, 86.5 mmol) in dry dioxane (145 ml) over a 40 minute period. The solution was then stirred at rt for 15 minutes before addition of 3,6-dibromo-9-(oxiran-2-ylmethyl)-9H-carbazole (25.05 g, 65.7 mmol), followed by heating at 90° C. for an hour. These conditions were optimized to maximize conversion while minimizing formation of an aziridene by-product. The reaction was allowed to cool to rt then diluted with 1.2 L ethyl acetate and washed several times with water and finally brine. The organic layer was dried over MgSO$_4$, filtered and condensed to give an orange viscous mixture. To this mixture was added 150 ml of 60% methylene chloride/hexanes, and the solution was then concentrated to generate a yellow foam (presumably this procedure helps remove residual ethyl acetate and/or dioxane). A further 150 ml of 60% methylene chloride/hexanes was added and stirred overnight. The mixture was filtered and washed several times with 60% methylene chloride/hexanes until the solid was white giving 20.1 g of 99% purity. A second crop gave 2.98 g in 91% purity. Filtrates and washings were combined and found to contain a 2:2.6:1 mixture of SM: product: aziridene by-product. This mixture was subjected to amination conditions by heating the mixture (24 g in approximately 2 equal portions) in ammonia in methanol (7N, 11 and 8 ml, respectively) at 100° C. in sealed pressure tubes overnight. Epoxide SM is converted to β-hydroxy amine (MacMillan et al., *J. Am. Chem. Soc.* 2011, 133, 1428), which aids chromatographic purification. Column chromatography in 80% DCM/hexanes gave a further 9.7 g of product with an overall yield of 32.78 g and 78%.

$^1$H NMR (CDCl$_3$, 400 MHz) δ 8.13 (d, J=1.9 Hz, 2H), 7.54 (dd, J=8.7, 1.9 Hz, 2H), 7.33 (t, J=8.1 Hz, 1H), 7.22 (d, J=8.7 Hz, 2H), 6.95 (dd, J=8.4, 2.3 Hz, 1H), 6.88 (s, 1H), 4.56-4.10 (m, 4H), 3.99 (m, 1H), 3.81 (s, 3H), 1.98 (d, J=4.2 Hz, 1H).

MS (ESI), m/z: calculated 633.94, found 678.6 (M+HCOO$^-$)$^-$.

3,6-dibromo-9-((1-(3-methoxyphenyl)aziridin-2-yl)methyl)-9H-carbazole

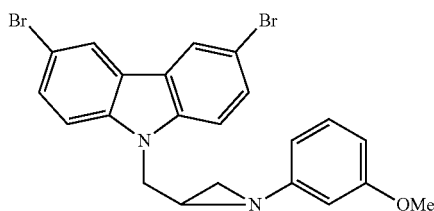 [SMILES: COc1cccc(N2CC2Cn2c3ccc(Br)cc3c3cc(Br)ccc32)c1]

$^1$H NMR (400 MHz, CDCl$_3$) δ 7.94 (d, J=1.9 Hz, 2H), 7.40 (dd, J=8.7, 1.9 Hz, 2H), 7.26 (d, J=8.7 Hz, 2H), 6.84 (t, J=8.1 Hz, 1H), 6.31 (dd, J=8.2, 2.4 Hz, 1H), 6.12-5.94 (m, 1H), 5.84 (t, J=2.2 Hz, 1H), 4.42 (dd, J=15.4, 2.8 Hz, 1H), 3.94 (dd, J=15.4, 8.0 Hz, 1H), 3.33 (s, 3H), 2.22 (dq, J=8.7, 3.0 Hz, 1H), 2.16 (d, J=3.3 Hz, 1H), 2.02 (d, J=6.3 Hz, 1H).

MS (ESI), m/z: calculated 483.98, found 484.7 (M+1)$^+$.

N-(3-(3,6-dibromo-9H-carbazol-9-yl)-2-fluoropropyl)-1,1,1-trifluoro-N-(3-methoxyphenyl)methanesulfonamide (P7C3-S241)

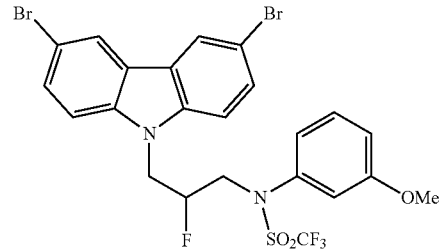

Morpho-Dast (14.0 ml, 115 mmol) was added to a solution of N-(3-(3,6-dibromo-9H-carbazol-9-yl)-2-hydroxypropyl)-1,1,1-trifluoro-N-(3-ethoxyphenyl)methanesulfonamide (20.6 g, 32.4 mmol) in anhydrous methylene chloride (315 ml) and stirred overnight. The solution, in a water bath at ambient temperature, was neutralized by dropwise addition of 375 ml saturated bicarbonate solution. The biphasic mixture was extracted with methylene chloride twice. The combined organics were dried over MgSO$_4$, filtered and condensed to give 21.5 g of off-white foam in quantitative yield.

$^1$H NMR (400 MHz, CDCl$_3$) δ 8.15 (d, J=1.9 Hz, 2H), 7.56 (dd, J=8.7, 1.9 Hz, 2H), 7.32 (t, J=8.2 Hz, 1H), 7.21 (d, J=8.6 Hz, 2H), 6.99-6.90 (m, 2H), 6.86 (m, 1H), 5.08-4.86 (dm, 1H), 4.57-4.44 (m, 2H), 4.09 (m, 2H), 3.79 (s, 3H).

MS (ESI), m/z: calculated 635.93, found 680.6 (M+HCOO$^-$)$^-$.

P7C3-S10 (P7C3A20): N-3-(3,6-dibromo-9H-carbazol-9-yl)-2-fluoropropyl)-3-methoxyaniline

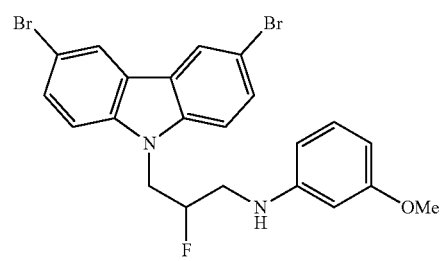 [SMILES: COc1cccc(NCC(F)Cn2c3ccc(Br)cc3c3cc(Br)ccc32)c1]

A two neck flask containing N-(3-(3,6-dibromo-9H-carbazol-9-yl)-2-fluoropropyl)-1,1,1-trifluoro-N-(3-methoxyphenyl)methanesulfonamide (5.00 g, 7.83 mmol) was purged with N$_2$ before addition of degassed xylene (52.0 ml). The solution was cooled in a dry-ice acetone bath before the dropwise addition of Red-Al®(sodium bis(2-methoxyethoxy)aluminum hydride solution, 65% wt in toluene, 11.0 ml, 36.1 mmol) during which the internal temperature was maintained between −50 to −40° C. The cold bath was removed immediately upon completion of Red-Al addition. The reaction was allowed to warm slowly to about −23° C. at which time the reaction flask was transferred to a heating block. The reaction flask was heated until the internal temperature was 59.3-62.0° C. Heating was continued for an hour, and then the mixture was allowed to cool to ambient temperature over 30 minutes. Analysis by HPLC/MS-ESI revealed the following: 92% consumption of SM, 75% product (N-(3-(3,6-dibromo-9H-carbazol-9-yl)-2-fluoropropyl)-3-methoxyaniline), 1% carbazole and 7% des-bromo decomposition products, 3% N-(3-(3,6-dibromo-9H-carbazol-9-yl)-2-hydroxypropyl)-1,1,1-trifluoro-N-(3-methoxyphenyl)methanesulfonamide and less than 5% elimination products (P7C3-S179). The reaction mixture was diluted with EtOAc and washed with water until white solid Al salts were no longer observed. The organic layer was then washed with 6M HCl a few times until yellow precipitate formed. The hydrochloride salt was filtered to give 3.60 g (85% yield). This salt formation removes the carbazole decomposition product, unreacted SM and some elimination products from the crude reaction mixture. The salt was free-based by vigorously stirring in a 1:1 mixture of methylene chloride and saturated bicarbonate solution until a translucent two-phase mixture was obtained. The organic layer was separated, and the aqueous phase was extracted 3 times with methylene chloride. The combined organics were dried over MgSO$_4$, filtered and condensed to give a solid that contained the des-brominated product as a minor impurity (ca. 3%). The solid was washed several times by stirring successively overnight in 40% Et$_2$O/hexanes and 30% DCM/hexanes and filtering the solid. For the final purification, solids from 3 reactions (19.5 g triflate SM total) were combined and assessed at 96% purity. The solid was stirred in 30% DCM/hexanes overnight and filtered to give 10.6 g of product in 98% purity and 69% yield.

$^1$H NMR (CDCl$_3$, 500 MHz) δ 8.16 (d, J=2.0 Hz, 2H), 7.56 (dd, J=1.9, 8.7 Hz, 2H), 7.31 (d, J=8.6 Hz, 2H), 7.11 (t, J=8.1 Hz, 1H), 6.36 (dd, J=2.2, 8.1 Hz, 1H), 6.23 (dd, J=2.0, 8.0 Hz, 1H), 6.15 (t, J=2.3 Hz, 1H), 5.11 (dddd, J=4.6, 5.8, 10.4, 47.7 Hz, 1H), 4.60 (dm, 2H), 3.95 (t, J=6.3 Hz, 1H), 3.75 (s, 3H), 4.39 (dm, 2H).

$^{13}$C NMR (CDCl$_3$, 100.5 MHz) δ 161.0, 148.6, 139.6, 130.4, 129.6, 123.9, 123.5, 112.9, 110.6 (d, $^4$J=2.0 Hz), 106.5, 103.9, 99.7, 90.7 (d, $^1$J=176.9 Hz), 55.3, 45.6 (d, $^2$J=22.1 Hz), 45.1 (d, $^2$J=25.1 Hz),

MS (ESI), m/z: calculated 503.98, found 504.9 (M+1)$^+$.

(E)-N-(3-(3,6-dibromo-9H-carbazol-9-yl)prop-1-en-1-yl)-1,1,1-trifluoro-N-(3-methoxyphenyl)methanesulfonamide (P7C3-S179)

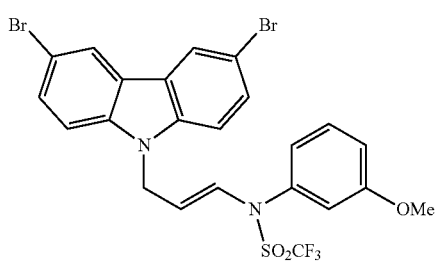

$^1$H NMR (CDCl$_3$, 400 MHz) δ 8.13 (d, J=1.9 Hz, 2H), 7.55 (dd, J=8.6, 2.0 Hz, 2H), 7.32 (t, J=8.2 Hz, 1H), 7.21 (d, J=8.7 Hz, 2H), 7.01 (d, J=13.4 Hz, 1H [olefin CH]), 6.98-6.93 (m, 1H), 6.80 (dd, J=7.9, 1.9 Hz, 1H), 6.73 (t, J=2.3 Hz, 1H), 4.83 (d, J=6.7 Hz, 2H), 4.76 (ddd, J=12.8, 7.2, 5.4 Hz, 1H), 3.75 (s, 3H).

MS (ESI), m/z: calculated 615.93, found 660.5 (M+HCOO)$^-$.

Example 6b

P7C3-S11: N-(3-(3,6-dibromo-9H-carbazol-9-yl)-2-fluoropropyl)-3-methoxy-N-methylaniline

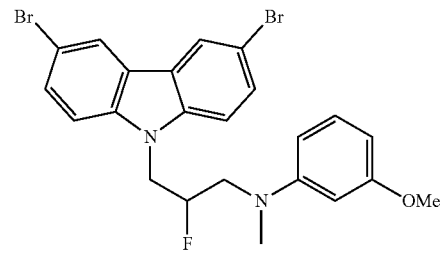 [SMILES: COc1cccc(N(C)CC(F)Cn2c3ccc(Br)cc3c3cc(Br)ccc32)c1]

The title compound of Example 6b was prepared according to the procedure described in Representative Procedure 4 except using 1-(3,6-dibromo-9H-carbazol-9-yl)-3-((3-methoxyphenyl)(methyl)-amino)propan-2-ol (see Example 23)

$^1$H NMR (CDCl$_3$, 500 MHz) δ 8.13 (d, 2H, J=1.9 Hz), 7.54 (dd, 2H, J=1.9, 8.8 Hz), 7.23 (d, 2H, J=8.7 Hz), 7.12 (t, 1H, J=8.2 Hz), 6.32 (dd, 1H, J=2.2, 8.1 Hz), 6.26 (dd, 1H, J=2.3, 8.0 Hz), 6.17 (t, 1H, J=2.4 Hz), 5.10 (dddd, 1H, J=4.6, 6.4, 10.7, 48.5 Hz), 4.37-4.48 (m, 2H), 3.72 (s, 3H), 3.60-3.71 (m, 1H), 3.53 (td, 1H, J=6.9, 15.9 Hz), 2.99 (s, 3H).

MS (ESI), m/z: 518.9 [M+1]$^+$ ([M+H]+ for C23H21Br2FN2O requires 519.0.)

Example 7a

P7C3-S3: 1-(3,6-dibromo-9H-carbazol-9-yl)-3-(3-methoxyphenylamino)-propan-2-one

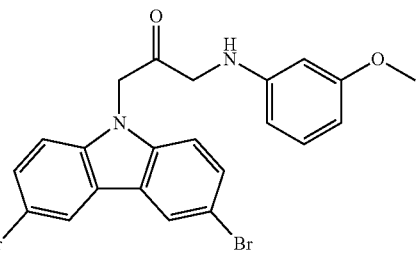

Trietheylamine (1.65 ml, 11.8 mmol) was added to a stirring solution of 1-(3,6-dibromo-9H-carbazol-9-yl)-3-(3-methoxyphenylamino)propan-2-ol (1.02 g, 2.02 mmol) in DMSO (21 ml). The solution was stirred for 30 minutes before addition of sulfur trioxide pyridine complex (0.659 g, 4.14 mmol). After stirring overnight, additional triethylamine (1.0 ml, 7.17 mmol) was added, followed by sulfur trioxide pyridine complex (0.663 mg, 4.17 mmol) an hour later. After stirring for 1 h, the orange solution was diluted with ~150 ml ethyl acetate and washed several times with water and then brine. The organic layer was dried over Na$_2$SO4, filtered and concentrated to yield brown foam. Flash chromatography on SiO$_2$ 100% (CH$_2$Cl$_2$+0.2% TEA) provided a higher R$_f$ ketone (thioether, 18%) and a lower R$_f$ ketone (Yield=40%).

Major product: $^1$H NMR (CDCl$_3$, 400 MHz) δ 8.18 (2H, J=1.9 Hz), 7.56 (dd, 2H, J=1.9, 8.7 Hz), 7.11 (d, 2H, J=8.8 Hz), 7.06 (t, 1H, J=8.1 Hz), 6.30 (dd, 1H, J=2.3, 8.2 Hz), 6.07 (d, 1H, J=2.0, 8.0 Hz), 6.11 (t, 1H, J=2.2 Hz), 5.08 (s, 2H,), 4.41 (t, 1H, J=4.8 Hz), 3.90 (d, 2H, J=5.1 Hz), 3.72 (s, 3H)

$^{13}$C NMR (CDCl$_3$, 126 MHz) δ=202.9, 161.1, 147.9 (2C), 139.5, 130.6 (2C), 129.9 (2C), 124.1 (2 C), 123.9 (2C), 113.5, 110.1 (2C), 103.7, 99.3, 55.4, 51.9, 51.0.

MS (ESI), m/z: 500.9 (M+1)$^+$ ([M+1]+ for C22H18Br2N2O2 requires 501.0)

Example 7b

P7C3-S4: 3-(3,6-dibromo-9H-carbazol-9-yl)-1-(3-methoxyphenylamino)-1-(methylthio)propan-2-one

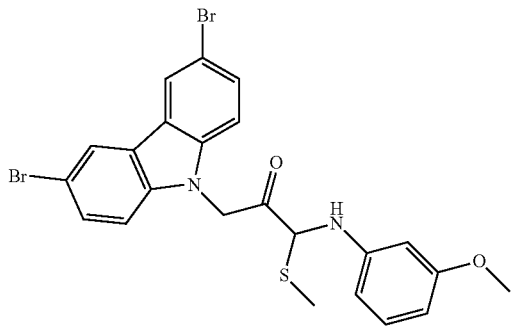 [SMILES: COc1cccc(NC(SC)C(=O)Cn2c3ccc(Br)cc3c3cc(Br)ccc32)c1]

The title compound of Example 7b was obtained as a minor product in the preparation of the title compound of Example 7a.

$^1$H NMR (CDCl$_3$, 400 MHz): δ 8.16 (d, 2H, J=2.0 Hz), 7.55 (dd, 2H, J=1.7, 8.8 Hz), 7.25 (d, J=8.8 Hz, 2H), 7.12 (t, 1H, J=8.4 Hz), 6.39 (dd, 1H, J=2.2, 8.2 Hz), 6.33 (dd, 1H, J=2.2, 8.0 Hz), 6.29 (t, 1H, J=2.2 Hz), 5.50 (d, 1H, J=18.0 Hz), 5.22 (d, 1H, J=18.4 Hz), 5.25 (d, J=8.0 Hz, 1H), 4.50 (d, J=8.0 Hz, 1H, exchangeable), 3.76 (s, 3H), 1.74 (s, 3H)

$^{13}$C NMR (CDCl$_3$, 126 MHz) δ=193.2, 160.9, 143.9 (2C), 139.8 (2C), 130.4, 129.8 (2C), 124.1, 123.7 (2C), 113.4 (2C), 110.3 (2C), 107.8, 104.7, 101.0, 60.3, 55.4, 48.9, 9.0

ESI m/z 498.9 [M-SMe+H]$^+$ ([M-SMe+H]+ for C$_{23}$H$_{20}$Br$_2$N$_2$O$_2$S requires 499.0.

HRMS m/z: 546.9675 [M+H]+ ([M+H]+ for C$_{23}$H$_{20}$Br$_2$N$_2$O$_2$S requires 545.9612.

Example 8

P7C3-S13: N-(3-(3,6-dibromo-9H-carbazol-9-yl)-2-methoxypropyl)-3-methoxyaniline

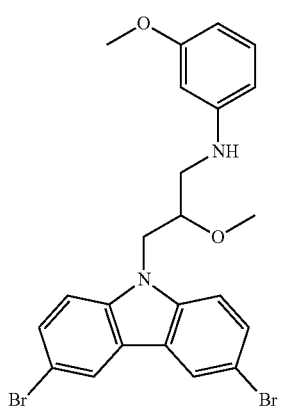 [SMILES: COc1cccc(NCC(Cn2c3ccc(Br)cc3c3cc(Br)ccc32)OC)c1]

Sodium hydride (9.0 mg, 0.23 mmol) was added to a stirring solution of 1-(3,6-dibromo-9H-carbazol-9-yl)-3-(3-methoxyphenylamino)propan-2-ol (99.3 mg, 0.20 mmol) in DMF 0.5 ml, 0.39 M). The solution was stirred at room temperature for about 70 minutes before the dropwise addition of a solution of methyl iodide (14 ml. 0.22 mol) in DMF (1.0 ml). The reaction was monitored by lc/ms for the consumption of SM and the appearance of O and N-methyl products. After 2.5 hours of stirring at r.t, conversion was about 30% and about 5% N-methyl product had formed. The reaction was stopped when an increase of N-Me to O-Me had been observed and conversion was about 50%. The brown solution was diluted with ethyl acetate and washed several times with water and finally brine. The organic layer was dried over Na$_2$SO$_4$, filtered and condensed. The mixture was purified by preparative TLC 30% EtOAc/hexanes.

$^1$H NMR (CDCl$_3$, 400 MHz) Λ 8.13 (s, 2H), 7.51 (dd, 2H, J=1.8, 8.8 Hz), 7.31 (d, 2H, J=8.7 Hz), 7.09 (t, 1H, J=8.2 Hz), 6.33 (dd, 1H, J=2.3, 8.3 Hz), 6.21 (dd, 1H, J=2.1, 8.0 Hz), 6.12 (m, 1H), 4.42 (m, 1H), 4.03 (bs, 1H), 3.85 (m, 1H), 3.74 (s, 3H), 3.29 (s, 3H), 3.09 (m, 2H)

$^{13}$C NMR (CDCl$_3$, 126 MHz) δ 161.0, 149.4, 139.8, 130.4, 129.5, 123.8, 123.5, 112.7, 110.9, 106.7, 103.6, 99.7, 78.2, 58.3, 55.3, 45.3, 44.3.

MS (ESI), m/z: 516.9 (M+1)$^+$ ([M+1]+ for C$_{23}$H$_{22}$Br$_2$N$_2$O$_2$ requires 517.0).

Example 9

P7C3-S2: 1-(3,6-Dimethyl-9H-carbazol-9-yl)-3-(3-methoxyphenylamino)propan-2-ol

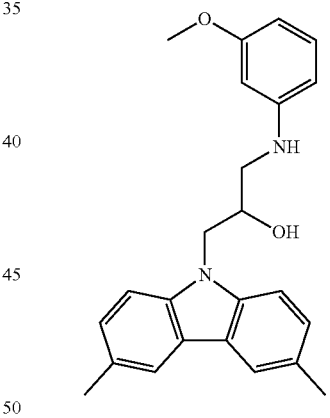

Step 1. Synthesis of 3,6-Dimethyl-9-(oxiran-2-ylmethyl)-9H-carbazole

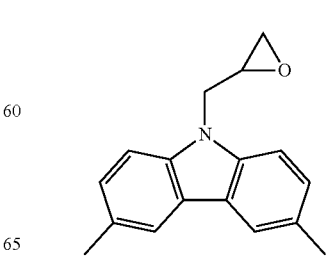

Following Representative Procedure 1, 3,6-dimethyl carbazole (Beyer et al., O. *J. Org. Chem.* 2003, 68, 2209-2215) was added to epichlorohydrin in 69% yield.

$^1$H NMR (CDCl$_3$, 500 MHz) Λ 7.84 (d, 2H, J=1.0 Hz), 7.30 (d, 2H, J=8.5 Hz), 7.26 (dd, 2H, J=1.0, 8.5 Hz), 4.54 (dd, 1H, J=3.5, 16.0 Hz), 4.35 (dd, 1H, J=4.5, 16.0 Hz), 3.30 (m, 1H), 2.76 (dd, 1H, J=4.0, 5.0 Hz), 2.52 (s, 6H), 2.51 (m, 1H)

Step 2. Synthesis of 1-(3,6-Dimethyl-9H-carbazol-9-yl)-3-(3-methoxyphenylamino)propan-2-ol

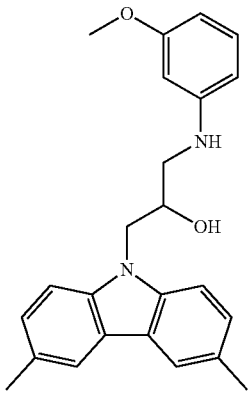

Following Representative procedure 2, 1-(3,6-Dimethyl-9H-carbazol-9-yl)-3-(3-methoxyphenylamino)propan-2-ol was prepared from 3,6-Dimethyl-9-(oxiran-2-ylmethyl)-9H-carbazole in 22% following purification by preparative TLC.

$^1$H NMR (CDCl$_3$, 500 MHz) δ 7.84 (d, 2H, J=0.5 Hz), 7.30 (d, 2H, J=8.0 Hz), 7.23 (d, 2H, J=8.0 Hz), 7.05 (t, 1H, J=8.0 Hz), 6.28 (dd, 1H, J=2.5, 8.0 Hz), 6.21 (dd, 1H, J=2.5, 8.0 Hz), 6.12 (dd, 1H, J=2.0, 2.5 Hz), 4.39 (m, 3H), 4.01 (br s, 1H), 3.68 (s, 3H), 3.31 (dd, 1H, J=3.0, 11.5 Hz), 3.17 (dd, 1H, J=6.5, 13.0 Hz), 2.51 (s, 6H), 2.13 (br s, 1H)

$^{13}$C NMR (CDCl$_3$, 125 MHz) δ 161.0, 149.5, 139.5 (2C), 130.3 (2C), 128.7, 127.3 (2C), 123.2 (2C), 120.5 (2C), 108.7 (2C), 106.7, 103.7, 99.5, 69.7, 55.2, 48.0, 47.4, 21.6 (2C).

ESI m/z 375.2 ([M+H]$^+$, C$_{24}$H$_{27}$N$_2$O$_2$ requires 375.2)

Example 10

P7C3-S14: 1-(3-Bromo-6-methyl-9H-carbazol-9-yl)-3-(3-methoxyphenylamino)-propan-2-ol

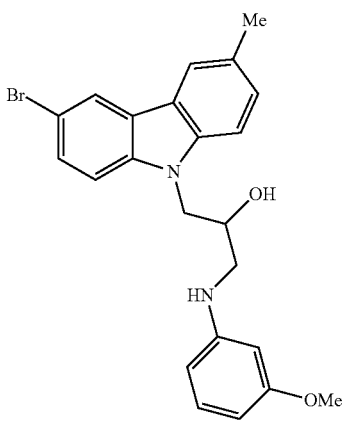 [SMILES: COc1cccc(NCC(O)Cn2c3ccc(C)cc3c3cc(Br)ccc32)c1]

Step 1. Synthesis of 3-Bromo-6-methyl-9-(oxiran-2-ylmethyl)-9H-carbazole

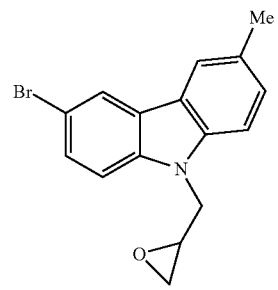 [SMILES: Cc1ccc2c(c1)c1cc(Br)ccc1n2CC1CO1]

Following Representative Procedure 2, Example 14 was prepared in 74% yield.

$^1$H NMR (CDCl$_3$, 500 MHz) δ 8.13 (d, 1H, J=1.5 Hz), 7.80 (d, 1H, J=1.0 Hz), 7.50 (dd, 1H, J=2.0, 8.5 Hz), 7.33-7.28 (m, 3H), 4.57 (dd, 1H, J=3.0, 15.5 Hz), 4.29 (dd, 1H, J=5.0, 15.5 Hz), 3.29 (m, 1H), 2.77 (dd, 1H, J=4.0, 4.5 Hz), 2.51 (s, 3H), 2.48 (dd, 1H, J=2.5, 4.5 Hz)

Step 2. Synthesis of 1-(3-Bromo-6-methyl-9H-carbazol-9-yl)-3-(3-methoxyphenylamino)-propan-2-ol

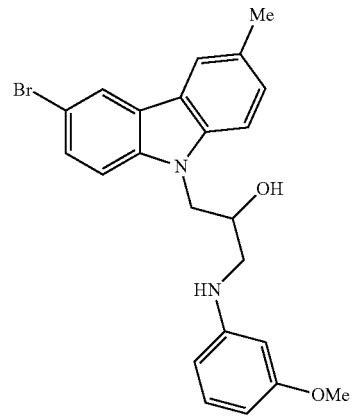 [SMILES: COc1cccc(NCC(O)Cn2c3ccc(C)cc3c3cc(Br)ccc32)c1]

Following Representative Procedure 2, Example was prepared 3-Bromo-6-methyl-9-(oxiran-2-ylmethyl)-9H-carbazole in 41% yield.

$^1$H NMR (CDCl$_3$, 500 MHz) δ 8.14 (d, 1H, J=2.0 Hz), 7.81 (s, 1H), 7.48 (dd, 1H, J=2.0, 8.5 Hz), 7.31 (d, 1H, J=5.0 Hz), 7.29 (br s, 1H), 7.06 (t, 1H, J=8.5 Hz), 6.29 (dd, 1H, J=2.0, 8.0 Hz), 6.21 (dd, 1H, J=2.0, 8.0 Hz), 6.11 (t, 1H, J=2.0 Hz), 4.37 (m, 3H), 3.99 (br s, 1H), 3.70 (s, 3H), 3.30 (dd, 1H, J=3.5, 13.5 Hz), 3.16 (dd, 1H, J=6.5, 13.5 Hz), 2.51 (s, 3H), 2.14 (br s, 1H)

$^{13}$C NMR (CDCl$_3$, 125 MHz) δ 161.0, 149.4, 139.8, 139.5, 130.3, 129.4, 128.5, 128.2, 124.7, 123.2, 122.3 120.7, 112.1, 110.6, 109.0, 106.7, 103.7, 99.6, 69.5, 55.3, 47.9, 47.4, 21.5.

ESI m/z 439.1 ([M+H]$^+$, C$_{23}$H$_{24}$BrN$_2$O$_2$ requires 439.1)

Example 11

P7C3-S15: 1-(3,6-Dichloro-9H-carbazol-9-yl)-3-(3-methoxyphenylamino)propan-2-ol

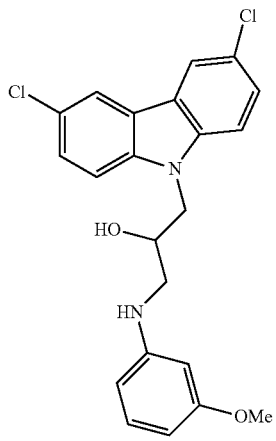 [SMILES: COc1cccc(NCC(O)Cn2c3ccc(Cl)cc3c3cc(Cl)ccc32)c1]

Step 1. Synthesis of 3,6-Dichloro-9-(oxiran-2-ylmethyl)-9H-carbazole

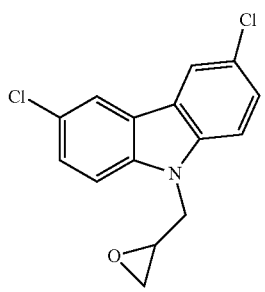 [SMILES: Clc1ccc2c(c1)c1cc(Cl)ccc1n2CC1CO1]

Following Representative Procedure 1, 3,6-Dichloro-9-(oxiran-2-ylmethyl)-9H-carbazole was prepared in 23% yield.

$^1$H NMR (CDCl$_3$, 600 MHz) δ 7.92 (d, 2H, J=1.8 Hz), 7.40 (dd, 2H, J=1.8, 9.0 Hz), 7.32 (d, 2H, J=9.0 Hz), 4.59 (dd, 1H, J=3.0, 16.2 Hz), 4.22 (dd, 1H, J=5.4, 16.2 Hz), 3.27 (m, 1H), 2.78 (dd, 1H, J=4.2, 4.8 Hz), 2.46 (dd, 1H, J=2.4, 4.8 Hz)

Step 2. Synthesis of 1-(3,6-Dichloro-9H-carbazol-9-yl)-3-(3-methoxyphenylamino)propan-2-ol

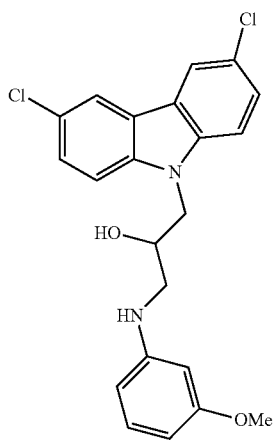 [SMILES: COc1cccc(NCC(O)Cn2c3ccc(Cl)cc3c3cc(Cl)ccc32)c1]

Following Representative Procedure 2, 1-(3,6-dichloro-9H-carbazol-9-yl)-3-(3-methoxyphenylamino)propan-2-ol was prepared from 3,6-Dichloro-9-(oxiran-2-ylmethyl)-9H-carbazole in 37% yield.

$^1$H NMR (CDCl$_3$, 500 MHz) δ 7.95 (d, 2H, J=2.0 Hz), 7.38 (dd, 2H, J=2.0, 8.5 Hz), 7.33 (d, 2H, J=9.0 Hz), 7.06 (t, 1H, J=8.0 Hz), 6.30 (dd, 1H, J=2.0, 8.0 Hz), 6.20 (dd, 1H, J=2.0, 8.0 Hz), 6.11 (dd, 1H, J=2.0, 2.5 Hz), 4.30-4.35 (m, 3H), 3.70 (s, 3H), 3.28 (dd, 1H, J=3.5, 13.0 Hz), 3.13 (dd, 1H, J=6.5, 13.0 Hz)

$^{13}$C NMR (CDCl$_3$, 150 MHz) δ 161.0, 149.3, 139.7, 130.4 (2C), 126.9 (2C), 125.5 (2C), 123.4 (2C), 120.4 (2C), 110.5 (2C), 106.7, 103.8, 99.8, 69.6, 55.3, 48.0, 47.5.

ESI m/z 415.0 ([M+H]$^+$, C$_{22}$H$_{20}$Cl$_2$N$_2$O$_2$ requires 415.1)

Example 12

P7C3-S18: 1-(5-bromo-2,3-dimethyl-1H-indol-1-yl)-3-(phenylamino)propan-2-ol

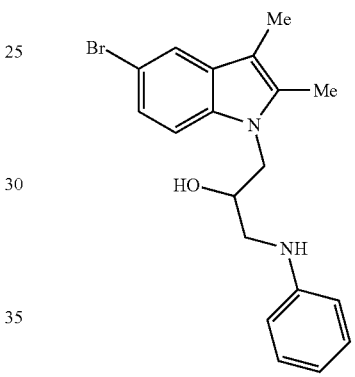

Step 1. Synthesis of 5-Bromo-2,3-dimethyl-1H-indole

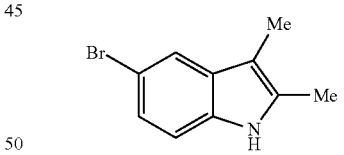

Following a published procedure (Gundersen, E. G. U.S. Patent App. Publ. US 2005/070592) 2-Butanone (0.11 mL, 1.278 mmol) was added to a solution of 4-bromophenylhydrazine hydrochloride (0.300 g, 1.342 mmol in EtOH (3.8 mL). The mixture was heated to reflux for 22 h, concentrated in vacuo, and partitioned between EtOAc and 1N HCl. The organic layer was washed with H$_2$O and saturated aqueous NaHCO$_3$, dried over Na$_2$SO$_4$, filtered, and concentrated. The crude residue was purified by chromatography (SiO$_2$, 0-20% EtOAc/Hexane) to afford the desired indole as a pink powder (200 mg, 67%).

$^1$H NMR (CDCl$_3$, 500 MHz) δ 7.69 (br s, 1H), 7.55 (d, 1H, J=2.0 Hz), 7.15 (dd, 1H, J=2.0, 8.5 Hz), 7.09 (dd, 1H, J=0.5, 8.5 Hz), 2.34 (s, 3H), 2.15 (d, 3H, J=0.5 Hz). ESI m/z 224.0 ([M+H]$^+$, C$_{10}$H$_{11}$BrN requires 224.0)

Step 2. Synthesis of 5-Bromo-2,3-dimethyl-1-(oxiran-2-ylmethyl)-1H-indole

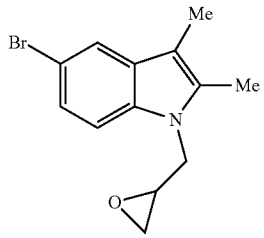 [SMILES: Cc1c(C)n(CC2CO2)c2ccc(Br)cc12]

Following Representative Procedure 1, 5-bromo-2,3-dimethyl-1-(oxiran-2-ylmethyl)-1H-indole was prepared from 5-Bromo-2,3-dimethyl-1H-indole in 48% yield.

$^1$H NMR (CDCl$_3$, 500 MHz) δ 7.58 (d, 1H, J=2.0 Hz), 7.20 (dd, 1H, J=2.0, 8.5 Hz), 7.10 (d, 1H, J=8.5 Hz), 4.35 (dd, 1H, J=3.0, 16.0 Hz), 4.09 (dd, 1H, J=4.5, 16.0 Hz), 3.17 (m, 1H), 2.72 (t, 1H, J=4.5 Hz), 2.35 (dd, 1H, J=3.0, 5.0 Hz), 2.33 (s, 3H), 2.19 (s, 3H). ESI m/z 280.0 ([M+H]$^+$, C$_{13}$H$_{15}$BrNO requires 280.0)

Step 3. Synthesis of 1-(5-bromo-2,3-dimethyl-1H-indol-1-yl)-3-(phenylamino)propan-2-ol

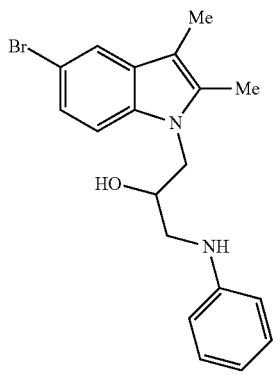 [SMILES: Cc1c(C)n(CC(O)CNc2ccccc2)c2ccc(Br)cc12]

Following Representative Procedure 2, 1-(5-bromo-2,3-dimethyl-1H-indol-1-yl)-3-(phenylamino)propan-2-ol was prepared from 5-Bromo-2,3-dimethyl-1-(oxiran-2-ylmethyl)-1H-indole in 39% yield.

$^1$H NMR (CDCl$_3$, 500 MHz) δ 7.58 (d, 1H, J=2.0 Hz), 7.17 (dd, 2H, J=7.0, 8.5 Hz), 7.11 (d, 1H, J 8.5 Hz), 6.75 (t, 1H, J=7.0 Hz), 6.60 (d, 2H, J=8.5 Hz), 4.17 (m, 1H), 4.15 (m, 2H), 3.27 (dd, 1H, J 3.0, 8.5 Hz), 3.12 (dd, 1H, J=7.0, 13.0 Hz), 2.34 (s, 3H), 2.19 (s, 3H)

$^{13}$C NMR (CDCl$_3$, 125 MHz) δ 147.9, 135.1, 134.3, 130.6, 129.6 (2C), 123.6, 120.9, 118.6, 113.7 (2C), 112.5, 110.5, 107.1, 69.9, 47.7, 47.4, 10.7, 9.0. ESI m/z 373.0 ([M+H]$^+$, C$_{19}$H$_{22}$BrN$_2$O requires 373.1).

Example 13

P7C3-S26: 1-(3,6-Dibromo-9H-pyrido[3,4-b]indol-9-yl)-3-(phenylamino)propan-2-ol

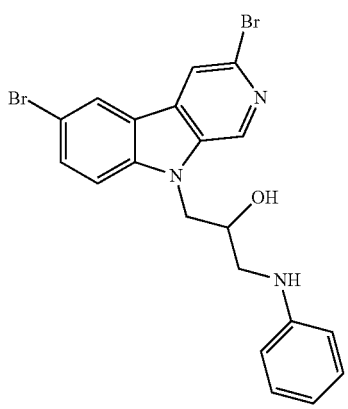 [SMILES: OC(CNc1ccccc1)Cn1c2ccc(Br)cc2c2cc(Br)ncc21]

Step 1. Synthesis of 3,6-Dibromo-β-carboline

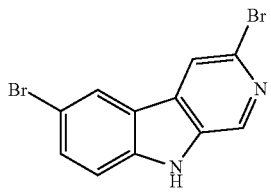 [SMILES: Brc1ccc2[nH]c3cnc(Br)cc3c2c1]

Following a literature procedure (Ponce, M. A.; Erra-Balsells, R. *J. Heterocyclic Chem.* 2001, 38, 1087) β-Carboline (0.100 g, 0.595 mmol) and SiO$_2$ (1.00 g) were suspended in CH$_2$Cl$_2$ (15 mL). N-Bromosuccinimde (0.212 g, 1.189 mmol) was dissolved in CH$_2$Cl$_2$ (15 mL) and the solution was added to the carboline mixture slowly via syringe in the absence of light. The reaction was stirred at ambient temperature for 2.5 h, after which the silica gel was filtered off and washed 3× CH$_2$Cl$_2$. The combined organic layer was extracted with 0.1 M NaOH and saturated aqueous NaCl, dried over Na$_2$SO$_4$, filtered, and concentrated in vacuo. The crude product was purified by chromatography (SiO$_2$, 0-100% EtOAc/Hexane) to afford the desired 3,6-dibrominated carboline (25 mg, 13%) as well as 6,8-dibrominated carboline (15 mg, 8%) and the tribrominated carboline (36 mg, 19%).

$^1$H NMR (d$_6$-DMSO, 500 MHz) δ 8.72 (s, 1H), 8.58 (d, 1H, J=1.5 Hz), 8.48 (s, 1H), 7.70 (dd, 1H, J 1.5, 9.0 Hz), 7.58 (d, 1H, J=9.0 Hz). ESI m/z 326.9 ([M+H]$^+$, C$_{11}$H$_7$Br$_2$N$_2$ requires 326.9).

Step 2. Synthesis of 3,6-Dibromo-9-(oxiran-2-ylmethyl)-9H-pyrido[3,4-b]indole

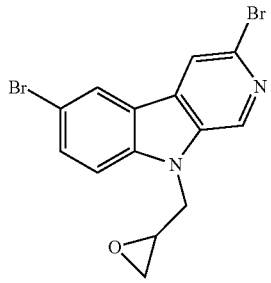 [SMILES: Brc1ccc2c(c1)c1cc(Br)ncc1n2CC1CO1]

Following Representative Procedure 1, 3,6-dibromo-9-(oxiran-2-ylmethyl)-9H-pyrido[3,4-b]indole was prepared from 3,6-dibromo-1-carboline in 73% yield.

$^1$H NMR (CDCl$_3$, 400 MHz) δ 8.62 (d, 1H, J=0.8 Hz), 8.17 (d, 1H, J=2.0 Hz), 8.02 (d, 1H, J=1.2 Hz), 7.69 (dd, 1H, J=2.0, 8.8 Hz), 7.41 (d, 1H, J=8.8 Hz), 5.34 (br s, 1H), 4.73 (dd, 1H, J=2.4, 16.0 Hz), 4.27 (dd, 1H, J=5.2, 16.0 Hz), 3.32 (m, 1H), 2.83 (dd, 1H, J=4.0, 4.4 Hz), 2.49 (dd, 1H, J=2.4, 4.4 Hz).

ESI m/z 382.9 ([M+H]$^+$, C$_{14}$H$_{11}$Br$_2$N$_2$O requires 382.9).

Step 3. Synthesis of 1-(3,6-Dibromo-9H-pyrido[3,4-b]indol-9-yl)-3-(phenylamino)propan-2-ol

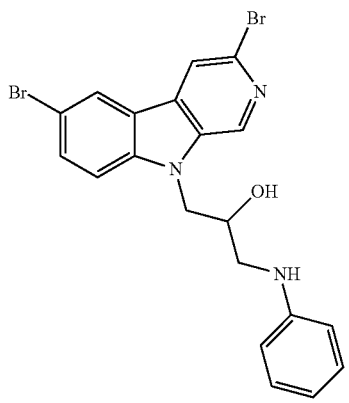

Following Representative Procedure 2, 1-(3,6-dibromo-9H-pyrido[3,4-b]indol-9-yl)-3-(phenylamino)propan-2-ol was prepared from 3,6-dibromo-9-(oxiran-2-ylmethyl)-9H-pyrido[3,4-b]indole in 14% yield after purification by preparative TLC.

$^1$H NMR (CDCl$_3$, 500 MHz) δ 8.64 (s, 1H), 8.18 (d, 1H, J=2.0 Hz), 7.99 (s, 1H), 7.66 (dd, 1H, J=1.5, 9.0 Hz), 7.40 (d, 1H, J=9.0 Hz), 7.18 (dd, 2H, J=7.5 Hz), 6.76 (t, 1H, J=7.5 Hz), 6.63 (d, 2H, J=8.5 Hz), 5.33 (br s, 1H), 4.38-4.49 (m, 3H), 3.37 (dd, 1H, J=4.0, 13.0 Hz), 3.21 (dd, 1H, J=7.0, 13.0 Hz)

$^{13}$C NMR (CDCl$_3$, 125 MHz) δ 147.7, 141.2, 137.0, 132.6, 132.5, 130.9, 130.1, 129.7 (2C), 125.0, 122.0, 119.0, 118.6, 113.8 (2C), 113.4, 111.9, 69.6, 48.1, 47.9. ESI m/z 475.9 ([M+H]$^+$, C$_{20}$H$_{18}$Br$_2$N$_3$O requires 476.0)

Example 14

P7C3-S36: 1-(3-Azidophenylamino)-3-(3,6-dibromo-9H-carbazol-9-yl)propan-2-ol

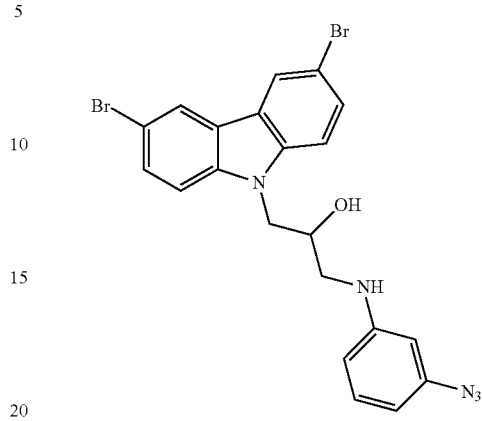

Following Representative Procedure 2, Example 14 was prepared in 14% yield.

$^1$H NMR (CDCl$_3$, 500 MHz) δ 8.13 (d, 2H, J=2.0 Hz), 7.53 (dd, 2H, J=2.0, 8.5 Hz), 7.31 (d, 2H, J=8.5 Hz), 7.12 (t, 1H, J=8.0 Hz), 6.44 (dd, 1H, J=1.5, 8.0 Hz), 6.36 (dd, 1H, J=1.5, 8.0 Hz), 6.20 (dd, 1H, J=2.0 Hz), 4.35-4.41 (m, 3H), 4.10 (br s, 1H), 3.31 (dd, 1H, J=3.0, 13.0 Hz), 3.17 (dd, 1H, J=6.5, 13.0 Hz), 2.11 (br s, 1H)

ESI m/z 513.9 ([M+H]$^+$, C$_{21}$H$_{18}$Br$_2$N$_5$O requires 514.0)

Example 15

P7C3-S34: 1,3-Bis(3,6-dibromo-9H-carbazol-9-yl)propan-2-ol

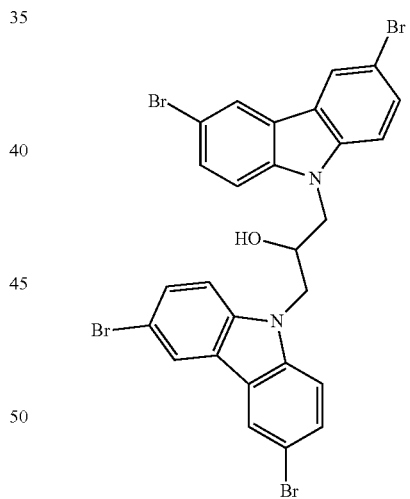

3,6-Dibromocarbazole (0.050 g, 0.154 mmol) was dissolved in DMF (1.5 mL) and cooled to 0° C. NaH (60% dispersion in mineral oil, 0.007 g, 0.169 mmol) was added and the reaction was stirred for 45 min at 0° C. 3,6-Dibromo-9-(oxiran-2-ylmethyl)-9H-carbazole (0.059 g, 0.154 mmol) was added and the reaction was stirred at ambient temperature for 24 h. Upon consumption of the starting material by TLC, the reaction was partitioned between EtOAc and H$_2$O. The aqueous layer was washed 3× with EtOAc, and the combined organics were washed with saturated aqueous NaCl, dried over Na$_2$SO$_4$, filtered, and concentrated in vacuo. The crude residue was purified by chromatography (SiO$_2$, 0-50% EtOAc/Hexane) to afford the desired product (37 mg, 34%).

¹H NMR (acetone-d₆, 400 MHz) δ 8.36 (d, 4H, J=2.0 Hz), 7.64 (d, 4H, J=8.8 Hz), 7.56 (dd, 4H, J 2.0, 8.8 Hz), 4.72 (m, 5H), 2.78 (br s, 1H)
¹³C NMR (acetone-d₆, 100 MHz) δ 141.2 (4C), 129.8 (4C), 124.6 (4C), 124.1 (4C), 112.9 (4C), 112.7 (4C), 70.3, 48.3 (2C). ESI m/z 747.0 ([M+CO₂H]⁻, $C_{28}H_{19}Br_4N_2O_3$ requires 746.8)

Example 16

P7C3-S35: 1-(9H-Carbazol-9-yl)-3-(3,6-dibromo-9H-carbazol-9-yl)propan-2-ol

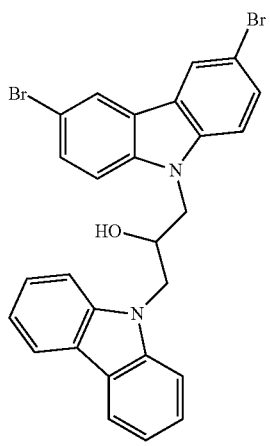 [SMILES: OC(Cn1c2ccccc2c2ccccc21)Cn1c2ccc(Br)cc2c2cc(Br)ccc21]

Following a procedure analogous to that used to prepare Example 15, Example 16 was prepared in 48% yield.
¹H NMR (acetone-d₆, 400 MHz) δ 8.36 (m, 2H), 8.14 (d, 2H, J=8.0 Hz), 7.63 (d, 2H, J=8.4 Hz), 7.55 (s, 2H), 7.42 (dt, 2H, J=1.2, 7.2 Hz), 7.20 (dt, 2H, J=0.8, 7.2 Hz), 4.76 (m, 1H), 4.64-4.72 (m, 4H), 2.77 (br s, 1H).
¹³C NMR (acetone-d₆, 100 MHz) δ 142.0 (2C), 141.0 (2C), 129.8 (2C), 126.6 (2C), 124.5 (2C), 124.1 (2C), 123.8 (2C), 121.0 (2C), 119.9 (2C), 112.7 (2C), 112.6 (2C), 110.5 (2C), 70.3, 48.4, 48.1.
ESI m/z 591.0 ([M+CO₂H]⁻, $C_{28}H_{21}Br_2N_2O_3$ requires 591.0).

Example 17

P7C3-S31: 3-(3,6-Dibromo-9H-carbazol-9-yl)-2-hydroxy-N-(3-methoxyphenyl)-propanamide

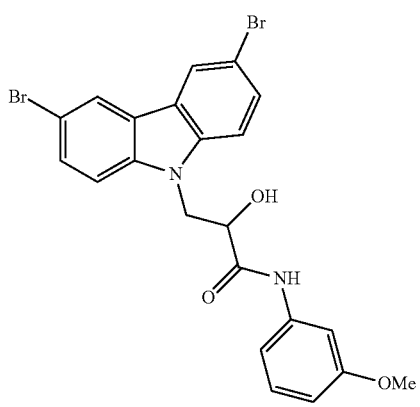 [SMILES: COc1cccc(NC(=O)C(O)Cn2c3ccc(Br)cc3c3cc(Br)ccc32)c1]

Step 1. Synthesis of Methyl 3-(3,6-Dibromo-9H-carbazol-9-yl)-2-hydroxypropanoate

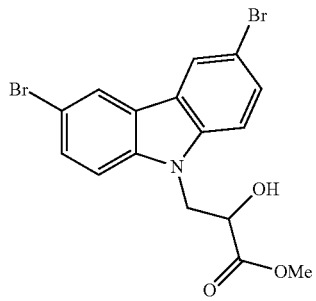 [SMILES: COC(=O)C(O)Cn1c2ccc(Br)cc2c2cc(Br)ccc21]

3,6-Dibromocarbazole (0.300 g, 0.923 mmol) was dissolved in DMF (1.2 mL) and cooled to 0° C. NaH (60% dispersion in mineral oil, 0.074 g, 1.846 mmol) was added and the reaction stirred for 1 h at 0° C. Methyl glycidate (0.471 g, 4.615 mmol) was added and the reaction was stirred and warmed to ambient temperature over 3.5 h. Upon completion by TLC the reaction mixture was partitioned between EtOAc and H₂O. The aqueous layer was extracted 3× with EtOAc, and the combined organics were washed with saturated aqueous NaCl, dried over Na₂SO₄, filtered, and concentrated in vacuo. The crude residue was purified by chromatography (SiO₂, 0-30% EtOAc/Hexane) to afford the desired product (125 mg, 32%).
¹H NMR (CDCl₃, 500 MHz) δ 8.10 (d, 2H, J=2.0 Hz), 7.53 (dd, 2H, J=2.0, 9.0 Hz), 7.36 (d, 2H, J=9.0 Hz), 4.63-4.55 (m, 3H), 3.69 (s, 3H), 2.94 (d, 1H, J=5.5 Hz).
ESI m/z 425.8 ([M+H]⁺, $C_{16}H_{14}Br_2NO_3$ requires 425.9)

Step 2. Synthesis of 3-(3,6-Dibromo-9H-carbazol-9-yl)-2-hydroxypropanoic acid

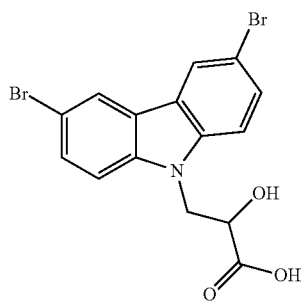 [SMILES: O=C(O)C(O)Cn1c2ccc(Br)cc2c2cc(Br)ccc21]

NaOH (0.64 mL, 1M solution in H₂O) was added to a suspension of methyl 3-(3,6-dibromo-9H-carbazol-9-yl)-2-hydroxypropanoate (0.055 g, 0.129 mmol) in EtOH (2.6 mL) and the reaction was stirred at ambient temperature for 2.5 h. The reaction was concentrated in vacuo and the residue was acidified with 1N aqueous HCl. The mixture was extracted with EtOAc (3×), and the combined organics were washed with saturated aqueous NaCl, dried over Na₂SO₄, filtered, and concentrated in vacuo to afford the desired product as a white solid (53 mg, 99%).
¹H NMR (CDCl₃, 500 MHz) δ 8.10 (d, 2H, J=1.5 Hz), 7.52 (dd, 2H, J=1.5, 8.5 Hz), 7.40 (d, 2H, J=9.0 Hz), 4.68 (m, 2H), 4.60 (dd, 1H, J=6.5, 15.5 Hz).
ESI m/z 411.9 ([M+H]⁺, $C_{15}H_{12}Br_2NO_3$ requires 411.9)

Step 3. Synthesis of 3-(3,6-Dibromo-9H-carbazol-9-yl)-2-hydroxy-N-(3-methoxyphenyl)-propanamide

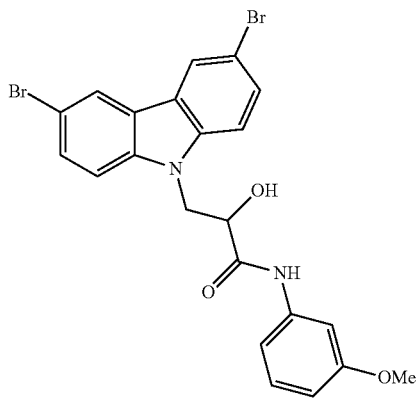 [SMILES: COc1cccc(NC(=O)C(O)Cn2c3ccc(Br)cc3c3cc(Br)ccc32)c1]

3-(3,6-Dibromo-9H-carbazol-9-yl)-2-hydroxypropanoic acid (0.025 g, 0.061 mmol) was suspended in anhydrous CH$_2$Cl$_2$ and cooled to 0° C. Thionyl chloride (0.005 mL, 0.073 mmol) was added dropwise and the reaction was stirred at 0° C. for 1 h. m-Anisidine (0.008 mL, 0.073 mmol) and Et$_3$N (0.010 mL, 0.073 mmol) were added and the reaction was allowed to warm to ambient temperature over 2.5 h. Upon completion, the solution was partitioned between EtOAc and H$_2$O. The aqueous layer was washed 3× with EtOAc, and the combined organics were washed with saturated aqueous NaCl, dried over Na$_2$SO$_4$, filtered, and concentrated in vacuo. The crude residue was purified by chromatography (SiO$_2$, 0-30% EtOAc/Hexane) to afford the desired product (15 mg, 48%).

$^1$H NMR (acetone-d$_6$, 500 MHz) δ 9.22 (br s, 1H), 8.34 (d, 2H, J=1.5 Hz), 7.65 (d, 2H, J=8.5 Hz), 7.59 (dd, 2H, J=4.0, 8.5 Hz), 7.42 (dd, 1H, J=2.0 Hz), 7.24 (m, 1H), 7.20 (dd, 1H, J=8.0 Hz), 6.67 (dd, 1H, J=2.0, 8.0 Hz), 5.56 (br s, 1H), 4.82 (m, 1H), 4.73 (m, 2H), 3.77 (s, 3H)

$^{13}$C NMR (CDCl$_3$, 100 MHz) δ 170.9, 161.1, 141.1, 140.3, 130.3 (2C), 129.8 (2C), 124.6 (2C), 124.0 (2C), 113.1 (2C), 112.8 (2C), 112.7, 110.5, 106.4, 72.7, 55.6, 48.4.

ESI m/z 514.9 ([M–H]$^-$, C$_{22}$H$_{17}$Br$_2$N$_2$O$_3$ requires 515.0)

Example 18

Ethyl 5-(2-Hydroxy-3-(3-methoxyphenylamino)propyl)-8-methyl-3,4-dihydro-1H-pyrido[4,3-b]indole-2(5H)-carboxylate

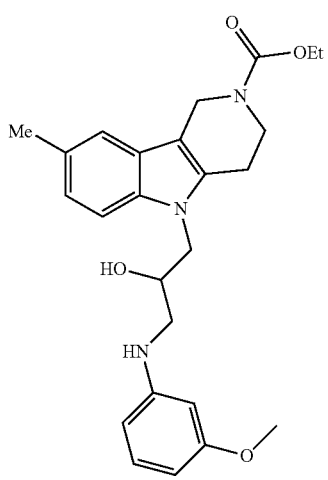 [SMILES: CCOC(=O)N1CCc2c(c3cc(C)ccc3n2CC(O)CNc2cccc(OC)c2)C1]

Step 1. Synthesis of Ethyl 8-Methyl-3,4-dihydro-1H-pyrido[4,3-b]indole-2(5H-carboxylate

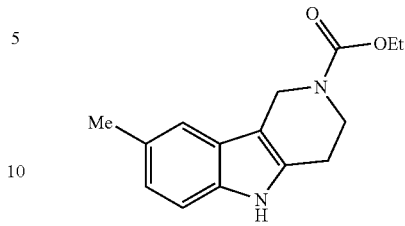

Following a literature procedure (Harbert et al., *J Med. Chem.* 1980, 23, 635-643) p-tolylhydrazine hydrochloride (0.500 g, 3.15 mmol) and 1-carbethoxy-4-piperidone (0.18 mL, 1.17 mmol) were suspended in EtOH (0.880 mL) and heated to reflux for 2 hours. The reaction mixture was removed from heat and allowed to stand overnight at ambient temperature. The resulting mixture was filtered and washed with 50% aqueous EtOH to afford the desired product as a beige powder (259 mg, 86%).

$^1$H NMR (CDCl$_3$, 500 MHz) δ 7.73 (br s, 1H), 7.23 (s, 1H), 7.18 (d, 1H, J=8.0 Hz), 6.96 (d, 1H, J=8.0 Hz), 4.64 (br s, 2H), 4.18 (q, 2H, J=7.0 Hz), 3.85 (m, 2H), 2.81 (br s, 2H), 2.42 (s, 3H), 1.28 (t, 3H, J=7.0 Hz).

Step 2. Synthesis of Ethyl 8-Methyl-5-(oxiran-2-ylmethyl)-3,4-dihydro-1H-pyrido[4, 3-b]indole-2(5H)-carboxylate

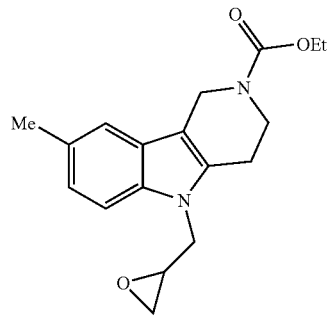 [SMILES: CCOC(=O)N1CCc2c(c3cc(C)ccc3n2CC2CO2)C1]

Ethyl 8-methyl-3,4-dihydro-1H-pyrido[4,3-b]indole-2(5H)-carboxylate (0.025 g, 0.097 mmol) was dissolved in anhydrous degassed THF and was cooled to −78° C. A solution of n-BuLi (0.082 mL, 1.78 M in hexanes) was added dropwise and the reaction was stirred at −78° C. for 30 min. Epibromohydrin (0.016 mL, 0.194 mmol) was added and the reaction was allowed to warm slowly to ambient temperature. After 3.5 h, epibromohydrin (0.008 mL, 0.097 mmol) was added and the reaction was stirred overnight at ambient temperature. Upon completion, saturated aqueous NH4Cl was added to quench the reaction and the mixture was extracted with EtOAc (3×). The combined organic layers were washed with brine, dried over Na$_2$SO$_4$, filtered, and concentrated. The crude residue was purified by chromatography (SiO$_2$, 0-50% EtOAc/Hexane) to afford the desired product (15 mg, 49%).

$^1$H NMR (CDCl$_3$, 500 MHz) δ 7.19 (m, 1H), 7.00 (d, 1H, J=8.5 Hz), 4.65 (br s, 2H), 4.32 (dd, 1H, J=3.0, 15.5 Hz), 4.18 (q, 2H, J=7.0 Hz), 4.08 (dd, 1H, J=5.0, 15.5 Hz), 3.85 (m, 2H), 3.18 (m, 1H), 2.81 (br s, 2H), 2.73 (dd, 1H, J=4.0, 4.5 Hz), 2.44 (s, 3H), 2.38 (br s, 1H), 1.29 (t, 3H, J=7.0 Hz)

Step 3. Synthesis of Ethyl 5-(2-Hydroxy-3-(3-methoxyphenylamino)propyl)-8-methyl-3,4-dihydro-1H-pyrido[4, 3-b]indole-2(5H)-carboxylate

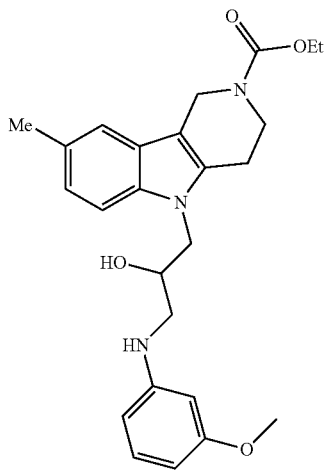 [SMILES: CCOC(=O)N1CCc2c(c3cc(C)ccc3n2CC(O)CNc2cccc(OC)c2)C1]

Following a literature procedure (Chakraborti et al., *Eur. J. Org. Chem.* 2004, 3597-3600) LiBr (0.001 g, 0.010 mmol) and m-anisidine (0.011 mL, 0.102 mmol) were added to ethyl 8-Methyl-5-(oxiran-2-ylmethyl)-3,4-dihydro-1H-pyrido[4,3-b]indole-2(5H)-carboxylate (0.032 g, 0.102 mmol) and stirred vigorously at ambient temperature overnight. Upon completion the reaction was partitioned between EtOAc/H$_2$O, and the organic layer was concentrated to an orange oil. The crude residue was purified by chromatography (SiO$_2$, 0-50% EtOAc/Hexane) to afford the desired product (30 mg, 67%).

$^1$H NMR (CDCl$_3$, 500 MHz) δ 7.23 (br s, 1H), 7.17 (d, 1H, J=8.0 Hz), 7.05 (dd, 1H, J=8.0 Hz), 6.97 (d, 1H, J=8.5 Hz), 6.28 (dd, 1H, J=1.5, 8.0 Hz), 6.19 (d, 1H, J=8.0 Hz), 6.11 (br s, 1H), 4.64 (br s, 2H), 4.18 (m, 1H), 4.16 (q, 2H, J=7.5 Hz), 4.12 (m, 1H), 3.80 (br s, 2H), 3.71 (s, 3H), 3.23 (dd, 1H, J=3.5, 13.0 Hz), 3.07 (dd, 1H, J=7.5, 13.0 Hz), 2.83 (m, 1H), 2.76 (m, 1H), 2.42 (s, 3H), 1.27 (t, 3H, J=7.0 Hz).

ESI m/z 438.2 ([M+H]$^+$, C$_{25}$H$_{32}$N$_3$O$_4$ requires 438.2).

Example 19

P7C3-S26: 4-(3,6-dibromo-9H-carbazol-9-yl)-1-(phenylamino)butan-2-ol

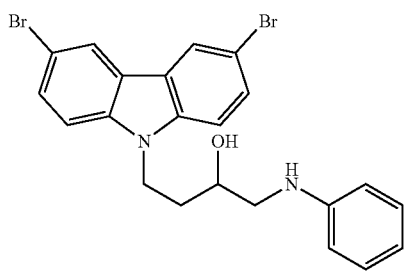 [SMILES: OC(CCn1c2ccc(Br)cc2c2cc(Br)ccc21)CNc1ccccc1]

Step 1. Synthesis of 3,6-dibromo-9-(2-(oxiran-2-yl)ethyl)-9H-carbazole

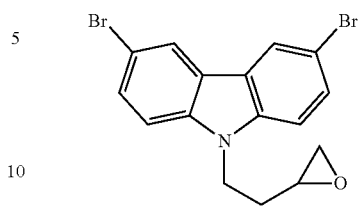

Crushed KOH (0.0054 g, 0.0954 mmol, 1.2 equiv) was added to 3,6-dibromocarbazole (0.0258 g, 0.0795 mmol, 1 equiv.) in 0.5 mL DMF solution and the mixture was stirred for 30 min. 1-Bromo-3,4-epoxybutane (0.0300 g, 0.199 mmol) in 0.5 mL DMF solution was dropwise added into the mixture and it was stirred at room temperature for overnight. Reaction crude was diluted with 20 mL EtOAc and washed with water 5×10 mL. The organic layer was dried over anhydrous Na$_2$SO$_4$ and evaporated to afford 31.2 mg white solid as product, yield 97.9%.

$^1$H NMR (CDCl$_3$, 400 MHz) δ ppm 1.65-1.81 (m, 1H) 2.13-2.27 (m, 1H) 2.34 (dd, J=4.88, 2.64 Hz, 1H) 2.64 (dd, J=4.78, 4.05 Hz, 1H) 2.69-2.80 (m, 1H) 4.26-4.54 (m, 2H) 7.27 (d, J=8.69 Hz, 2H) 7.50 (dd, J=8.69, 1.90 Hz, 2H) 8.08 (d, J=1.90 Hz, 2H)

Step 2. Synthesis of 4-(3,6-dibromo-9H-carbazol-9-yl)-1-(phenylamino)butan-2-ol

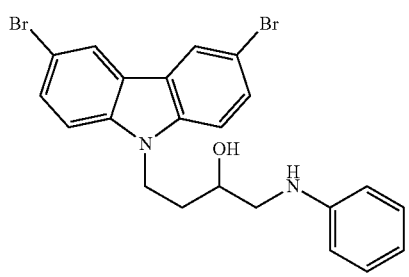 [SMILES: OC(CCn1c2ccc(Br)cc2c2cc(Br)ccc21)CNc1ccccc1]

According to Representative Procedure 2, Example 19 was isolated as a white solid in 31% yield.

$^1$H NMR (CDCl$_3$, 400 MHz) δppm 1.87-1.98 (m, 1H) 2.05-2.14 (m, 1H) 2.99-3.07 (dd, J=13.24, 3.43 Hz, 1H) 3.09-3.17 (dd, J=13.24, 8.27 Hz, 1H) 3.60-3.74 (m, 1H) 4.39-4.48 (m, 1H) 4.51-4.60 (m, 1H) 6.57 (d, J=7.71 Hz, 2H) 6.74 (t, J=7.34 Hz, 1H) 7.15 (dd, J=8.27, 7.59 Hz, 2H) 7.38 (d, J=8.69 Hz, 2H) 7.56 (dd, J=8.69, 1.90 Hz, 2H) 8.14 (d, J=1.85 Hz, 2H)

$^{13}$C NMR (CDCl$_3$, 500 MHz) δ=148.1, 139.6, 129.6, 129.4, 123.8, 123.6, 118.7, 113.6, 112.4, 110.8, 67.7, 51.0, 39.9, 33.7.

m/z (ESI): 486.9 (M+H$^+$) ([M+1] for C22H20Br2N2O requires 467.0)

Example 20

P7C3-S33: N-(3-(3,6-dibromo-9H-carbazol-9-yl)propyl)aniline

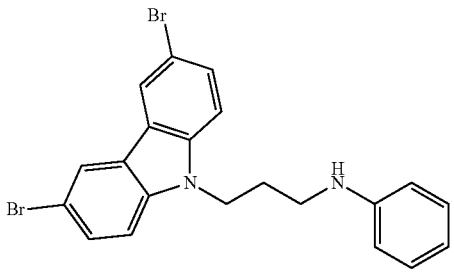 [SMILES: Brc1ccc2c(c1)c1cc(Br)ccc1n2CCCNc1ccccc1]

Step 1. Synthesis of 3,6-dibromo-9-(3-bromopropyl)-9H-carbazole

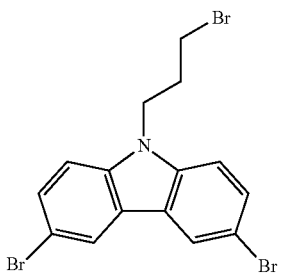 [SMILES: BrCCCn1c2ccc(Br)cc2c2cc(Br)ccc21]

Crushed KOH (0.0673 g, 1.20 mmol, 1.2 equiv) was added to 3,6-dibromocarbazole (0.3250 g, 1.00 mmol) in 2 mL DMF solution and the mixture was stirred for 30 min. 1,3-dibromopropane (0.5047 g, 2.50 mmol, 2.5 equiv) in 3 mL DMF solution was added dropwise into the mixture and it was stirred at room temperature overnight. The crude reaction mixture was diluted with 30 mL EtOAc and washed with 1M HCl 2×10 mL and water 3×10 mL. The organic layer was dried over anhydrous $Na_2SO_4$ and evaporated to afford the crude product, which was subjected to silica gel chromatography using Hexanes/EtOAc to afford 0.1275 g colorless oil as product, yield 28.6%.

$^1$H NMR (CDCl$_3$, 400 MHz) δppm 2.24-2.44 (m, 2H) 3.29 (t, J=6.05 Hz, 2H) 4.33 (t, J=6.59 Hz, 2H) 7.26 (d, J=8.83 Hz, 2H) 7.51 (dd, J=8.69, 1.95 Hz, 2H) 8.02 (d, J=1.71 Hz, 2H)

Step 2. Synthesis of N-(3-(3,6-dibromo-9H-carbazol-9-yl)propyl)-2-nitro-N-phenylbenzenesulfonamide

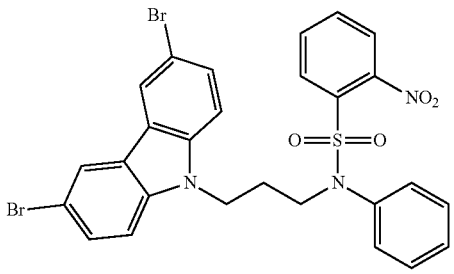 [SMILES: O=[N+]([O-])c1ccccc1S(=O)(=O)N(CCCn1c2ccc(Br)cc2c2cc(Br)ccc21)c1ccccc1]

Crushed KOH (0.0024 g, 0.0431 mmol) was added to 2-nitro-N-phenylbenzenesulfonamide (0.0100 g, 0.0359 mmol) in 0.2 mL DMF solution and the mixture was stirred for 30 min. 3,6-dibromo-9-(3-bromopropyl)-9H-carbazole (Example 35, 0.0240 g, 0.0538 mmol) in 0.3 mL DMF solution was added dropwise into the mixture and it was stirred at room temperature overnight. The crude reaction mixture was diluted with 20 mL EtOAc and washed with water 5×10 mL. The organic layer was dried over anhydrous $Na_2SO_4$ and evaporated to afford the crude product, which was subjected to silica gel chromatography using Hexanes/EtOAc to afford 0.0082 g white solid as impure product, purity 66.9% (impurity is starting Ns-aniline; used without additional purification), yield 35.5%.

$^1$H NMR (CDCl$_3$, 400 MHz) δppm 1.89-2.01 (m, 2H) 3.95 (t, J=6.61 Hz, 2H) 4.32-4.38 (m, 2H) 7.15 (s, 1H) 7.17 (s, 1H) 7.18-7.25 (m, 3H) 7.32 (d, J=3.66 Hz, 2H) 7.41-7.44 (m, 2H) 7.51 (dd, J=8.69, 1.95 Hz, 2H) 7.59-7.71 (m, 2H) 8.09 (d, J=1.90 Hz, 2H)

Step 3. Synthesis of N-(3-(3,6-dibromo-9H-carbazol-9-yl)propyl)aniline

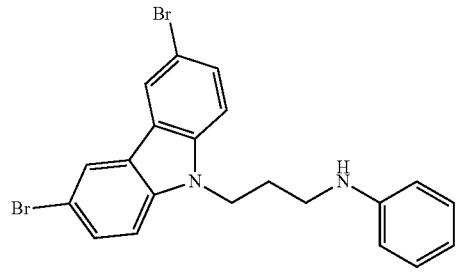 [SMILES: Brc1ccc2c(c1)c1cc(Br)ccc1n2CCCNc1ccccc1]

N-(3-(3,6-dibromo-9H-carbazol-9-yl)propyl)-2-nitro-N-phenylbenzenesulfonamide (0.0378 g, 0.0588 mmol, 1 equiv), cesium carbonate (0.0574 g, 0.176 mmol, 3 equiv) and benzenethiol (0.0194 g, 0.176 mmol) were mixed in 1 mL anhydrous THF. The mixture was stirred at room temperature for 3 hours. THF was removed under vacuum and the residue was purified by silica gel chromatography using Hexanes/EtOAc to afford 0.0164 g colorless oil as product, yield 60.9%.

$^1$H NMR (CDCl$_3$, 400 MHz) δppm 2.08-2.29 (m, 2H) 3.09 (t, J=6.56 Hz, 2H) 3.55 (br. s., 1H) 4.37 (t, J=6.69 Hz, 2H) 6.53 (dd, J=8.56, 0.95 Hz, 2H) 6.73 (t, J=7.32 Hz, 1H) 7.16 (dd, J=8.49, 7.37 Hz, 2H) 7.25 (d, J=8.69 Hz, 2H) 7.51 (dd, J=8.69, 1.95 Hz, 2H) 8.12 (d, J=1.85 Hz, 2H)

$^{13}$C NMR (CDCl$_3$, 400 MHz) δ=148.0, 139.5, 129.6, 129.4, 123.7, 123.6, 118.2, 113.3, 112.4, 110.5, 41.4, 40.9, 28.9

MS (ESI), m/z: 456.9 [M+H]+ ([M+H]+ for C21H18Br2N2 requires 457.0)

Example 21

P7C3-S32: 1-(3,6-dibromo-9H-carbazol-9-yl)-4-(phenylamino)butan-2-ol

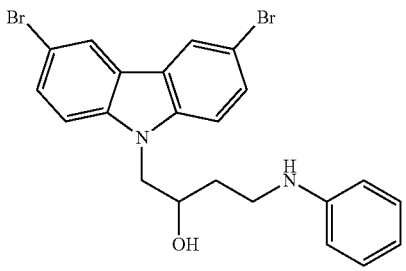 [SMILES: OC(CCNc1ccccc1)Cn1c2ccc(Br)cc2c2cc(Br)ccc21]

Step 1. Synthesis of N-(but-3-enyl)-2-nitro-N-phenylbenzenesulfonamide

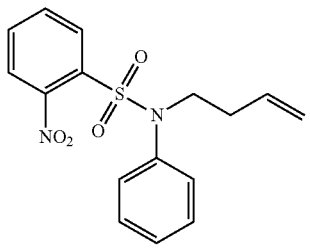 [SMILES: C=CCCN(c1ccccc1)S(=O)(=O)c1ccccc1[N+](=O)[O-]]

Crushed KOH (0.0484 g, 0.862 mmol, 1.2 equiv) was added to 2-nitro-N-phenylbenzenesulfonamide (0.200 g, 0.719 mmol) in 1 mL DMF, and the mixture was stirred for 30 min. 4-Bromo-1-butene (0.2426 g, 1.80 mmol) in 2 mL DMF solution was added dropwise into the mixture and it was stirred at room temperature overnight. The reaction mixture was diluted with 30 mL EtOAc and washed with 1M HCl 2×10 mL and water 3×10 mL. The organic layer was dried over anhydrous $Na_2SO_4$ and evaporated to afford the crude product, which was subjected to silica gel chromatography using Hexanes/EtOAc to afford 0.1546 g white solid, yield 63.5%.

$^1$H NMR (CDCl$_3$, 400 MHz) δppm 2.20 (q, J=6.90 Hz, 2H) 3.83 (t, J=7.15 Hz, 2H) 5.00 (d, J=4.39 Hz, 1H) 5.03 (s, 1H) 5.64-5.83 (m, 1H) 7.14-7.21 (m, 3H) 7.30 (d, J=1.85 Hz, 2H) 7.42-7.46 (m, 2H) 7.52-7.58 (m, 1H) 7.60-7.66 (m, 1H)

Step 2. Synthesis of 2-nitro-N-(2-(oxiran-2-yl)ethyl)-N-phenylbenzenesulfonamide

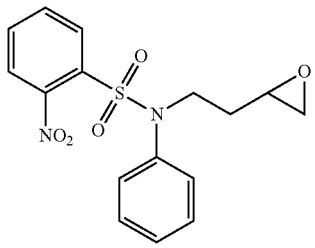 [SMILES: O=[N+]([O-])c1ccccc1S(=O)(=O)N(CCC1CO1)c1ccccc1]

mCPBA (77%, 0.0550 g, 0.246 mmol) was added to N-(but-3-enyl)-2-nitro-N-phenylbenzenesulfonamide (0.0653 g, 0.196 mmol) in 1 mL CHCl$_3$ at 0° C. The mixture was stirred at 0° C. for 30 min, then gradually warmed up to room temperature and continued to stir for 18 hr. After TLC showed the disappearance of starting material, the reaction mixture was diluted with a 1:1 mixture of water and saturated NaHCO$_3$ (2×10 mL) and water (10 mL). The organic layer was dried over anhydrous Na$_2$SO$_4$ and evaporated to afford the crude product, which was subjected to silica gel chromatography using Hexanes/EtOAc to afford 0.0662 g colorless oil as product, yield 96.9%.

$^1$H NMR (CDCl$_3$, 400 MHz) δppm 1.66-1.79 (m, 2H) 2.46 (dd, J=4.95, 2.66 Hz, 1H) 2.70-2.80 (m, 1H) 2.93-3.03 (m, 1H) 3.87-4.07 (m, 2H) 7.19-7.23 (m, 2H) 7.28-7.34 (m, 3H) 7.43-7.47 (m, 2H) 7.57-7.66 (m, 2H).

MS (ESI) m/z: 371.0 (M+Na$^+$) ([M+Na]+ for C$_{16}$H$_{16}$N$_2$O$_5$S requires 371.1)

Step 3. Synthesis of N-(2-(oxiran-2-yl)ethyl)aniline

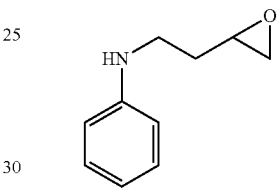

Prepared from 2-nitro-N-(2-(oxiran-2-yl)ethyl)-N-phenylbenzenesulfonamide using an analogous procedure as used to prepare the compound of Example 20.

$^1$H NMR (CDCl$_3$, 400 MHz) δppm 1.64-1.79 (m, 1H) 1.98-2.15 (m, 1H) 2.55 (dd, J=4.90, 2.71 Hz, 1H) 2.79 (t, J=4.44 Hz, 1H) 3.00-3.10 (m, 1H) 3.31 (t, J=6.64 Hz, 2H) 3.87 (br. s., 1H) 6.62 (d, J=7.71 Hz, 2H) 6.71 (t, J=7.32 Hz, 1H) 7.18 (dd, J=8.49, 7.37 Hz, 2H)

MS (ESI) m/z: 164.1 (M+H$^+$) ([M+1]+ for C$_{10}$H$_{13}$NO requires 164.1)

Step 4. Synthesis of 1-(3,6-dibromo-9H-carbazol-9-yl)-4-(phenylamino)butan-2-ol

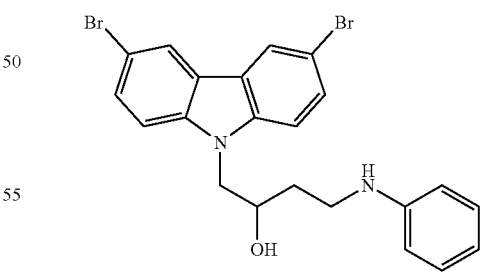

NaH (60% dispersed in mineral oil, 0.0018 g, 0.0452 mmol) was added to a solution of 3,6-dibromocarbazole (0.0147 g, 0.0452 mmol) in 0.5 mL anhydrous THF and the mixture was stirred for 15 min. N-(2-(oxiran-2-yl)ethyl)aniline (0.0067 g, 0.0410 mmol) in 1.5 mL anhydrous THF solution was added dropwise and the resulting mixture was stirred at 60° C. overnight. THF was removed under vacuum and the residue was dissolved in 10 mL EtOAc and washed with water 2×5 mL. The organic layer was dried over anhydrous Na₂SO₄ and evaporated to afford the crude product, which was subjected to silica gel chromatography using Hexanes/EtOAc to afford 0.0115 g colorless oil; yield 57.5%.

¹H NMR (CDCl₃, 400 MHz) δ ppm 1.76-1.95 (m, 2H) 3.22-3.41 (m, 2H) 4.20-4.38 (m, 3H) 6.63 (d, J=8.49 Hz, 2H) 6.76 (t, J=7.32 Hz, 1H) 7.18 (t, J=7.95 Hz, 2H) 7.31 (d, J=8.74 Hz, 2H) 7.54 (dd, J=8.69, 1.95 Hz, 2H) 8.12 (d, J=1.95 Hz, 2H)

¹³C NMR (CDCl₃, 400 MHz) δ=148.1, 139.9, 129.6, 129.5, 123.8, 123.5, 118.7, 113.9, 112.7, 111.1, 70.7, 50.0, 42.2, 34.1.

MS (ESI) m/z: 531.0 [M+HCOO]⁻ 486.9 [M+H]⁺ ([M+H]+ for C₂₂H₂₀Br₂N₂O requires 487.0)

Example 22

P7C3-S38: 1-(3,6-dibromo-9H-carbazol-9-yl)-3-(pyridin-2-ylamino)propan-2-ol

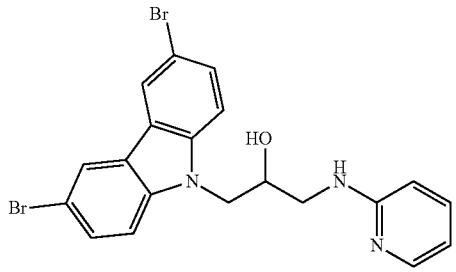 [SMILES: OC(CNc1ccccn1)Cn1c2ccc(Br)cc2c2cc(Br)ccc21]

Step 1. Synthesis of 1-amino-3-(3,6-dibromo-9H-carbazol-9-yl)propan-2-ol

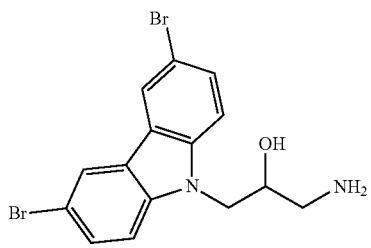 [SMILES: NCC(O)Cn1c2ccc(Br)cc2c2cc(Br)ccc21]

A solution of NH₃ (9.4 mL of 7M in MeOH, 65.6 mmol) was added to 3,6-dibromo-9-(oxiran-2-ylmethyl)-9H-carbazole (0.500 g, 1.31 mmol,). The vial was tightly sealed and the reaction mixture was heated to 100° C. and stirred for 1 hour. Volatile components were removed under vacuum. The residue was suspended in CH₂Cl₂ and the white precipitate was filtered. The filtrate was saved and CH₂Cl₂ was removed under vacuum to afford 0.3413 g white solid as crude product, which contained about 50% unidentified side-product. This crude product was used as is in next step without any further purification. Purification by flash chromatography on silica gel provided pure material.

¹H NMR (CDCl₃, 400 MHz) δ ppm 2.61 (dd, J=12.66, 7.78 Hz, 1H) 2.90 (dd, J=12.52, 4.03 Hz, 1H) 3.96-4.06 (m, 1H) 4.32 (d, J=5.81 Hz, 2H) 7.36 (d, J=8.74 Hz, 2H) 7.55 (dd, J=8.69, 1.95 Hz, 2H) 8.13 (d, J=1.90 Hz, 2H)

MS (ESI) m/z: 396.9 (M+H⁺) ([M+H]+ for C15H14Br2N2O requires 397.0)

Step 2. Synthesis of 5-((3,6-dibromo-9H-carbazol-9-yl)methyl)oxazolidin-2-one

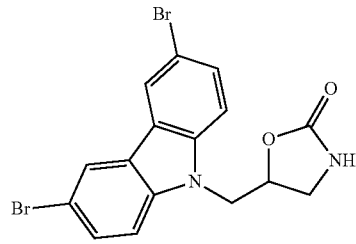 [SMILES: O=C1NCC(Cn2c3ccc(Br)cc3c3cc(Br)ccc32)O1]

A solution of triphosgene (0.0890 g, 0.300 mmol, 0.35 equiv) in 2 mL anhydrous CH₂Cl₂ was added dropwise to a solution of 1-amino-3-(3,6-dibromo-9H-carbazol-9-yl)propan-2-ol (0.3413 g, 0.857 mmol) and Et₃N (0.1909 g, 1.886 mmol) in 1 mL CH₂Cl₂ under N₂ atmosphere at 4° C. The reaction mixture was stirred for 15 min at 4° C. and then warmed to room temperature and stirred for 1 hour. CH₂Cl₂ was removed under vacuum. Saturated NH₄Cl (5 mL) and 10 mL EtOAc was added to the residue and stirred for 20 min. Then the aqueous layer was separated and the organic layer was washed with water 2×10 mL. The combined aqueous layers were extracted with EtOAc, dried over anhydrous Na₂SO₄ and evaporated to afford the crude product, which was subjected to silica gel chromatography using CH₂Cl₂/EtOAc to afford 0.1173 g white solid, yield 20.0% over 2 steps.

¹H NMR (CDCl₃, 400 MHz) δ ppm 3.37 (dd, J=8.98, 6.34 Hz, 1H) 3.67 (t, J=8.49 Hz, 1H) 4.54 (dd, J=5.22, 1.81 Hz, 2H) 5.02 (br. s., 1H) 5.05-5.14 (m, 1H) 7.31 (d, J=8.69 Hz, 2H) 7.58 (dd, J=8.69, 1.85 Hz, 2H) 8.14 (d, J=1.85 Hz, 2H)

MS (ESI) m/z: 466.9 [M+HCOO]⁻ ([M+HCOO]– for C₁₆H₁₂Br₂N₂O₂ requires 466.9.

Step 3. Synthesis of 5-((3,6-dibromo-9H-carbazol-9-yl)methyl)-3-(pyridin-2-yl)oxazolidin-2-one

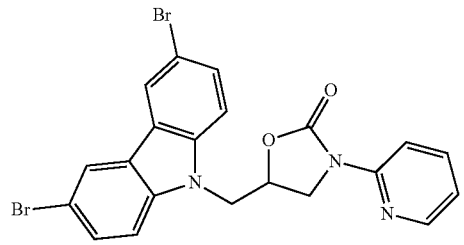 [SMILES: O=C1OC(Cn2c3ccc(Br)cc3c3cc(Br)ccc32)CN1c1ccccn1]

A mixture of 5-((3,6-dibromo-9H-carbazol-9-yl)methyl) oxazolidin-2-one (0.0195 g, 0.0460 mmol), 2-iodopyridine (0.0209 g, 0.102 mmol), CuI (0.0009 g, 0.00460 mmol), and K₂CO₃ (0.0058 g, 0.0418 mmol,) in 0.5 mL of DMSO was sealed tightly in a vial and heated at 130° C. for 12 hours. The reaction mixture was cooled and diluted with 20 mL EtOAc and washed with water 5×10 mL. The organic layer was dried over anhydrous Na₂SO₄ and evaporated to afford the crude product, which was subjected to silica gel chromatography using CH₂Cl₂/EtOAc as elute to afford 0.0183 g white solid as product, yield 79.4%.

¹H NMR (CDCl₃, 400 MHz) δppm 4.04 (dd, J=10.79, 7.08 Hz, 1H) 4.36 (dd, J=10.69, 8.74 Hz, 1H) 4.60 (d, J=5.03 Hz, 2H) 5.02-5.16 (m, 1H) 7.02 (t, J=6.08 Hz, 1H) 7.35 (d, J=8.69 Hz, 2H) 7.59 (dd, J=8.66, 1.73 Hz, 2H) 7.68 (t, J=7.88 Hz, 1H) 8.11 (s, 1H) 8.13 (d, J=1.32 Hz, 2H) 8.25 (d, J=4.93 Hz, 1H)

MS (ESI) m/z: 543.9 [M+HCOO]⁻ ([M+HCOO]– for C₂₁H₁₅Br₂N₃O₂ requires 544.0)

Step 4. Synthesis of 1-(3,6-dibromo-9H-carbazol-9-yl)-3-(pyridin-2-ylamino)propan-2-ol

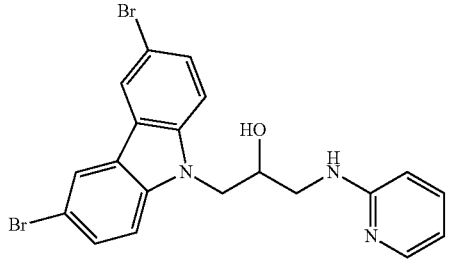 [SMILES: OC(CNc1ccccn1)Cn1c2ccc(Br)cc2c2cc(Br)ccc21]

LiOH·H₂O (0.0076 g, 0.182 mmol, 10 equiv) was added to 5-((3,6-dibromo-9H-carbazol-9-yl)methyl)-3-(pyridin-2-yl)oxazolidin-2-one (0.0091 g, 0.0182 mmol) in a mixture of 208 μL THF and 23 μL H₂O (v/v=9:1). The mixture was stirred at room temperature for 7 days. The reaction mixture was purified by silica gel chromatography using CH₂Cl₂/EtOAc as elute to afford 0.0071 g white solid as product, yield 41.0%.

¹H NMR (CDCl₃, 400 MHz) δppm 2.27-2.44 (m, 1H) 3.15-3.32 (m, 1H) 3.44 (dd, J=15.23, 5.03 Hz, 1H) 4.26-4.41 (m, 3H) 4.52 (t, J=5.00 Hz, 1H) 6.46 (d, J=8.00 Hz, 1H) 6.66 (t, J=6.20 Hz, 1H) 7.37 (d, J=8.74 Hz, 2H) 7.40-7.48 (m, 1H) 7.56 (dd, J=8.69, 1.90 Hz, 2H) 8.04 (d, J=4.49 Hz, 1H) 8.14 (d, J=1.85 Hz, 2H)

¹³C NMR (CDCl₃, 400 MHz) δ=158.6, 146.7, 139.5, 138.1, 129.2, 123.6, 123.3, 113.9, 112.3, 110.9, 109.6, 70.5, 47.4, 46.8

MS (ESI) m/z: 518.0 [M+HCOO]⁻ ([M+HCOO]– for C₂₀H₁₇Br₂N₃O requires 518.0.

Example 23

P7C3-S1: 1-(3,6-dibromo-9H-carbazol-9-yl)-3-((3-methoxyphenyl)(methyl)-amino)propan-2-ol

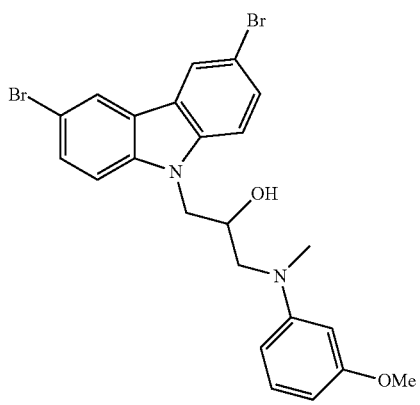 [SMILES: COc1cccc(N(C)CC(O)Cn2c3ccc(Br)cc3c3cc(Br)ccc32)c1]

Synthesized using a similar synthetic procedure analogous to Representative Procedure 2.

Example 25

P7C3-S6: 3-amino-1-(3-(3,6-dibromo-9H-carbazol-9-yl)-2-hydroxypropyl)pyridinium

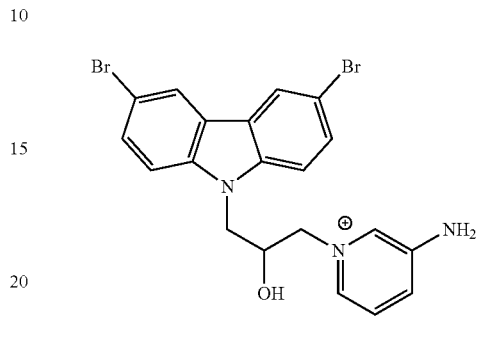

Example 25 was synthesized using a similar synthetic procedure analogous to Representative Procedure 2.

Example 26

P7C3-S8: 1-(3,6-dibromo-9H-carbazol-9-yl)-3-(pyrimidin-2-ylamino)propan-2-ol

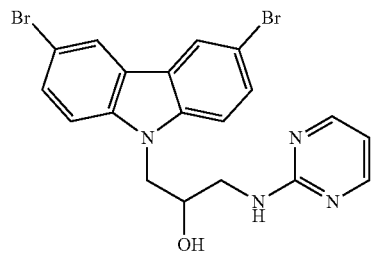 [SMILES: OC(CNc1ncccn1)Cn1c2ccc(Br)cc2c2cc(Br)ccc21]

To a 4 ml vial was added the corresponding primary amine (34.8 mg, 0.087 mmol), 2-chloropyrimidine (10.3 mg, 0.090 mmol) and dimethylformamide (1.5 ml, 0.058 M). The reaction was heated at 100° C. overnight. The cooled reaction mixture was diluted with EtOAc and washed several times with water and brine. The organic layer was dried over Na₂SO₄, filtered and condensed. The crude mixture was subjected to chromatography on silica gel (20% MeOH/CH₂Cl₂).

¹H NMR (CDCl₃, 400 MHz) δ 8.26 (d, 2H, J=4.94 Hz), 8.14 (d, 2H, J=1.88 Hz), 7.56 (dd, 2H, J=6.7, 1.9 Hz), 7.37 (d, 2H, J=8.7 Hz), 6.63 (t, 1H, J=4.9 Hz), 5.43 (t, 1H, J=5.71 Hz), 4.36 (s, 3H), 3.56 (m, 1H), 3.30-3.38 (m, 1H).

¹³C NMR (CDCl₃, 126 MHz) §□139.4, 29.5 (2C), 129.3 (2C), 123.7 (2C), 123.4 (2C), 118.6 (2) (2C), 113.5 (2C), 112.3, 110.7 (2C), 67.6, 50.9, 33.6.

MS (ESI) m/z: 474.9 [(M+1)⁺; C19H16Br2N4O (M) requires 474)].

The title compound of Example 26 can also be synthesized using a procedure analogous to that described in Representative Procedure 2.

Example 28

P7C3-S19: 1-(3,6-dibromo-9H-carbazol-9-yl)-3-methoxypropan-2-ol

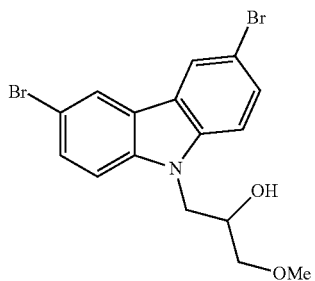 [SMILES: COCC(O)Cn1c2ccc(Br)cc2c2cc(Br)ccc21]

Following Representative Procedure 1, Example 28 was prepared from dibromocarbazole and methoxymethyloxirane.

Example 29

P7C3-S21: 1-(3,6-dibromo-9H-carbazol-9-yl)-4-phenylbutan-2-ol

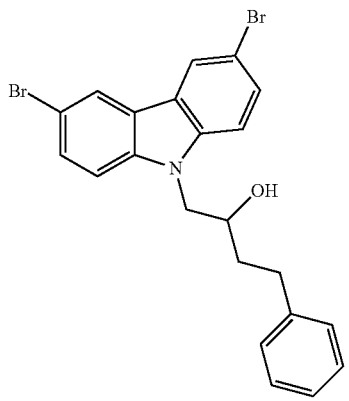 [SMILES: OC(CCc1ccccc1)Cn1c2ccc(Br)cc2c2cc(Br)ccc21]

Following Representative Procedure 1, Example 29 was prepared from dibromocarbazole and 2-phenethyloxirane.

Example 30

P7C3-S22: 1-(3,6-dibromo-9H-carbazol-9-yl)-3-(1H-indol-1-yl)propan-2-ol

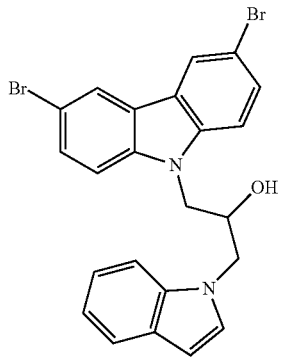 [SMILES: OC(Cn1ccc2ccccc21)Cn1c2ccc(Br)cc2c2cc(Br)ccc21]

Following Representative Procedure 1, Example 30 was prepared from dibromocarbazole and 1-(oxiran-2-ylmethyl)-1H-indole.

Example 31

P7C3-S23: 3-(1-(3-(3,6-dibromo-9H-carbazol-9-yl)-2-hydroxypropyl)-1H-1,2,3-triazol-4-yl)propan-1-ol

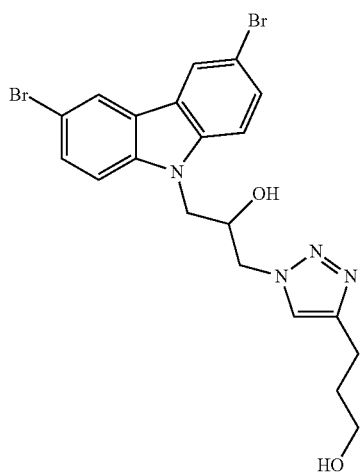 [SMILES: OCCCc1cn(CC(O)Cn2c3ccc(Br)cc3c3cc(Br)ccc32)nn1]

Example 31 was synthesized using a similar synthetic procedure analogous to Representative Procedure 2. Example 32. P7C3-S24: 1-(3,6-dibromo-9H-carbazol-9-yl)-3-(3-ethoxyphenylamino)propan-2-ol

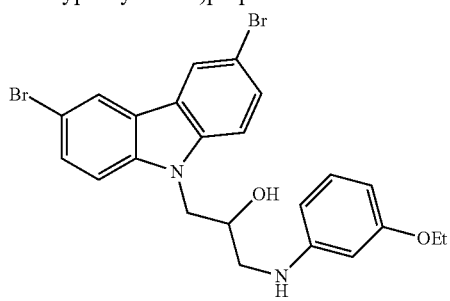

Example 32 was synthesized using a similar synthetic procedure analogous to Representative Procedure 2. Example 33. P7C3-S25: 1-(3,6-dibromo-9H-carbazol-9-yl-3-(3,5-dimethyl-1H-pyrazol-1-yl)propan-2-ol

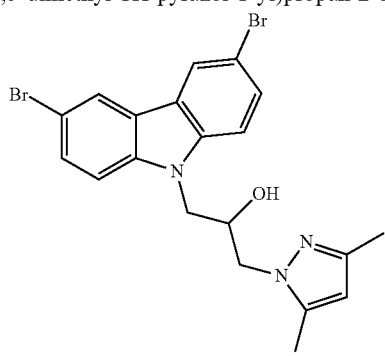

Example 33 was synthesized using a similar synthetic procedure analogous to Representative Procedure 2.

Example 36

P7C3-S29: 1-(3-bromo-9H-carbazol-9-yl)-3-(3-methoxyphenylamino)propan-2-ol

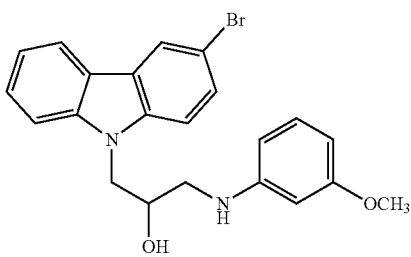 [SMILES: COc1cccc(NCC(O)Cn2c3ccccc3c3cc(Br)ccc32)c1]

Step 1.
3-bromo-9-(oxiran-2-ylmethyl)-9H-carbazole

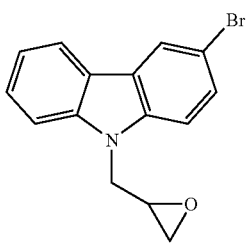 [SMILES: Brc1ccc2c(c1)c1ccccc1n2CC1CO1]

The title compound of Example 36, step 1 was prepared using a procedure analogous to that described in representative procedure 1.

$^1$H NMR (CDCl$_3$, 400 MHz) δ=2.52 (dd, J=4.6, 2.6 Hz, 1H) 2.80 (t, J=4.3 Hz, 1H) 3.33 (td, J=5.3, 2.2 Hz, 1H) 4.34 (dd, J=15.9, 4.9 Hz, 1H) 4.64 (dd, J=15.9, 2.9 Hz, 1H) 7.26 (t, J=7.3 Hz, 1H) 7.35 (d, J=8.7 Hz, 1H) 7.58-7.42 (m, 3H) 8.02 (d, J=5.1 Hz, 1H) 8.19 (d, J=1.7 Hz, 1H).

Step 2

The title compound was prepared from 3-bromo-9-(oxiran-2-ylmethyl)-9H-carbazole using a procedure similar to that described in representative procedure 2.

$^1$H NMR (CDCl$_3$, 400 MHz) δ=2.13 (d, J=3.0 Hz, 1H) 3.21 (dd, J=13.0, 6.5 Hz, 1H) 3.35 (dd, J=13.0, 3.2 Hz, 1H) 3.72 (s, 3H) 4.03 (s, br, 1H) 4.50-4.36 (m, 3H) 6.15 (t, J=2.3 Hz, 1H) 6.24 (dd, J=8.0, 2.2 Hz, 1H) 6.32 (dd, J=8.2, 2.3 Hz, 1H) 7.08 (t, J=8.1 Hz, 1H) 7.30-7.24 (m, 1H) 7.36 (d, J=8.7 Hz, 1H) 7.51-7.44 (m, 2H) 7.53 (dd, J=8.7, 1.9 Hz, 1H) 8.05 (d, J=7.9 Hz, 1H) 8.21 (d, J=1.9 Hz, 1H)

$^{13}$C NMR (CDCl$_3$, 400 MHz) δ=161.0, 149.4, 141.2, 139.6, 130.4, 128.8, 126.9, 125.0, 123.3, 122.2, 120.8, 120.1, 112.4, 110.7, 109.4, 106.7, 103.8, 99.7, 69.6, 55.3, 48.0, 47.4.

ESI m/z: 425.0 [(M+H$^+$), C$_{22}$H$_{21}$BrN$_2$O$_2$ (M) requires 421.1].

Example 37

P7C3-S37: N-(5-(3-(3-(3,6-dibromo-9H-carbazol-9-yl)-2-hydroxypropylamino)phenoxy)pentyl)-2-(7-(dimethylamino)-2-oxo-2H-chromen-4-yl)acetamide

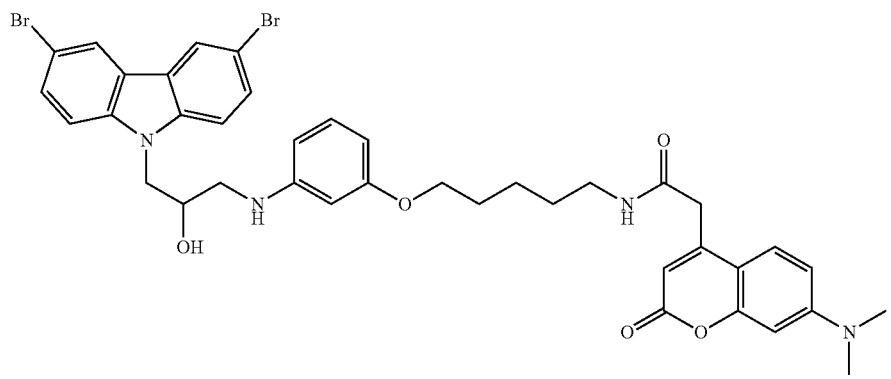 [SMILES: CN(C)c1ccc2c(CC(=O)NCCCCCOc3cccc(NCC(O)Cn4c5ccc(Br)cc5c5cc(Br)ccc54)c3)cc(=O)oc2c1]

The coumarin was attached to Example 62 Compound using a known procedure (Alexander, et al., *ChemBioChem*, 2006, 7, 409-416.

Example 39

P7C3-S43: N-(2-(3-(3,6-dibromo-9H-carbazol-9-yl)-2-hydroxypropoxy)ethyl)-acetamide

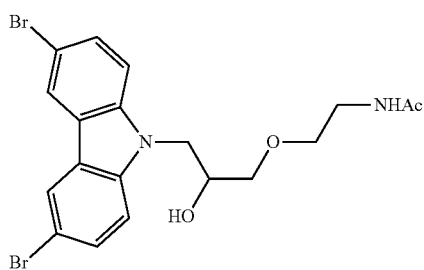 [SMILES: CC(=O)NCCOCC(O)Cn1c2ccc(Br)cc2c2cc(Br)ccc21]

145

Step 1. 2-(2-(3-(3,6-dibromo-9H-carbazol-9-yl)-2-hydroxypropoxy)ethyl) isoindoline-1, 3-dione

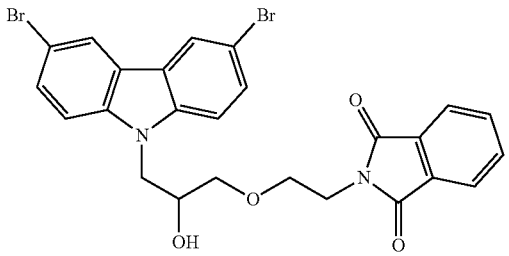 [SMILES: O=C1c2ccccc2C(=O)N1CCOCC(O)Cn1c2ccc(Br)cc2c2cc(Br)ccc21]

Sodium hydride dispersion (31.6 mg, 0.79 mmol) was added to a solution of N-(2-hydroxyethyl)-phthalimide (153.7 mg, 0.80 mmol) in anhydrous THF (1.2 ml, 0.67 M). The suspension is stirred for 15 minutes before the addition of carbazole epoxide 2-A. The reaction was stirred at room temperature for five minutes and then at 60° C. for 1 hour. The cooled reaction was diluted with EtOAc and washed with water. The aqueous layer was extracted and the combined organics were filtered over a celite pad. The Crude product was used without further purification. Yield=44%

$^1$H NMR (CDCl$_3$, 500 MHz) ☐ 8.12 (s, 2H), 7.85 (s, 2H), 7.72 (m, 2H), 7.55 (d, 2H, J=8.5 Hz), 7.33 (d, 2H, J=8.7 Hz), 4.64 (d, 1H, J=16.1 Hz), 4.27 (d, 1H), 3.88 (m, 4H), 3.31 (bs, 1H), 2.80 (m, 1H), 2.48 (m, 1H), 2.04 (s, 1H).

MS (ESI), m/z: 614.9 [(M+HCOO)$^-$; C25H20Br2N2O4 (M) requires 570].

Step 2. 1-(2-aminoethoxy)-3-(3,6-dibromo-9H-carbazol-9-yl)propan-2-ol

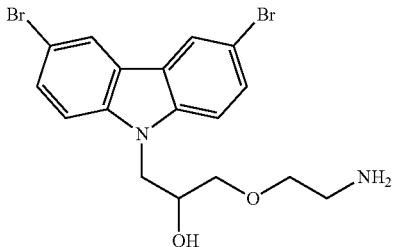 [SMILES: NCCOCC(O)Cn1c2ccc(Br)cc2c2cc(Br)ccc21]

Hydrazine hydrate (400 ul, 8.22 mmol) was added to a solution of the phthalimide prepared in step 1 above (53 mg, 0.093 mmol) in ethanol (2.0 ml, 0.046 M). The reaction was stirred overnight, condensed and purified in 5-10% MeOH/DCM.

$^1$H NMR (CDCl$_3$, 500 MHz) ☐ 8.11 (s, 2H), 7.53 (dd, 2H, J=8.7, 1.8 Hz), 7.38 (d, 2H, J=8.5 Hz), 4.37 (dm, 5H), 4.05 (t, 1H, J=6.8 Hz), 2.84 (m, 2H), 2.62 (m, 1H)

MS (ESI), m/z: 440.9 [(M+1)$^+$; C17H18Br2N2O2 (M) requires 440.0].

Step 3

The title compound of Example 39 was prepared as follows. Triethylamine (33.5 ul, 0.26 mmol) and acetic anhydride (17 ul, 0.18 mmol) were added to a solution of amine XIII (71 mg, 0.16 mmol) in THF (3.0 ml, 0.053 M). The reaction was stirred overnight. The reaction mixture was diluted with EtOAc, washed with water, dried over Na$_2$SO$_4$, filtered and condensed. The crude mixture was subjected to flash chromatography (5% MeOH/CH$_2$Cl$_2$).

$^1$H NMR (CDCl$_3$, 500 MHz) ☐ 8.13 (d, 2H, J=1.7 Hz, 7.55 (dd, 2H, J=8.7, 1.8 Hz), 7.34 (d, 2H, 9.1 Hz), 5.78 (bs, 1H), 4.35 (ddd, 3H, J=6.2, 6.8 Hz), 4.22 (m, 1H), 3.46 (m, 4H), 3.33 (dd, 1H, J=9.7, 5.4 Hz), 2.80 (bs, 1H), 1.98 (s, 3H)

MS (ESI), m/z: 482.9 [(M+1)$^+$; C19H20Br2N2O3 (M) requires 482.0]

Example 40

P7C3-S44: 1-(3,6-dibromo-9H-carbazol-9-yl)-3-(pyridin-3-ylamino)propan-2-ol

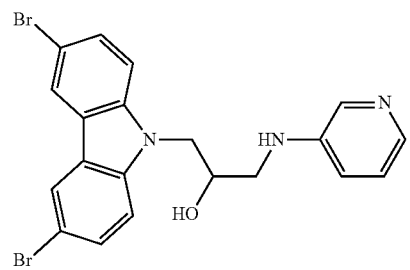 [SMILES: OC(CNc1cccnc1)Cn1c2ccc(Br)cc2c2cc(Br)ccc21]

Step 1. 5-((3,6-dibromo-9H-carbazol-9-yl)methyl)-3-(pyridin-3-yl)oxazolidin-2-one

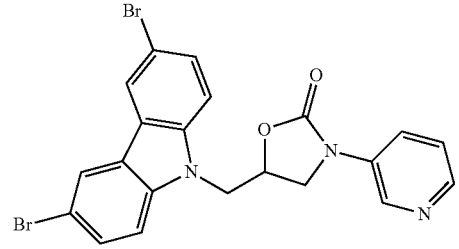 [SMILES: O=C1OC(Cn2c3ccc(Br)cc3c3cc(Br)ccc32)CN1c1cccnc1]

A mixture of the corresponding N—H oxazolidinone (0.0390 g, 0.0920 mmol), 3-iodopyridine (0.0419 g, 0.204 mmol), CuI (0.0018 g, 0.00920 mmol), and K$_2$CO$_3$ (0.0116 g, 0.0837 mmol) in 0.5 mL of DMSO was heated at 130° C. for 12 hours in a sealed vial. The reaction mixture was cooled and diluted with 20 mL EtOAc and washed with water 2×10 mL and brine 2×10 mL. The organic layer was dried over anhydrous Na$_2$SO$_4$ and evaporated to afford the crude product (0.0383 g white solid, yield 83.7%), which was used without further purification.

$^1$H NMR (CDCl$_3$, 400 MHz) δ=3.82 (dd, J=9.1, 6.6 Hz, 1H) 4.12 (dd, J=10.0, 7.9 Hz, 1H) 4.72-4.55 (m, 2H) 5.15 (td, J=11.8, 5.4 Hz, 1H) 7.27 (dd, J=8.3, 4.9 Hz, 1H) 7.34 (d, J=8.7 Hz, 2H) 7.59 (dd, J=8.7, 1.9 Hz, 2H) 8.03 (ddd, J=8.5, 2.6, 1.2 Hz, 1H) 8.14 (d, J=1.9 Hz, 2H) 8.37 (d, J=4.2 Hz, 1H) 8.44 (s, 1H). ESI m/z: 543.9 [(M+HCOO$^-$); C21H15Br2N3O2 (M) requires 499].

Step 2

The title compound of Example 40 was prepared as follows. LiOH·H$_2$O (0.0097 g, 0.231 mmol) was added to 5-((3,6-dibromo-9H-carbazol-9-yl)methyl)-3-(pyridin-3-yl)oxazolidin-2-one (0.0116 g, 0.0231 mmol) in a mixture of 265 μL THF and 29 μL H₂O (v/v=9:1). The mixture was stirred at room temperature for 7 days. The reaction mixture purified by silica gel chromatography using CHCl₃/MeOH as elute to afford 0.0087 g white solid as product, yield 79.3%.

¹H NMR (CDCl₃, 600 MHz) δ=3.15 (dd, J=12.6, 6.2 Hz, 1H) 3.30 (d, J=11.8 Hz, 1H) 4.45-4.33 (m, 3H) 6.81 (d, J=7.4 Hz, 1H) 7.02 (s, br, 1H) 7.32 (d, J=8.7 Hz, 2H) 7.52 (dd, J=8.7, 1.8 Hz, 2H) 7.83 (s, br, 2H) 8.11 (d, J=1.6 Hz, 2H)

¹³C NMR (CDCl₃, 400 MHz) δ=139.8, 139.5, 136.2, 130.0, 129.5, 124.1, 123.8, 123.5, 119.7, 112.8, 110.9, 69.0, 47.6, 47.3

ESI m/z: 517.9 [(M+HCOO⁻); C20H17Br2N3O (M) requires 473].

Example 41

P7C3-S45: 1-(3,6-dibromo-9H-carbazol-9-yl)-3-(pyridin-4-ylamino)propan-2-ol

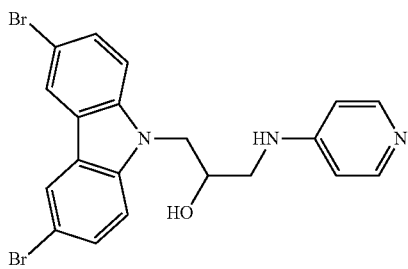 [SMILES: OC(CNc1ccncc1)Cn1c2ccc(Br)cc2c2cc(Br)ccc21]

Step 1. 5-((3,6-dibromo-9H-carbazol-9-yl)methyl)-3-(pyridin-4-yl)oxazolidin-2-one

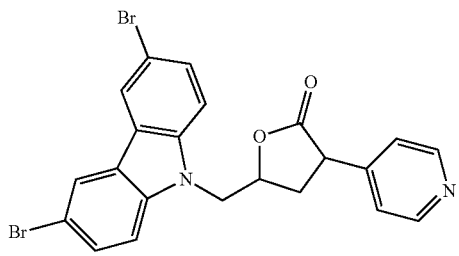 [SMILES: O=C1OC(Cn2c3ccc(Br)cc3c3cc(Br)ccc32)CC1c1ccncc1]

A mixture of the corresponding N—H oxazolidinone (0.0195 g, 0.0460 mmol), 4-iodopyridine (0.0209 g, 0.102 mmol), CuI (0.0009 g, 0.00460 mmol), and K₂CO₃ (0.0058 g, 0.0418 mmol) in 0.5 mL of DMSO was at 130° C. for 12 hours in a sealed vial. The reaction mixture was cooled and diluted with 20 mL EtOAc and washed with brine (3×10 mL). The organic layer was dried over anhydrous Na₂SO₄ and evaporated to afford the crude product, which was further triturated from CH₂Cl₂ suspension by hexane to afford 0.0187 g white solid as product, yield 74.6%.

¹H NMR (CDCl₃, 400 MHz) δ=3.77 (dd, J=9.4, 6.8 Hz, 1H) 4.08 (t, J=9.0 Hz, 1H) 4.64 (t, J=4.6 Hz, 2H) 5.23-5.10 (m, 1H) 7.34 (d, J=8.7 Hz, 2H) 7.37 (s, br, 2H) 7.61 (dd, J=8.6, 1.8 Hz, 2H) 8.16 (d, J=1.8 Hz, 2H) 8.55 (s, br, 2H).

ESI m/z: 544.0 [(M+HCOO⁻); C21H15Br2N3O2 (M) requires 499].

Step 2

The title compound of Example 41 was prepared as follows. LiOH·H₂O (0.0157 g, 0.373 mmol) was added to 5-((3,6-dibromo-9H-carbazol-9-yl)methyl)-3-(pyridin-4-yl)oxazolidin-2-one (0.0187 g, 0.0373 mmol) in a mixture of 428 μL THF and 48 μL H₂O (v/v=9:1). The mixture was stirred at room temperature for 3 days. The reaction mixture was diluted with 30 mL EtOAc and washed with brine 3×30 mL. The organic layer was dried over anhydrous Na₂SO₄ and evaporated to afford the crude product, which did not require purification (0.0013 g white solid, 7.3%).

¹H NMR (d₆-Acetone, 400 MHz) δ=3.33 (dd, J=13.1, 6.4 Hz, 1H) 3.49 (dd, J=13.2, 4.4 Hz, 1H) 4.41 (td, J=7.6, 4.1 Hz, 1H) 4.51 (dd, J=15.0, 7.6 Hz, 1H) 4.61 (dd, J=14.8, 3.4 Hz, 1H) 6.61 (s, 2H) 7.56 (d, J=8.6 Hz, 2H) 7.62 (d, J=8.7 Hz, 2H) 8.10 (s, br, 2H) 8.37 (s, 2H)

¹³C NMR (d-Acetone, 400 MHz) δ=179.0, 149.6, 140.4, 129.0, 123.8, 123.3, 112.1, 111.8, 107.8, 68.8, 47.6, 46.4

ESI m/z: 517.9 [(M+HCOO⁻); C20H17Br2N3O (M) requires 473].

Example 42

P7C3-S46: 1-(2,8-dimethyl-3,4-dihydro-1H-pyrido[4,3-b]indol-5(2H)-yl)-3-(phenylamino)propan-2-ol

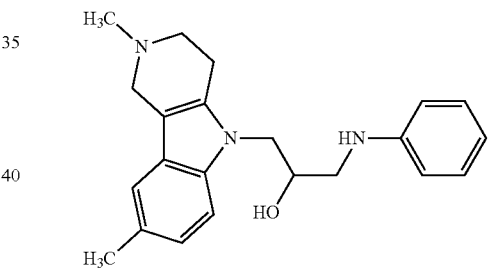

Example 42 was synthesized using a similar synthetic procedure analogous to Representative Procedure 2.

Example 43

P7C3-S59: N-(3-(3,6-dibromo-9H-carbazol-9-yl)-2,2-difluoropropyl)-3-methoxyaniline

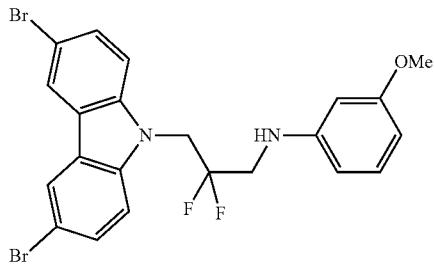 [SMILES: COc1cccc(NCC(F)(F)Cn2c3ccc(Br)cc3c3cc(Br)ccc32)c1]

Step 1. N-(3-(3,6-dibromo-9H-carbazol-9-yl)-2-oxopropyl)-N-(3-methoxyphenyl)-4-nitrobenzenesulfonamide

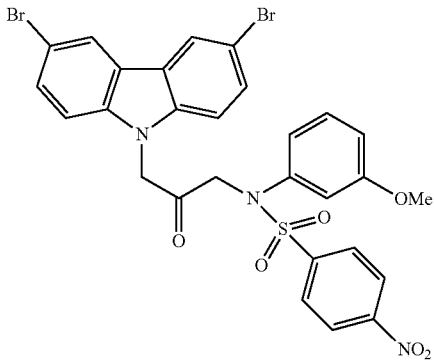 [SMILES: COc1cccc(N(CC(=O)Cn2c3ccc(Br)cc3c3cc(Br)ccc32)S(=O)(=O)c2ccc([N+](=O)[O-])cc2)c1]

The nosylate of the title compound of Example 62 (prepared according to the procedures described herein) was oxidized with Dess-Martin periodinane using a procedure similar to that described in Example 103. Quantitative yield.

$^1$H NMR (CDCl$_3$, 500 MHz) δ 8.24 (d, 2H, J=8.9 Hz), 8.14 (s, 2H), 7.68 (d, 2H, J=9.1 Hz), 7.53 (d, 2H, J=8.6 Hz), 7.18 (t, 1H, J=8.7 Hz), 7.05 (t, 2H, J=8.1 Hz), 6.87 (dd, 1H, J=8.3, 2.5 Hz) 5.21, (s, 2H), 4.30 (s, 2H), 2.48 (s, 3H). MS (ESI), m/z: 683.9 [(M−1)$^-$; C28H21Br2N3O6S (M) require 685.0].

Step 2. N-(3-(3,6-dibromo-9H-carbazol-9-yl)-2,2-difluoropropyl)-N-(3-methoxyphenyl)-4-nitrobenzenesulfonamide

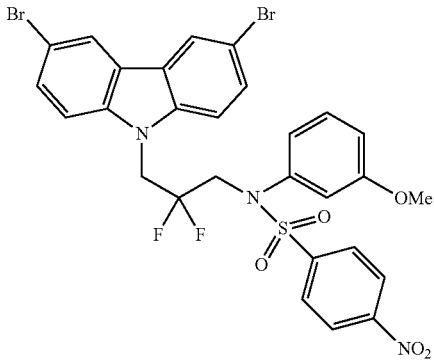 [SMILES: COc1cccc(N(CC(F)(F)Cn2c3ccc(Br)cc3c3cc(Br)ccc32)S(=O)(=O)c2ccc([N+](=O)[O-])cc2)c1]

The title compound of Example 43, step 2 was prepared from the ketone prepared in step 1 above using a procedure similar to that described in Example 103. Yield was quantitative and crude product was used without additional purification.

$^1$H NMR (CDCl$_3$, 500 MHz) δ 8.31 (d, 2H, J=8.9 Hz), 8.11 (s, 2H), 7.77 (d, 2H, J=8.9 Hz), 7.55 (dd, 2H, J=8.7, 1.8 Hz), 7.25 (m, 3H), 6.92 (dd, 1H, J=8.3, 2.0 Hz), 6.73 (m, 1H) 6.61, (d, 1H, J=7.7 Hz), 4.78 (t, 2H, T=14.7 Hz), 4.18 (t, 2H, J=11.2 Hz), 3.78 (s, 3H).

MS (ESI), m/z: 751.9 [(M+HCOO)$^-$; C28H21Br2F2N3O5S (M) requires 707.0].

Step 3

The title compound of Example 43 was prepared as follows. The nosyl group on N-(3-(3,6-dibromo-9H-carbazol-9-yl)-2,2-difluoropropyl)-N-(3-methoxyphenyl)-4-nitrobenzenesulfonamide was removed using the procedure described in Representative Procedure 5.

$^1$H NMR (CDCl$_3$, 400 MHz) δ 8.11 (d, 2H, J=1.6 Hz), 7.49 (dd, 2H, J=8.7, 2.0 Hz), 7.32 (d, 2H, J=8.9 Hz), 7.11 (t, 1H, J=8.2 Hz) 6.39 (dd, 1H, J=8.2, 2.3 Hz), 4.68 (t, 2H, J=13.2 Hz), 3.89 (t, 1H, J=7.0 Hz), 3.74 (s, 3H), 3.47 (m, 2H)

MS (ESI), m/z: 566.9 [(M+HCOO)$^-$; C22H18Br2F2N2O (M) requires 522.0].

Example 45

P7C3: 1-(3,6-dibromo-9H-carbazol-9-yl)-3-(phenylamino)propan-2-ol

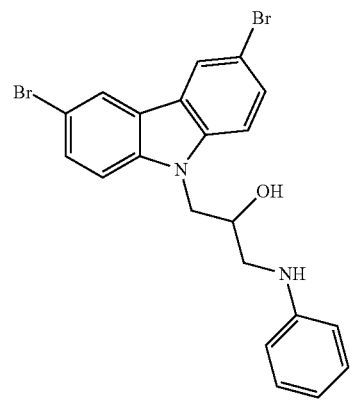

This compound can be purchased from ChemBridge Corporation.

Example 46

1-(3,6-dibromo-9H-carbazol-9-yl)-3-(o-tolylamino)propan-2-ol

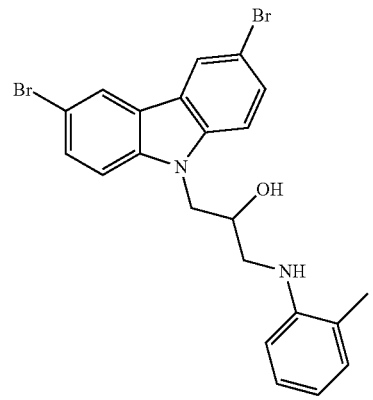 [SMILES: Cc1ccccc1NCC(O)Cn1c2ccc(Br)cc2c2cc(Br)ccc21]

This compound can be purchased from ChemBridge Corporation.

Example 47

1-(3,6-dibromo-9H-carbazol-9-yl)-3-(m-tolylamino)propan-2-ol

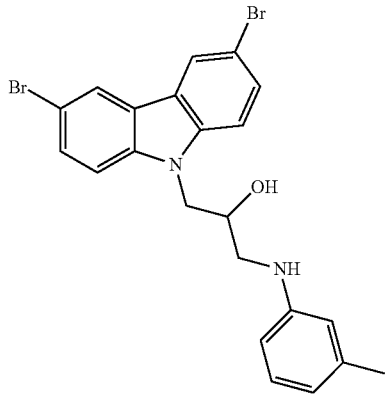 [SMILES: Cc1cccc(NCC(O)Cn2c3ccc(Br)cc3c3cc(Br)ccc32)c1]

This compound can be purchased from ChemBridge Corporation.

Example 48

1-(3,6-dibromo-9H-carbazol-9-yl)-3-(2-methoxyphenylamino)propan-2-ol

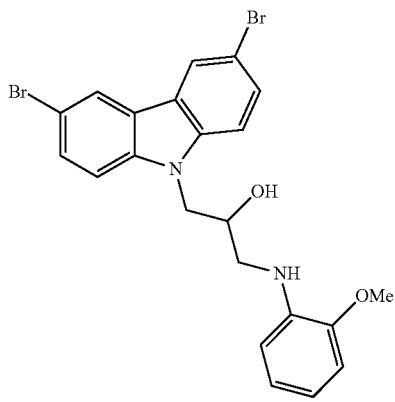 [SMILES: COc1ccccc1NCC(O)Cn1c2ccc(Br)cc2c2cc(Br)ccc21]

This compound can be purchased from ChemBridge Corporation.

Example 50

1-(4-bromophenylamino)-3-(3,6-dichloro-9H-carbazol-9-yl)propan-2-ol

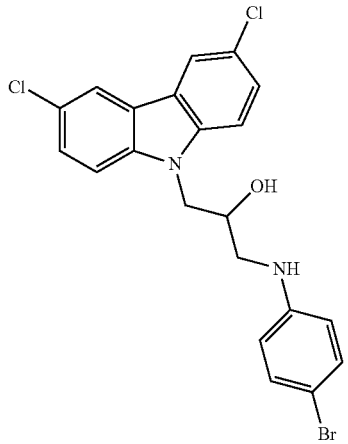

This compound can be purchased from ChemBridge Corporation.

Example 51

1-(4-bromophenylamino)-3-(3,6-dibromo-9H-carbazol-9-yl)propan-2-ol

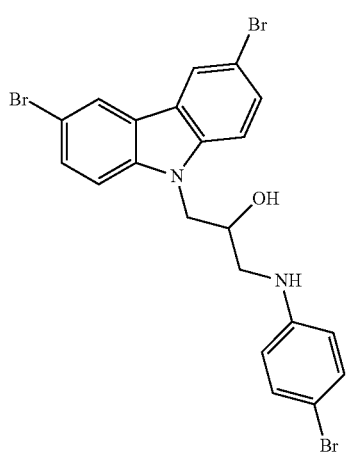 [SMILES: OC(CNc1ccc(Br)cc1)Cn1c2ccc(Cl)cc2c2cc(Cl)ccc21]

This compound can be purchased from ChemBridge Corporation.

Example 52

1-(3,6-dibromo-9H-carbazol-9-yl)-3-(4-ethoxyphenylamino)propan-2-ol

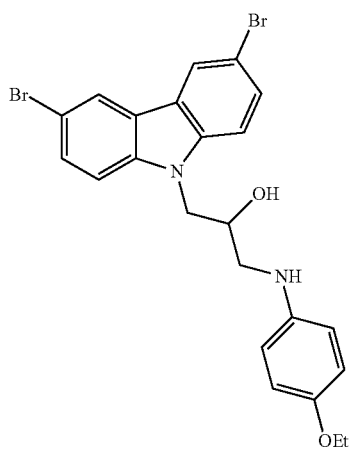 [SMILES: CCOc1ccc(NCC(O)Cn2c3ccc(Br)cc3c3cc(Br)ccc32)cc1]

This compound can be purchased from ChemBridge Corporation.

Example 53

1-(4-chlorophenylamino)-3-(3,6-dibromo-9H-carbazol-9-yl)propan-2-ol

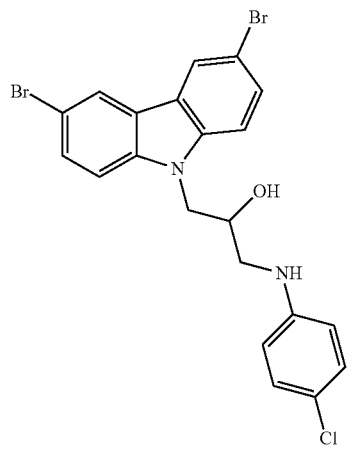

This compound can be purchased from ChemBridge Corporation.

Example 54

1-(3,6-dibromo-9H-carbazol-9-yl)-3-(phenethylamino)propan-2-ol

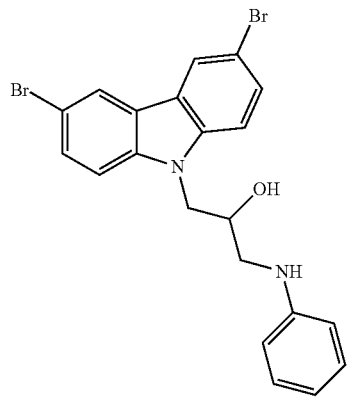

This compound can be purchased from ChemBridge Corporation.

Example 55

1-(3,6-dibromo-9H-carbazol-9-yl)-3-(2-hydroxyethylamino)propan-2-ol

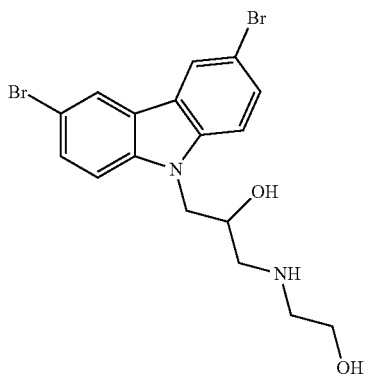 [SMILES: OCCNCC(O)Cn1c2ccc(Br)cc2c2cc(Br)ccc21]

This compound can be purchased from ChemBridge Corporation.

Example 56

1-(3,6-dibromo-9H-carbazol-9-yl)-3-(2,4-dimethoxyphenylamino)propan-2-ol

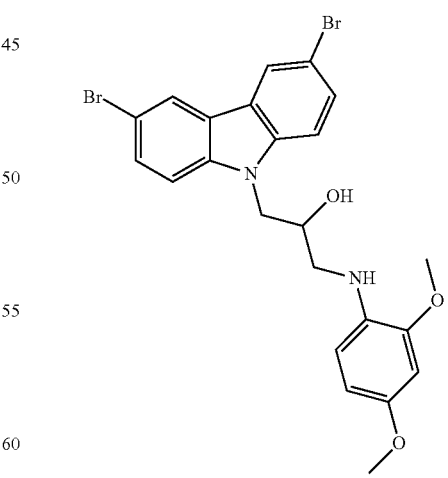

This compound can be purchased from ChemBridge Corporation.

Example 57

1-(3,6-dibromo-9H-carbazol-9-yl)-3-(2,3-dimethyl-phenylamino)propan-2-ol

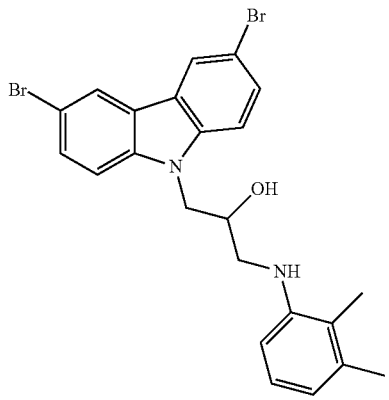 [SMILES: Cc1cccc(NCC(O)Cn2c3ccc(Br)cc3c3cc(Br)ccc32)c1C]

This compound can be purchased from ChemDiv, Inc.

Example 58

1-(2-chlorophenylamino)-3-(3,6-dibromo-9H-carbazol-9-yl)propan-2-ol

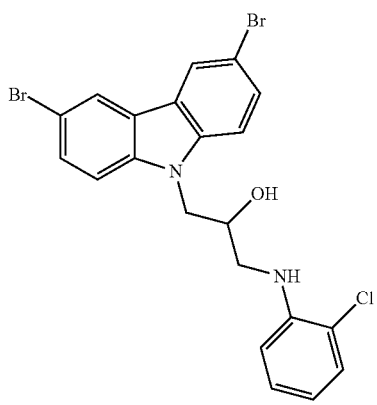 [SMILES: OC(CNc1ccccc1Cl)Cn1c2ccc(Br)cc2c2cc(Br)ccc21]

This compound can be purchased from ChemDiv, Inc.

Example 59

1-(tert-butylamino)-3-(3,6-dibromo-9H-carbazol-9-yl)propan-2-ol

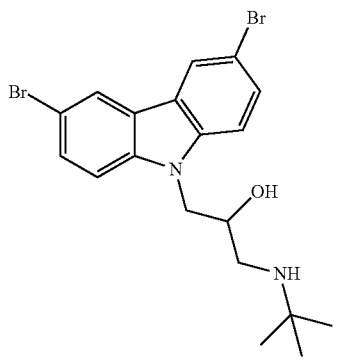 [SMILES: CC(C)(C)NCC(O)Cn1c2ccc(Br)cc2c2cc(Br)ccc21]

This compound can be purchased from ChemDiv, Inc.

Example 60

1-(3,6-dibromo-9H-carbazol-9-yl)-3-(isopropylamino)propan-2-ol

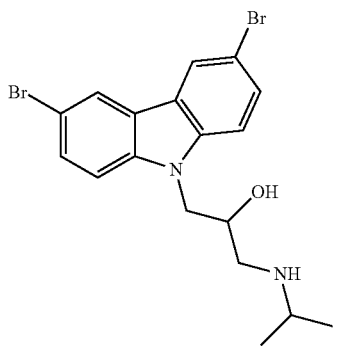 [SMILES: CC(C)NCC(O)Cn1c2ccc(Br)cc2c2cc(Br)ccc21]

This compound can be purchased from ChemDiv, Inc.

Example 61

1-(3,6-dibromo-9H-carbazol-9-yl)-3(4-methoxyphenylamino)propan-2-ol

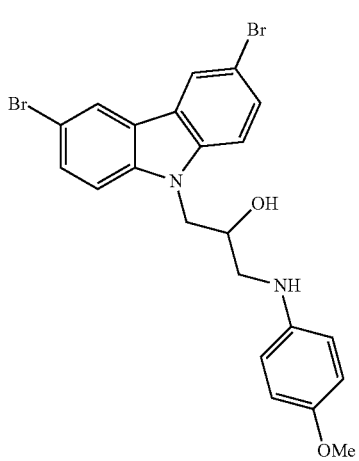 [SMILES: COc1ccc(NCC(O)Cn2c3ccc(Br)cc3c3cc(Br)ccc32)cc1]

This compound can be purchased from ChemDiv, Inc.

Example 62

1-(3,6-dibromo-9H-carbazol-9-yl)-3-(3-methoxyphenylamino)propan-2-ol

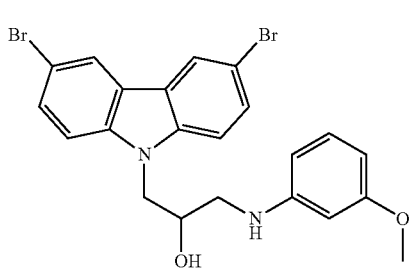 [SMILES: COc1cccc(NCC(O)Cn2c3ccc(Br)cc3c3cc(Br)ccc32)c1]

This compound can be purchased from ChemDiv, Inc.

Example 63

1-(3,6-dibromo-9H-carbazol-9-yl)-3-(m-tolylamino)propan-2-ol

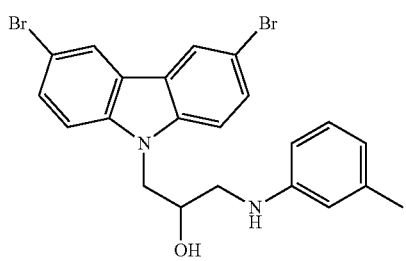 [SMILES: Cc1cccc(NCC(O)Cn2c3ccc(Br)cc3c3cc(Br)ccc32)c1]

This compound can be purchased from ChemDiv, Inc.

Example 64

1-(3,6-dibromo-9H-carbazol-9-yl)-3-(3,5-dimethylphenylamino)propan-2-ol

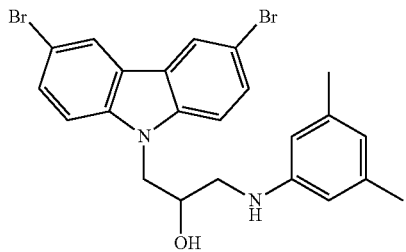 [SMILES: Cc1cc(C)cc(NCC(O)Cn2c3ccc(Br)cc3c3cc(Br)ccc32)c1]

This compound can be purchased from ChemDiv, Inc.

Example 65

1-(3,6-dibromo-9H-carbazol-9-yl)-3-(3,4-dimethylphenylamino)propan-2-ol

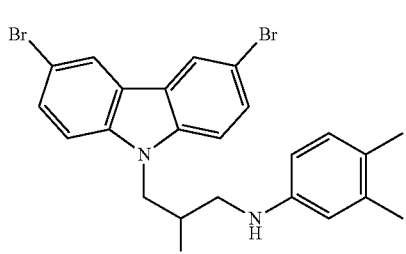

This compound can be purchased from ChemDiv, Inc.

Example 66

1-(3,6-dibromo-9H-carbazol-9-yl)-3-(3,4-dimethylphenylamino)propan-2-ol

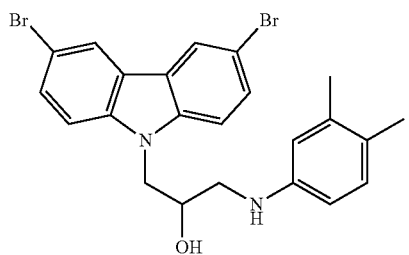 [SMILES: Cc1ccc(NCC(O)Cn2c3ccc(Br)cc3c3cc(Br)ccc32)cc1C]

This compound can be purchased from ChemDiv, Inc.

Example 67

1-(3,6-dibromo-9H-carbazol-9-yl)-3-(2,5-dimethylphenylamino)propan-2-ol

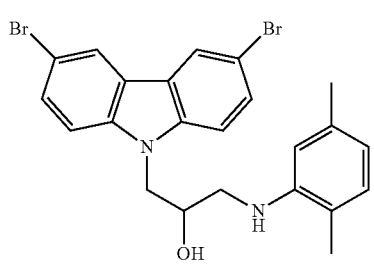 [SMILES: Cc1ccc(C)c(NCC(O)Cn2c3ccc(Br)cc3c3cc(Br)ccc32)c1]

This compound can be purchased from ChemDiv, Inc.

Example 68

1-(4-bromophenylamino)-3-(2,3-dimethyl-1H-indol-1-yl)propan-2-ol

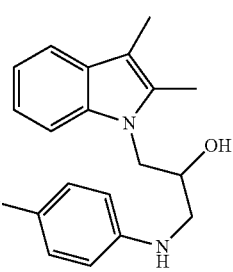

This compound can be purchased from ChemBridge Corporation.

Example 69

1-(2,3-dimethyl-1H-indol-1-yl)-3-(4-methoxyphenylamino)propan-2-ol

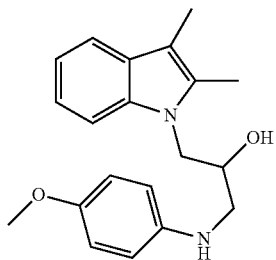 [SMILES: COc1ccc(NCC(O)Cn2c(C)c(C)c3ccccc32)cc1]

This compound can be purchased from ChemBridge Corporation.

Example 70

1-(2,3-dimethyl-1H-indol-1-yl)-3-(4-ethoxyphenylamino)propan-2-ol

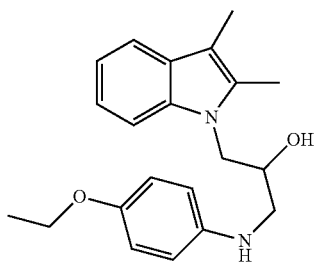 [SMILES: CCOc1ccc(NCC(O)Cn2c(C)c(C)c3ccccc32)cc1]

This compound can be purchased from ChemBridge Corporation.

Example 71

1-(2,3-dimethyl-1H-indol-1-yl)-3-(p-tolylamino)propan-2-ol

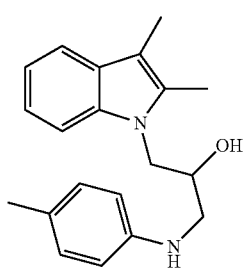 [SMILES: Cc1ccc(NCC(O)Cn2c(C)c(C)c3ccccc32)cc1]

This compound can be purchased from ChemBridge Corporation.

Example 72

1-(2,3-dimethyl-1H-indol-1-yl)-3-(phenylamino)propan-2-ol oxalate

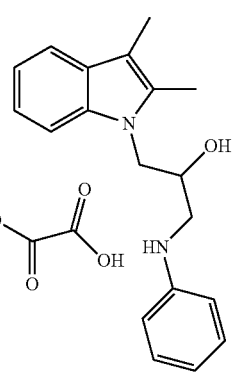

This compound can be purchased from ChemBridge Corporation.

Example 73

1-(1H-indol-1-yl)-3-(4-methoxyphenylamino)propan-2-ol hydrochloride

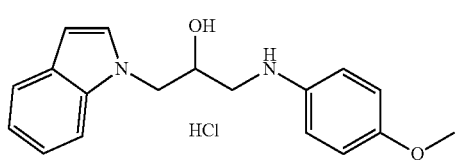 [SMILES: COc1ccc(NCC(O)Cn2ccc3ccccc32)cc1 ; Cl]

This compound can be purchased from ChemBridge Corporation.

Example 74

1-(1H-indol-1-yl)-3-(phenylamino)propan-2-ol oxalate

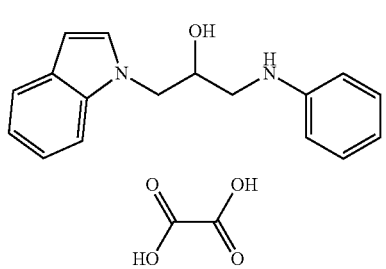 [SMILES: OC(CNc1ccccc1)Cn1ccc2ccccc21 ; O=C(O)C(=O)O]

This compound can be purchased from ChemBridge Corporation.

Example 75

1-(3,4-dihydro-1H-carbazol-9(2H)-yl)-3-(m-tolylamino)propan-2-ol

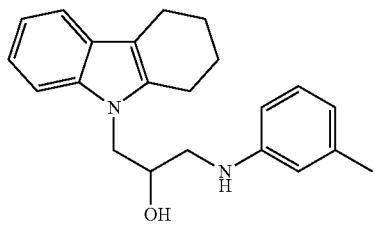 [SMILES: Cc1cccc(NCC(O)Cn2c3c(c4ccccc42)CCCC3)c1]

This compound can be purchased from ChemBridge Corporation.

Example 76

P7C3-S229: 1-(9H-carbazol-9-yl)-3-(phenylamino)propan-2-ol

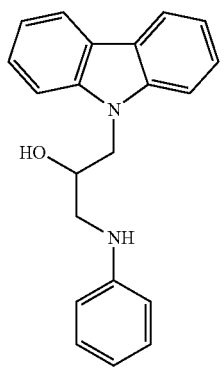 [SMILES: OC(CNc1ccccc1)Cn1c2ccccc2c2ccccc21]

This compound can be purchased from ChemBridge Corporation.

A separate batch was also synthesized independently. Specifically, following representative procedure 2, 1-(9H-carbazol-9-yl)-3-(phenylamino)propan-2-ol was prepared in 80% yield.

$^1$H NMR (500 MHz, CDCl$_3$) δ 8.09 (d, J=7.7 Hz, 2H), 7.45 (q, J=8.2 Hz, 4H), 7.24 (d, J=6.6 Hz, 2H), 7.17 (t, J=7.6 Hz, 2H), 6.80 (t, J=7.5 Hz, 2H), 6.71 (d, J=7.8 Hz, 2H), 4.49 (s, 1H), 4.46 (d, J=5.1 Hz, 2H), 3.40 (d, J=12.9 Hz, 1H), 3.28 (dd, J=12.3, 7.5 Hz, 1H). ESI m/z: 317.1 ([M+H]$^+$, C$_{21}$H$_{20}$N$_2$O requires 317.16)

Example 77

1-(3,6-dichloro-9H-carbazol-9-yl)-3-(phenylamino)propan-2-ol

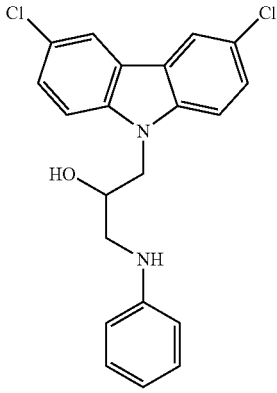 [SMILES: OC(CNc1ccccc1)Cn1c2ccc(Cl)cc2c2cc(Cl)ccc21]

This compound can be purchased from ChemBridge Corporation.

Example 78

1-(9H-carbazol-9-yl)-3-(p-tolylamino)propan-2-ol

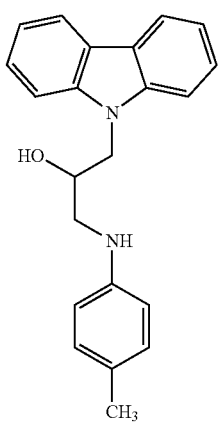 [SMILES: Cc1ccc(NCC(O)Cn2c3ccccc3c3ccccc32)cc1]

This compound can be purchased from ChemBridge Corporation.

Example 79

1-(3,6-dichloro-9H-carbazol-9-yl)-3-(p-tolylamino)propan-2-ol

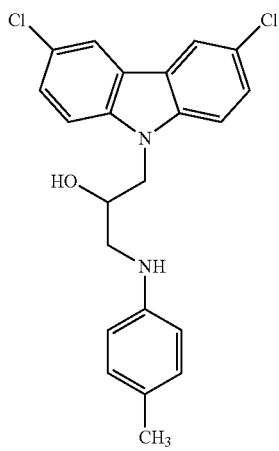 [SMILES: Cc1ccc(NCC(O)Cn2c3ccc(Cl)cc3c3cc(Cl)ccc32)cc1]

This compound can be purchased from ChemBridge Corporation.

Example 80

1-(3,6-dibromo-9H-carbazol-9-yl)-3-(p-tolylamino)propan-2-ol

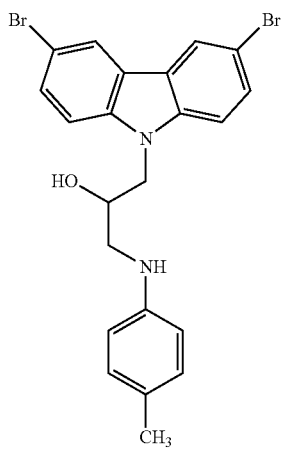 [SMILES: Cc1ccc(NCC(O)Cn2c3ccc(Br)cc3c3cc(Br)ccc32)cc1]

This compound can be purchased from ChemBridge Corporation.

Example 81

N-(4-(3-(9H-carbazol-9-yl)-2-hydroxypropoxy)phenyl)acetamide

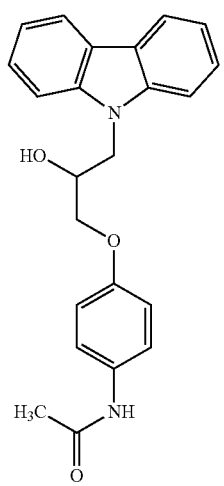 [SMILES: CC(=O)Nc1ccc(OCC(O)Cn2c3ccccc3c3ccccc32)cc1]

This compound can be purchased from ChemBridge Corporation.

Example 82

1-(9H-carbazol-9-yl)-3-phenoxypropan-2-ol

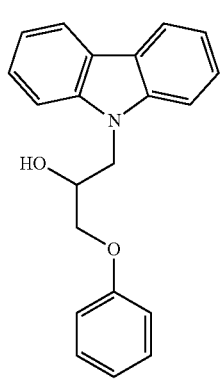 [SMILES: OC(COc1ccccc1)Cn1c2ccccc2c2ccccc21]

This compound can be purchased from ChemBridge Corporation.

Example 83

1-(9H-carbazol-9-yl)-3-(4-methoxyphenylamino)propan-2-ol

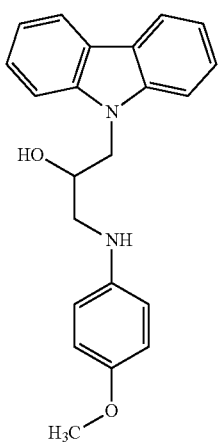 [SMILES: COc1ccc(NCC(O)Cn2c3ccccc3c3ccccc32)cc1]

This compound can be purchased from ChemBridge Corporation.

Example 84

1-(benzylamino)-3-(9H-carbazol-9-yl)propan-2-ol

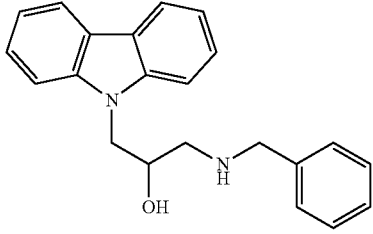 [SMILES: OC(CNCc1ccccc1)Cn1c2ccccc2c2ccccc21]

This compound can be purchased from ChemBridge Corporation.

Example 85 methyl 4-(3-(9H-carbazol-9-yl)-2-hydroxypropoxy)benzoate

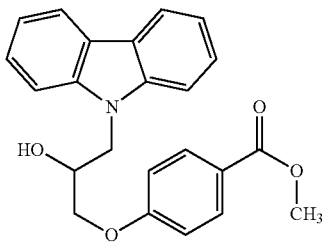 [SMILES: COC(=O)c1ccc(OCC(O)Cn2c3ccccc3c3ccccc32)cc1]

This compound can be purchased from ChemBridge Corporation.

Example 86

1-(9H-carbazol-9-yl)-3-(4-methoxyphenoxy)propan-2-ol

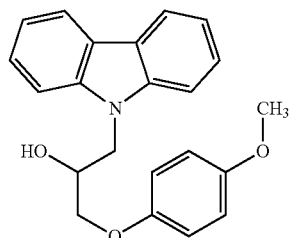

This compound can be purchased from ChemBridge Corporation.

Example 87

P7C3-S20: 1-amino-3-(3,6-dibromo-9H-carbazol-9-yl)propan-2-ol

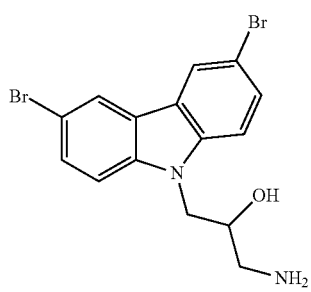 [SMILES: NCC(O)Cn1c2ccc(Br)cc2c2cc(Br)ccc21]

This compound can be purchased from ChemBridge Corporation.

Example 88a

P7C3-S40: (S)-1-(3,6-dibromo-9H-carbazol-9-yl)-3-phenoxypropan-2-ol

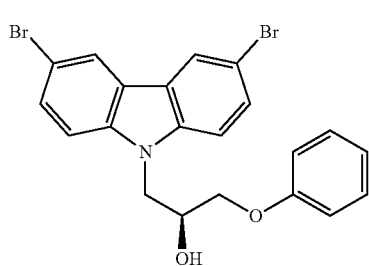 [SMILES: O[C@H](COc1ccccc1)Cn1c2ccc(Br)cc2c2cc(Br)ccc21]

Example 88b

P7C3-S41: (R)-1-(3,6-dibromo-9H-carbazol-9-yl)-3-phenoxypropan-2-ol

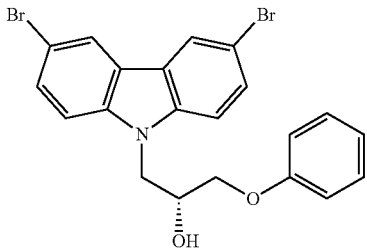 [SMILES: O[C@@H](COc1ccccc1)Cn1c2ccc(Br)cc2c2cc(Br)ccc21]

The title compounds of Examples 88a and 88b were prepared according to the procedure described in Example 3b except using the appropriate commercially available optically active phenoxymethyl oxirane as the epoxide starting material.

Example 89

P7C3-S42: 3,6-dibromo-9-(2-fluoro-3-phenoxypropyl)-9H-carbazole

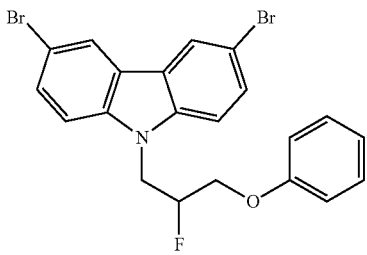

The title compound of Example 89 was prepared according to the procedure described in Representative Procedure 4 except using the title compound of Example 3b as the starting material. The crude mixture was purified in 100% DCM (+0.2% TEA). Isolated yield=97%.

$^1$H NMR (CDCl$_3$, 400 MHz) δ 8.13 (d, 2H, J=1.7 Hz), 7.51 (dd, 2H, J=8.7, 1.9 Hz), 7.29-7.35 (m, 4H), 7.01 (t, 1H, J=7.5 Hz), 6.91 (d, 1H, J=7.8 Hz), 5.16 (dddd, 1H, J=4.5, 5.4, 9.7, 46.0 Hz), 4.59-4.79 (m, 2H), 4.03-4.17 (m, 2H).

MS (ESI), m/z: 519.9 [(M+HCOO)$^-$; C21H16Br2FNO (M) requires 475.0].

Example 90

P7C3-S54: 1-(3,6-dibromo-9H-carbazol-9-yl)-3-(3-methoxyphenylamino)-2-methylpropan-2-ol

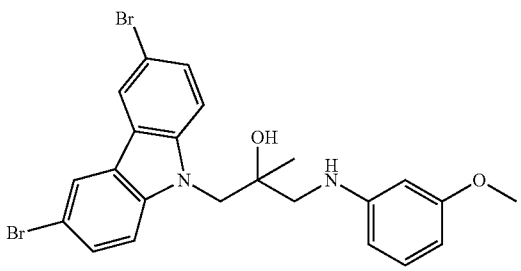 [SMILES: COc1cccc(NCC(C)(O)Cn2c3ccc(Br)cc3c3cc(Br)ccc32)c1]

Step 1. Chlorohydrin-19

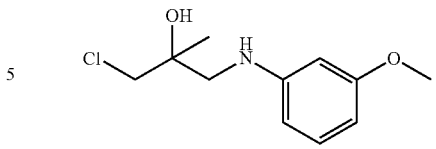

m-Anisidine (0.18 mL, 1.62 mmol) was added to 2-chloromethyl-2-methyl oxirane (0.154 mL, 1.62 mmol) in acetic acid (2 mL) and the mixture was heated to 75° C. Upon completion the reaction was neutralized with saturated sodium bicarbonate to pH 7, then extracted 3× with EtOAc, washed with brine and dried with MgSO$_4$ filtered, and concentrated in vacuo. The crude residue was purified by chromatography (SiO$_2$, 0-25% EtOAc/Hexane) to afford the desired alcohol (332 mg, 89%).

$^1$H NMR (CDCl$_3$, 400 MHz) δ 7.08 (t, 1H, J=8.1 Hz), 6.29 (m, 2H), 6.23 (t, 1H, J=2.3 Hz), 3.95 (s, NH), 3.77 (s, 3H), 3.60 (dd, 2H, J=35.1, 11.0 Hz), 3.25 (dd, 2H, J=44.8, 13.0 Hz), 2.31 (apparent d, OH), 1.36 (s, 3H) ESI m/z 230.1 ([M+H]$^+$).

Step 2. Epoxide-20

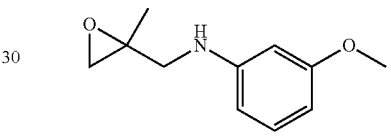

Chlorohydrin-19 (0.166 g, 0.722 mmol) was dissolved in dioxane (1 mL) and added to a solution of KOH (0.168 mgs, 3.0 mmol). The reaction was followed by TLC (20% EtOAc/Hexane) until the starting material was consumed and the less polar product was obtained. After aqueous workup, the crude product was used without purification.

$^1$H NMR (CDCl$_3$, 400 MHz) δ 7.07 (t, 1H, J=8.1 Hz), 6.27 (dd, 1H, J=8.2, 0.8 Hz), 6.22 (dd, 1H, J=8.2, 0.8 Hz), 6.16 (t, 1H, J=2.3 Hz), 3.83 (s, NH), 3.32 (br s, 2H), 2.82 (d, 1H, J=4.5 Hz), 2.63 (d, 1H, J=4.5 Hz).

Reference: Chemistry of Heterocyclic Compounds volume 41, No 4, 2005, pg 426.

Step 3

The title compound of Example 90 was prepared in 83% yield using 3,6-dibromocarbazole, sodium hydride (NaH), and epoxide 20. See, e.g., the procedure described in Example 21, step 4.

$^1$H NMR (CDCl$_3$, 400 MHz): δ 8.14 (s, 2H), 7.53 (d, 2H, J=8.9 Hz), 7.42 (d, 2H, J=8.4 Hz), 7.09 (t, 1H, J=8.4 Hz), 6.33 (d, 1H, J=6.3 Hz), 6.27 (d, 1H, J=6.3 Hz), 6.18 (s, 1H), 4.41 (d, 1H, J=15.3 Hz), 4.32 (d, 1H, J=15.3 Hz) 3.74 (s, NH), 3.49 (s, 3H), 3.28 (d, 1H, 12.4 Hz), 3.22 (d, 1H, 12.4 Hz), 2.03 (s, OH), 1.33 (s, 3H) ESI m/z 518.9 ([M+H]$^+$).

$^{13}$C NMR (CDCl$_3$, 100 MHz) δ 161.0, 149.8, 140.6 (2C), 130.4 (2C), 129.4 (2C), 123.8 (2C), 123.2 (2C), 112.8, 111.8 (2C), 106.9, 103.8, 99.8, 75.0, 55.4, 52.5, 51.5, 25.1

ESI m/z 516.9 ([M+H]$^+$, C$_{23}$H$_{22}$Br$_2$N$_2$O$_2$ requires 516.04

Example 91

1-(2,8-dimethyl-3,4-dihydro-1H-pyrido[4,3-b]indol-5(2H)-yl)-3-(3-methoxyphenylamino)propan-2-ol

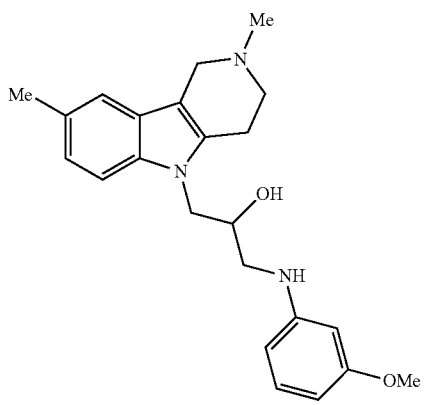 [SMILES: COc1cccc(NCC(O)Cn2c3c(c4cc(C)ccc42)CN(C)CC3)c1]

Following a literature procedure (Zoidis et al., *Bioorg. Med. Chem.* 2009, 17, 1534-1541), the title compound of Example 18 (0.015 g, 0.034 mmol) was dissolved in anhydrous THF (0.34 mL) and cooled to 0° C. A solution of LAH (0.10 mL, 1.0 M in THF) was added dropwise, and the reaction was stirred for 2 h at 0° C. MeOH was added to quench the remaining LAH and after 45 min, the mixture was partitioned between EtOAc/H2O. The organic layer was separated and the aqueous layer was extracted with EtOAc (3×), and the combined organic layers were washed with satd. aq. NaCl, dried over $Na_2SO_4$, filtered, and concentrated. The crude residue was purified by column chromatography ($SiO_2$, 0-20% MeOH/Acetone+1% $Et_3N$), followed by PTLC (10% MeOH/Acetone+1% $Et_3N$) to afford the desired product (0.6 mg, 5%).

$^1$H NMR (CDCl$_3$, 500 MHz) δ=7.14 (m, 2H), 7.04 (dd, 1H, J=8.0, 8.0 Hz), 6.98 (d, 1H, J=8.5 Hz), 6.27 (d, 1H, J=8.0 Hz), 6.18 (d, 1H, J=8.0 Hz), 6.12 (s, 1H), 4.14 (m, 1H), 4.10 (m, 1H), 4.01 (m, 1H), 3.72 (s, 3H), 3.20 (m, 1H), 3.06 (m, 1H), 2.72 (s, 3H), 2.41 (s, 3H).

ESI m/z 380.2 ([M+H]$^+$, $C_{23}H_{30}N_3O_2$ requires 380.2).

Example 92

P7C3-S48: 1-(4-azidophenylamino)-3-(3,6-dibromo-9H-carbazol-9-yl)propan-2-ol

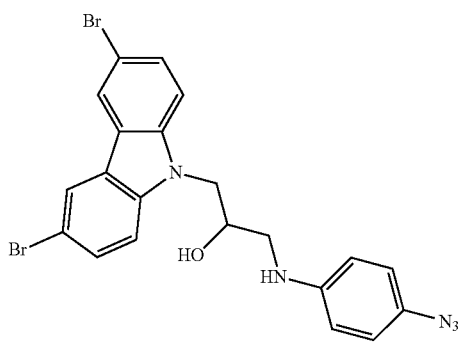 [SMILES: [N-]=[N+]=Nc1ccc(NCC(O)Cn2c3ccc(Br)cc3c3cc(Br)ccc32)cc1]

4-Azidoaniline (0.038 g, 0.283 mmol) was added to a solution of 3,6-dibromo-9-(oxiran-2-ylmethyl)-9H-carbazole (0.100 g, 0.262 mmol) in THF (0.10 mL). LiBr (0.001 g, 0.013 mmol) was added and the reaction was stirred at room temperature for 3 days. The reaction was purified directly by chromatography ($SiO_2$, 0-25% EtOAc/Hexane) to afford the desired product (31 mg, 23%).

$^1$H NMR (d$_6$-acetone, 500 MHz) δ=8.36 (d, 2H, J=2.0 Hz), 7.61 (m, 2H), 7.55 (m, 2H), 6.85 (m, 2H), 6.74 (m, 2H), 5.19 (br s, 1H), 4.61 (dd, 1H, J=4.0, 15.0 Hz), 4.56 (br s, 1H), 4.50 (dd, 1H, J=8.0, 15.0 Hz), 4.39 (m, 1H), 3.39 (dd, 1H, J=4.5, 13.0 Hz), 3.25 (dd, 1H, J=6.5, 13.0 Hz).

$^{13}$C NMR (acetone-d$_6$, 100 MHz) δ=147.7, 141.1, 129.8 (2C), 128.9, 124.5, 124.0 (2C), 120.7 (2C), 114.9 (2C), 112.8 (2C), 112.6, 111.9, 69.6, 48.5, 48.4.

ESI m/z 513.9 ([M+H]$^+$, $C_{21}H_{18}Br_2N_5O$ requires 514.0).

Example 93

P7C3-S47: 1-(3-azido-6-bromo-9H-carbazol-9-yl)-3-(3-methoxyphenylamino)propan-2-ol

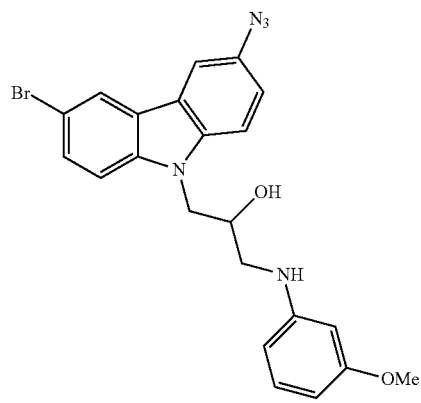 [SMILES: COc1cccc(NCC(O)Cn2c3ccc(Br)cc3c3cc(N=[N+]=[N-])ccc32)c1]

Step 1. 3-azido-6-bromo-9H-carbazole

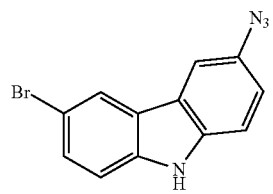 [SMILES: [N-]=[N+]=Nc1ccc2[nH]c3ccc(Br)cc3c2c1]

3,6-Dibromocarbazole (0.500 g, 1.538 mmol), NaN$_3$ (0.120 g, 1.846 mmol), CuI (0.029 g, 0.154 mmol), L-proline (0.053 g, 0.461 mmol) and NaOH (0.019 g, 0.461 mmol) were dissolved in 7:3 EtOH/H$_2$O (3.0 mL) and heated to 95° C. under a N$_2$ atmosphere for 24 h. The completed reaction was partitioned between EtOAc/H2O (3×) and the combined organics were washed with satd. aq. NaCl, dried over Na$_2$SO$_4$, filtered, and concentrated. The crude residue was purified by chromatography (SiO$_2$, 0-15% EtOAc/toluene), followed by HPLC (Phenomenex SiO$_2$ Luna 10μ, 250×21.2 mm column, 50% EtOAc/Hexane, 21 mL/min, retention time=48 min) to afford the desired product.

¹H NMR (CDCl₃, 500 MHz) δ 8.14 (s, 1H), 8.08 (br s, 1H), 7.64 (s, 1H), 7.50 (d, 1H, J=8.5 Hz), 7.38 (d, 1H, J=9.0 Hz), 7.29 (d, 1H, J=8.5 Hz), 7.10 (d, 1H, J=9.0 Hz).

ESI m/z 285.0 ([M−H]⁻, $C_{12}H_6BrN_4$ requires 285.0).

Step 2 The title compound of Example 93 was synthesized from 3-azido-6-bromo-9H-carbazole in 46% yield using a procedure analogous to that described in Example 90, step 3.

¹H NMR (CDCl₃, 500 MHz) δ 8.14 (d, 1H, J=1.5 Hz), 7.64 (d, 1H, J=2.0 Hz), 7.52 (dd, 1H, J=1.5, 8.5 Hz), 7.40 (d, 1H, J=9.0 Hz), 7.31 (d, 1H, J=8.5 Hz), 7.12 (dd, 1H, J=2.0, 8.5 Hz), 7.07 (dd, 1H, J=8.0, 8.0 Hz), 6.31 (dd, 1H, J=2.0, 8.0 Hz), 6.21 (dd, 1H, J=1.5, 8.0 Hz), 6.13 (dd, 1H, J=2.0, 2.5 Hz), 4.39-4.35 (m, 3H), 3.71 (s, 3H), 3.31 (dd, 1H, J=3.5, 13.0 Hz), 3.16 (dd, 1H, J=7.0, 13.0 Hz), 2.17 (br s, 1H).

ESI m/z 466.0 ([M+H]⁺, $C_{22}H_{21}BrN_5O_2$ requires 466.1).

Example 94

P7C3-S49: 1-(3,6-dibromo-9H-carbazol-9-yl)-3-(4-methoxyphenoxy) propan-2-ol

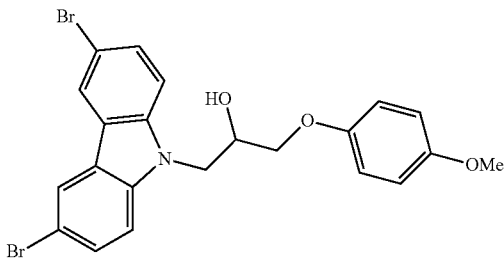 [SMILES: COc1ccc(OCC(O)Cn2c3ccc(Br)cc3c3cc(Br)ccc32)cc1]

The title compound of Example 93 was synthesized from dibromocarbazole and (p-methoxyphenyl)-glycidyl ether in 47% yield using a procedure analogous to those described in Example 90, step 3 and Example 93, Step 2

¹H NMR (CDCl₃, 500 MHz) δ 8.12 (d, 2H, J=2.0 Hz), 7.50 (dd, 2H, J=2.0, 8.5 Hz), 7.34 (d, 2H, J 8.5 Hz), 6.81 (m, 2H), 6.79 (m, 2H), 4.56 (m, 1H), 4.42 (m, 3H), 3.93 (dd, 1H, J=4.5, 9.5 Hz), 3.81 (dd, 1H, J=4.5, 9.5 Hz), 3.76 (s, 3H), 2.39 (d, 1H, J=6.0 Hz).

¹³C NMR (acetone-d₆, 100 MHz) δ 155.2, 153.8, 141.2 (2C), 129.8 (2C), 124.5 (2C), 124.0 (2C), 116.4 (2C), 115.5 (2C), 112.9 (2C), 112.5 (2C), 71.1, 69.8, 55.9, 47.4.

ESI m/z 547.9 ([M+CO₂H]⁻, $C_{23}H_{20}Br_2NO_5$ requires 548.0).

Example 95

P7C3-S52: 1-(3,6-dichloro-9H-carbazol-9-yl)-3-(phenylsulfonyl)propan-2-ol

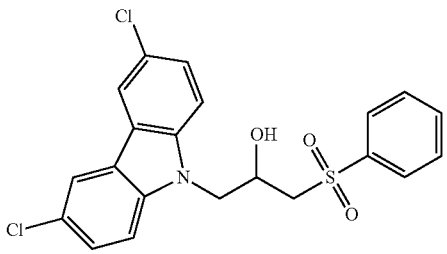 [SMILES: O=S(=O)(CC(O)Cn1c2ccc(Cl)cc2c2cc(Cl)ccc21)c1ccccc1]

Step 1. 1-(3,6-dichloro-9H-carbazol-9-yl)-3-(phenylthio)propan-2-ol

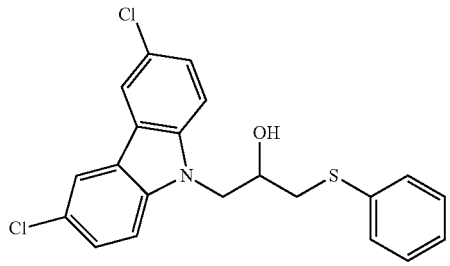 [SMILES: OC(CSc1ccccc1)Cn1c2ccc(Cl)cc2c2cc(Cl)ccc21]

The title compound of Example 95, step 1 was prepared using a procedure analogous to that described in Example 3a (white solid, 0.0293 g, yield 99.0%).

¹H NMR (CDCl₃, 400 MHz) δ=2.55 (s, 1H) 2.97 (dd, J=13.8, 7.2 Hz, 1H) 3.09 (dd, J=13.9, 5.2 Hz, 1H) 4.20-4.06 (m, 1H) 4.28 (dd, J=15.0, 7.0 Hz, 1H) 4.41 (dd, J=15.0, 4.1 Hz, 1H) 7.46-7.14 (m, 9H) 7.93 (d, J=1.8 Hz, 2H)

¹³C NMR (CDCl₃, 400 MHz) δ=139.7, 134.5, 130.3, 129.5, 127.3, 126.8, 125.4, 123.3, 120.4, 110.6, 69.3, 48.2, 39.4

ESI m/z: 446.0, 436.0 [(M+HCOO⁻), (M+Cl⁻); C21H17C12NOS (M) requires 401.0].

Step 2

The title compound of Example 95 was prepared as follows. To a solution of 1-(3,6-dichloro-9H-carbazol-9-yl)-3-(phenylthio)propan-2-ol (0.0081 g, 0.0201 mmol) in 0.2 mL CH₂Cl₂, a solution of mCPBA (77%, 0.0113 g, 0.0503 mmol) in 0.2 mL CH₂Cl₂ was added dropwise. The mixture was sealed and stirred at rt overnight. The crude was diluted with 30 mL EtOAc and washed with saturated NaHCO₃ (3×30 mL) and brine 1×30 mL. The organic layer was dried over anhydrous Na₂SO₄ and evaporated to afford the crude product, which was subjected to silica gel chromatography using Hexanes/EtOAc to afford white solid as product (0.0080 g, yield 91.3%).

¹H NMR (CDCl₃, 400 MHz) δ=3.17 (dd, J=14.2, 3.0 Hz, 1H) 3.28 (dd, J=14.3, 8.3 Hz, 1H) 3.29 (d, J=2.9 Hz, 1H) 4.39 (d, J=6.3 Hz, 2H) 4.67 (dtt, J=8.7, 5.9, 3.0 Hz, 1H) 7.31 (d, J=8.7 Hz, 2H) 7.40 (dd, J=8.7, 2.0 Hz, 2H) 7.52 (t, J=7.9 Hz, 2H) 7.66 (t, J=7.5 Hz, 1H) 7.80 (d, J=7.3 Hz, 2H) 7.96 (d, J=2.0 Hz, 2H).

¹³C NMR (CDCl₃, 400 MHz) δ=139.6, 138.8, 134.5, 129.8, 128.0, 127.0, 125.7, 123.5, 120.5, 110.5, 65.8, 60.0, 48.5

ESI m/z: 477.9 [(M+HCOO⁻); C21H17C12NO3S (M) requires 433.0].

Example 96

P7C3-S53: 3,6-dibromo-9-(2-fluoro-3-(phenylsulfonyl)propyl)-9H-carbazole

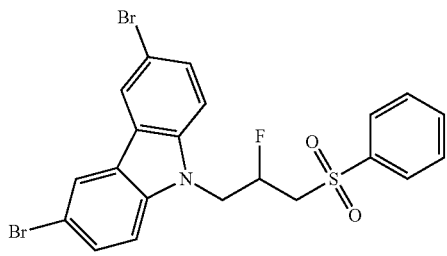 [SMILES: O=S(=O)(CC(F)Cn1c2ccc(Br)cc2c2cc(Br)ccc21)c1ccccc1]

Step 1. 3,6-dibromo-9-(2-fluoro-3-(phenylthio)propyl)-9H-carbazole

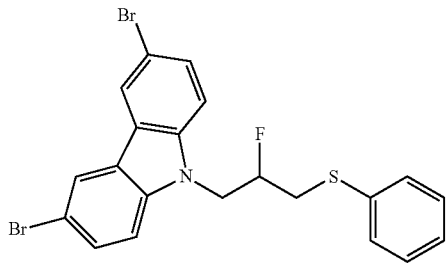 [SMILES: FC(CSc1ccccc1)Cn1c2ccc(Br)cc2c2cc(Br)ccc21]

The title compound of Example 96, step 1 was prepared by fluorination of the title compound of Example 31 using a procedure similar to that described in Representative Procedure 4.

$^1$H NMR (CDCl$_3$, 400 MHz) δ=3.09 (ddd, J=14.2, 11.3, 8.4 Hz, 1H) 3.37-3.23 (m, 1H) 4.53 (ddd, J=20.8, 15.9, 6.7 Hz, 1H) 4.66 (ddd, J=26.6, 15.9, 2.8 Hz, 1H) 5.04-4.81 (m, 1H) 7.36-7.27 (m, 5H) 7.42 (dt, J=3.2, 2.0 Hz, 2H) 7.54 (dd, J=8.7, 1.9 Hz, 2H) 8.13 (d, J=1.9 Hz, 2H)

$^{13}$C NMR (CDCl$_3$, 400 MHz) δ=139.8, 134.3, 129.6, 129.5, 127.6, 123.9, 123.4, 112.9, 110.91 (d, J=2.1 Hz, 1C) 92.2, 90.4, 46.16 (d, J=22.8 Hz, 1C) 35.63 (d, J=23.3 Hz, 1C)

Step 2

The title compound of Example 96 was prepared as follows. To a solution of 3,6-dibromo-9-(2-fluoro-3-(phenylthio)propyl)-9H-carbazole (0.0143 g, 0.0290 mmol) in 0.5 mL CH$_2$Cl$_2$, a solution of mCPBA (77%, 0.0162 g, 0.0725 mmol) in 0.5 mL CH$_2$Cl$_2$ was added dropwise. The mixture was sealed and stirred at rt overnight. The crude was diluted with 30 mL EtOAc and washed with saturated NaHCO$_3$ 3×30 mL and brine 1×30 mL. The organic layer was dried over anhydrous Na$_2$SO$_4$ and evaporated to afford the crude product, which was subjected to silica gel chromatography using Hexanes/EtOAc as elute to afford white solid as product (0.0114 g, yield 74.8%).

$^1$H NMR (CDCl$_3$, 400 MHz) δ=3.61-3.40 (m, 2H) 4.56 (ddd, J=22.4, 16.0, 6.6 Hz, 1H) 4.72 (dd, J=26.8, 15.9 Hz, 1H) 5.38 (dd, J=47.1, 5.9 Hz, 1H) 7.34 (d, J=8.7 Hz, 2H) 7.63-7.53 (m, 4H) 7.68 (t, J=7.4 Hz, 1H) 7.90 (d, J=8.0 Hz, 2H) 8.12 (s, J=2.0 Hz, 2H)

$^{13}$C NMR (CDCl$_3$, 400 MHz) δ=139.8, 134.7, 129.84, 129.79, 128.2, 124.1, 123.5, 113.3, 110.91, 110.89, 88.1, 86.3, 58.4, 58.1, 47.3, 47.1

ESI m/z: 557.9 [(M+C1); C21H16Br2FNO2S (M) requires 522.9].

Example 97a

P7C3-S50: (S)-1-(3,6-dibromo-9H-carbazol-9-yl)-3-(phenylsulfonyl) propan-2-ol

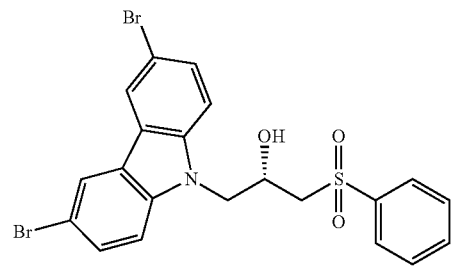 [SMILES: O=S(=O)(C[C@@H](O)Cn1c2ccc(Br)cc2c2cc(Br)ccc21)c1ccccc1]

Example 97b

P7C3-S51: (R)-1-(3,6-dibromo-9H-carbazol-9-yl)-3-(phenylsulfonyl) propan-2-ol

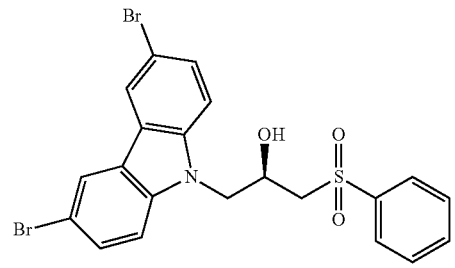 [SMILES: O=S(=O)(C[C@H](O)Cn1c2ccc(Br)cc2c2cc(Br)ccc21)c1ccccc1]

The title compounds of Examples 97a and 97b were prepared from (S)- or (R)-3,6-dibromo-9-(oxiran-2-ylmethyl)-9H-carbazole using a procedure similar to that described in Example 3d.

Preparation of (S)-3,6-dibromo-9-(oxiran-2-ylmethyl)-9H-carbazole [(S)-epoxide A]

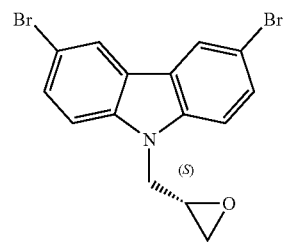

To a solution of 3,6-dibromocarbazole (0.2194 g, 0.675 mmol) and triphenylphosphine (0.1770 g, 0.675 mmol) in THF (5.4 mL) was added S-(−)-glycidol (44.8 µL, 0.0500 g, 0.675 mmol). The reaction mixture was cooled in an ice bath and diethyl azodicarboxylate (106.3 μL, 0.1175 g, 0.675 mmol) was added. The reaction mixture was allowed to warm to room temperature and stir overnight. THF was removed under vacuum and the residue was dissolved in 30 mL EtOAc and washed with brine (3×30 mL). The organic layer was dried over anhydrous $Na_2SO_4$ and evaporated to afford the crude product, which was subjected to silica gel chromatography using Hexanes/EtOAc to afford white solid as product (0.0514 g, yield 20.0%).

Example 98

P7C3-S62: 1-(3,6-dicyclopropyl-9H-carbazol-9-yl)-3-(phenylamino) propan-2-ol

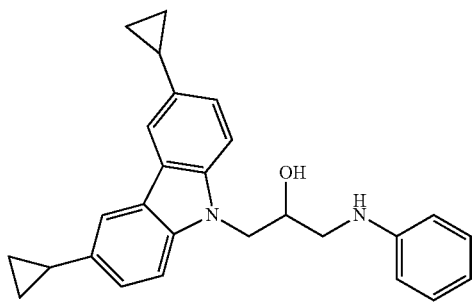 [SMILES: OC(CNc1ccccc1)Cn1c2ccc(C3CC3)cc2c2cc(C3CC3)ccc21]

Step 1. tert-butyl 3,6-dibromo-9H-carbazole-9-carboxylate

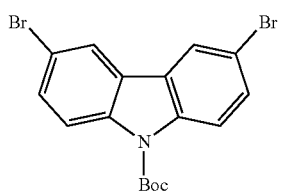 [SMILES: CC(C)(C)OC(=O)n1c2ccc(Br)cc2c2cc(Br)ccc21]

A solution of 3,6-dibromocarbazole (0.8288 g, 2.55 mmol) in 20 mL THF was added to a suspension of NaH (60%, 0.1122 g, 2.81 mmol) in 10 mL THF at −78° C. After stirring for 1 h, a solution of $(Boc)_2O$ anhydride (0.6122 g, 2.81 mmol) in 20 mL THF was added dropwise into the mixture. The reaction was allowed to warm to room temperature and stir overnight. THF was removed under vacuum and the residue was dissolved in 30 mL EtOAc and washed with 1M HCl (2×30 mL) and brine (1×30 mL). The organic layer was dried over anhydrous $Na_2SO_4$ and evaporated and the crude product was subjected to silica gel chromatography using Hexanes/EtOAc to afford white solid as product (0.9890 g, yield 91.7%).

$^1$H NMR (CDCl$_3$, 400 MHz) δ=1.75 (s, 9H) 7.58 (dd, J=8.9, 2.0 Hz, 1H) 8.05 (d, J=1.8 Hz, 1H) 8.16 (d, J=8.9 Hz, 1H).

$^{13}$C NMR (CDCl$_3$, 400 MHz) δ=150.5, 137.5, 130.5, 126.3, 122.6, 117.9, 116.4, 84.9, 28.5.

Step 2. tert-butyl 3,6-dicyclopropyl-9H-carbazole-9-carboxylate

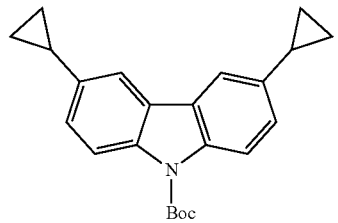 [SMILES: CC(C)(C)OC(=O)n1c2ccc(C3CC3)cc2c2cc(C3CC3)ccc21]

Following a literature procedure (Petit et al., ChemMedChem 2009, 4, 261-275.), tert-butyl 3,6-dibromo-9H-carbazole-9-carboxylate (0.0200 g, 0.0470 mmol), cyclopropyl boronic acid (0.0202 g, 0.235 mmol), palladium acetate (10 mol %, 0.0011 g, 0.00470 mmol), potassium phosphate tribasic (0.0350 g, 0.165 mmol), tricyclohexylphosphine (0.0026 g, 0.00941 mmol), water (12.2 μL) and a stir bar were combined in a sealed vial. The vial was sparged with $N_2$ and charged with 0.22 mL degassed toluene. The mixture was stirred at 100° C. for 65 h. The crude reaction mixture was diluted with 10 mL EtOAc and washed with brine (3×10 mL). The organic layer was dried over anhydrous $Na_2SO_4$ and evaporated to afford the crude product, which was used as is without further purification.

$^1$H NMR (CDCl$_3$, 400 MHz) δ=0.82-0.76 (m, 4H) 1.02 (ddd, J=8.4, 6.4, 4.4 Hz, 4H) 1.74 (s, 9H) 2.11-2.01 (m, 2H) 7.19 (dd, J=8.6, 1.9 Hz, 2H) 7.65 (d, J=1.7 Hz, 2H) 8.14 (d, J=8.5 Hz, 2H)

Step 3. 3, 6-dicyclopropyl-9H-carbazole

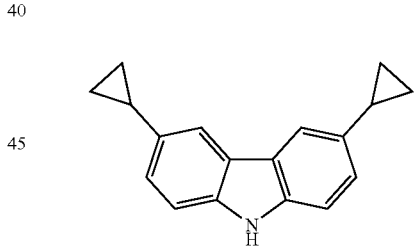

To a solution of the corresponding N-Boc carbazole (0.0163 g, 0.0469 mmol) in 1 mL $CH_2Cl_2$, TFA (144.8 μL, 1.876 mmol) was added dropwise. The mixture was sealed and stirred at rt for 6 h. $CH_2Cl_2$ and TFA were removed under vacuum. The residue was diluted with 30 mL EtOAc and washed with saturated $NaHCO_3$ 3×30 mL. The organic layer was dried over anhydrous $Na_2SO_4$ and evaporated to afford the crude product, which was subjected to silica gel chromatography using Hexanes/EtOAc as elute to afford white solid as product (0.0139 g).

$^1$H NMR (CDCl$_3$, 400 MHz) δ=0.77 (dt, J=6.4, 4.5 Hz, 4H) 0.99 (ddd, J=8.4, 6.2, 4.4 Hz, 4H) 2.13-2.03 (m, 2H) 7.16 (dd, J=8.4, 1.7 Hz, 2H) 7.28 (d, J=8.4 Hz, 2H) 7.76 (d, J=1.1 Hz, 2H) 7.83 (s, br, 1H).

Step 4. 3,6-dicyclopropyl-9-(oxiran-2-ylmethyl)-9H-carbazole

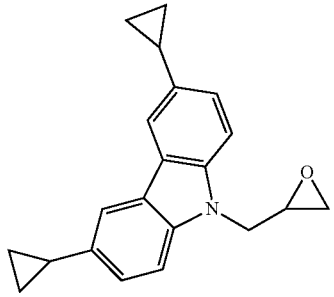 [SMILES: c1cc2c(cc1C1CC1)c1cc(C3CC3)ccc1n2CC1CO1]

The title compound of Example 98, step 4 was prepared from 3,6-dicyclopropyl-9H-carbazole using a procedure similar to that described in Representative Procedure 1.

¹H NMR (CDCl₃, 400 MHz) δ=0.81-0.74 (m, 4H) 1.03-0.96 (m, 4H) 2.09 (ddd, J=14.4, 8.9, 5.6 Hz, 2H) 2.53 (dd, J=4.8, 2.6 Hz, 1H) 2.77 (t, J=4.3 Hz, 1H) 3.30 (dt, J=7.4, 3.9 Hz, 1H) 4.35 (dd, J=15.8, 4.6 Hz, 1H) 4.54 (dd, J=15.8, 3.4 Hz, 1H) 7.22 (dd, J=8.4, 1.7 Hz, 2H) 7.31 (d, J=8.4 Hz, 2H) 7.78 (d, J=1.1 Hz, 2H).

Step 5

The title compound of Example 98 was prepared from 3,6-dicyclopropyl-9-(oxiran-2-ylmethyl)-9H-carbazole using a procedure similar to that described in Representative Procedure 2.

¹H NMR (CDCl₃, 600 MHz) δ=0.79-0.75 (m, 4H) 0.99 (td, J=6.2, 4.6 Hz, 4H) 2.08 (ddd, J=13.6, 8.5, 5.1 Hz, 2H) 3.21 (dd, J=12.9, 5.6 Hz, 1H) 3.35 (d, J=13.8 Hz, 1H) 4.39 (s, J=23.7 Hz, 3H) 6.62 (d, J=8.4 Hz, 2H) 6.75 (t, J=7.3 Hz, 1H) 7.17 (t, J=7.9 Hz, 2H) 7.20 (dd, J=8.4, 1.1 Hz, 2H) 7.32 (d, J=8.4 Hz, 2H) 7.78 (s, 2H)

¹³C NMR (CDCl₃, 500 MHz) δ=148.2, 139.8, 134.9, 129.6, 124.8, 123.2, 118.5, 117.5, 113.7, 108.8, 69.8, 48.0, 47.6, 15.7, 9.1

ESI m/z: 441.2 [(M+HCOO⁻); C27H28N2O (M) requires 396.2].

Example 99

P7C3-S63: 1-(3,6-diiodo-9H-carbazol-9-yl)-3-(phenylamino)propan-2-ol

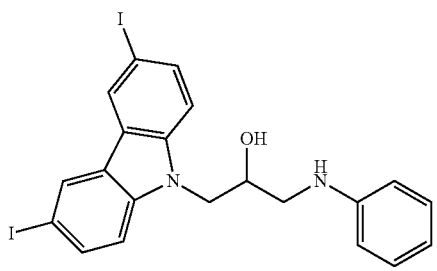 [SMILES: OC(CNc1ccccc1)Cn1c2ccc(I)cc2c2cc(I)ccc21]

Step 1. 3,6-diiodo-9-(oxiran-2-ylmethyl)-9H-carbazole

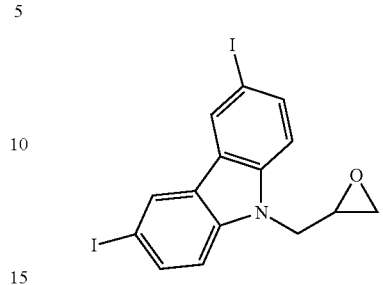

The title compound of Example 99, step 1 was prepared from 3,6-diiodo carbazole (Maegawa et al., *Tetrahedron Lett.* 2006, 47, 6957-6960) using a procedure similar to that described in Representative Procedure 1.

¹H NMR (CDCl₃, 400 MHz) δ=2.48 (dd, J=4.6, 2.6 Hz, 1H) 2.80 (t, J=4.3 Hz, 1H) 3.37-3.24 (m, 1H) 4.28 (dd, J=16.0, 5.1 Hz, 1H) 4.64 (dd, J=15.9, 2.7 Hz, 1H) 7.24 (d, J=8.6 Hz, 2H) 7.73 (dd, J=8.6, 1.6 Hz, 2H) 8.33 (d, J=1.7 Hz, 2H)

¹³C NMR (CDCl₃, 500 MHz) δ=140.0, 135.0, 129.5, 124.3, 111.3, 82.6, 50.6, 45.2, 44.9

Step 2

The title compound of Example 99 was prepared from 3,6-diiodo-9-(oxiran-2-ylmethyl)-9H-carbazole using a procedure similar to that described in Representative Procedure 1.

¹H NMR (CDCl₃, 400 MHz) δ=2.92 (s, br, 1H) 3.19 (dd, J=12.8, 6.1 Hz, 1H) 3.33 (d, J=10.9 Hz, 1H) 4.49-4.29 (m, 3H) 6.63 (d, J=8.3 Hz, 2H) 6.78 (t, J=7.3 Hz, 1H) 7.20 (t, J=7.7 Hz, 2H) 7.28 (d, J=2.5 Hz, 2H) 7.72 (d, J=8.6 Hz, 2H) 8.35 (s, 2H).

¹³C NMR (CDCl₃, 400 MHz) δ=147.9, 140.1, 135.1, 129.65, 129.63, 124.4, 118.9, 113.7, 111.5, 82.6, 69.6, 48.0, 47.3

ESI m/z: 613.0 [(M+HCOO⁻); C21H18I2N2O (M) requires 568.0]. Example 100. P7C3-S64: 1-(3,6-diethynyl-9H-carbazol-9-yl)-3-(3-methoxyphenylamino) propan-2-ol

Step 1. 1-(3,6-bis((triisopropylsilyl)ethynyl)-9H-carbazol-9-yl)-3-(3-methoxyphenylamino)propan-2-ol

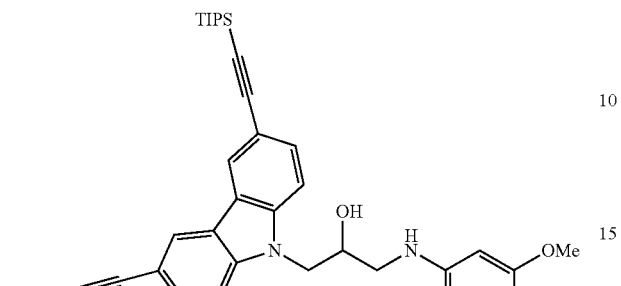

The title compound of Example 62 (0.0112 g, 0.0222 mmol), bis(benzonitrile)dichloropalladium (3 mol %, 0.0003 g, 0.0007 mmol), [(tBu)$_3$PH]BF$_4$ (6.2 mol %, 0.0004 g, 0.0014 mmol), copper(I) iodide (2 mol %, 0.0001 g, 0.0004 mmol), DABCO (0.0060 g, 0.0533 mmol) were combined under an N$_2$ atmosphere. Degassed dioxane (0.1 mL) was added, and the resulting solution was stirred at room temperature for 10 min. Trimethylsilylacetylene (11.8 µL, 0.0533 mmoL) was added into the mixture via microsyringe. The mixture was then stirred at rt overnight. The crude reaction mixture was diluted with 10 mL EtOAc and washed with brine (3×10 mL). The organic layer was dried over anhydrous Na$_2$SO$_4$ and evaporated to afford the crude product, which was subjected to silica gel chromatography using Hexanes/EtOAc to afford colorless oil as product (0.0152 g, yield 96.8%).

$^1$H NMR (CDCl$_3$, 400 MHz) δ=1.22-1.13 (m, 42H) 2.24 (s, br, 1H) 3.17 (dd, J=12.6, 6.7 Hz, 1H) 3.31 (d, J=12.1 Hz, 1H) 3.71 (s, 3H) 4.48-4.31 (m, 3H) 6.12 (t, J=2.1 Hz, 1H) 6.22 (dd, J=8.0, 1.8 Hz, 1H) 6.31 (dd, J=8.1, 2.1 Hz, 1H) 7.07 (t, J=8.1 Hz, 1H) 7.37 (d, J=8.5 Hz, 2H) 7.58 (dd, J=8.5, 1.5 Hz, 2H) 8.22 (d, J=1.4 Hz, 2H)

$^{13}$C NMR (CDCl$_3$, 400 MHz) δ=171.5, 161.0, 149.3, 140.9, 130.6, 130.4, 124.9, 122.7, 115.1, 109.3, 108.2, 106.7, 103.9, 99.7, 88.7, 69.5, 55.3, 47.4, 19.0, 11.6

Step 2

The title compound of Example 100 was prepared as follows. To a solution of 1-(3,6-bis((triisopropylsilyl)ethynyl)-9H-carbazol-9-yl)-3-(3-methoxyphenylamino)propan-2-ol (0.0152 g, 0.0215 mmol) in 200 µL anhydrous THF, a solution of TBAF in THF (1 M, 64.5 µL, 0.0645 mmol) and acetic acid (2.5 µL, 0.0430 mmol) were added. The mixture was sealed and stirred under N$_2$ atmosphere at rt for 27 h until TLC showed the complete disappearance of starting material. The crude was diluted with 10 mL EtOAc and washed with saturated NaHCO$_3$ (3×10) mL. The organic layer was dried over anhydrous Na$_2$SO$_4$ and evaporated to afford the crude product, which was subjected to silica gel chromatography using Hexanes/EtOAc to afford white solid as product (0.0061 g, yield 71.9%).

$^1$H NMR (CDCl$_3$, 400 MHz) δ=2.24 (s, br, 1H) 3.09 (s, 2H) 3.20 (s, br, 1H) 3.32 (s, br, 1H) 3.72 (s, 3H) 4.48-4.27 (m, 3H) 6.14 (s, 1H) 6.23 (dd, J=8.0, 1.4 Hz, 1H) 6.32 (dd, J=8.2, 1.8 Hz, 1H) 7.08 (t, J=8.1 Hz, 1H) 7.40 (d, J=8.5 Hz, 2H) 7.59 (dd, J=8.5, 1.4 Hz, 2H) 8.21 (d, J=1.1 Hz, 2H)

$^{13}$C NMR (CDCl$_3$, 500 MHz) δ=161.1, 149.3, 141.2, 130.7, 130.4, 125.0, 122.7, 113.6, 109.6, 106.7, 103.8, 99.8, 84.7, 76.0, 69.6, 55.3, 48.0, 47.4

ESI m/z: 439.1 [(M+HCOO$^-$); C26H22N2O2 (M) requires 394.2].

Example 101

P7C3-S65: 9-(2-hydroxy-3-(3-methoxyphenylamino)propyl)-9H-carbazole-3,6-dicarbonitrile

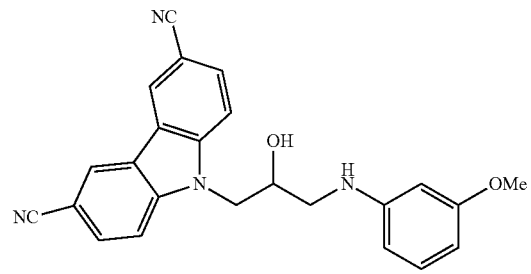 [SMILES: COc1cccc(NCC(O)Cn2c3ccc(C#N)cc3c3cc(C#N)ccc32)c1]

Following a literature procedure (Weissman et al., *J. Org. Chem.* 2005, 70, 1508-1510), the title compound of Example 62 (0.0252 g, 0.05 mmol), potassium hexacyanoferrate(II) trihydrate (0.0106 g, 0.025 mmol), sodium bicarbonate (0.0106 g, 0.1 mmol) and palladium acetate (1 mol %, 0.0001 g) were combined under a N$_2$ atmosphere. Anhydrous dimethylacetamide (0.1 mL) was added, and the reaction mixture was stirred at 120° C. overnight. The crude reaction mixture was diluted with 10 mL EtOAc and washed with water (2×10 mL) and brine (1×30 mL). The organic layer was dried over anhydrous Na$_2$SO$_4$ and evaporated to afford the crude product, which was subjected to silica gel chromatography using Hexanes/EtOAc to afford white solid as product (0.0110 g, yield 54.6%).

$^1$H NMR (d$_6$-acetone, 400 MHz) δ=2.81 (s, 1 H) 3.36-3.28 (m, 1H) 3.50-3.43 (m, 1H) 3.71 (s, 3 H) 4.44 (s, br, 1 H) 4.66 (dd, J=15.0, 8.5 Hz, 1 H) 4.77 (dd, J=15.1, 3.4 Hz, 1 H) 5.16 (t, J=5.8 Hz, 1H) 6.22 (dd, J=8.1, 2.1 Hz, 1H) 6.27 (t, J=2.0 Hz, 1H) 6.31 (dd, J=8.1, 1.2 Hz, 1H) 7.01 (t, J=8.1 Hz, 1H) 7.84 (dd, J=8.6, 1.2 Hz, 2H) 7.91 (d, J=8.6 Hz, 2H) 8.74 (s, 2H)

$^{13}$C NMR (d-acetone, 500 MHz) δ=161.3, 150.4, 143.9, 130.02, 129.95, 126.0, 122.4, 119.8, 112.0, 106.0, 103.3, 102.5, 98.9, 69.0, 54.5, 48.0, 47.7

ESI m/z: 441.1 [(M+HCOO$^-$); C24H20N4O2 (M) requires 396.2).

Example 102

P7C3-S55: N-(3-(3,6-dibromo-9H-carbazol-9-yl)-2-fluoropropyl)aniline

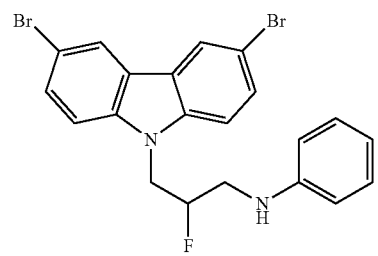

Step 1 N-(3-(3,6-dibromo-9H-carbazol-9-yl)-2-fluoropropyl)-4-nitro-N-phenylbenzenesulfonamide

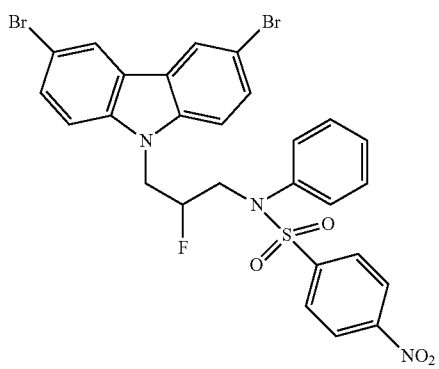 [SMILES: O=[N+]([O-])c1ccc(S(=O)(=O)N(CC(F)Cn2c3ccc(Br)cc3c3cc(Br)ccc32)c2ccccc2)cc1]

The title compound of Example 102, step 1 was prepared from epoxide 2-A and Ns-aniline using procedures similar to those described in representative procedures 3 and 4. The crude mixture was purified in 40% EtOAc/hexanes (+0.1% TEA). The isolated yield was 60%.

$^1$H NMR ((CD$_3$)$_2$CO)$_3$, 400 MHz) δ 8.37 (m, 2H), 7.90 (m, 2H), 7.68 (m, 1H), 7.53-7.60 (m, 6H), 7.32-7.40 (m, 5H), 5.03 (dm, 1H), 4.71-4.93 (m, 2H), 4.27-4.41 (m, 2H).

MS (ESI), m/z: 703.9 [(M+HCOO)$^-$; C27H20Br2FN3O4S (M) requires 659.0]

Step 2

The title compound of Example 102 was prepared as follows. Cesium carbonate (11.5 mg, 0.036 mmol), the nosylate prepared in step 1 above (7.9 mg, 0.012 mmol), THF (0.7 ml, 0.017 M) and benezenthiol (3.8 ul, 0.037 mmol) were combined and stirred overnight. The crude reaction mixture was diluted with EtOAc, washed with water and brine. The organic layer was dried over Na$_2$SO$_4$, filtered and condensed. Chromatographic purification on SiO2 (20% EtOAc/hexanes (0.2% TEA)) provided 74% (4.2 mg).

$^1$H NMR (CDCl$_3$, 500 MHz) δ=8.16 (s, 2H), 7.56 (d, 2H, J=8.5 Hz), 7.31 (d, 2H, J=8.5 Hz), 7.21 (t, 2H, J=7.4 Hz), 6.80 (t, 1H, J=7.3 Hz), 6.62 (d, 2H, J=8.5 Hz), 5.11 (dddd, 1H, J=5.4, 5.4, 10.4, 47.4 Hz), 4.52-4.68 (m, 2H), 3.94 (t, 1H, J=6.02 Hz), 3.30-3.51, (dm, 2H).

MS (ESI), m/z: 475.0 [(M+1)−; C21H17Br2FN2 (M) requires 474.0].

Example 103

P7C3-S56: 3,6-dibromo-9-(2,2-difluoro-3-phenoxypropyl)-9H-carbazole

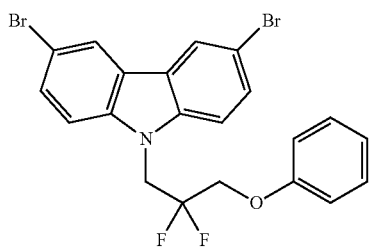 [SMILES: FC(F)(COc1ccccc1)Cn1c2ccc(Br)cc2c2cc(Br)ccc21]

Step 1. 1-(3,6-dibromo-9H-carbazol-9-yl)-3-phenoxypropan-2-one

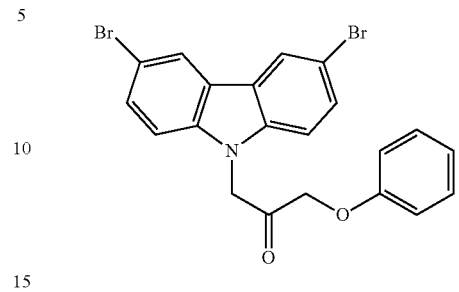

Dess-Martin periodinane (58.2 mg, 0.137 mmol) was charged to a solution of the title compound of Example 3b (45.0 mg, 0.095 mmol) in dichloromethane (1.0 ml, 0.095 M). After two hours the reaction mixture was diluted with EtOAc and washed with saturated sodium thiosulfate solution, water and brine. The organic layer was dried over Na$_2$SO$_4$, filtered and condensed. The crude product was used without additional purification. Yield=74%

$^1$H NMR (CDCl$_3$, 400 MHz) δ 8.15 (d, 2H, J=1.9 Hz), 7.52 (dd, 2H, J=8.6, 1.9 Hz) 7.35 (m, 2H), 7.08 (t, 1H, J=7.3 Hz), 7.04 (d, 2H, J=8.9 Hz), 6.91 (m, 2H), 5.29 (s, 2H), 4.68 (m, 2H)

MS (ESI), m/z: 469.9 [(M−1)$^-$; C21H15Br2NO2 (M) requires 570.9].

Step 2

The title compound of Example 103 was prepared as follows. Diethylaminosulfur trifluoride (39 ul, 0.30 mmol) was added dropwise to a solution of 1-(3,6-dibromo-9H-carbazol-9-yl)-3-phenoxypropan-2-one (33.3 mg, 0.070 mmol) in anhydrous dichloromethane (1.5 ml, 0.047M). The reaction was quenched with saturated sodium bicarbonate solution, and then extracting three times with dichloromethane. The organic layer is dried over Na$_2$SO$_4$, filtered and condensed. The crude mixture was purified on SiO2 (10% EtOAc/hexanes+0.2% TEA. Isolated yield was 69%.

$^1$H NMR (CDCl$_3$, 400 MHz) δ 8.09 (d, 2H, J=1.9 Hz), 7.48 (dd, 2H, J=8.7, 1.8 Hz) 7.30-7.4 (m, 4H), 7.06 (t, 1H, J=7.3 Hz), 6.91 (d, 2H, J=7.9 Hz), 4.79 (t, 2H, J=12.4 Hz), 4.07 (t, 2H, J=11.1 Hz).

MS (ESI), m/z: 537.9 [(M+HCOO)$^-$; C21H15Br2F2NO (M) requires 492.9].

Example 104

P7C3-S60: N-(3-(3,6-dibromo-9H-carbazol-9-yl)-2-fluoropropyl)-4-methoxyaniline

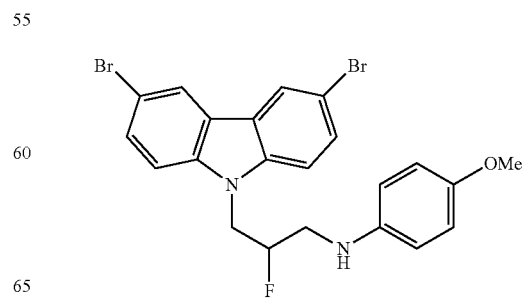

Step 1. N-(3-(3,6-dibromo-9H-carbazol-9-yl)-2-hydroxypropyl)-N-(4-methoxyphenyl)-4-nitrobenzenesulfonamide

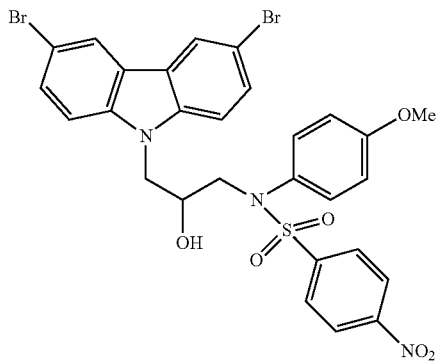

The title compound of Example 104, step 1 was prepared from epoxide 2-A and Ns-anisidine according to Representative Procedure 3. Yield=71%

$^1$H NMR (CDCl$_3$, 400 MHz) δ 8.29 (d, 2H, J=8.7 Hz), 8.11 (d, 2H, J=1.9 Hz), 7.71 (, 2H, J=8.6 Hz), 7.52 (dd, 2H, J=8.6, 1.9 Hz), 7.23 (d, 2H, J=8.9 Hz), 6.94 (d, 2H, J=8.9 Hz), 6.82 (d, 2H, J=8.9 Hz), 4.44 (dd, 1H, J=14.8, 3.8 Hz), 4.30 (m, 1H), 4.21 (bs, 1H), 3.81 (s, 3H), 3.69 (m, 2H).

MS (ESI), m/z: 732.0 [(M+HCOO$^-$); C28H23Br2N3O6S (M) requires 687.0]

Step 2. N-(3-(3,6-dibromo-9H-carbazol-9-yl)-2-fluoropropyl)-N-(4-methoxyphenyl)-4-nitrobenzenesulfonamide

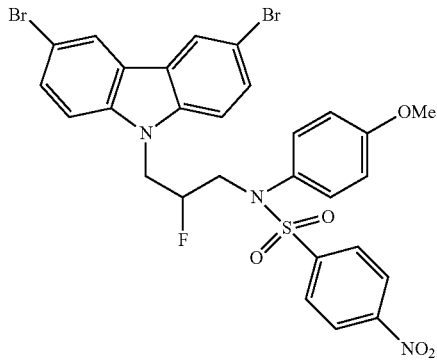 [SMILES: COc1ccc(N(CC(F)Cn2c3ccc(Br)cc3c3cc(Br)ccc32)S(=O)(=O)c2ccc([N+](=O)[O-])cc2)cc1]

The title compound of Example 104, step 2 was prepared from the nosylate prepared in step 1 above according to General Procedure 4. Yield=61.5%

$^1$H NMR (CDCl$_3$, 400 MHz) δ 8.27 (m, 2H), 8.09 (m, 2H), 7.71 (d, 2H, J=7.41 Hz), 7.53 (m, 2H), 7.19 (m, 2H), 6.95 (d, 2H, J=8.8 Hz), 6.82 (d, 2H, J=8.8 Hz), 4.92 (dm, 1H, J$_d$=48.3 Hz), 4.55 (m, 2H), 3.88 (m, 2H), 3.79 (s, 3H).

MS (ESI), m/z: 734.0 (M+HCOO$^-$); C28H22Br2FN3O5S (M) requires 689.0]

Step 3

The title compound of Example 104 was prepared according to Representative Procedure 5. Isolated yield 70%.

$^1$H NMR (CDCl$_3$, 400 MHz) δ 8.14 (m, 2H0, 7.53 (dt, 2H, J=8.8, 1.6 Hz), 7.30 (d, 2H, 8.6 Hz), 6.78 (d, 2H, J=7.9 Hz), 6.57 (d, 2H, J=7.9 Hz), 5.07 (dddd, 1H, J=4.7, 6.1, 9.4, 47.7), 4.58 (m, 2H), 3.75 (s, 3H), 3.32 (m, 2H).

MS (ESI), m/z: 549.0 [(M+HCOO)$^-$; C22H19Br2FN2O (M) requires 505.0).

Example 105

P7C3-S67: N-(2-bromo-3-(3,6-dibromo-9H-carbazol-9-yl)propyl)-N-(4-methoxyphenyl)-4-nitrobenzenesulfonamide

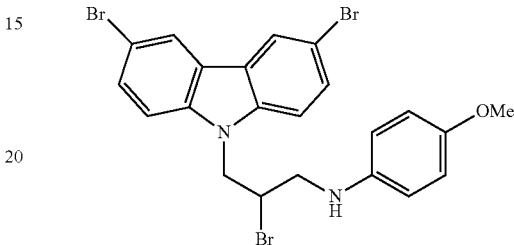

Step 1. N-(2-bromo-3-(3,6-dibromo-9H-carbazol-9-yl)propyl)-N-(4-methoxyphenyl)-4-nitrobenzenesulfonamide

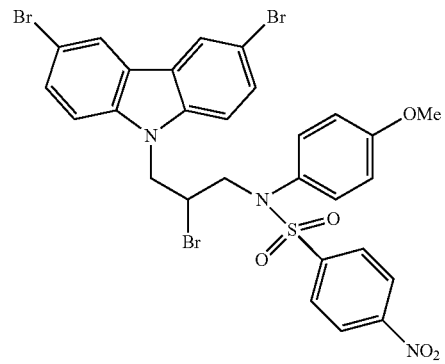 [SMILES: COc1ccc(N(CC(Br)Cn2c3ccc(Br)cc3c3cc(Br)ccc32)S(=O)(=O)c2ccc([N+](=O)[O-])cc2)cc1]

A solution of the title compound Example 104, Step 1 (20.5 mg, 0.030 mmol) in anhydrous dichloromethane (1.0 ml, 0.03 M) was cooled in an ice bath before the addition of BBr$_3$ (7 ul, 0.074 mmol). After 1 h the reaction was diluted with EtOAc, washed twice with water, saturated sodium bicarbonate solution and brine. The organic layer was dried over Na$_2$SO$_4$, filtered and condensed. The crude mixture was purified in 100% CH$_2$Cl$_2$ (+0.2% TEA). Isolated yield=56%.

$^1$H NMR (CDCl$_3$, 500 MHz) δ 8.26 (d, 2H, J=8.9 Hz), 8.12 (d, 2H, J=1.7 Hz), 7.60 (d, 2H, J=8.8 Hz) 7.53 (dd, 2H, J=8.7, 1.9 Hz), 7.18 (d, 2H, J=8.7 Hz), 6.89 (d, 2H, J=8.9 Hz) 6.81 (d, 2H, J=9.0 Hz), 4.86 (dd, 1H, J=15.6, 5.4 Hz), 4.57 (m, 1H), 4.44 (m, 1H), 3.92 (m, 2H), 3.82 (s, 3H). MS (ESI), m/z: 747.9 [(M−1)$^-$; C28H22Br3N3O5S (M) requires 748.9]

Step 2

The title compound of Example 105 was prepared from the nosylate prepared in step 1 above according to Representative Procedure 5. Isolated yield=43% in approximately 90% purity.

¹H NMR (CDCl₃, 400 MHz) δ 8.14 (d, 2H, J=1.7 Hz), 7.51 (dd, 2H, J=8.6, 1.9 Hz), 7.28 (d, 2H, J=8.7 Hz), 6.71 (d, 2H, J=8.9 Hz), 6.41 (d, 2H, J=8.8 Hz), 4.84 (m, 1H), 4.63 (m, 3H), 3.82 (m, 1H), 3.73 (s, 3H).

MS (ESI), m/z: 564.8 [(M+1)⁺; C22H19Br3N2O requires 563.9].

The title compounds of Examples 106-109 can be prepared using the methods described herein and/or using conventional synthesis methods.

Example 106

P7C3-S61: Ethyl 2-(4-(3-(3,6-dibromo-9H-carbazol-9-yl)-2-fluoropropylamino)phenoxy)acetate

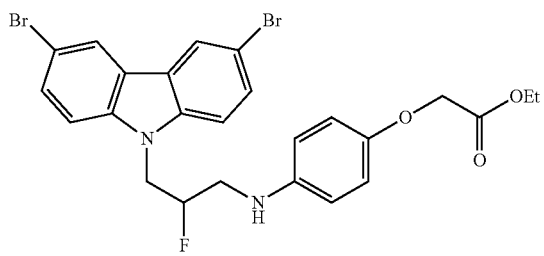 [SMILES: CCOC(=O)COc1ccc(NCC(F)Cn2c3ccc(Br)cc3c3cc(Br)ccc32)cc1]

Example 107

P7C3-S66: N-(3-(3,6-dibromo-9H-carbazol-9-yl)-2-fluoropropyl)-4-(2-(2-methoxyethoxy)ethoxy)aniline

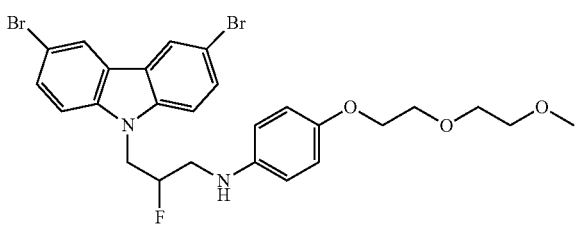 [SMILES: COCCOCCOc1ccc(NCC(F)Cn2c3ccc(Br)cc3c3cc(Br)ccc32)cc1]

Step 1. N-(3-(3,6-dibromo-9H-carbazol-9-yl)-2-hydroxypropyl)-N-(4-methoxyphenyl)-4-nitrobenzenesulfonamide

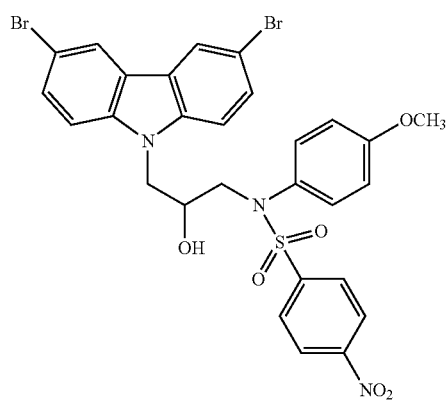 [SMILES: COc1ccc(N(CC(O)Cn2c3ccc(Br)cc3c3cc(Br)ccc32)S(=O)(=O)c2ccc([N+](=O)[O-])cc2)cc1]

The title compound was prepared according to Representative Procedure 3.

Step 2. N-(3-(3,6-dibromo-9H-carbazol-9-yl)-2-hydroxypropyl)-N-(4-hydroxyphenyl)-4-nitrobenzenesulfonamide

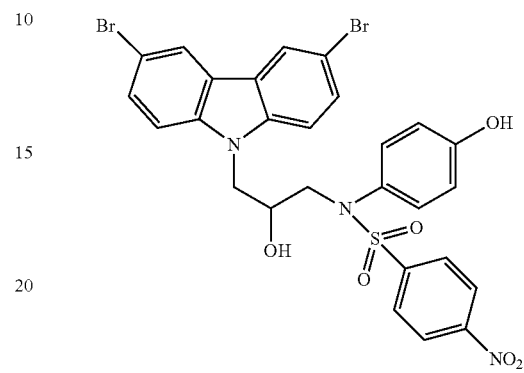

Boron tribromide (290 ul, 3.06 mmol) was added to solution of the product of Step 1 (598 mg, 0.87 mmol) in anhydrous dichloromethane (17.0 ml) at 0° C. The reaction mixture was condensed, diluted with ethyl acetate and washed with water, saturated sodium bicarbonate, water and then brine. Pure product was isolated from column chromatography of the crude mixture in 1% MeOH/DCM. Yield=59%

¹H NMR (CD₃)₂CO, 500 MHz) δ 8.42 (d, 2H, J=8.8 Hz), 8.35 (s, 2H), 7.87 (d, 2H, J=8.8 Hz), 7.56 (dd, 2H, J=1.7, 8.8 Hz), 7.49 (d, 2H, J=8.9 Hz) 7.05 (d, 2H, J=8.7 Hz), 6.81 (d, 2H, J=8.6 Hz), 4.59 (dd, 1H, J=2.9, 15.2 Hz), 4.53 (d, 1H, J=5.5 Hz), 4.15 (m, 1H), 3.87 (m, 1H).

Step 3. N-(3-(3,6-dibromo-9H-carbazol-9-yl)-2-fluoropropyl)-N-(4-hydroxyphenyl)-4-nitrobenzenesulfonamide

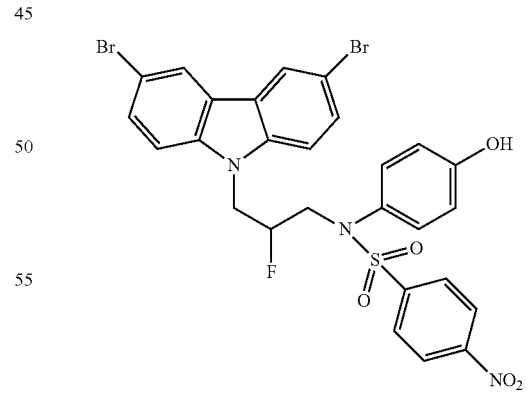

The product of Step 2 was fluorinated according to Representative Procedure 4. Pure product was obtained after column chromatography in 1% MeOH/DCM (+0.2% TEA). Yield=89%.

¹H NMR (CD₃)₂CO, 400 MHz) δ 8.48 (d, 2H, J=9.0 Hz), 8.41 (d, 2H, J=1.7 Hz), 7.94 (d, 2H, J=8.6 Hz), 7.66 (dd, 2H,

J=1.9, 8.8 Hz), 7.60 (d, 2H, J=8.8 Hz), 7.10 (d, 2H, J=9.0 Hz), 6.89 (d, 2H, J=8.8 Hz), 5.10 (dm, 1H), 4.74-4.94 (m, 2H), 4.20-4.32 (m, 2H).

Step 4. N-(3-(3,6-dibromo-9H-carbazol-9-yl)-2-fluoropropyl)-N-(4-(2-(2-methoxyethoxy)ethoxy)phenyl)-4-nitrobenzenesulfonamide

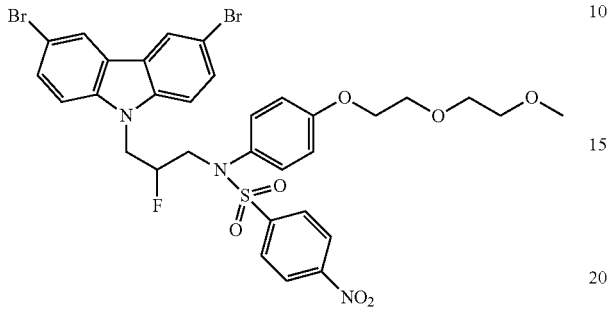

A solution of the product of Step 3 (15.9 mg, 0.023 mmol), potassium carbonate (13.6 mg, 0.098 mmol) and 1-bromo-2-(2-methoxyethoxy)ethane (8.5 mg, 0.041 mmol) in dimethylformamide (1.0 ml) was heated at 70° C. overnight. The reaction was diluted with EtOAc and washed with water several times, then brine. Column chromatography in 100% DCM (+0.2% TEA)-1% MeOH/DCM (+0.2% TEA) gave the pure product. Yield=43%.

$^1$H NMR (CDCl$_3$, 500 MHz) δ 8.30 (d, 2H, J=8.9 Hz), 8.14 (d, 2H, J=1.7 Hz), 7.72 (d, 2H, J=8.8 Hz), 7.56 (dd, 2H, J=1.8, 8.6 Hz), 7.23 (d, 2H, J=8.8 Hz), 6.95 (d, 2H, J=8.7 Hz), 6.85 (d, 2H, J=8.7 Hz), 4.93 (dm, 1H), 4.46-4.69 (m, 2H), 4.13 (t, 2H, J=5.2 Hz), 3.85-3.91 (m, 3H), 3.72 (m, 2H), 3.58 (m, 2H), 3.46-3.50 (m, 1H), 3.39 (s, 3H). MS (ESI), m/z: 824.0 (M+HCOO)

Step 5. P7C3-S66: N-(3-(3,6-dibromo-9H-carbazol-9-yl)-2-fluoropropyl)-4-(2-(2-methoxyethoxy)ethoxy)aniline

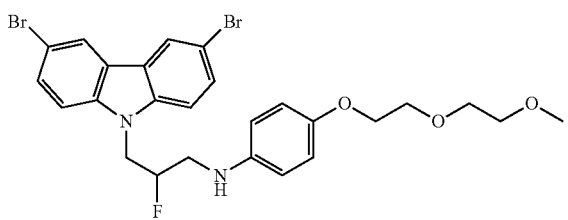 [SMILES: COCCOCCOc1ccc(NCC(F)Cn2c3ccc(Br)cc3c3cc(Br)ccc32)cc1]

The nitrosulfonyl group was removed from the product of Step 4 via Representative Procedure 5. Pure product was isolated following preparative TLC. Yield=92% $^1$H NMR (CDCl$_3$, 400 MHz) δ 8.15 (d, 2H, J=1.8 Hz), 7.55 (dd, 2H, J=1.9, 8.7 Hz), 7.30 (d, 2H, J=8.6 Hz), 6.81 (d, 2H, J=8.9 Hz), 6.57 (d, 2H, J=9.2 Hz), 5.08 (dm, 1H, $^1J_{H-F}$=47.8 Hz), 4.50-4.69 (m, 2H), 4.08 (m, 2H), 3.84 (m, 2H), 3.66-3.75 (m, 2H), 3.59 (m, 2H), 3.40 (s, 3H), 3.27-3.45 (m, 2H). MS (ESI), m/z: calculated 594.31, found 595 (M+1)$^+$.

Example 108

P7C3-S68: N-(2-(2-(4-(3-(3,6-dibromo-9H-carbazol-9-yl)-2-fluoropropylamino)phenoxy)acetamido)ethyl)-5-(2-oxohexahydro-H-thieno[3,4-d]imidazol-4-yl)pentanamide

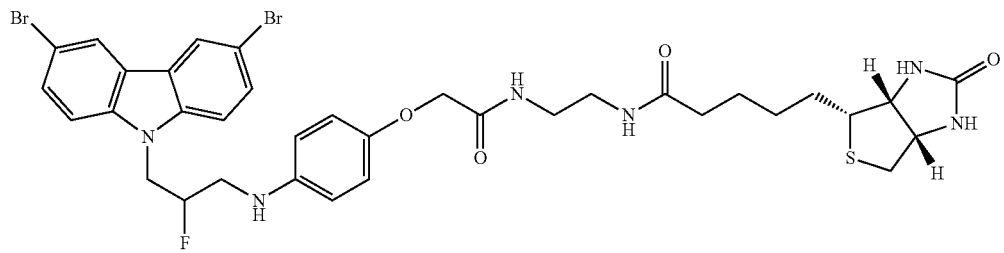 [SMILES: O=C(CCCC[C@H]1SC[C@H]2NC(=O)N[C@H]21)NCCNC(=O)COc1ccc(NCC(F)Cn2c3ccc(Br)cc3c3cc(Br)ccc32)cc1]

The title compound of Example 108 (P7C3-S68) was prepared via alkylation of the product of Step 3 in the synthesis of Example 107 Compound (P7C3-S66) with iodoethyl acetate and subsequent amidation and desulfonylation. The product was purified by preparative TLC in 10% MeOH/CH$_2$Cl$_2$ (+0.2% TEA). $^1$H NMR (CD$_3$OD, 500 MHz) δ=8.23 (s, 2H), 7.51 (dd, 4H, J=31.0, 8.8, Hz), 6.84 (d, 2H, J=8.9 Hz) 6.67 (d, 2H, J=8.6 Hz), 5.04 (dm, 1H, J=48.9 Hz), 4.69 (d, 1H, J=5.2 Hz) 4.65 (m, 1H), 3.37-3.42 (m, 3H), 4.17 (m, 1H), 3.42-3.52 (m, 1H), 3.37 (m, 4H) 3.05 (m, 1H), 2.82 (dm, 1H), 2.69 (m, 1H), 2.63 (d, 1H, J=12.7 Hz), 2.13-2.18 (m, 2H), 1.15-1.69 (m, 6H). $^{13}$C NMR (CDCl$_3$, 126 MHz) δ=176.6, 166.0, 151.7, 144.6, 141.2, 130.3, 124.9, 124.1, 117.1, 115.5, 113.4, 112.4, 106.2, 92.6 (d, $^1$J=176.7 Hz), 69.2, 63.3, 61.6, 56.9, 47.2 (d, $^2$J=22.2 Hz), 46.1 (d, $^2$J=24.1 Hz), 41.0, 40.2, 39.7, 36.8, 29.7, 29.4, 26.8. MS (ESI), m/z: calculated 816.11. found 817.1 (M+1)$^+$.

Example 109

P7C3-S57

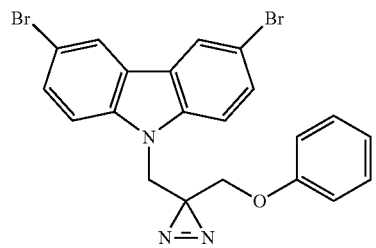 [SMILES: Brc1ccc2c(c1)c1cc(Br)ccc1n2CC1(COc2ccccc2)N=N1]

Example 110

P7C3-S70: 2-(4-(3-(3,6-dibromo-9H-carbazol-9-yl)-2-fluoropropylamino)phenoxy)-N,N-dimethylacetamide

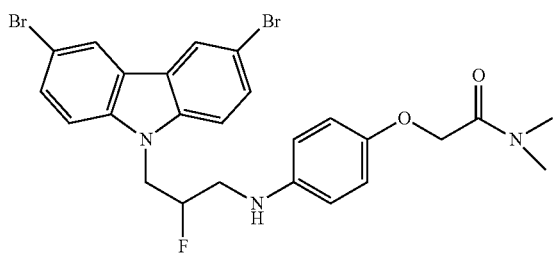 [SMILES: CN(C)C(=O)COc1ccc(NCC(F)Cn2c3ccc(Br)cc3c3cc(Br)ccc32)cc1]

The title compound was prepared analogously to P7C3-S66. $^1$H NMR (CDCl$_3$, 400 MHz) δ=8.04 (d, 2H, J=8.6 Hz), 7.45 (dd, 2H, J=1.9, 8.6 Hz), 7.20 (d, 2H, J=9.7 Hz), 6.75 (d, 2H, J=8.8 Hz), 6.47 (d, 2H, J=9.1 Hz), 4.97 (dm, 1H, $^1J_{H-F}$=47.2 Hz), 4.53 (s, 2H), 4.38-4.60 (m, 2H), 3.11-3.36 (m, 2H), 3.00 (s, 3H), 2.89 (s, 3H). $^{13}$C NMR (CDCl$_3$, 100 MHz) δ=184.0, 168.3, 151.4, 142.0, 139.6, 129.5, 123.4, 116.1, 112.9, 110.7 (d, $^4J$=1.8 Hz), 90.8 (d, $^1J$=175.5 Hz), 68.4, 46.4 (d, $^2J$=24.7 Hz), 45.0 (d, $^2J$=92.3 Hz), 29.8, 32.9. MS (ESI), m/z: calculated 575.02, found 622.0 (M+HCOO)$^-$.

Example 111

P7C3-S71: 2-(4-(3-(3,6-dibromo-9H-carbazol-9-yl)-2-fluoropropylamino)phenoxy)-N-(2-hydroxyethyl)acetamide

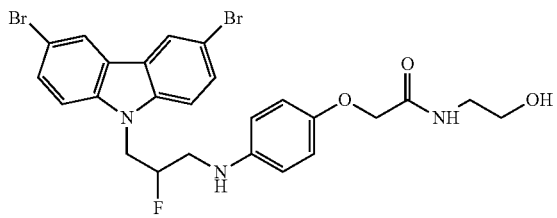 [SMILES: O=C(COc1ccc(NCC(F)Cn2c3ccc(Br)cc3c3cc(Br)ccc32)cc1)NCCO]

The title compound was prepared analogously to P7C3-S66 and was purified by chromatography on silica gel (5% MeOH/DCM+0.2% TEA). $^1$H NMR (CDCl$_3$, 400 MHz) δ=12.07 (bs, 1H), 8.15 (d, 2H), 7.55 (dd, 2H, J=2.0, 8.5 Hz), 7.31 (d, 2H, J=8.8 Hz), 7.06 (bm, 1H), 6.80 (d, 2H, J=9.1 Hz), 6.57 (d, 2H, 9.2 Hz), 5.09 (dm, 1H, $^1J_{H-F}$=47.2 Hz), 4.51-4.68 (m, 2H), 4.51-4.68 (m, 2H), 4.45 (s, 2H), 3.78 (t, 3H, J=4.9 Hz), 3.53 (q, 2H, J=5.4 Hz), 3.22-3.45 (m, 2H), 2.57 (bs, 1H). $^{13}$C NMR (CDCl$_3$, 100 MHz).

δ=169.9, 150.5, 142.5, 139.7, 129.6, 123.5, 116.2, 110.7 (d, $^4J$=1.2 Hz), 90.8 (d, $^1J$=176.5 Hz), 68.3, 62.4, 46.3 (d, $^2J$=21.8 Hz), 45.0 (d, $^2J$=25.7 Hz), 42.2. MS (ESI), m/z: calculated 591.02. found 638.0 (M+HCOO)$^-$.

Example 112

P7C3-S72: 1-(bis(4-bromophenyl)amino)-3-(phenylamino)propan-2-ol

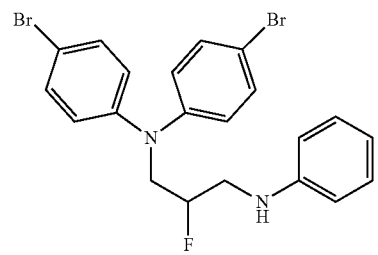 [SMILES: FC(CNc1ccccc1)CN(c1ccc(Br)cc1)c1ccc(Br)cc1]

P7C3-S72 was synthesized from di-(4-bromophenyl)amine, epibromohydrin and aniline following Representative Procedures 1 and 2. $^1$H NMR (CDCl$_3$, 400 MHz) δ=7.38 (d, 4H, J=8.8 Hz), 7.19 (d, 2H, J=7.4 Hz), 6.95 (d, 4H, J=8.8 Hz), 6.76 (t, 1H, J=7.4 Hz), 6.62 (d, 2H, J=7.9 Hz), 4.17 (bm, 1H), 3.89 (dd, 1H, J=4.3, 15.2 Hz), 3.72-3.81 (m, 1H), 3.32 (dd, 1H, J=3.2, 12.8 Hz), 3.08-3.18 (m, 1H). $^{13}$C NMR (CDCl$_3$, 100 MHz) δ=148.0, 147.0, 132.6, 129.5, 123.1, 118.4, 114.9, 113.5, 67.9, 56.6, 47.8. MS (ESI), m/z: calculated 473.99, found 521 (M+HCOO)$^-$.

Example 113

P7C3-S73: (E)-3,6-dibromo-9-(3-phenoxyallyl)-9H-carbazole and (E)-3,6-dibromo-9-(3-phenoxyprop-1-en-1-yl)-9H-carbazole Step 1. 3,6-dibromo-9-(2-bromo-3-phenoxypropyl)-9H-carbazole

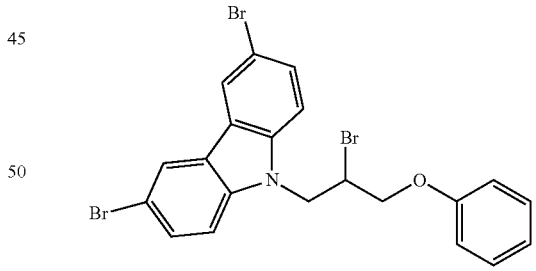

To an ice-cold solution of P7C3-S39 (95.0 mg, 0.20 mmol, 1 equiv) and triphenylphosphine (78.7 mg, 0.30 mmol, 1.5 equiv) in dichloromethane (0.6 mL) was added tetrabromomethane (73.0 mg, 0.22 mmol, 1.1 equiv). The mixture was stirred at rt for 3 hours. Dichloromethane was and the crude residue was purified by silica gel chromatography using 9% EtOAc/Hex to afford 7.4 mg white solid as product, yield 6.9%. $^1$H NMR (CDCl$_3$, 400 MHz) δ=4.22-4.11 (m, 2H) 4.61 (dt, J=12.2, 6.2 Hz, 1H) 4.68 (dd, J=15.2, 6.4 Hz, 1H) 4.98 (dd, J=15.2, 7.1 Hz, 1H) 6.88 (d, J=7.8 Hz, 2H) 7.02 (t, J=7.4 Hz, 1H) 7.37-7.26 (m, 4H) 7.49 (dd, J=8.7, 1.8 Hz, 2H) 8.12 (d, J=1.8 Hz, 2H)

Step 2. P7C3-S73. (E)-3,6-dibromo-9-(3-phenoxyal-lyl)-9H-carbazole and (E)-3,6-dibromo-9-(3-phe-noxyprop-1-en-1-yl)-9H-carbazole

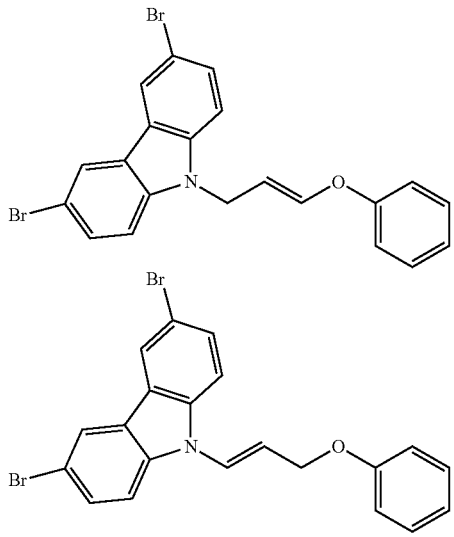

To a 4-mL vial were added the product of Step 1, kryptofix 222 (4.8 mg, 0.0130 mmol, 1 equiv), KF (0.5 mg, 0.0090 mmol, 0.7 equiv), K$_2$CO$_3$ (0.3 mg, 0.0019 mmol, 0.15 equiv) and acetonitrile (0.15 mL). The vial was tightly sealed and heated to 80° C. for 20 min. The crude was purified by silica gel chromatography using 9% EtOAc/Hex to afford 4.9 mg white solid in one fraction as a mixture of these two olefins in a 45:55 ratio, total yield 83.6%. $^1$H NMR (CDCl$_3$, 400 MHz) δ=4.51 (dd, J=6.5, 1.4 Hz, 0.45×1H) 4.83 (dd, J=6.2, 1.2 Hz, 0.55×1H) 6.21 (dt, J=8.0, 6.6 Hz, 0.45×1H) 6.31 (dt, J=14.2, 6.1 Hz, 0.55×1H) 6.74 (d, J=7.9 Hz, 1H) 6.94-6.85 (m, 1H) 7.05-6.98 (m, 2H) 7.38-7.15 (m, 4H) 7.49 (d, J=8.7 Hz, 1H) 7.57 (ddd, J=8.6, 4.1, 1.9 Hz, 2H) 8.14 (dd, J=13.0, 1.8 Hz, 2H).

Example 114

P7C3-S75: 1-(3,6-bis(trifluoromethyl)-9H-carbazol-9-yl)-3-(phenylamino)propan-2-ol Step 1. 4-(trifluoromethyl)phenyl trifluoromethanesulfonate

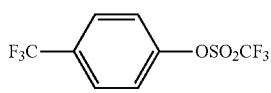

To a solution of 4-trifluoromethylphenol (324.2 mg, 2.0 mmol, 1 equiv) in dichloromethane (1.2 mL) was added pyridine (194.1 μL, 2.4 mmol, 1.2 equiv). A solution of triflic anhydride (370.1 μL, 2.2 mmol, 1.1 equiv) in dichloromethane (1.2 mL) was added dropwise at 0° C. The mixture was stirred at 0° C. for 1 hour, and then rt for 2.5 hours. The reaction was quenched with 1 mL of water. The organic phase was washed with saturated NaHCO$_3$, 1M HCl and brine, then dried with MgSO$_4$ and concentrated to give crude product. It was further purified by silica gel chromatography using 5% EtOAc/Hex to afford 449.4 mg colorless oil as product, yield 76.4%.
$^1$H NMR (CDCl$_3$, 400 MHz) δ=7.42 (d, J=8.8 Hz, 2H) 7.75 (d, J=9.0 Hz, 1H).

Step 2. 3, 6-bis(trifluoromethyl)-9H-carbazole

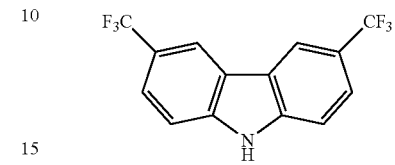

Following methods in Watanabe et al., *J. Org. Chem.* 2009, 74, 4720-4726, to a vial under argon atmosphere containing the product of Step 1, (29.4 mg, 0.10 mmol, 1 equiv), 4-(trifluoromethyl)aniline (17.7 mg, 0.11 mmol, 1.1 equiv), Pd(OAc)$_2$ (2.2 mg, 0.01 mmol, 0.1 equiv), XPhos (7.2 mg, 0.015 mmol, 0.15 equiv) and Cs$_2$CO$_3$ (39.1 mg, 0.12 mmol, 1.2 equiv) was added toluene (0.2 mL). The mixture was stirred at 100° C. for 1.5 hour. After cooling, the crude mixture was diluted with ethyl acetate and washed with brine. The organic layer was dried with MgSO$_4$ and concentrated. The crude product was further purified by silica gel chromatography using 0-5% of EtOAc/Hex to afford 22.2 mg of the diaryl amine as a colorless oil as, yield 69.2%. To this intermediate was added acetic acid (0.8 mL) and Pd(OAc)$_2$ (2.5 mg). The mixture was heated to 90° C. for 12 h under an oxygen balloon. Solid NaHCO$_3$ was added to quench the reaction. The mixture was diluted with ethyl acetate and washed with NaHCO$_3$. The organic layer was dried with MgSO$_4$ and concentrated to give crude product. It was further purified by silica gel chromatography using 25% EtOAc/Hex to afford 9.2 mg white solid yield 41.7%.
$^1$H NMR (CDCl$_3$, 400 MHz) δ=7.54 (d, J=8.6 Hz, 2H) 7.72 (dd, J=8.6, 1.5 Hz, 2H) 8.38 (s, 2H) 8.47 (s, br, 1H). ESI (m/z): 302.0 (M−H$^+$).

Step 3. 1-chloro-3-(phenylamino)propan-2-ol

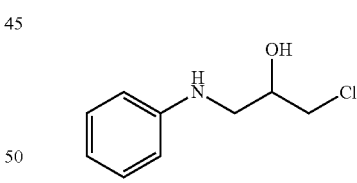

Acetic acid (0.56 mL), aniline (456 μL, 5.0 mmol, 1 equiv) and epichlorohydin (469 μL, 6.0 mmol, 1.2 equiv) were combined and stirred at 75° C. for 3 h in a sealed vial. The reaction was quenched with solid NaHCO$_3$ (0.8218 g) and the mixture was diluted with ethyl acetate and washed with saturated NaHCO$_3$. The combined organic extracts were dried with MgSO$_4$ and concentrated to give crude product. It was further purified by silica gel chromatography using 30% EtOAc/Hex to afford 495.5 mg colorless oil as product, yield 53.4%. $^1$H NMR (CDCl$_3$, 400 MHz) δ=2.10 (d, J=0.9 Hz, 1H) 3.25 (dd, J=13.3, 7.1 Hz, 1H) 3.39 (dd, J=13.3, 4.5 Hz, 1H) 3.77-3.56 (m, 2H) 4.17-4.03 (m, 1H) 6.67 (dd, J=8.6, 1.0 Hz, 2H) 6.76 (tt, J=7.4, 1.0 Hz, 1H) 7.20 (dd, J=8.5, 7.4 Hz, 2H). ESI (m/z): 186.1 (M+H$^+$); 230.1 (M+HCOO$^-$).

Step 4. N-(oxiran-2-ylmethyl)aniline

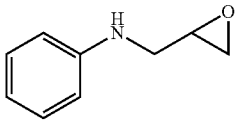 [SMILES: c1ccc(NCC2CO2)cc1]

To a solution of the product of Step 3 (185.7 mg, 1.0 mmol, 1 equiv) in 1,4-dioxane (3.3 mL) was added KOH powder (67.3 mg, 1.2 mmol, 1.2 equiv). The mixture was stirred at room temperature for 24 hours. The mixture was diluted with EtOAc and washed with 1M HCl and brine. The organic layer was dried with $MgSO_4$ and concentrated to give crude product. It was further purified by silica gel chromatography using 20% EtOAc/Hex to afford 141.8 mg colorless oil as product, yield 95.0%. $^1$H NMR (CDCl$_3$, 400 MHz) δ=2.70 (dd, J=4.9, 2.3 Hz, 1H) 2.87-2.77 (m, 1H) 3.23-3.18 (m, 1H) 3.26 (t, J=4.9 Hz, 1H) 3.59-3.48 (m, 1H) 3.87 (s, 1H) 6.64 (d, J=7.7 Hz, 2H) 6.73 (t, J=7.3 Hz, 1H) 7.18 (dd, J=8.3, 7.5 Hz, 2H).

Step 5. P7C3-S75: 1-(3,6-bis(trifluoromethyl)-9H-carbazol-9-yl)-3-(phenylamino)propan-2-ol

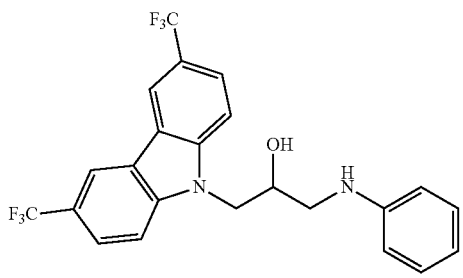 [SMILES: OC(CNc1ccccc1)Cn1c2ccc(C(F)(F)F)cc2c2cc(C(F)(F)F)ccc21]

To a solution of the product of Step 2 (4.6 mg, 0.0152 mmol, 1 equiv) in THF (0.25 mL) was added NaH (60% dispersion in mineral oil, 0.7 mg, 0.0167 mmol, 1.1 equiv) and the mixture was stirred at room temperature for 15 min. The product of Step 4 (2.7 mg, 0.0182 mmol, 1.2 equiv) was added and the resulting mixture was stirred at room temperature overnight and then heated at 65° C. for 4 hours. Brine was added and the crude reaction was extracted 3 times with EtOAc. The combined organic extracts were dried with $MgSO_4$ and concentrated to give crude product. It was further purified by silica gel chromatography using 30% EtOAc/Hex to afford 4.1 mg white solid as product, yield 59.6%. $^1$H NMR (CDCl$_3$, 400 MHz) δ=2.33 (s, 1H) 3.25 (dd, J=13.1, 7.1 Hz, 1H) 3.40 (dd, J=13.1, 4.0 Hz, 1H) 4.43 (ddd, J=11.3, 6.8, 4.6 Hz, 1H) 4.62-4.46 (m, 2H) 6.64 (d, J=8.3 Hz, 2H) 6.79 (t, J=7.3 Hz, 1H) 7.23-7.12 (m, 2H) 7.60 (d, J=8.6 Hz, 2H) 7.75 (dd, J=8.6, 1.4 Hz, 2H) 8.41 (s, 2H). $^{13}$C NMR (CDCl$_3$, 400 MHz) δ=147.8, 143.1, 129.7, 123.9 (dd, J=7.0, 3.5 Hz, 1C), 123.0, 122.7, 122.5, 119.0, 118.5 (q, J=4.2 Hz, 1C), 113.8, 110.0, 69.7, 48.1, 47.5. ESI (m/z): 497.1 (M+HCOO$^-$).

Example 115

P7C3-S77: 1-(3,6-Dibromo-9H-carbazol-9-yl)-3-(3-methoxyphenylthio)propan-2-ol

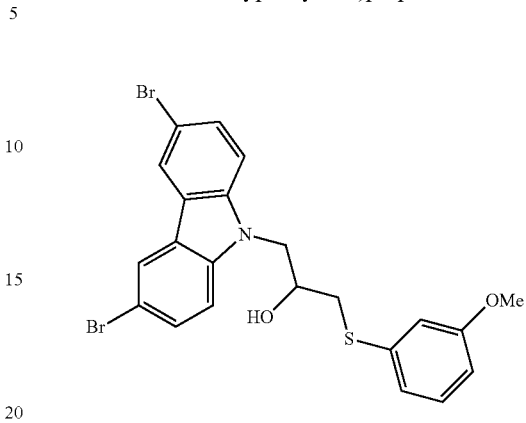

Prepared analogously to Example 3a. Chromatography (0-50% EtOAc in hexanes) provided 242 mg (88% yield) of an off-white foam. $^1$H NMR (CDCl$_3$, 500 MHz) δ=8.01 (d, J=1.5 Hz, 2H), 7.46 (dd, J=1.5, 8.5 Hz, 2H), 7.21 (d, J=9.0 Hz, 2H), 7.14 (dd, J=8.0, 8.0 Hz, 1H), 6.85 (d, J=7.5 Hz, 1H), 6.80 (m, 1H), 6.72 (dd, J=2.0, 8.0 Hz, 1H), 4.32 (dd, J=4.0, 15.0 Hz, 1H), 4.20 (dd, J=7.0, 15.0 Hz, 1H), 4.09 (m, 1H), 3.69 (s, 3H), 3.03 (dd, J=5.0, 14.0 Hz, 1H), 2.91 (dd, J=7.5, 14.0 Hz, 1H), 2.55 (d, J=3.0 Hz, 1H). $^{13}$C NMR (CDCl$_3$, 125 MHz) δ=160.1, 139.7, 135.7, 130.3, 129.3 (2C), 123.6, 123.3 (2C), 122.0, 115.4, 112.7, 112.6, 111.0 (2C), 69.2, 55.4, 48.0, 39.0. ESI m/z: 563.6 ([M+HCOO]$^-$).

Example 116

P7C3-S78: 1-(3,6-Dibromo-9H-carbazol-9-yl)-3-(4-methoxyphenylthio)propan-2-ol

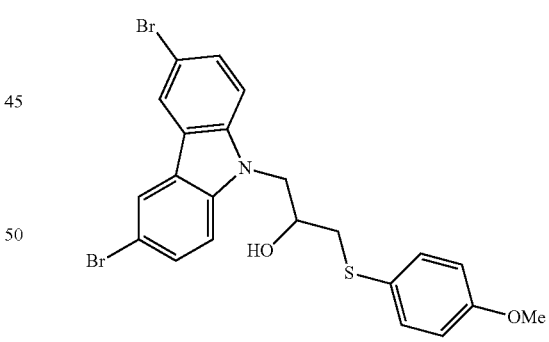

Prepared analogously to Example 3a. Chromatography (0-50% EtOAc in hexanes) provided 263 mg (96% yield) of an off-white solid. $^1$H NMR (CDCl$_3$, 500 MHz) δ=8.02 (d, J=2.0 Hz, 2H), 7.47 (dd, J=2.0, 8.5 Hz, 2H), 7.28 (d, J=8.5 Hz, 2H), 7.22 (d, J=9.0 Hz, 2H), 6.77 (d, J=9.0 Hz, 2H), 4.31 (dd, J=4.0, 15.0 Hz, 1H), 4.18 (dd, J=7.0, 15.5 Hz, 1H), 4.01 (m, 1H), 3.75 (s, 3H), 2.93 (dd, J=5.0, 14.0 Hz, 1H), 2.79 (dd, J 7.5, 13.5 Hz, 1H), 2.6 (d, J=3.5 Hz, 1H). $^{13}$C NMR (CDCl$_3$, 125 MHz) δ=159.7, 139.8 (2C), 133.9 (2C), 129.3 (2C), 124.4, 123.6 (2C), 123.3 (2C), 115.1 (2C), 112.6 (2C), 111.0 (2C), 69.1, 555.5, 48.0, 41.3. ESI m/z: 563.5 ([M+HCOO]$^-$).

Example 117

P7C3-S79: 3,6-Dibromo-9-(2-fluoro-3-(3-methoxyphenylthio)propyl)-9H-carbazole

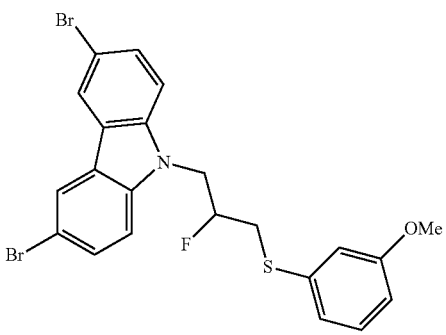 [SMILES: COc1cccc(SCC(F)Cn2c3ccc(Br)cc3c3cc(Br)ccc32)c1]

Prepared analogously to Example 96 from P7C3-S77. Chromatography (0-5% EtOAc in hexanes) provided 32 mg (32% yield) of an off-white solid. $^1$H NMR (CDCl$_3$, 500 MHz) δ=8.07 (d, J=1.5 Hz, 2H), 7.50 (dd, J=1.5, 8.5 Hz, 2H), 7.26 (d, J=8.5 Hz, 2H), 7.21 (t, J=8.0 Hz, 1H), 6.96 (d, J=7.5 Hz, 1H), 6.92 (br s, 1H), 6.77 (dd, J=2.0, 8.5 Hz, 1H), 4.90 (dm, J=47.5 Hz, 1H), 4.59 (ddd, J=2.5, 16.0, 26.5 Hz, 1H), 4.45 (ddd, J=7.0, 16.0, 22.0 Hz, 1H), 3.76 (s, 3H), 3.26 (ddd, J=4.5, 15.0, 15.0 Hz, 1H), 3.06 (m, 1H). $^{13}$C NMR (CDCl$_3$, 125 MHz) δ=160.2, 139.8 (2C), 135.5, 130.5, 129.5 (2C), 123.9 (2C), 123.4 (2C), 122.2 (2C), 115.8, 113.0, 112.9, 110.9 (d, J=2.1 Hz, 2C), 104.9, 91.3 (d, J=180 Hz), 55.5, 46.1 (d, J=22.9 Hz), 35.4 (d, J=23.9 Hz). ESI m/z: 565.7 ([M+HCOO]$^-$).

Example 118

P7C3-S80: 3,6-Dibromo-9-(2-fluoro-3-(4-methoxyphenylthio)propyl)-9H-carbazole

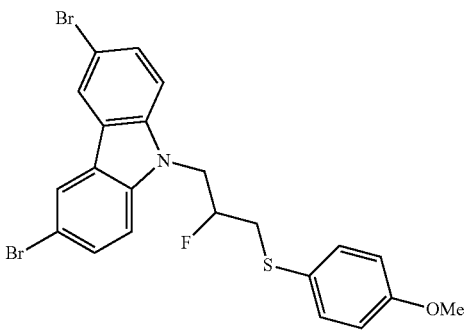 [SMILES: COc1ccc(SCC(F)Cn2c3ccc(Br)cc3c3cc(Br)ccc32)cc1]

Prepared analogously to Example 96 from P7C3-S78. Chromatography (0-5% EtOAc in hexanes) provided 23 mg (23% yield) of an off-white solid. $^1$H NMR (CDCl$_3$, 500 MHz) δ=8.08 (d, J=1.5 Hz, 2H), 7.52 (dd, J=1.5, 8.5 Hz, 2H), 7.39 (d, J=9.0 Hz, 2H), 7.28 (d, J=8.5 Hz, 2H), 6.84 (d, J=9.0 Hz, 2H), 4.83 (dm, J=48.0 Hz, 1H), 4.58 (ddd, J=2.5, 15.5, 27.0 Hz, 1H), 4.45 (ddd, J=7.0, 16.0, 20.5 Hz, 1H), 3.78 (s, 3H), 3.13 (ddd, J=4.5, 14.5, 14.5 Hz, 1H), 2.96 (m, 1H). $^{13}$C NMR (CDCl$_3$, 125 MHz) δ=159.9, 134.2, 129.5, 124.4, 123.9, 123.4, 115.2, 112.9, 110.9 (d, J=2.1 Hz, 2C), 104.9, 91.5 (d, J=179.6 Hz), 55.6, 46.1 (d, J=22.6 Hz), 37.6 (d, J=22.4 Hz). ESI m/z: 565.7 ([M+HCOO]$^-$ 565.9).

Example 119

P7C3-S81: 3,6-Dibromo-9-(2-fluoro-3-(3-methoxyphenylsulfonyl)propyl)-9H-carbazole

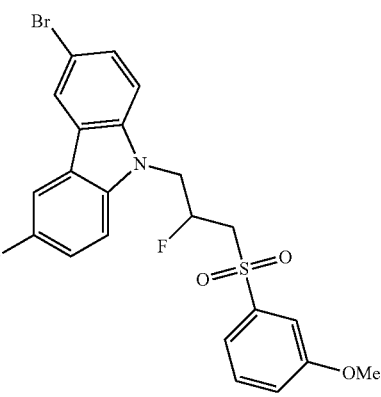

Prepared analogously to Example 96 from P7C3-S77. Chromatography (0-30% EtOAc in hexanes) provided 17.7 mg (84% yield) of an off-white solid. $^1$H NMR (CDCl$_3$, 500 MHz) δ=8.11 (d, J=1.5 Hz, 2H), 7.55 (dd, J=1.5, 8.5 Hz, 2H), 7.43 (m, 2H), 7.34 (d, J=8.5 Hz, 2H), 7.33 (m, 1H), 7.16-7.14 (m, 1H), 5.34 (dm, J=49.0 Hz, 1H), 4.71 (ddd, J=2.5, 16.0, 26.5 Hz, 1H), 4.56 (ddd, J=7.0, 16.0, 22.5 Hz, 1H), 3.81 (s, 3H), 3.48 (m, 2H). $^{13}$C NMR (CDCl$_3$, 125 MHz) δ=160.4, 140.0, 139.7 (2C), 130.9, 129.7 (2C), 124.0 (2C), 123.5 (2C), 121.1 (2C), 120.2, 113.2, 112.6, 110.9 (d, J=2.1 Hz, 2C), 87.1 (d, J=181.3 Hz), 58.1 (d, J=23.4 Hz), 56.0, 47.1 (d, J=22.0 Hz). ESI m/z: 531.7 ([M–H$_2$F]$^-$).

Example 120

P7C3-S82: 1-(3,6-Dibromo-9H-carbazol-9-yl)-3-(3-methoxyphenylsulfonyl)propan-2-ol

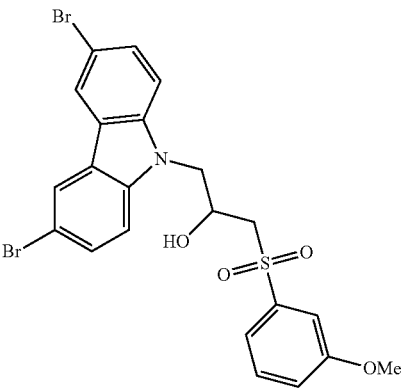 [SMILES: COc1cccc(S(=O)(=O)CC(O)Cn2c3ccc(Br)cc3c3cc(Br)ccc32)c1]

Prepared analogously to Example 3d from P7C3-S77. Chromatography (0-25% EtOAc in hexanes) provided 30 mg (94% yield) of an off-white solid. $^1$H NMR (CDCl$_3$, 500 MHz) δ=8.06 (d, J=2.0 Hz, 2H), 7.49 (dd, J=2.0, 9.0 Hz, 2H), 7.36 (apparent t, J=8.0 Hz, 1H), 7.31 (m, 1H), 7.22 (d, J=9.0 Hz, 2H), 7.20 (m, 1H), 7.10 (m, 1H), 4.61 (m, 1H), 4.33 (m, 2H), 3.78 (s, 3H), 3.32 (br s, 1H), 3.23 (dd, J=8.0, 14.0 Hz, 1H), 3.12 (dd, J=3.0, 14.5 Hz, 1H). $^{13}$C NMR (CDCl$_3$, 125 MHz) δ=160.3, 139.7, 139.6 (2C), 130.8, 129.6 (2C), 123.8, 123.4 (2C), 120.8, 119.9, 113.0 (2C), 112.3 (2C), 110.9 (2C), 65.6, 59.9, 55.9, 48.2. ESI m/z: 595.6 ([M+HCOO]$^-$).

Example 121

P7C3-S83: 3,6-Dibromo-9-(2-fluoro-3-(4-methoxyphenylsulfonyl)propyl)-9H-carbazole

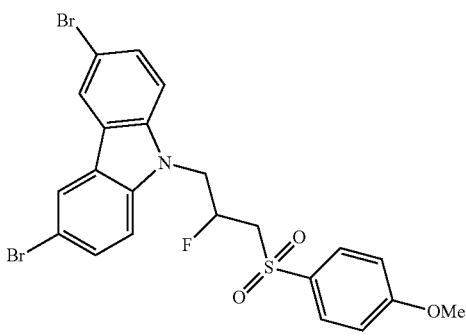 [SMILES: COc1ccc(S(=O)(=O)CC(F)Cn2c3ccc(Br)cc3c3cc(Br)ccc32)cc1]

Prepared analogously to Example 96 from P7C3-S78. Chromatography (0-30% EtOAc in hexanes) provided 18.9 mg (89% yield) of an off-white solid. $^1$H NMR (CDCl$_3$, 500 MHz) δ=8.10 (d, J=2.0 Hz, 2H), 7.78 (d, J=8.5 Hz, 2H), 7.54 (dd, J=1.5, 8.5 Hz, 2H), 7.32 (d, J=8.5 Hz, 2H), 6.96 (d, J=9.0 Hz, 2H), 5.32 (dm, J=47.5 Hz, 1H), 4.69 (ddd, J=2.5, 16.0, 27.0 Hz, 1H), 4.54 (ddd, J=7.0, 16.0, 22.5 Hz, 1H), 3.85 (s, 3H), 3.49-3.42 (m, 2H). $^{13}$C NMR (CDCl$_3$, 125 MHz) δ=164.5, 139.7 (2C), 130.5 (2C), 130.3, 129.7 (2C), 124.0 (2C), 123.5 (2C), 114.9 (2C), 113.2 (2C), 110.9 (d, J=2.25 Hz, 2C), 87.4 (d, J=181.1 Hz), 58.5 (d, J 23.1 Hz), 56.0, 47.2 (d, J=22.0 Hz). ESI m/z: 531.5 ([M–H$_2$F]$^-$.

Example 122

P7C3-S84: 1-(3,6-Dibromo-9H-carbazol-9-yl)-3-(4-methoxyphenylsulfonyl)propan-2-ol

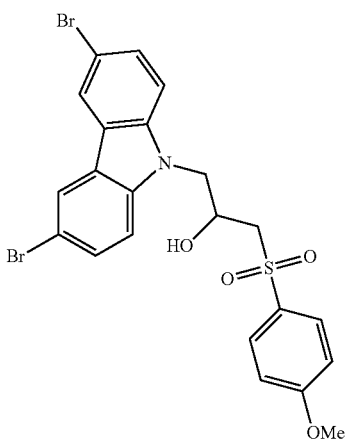 [SMILES: COc1ccc(S(=O)(=O)CC(O)Cn2c3ccc(Br)cc3c3cc(Br)ccc32)cc1]

Prepared analogously to example 3d from P7C3-S78. Chromatography (0-30% EtOAc in hexanes) provided 27 mg (85% yield) of an off-white solid. $^1$H NMR (CDCl$_3$, 500 MHz) δ=8.09 (d, J=2.0 Hz, 2H), 7.67 (d, J=9.0 Hz, 2H), 7.50 (dd, J=2.0, 9.0 Hz, 2H), 7.25 (d, J=8.0 Hz, 2H), 6.92 (d, J=9.0 Hz, 2H), 4.61 (m, 1H), 4.36 (d, J=6.0 Hz, 2H), 3.86 (s, 3H), 3.35 (d, J=2.5 Hz, 1H), 3.20 (dd, J=8.5, 14.0 Hz, 1H), 3.10 (dd, J=2.5, 14.0 Hz, 1H). $^{13}$C NMR (d$_6$-acetone, 125 MHz) δ=164.7, 141.0 (2C), 132.8, 131.2 (2C), 129.8 (2C), 124.5 (2C), 124.0 (2C), 115.2 (2C), 112.74 (2C), 112.68 (2C), 66.6, 61.0, 56.3, 49.7. ESI m/z: 595.6 ([M+HCOO]$^-$).

Example 123

P7C3-S91: 3-(3-(3,6-Dibromo-9H-carbazol-9-yl)-2-hydroxypropylthio)phenol

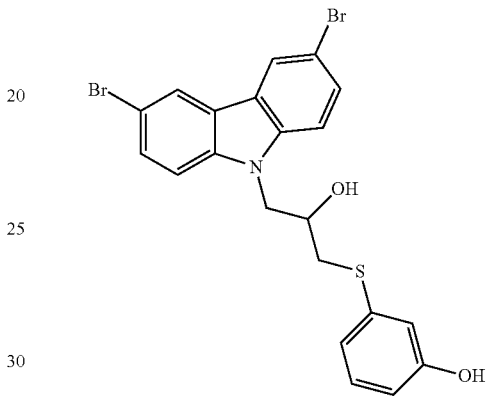

Prepared analogously to example 3a. Silica chromatography (0-40% EtOAc in hexanes) followed by HPLC purification (75% MeCN/H$_2$O+0.1% HCO$_2$H, Phenomenex C18 Luna, 10×250 mm, 3 mL/min) provided 9.9 mg (21% yield) of an off-white solid. $^1$H NMR (d$_6$-acetone, 400 MHz) δ=8.35 (br s, 2H), 7.56 (m, 4H), 7.13 (apparent t, J=8.0 Hz, 1H), 6.94 (br s, 1H), 6.88 (d, J=7.6 Hz, 1H), 6.69 (dd, J=1.6, 8.0 Hz, 1H), 4.66 (dd, J=3.2, 15.2 Hz, 1H), 4.47 (dd, J=8.4, 14.8 Hz, 1H), 4.26 (m, 1H), 3.22 (d, J=6.4 Hz). $^{13}$C NMR (d$_6$-acetone, 125 MHz) δ=158.8, 141.1 (2C), 138.2, 130.9, 129.7 (2C), 124.4 (2C), 124.0 (2C), 120.7 (2C), 116.5, 114.2, 112.8 (2C), 112.5, 70.2, 49.2, 38.5. ESI m/z: 549.7 ([M+HCOO]$^-$).

Example 124

P7C3-S92: 4-(3-(3,6-Dibromo-9H-carbazol-9-yl)-2-hydroxypropylthio)phenol

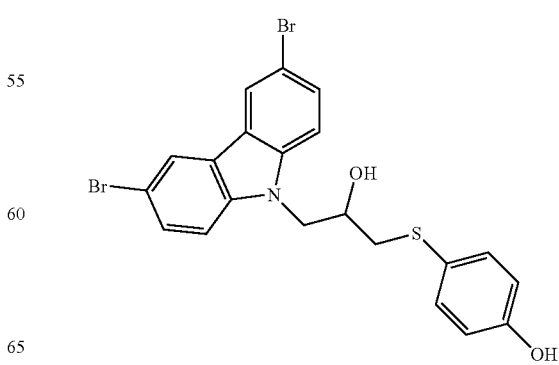

Prepared analogously to example 3a. Chromatography (0-3% acetone in dichloromethane) followed by HPLC purification (75% MeCN/H$_2$O+0.1% HCO$_2$H, Phenomenex C18 Luna, 10×250 mm, 3 mL/min) provided 11.4 mg (25% yield) of an off-white solid. $^1$H NMR (d$_6$-acetone, 500 MHz) δ=8.64 (br s, 1H), 8.34 (s, 2H), 7.56 (m, 4H), 7.36 (d, J=8.5 Hz, 2H), 6.82 (d, J=8.5 Hz, 2H), 4.62 (dd, J=3.5, 15.0 Hz, 1H), 4.54 (br s, 1H), 4.43 (dd, J=8.5, 15.0 Hz, 1H), 4.16 (m, 1H), 3.09 (d, J=6.5 Hz, 2H). $^{13}$C NMR (d$_6$-acetone, 125 MHz) δ=158.0, 141.1 (2C), 134.3 (2C), 129.7 (2C), 125.3, 124.4 (2C), 124.0 (2C), 117.1 (2C), 112.9 (2C), 112.5 (2C), 70.3, 49.1, 41.2. ESI m/z: 503.6 ([M–H]$^-$, C$_{21}$H$_{16}$Br$_2$NO$_2$S requires 503.9).

Example 125

P7C3-S93: 3-(3-(3,6-Dibromo-9H-carbazol-9-yl)-2-hydroxypropylsulfonyl)phenol

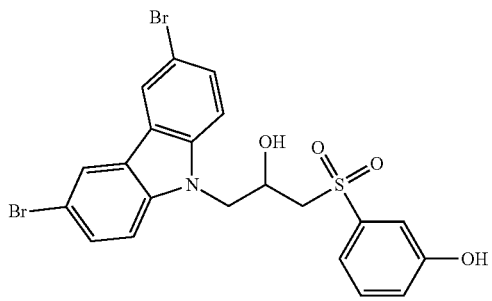 [SMILES: O=S(=O)(CC(O)Cn1c2ccc(Br)cc2c2cc(Br)ccc21)c1cccc(O)c1]

Prepared analogously to example 3d from P7C3-S91. Chromatography (0-40% EtOAc in hexanes) followed by HPLC purification (75% MeCN/H$_2$O+0.1% HCO$_2$H, Phenomenex C18 Luna, 10×250 mm, 3 mL/min) provided 9.9 mg (46% yield) of an off-white solid. $^1$H NMR (d$_6$-acetone, 500 MHz) δ=9.28 (br s, 1H), 8.36 (s, 2H), 7.59 (m, 4H), 7.44 (apparent t, J=8.0 Hz, 1H), 7.43 (m, 1H), 7.38 (br s, 1H), 7.16 (d, J=8.0 Hz, 1H), 4.72 (br s, 1H), 4.64 (dd, J=2.5, 14.0 Hz, 1H), 4.76 (m, 1H), 4.54 (dd, J=8.5, 14.0 Hz, 1H), 3.66 (dd, J=5.0, 14.5 Hz, 1H), 3.58 (dd, J=6.5, 14.5 Hz, 1H). $^{13}$C NMR (d$_6$-acetone, 125 MHz) δ=158.9, 142.5, 141.0 (2C), 131.4, 129.8, 124.5 (2C), 124.1 (2C), 121.7, 119.8, 115.3, 112.8 (2C), 112.7 (2C), 66.5, 60.7, 49.7. ESI m/z: 535.5 ([M–H]$^-$, C$_{21}$H$_{16}$Br$_2$NO$_4$S requires 535.9).

Example 126

P7C3-S94: 4-(3-(3,6-Dibromo-9H-carbazol-9-yl)-2-hydroxypropylsulfonyl)phenol

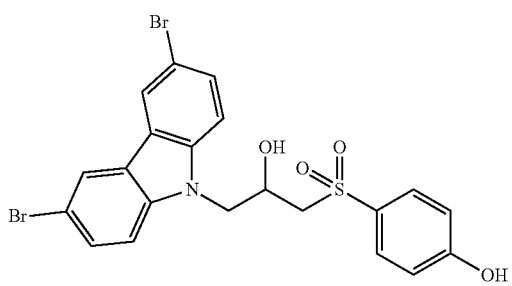 [SMILES: O=S(=O)(CC(O)Cn1c2ccc(Br)cc2c2cc(Br)ccc21)c1ccc(O)cc1]

Prepared analogously to example 3d from P7C3-S92. Chromatography (0-40% EtOAc in hexanes) provided 5.5 mg (23% yield) of an off-white solid. $^1$H NMR (d$_6$-acetone, 500 MHz) δ=8.36 (s, 2H), 7.79 (d, J=9.0 Hz, 2H), 7.60 (m, 4H), 7.01 (d, J=9.0 Hz, 2H), 4.66-4.50 (m, 3H), 3.61 (dd, J=5.0, 14.5 Hz, 1H), 3.52 (dd, J=6.0, 14.5 Hz, 1H). $^{13}$C NMR (d$_6$-acetone, 125 MHz) δ=163.2, 141.0 (2C), 131.7, 131.4 (2C), 129.8 (2C), 124.5 (2C), 124.0 (2C), 116.7 (2C), 112.8 (2C), 112.7 (2C), 66.6, 61.1, 49.7. ESI m/z: 535.5 ([M–H]$^-$, C$_{21}$H$_{16}$Br$_2$NO$_4$S requires 535.9).

Example 127

P7C3-S95: 1-(3-Aminophenylthio)-3-(3,6-dibromo-9H-carbazol-9-yl)propan-2-ol

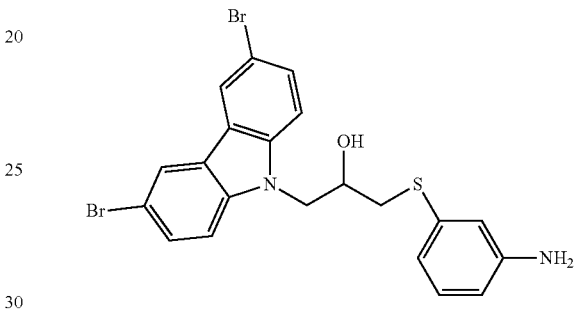

Prepared analogously to example 3a. Chromatography (0-50% EtOAc in hexanes) provided 5.5 mg (23% yield) of an off-white solid. $^1$H NMR (CDCl$_3$, 400 MHz) δ=8.08 (s, 2H), 7.50 (d, J=8.8 Hz, 2H), 7.26 (d, J=8.8 Hz, 2H), 7.01 (apparent t, J=8.0 Hz, 1H), 6.66 (d, J=8.0 Hz, 1H), 6.49 (m, 2H), 4.39 (dd, J=4.8, 15.2 Hz, 1H), 4.27 (dd, J=6.8, 15.6 Hz, 1H), 4.13 (m, 1H), 3.58 (br s, 2H), 3.01 (dd, J=5.2, 14.0 Hz, 1H), 2.88 (dd, J=7.6, 14.0 Hz, 1H), 2.53 (br s, 1H). $^{13}$C NMR (CDCl$_3$, 125 MHz) δ=147.3, 139.8 (2C), 135.2, 130.3 (2C), 129.4 (2C), 123.7, 123.4 (2C), 120.0 (2C), 116.1, 114.0, 112.7, 111.1 (2C), 69.2, 48.1, 39.0. ESI m/z: 504.6 ([M+H]$^+$, C$_{21}$H$_{19}$Br$_2$N$_2$OS requires 505.0).

Example 128

P7C3-S96: 1-(4-Aminophenylthio)-3-(3,6-dibromo-9H-carbazol-9-yl)propan-2-ol

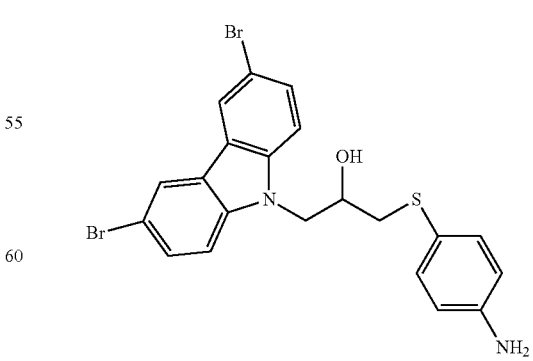

Prepared analogously to example 3a. Chromatography (0-50% EtOAc in hexanes) provided 31 mg (23% yield) of an off-white solid. ¹H NMR (CDCl₃, 400 MHz) δ=8.09 (s, 2H), 7.50 (d, J=8.8, 2H), 7.28 (d, J=8.4 Hz, 2H), 7.18 (d, J=8.4 Hz, 2H), 6.55 (d, J=8.4 Hz, 2H), 4.36 (dd, J=4.0, 15.6 Hz, 1H), 4.23 (dd, J=6.8, 15.2 Hz, 1H), 4.03 (m, 1H), 3.73 (br s, 2H), 2.91 (dd, J=5.2, 14.0 Hz, 1H), 2.75 (dd, J=8.0, 13.6 Hz, 1H), 2.59 (br s, 1H). ¹³C NMR (CDCl₃, 125 MHz) δ=146.9, 139.9 (2C), 134.6 (2C), 129.3 (2C), 123.7, 123.3 (2C), 121.0 (2C), 115.9 (2C), 112.6 (2C), 111.2 (2C), 69.1, 48.1, 41.9. ESI m/z: 504.7 ([M+H]⁺, C₂₁H₁₉Br₂N₂OS requires 505.0).

Example 129

P7C3-S97: 1-(3,6-dibromo-9H-carbazol-9-yl)-3-phenoxypropan-2-amine

Step 1. 1-(3,6-dibromo-9H-carbazol-9-yl)-3-phenoxypropan-2-one

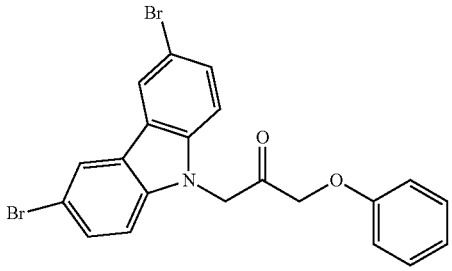 [SMILES: O=C(COc1ccccc1)Cn1c2ccc(Br)cc2c2cc(Br)ccc21]

To a solution of P7C3-S39 (87.2 mg, 0.1835 mmol, 1 equiv) in CHCl₃ (3 mL) was added Dess-Martin periodinane (DMP, 77.8 mg, 0.1835 mmol, 1 equiv). The mixture was stirred at room temperature. After 1 hour, a second batch of DMP (31.1 mg, 0.0734 mmol, 0.4 mmol) was added to the reaction mixture and further stirred for another 4 hours. Solvent was removed on the vacuum and the crude residue was purified by silica gel chromatography using 28% EtOAc to afford 31.7 mg white solid as product, yield 36.9%. ¹H NMR (CDCl₃, 400 MHz) δ=4.69 (s, 2H) 5.30 (s, 2H) 6.92 (d, J=8.7 Hz, 2H) 7.04 (d, J=8.6 Hz, 2H) 7.08 (t, J=8.7 Hz, 1H) 7.36 (t, J=8.0 Hz, 2H) 7.53 (d, J=8.7 Hz, 2H) 8.16 (s, 2H)

Step 2. (Z)-1-(3,6-dibromo-9H-carbazol-9-yl)-3-phenoxypropan-2-one O-benzyl oxime

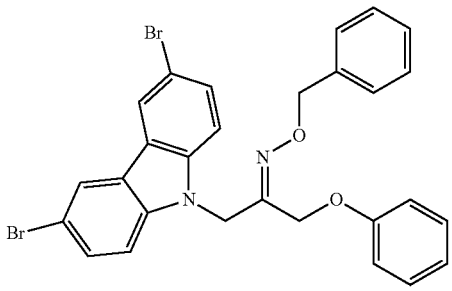 [SMILES: Brc1ccc2c(c1)c1cc(Br)ccc1n2C/C(COc1ccccc1)=N/OCc1ccccc1]

To a solution of the product of Step 1 (17.7 mg, 0.0374 mmol, 1.0 equiv) in THF (400 μL) were added 2,6-lutidine (4.4 μL, 0.0374 mmol, 1.0 equiv), O-benzylhydroxylamine hydrochloride (14.3 mg, 0.0898 mmol, 2.4 equiv) and 4 A molecular sieves (15.8 mg). The mixture was stirred for 12 h until TLC indicated complete consumption of starting material. The reaction mixture was quenched with saturated NaHCO₃ and extracted 3 times with dichloromethane. The combined organic extracts were dried with MgSO₄ and concentrated to give crude product. It was further purified by silica gel chromatography (5-10% EtOAc/Hex) to afford 20.2 mg white solid as product, yield 93.4%. ¹H NMR (CDCl₃, 400 MHz) δ=4.68 (s, 2H) 5.00 (s, 2H) 5.14 (s, 2H) 6.72 (d, J=8.2 Hz, 2H) 6.94 (t, J=7.3 Hz, 1H) 7.47-7.16 (m, 11H) 8.06 (s, 2H)

Step 3. P7C3-S97: 1-(3,6-dibromo-9H-carbazol-9-yl)-3-phenoxypropan-2-amine

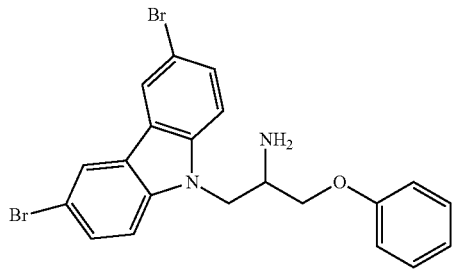 [SMILES: NC(COc1ccccc1)Cn1c2ccc(Br)cc2c2cc(Br)ccc21]

To a stirred solution containing the product of Step 2 (5.8 mg, 0.01 mmol, 1 equiv) in anhydrous THF (0.2 mL) at 0° C. was added borane-THF complex (1M in THF, 150 μL, 0.15 mmol, 15.0 equiv). The mixture was stirred at rt overnight. The reaction mixture was quenched with methanol and concentrated under vacuum. 10% Pd-C (4.0 mg) and anhydrous methanol were added and the mixture was stirred at rt for 5 hours under a hydrogen balloon. The mixture was filtered through a plug of silica-gel and NaHCO₃ was further purified by silica gel chromatography (1-5% MeOH/0.2% Et₃N/dichloromethane) to afford 4.1 mg white solid as product, yield 58.1%. ¹H NMR (CD₃OD, 500 MHz) δ=3.61 (td, J=9.7, 4.0 Hz, 1H) 3.72 (dd, J=9.6, 4.0 Hz, 1H) 3.89 (dd, J=9.5, 4.2 Hz, 1H) 4.39 (dd, J=14.9, 5.9 Hz, 1H) 4.59 (dd, J=14.9, 8.2 Hz, 1H) 6.88 (d, J=8.0 Hz, 2H) 6.94 (t, J=7.4 Hz, 1H) 7.26 (t, J=8.0 Hz, 2H) 7.46 (dd, J=8.8, 1.7 Hz, 2H) 7.49 (d, J=8.7 Hz, 2H) 8.21 (s, 2H). ¹³C NMR (CD₃OD, 500 MHz) δ=159.8, 141.0, 130.5, 130.2, 124.9, 124.2, 122.2, 115.5, 113.3, 112.2, 69.8, 51.2, 46.9 ESI (m/z): 472.7 (M+H⁺).

Example 130

P7C3-S98: N-Benzyl-2-(3-(3-(3,6-dibromo-9H-carbazol-9-yl)-2-hydroxypropylthio)-phenoxy)acetamide

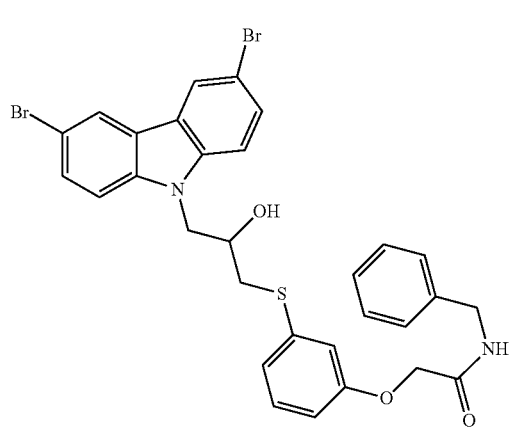 [SMILES: O=C(COc1cccc(SCC(O)Cn2c3ccc(Br)cc3c3cc(Br)ccc32)c1)NCc1ccccc1]

Prepared analogously to P7C3-S66 from P7C3-S91. Chromatography (0-50% EtOAc in hexanes) provided 6.6 mg (23% yield) of an off-white solid. $^1$H NMR (CDCl$_3$, 500 MHz) δ=8.05 (d, J=1.5 Hz, 2H), 7.47 (dd, J=1.5, 8.5 Hz, 2H), 7.30-7.23 (m, 5H), 7.18-7.15 (m, 2H), 6.92 (d, J=7.5 Hz, 1H), 6.81 (br s, 1H), 6.72-6.69 (m, 2H), 4.43 (s, 2H), 4.41-4.35 (m, 3H), 4.28 (dd, J=7.0, 15.0 Hz, 1H), 4.12 (m, 1H), 3.04 (dd, J=6.0, 14.0 Hz, 1H), 2.97 (dd, J=7.0, 14.0 Hz, 1H), 2.75 (br s, 1H). $^{13}$C NMR (CDCl$_3$, 125 MHz) δ=169.3, 168.1, 157.7, 139.8, 137.7, 136.7, 130.6, 129.4, 129.0, 127.92, 127.90, 123.8, 123.4, 123.2, 115.5, 113.2, 112.7, 111.1, 69.3, 67.5, 48.1, 43.2, 38.7. ESI m/z: 696.6 ([M+HCOO]$^-$.

Example 131

P7C3-S99: N-Benzyl-2-(4-(3-(3,6-dibromo-9H-carbazol-9-yl)-2-hydroxypropylthio)-phenoxy)acetamide

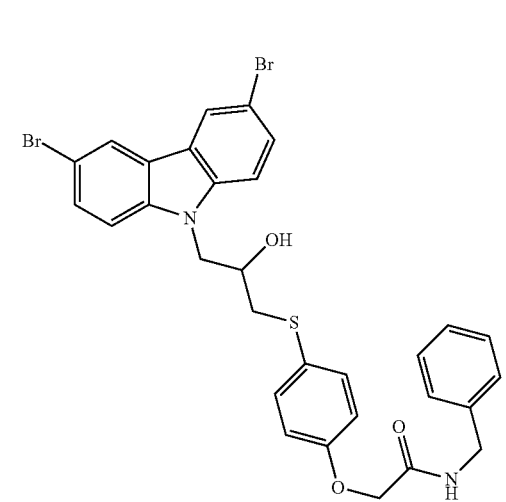 [SMILES: O=C(COc1ccc(SCC(O)Cn2c3ccc(Br)cc3c3cc(Br)ccc32)cc1)NCc1ccccc1]

Prepared analogously to P7C3-S66 from P7C3-S92. Chromatography (0-70% EtOAc in hexanes, followed by 0-10% EtOAC in dichloromethane) provided 8.7 mg (22% yield) of an off-white solid. $^1$H NMR (CDCl$_3$, 500 MHz) δ=8.10 (s, 2H), 7.50 (dd, J=1.5, 8.5 Hz, 2H), 7.32-7.26 (m, 8H), 6.79 (m, 3H), 4.51 (d, J=6.0 Hz, 2H), 4.48 (s, 2H), 4.40 (dd, J=4.5, 15.0 Hz, 1H), 4.29 (dd, J=7.0, 15.5 Hz, 1H), 4.07 (m, 1H), 2.99 (dd, J=5.0, 14.0 Hz, 1H), 2.85 (dd, J=7.5, 13.5 Hz, 1H), 2.54 (br s, 1H). $^{13}$C NMR (CDCl$_3$, 125 MHz) δ=167.8, 157.0, 139.9, 133.7, 129.4, 129.0, 128.0, 127.9, 123.9, 123.8, 123.5, 115.8, 112.7, 111.1, 69.2, 67.6, 48.1, 43.2, 41.1. ESI m/z: 696.5 ([M+HCOO]$^-$, C$_{31}$H$_{27}$Br$_2$N$_2$O$_5$S requires 697.0).

Example 132

P7C3-S100

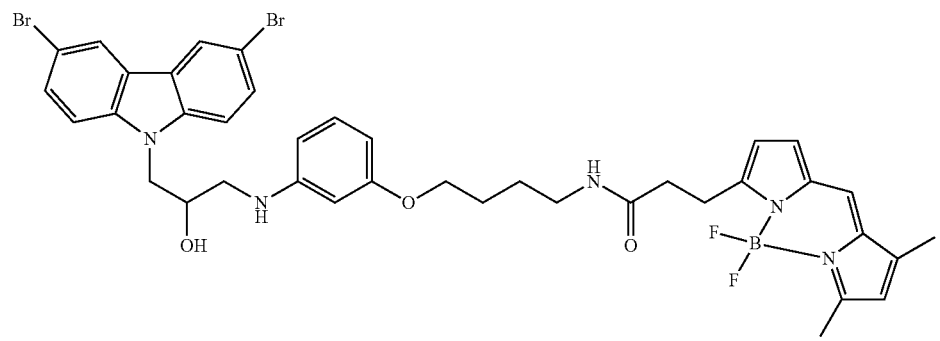

A solution of amine-terminated P7C3 analog (prepared via alkylation of the phenol analogously to P7C3-S66) (5.0 mg, 0.0087 mmol) in 300 μl DMF was added to 4,4-difluoro-5,7-dimethyl-4-bora-3a,4a-diaza-s-indacene-3-propionic acid succinimidyl ester (Bodipy-OSu, 4.0 mg, 0.010 mmol), followed by the addition of diisopropylethyl amine (25 μl, 0.14 mmol). The reaction was stirred overnight in the absence of light. The reaction was diluted with EtOAc and washed several times with water and then brine. The organic layer was dried over Na$_2$SO$_4$, filtered and condensed. The crude mixture was purified by preparative TLC in the absence of light in 100% EtOAc to give the desired product. Yield=54%. MS (ESI), m/z: calculated 848.18. found 848.7 (M+1)$^+$.

Example 133

P7C3-S101: 3-(3,6-Dibromo-9H-carbazol-9-yl)-2-fluoropropylsulfonyl)phenol

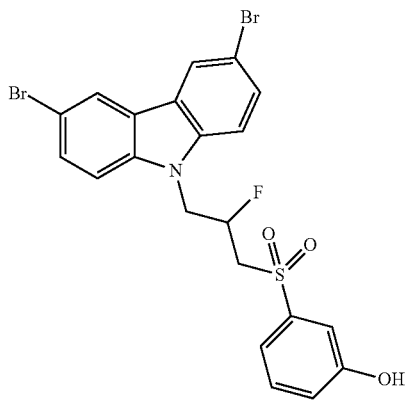 [SMILES: O=S(=O)(CC(F)Cn1c2ccc(Br)cc2c2cc(Br)ccc21)c1cccc(O)c1]

Prepared analogously to example 96 from P7C3-S91. Chromatography (0-50% EtOAc in hexanes) followed by HPLC purification (30% EtOAc/hexanes, Phenomenex Silica Luna, 10×250 mm, 3 mL/min) provided 13.9 mg (14% yield) of a pale yellow solid. $^1$H NMR (d$_6$-acetone, 500 MHz) δ=9.41 (br s, 1H), 8.38 (s, 2H), 7.60 (m, 4H), 7.45 (apparent t, J=8.0 Hz, 1H), 7.39 (d, J=8.0 Hz, 1H), 7.35 (br s, 1H), 7.16 (dd, J=2.0, 8.0 Hz, 1H), 5.42 (dm, J=47.0 Hz, 1H), 4.89-4.78 (m, 2H), 3.92 (d, J=5.5 Hz, 1H), 3.87 (m, 1H). $^{13}$C NMR (d$_6$-acetone, 125 MHz) δ=159.0, 142.2, 140.8, 131.5, 130.1, 124.7, 124.3, 122.0, 119.8, 115.4, 113.2, 112.5 (d, J=1.75 Hz), 88.6 (d, J=178.8 Hz), 58.5 (d, J=21.8 Hz), 47.1 (d, J=21.1 Hz). ESI m/z: 537.7 ([M−H]$^−$.

Example 134

P7C3-S102: N-Benzyl-2-(3-(3-(3,6-dibromo-9H-carbazol-9-yl)-2-hydroxypropylsulfonyl)-phenoxy) acetamide

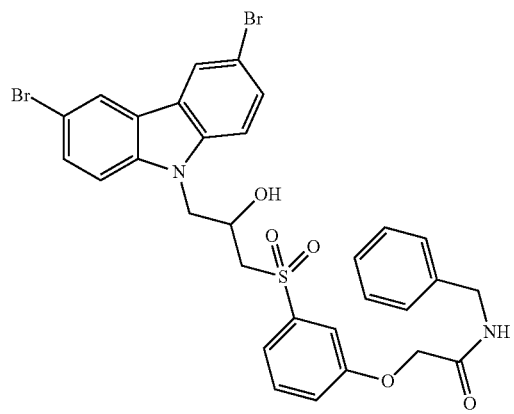 [SMILES: O=C(COc1cccc(S(=O)(=O)CC(O)Cn2c3ccc(Br)cc3c3cc(Br)ccc32)c1)NCc1ccccc1]

Prepared analogously to P7C3-S66 from P7C3-S93. Chromatography (0-50% acetone in hexanes) provided 10.1 mg (20% yield) of an off-white solid. $^1$H NMR (d$_6$-acetone, 500 MHz, 45° C.) δ=8.32 (s, 2H), 8.00 (br s, 1H), 7.57 (s, 3H), 7.55-7.52 (m, 2H), 7.32-7.30 (m, 1H), 7.29 (m, 2H), 7.22 (m, 1H), 4.65 (s, 2H), 4.63-4.60 (m, 2H), 4.53 (m, 1H), 4.47 (d, J=6.0 Hz, 1H), 3.61 (m, 2H), 3.32 (d, J=5.5 Hz, 1H). $^{13}$C NMR (d$_6$-acetone, 125 MHz) δ=168.1, 159.0, 142.7, 141.0, 140.2, 131.5, 129.9, 129.2, 128.4, 127.8, 124.5, 124.1, 121.7, 121.0 115.2, 112.8, 112.7, 68.3, 66.5, 60.7, 49.6, 43.1. ESI m/z: 728.5 ([M+HCOO]$^−$.

Example 135

P7C3-S103:4-(3-(3,6-Dibromo-9H-carbazol-9-yl)-2-fluoropropylsulfonyl)phenol

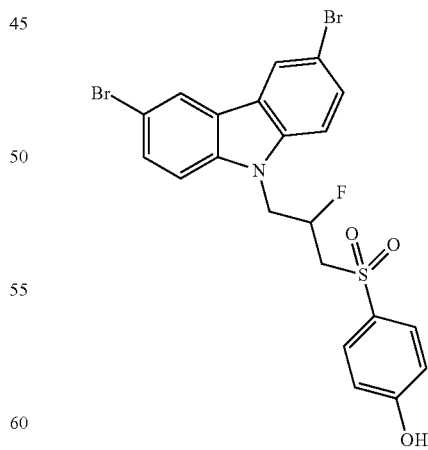

Prepared analogously to example 96 from P7C3-S94. HPLC purification (40% EtOAc/hexanes, Phenomenex Silica Luna, 21.2×250 mm, 13.5 mL/min) provided 11.4 mg (16% yield) of an off-white solid. $^1$H NMR (d$_6$-acetone, 500 MHz) δ=8.39 (s, 2H), 7.76 (d, J=8.5 Hz, 2H), 7.60 (m, 4H), 7.00 (d, J=8.5 Hz, 2H), 5.39 (dm, J=51.5 Hz, 1H), 4.89-4.81 (m, 2H), 3.85 (m, 1H), 3.80 (d, J=5.5 Hz). $^{13}$C NMR (d$_6$-acetone, 125 MHz) δ=163.5, 140.8 (2C), 131.5 (2C), 131.3, 130.1 (2C), 124.7 (2C), 124.3 (2C), 116.8 (2C), 113.2 (2C), 112.5 (d, J=1.9 Hz, 2C), 88.8 (d, J=178.5 Hz), 58.8 (d, J=21.6 Hz), 47.2 (d, J=21.3 Hz). ESI m/z: 537.6 ([M–H]$^-$.

Example 136

P7C3-S104: 5-(5-(3-(3-(3,6-dibromo-9H-carbazol-9-yl)-2-hydroxypropylamino)phenoxy)pentylcarbamoyl)-2-(6-hydroxy-3-oxo-3H-xanthen-9-yl)benzoic acid

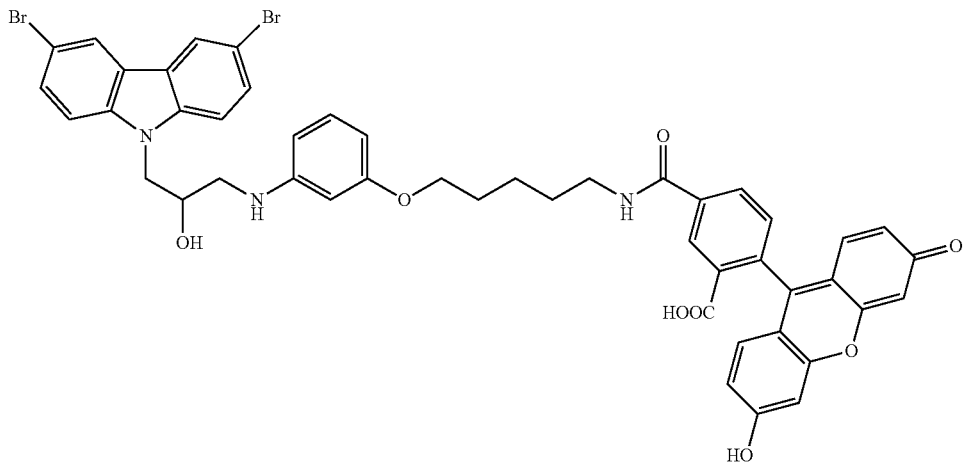 [SMILES: O=C(NCCCCCOc1cccc(NCC(O)Cn2c3ccc(Br)cc3c3cc(Br)ccc32)c1)c1ccc(-c2c3ccc(=O)cc-3oc3cc(O)ccc23)c(C(=O)O)c1]

The title compound was synthesized analogously to P7C3-S100. MS (ESI), m/z: calculated 931.1, found 931.6 (M)$^+$.

Example 137

P7C3-S105: 1-(8-bromo-3,4-dihydro-1H-pyrido[4,3-b]indol-5(2H)-yl)-3-phenoxypropan-2-ol Step 1. tert-butyl 8-bromo-3,4-dihydro-1H-pyrido[4, 3-b]indole-2(5H)-carboxylate

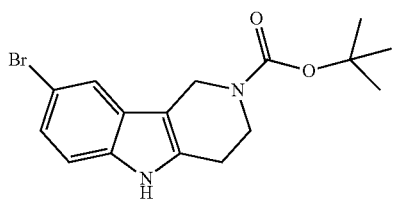 [SMILES: CC(C)(C)OC(=O)N1CCc2[nH]c3ccc(Br)cc3c2C1]

A solution of 8-bromo-2,3,4,5-tetrahydro-1H-pyrido[4,3-b]indole (813 mg, 3.2 mmol), dimethylaminopyridine (53.5 mg, 0.14 mmol) and di-tert butyl dicarbonate (1.46 g, 6.7 mmol) in methylene chloride (10 ml) and methanol (5.0 ml) with triethlamine (0.95 ml, 6.8 mmol) was stirred overnight. The reaction was condensed to a dark red semi-solid before dilution with methylene chloride. The organic layer was washed twice with water and brine, then dried over Na$_2$SO$_4$, filtered and condensed. The crude reaction product was purified in 50% EtOAc/hexanes to give 931.8 mg of product (82%). $^1$H NMR (CDCl$_3$, 500 MHz) δ=7.88 (bs, 1H), 7.58 (s, 1H), 7.22 (dd, 2H, J=8.3, 28.1 Hz), 4.58 (s, 2H), 3.82 (s, 2H), 2.83 (s, 2H), 1.51 (s, 9H). (ESI m/z): 350.8 (M+1)$^+$.

Step 2: tert-butyl 8-bromo-5-(2-hydroxy-3-phenoxypropyl)-3,4-dihydro-1H-pyrido[4, 3-b]indole-2(5H)-carboxylate

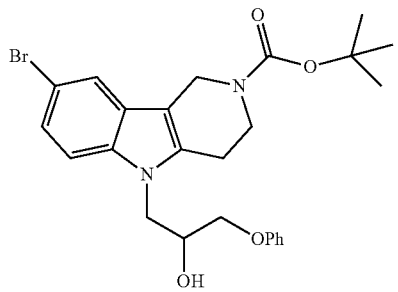 [SMILES: CC(C)(C)OC(=O)N1CCc2c(c3cc(Br)ccc3n2CC(O)COc2ccccc2)C1]

A solution of tert-butyl 8-bromo-3,4-dihydro-1H-pyrido[4,3-b]indole-2(5H)-carboxylate (449.7 mg, 1.28 mmol) and powdered potassium hydroxide (86.9 mg, 1.54 mmol) in acetone (4.0 ml) was stirred for 15 minutes before the addition of 2-(phenoxymethyl)oxirane (254 mg, 1.69 mmol). After 1 h the reaction was condensed, diluted with EtOAc and washed twice with water and then brine. The organic layer was then dried over Na$_2$SO$_4$, filtered and condensed. The crude mixture was purified by silica gel chromatography (1% MeOH/CH$_2$Cl$_2$+0.1% Et$_3$N). Yield=21%. ESI (m/z): 546.6 (M+CHCOO$^-$).

Step 3. P7C3-S105: 1-(8-bromo-3,4-dihydro-1H-pyrido[4, 3-b]indol-5(2H)-yl)-3-phenoxypropan-2-ol

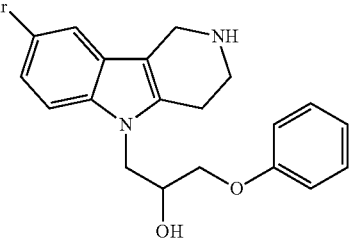

Trifluoroactetic acid (31 ul, 0.40 mmol) was added to a solution of the product of Step 2 (20.1 mg, 0.04 mmol) in methylene chloride (0.3 ml). After 100 minutes the reaction mixture was condensed and purified by preparative TLC (10% MeOH/CH$_2$Cl$_2$). Yield=96%. $^1$H NMR (CDCl$_3$, 400

MHz)) δ=7.43 (s, 1H), 7.27 (s, 1H), 7.17 (dd, 2H, J=8.5, 26.7 Hz), 6.97 (t, 1H, 4.58 J=7.0 Hz), 6.86 (d, 2H, J=6.9 Hz), 4.24 (dm, 5H), 4.06 (m, 1H), 3.88 (m, 2H), 3.34 (m, 2H), 3.16 (m, 1H), 2.96 (m, 1H). ESI (m/z): 400.8 (M+1)+.

Example 138

P7C3-S106: 1-(8-bromo-2-cyclopropyl-3,4-dihydro-1H-pyrido[4,3-b]indol-5(2H)-yl)-3-phenoxypropan-2-ol

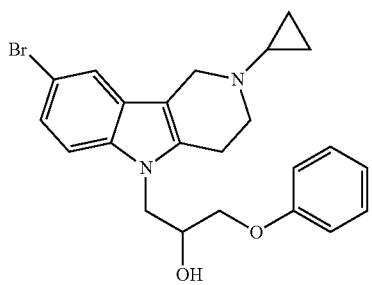 [SMILES: OC(COc1ccccc1)Cn1c2c(c3cc(Br)ccc31)CN(C1CC1)CC2]

Following a literature procedure (Barta, Thomas E. et al. WO 2003/091247 A2), ethoxycyclopropyl-oxy trimethylsilane (30 µl, 0.15 mmol) was added to a solution of P7C3-S105 (45.9 mg, 0.114 mmol) in methanol (1.0 ml) and acetic acid (70 µl, 1.2 mmol). The reaction was stirred for 10 minutes before the addition of sodium cyanoborohydride (37.0 mg, 0.59 mmol). The sealed vial was heated to reflux for 2.5 hours after which it was condensed, diluted with EtOAc, washed with 1 N NaOH solution, water and brine. The organic layer was then dried over Na$_2$SO$_4$, filtered and condensed. Purification by preparative TLC (5% MeOH/CH$_2$Cl$_2$) provided the product in 8% yield. $^1$H NMR (CDCl$_3$, 400 MHz)) δ 7.54 (s, 1H), 7.30 (t, 1H, J=7.7 Hz), 7.18 (s, 2H), 7.00 (t, 1H, J=7.3 Hz), 6.88 (d, 2H, J=8.4 Hz), 4.29 (m, 2H), 4.15 (m, 1H), 3.92 (m, 4H), 3.00 (m, 4H), 1.98 (bs, 1H), 1.33 (m, 4H), 0.6 (m, 4H). $^{13}$C NMR (CDCl$_3$, 126 MHz) δ158.1, 135.7, 125.2, 129.8, 127.6, 123.9, 121.7, 120.5, 114.6, 112.7, 110.7, 69.6, 38.8, 50.8, 49.6, 45.7, 45.7, 38.0, 8.7, 6.4. ESI (m/z): calculated 440.11, found 440.9 (M+1)+.

Example 139

P7C3-S107: 8-bromo-5-(2-hydroxy-3-phenoxypropyl)-3,4-dihydro-1H-pyrido[4,3-b]indole-2(5H)-carbonitrile

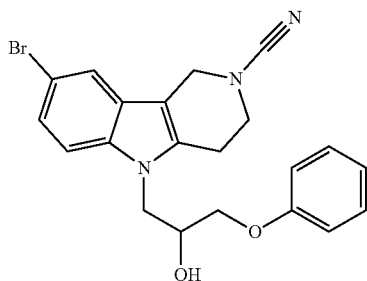 [SMILES: N#CN1CCc2c(c3cc(Br)ccc3n2CC(O)COc2ccccc2)C1]

Following a literature procedure (Kong, Chan Chun et al.; WO2004/52885) cyanogen bromide (5.0 M in CH$_3$CN, 44 µl) was added to a solution of P7C3-S105 (88.1 mg, 0.22 mmol) and potassium carbonate (45.4 mg, 0.33 mmol) in methylene chloride (2.1 ml). The reaction was stirred at ambient temperature then at reflux overnight. The cooled reaction mixture was filtered through a small celite plug directly into a separatory funnel. The organic layer was washed with water and brine, dried over Na$_2$SO$_4$, filtered and condensed. Chromatography on silica gel (1% MeOH/CH$_2$Cl$_2$) provided the purified product. Yield=12% $^1$H NMR (CDCl$_3$, 400 MHz)) δ=7.52 (s, 1H), 7.32 (t, 1H, J=8.2 Hz), 7.25 (m, 2H), 7.02 (t, 1H, J=7.3 Hz), 6.90 (d, 2H, J=7.8 Hz), 4.46 (s, 2H), 4.34 (m, 2H), 4.19 (m, 1H), 4.00 (dd, 1H, J=4.4, 9.5 Hz), 3.87 (dd, 1H, J=4.8, 9.7 Hz), 3.55 (m, 2H), 3.01 (m, 2H) 2.49 (bs, 1H). $^{13}$C NMR (CDCl$_3$, 126 MHz) δ160.0, 125.4, 133.9, 129.9, 124.9, 120.5, 118.2, 113.3, 111.0, 104.8, 69.5, 68.8, 46.7, 46.3, 45.9, 22.1.

ESI (m/z): calculated 425.07, found 471.8 (M+CH$_3$COO)−.

Example 140

P7C3-S108: 8-bromo-5-(2-fluoro-3-phenoxypropyl)-2,3,4,5-tetrahydro-1H-pyrido[4,3-b]indole Step 1. tert-butyl 8-bromo-5-(2-fluoro-3-phenoxypropyl)-3,4-dihydro-1H-pyrido[4, 3-b]indole-2(5H)-carboxylate

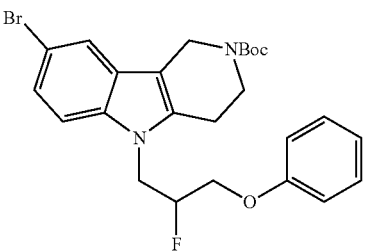 [SMILES: CC(C)(C)OC(=O)N1CCc2c(c3cc(Br)ccc3n2CC(F)COc2ccccc2)C1]

Following Representative Procedure 4, the title compound was synthesized from the product of Step 2 in the synthesis of P7C3-S105. The crude reaction product used without purification.

Step 2. P7C3-S108: 8-bromo-5-(2-fluoro-3-phenoxypropyl)-2, 3, 4, 5-tetrahydro-1H-pyrido[4, 3-b]indole

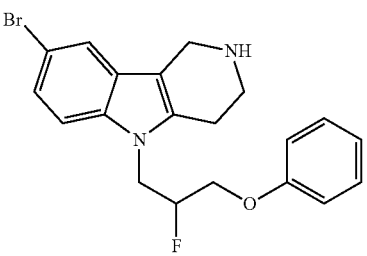 [SMILES: FC(COc1ccccc1)Cn1c2c(c3cc(Br)ccc31)CNCC2]

Trifluoroactetic acid (15 µl, 0.20 mmol) was added to a solution of the product of Step 1(20.6 mg, 0.04 mmol) in methylene chloride (0.4 ml). A further 25 µl trifluoroactetic acid (0.32 mmol) was added after 3 hours. The reaction was diluted with methylene chloride, washed with twice with water and twice with 10% NaCl solution. The organic layer was dried over Na$_2$SO$_4$, filtered and condensed. The crude was purified by preparative TLC (7% MeOH/DCM+0.15% TEA) and isolated in quantitative yield.

$^1$H NMR (CD$_3$OD, 500 MHz)) δ=7.62 (m, 1H), 7.38 (d, 1H, J=9.9 Hz), 7.25 (m, 3H), 6.92 (m, 2H), 5.06 (dm, 1H), 4.56 (m, 2H), 4.37 (s, 2H), 4.08-4.24 (m, 2H), 3.57 (m, 2H), 3.27 (m, 1H), 3.18 (m, 2H). $^{13}$C NMR (CD$_3$OD, 126 MHz) δ=159.7, 137.1, 134.5, 130.7, 126.0, 121.4, 115.6, 114.3, 112.6, 103.2, 91.7 (d, $^1$J=177.1 Hz), 68.0 (d, $^2$J=23.5 Hz), 47.9, 45.0 (d, $^2$J=22.9 Hz), 42.9, 41.9, 20.8, 9.2. MS (ESI), m/z: calculated 402.07, found 402.8 (M+1)$^+$.

Example 141

P7C3-S109: 1-(cyclohexylamino)-3-(3,6-dibromo-9H-carbazol-9-yl)propan-2-ol

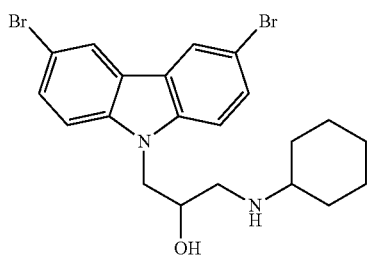 [SMILES: OC(CNC1CCCCC1)Cn1c2ccc(Br)cc2c2cc(Br)ccc21]

Cyclohexylamine (152 μl, 1.3 mmol) was added to a heterogeneous solution of 3,6-dibromo-9-(oxiran-2-ylmethyl)-9H-carbazole (102.5 mg, 0.27 mmol) in ethanol (2.6 ml). The reaction mixture was heated to reflux for 1 h and then condensed to yield pure desired product. Yield=97%. $^1$H NMR (CDCl$_3$, 500 MHz)) δ 8.13 (d, 2H, J=1.5 Hz), 7.55 (dd, 2H, J=1.8, 8.6 Hz), 7.36 (d, 2H, J=8.8 Hz), 4.28 (d, 2H, J=5.5 Hz), 4.01 (m, 1H), 2.81 (dd, 1H, J=3.5, 12.0 Hz), 2.50 (m, 1H), 2.29 (m, 1H), 1.77 (d, 2H, J=11.4 Hz), 1.63 (m, 3H), 0.84-1.28 (m, 6H). $^{13}$C NMR (CDCl$_3$, 500 MHz) δ140.0, 129.3, 123.7, 123.3, 112.4, 111.1, 69.2, 56.8, 50.0, 47.6, 34.1, 33.7, 26.0, 25.1 ESI (m/z): calculated 478.03, found 524.7 (M+CHCOO)$^-$.

Example 142

P7C3-S110: (9-(2-hydroxy-3-(phenylthio)propyl)-9H-carbazole-3,6-dicarbonitrile

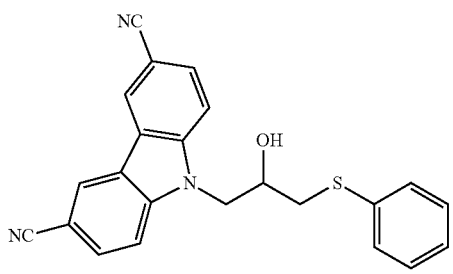 [SMILES: N#Cc1ccc2c(c1)c1cc(C#N)ccc1n2CC(O)CSc1ccccc1]

Prepared from P7C3-S7 5.3% yield analogously to Example 101. $^1$H NMR (d$_6$-Acetone, 400 MHz) δ=3.40-3.24 (m, 2H) 4.30 (tdd, J=9.0, 6.1, 2.9 Hz, 1H) 4.66 (dd, J=15.1, 8.7 Hz, 1H) 4.74 (d, J=5.1 Hz, 1H) 4.82 (dd, J=15.1, 3.0 Hz, 1H) 7.22 (t, J=7.4 Hz, 1H) 7.33 (t, J=7.6 Hz, 2H) 7.47 (dd, J=8.3, 1.0 Hz, 2H) 7.92-7.77 (m, 4H) 8.73 (s, 2H)$^{13}$C NMR (d$_6$-Acetone, 500 MHz) δ=143.8, 136.3, 130.1, 129.4, 129.2, 126.4, 126.0, 122.4, 119.8, 111.9, 103.2, 69.4, 48.7, 37.9 ESI (m/z): 427.8 (M+HCOO).

Example 143

P7C3-S111: 9-(2-hydroxy-3-phenoxypropyl)-9H-carbazole-3,6-dicarbonitrile

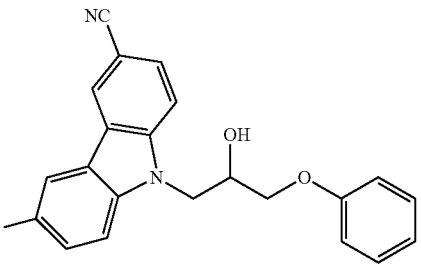

Prepared from P7C3-S39 in 16.5% yield, analogously to Example 101. $^1$H NMR (d$_6$-Acetone, 400 MHz) δ=4.15 (d, J=5.4 Hz, 2H) 4.56 (dt, J=9.2, 5.1 Hz, 1H) 4.76 (dd, J=15.1, 7.6 Hz, 1H) 4.86 (dd, J=15.1, 3.9 Hz, 1H) 6.98 (dd, J=16.4, 8.0 Hz, 3H) 7.31 (t, J=8.0 Hz, 2H) 7.85 (dd, J=8.6, 1.4 Hz, 2H) 7.96 (d, J=8.6 Hz, 2H) 8.75 (s, 1H). $^{13}$C NMR (d$_6$-Acetone, 500 MHz) δ=158.9, 143.9, 130.1, 129.7, 126.0, 122.5, 121.2, 119.7, 114.7, 112.0, 103.3, 69.7, 69.0, 46.9. ESI (m/z): 411.9 (M+HCOO$^-$).

Example 144a and 144b

P7C3-S113 and P7C3-S114: N-(3-(3,6-dibromo-9H-carbazol-9-yl)-2-fluoropropyl)-3-methoxyaniline (R- and S-enantiomers)

Step 1: (2R)—N-(3-(3,6-dibromo-9H-carbazol-9-yl)-2-fluoropropyl)-3, 3, 3-trifluoro-2-methoxy-N-(3-methoxyphenyl)-2-phenylpropanamide

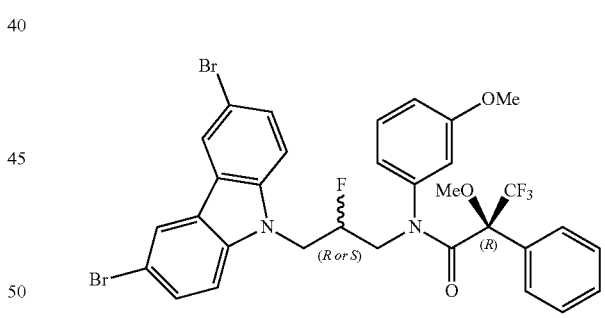

To a solution of P7C3-S10 (20.0 mg, 0.0395 mmol, 1.0 equiv) in dichloromethane (790 μL) was added NaH (60% dispersion in mineral oil, 0.9 mg, 0.0395 mmol, 1.0 equiv). The mixture was stirred at room temperature for 15 minutes. (S)-(+)-α-methoxy-α-trifluoromethyl-phenylacetyl chloride (14.8 μL, 0.0790 mmol, 2.0 equiv) was added dropwise into the reaction mixture. 4-(dimethylamino)pyridine (DMAP, catalytic) was added to the above mixture after 1 hour. The mixture was stirred at room temperature overnight and then quenched by water. The crude reaction was diluted with ethyl acetate and washed with brine. The organic layer was dried with MgSO$_4$ and concentrated to give crude product. It was further purified by silica gel preparative HPLC (20-25% EtOAc/Hex) to afford 10.1 mg white solid of the faster eluting diastereomer and 6.8 mg white as the slower eluting diasteromer, yield 59.2%. $^1$H NMR (CDCl$_3$, 400 MHz) Faster eluting diasteromer: δ=3.39 (s, 3H) 3.54 (s, 3H) 3.70-3.61 (m, 1H) 4.34 (dd, J=30.0, 14.2 Hz, 1H) 4.61-4.44 (m, 2H) 5.24 (d, J=50.4 Hz, 1H) 6.66 (d, J=8.1 Hz, 1H) 7.40-7.23 (m, 10H) 7.54 (d, J=8.6 Hz, 2H) 8.12 (s, 2H) Slower diastereomer: δ=3.25 (s, 3H) 3.50 (s, 3H) 3.61-3.53 (m, 1H) 4.27 (dd, J=32.4, 14.4 Hz, 1H) 4.61-4.40 (m, 2H) 5.32 (d, J=50.3 Hz, 1H) 6.65 (d, J=7.9 Hz, 1H) 7.42-7.20 (m, 10H) 7.56 (d, J=8.6 Hz, 2H) 8.12 (s, 2H). P7C3-S113 (see below) was derived from the diastereomer that elutes faster on reverse phase HPLC (C18 column) and elutes slower by normal phase (silica gel) HPLC.

Step 2. P7C3-S113 and P7C3-S114: N-(3-(3,6-dibromo-9H-carbazol-9-yl)-2-fluoropropyl)-3-methoxyaniline (absolute stereochemistry unassigned)

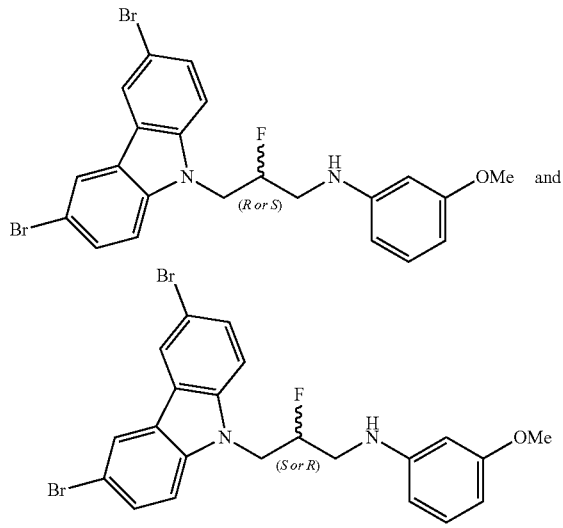

To dry and nitrogen flushed vials containing the separated products of Step 1 (4.0 mg, 0.00554 mmol, 1 equiv) was added anhydrous and degassed diethyl ether (206 μL). The suspension was chilled to 0° C. Lithium aluminum hydride solution (1M in THF, 60 μL, 0.06 mmol, 3 equiv) was added to the above chilled suspension. The mixture was stirred in ice bath for 1 hour and further at room temperature for another 1 hour. Water (0.4 μL), 15% NaOH (0.4 μL) and water (1.2 μL) were added successively to the mixture to quench the reaction. The crude was diluted with ethyl acetate and washed with brine. The organic layer was dried with MgSO$_4$ and concentrated. It was further purified by silica gel chromatography (30% EtOAC/Hex) to afford 1.5 mg white solid as product, yield 50-55%. P7C3-S113 and -S114 displayed identical LC/MS chromtograms and NMR spectra as P7C3-S10. P7C3-S113 was found to have >99% ee by HPLC (Chiralcel OD-H, 1 mL/min, 100% Acetonitrile $t_{S113}$=5.45 min, $t_{S114}$=5.74 min). P7C3-S114 was found to have 79% ee.

It should be appreciated by one skilled in the art, as generally known, that different enantiomers may have different activity. One enantiomer can be more active than another enantiomer. Two enantiomers combined can have another level of activity that is different than either substantially pure enantiomer. Preliminary experiments suggest P7C3-S113 is more active than P7C3-S114 in pro-neurogenic and/or anti-apoptotic activities in an in vivo assay where 12 week old adult male C57/B16 mice were treated with 10 μM of either compound. It should be noted that such difference in enantiomer activity may also be observed in other compounds of the presently disclosed embodiments. It should also be noted that such activity may depend on assay mode, compound concentration, compound purity, compound stability, as well as other parameters. It is possible that when tested at a different concentration, a less active enantiomer may show increased activity, and vice versa.

Example 145

P7C3-S115: N-(2-(3,6-dibromo-9H-carbazol-9-yl)ethyl)aniline

Step 1. ethyl 2-(3,6-dibromo-9H-carbazol-9-yl)acetate

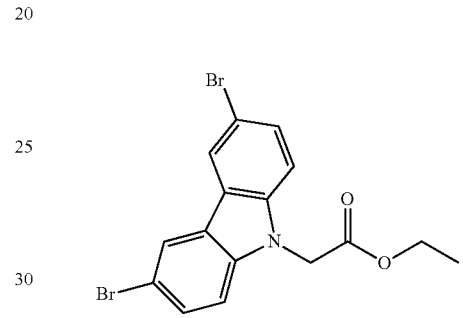

To a solution of 3,6-dibromocarbazole (325.0 mg, 1.0 mmol, 1 equiv) in anhydrous N,N-dimethylformamide (5 mL) was added crushed KOH (67.3 mg, 1.2 mmol, 1.2 equiv). The mixture was stirred for 30 minutes. Ethyl bromoacetate (277.2 μL, 2.5 mmol, 2.5 equiv) was added into the mixture and it was stirred at room temperature overnight. The reaction crude was diluted with ethyl acetate (30 mL) and washed with 1M HCl and water. The organic layer was dried with MgSO$_4$ and the concentrated to afford 396.3 mg white solid as product (96.4%).

$^1$H NMR (CDCl$_3$, 400 MHz) δ=1.22 (t, J=7.1 Hz, 3H) 4.20 (q, J=7.1 Hz, 2H) 4.94 (s, 2H) 7.21 (d, J=8.7 Hz, 2H) 7.57 (dd, J=8.6, 1.1 Hz, 2H) 8.16 (s, 2H). ESI (m/z): 407.6 (M–H$^+$).

Step 2. 2-(3,6-dibromo-9H-carbazol-9-yl)acetic acid

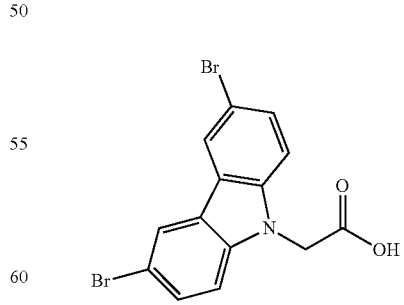

To a solution of the product of Step 1 (41.1 mg, 0.1 mmol, 1 equiv) in THF-methanol-water (3:2:1, total 1.2 mL) was added LiOH (12.0 mg, 0.5 mmol, 5 equiv). The mixture was stirred at room temperature for 1 hour. The reaction was diluted with 1M HCl (10 mL) and extracted with ethyl acetate (10 mL). The organic layer was washed with water (10 mL) twice and dried with MgSO₄ to afford 38.3 mg white solid as product, yield 99%. ¹H NMR (CDCl₃, 400 MHz) δ=5.02 (s, 2H) 7.22 (d, J=8.8 Hz, 2H) 7.58 (dd, J=8.7, 1.2 Hz, 2H) 8.16 (d, J=1.6 Hz, 2H). ESI (m/z): 379.6 (M−H⁺).

Step 3.
2-(3,6-dibromo-9H-carbazol-9-yl)-N-phenylacetamide

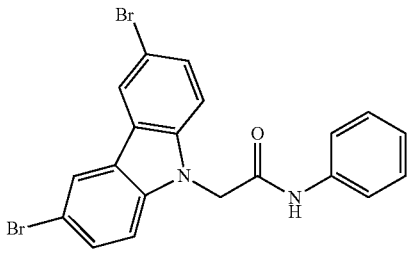 [SMILES: O=C(Cn1c2ccc(Br)cc2c2cc(Br)ccc21)Nc1ccccc1]

To a solution of the product of Step 3 (9.6 mg, 0.025 mmol, 1 equiv) in anhydrous dichloromethane (1.5 mL) was added N-(3-Dimethylaminopropyl)-N'-ethylcarbodiimide hydrochloride (EDC, 5.8 mg, 0.03 mmol, 1.2 equiv), 1-hydroxybenzotriazole hydrate (HOBt, 4.1 mg, 0.03 mmol, 1.2 equiv) and 4-(dimethylamino)pyridine (DMAP, 1 crystal). After the mixture was stirred at rt for 20 min, aniline (3.4 μL, 0.0375 mmol, 1.5 equiv) was added. The resulting mixture was heated at 80° C. overnight. The reaction mixture was diluted with ethyl acetate (20 mL) and washed successively with 1M NaOH, 1M HCl and water.

The organic layer was dried with MgSO₄ and the concentrated to give a poorly soluble white solid, which was pure enough to be used in the next step. ¹H NMR (d₆-DMSO, 400 MHz) δ=5.29 (s, 2H) 7.06 (t, J=7.3 Hz, 1H) 7.31 (t, J=7.8 Hz, 2H) 7.66-7.55 (m, 6H) 8.50 (s, 2H) 10.55 (s, 1H). ESI (m/z): 454.6 (M−H).

Step 4. P7C3-S115. N-(2-(3,6-dibromo-9H-carbazol-9-yl)ethyl)aniline

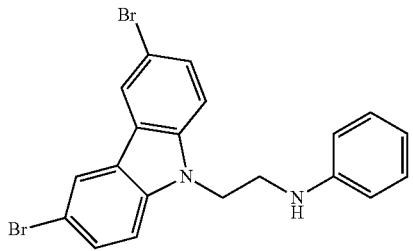 [SMILES: Brc1ccc2c(c1)c1cc(Br)ccc1n2CCNc1ccccc1]

To a dry and nitrogen flushed vial with the product of Step 3 (9.2 mg, 0.02 mmol, 1 equiv) was added anhydrous and degassed diethyl ether (750 μL). The suspension was chilled to 0° C. Lithium aluminum hydride (1M in THF, 60 μL, 0.06 mmol, 3 equiv) was added and the mixture was stirred in ice bath for 1 hour and at rt overnight. Water (3.6 μL), 15% NaOH (3.6 μL) and water (10.8 μL) were added successively to the mixture to quench the reaction. The crude mixture was diluted with ethyl acetate and washed with brine. The organic layer was dried with MgSO₄ and concentrated to give crude product. It was further purified by silica gel chromatography (60% of dichloromethane/Hex) to afford 2.7 mg white solid as product, yield 28.8%. ¹H NMR (CDCl₃, 400 MHz) δ=3.70-3.56 (m, 2H) 4.46 (t, J=5.5 Hz, 2H) 6.55 (d, J=7.8 Hz, 2H) 6.76 (t, J=7.4 Hz, 1H) 7.16 (d, J=8.8 Hz, 2H) 7.20 (t, J=7.9 Hz, 2H) 7.50 (dd, J=8.7, 1.9 Hz, 2H) 8.14 (d, J=1.7 Hz, 2H). ¹³C NMR (CDCl₃, 500 MHz) δ=146.8, 139.5, 129.7, 129.4, 123.7, 123.5, 118.4, 113.1, 112.6, 110.5, 42.7, 42.5. ESI (m/z): 486.7 (M+HCOO⁻); 476.7 (M+Cl⁻).

Example 146

P7C3-S129: 2-(6-Amino-3-imino-3H-xanthen-9-yl)-4-(6-(5-(3-(3-(3,6-dibromo-9H-carbazol-9-yl)-2-hydroxypropylamino)phenoxy)pentylamino)-6-oxohexylcarbamoyl)benzoic acid AND 2-(6-amino-3-imino-3H-xanthen-9-yl)-5-(6-(5-(3-(3-(3,6-dibromo-9H-carbazol-9-yl)-2-hydroxypropylamino)phenoxy)pentylamino)-6-oxohexylcarbamoyl)benzoic acid

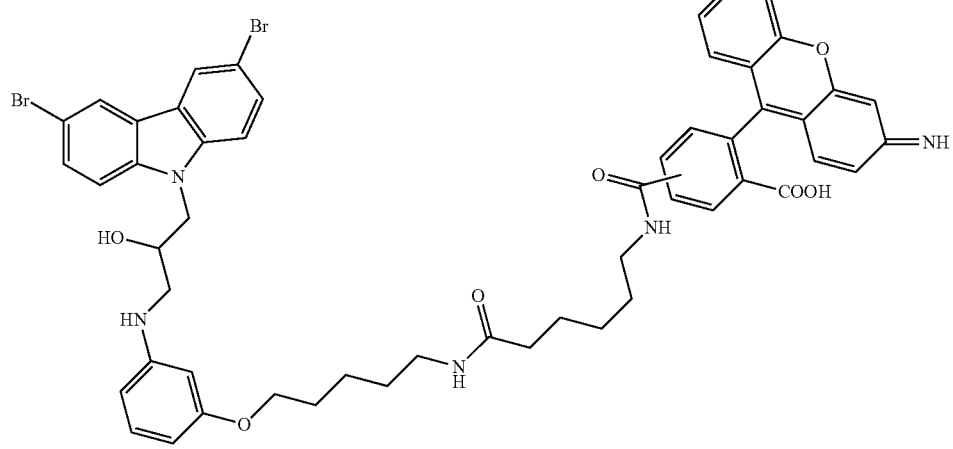

Prepared analogously to P7C3-S100. HPLC purification (45% MeCN/H$_2$O+0.1% HCO$_2$H, Phenomenex C18 Luna, 10×250 mm, 3 mL/min) provided 1.7 mg (50% yield) as a mixture of isomers. ESI m/z: 1043.2 ([M+H]$^+$, C$_{53}$H$_{53}$Br$_2$N$_6$O$_7$ requires 1043.2).

Example 147

P7C3-S130

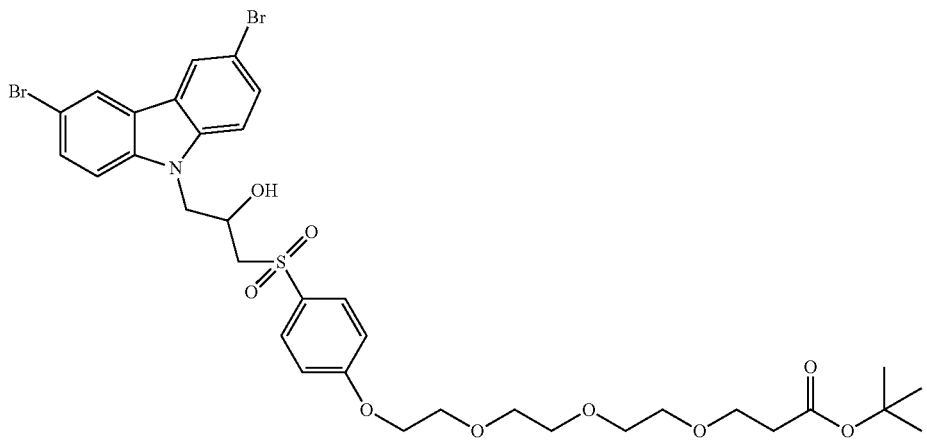 [SMILES: CC(C)(C)OC(=O)CCOCCOCCOCCOc1ccc(S(=O)(=O)CC(O)Cn2c3ccc(Br)cc3c3cc(Br)ccc32)cc1]

Prepared analogously to example P7C3-S66 from P7C3-S94. Chromatography (1% MeOH in dichloromethane) then trituration with hexanes provided 1.2 mg (5.3% yield) of an off-white solid. $^1$H NMR (CDCl$_3$, 500 MHz) d=8.12 (s, 2H), 7.71 (d, J=7.0 Hz, 2H), 7.54 (d, J=9.0 Hz, 2H), 7.29 (m, 2H), 6.98 (d, J=7.0 Hz, 2H), 4.62 (br s, 1H), 4.39 (s, 2H), 4.19 (s, 2H), 3.88 (s, 2H), 3.72 (m, 11H), 3.42 (s, 1H), 3.23 (d, J=5.0 Hz, 1H), 3.16 (s, 1H), 2.49 (t, J=14.0 Hz, 2H), 1.43 (s, 9H). ESI m/z: 841.6 ([M+HCOO], C$_{35}$H$_{42}$Br$_2$NO$_{11}$S requires 842.1).

Example 148

P7C3-S131: 1-(8-bromo-2-methyl-3,4-dihydro-1H-pyrido[4,3-b]indol-5(2H)-yl)-3-phenoxypropan-2-ol

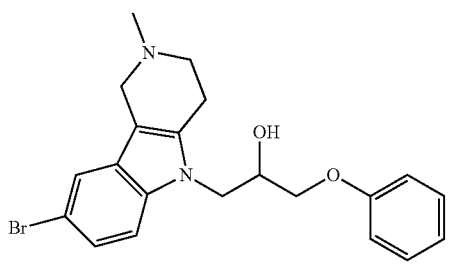 [SMILES: CN1CCc2c(c3cc(Br)ccc3n2CC(O)COc2ccccc2)C1]

Powdered KOH (13.6 mg, 0.24 mmol) was added to a solution of 8-bromo-2-methyl-2,3,4,5-tetrahydro-1H-pyrido[4,3-b]indole (Boekelheide, V.; Ainsworth, C. *J. Am. Chem. Soc.* 1950, 72, 2134) (52.5 mg, 0.20 mmol) in DMF (1.0 mL) at ambient temperature and stirred for 30 min until dissolved. 2-(Phenoxymethyl)oxirane was added via syringe and the reaction was stirred at room temperature overnight. Upon completion, the solution was diluted with EtOAc. The mixture was washed with H$_2$O and brine. The organic layer was dried over Na$_2$SO$_4$, filtered, and concentrated in vacuo. The crude residue was purified by flash column chromatography to afford the product as a white foam (35.3 mg, 43%). $^1$H NMR (CDCl$_3$) δ=7.49 (s, 1H), 7.27 (t, J=7.9 Hz, 2H), 7.18-7.15 (m, 2H), 6.98 (t, J=7.8 Hz, 1H), 6.81 (d, J=8.0 Hz, 2H), 4.23 (dd, J=14.6, 4.5 Hz, 1H), 4.15-4.08 (m, 1H), 4.03 (dd, J=14.6, 7.1 Hz, 1H), 3.83-3.75 (m, 2H), 3.53-3.43 (m, 2H), 2.85-2.63 (m, 4H), 2.47 (s, 3H). $^{13}$C NMR (CDCl$_3$, 126 MHz) δ=158.0, 135.4, 135.0, 123.6, 121.3, 114.4, 110.7, 107.7, 69.1, 68.9, 52.2, 51.3, 46.0, 45.6, 23.0. ESI m/z: 414.8 ([M+H]$^+$, C$_{21}$H$_{23}$BrN$_2$O$_2$ requires 415.0).

Example 149

P7C3-S137: Synthesis of 1-(3-(3,6-dibromo-9H-carbazol-9-yl)-2-hydroxypropyl)pyridin-2(1H)-one

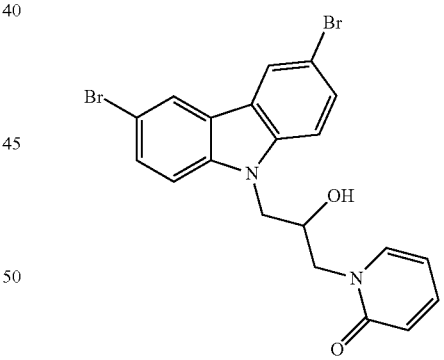

n-BuLi (2.5 M in hexanes, 80 µl, 0.2 mmol) was added to a solution of 3,6-dibromo-9H-carbazole (32.1 mg, 0.10 mmol) in THF (1.0 mL) at −78° C. and stirred for 30 min. 1-(Oxiran-2-ylmethyl)pyridin-2(1H)-one$^1$ was added at −78° C. and the reaction was stirred at room temperature overnight. Upon completion, the solution was quenched with H$_2$O. CH$_2$Cl$_2$ was added and the mixture was washed with H$_2$O, and saturated aqueous NaCl. The organic layer was dried over Na$_2$SO$_4$, filtered, and concentrated in vacuo. The crude residue was purified by flash column chromatography to afford the product as a white solid (42.2 mg, 89%).
$^1$H NMR (d$_6$-DMSO, 500 MHz) δ 8.47 (s, 2H), 7.64-7.53 (m, 5H), 7.40 (t, 1H, J=7.2 Hz), 6.35 (d, 1H, J=9.0 Hz), 6.19

(t, 1H, J=6.2 Hz), 5.33 (d, 1H, J=5.5 Hz), 4.44 (d, 1H, J=14.8 Hz), 4.35 (dd, 1H, J=7.9, 14.8 Hz), 4.28 (d, 1H, J=13.0 Hz), 4.25-4.17 (m, 1H), 3.74 (dd, 1H, J=8.8, 12.5 Hz). MS (ESI) m/z: 474.6 ([M+H]$^+$, $C_{20}H_{17}Br_2N_2O_2$ requires 475.0).

Example 150

P7C3-S138: 9-(2-hydroxy-3-phenoxypropyl)-9H-carbazole-3-carbonitrile

Step 1. Synthesis of 9H-carbazole-3-carbonitrile

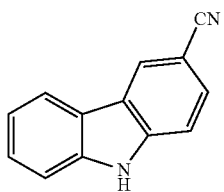 [SMILES: N#Cc1ccc2[nH]c3ccccc3c2c1]

A solution of 3-bromo-9H-carbazole (123.4 mg, 0.50 mmol) and CuCN (49.9 mg, 0.56 mmol) in N-methylpyrrolidone (2 mL) was heated at 200° C. for 5 h. The cooled reaction mixture was poured into water and the precipitate was filtered and washed with ethyl acetate. The filtrate was extracted with ethyl acetate and the combined ethyl acetate extracts were washed with water, brine, dried ($Na_2SO_4$), filtered, and concentrated in vacuo. The crude residue was purified by flash column chromatography to afford the product as a white solid (84.7 mg, 88%).

$^1$H NMR (CD$_3$OD, 500 MHz) δ 8.46 (s, 1H), 8.13 (d, 1H, J=7.9 Hz), 7.65 (d, 1H, J=8.4 Hz), 7.55 (d, 1H, J=8.4 Hz), 7.51 (d, 1H, J=8.1 Hz), 7.47 (t, 1H, J=7.5 Hz), 7.24 (t, 1H, J=7.5 Hz), 3.35 (s, 1H). MS (ESI) m/z: 193.0 ([M+H]$^+$, $C_{13}H_9N_2$ requires 193.1).

Step 2. Synthesis of 9-2-hydroxy-3-phenoxypropyl)-9H-carbazole-3-carbonitrile

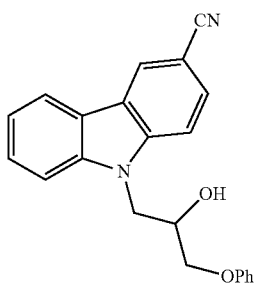 [SMILES: N#Cc1ccc2c(c1)c1ccccc1n2CC(O)COc1ccccc1]

P7C3-S138 was synthesized and isolated in 61% yield analogously to P7C3-S137 except 9H-carbazole-3-carbonitrile and 2-(phenoxymethyl)oxirane were used.

$^1$H NMR (CD$_3$OD, 400 MHz) δ 8.45 (s, 1H), 8.14 (d, 1H, J=7.8 Hz), 7.73-7.56 (m, 3H), 7.47 (t, 1H, J=7.7 Hz), 7.27 (td, 3H, J=2.0, 7.9 Hz), 6.94 (t, 3H, J=8.6 Hz), 4.66 (dd, 1H, J=5.0, 15.0 Hz), 4.52 (dd, 1H, J=6.8, 15.0 Hz), 4.43-4.34 (m, 1H), 3.99 (dd, 1H, J=5.4, 9.8 Hz), 3.93 (dd, 1H, J=4.6, 9.8 Hz). MS (ESI) m/z: 342.9 ([M+H]$^+$, $C_{22}H_{19}N_2O_2$ requires 343.1).

Example 151

P7C3-S141: tert-butyl (5-(4-((3-(3,6-dibromo-9H-carbazol-9-yl)-2-hydroxypropyl)sulfonyl)phenoxy)pentyl)carbamate

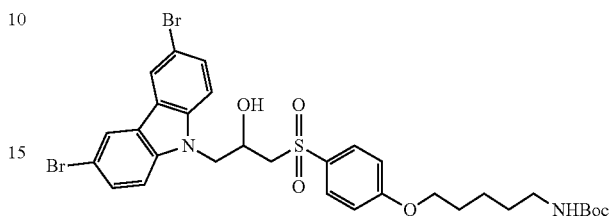

The title compound was synthesized analogously to P7C3-S98.

MS (ESI) m/z: 766.6 [M+ formate]$^-$, $C_{31}H_{36}Br_2N_2O_6S$ requires 722.1.

Example 152

P7C3-S142: 6-bromo-9-(2-hydroxy-3-phenoxypropyl)-9H-carbazole-3-carbonitrile

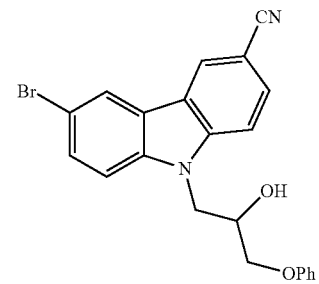 [SMILES: N#Cc1ccc2c(c1)c1cc(Br)ccc1n2CC(O)COc1ccccc1]

N-bromosuccinimide (8.0 mg, 0.09 mmol) was added to a solution of P7C3-S138 (14.0 mg, 0.04 mmol) in toluene (0.7 mL) and ethyl acetate (0.3 mL) at room temperature. The reaction was stirred at 70° C. for 2 days, and then cooled to room temperature at which point additional N-bromosuccinimide (8.1 mg, 0.09 mmol) was added. The reaction was stirred at 70° C. for another 2 days. Upon completion of the reaction as monitored by $^1$H NMR, the suspension was washed with water, and dried ($Na_2SO_4$), filtered, and concentrated in vacuo. The crude residue was purified by flash column chromatography to afford the product as a white solid (9.7 mg, 56%).

$^1$H NMR (CDCl$_3$, 400 MHz) δ 8.31 (s, 1H), 8.20 (d, 1H, J=1.7 Hz), 7.66 (d, 1H, J=8.6 Hz), 7.63-7.53 (m, 2H), 7.43 (d, 1H, J=8.7 Hz), 7.31 (t, 2H, J=8.0 Hz), 7.02 (t, 1H, J=7.4 Hz), 6.89 (d, 2H, J=8.6 Hz), 4.63 (dd, 1H, J=5.0, 14.4 Hz), 4.57-4.41 (m, 2H), 4.04 (dd, 1H, J=4.5, 9.4 Hz), 3.91 (dd, 1H, J=4.5, 9.4 Hz), 2.49 (d, 1H, J=5.6 Hz). MS (ESI) m/z: 420.8 ([M+H]$^+$, $C_{22}H_{18}BrN_2O_2$ requires 421.1).

Example 153

P7C3-S146: 6-bromo-9-(2-hydroxy-3-phenoxypropyl)-9H-carbazole-3-carboxamide

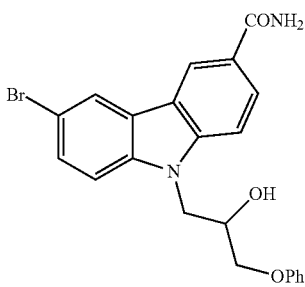

A mixture of P7C3-S142 (4.5 mg, 0.01 mmol), 50% hydrogen peroxide (0.008 mL) and 1N aqueous NaOH (0.007 mL) in ethanol (1 mL) was stirred at 30° C. for 30 h. Then additional 50% hydrogen peroxide (0.008 mL) and 1N aqueous NaOH (0.007 μL) were added, and the reaction completed after 15 h at 30° C. The solution was concentrated and the crude residue was purified by preparative thin layer chromatography to afford the product (3.9 mg, 72%).

$^1$H NMR (CDCl$_3$, 400 MHz) δ 8.48 (s, 1H), 8.19 (d, 1H, J=1.6 Hz), 7.86 (dd, 1H, J=1.6, 8.6 Hz), 7.58-7.46 (m, 2H), 7.40 (d, 1H, J=8.7 Hz), 7.33-7.28 (m, 2H), 7.01 (t, 1H, J=7.4 Hz), 6.90 (d, 2H, J=7.8 Hz), 6.08 (s, 1H), 5.61 (s, 1H), 4.61 (t, 1H, J=8.5 Hz), 4.55-4.40 (m, 2H), 4.03 (dd, 1H, J=4.6, 9.5 Hz), 3.93 (dd, 1H, J=4.6, 9.5 Hz), 2.73 (s, 1H). MS (ESI) m/z: 438.8 ([M+H]$^+$, C$_{22}$H$_{20}$BrN$_2$O$_3$ requires 439.1).

Example 154

P7C3-S147: 1-(3,6-dibromo-9H-carbazol-9-yl)-3-(pyridin-2-yloxy)propan-2-ol

Step 1. Synthesis of 3-(pyridin-2-yloxy)propane-1,2-diol

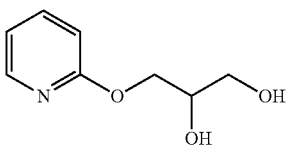 [SMILES: OCC(O)COc1ccccn1]

Following a literature procedure$^2$, a solution of solketal (1.25 mL, 0.01 mol) in THF (20 mL) was stirred and cooled to 0° C. under N$_2$ and KO$^t$Bu (1.349 g, 0.012 mol) was added. The mixture was stirred 15 min, 2-bromopyridine (1.1 mL, 0.011 mol) was added, and the mixture was stirred 18 h at room temperature, diluted with H$_2$O, and extracted with CH$_2$Cl$_2$. The combined extracts were dried (Na$_2$SO$_4$), filtered, and evaporated to give the crude title product (288.1 mg, 17%).

$^1$H NMR (CDCl$_3$, 400 MHz) δ 7.98 (d, 1H, J=3.2 Hz), 7.50 (t, 1H, J=6.8 Hz), 6.81 (t, 1H, J=5.8 Hz), 6.69 (d, 1H, J=8.3 Hz), 4.35 (d, 2H, J=4.5 Hz), 4.09 (s, 1H), 3.95-3.83 (m, 1H), 3.63-3.46 (m, 2H), 2.81 (s, 1H). MS (ESI) m/z: 170.0 ([M+H]$^+$, C$_8$H$_{12}$NO$_3$ requires 170.1).

Step 2. 1-(mesityloxy)-3-(pyridin-2-yloxy)propan-2-ol

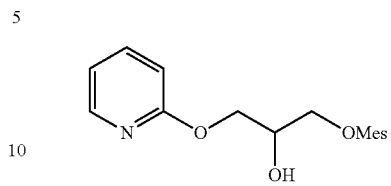

2-Mesitylenesulfonyl chloride (120.8 mg, 0.55 mmol), Bu$_2$SnO (63.1 mg, 0.25 mmol), DMAP (61.9 mg, 0.51 mmol) and Et$_3$N (1 mL) were added to a solution of 3-(pyridin-2-yloxy)propane-1,2-diol (83.7 mg, 0.50 mmol) in toluene (5 mL). The reaction mixture was stirred at room temperature for 2 h. Following the addition of water, the mixture was extracted with CH$_2$Cl$_2$. The organic layers were dried with Na$_2$SO$_4$, and the solvent was removed under reduced pressure. The residue was purified by flash column chromatography to give the title product (123.9 mg, 71%).

$^1$H NMR (CDCl$_3$, 400 MHz) δ 8.05 (dd, 1H, J=1.9, 5.1 Hz), 7.65-7.56 (m, 1H), 7.01-6.87 (m, 3H), 6.74 (d, 1H, J=7.8 Hz), 4.98 (s, 1H), 4.43 (qd, 2H, J=4.1, 12.2 Hz), 4.15 (s, 1H), 4.02 (d, 2H, J=5.6 Hz), 2.61 (s, 6H), 2.27 (s, 3H). MS (ESI) m/z: 351.9 ([M+H]$^+$, C$_{17}$H$_{22}$SNO$_5$ requires 352.1).

Step 3. Synthesis of 1-(3,6-dibromo-9H-carbazol-9-yl)-3-(pyridin-2-yloxy)propan-2-ol (P7C3-S147)

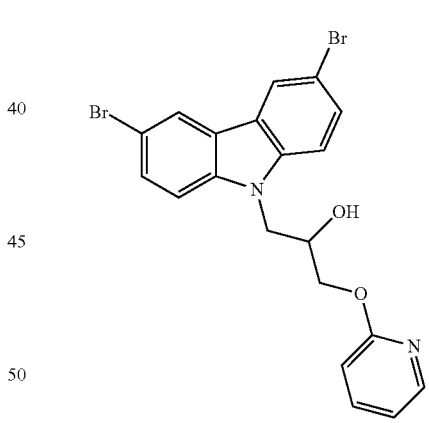

Following Representative Procedure 1, a solution of 1,3,6-dibromo-9H-carbazole (32.4 mg, 0.10 mmol) in dry DMF (0.5 mL), was treated KOH (10.2 mg, 0.15 mmol) and 1-(mesityloxy)-3-(pyridin-2-yloxy)propan-2-ol (47.5 mg, 0.14 mmol) in dry DMF (1.0 mL) to afford the title product (34.1 mg, 72%).

$^1$H NMR (d$_6$-DMSO, 400 MHz) δ 8.46 (d, 2H, J=1.8 Hz), 8.15-8.10 (m, 1H), 7.79-7.67 (m, 1H), 7.62 (d, 2H, J=8.8 Hz), 7.56 (dd, 2H, J=1.9, 8.7 Hz), 7.04-6.93 (m, 1H), 6.86 (d, 1H, J=8.3 Hz), 5.39 (d, 1H, J=3.6 Hz), 4.53 (dd, 1H, J=3.6, 14.8 Hz), 4.44 (dd, 1H, J=6.9, 14.8 Hz), 4.31-4.19 (m, 3H). MS (ESI) m/z: 474.7 ([M+H]$^+$, C$_{20}$H$_{17}$Br$_2$N$_2$O$_2$ requires 475.0).

Example 155

P7C3-S150: 1-(3-bromo-9H-carbazol-9-yl)-3-phenoxypropan-2-ol

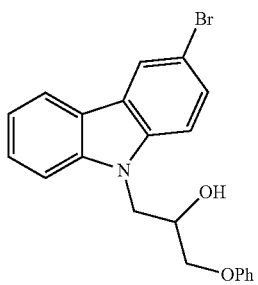 [SMILES: OC(COc1ccccc1)Cn1c2ccccc2c2cc(Br)ccc21]

Following Representative Procedure 1, a solution of bromocarbazole (24.7 mg, 0.10 mmol) in dry DMF (0.6 mL), was treated KOH (10.0 mg, 0.15 mmol) and 2-(phenoxymethyl)oxirane (30.8 mg, 0.21 mmol) in dry DMF (0.4 mL) to afford the title product (10.5 mg, 31%).

$^1$H NMR (CDCl$_3$, 400 MHz) δ 8.19 (d, 1H, J=1.8 Hz), 8.03 (d, 1H, J=7.8 Hz), 7.54-7.42 (m, 3H), 7.36 (d, 1H, J=8.7 Hz), 7.34-7.21 (m, 3H), 7.00 (t, 1H, J=7.4 Hz), 6.89 (d, 2H, J=7.8 Hz), 4.60 (dd, 1H, J=8.1, 16.1 Hz), 4.53-4.43 (m, 2H), 4.01 (dd, 1H, J=4.2, 9.5 Hz), 3.91 (dd, 1H, J=4.5, 9.5 Hz), 2.44 (d, 1H, J=5.6 Hz). MS (ESI) m/z: 395.8 ([M+H]$^+$, C$_{21}$H$_{19}$BrNO$_2$ requires 396.1).

Example 156

P7C3-S151: methyl 6-bromo-9-(2-hydroxy-3-phenoxypropyl)-9H-carbazole-3-carboxylate Step 1. Synthesis of 6-bromo-9-(2-hydroxy-3-phenoxypropyl)-9H-carbazole-3-carboxylic acid

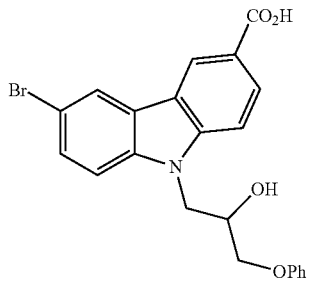 [SMILES: O=C(O)c1ccc2c(c1)c1cc(Br)ccc1n2CC(O)COc1ccccc1]

Concentrated HCl (773 μL) was added to a solution of P7C3-S142 (10.8 mg, 0.026 mmol) in dioxane (3.1 mL) at room temperature. The mixture was irradiated at 150° C. for 4 h in a microwave reactor. Upon completion 1 N NaOH aqueous was added to make pH value about 4. The solution was diluted with EtOAc. The mixture was washed with H$_2$O, and saturated aqueous NaCl. The organic layer was dried over Na$_2$SO$_4$, filtered, and concentrated in vacuo to give the crude title product.

Step 2. Synthesis of methyl 6-bromo-9-(2-hydroxy-3-phenoxypropyl)-9H-carbazole-3-carboxylate (P7C3-S151)

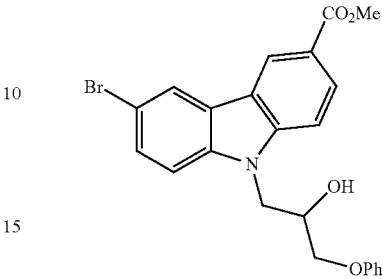

Concentrated H$_2$SO$_4$ (20 μL) was added to a solution of the above crude acid in MeOH (1 mL) at room temperature. Then the solution was stirred at 70° C. overnight. Upon completion, the solution was concentrated in vacuo. The crude residue was purified by flash column chromatography to afford the product (5.8 mg, 50% with two steps).

$^1$H NMR (CDCl$_3$, 400 MHz) δ 8.75 (s, 1H), 8.25 (d, J=1.7 Hz, 1H), 8.13 (dd, J=8.7, 1.5 Hz, 1H), 7.54 (dd, J=8.7, 1.9 Hz, 1H), 7.49 (d, J=8.7 Hz, 1H), 7.40 (d, J=8.7 Hz, 1H), 7.31 (t, J=8.0 Hz, 2H), 7.01 (t, J=7.3 Hz, 1H), 6.89 (d, J=7.9 Hz, 2H), 4.70-4.57 (m, 1H), 4.56-4.40 (m, 2H), 4.04 (dd, J=9.6, 4.4 Hz, 1H), 4.00-3.86 (m, 4H), 2.51 (d, J=5.2 Hz, 1H). MS (ESI) m/z: 453.8 ([M+H]$^+$, C$_{23}$H$_{21}$BrNO$_4$ requires 454.1).

Example 157

P7C3-S153: 6-bromo-9-(2-hydroxy-3-phenoxypropyl)-9H-carbazole-3-carboxylic acid

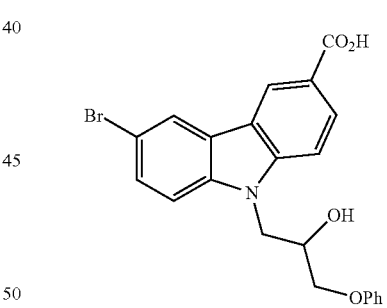

LiOH·H$_2$O was added to a solution of P7C3-S151 in 2 mL THF/H$_2$O/MeOH (v/v/v=3/1/1) at room temperature and stirred at 60° C. for 3 h. Upon completion, the solution was treated with 1.0 N HCl to make pH value about 3. The mixture was extracted with ethyl acetate and the ethyl acetate extracts were washed with H$_2$O, and saturated aqueous NaCl. The organic layer was dried over Na$_2$SO$_4$, filtered, and concentrated in vacuo. The crude residue was purified by preparative thin layer chromatography to afford the product as a white solid (2.2 mg, 67%).

$^1$H NMR (d$_6$-DMSO, 400 MHz) δ 8.84 (d, 1H, J=1.3 Hz), 8.54 (d, 1H, J=1.8 Hz), 8.03 (dd, 1H, J=1.6, 8.7 Hz), 7.68 (dd, 2H, J=8.8, 14.4 Hz), 7.59 (dd, 1H, J=1.9, 8.7 Hz), 7.33-7.26 (m, 2H), 6.99-6.91 (m, 3H), 5.45 (s, 1H), 4.61 (dd, 1H, J=4.1, 14.7 Hz), 4.49 (dd, 1H, J=4.1, 14.8 Hz), 4.31-

4.22 (m, 1H), 4.05-3.93 (m, 2H). MS (ESI) m/z: 437.8 ([M−H]⁻, C$_{22}$H$_{17}$BrNO$_4$ requires 438.0).

Examples 158a and 158b.

P7C3-S154: 6-bromo-9-(2-hydroxy-3-phenoxypropyl)-9H-pyrido[2,3-b]indole-3-carbonitrile and P7C3-S155: 9-(2-hydroxy-3-phenoxypropyl)-9H-pyrido[2,3-b]indole-3-carbonitrile Step 1. Synthesis of 6-amino-5-bromonicotinonitrile

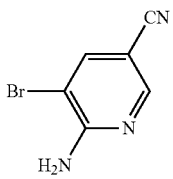

Br$_2$ (0.52 mL, 0.01 mol) was added to a solution of 6-aminonicotinonitrile (1.1901 g, 0.01 mol) in AcOH (10 mL) at room temperature. The mixture was stirred at room temperature for 2 h. Then the mixture was concentrated and the residue was purified by flash column chromatography to give the title product (980.0 mg, 49%).

$^1$H NMR (d$_6$-DMSO, 400 MHz) δ 8.36 (s, 1H), 8.19 (s, 1H), 7.33 (bs, 2H). MS (ESI) m/z: 197.9 ([M+H]⁺, C$_6$H$_5$BrN$_3$ requires 198.0).

Step 2. Synthesis of 5,6-dibromonicotinonitrile

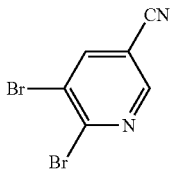

$^t$-BuONO (77.4 mg, 0.75 mmol) was added to a solution of anhydrous CuBr$_2$ (135.2 mg, 0.61 mmol) in CH$_3$CN (3 mL) at room temperature. The mixture was heated to 65° C. and then added a suspension of 6-amino-5-bromonicotinonitrile (98.1 mg, 0.50 mmol) in CH$_3$CN (2 mL). The mixture was stirred at 65° C. for 3 h. Then the mixture was poured into 3M HCl and extracted with ethyl acetate. The organic layer was dried over anhydrous Na$_2$SO$_4$, filtered, and concentrated. The residue was purified by flash column chromatography to give the title product (81.0 mg, 62%).

$^1$H NMR (CD$_3$OD, 400 MHz) δ 8.70 (d, 1H, J=2.0 Hz), 8.53 (d, 1H, J=2.0 Hz). MS (ESI) m/z: 260.7 ([M+H]⁺, C$_6$H$_3$Br$_2$N$_2$ requires 260.9).

Step 3. Synthesis of 5-bromo-6-((4-bromophenyl)amino)nicotinonitrile

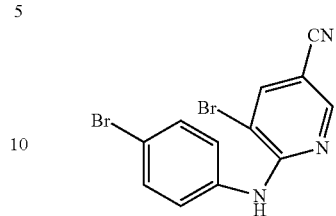

Following a literature procedure[3], a mixture of 2,4-bromoaniline (59.0 mg, 0.34 mmol), 5,6-dibromonicotinonitrile (81.0 mg, 0.31 mmol), Pd(OAc)$_2$ (3.6 mg, 0.016 mmol), PPh$_3$ (8.2 mg, 0.03 mmol), and NaO$^t$-Bu (36.1 mg, 0.38 mmol) in o-xylene (3 mL) was sparged with N$_2$ for about 5 min at room temperature, placed under N$_2$ atmosphere, and heated at 120° C. for 3 h in a screw-capped sample vial. The reaction mixture was allowed to cool to room temperature and concentrated in vacuo. The crude residue was purified by flash column chromatography to afford the product as a white solid (56.4 mg, 52%).

$^1$H NMR (CDCl$_3$, 400 MHz) δ 8.41 (d, 1H, J=1.7 Hz), 7.94 (d, 1H, J=1.7 Hz), 7.55-7.46 (m, 4H), 7.34 (s, 1H). MS (ESI) m/z: 351.7 ([M+H]⁺, C$_{12}$H$_8$Br$_2$N$_3$ requires 351.9).

Step 4. Synthesis of the mixture bromo and des-bromo carbolines

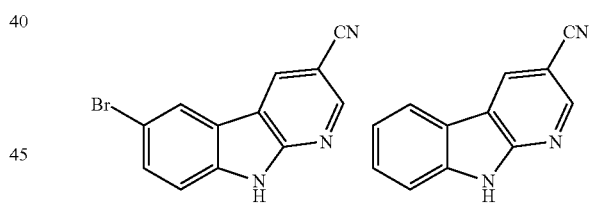

Following a literature procedure[3], Pd(OAc)$_2$ (1.3 mg, 0.006 mmol), PCy$_3$ (3.3 mg, 0.012 mmol), and DBU (16.0 mg, 0.11 mmol were added to the solution of 5-bromo-6-((4-bromophenyl)amino)nicotinonitrile (36.0 mg, 0.10 mmol) in DMA (2 mL) at room temperature. The reaction mixture was sparged for about 5 min, placed under N2 atmosphere, and heated at 145° C. for about 16 h. The reaction mixture was concentrated under reduced pressure. The residue was dissolved in ethyl acetate with heating at 40-50° C. The mixture was washed several times with water and then brine, dried over anhydrous Na$_2$SO$_4$, filtered, and concentrated. The residue was purified by flash column chromatography to give the mixture of 6-bromo-9H-pyrido[2,3-b]indole-3-carbonitrile and 9H-pyrido[2,3-b]indole-3-carbonitrile (5.9 mg) and recovered 5-bromo-6-((4-bromophenyl)amino)nicotinonitrile (19.8 mg).

Step 5. Synthesis of 6-bromo-9-(2-hydroxy-3-phenoxypropyl)-9H-pyrido[2,3-b]indole-3-carbonitrile (P7C3-S154) and 9-(2-hydroxy-3-phenoxypropyl)-9H-pyrido[2,3-b]indole-3-carbonitrile (P7C3-S155)

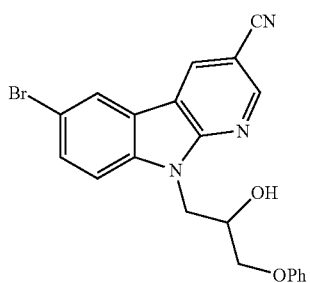

P7C3-S154

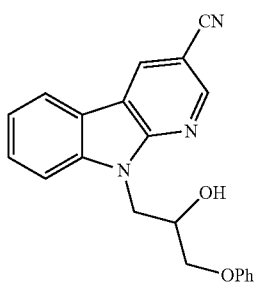

-continued

P7C3-S155

MeLi (1.6 M in Et$_2$O, 108 µl, 0.17 mmol) was added to a solution of the mixture of 6-bromo-9H-carbazole-3-carbonitrile and 9H-carbazole-3-carbonitrile (24.1 mg) in THF (1.0 mL) at −78° C. and stirred for 40 min. Phenyl glycidyl ether (24.1 mg, 0.16 mmol) was added at −78° C. and the reaction was stirred at 45° C. overnight. Upon completion, the solution was quenched with H$_2$O. Ethyl acetate was added and the mixture was washed with H$_2$O, and saturated aqueous NaCl. The organic layer was dried over Na$_2$SO$_4$, filtered, and concentrated in vacuo. A small fraction was purified by reverse HPLC to afford the title products P7C3-S154 and P7C3-S155.

P7C3-S154: $^1$H NMR (d$_6$-DMSO, 400 MHz) δ 9.13 (d, 1H, J=1.9 Hz), 8.91 (d, 1H, J=1.9 Hz), 8.55 (d, 1H, J=1.7 Hz), 7.81 (d, 1H, J=8.8 Hz), 7.74 (dd, 1H, J=1.9, 8.8 Hz), 7.27 (t, 2H, J=7.9 Hz), 6.93 (t, 1H, J=7.3 Hz), 6.88 (d, 2H, J=8.0 Hz), 5.42 (s, 1H), 4.68 (dd, 1H, J=4.8, 14.3 Hz), 4.61 (dd, J=1H, 7.7, 14.2 Hz), 4.41-4.32 (m, 1H), 4.04 (dd, 1H, J=4.9, 9.9 Hz), 3.98 (dd, 1H, J=5.5, 9.9 Hz). MS (ESI) m/z: 421.8 ([M+H]$^+$, C$_{21}$H$_{17}$BrN$_3$O$_2$ requires 422.1).

P7C3-S155: $^1$H NMR (d$_6$-DMSO, 400 MHz) δ 9.11 (d, 1H, J=2.0 Hz), 8.87 (d, 1H, J=2.0 Hz), 8.29 (d, 1H, J=8.0 Hz), 7.82 (d, 1H, J=8.3 Hz), 7.60 (dt, 1H, J=0.8, 7.6 Hz), 7.38 (t, 1H, J=7.5 Hz), 7.29-7.23 (m, 2H), 6.92 (t, 1H, J=7.3 Hz), 6.88 (d, 2H, J=7.8 Hz), 5.41 (s, 1H), 4.68 (dd, 1H, J=5.2, 14.3 Hz), 4.62 (dd, 1H, J=7.4, 14.3 Hz), 4.44-4.34 (m, 1H), 4.04 (dd, 1H, J=4.8, 9.9 Hz), 3.98 (dd, 1H, J=5.4, 9.9 Hz). MS (ESI) m/z: 343.8 ([M+H]$^+$, C$_{21}$H$_{18}$N$_3$O$_2$ requires 344.1).

Example 159

P7C3-S157: tert-butyl 3-(2-(2-(2-(3-((3-(3,6-dibromo-9H-carbazol-9-yl)-2-hydroxypropyl)amino)phenoxy)ethoxy)ethoxy)ethoxy)propanoate

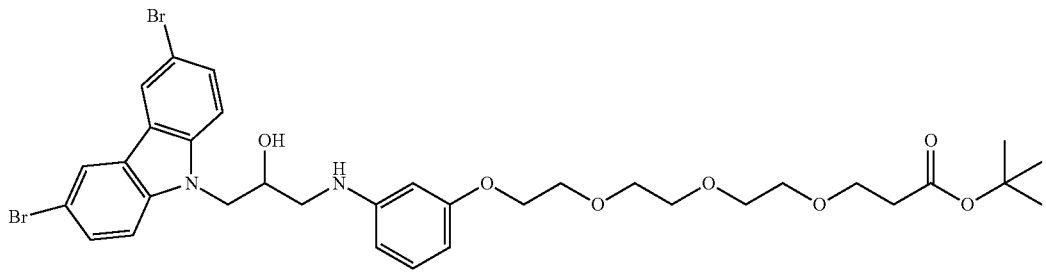 [SMILES: CC(C)(C)OC(=O)CCOCCOCCOCCOc1cccc(NCC(O)Cn2c3ccc(Br)cc3c3cc(Br)ccc32)c1]

The title compound was synthesized analogously to P7C3-S219 (see below).
MS (ESI) m/z: 748.7 [M+H]+, C$_{34}$H$_{42}$Br$_2$N$_2$O$_7$ requires 748.1.

Example 160

P7C3-S159: 1-(3-bromo-6-methoxy-9H-carbazol-9-yl)-3-(phenylamino)propan-2-ol

Representative Procedure 6: Bromination of Heterocycles

Step 1. Synthesis of 3-bromo-6-methoxy-9H-carbazole

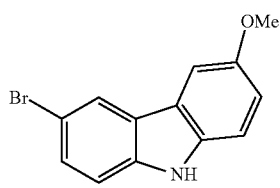 [SMILES: COc1ccc2[nH]c3ccc(Br)cc3c2c1]

3-Methoxy-9H-carbazole (Bedford, R. B.; Betham, M. J. Org. Chem. 2006, 71, 9403-9410) (0.029 g, 0.147 mmol) was dissolved in dry DMF (0.28 mL) and NBS (0.026 g, 0.147 mmol) was added to the solution. The reaction mixture was stirred at room temperature for 2 h under absence of light. The solution was poured into water (2 mL), filtered and washed with water. The title compound was isolated as a grey solid (0.033 g, 82%).

$^1$H NMR (CDCl$_3$, 400 MHz) δ 8.13 (s, 1H), 7.91 (brs, 1H), 7.50-7.43 (m, 2H), 7.30 (d, 1H, J=8.7 Hz), 7.25 (d, 1H, J=5.6 Hz), 7.08 (d, 1H, J=8.7 Hz), 3.91 (s, 3H). MS (ESI) m/z 276.9 [M+H]$^+$ ([M+H]$^+$, C$_{13}$H$_{11}$BrNO requires 276.0).

Representative Procedure 7: Alkylation of Carbazoles with NaH

Step 2. Synthesis of 1-(3-bromo-6-methoxy-9H-carbazol-9-yl)-3-(phenylamino)propan-2-ol (P7C3-S159)

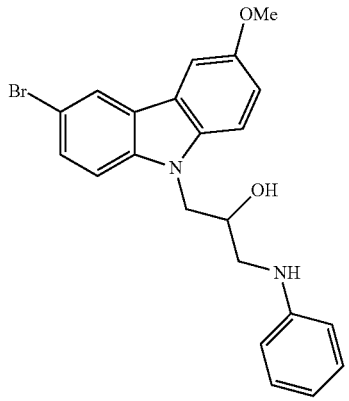 [SMILES: COc1ccc2c(c1)c1cc(Br)ccc1n2CC(O)CNc1ccccc1]

NaH (0.0023 g of 60% suspension (in oil), 0.093 mmol) was added to a solution of 3-bromo-6-methoxy-9H-carbazole (0.014 g, 0.052 mmol) in anhydrous THF (0.1 mL) at 0° C. and stirred for 30 min. A solution of N-(oxiran-2-ylmethyl)aniline (0.0093 g, 0.062 mmol) in anhydrous THF (0.1 mL) was added dropwise to the reaction mixture. The reaction was warmed to room temperature and stirred for 48 h. The reaction was quenched with saturated aqueous NH$_4$Cl and extracted with EtOAc. The combined organics were concentrated and purified by chromatography (SiO$_2$, 0-30% EtOAc/Hexane) to afford the title compound (0.007 g, 25%).

$^1$H NMR (CDCl$_3$, 500 MHz) δ 8.15 (s, 1H), 7.56-7.44 (m, 2H), 7.33 (dd, 2H, J=8.8, 22.6 Hz), 7.19 (t, 2H, J=7.7 Hz,), 7.11 (dd, 1H, J=2.2, 8.8 Hz), 6.80 (t, 1H, J=7.3 Hz), 6.67 (d, 2H, J=7.8 Hz), 4.41 (m$_c$, 1H), 4.39 (m$_c$, 2H), 3.91 (s, 3H), 3.34 (dd, 1H, J=3.0, 12.9 Hz), 3.20 (dd, 1H, J=6.9, 12.9 Hz). MS (ESI) m/z 424.8 [M+H]$^+$ ([M+H]$^+$, C$_{22}$H$_{22}$BrN$_2$O$_2$ requires 425.0).

Example 161

P7C3-S160: 1-(3,6-dibromo-1,4-dimethoxy-9H-carbazol-9-yl)-3-(phenylamino)propan-2-ol

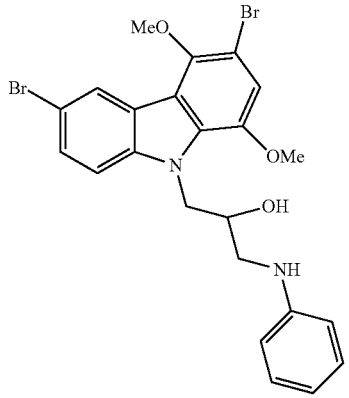 [SMILES: COc1c(Br)cc(OC)c2c1c1cc(Br)ccc1n2CC(O)CNc1ccccc1]

Representative Procedure 8: Synthesis of Carbazoles Via Consecutive Amination and C—H Activation Step 1. Synthesis of 1,4-dimethoxy-9H-carbazole

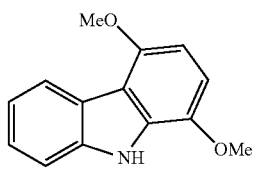 [SMILES: COc1ccc(OC)c2c1[nH]c1ccccc12]

Following a published procedure (Bedford, R. B.; Betham, M. J. Org. Chem. 2006, 71, 9403-9410), NaOtBu (0.754 g, 7.84 mmol), Pd(OAc)$_2$ (0.014 g, 0.06 mmol), and [HPtBu$_3$][BF$_4$](0.023 g, 0.078 mmol) were suspended in dry toluene (5 mL) in a microwave vial. 2-Chloroaniline (0.165 mL, 1.567 mmol) and 2-bromo-1,4-dimethoxybenzene (0.240 mL, 1.598 mmol) were then added, and the vial was sealed. The reaction was then heated in the microwave reactor at 170° C. for 4 h, allowed to cool, and then quenched by addition of 1M HCl. The aqueous phase was extracted with CH$_2$Cl$_2$, the organic layer was dried over Na$_2$SO$_4$, filtered and condensed. The crude mixture was purified by chromatography (SiO$_2$, 0-10% EtOAc/Hexane) to afford the title product (0.193 g, 55%).

$^1$H NMR (CDCl$_3$, 500 MHz) δ 8.19 (d, 1H, J=7.8 Hz), 8.15 (brs, 1H), 7.29-7.22 (m, 2H), 7.10 (t, 1H, J=7.2 Hz), 6.63 (d, 1H, J=8.4 Hz), 6.38 (d, 1H, J=8.4 Hz), 3.88 (s, 3H), 3.81 (s, 3H). MS (ESI) m/z 228.0 [M+H]$^+$ ([M+H]$^+$, C$_{14}$H$_{14}$NO$_2$ requires 228.2).

Step 2. Synthesis of 3,6-dibromo-1,4-dimethoxy-9H-carbazole

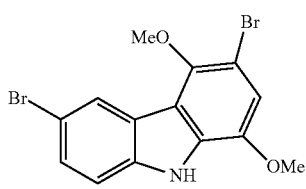 [SMILES: COc1cc(Br)c(OC)c2c1[nH]c1ccc(Br)cc12]

Following Representative Procedure 6, 1,4-dimethoxy-9H-carbazole (0.050 g, 0.22 mmol) was treated with NBS (0.078 g, 0.44 mmol) in dry CH$_2$Cl$_2$ (11 mL) to afford the title compound (0.073 g, 88%).

$^1$H NMR (CDCl$_3$, 400 MHz) δ 8.33 (brs, 1H), 8.31 (d, 2H, J=1.8 Hz), 7.52 (dd, 1H, J=1.8, 8.6 Hz), 7.32 (d, 1H, J=8.6 Hz), 6.99 (s, 1H), 4.03 (s, 3H), 3.97 (s, 3H). MS (ESI) m/z 383.7 [M−H]$^-$ ([M−H]$^-$, C$_{14}$H$_{10}$Br$_2$NO$_2$ requires 384.0).

Step 3. Synthesis of 1-(3,6-dibromo-1, 4-dimethoxy-9H-carbazol-9-yl)-3-(phenylamino)propan-2-ol

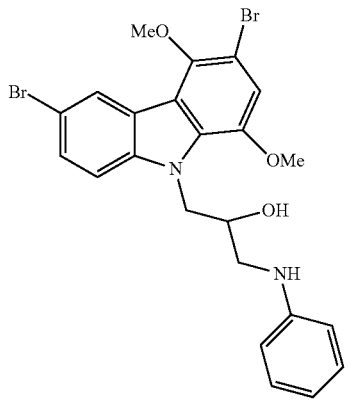 [SMILES: COc1c(Br)cc(OC)c2c1c1cc(Br)ccc1n2CC(O)CNc1ccccc1]

Following Representative Procedure 7, the title compound was prepared in 46% yield.

$^1$H NMR (CDCl$_3$, 500 MHz) δ 8.32 (s, 1H), 7.54 (dd, 1H, J=1.7, 8.8 Hz), 7.39 (d, 1H, J=8.8 Hz), 7.19 (t, 2H, J=7.8 Hz), 7.01 (s, 1H), 6.75 (t, 1H, J=7.3 Hz), 6.64 (d, 2H, J=7.8 Hz), 4.76 (dd, 1H, J=3.9, 14.7 Hz), 4.55 (dd, 1H, J=7.8, 14.7 Hz), 4.37 (m$_c$, 1H), 4.01 (s, 3H), 3.94 (s, 3H), 3.35 (dd, 1H, J=3.8, 13.0 Hz), 3.20 (dd, 1H, J=7.4, 13.0 Hz). MS (ESI) m/z 534.7 [M+H]$^+$ ([M+H]$^+$, C$_{23}$H$_{23}$Br$_2$N$_2$O$_3$ requires 535.2).

Example 162

P7C3-S161: 1-(3,6-dibromo-1,8-dimethyl-9H-carbazol-9-yl)-3-(phenylamino)propan-2-ol

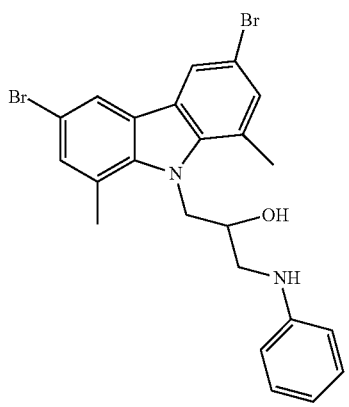 [SMILES: Cc1cc(Br)cc2c3cc(Br)cc(C)c3n(CC(O)CNc3ccccc3)c12]

The title compound was prepared analogously to P7C3-S160.

$^1$H NMR (CDCl$_3$, 500 MHz) δ 7.97 (s, 2H), 7.29 (s, 2H), 7.13 (t, 2H, J=7.7 Hz), 6.73 (t, 1H, J=7.3 Hz), 6.43 (d, 2H, J=8.1 Hz), 4.85 (dd, 1H, J=8.1, 15.6 Hz), 4.74 (dd, 1H, J=4.7, 15.6 Hz), 3.92 (m$_c$, 1H), 3.86 (m$_c$, 1H), 3.00 (dd, 1H, J=3.4, 13.2 Hz), 2.94 (dd, 1H, J=7.2, 13.2 Hz), 2.73 (s, 6H). MS (ESI) m/z 502.7 [M+H]$^+$ ([M+H]$^+$, C$_{23}$H$_{23}$Br$_2$N$_2$O requires 503.2).

Example 163

P7C3-S164: ethyl 2-(3,6-dibromo-9H-carbazol-9-yl)acetate

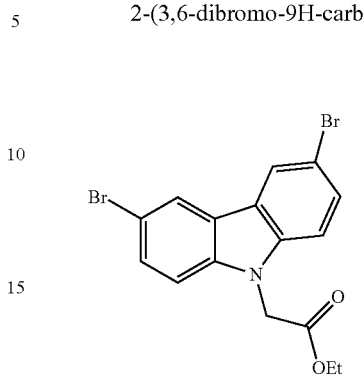

Sodium Hydride was added to a stirred solution of 3,6-dibromocarbazole (250 mg, 0.77 mmol) in DMF (4 ml). The solution was stirred for 30 minutes before the dropwise addition of ethyl chloroacetate. After 12 hours water was added and a fine white precipitate formed which was filtered and rinsed with water and hexanes to afford the desired ethyl ester in 93% yield.

$^1$H NMR (500 MHz, CDCl$_3$) δ 8.15 (s, 2H), 7.56 (d, J=8.6 Hz, 2H), 7.21 (d, J=8.5 Hz, 2H), 4.94 (s, 2H), 4.20 (q, J=6.3 Hz, 2H), 1.26-1.18 (m, 3H). ESI m/z: 409.7 ([M+H]$^+$, C$_{16}$H$_{13}$Br$_2$NO$_2$ requires 409.9)

Example 164

P7C3-S165: 2-(3,6-dibromo-9H-carbazol-9-yl)acetic acid

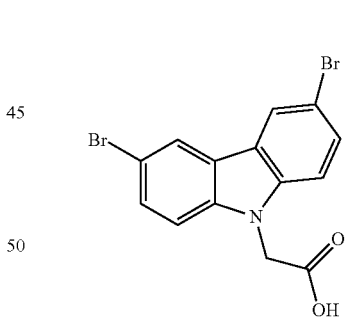

Ethyl 2-(3,6-dibromo-9H-carbazol-9-yl)acetate (50 mg, 0.12 mmol) was dissolved in 0.6 ml of THF. To this stirred solution was added 0.4 ml of methanol, 0.2 ml of water, and lithium hydroxide (14.5 mg, 0.6 mmol). After 1 hour all starting material had been consumed. The solution was acidified with 1N HCl. Upon reaching a pH of about 4 precipitate had formed which was collected and rinsed with fresh water to afford the desired acid in 95% yield.

$^1$H NMR (500 MHz, Acetone-d$_6$) δ 8.41 (s, 2H), 7.62 (dt, J=8.6, 1.7 Hz, 2H), 7.58 (dd, J=8.7, 1.5 Hz, 2H), 5.31 (d, J=1.6 Hz, 2H). ESI m/z: 381.7 ([M+H]$^+$, C$_{14}$H$_9$Br$_2$NO$_2$ requires 381.9)

Example 165

P7C3-S166: 1-(6-bromo-3-methoxy-1-methyl-9H-carbazol-9-yl)-3-(phenylamino)propan-2-ol

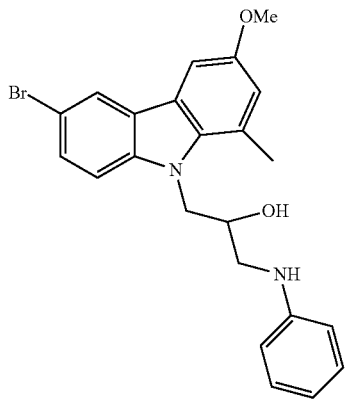 [SMILES: COc1cc(C)c2c(c1)c1cc(Br)ccc1n2CC(O)CNc1ccccc1]

The title compound was prepared analogously to P7C3-S160.

$^1$H NMR (CDCl$_3$, 400 MHz) δ 8.13 (d, 1H, J=1.9 Hz), 7.47 (dd, 1H, J=1.9, 8.7 Hz), 7.34 (d, 1H, J=2.5 Hz), 7.30 (d, 1H, J=8.7 Hz), 7.21-7.15 (m, 2H), 6.86 (d, 1H, J=1.9 Hz), 6.75 (t, 1H, J=7.3 Hz), 6.60 (d, 2H, J=7.7 Hz), 4.65 (dd, 1H, J=8.3, 15.4 Hz), 4.56 (dd, 1H, J=4.4, 15.4 Hz), 4.31 (m$_c$, 1H), 3.89 (s, 3H), 3.30 (dd, 1H, J=3.8, 13.0 Hz), 3.21 (dd, 1H, J=7.2, 13.0 Hz), 2.76 (s, 3H). MS (ESI) m/z 440.9 [M+H]$^+$ ([M+H]$^+$, C$_{23}$H$_{24}$BrN$_2$O$_2$ requires 440.3).

Example 166

P7C3-S167: 1-(4,6-dibromo-3-methoxy-1-methyl-9H-carbazol-9-yl)-3-(phenylamino)propan-2-ol

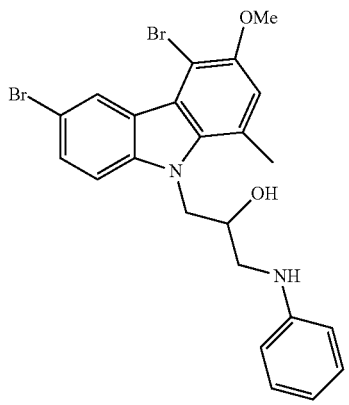 [SMILES: COc1cc(C)c2c(c1Br)c1cc(Br)ccc1n2CC(O)CNc1ccccc1]

The title compound was synthesized analogously to P7C3-S160.

$^1$H NMR (CDCl$_3$, 400 MHz) δ 9.03 (d, 1H, J=1.9 Hz), 7.53 (dd, 1H, J=1.9, 8.8 Hz), 7.29 (d, 1H, J=8.8 Hz), 7.22-7.15 (m, H), 6.86 (s, 1H), 6.76 (t, 1H, J=7.3 Hz), 6.60 (d, 2H, J=7.7 Hz), 4.65 (dd, 1H, J=8.4, 15.4 Hz), 4.53 (dd, 1H, J=4.1, 15.4 Hz), 4.27 (m$_c$, 1H), 3.94 (s, 3H), 3.29 (dd, 1H, J=3.9, 13.1 Hz), 3.20 (dd, 1H, J=7.2, 13.1 Hz), 2.77 (s, 3H). MS (ESI) m/z 518.7 [M+H]$^+$ ([M+H]$^+$, C$_{23}$H$_{23}$Br$_2$N$_2$O$_2$ requires 519.2).

Example 167

P7C3-S168: 1-(3,6-dibromo-4-methoxy-9H-carbazol-9-yl)-3-(phenylamino)propan-2-ol

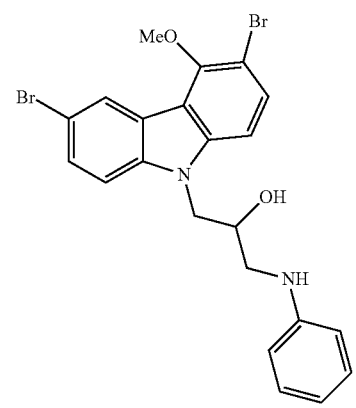 [SMILES: COc1c(Br)ccc2c1c1cc(Br)ccc1n2CC(O)CNc1ccccc1]

The title compound was synthesized analogously to P7C3-S160.

$^1$H NMR (CDCl$_3$, 500 MHz) δ 8.46 (s, 1H), 7.62-7.47 (m, 2H), 7.44 (d, 1H, J=8.7 Hz), 7.18 (t, 2H, J=7.6 Hz), 6.75 (t, 1H, J=7.2 Hz), 6.64 (d, 2H, J=8.2 Hz), 6.60 (d, 1H, J=8.5 Hz), 5.04 (dd, 1H, J=4.1, 15.2 Hz), 4.68 (dd, 1H, J=8.1, 15.2 Hz), 4.51 (m$_c$, 1H), 4.07 (s, 3H), 3.39 (dd, 1H, J=3.1, 13.0 Hz), 3.24 (dd, 1H, J=7.5, 13.0 Hz). MS (ESI) m/z 504.7 [M+H]$^+$ ([M+H]$^+$, C$_{22}$H$_{21}$Br$_2$N$_2$O$_2$ requires 505.2).

Example 168

P7C3-S172: 9-(2-hydroxy-3-phenoxypropyl)-9H-pyrido[3,4-b]indole-3-carboxylic acid Step 1: Ethyl 9-(2-hydroxy-3-phenoxypropyl)-9H-pyrido[3,4-b]indole-3-carboxylate

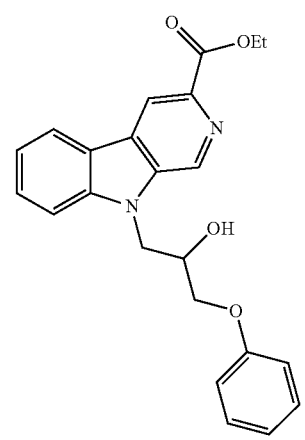 [SMILES: CCOC(=O)c1cc2c3ccccc3n(CC(O)COc3ccccc3)c2cn1]

Following Representative Procedure 1, the title compound ethyl 9-(2-hydroxy-3-phenoxypropyl)-9H-pyrido[3, 4-b]indole-3-carboxylate was prepared from Ethyl 9H-pyrido[3,4-b]indole-3-carboxylate and phenoxymethyloxirane in 67% yield.

1H NMR (500 MHz, DMSO-$d_6$) δ 9.12 (s, 1H), 8.92 (s, 1H), 8.43 (d, J=7.7 Hz, 1H), 7.80 (d, J=8.4 Hz, 1H), 7.66 (t, J=7.4 Hz, 1H), 7.37 (t, J=7.4 Hz, 1H), 7.30 (t, J=7.6 Hz, 2H), 6.96 (dd, J=12.0, 8.0 Hz, 3H), 5.50 (s, 1H), 4.75 (dd, J=14.8, 3.4 Hz, 1H), 4.64 (dd, J=14.8, 7.3 Hz, 1H), 4.38 (dd, J=14.2, 7.1 Hz, 1H), 4.31 (s, 1H), 4.03 (p, J=9.7 Hz, 2H), 1.41-1.32 (m, 3H). ESI m/z: 390.9 ([M+H]$^+$, $C_{23}H_{22}N_2O_4$ requires 391.16)

Step 2: P7C3-S172: 9-(2-hydroxy-3-phenoxypropyl)-9H-pyrido[3,4-b]indole-3-carboxylic acid

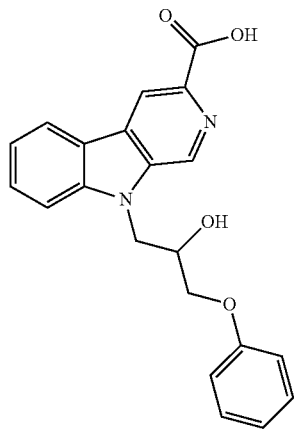 [SMILES: O=C(O)c1cc2c3ccccc3n(CC(O)COc3ccccc3)c2cn1]

Ethyl 9-(2-hydroxy-3-phenoxypropyl)-9H-pyrido[3,4-b]indole-3-carboxylate (42 mg, 0.107 mmol) was suspended in 10% NaOH$_{(aq)}$. and heated to reflux for 3 hours. Upon completion the reaction was cooled to room temperature and acidified with ice cold HCl$_{(conc)}$. The temperature was maintained at 0° C. and stirred for 1 hour. The precipitate was filtered, rinsed with water, and dried under vacuum to afford the desired compound in 92% yield.

$^1$H NMR (500 MHz, DMSO-$d_6$) δ 9.16 (s, 1H), 9.00 (s, 1H), 8.48 (d, J=7.7 Hz, 1H), 7.83 (d, J=8.4 Hz, 1H), 7.66 (t, J=7.4 Hz, 1H), 7.37 (t, J=7.4 Hz, 1H), 7.30 (t, J=7.6 Hz, 2H), 6.96 (dd, J=12.0, 8.0 Hz, 3H), 5.52 (s, 1H), 4.78 (dd, J=14.8, 3.4 Hz, 1H), 4.68 (dd, J=14.8, 7.3 Hz, 1H), 4.31 (s, 1H), 4.03 (p, J=9.7 Hz, 2H). ESI m/z: 362.9 ([M+H]$^+$, $C_{21}H_{18}N_2O_4$ requires 363.13)

Example 169

P7C3-S173: 6-bromo-9-(2-hydroxy-3-phenoxypropyl)-9H-pyrido[3,4-b]indole-3-carboxylic acid Step 1: Synthesis of ethyl 6-bromo-9H-pyrido[3,4-b]indole-3-carboxylate

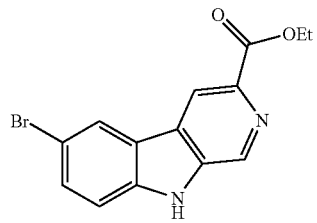 [SMILES: CCOC(=O)c1cc2c(cn1)[nH]c1ccc(Br)cc12]

Following a procedure in *Chem. Bio. Chem*, 2009, 10, 889-895, N-bromosuccinimide (37 mg, 0.208 mmol) was added to a solution of ethyl 9H-pyrido[3,4-b]indole-3-carboxylate (50 mg, 0.208 mmol) in acetic acid (1.5 ml) and stirred at room temperature. After 45 minutes the acetic acid was removed and the solid material was partitioned between EtOAc and NaHCO$_3$. The organic layer was washed with water, brine, and dried over Na$_2$SO$_4$ to afford the desired compound in 98% yield.

$^1$H NMR (500 MHz, DMSO-$d_6$) δ 8.99 (d, J=3.4 Hz, 2H), 8.70 (s, 1H), 7.67 (dd, J=24.8, 8.5 Hz, 2H), 4.37 (q, J=7.1 Hz, 2H), 1.37 (t, J=7.1 Hz, 3H). ESI m/z: 318.8 ([M+H]$^+$, $C_{14}H_{11}BrN_2O_2$ requires 319.0)

Step 2: ethyl 6-bromo-9-(2-hydroxy-3-phenoxypropyl)-9H-pyrido[3,4-b]indole-3-carboxylate (P7C3-S174)

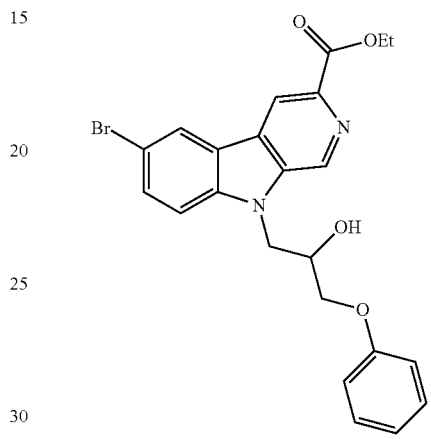

Following Representative Procedure 1, the title compound ethyl 6-bromo-9-(2-hydroxy-3-phenoxypropyl)-9H-pyrido[3,4-b]indole-3-carboxylate was prepared from ethyl 6-bromo-9H-pyrido[3,4-b]indole-3-carboxylate and phenoxymethyloxirane in 71% yield.

$^1$H NMR (500 MHz, DMSO-$d_6$) δ 9.26 (s, 1H), 9.19 (s, 1H), 8.87 (s, 1H), 7.90-7.80 (m, 2H), 7.30 (t, J=6.6 Hz, 2H), 6.96 (d, J=7.5 Hz, 3H), 4.81 (d, J=14.9 Hz, 1H), 4.73 (dd, J=15.7, 8.6 Hz, 1H), 4.44 (dd, J=13.8, 6.8 Hz, 2H), 4.29 (s, 1H), 4.03 (s, 2H), 1.40 (td, J=7.0, 2.6 Hz, 3H). ESI m/z: 468.8 ([M+H]$^+$, $C_{23}H_{21}BrN_2O_4$ requires 469.07)

Step 3: P7C3-S173: 6-bromo-9-(2-hydroxy-3-phenoxypropyl)-9H-pyrido[3,4-b]indole-3-carboxylic acid

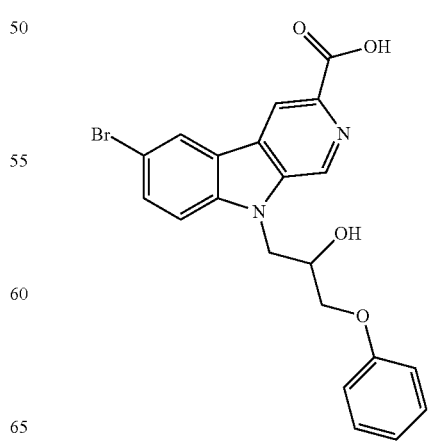

P7C3-S173 was synthesized analogously to P7C3-S172 except ethyl 6-bromo-9-(2-hydroxy-3-phenoxypropyl)-9H-pyrido[3,4-b]indole-3-carboxylate was used.

$^1$H NMR (500 MHz, DMSO-$d_6$) δ 9.35 (s, 1H), 9.27 (s, 1H), 8.91 (s, 1H), 7.90 (dd, J=24.1, 9.5 Hz, 2H), 7.30 (t, J=7.4 Hz, 2H), 6.96 (d, J=7.4 Hz, 3H), 4.89-4.73 (m, 3H), 4.29 (s, 1H), 4.04 (d, J=4.2 Hz, 2H). ESI m/z: 440.8 ([M+H]$^+$, $C_{21}H_{17}BrN_2O_4$ requires 441.0)

Example 170

P7C3-S174: ethyl 6-bromo-9-(2-hydroxy-3-phenoxypropyl)-9H-pyrido[3,4-b]indole-3-carboxylate

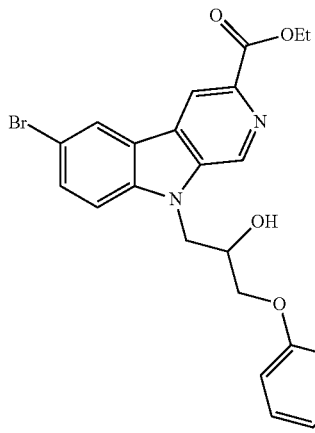

P7C3-S174 was an intermediate in the synthesis of P7C3-S173.

Example 171

P7C3-S175: 9-(2-fluoro-3-phenoxypropyl)-9H-carbazole-3,6-dicarbonitrile

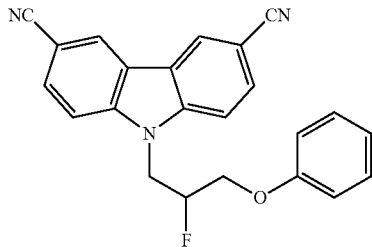 [SMILES: N#Cc1ccc2c(c1)c1cc(C#N)ccc1n2CC(F)COc1ccccc1]

The title compound was prepared according to the procedure described in Representative Procedure 4 with Morpho-Dast, except using P7C3-S111 as starting material. The crude mixture was purified on silica gel in 100% DCM (+0.2% TEA). Isolated yield=75%.

$^1$H NMR (THF-d, 400 MHz) δ 8.62 (s, 2H), 7.80 (s, 4H), 7.27 (t, J=8.2 Hz, 2H), 6.84 (dm, 1H, $J_{H-F}$=47.3 Hz), 4.84-5.04 (m, 2H), 4.16-4.34 (m, 2H). MS (ESI), m/z: calculated 369.13, found 413.9 (M+HCOO$^-$).

Example 172

P7C3-S176: 1-(cyclopentylamino)-3-(3,6-dibromo-9H-carbazol-9-yl)propan-2-ol

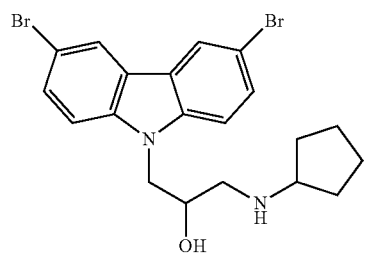 [SMILES: OC(CNC1CCCC1)Cn1c2ccc(Br)cc2c2cc(Br)ccc21]

A solution of 3,6-Dibromo-9-(oxiran-2-ylmethyl)-9H-carbazole (153 mg, 0.40 mmol) and cyclopentylamine (200 μl, 2.02 mmol) in ethanol (4.0 ml) was heated at 80° C. for 3 hours. The reaction was cooled and condensed to give desired in quantitative yield.

$^1$H NMR (CDCl$_3$, 400 MHz) δ 8.15 (d, J=1.9 Hz, 2H), 7.56 (dd, J=8.7, 2.0 Hz, 2H), 7.38 (d, J=8.7 Hz, 2H), 4.32 (d, J=5.6 Hz, 2H), 4.11-4.00 (m, 1H), 3.75 (q, J=6.6 Hz, 1H), 3.06-2.95 (m, 1H), 2.79 (dd, J=12.1, 3.7 Hz, 1H), 2.52 (dd, J=12.0, 8.8 Hz, 1H), 1.90-1.39 (m, 6H), 1.32-1.17 (m, 2H). MS (ESI), m/z: calculated 464.01. found 508.7 (M+HCOO$^-$).

Example 173

P7C3-S177: 9-(2-hydroxy-2-methyl-3-phenoxypropyl)-9H-carbazole-3,6-dicarbonitrile Step 1: 1-(3,6-dibromo-9H-carbazol-9-yl)-2-methyl-3-phenoxypropan-2-ol

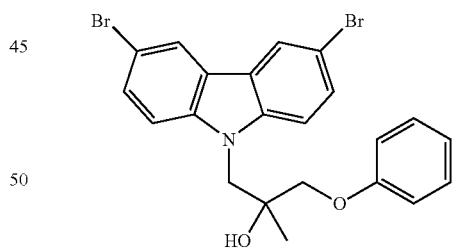

Methylmagnesium bromide (92 μl, 3.0 M in THF) was added to an ice-cooled solution of title compound of example 103, step 1, 1-(3,6-dibromo-9H-carbazol-9-yl)-3-phenoxypropan-2-one (86 mg, 0.18 mmol) in anhydrous THF (1.8 ml). The reaction was stirred in the gently warming ice bath for 6 hours, and then quenched by addition of water. The crude mixture was diluted with EtOAc and washed with saturated sodium bicarbonate, water and then brine. The organic layer was dried over Na$_2$SO$_4$, filtered and condensed. Some unreacted starting material was precipitated from ~50% acetone/hexanes. The condensed filtrate was carried forward. Yield=89%. MS (ESI), m/z: calculated 486.98, found 531.7 (M+HCOO$^-$).

Step 2: 9-(2-hydroxy-2-methyl-3-phenoxypropyl)-9H-carbazole-3,6-dicarbonitrile (P7C3-S177)

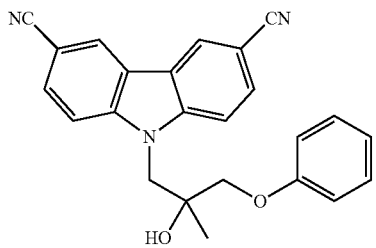 [SMILES: CC(O)(COc1ccccc1)Cn1c2ccc(C#N)cc2c2cc(C#N)ccc21]

An oven dried vial was charged with 1-(3,6-dibromo-9H-carbazol-9-yl)-2-methyl-3-phenoxypropan-2-ol (79.5 mg, 0.16 mmol), copper iodide (16 mg, 0.08 mmol), sodium cyanide (22 mg, 0.45 mmol) and potassium iodide (16 mg, 0.10 mmol). The sealed vial was nitrogen filled and evacuated three times before addition of N, N-dimethyl-1,2-ethanediamine (22.5 µl, 0.21 mmol) and anhydrous toluene (75 µl). The reaction was heated at 100° C. over 60 hours. The cooled mixture was diluted with EtOac, washed with water and brine. The organic layer was dried over Na$_2$SO$_4$, filtered and condensed. The crude mixture was purified on silica gel in 40% THF/hexanes. Yield=34%.

$^1$H NMR (THF-d$_8$, 400 MHz) δ 8.49 (d, J=1.0 Hz, 2H), 7.79 (d, J=8.6 Hz, 2H), 7.60 (dd, J=8.7, 1.5 Hz, 2H), 7.17 (d, J=8.0 Hz, 2H), 6.89-6.74 (m, 3H), 4.46-4.70 (m, 2H), 371-3.89 (m, 2H), 1.32 (s, 3H). MS (ESI), m/z: calculated 381.15, found 425.9 (M+HCOO).

Example 174

P7C3-S178: 1-(cyclohexyloxy)-3-(3,6-dibromo-9H-carbazol-9-yl)propan-2-ol

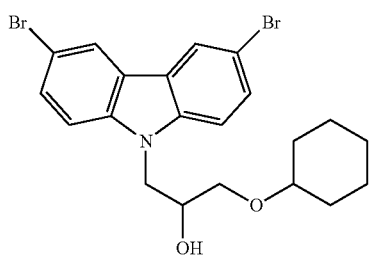 [SMILES: OC(COC1CCCCC1)Cn1c2ccc(Br)cc2c2cc(Br)ccc21]

A spatula tip of sodium hydride (60% suspension in mineral oil) was added to solution of 3,6-Dibromo-9-(oxiran-2-ylmethyl)-9H-carbazole (Epoxide 2-A) (145 mg, 0.38 mmol) in cyclohexanol (10 ml). The reaction was stirred overnight at 60° C. The mixture was washed with water and then dried over several days under vacuum. Yield=45%

$^1$H NMR (CDCl$_3$, 400 MHz) δ 8.14 (d, J=1.9 Hz, 2H), 7.56 (dd, J=8.7, 1.9 Hz, 2H), 7.39 (d, J=8.7 Hz, 2H), 4.43 (dd, J=15.0, 6.8 Hz, 1H), 4.32 (dd, J=14.9, 5.7 Hz, 1H), 4.18 (m, 1H), 3.49 (dd, J=9.4, 4.1 Hz, 1H), 3.27 (m, 2H), 2.53 (d, J=6.0 Hz, 1H), 1.89 (m, 2H), 1.79-1.69 (m, 2H), 1.56 (m, 2H), 1.40-1.17 (m, 4H). MS (ESI), m/z: calculated 479.01, found 523.7 (M+HCOO$^-$).

Example 175

P7C3-S179: (E)-N-(3-(3,6-dibromo-9H-carbazol-9-yl)prop-1-en-1-yl)-1,1,1-trifluoro-N-(3-methoxyphenyl)methanesulfonamide

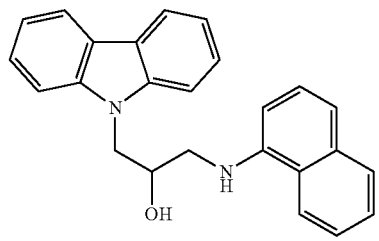 [SMILES: OC(CNc1cccc2ccccc12)Cn1c2ccccc2c2ccccc21]

The title compound was isolated as a by-product from the reaction of N-(3-(3,6-dibromo-9H-carbazol-9-yl)-2-fluoropropyl)-1,1,1-trifluoro-N-(3-methoxyphenyl)methanesulfonamide (P7C3-S241) in toluene with Red-Al at 80° C. It was purified with column chromatography in 10% EtOAc/hexanes.

$^1$H NMR (CDCl$_3$, 400 MHz) δ 8.13 (d, J=1.9 Hz, 2H), 7.55 (dd, J=8.6, 2.0 Hz, 2H), 7.32 (t, J=8.2 Hz, 1H), 7.21 (d, J=8.7 Hz, 2H), 7.01 (d, J=13.4 Hz, 1H), 6.98-6.93 (m, 1H), 6.80 (dd, J=7.9, 1.9 Hz, 1H), 6.73 (t, J=2.3 Hz, 1H), 4.83 (d, J=6.7 Hz, 2H), 4.76 (ddd, J=12.8, 7.2, 5.4 Hz, 1H), 3.75 (s, 3H). MS (ESI), m/z: calculated 615.93, found 660.5 (M+HCOO$^-$).

Example 176

P7C3-S180: 1-(9H-carbazol-9-yl)-3-(naphthalen-1-ylamino)propan-2-ol

The title compound was prepared using representative procedure 2 and 9-(oxiran-2-ylmethyl)-9H-carbazole. Chromatography in 10% EtOAc/hexanes gave desired in 49% yield.

$^1$H NMR (CDCl$_3$, 400 MHz) δ 8.13 (d, J=7.7 Hz, 2H), 7.83 (ddd, J=9.7, 6.8, 3.0 Hz, 2H), 7.57-7.43 (m, 6H), 7.37-7.27 (m, 4H), 6.58 (dd, J=6.6, 2.0 Hz, 1H), 4.77 (s, 1H), 4.68-4.50 (m, 3H), 3.55 (dd, J=12.6, 3.6 Hz, 1H), 3.41 (dd, J=12.7, 6.9 Hz, 1H), 2.23 (s, 1H). MS (ESI): m/z calculated 366.17. found 367.0 (M+1).

Example 177

P7C3-S183: 1-(8-bromo-5H-pyrido[4,3-b]indol-5-yl)-3-phenoxypropan-2-ol

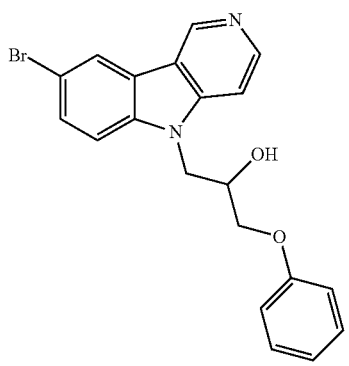 [SMILES: OC(COc1ccccc1)Cn1c2ccncc2c2cc(Br)ccc21]

The title compound was synthesized analogously to P7C3-S160 using phenyl glycidyl ether and the appropriate carboline (Sako, K. et al. *Bioorg. Med. Chem.* 2008, 16, 3780-3790)

$^1$H NMR (CDCl$_3$-MeOD [4:2], 500 MHz) δ 8.98 (s, 1H), 8.25 (d, 1H, J=5.9 Hz), 8.12 (d, 1H, J=1.5 Hz), 7.46 (d, 1H, J=8.6 Hz), 7.40-7.33 (m, 2H), 7.19 (t, 2H, J=7.8 Hz), 6.88 (t, 1H, J=7.3 Hz), 6.81 (d, 2H, J=8.5 Hz), 4.52 (dd, 1H, J=4.9, 14.8 Hz), 4.36 (dd, 1H, J=6.4, 14.8 Hz), 4.30 (m$_c$, 1H), 3.85 (m$_c$, 2H). MS (ESI) m/z 398.8 [M+H]$^+$ ([M+H]$^+$, C$_{20}$H$_{18}$BrN$_2$O$_2$ requires 398.2).

Example 178

P7C3-S184: 1-(3,6-dichloro-9H-carbazol-9-yl)-3-(naphthalen-1-ylamino)propan-2-ol

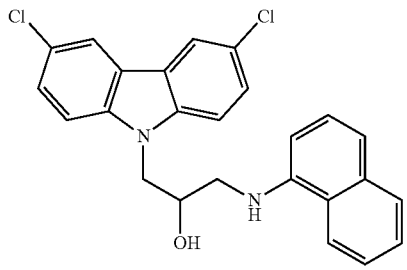 [SMILES: OC(CNc1cccc2ccccc12)Cn1c2ccc(Cl)cc2c2cc(Cl)ccc21]

The title compound was prepared analogously to P7C3-S180. Chromatography with 10% EtOAc/hexanes gave desired in 59% yield.

$^1$H NMR (400 MHz, Acetone-d6) δ 8.22 (d, J=2.0 Hz, 2H), 8.17-7.96 (m, 1H), 7.88-7.73 (m, 1H), 7.68 (d, J=8.8 Hz, 2H), 7.59-7.34 (m, 4H), 7.26 (m, 1H), 7.21 (d, J=8.1 Hz, 1H), 6.61 (d, J=7.4 Hz, 1H), 5.63 (d, J=5.1 Hz, 1H), 4.71 (m, 1H), 4.60 (m, 2H), 3.58 (dm, 3H). MS (ESI), m/z: calculated 434.10. found 434.9 (M−1).

Example 179

P7C3-S186: 1-(6-bromo-9H-pyrido[2,3-b]indol-9-yl)-3-phenoxypropan-2-ol

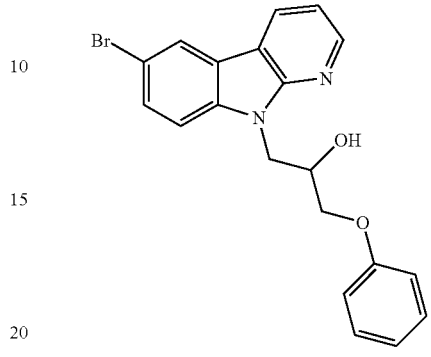

The title compound was synthesized analogously to P7C3-S160 using α-carboline (Sako, K. et al. *Bioorg. Med. Chem.* 2008, 16, 3780-3790) and phenyl glycidyl ether.

$^1$H NMR (CDCl$_3$, 500 MHz) δ 8.46 (d, 1H, J=4.7 Hz), 8.29 (d, 1H, J=7.6 Hz), 8.15 (s, 1H), 7.55 (d, 1H, J=8.7 Hz), 7.42 (d, 1H, J=8.7 Hz), 7.27 (t, 2H, J=7.9 Hz), 7.23 (dd, 1H, J=5.0, 7.5 Hz), 6.96 (t, 1H, J=7.3 Hz), 6.88 (d, 2H, J=8.1 Hz), 4.73 (dd, 1H, J=2.6, 14.9 Hz), 4.66 (dd, 1H, J=5.6, 14.9 Hz), 4.53 (m$_c$, 1H), 4.07 (dd, 1H, J=5.1, 9.1 Hz), 3.86 (dd, 1H, J=7.6, 9.1 Hz). MS (ESI) m/z 397.8 [M+H]$^+$ ([M+H]$^+$, C$_{20}$H$_{18}$BrN$_2$O$_2$ requires 398.2).

Example 180

P7C3-S187: 1-(3,6-dibromo-9H-pyrido[2,3-b]indol-9-yl)-3-phenoxypropan-2-ol

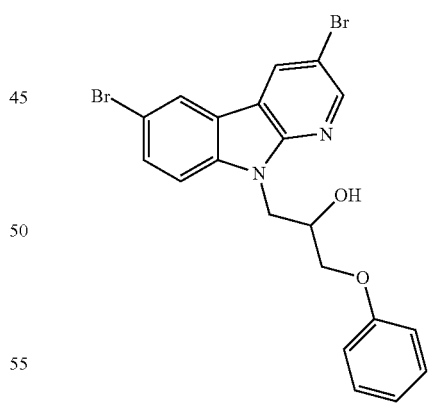

The title compound was synthesized analogously to P7C3-S186, except excess NBS was used in the bromination.

$^1$H NMR (CDCl$_3$-MeOD [4:2], 500 MHz) δ 8.39 (s, 1H), 8.33 (s, 1H), 8.05 (s, 1H), 7.52-7.43 (m, 1H), 7.43-7.32 (m, 1H), 7.18 (t, 2H, J=7.1 Hz), 6.87 (t, 1H, J=7.3 Hz), 6.78 (d, 2H, J=7.9 Hz), 4.60 (dd, 1H, J=4.6, 14.7 Hz), 4.53 (dd, 1H, J=6.0, 14.7 Hz), 4.38 (me, 1H), 3.89 (me, 2H). MS (ESI) m/z 476.7 [M+H]$^+$ ([M+H]$^+$, C$_{20}$H$_{17}$Br$_2$N$_2$O$_2$ requires 477.1).

Example 181

P7C3-S188: 1-(3,6-dibromo-9H-carbazol-9-yl)-3-((6-methoxypyridin-2-yl)amino)propan-2-ol

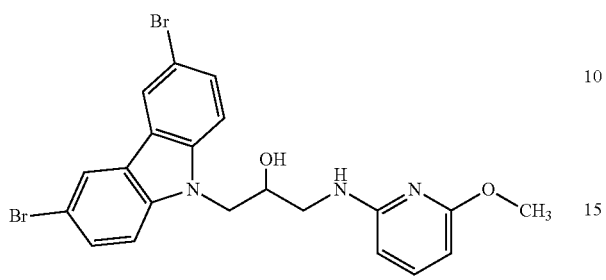

The title compound was prepared analogously to P7C3-S10, also known as P7C3A20.

MS (ESI) m/z: 503.7 [M+H]$^+$, $C_{21}H_{19}Br_2N_3O_2$ requires 503.0.

Example 182

P7C3-S190: 1-(6-bromo-3-methyl-9H-pyrido[3,4-b]indol-9-yl)-3-phenoxypropan-2-ol

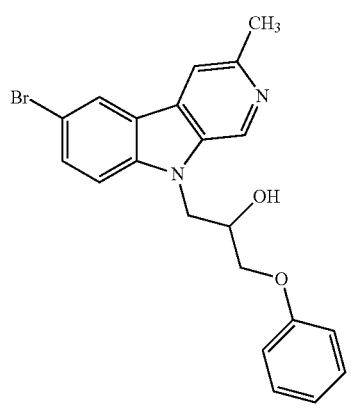

Step 1:
6-bromo-9H-pyrido[3,4-b]indol-3-yl)methanol (P7C3-S204)

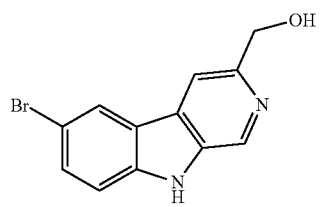 [SMILES: OCc1cc2c(cn1)[nH]c1ccc(Br)cc12]

Ethyl 6-bromo-9H-pyrido[3,4-b]indole-3-carboxylate (141 mg, 0.44 mmol) and lithium borohydride (19 mg, 0.88 mmol) were dissolved in THF (2 ml) and stirred at 60° C. overnight. Upon completion, the reaction was quenched with 1N HCl. The mixture was extracted with $CH_2Cl_2$ (3×), washed with brine, $H_2O$, and dried over $Na_2SO_4$. The material was used in the next step without purification.

$^1$H NMR (500 MHz, DMSO-$d_6$) δ 12.05 (s, 1H), 8.99 (s, 1H), 8.74 (s, 1H), 8.65 (s, 1H), 7.77 (d, J=8.7 Hz, 1H), 7.67 (d, J=8.7 Hz, 1H), 4.90 (s, 2H). ESI m/z: 276.8 ([M+H]$^+$, $C_{12}H_9BrN_2O$ requires 276.99)

Step 2:
6-bromo-9H-pyrido[3,4-b]indole-3-carbaldehyde

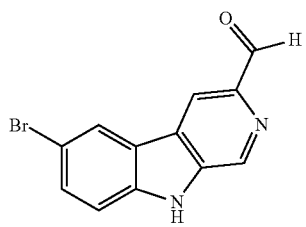 [SMILES: O=Cc1cc2c(cn1)[nH]c1ccc(Br)cc12]

Following a published procedure (*J. Med. Chem.*, 1982, 25, 1081) 6-bromo-9H-pyrido[3,4-b]indol-3-yl)methanol (253 mg, 1.27 mmol) and $MnO_2$ (300 mg, 3.44 mmol) were combined in acetonitrile (5 ml) and stirred at reflux overnight. The material was cooled to room temperature and filtered over a pad of celite. This was rinsed with hot $CH_3CN$ to give the desired aldehyde in 58% yield.

$^1$H NMR (500 MHz, DMSO-$d_6$) δ 12.36 (s, 1H), 10.11 (s, 1H), 9.10 (s, 1H), 8.90 (s, 1H), 8.73 (s, 1H), 7.75 (d, J=8.8 Hz, 1H), 7.67 (d, J=8.6 Hz, 1H). ESI m/z: 274.8 ([M+H]$^+$, $C_{12}H_7BrN_2O$ requires 274.97)

Step 3: 6-bromo-3-methyl-9H-pyrido[3,4-b]indole (P7C3-S226)

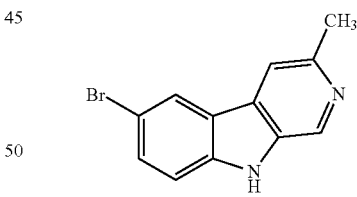

Following a published procedure (*Tetrahedron*, 2002, 5251) 6-bromo-9H-pyrido[3,4-b]indole-3-carbaldehyde (40 mg, 0.145 mmol), hydrazine hydrate (51 mg, 1.02 mmol) and KOH (29 mg, 0.509 mmol) were combined in 0.5 mL of ethylene glycol and heated to 150° C. overnight. The reaction was cooled to room temperature. Ice chips were added and the mixture was stirred in an ice bath for 1 hour. White precipitate formed which was filtered and dried to afford the desired compound in 73% yield.

$^1$H NMR (500 MHz, DMSO-$d_6$) δ 11.59 (s, 1H), 8.77 (s, 1H), 8.42 (s, 1H), 7.97 (s, 1H), 7.61 (d, J=8.4 Hz, 1H), 7.51 (d, J=8.0 Hz, 1H), 2.58 (s, 3H). ESI m/z: 260.8 ([M+H]$^+$, $C_{12}H_9BrN_2$ requires 260.99)

Step 4: P7C3-S190: 1-(6-bromo-3-methyl-9H-pyrido[3,4-b]indol-9-yl)-3-phenoxypropan-2-ol

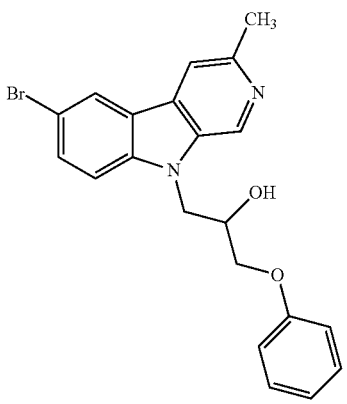 [SMILES: Cc1cc2c3cc(Br)ccc3n(CC(O)COc3ccccc3)c2cn1]

Following Representative Procedure 1, the title compound 1-(6-bromo-3-methyl-9H-pyrido[3,4-b]indol-9-yl)-3-phenoxypropan-2-ol was prepared from 6-bromo-3-methyl-9H-pyrido[3,4-b]indole and phenoxymethyloxirane in 78% yield after a precipitation from isopropanol.

$^1$H NMR (500 MHz, DMSO-$d_6$) δ 8.93 (s, 1H), 8.47 (s, 1H), 8.01 (s, 1H), 7.70-7.61 (m, 2H), 7.30 (t, J=7.7 Hz, 2H), 6.95 (d, J=7.1 Hz, 3H), 5.47 (s, 1H), 4.63 (d, J=15.7 Hz, 1H), 4.51 (dd, J=15.3, 6.7 Hz, 1H), 4.26 (s, 1H), 4.02-3.91 (m, 2H), 2.60 (s, 3H). ESI m/z: 410.8 ([M+H]$^+$, $C_{21}H_{19}BrN_2O_4$ requires 411.06)

Example 183

P7C3-S191: 6-bromo-9-(2-hydroxy-3-phenoxypropyl)-9H-pyrido[3,4-b]indole-3-carboxamide

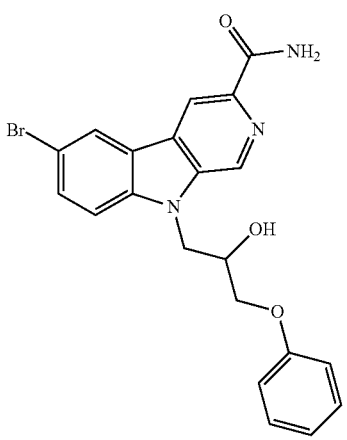 [SMILES: NC(=O)c1cc2c3cc(Br)ccc3n(CC(O)COc3ccccc3)c2cn1]

6-bromo-9-(2-hydroxy-3-phenoxypropyl)-9H-pyrido[3,4-b]indole-3-carboxylic acid (P7C3-S174) (30 mg, 0.068 mmol) was added to 0.5 mL CH$_2$Cl$_2$ with a catalytic amount of DMF. Oxalyl chloride (60 ul, 0.68 mmol) was added and the solution was stirred for 1 hour at room temperature. The reaction was concentrated to remove solvent, and NH$_3$ in dioxane was added. Upon completion of the reaction, the solvent was removed under vacuum to give the desired compound in 92% yield.

$^1$H NMR (500 MHz, DMSO-$d_6$) δ 9.06 (s, 1H), 8.90 (s, 1H), 8.66 (s, 1H), 7.98 (s, 1H), 7.73 (dt, J=8.8, 5.3 Hz, 2H), 7.34 (s, 1H), 7.33-7.25 (m, 2H), 6.96 (d, J=8.5 Hz, 3H), 5.41 (s, 1H), 4.73 (dd, J=15.0, 3.9 Hz, 1H), 4.63 (dd, J=15.0, 7.4 Hz, 1H), 4.31 (s, 1H), 4.03 (d, J=5.4 Hz, 2H). ESI m/z: 439.8 ([M+H]$^+$, $C_{21}H_{18}BrN_3O_3$ requires 440.05)

Example 184

P7C3-S192: 6-bromo-9-(2-hydroxy-3-phenoxypropyl)-9H-pyrido[3,4-b]indole-3-carbonitrile Step 1: 6-bromo-9H-pyrido[3,4-b]indole-3-carbonitrile (P7C3-S221)

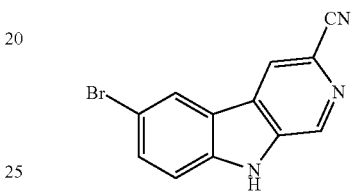

6-bromo-9H-pyrido[3,4-b]indole-3-carbaldehyde (30 mg, 0.11 mmol) was suspended in 100 ul of THF. Ammonium hydroxide (1 mL) and iodine (31 mg, 0.12 mmol) were added and the mixture was stirred at room temperature for 1 hour. Upon completion, Na$_2$S$_2$O$_3$ (5 ml) was added and was extracted 3× with diethyl ether. Material was used in the next step without further purification.

$^1$H NMR (500 MHz, DMSO-$d_6$) δ 12.26 (s, 1H), 9.05 (s, 1H), 8.92 (s, 1H), 8.62 (s, 1H), 7.77 (d, J=8.7 Hz, 1H), 7.68 (d, J=8.7 Hz, 1H). ESI m/z: 271.8 ([M+H]$^+$, $C_{12}H_6BrN_3$ requires 271.97)

Step 2: 6-bromo-9-(2-hydroxy-3-phenoxypropyl)-9H-pyrido[3,4-b]indole-3-carbonitrile (P7C3-S192)

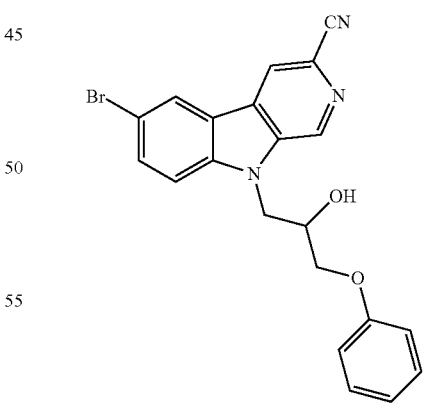

6-bromo-9H-pyrido[3,4-b]indole-3-carbonitrile (21.3 mg, 0.785 mmol) was added to a flask and purged with nitrogen. THF was added and the solution was cooled to −78° C. Methyl lithium (1.6 M in Et$_2$O) (1.1 eq) was added and was stirred for 30 minutes. 1,2-epoxy-3-phenoxypropane (0.011 mL, 0.824 mmol) was added with gradual warming to 45° C. Upon completion the reaction was quenched with 1 N HCl and extracted 3× with EtOAc. The organic layer was washed with H₂O, brine, and dried over Na₂SO₄. The crude mixture was purified on SiO₂ (0 to 50% EtOAc/hexanes to afford the desired product in 90% yield.

¹H NMR (500 MHz, DMSO-d₆) δ 9.24 (s, 1H), 8.94 (s, 1H), 8.66 (s, 1H), 7.86-7.77 (m, 2H), 7.30 (d, J=3.9 Hz, 2H), 6.95 (d, J=3.4 Hz, 3H), 5.50 (s, 1H), 4.77 (d, J=15.1 Hz, 1H), 4.71-4.62 (m, 1H), 4.28 (s, 1H), 4.01 (s, 2H). ESI m/z: 421.8 ([M+H]⁺, C₂₁H₁₈BrN₃O₃ requires 422.04)

Example 185

P7C3-S194: 1-(8-bromo-5H-pyrido[3,2-b]indol-5-yl)-3-phenoxypropan-2-ol

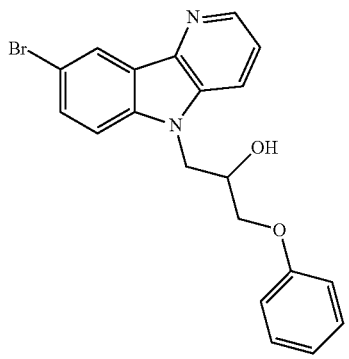 [SMILES: OC(COc1ccccc1)Cn1c2ccc(Br)cc2c2ncccc21]

The title compound was synthesized analogously to e P7C3-S186.

¹H NMR (CDCl₃, 500 MHz) δ 8.57 (d, 1H, J=4.5 Hz), 8.51 (d, 1H, J=1.6 Hz), 7.85 (d, 1H, J=8.3 Hz), 7.59 (dd, 1H, J=1.8, 8.7 Hz), 7.48 (d, 1H, J=8.7 Hz), 7.38-7.31 (m, 1H), 7.31-7.26 (m, 1H), 7.23-7.17 (m, 1H), 7.04 (t, 1H, J=7.3 Hz), 6.94 (d, 2H, J=8.0 Hz), 5.50 (me, 1H), 4.76 (dd, 1H, J=6.5, 15.2 Hz), 4.62 (dd, 1H, J=5.9, 15.2 Hz), 4.07 (dd, 1H, J=4.8, 10.4 Hz), 3.98 (dd, 1H, J=3.5, 10.4 Hz). MS (ESI) m/z 398.8 [M+H]⁺ ([M+H]⁺, C₂₀H₁₈BrN₂O₂ requires 398.2).

Example 186

P7C3-S195: 8-bromo-5-(2-hydroxy-3-phenoxypropyl)-5H-pyrido[4,3-b]indole 2-oxide

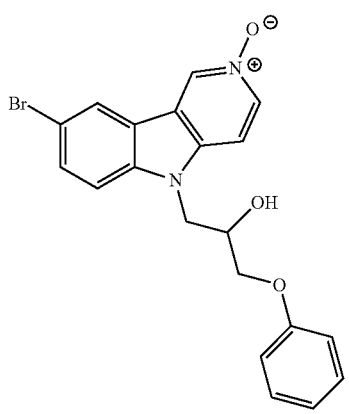 [SMILES: [O-][n+]1ccc2c(c1)c1cc(Br)ccc1n2CC(O)COc1ccccc1]

To a stirred solution of P7C3-S183 (0.029 g, 0.073 mmol) in CHCl₃:EtOH (1:1) (0.072 mL) was added mCPBA (0.057 g, 0.252 mmol). The mixture was stirred under reflux for 30 min. The cooled reaction was treated with 2M NaOH and the mixture stirred for 30 min at room temperature. The aqueous phase was extracted with CH₂Cl₂, the organic layer was dried over Na₂SO₄, filtered and condensed. The crude mixture was purified by chromatography (SiO₂, 0-10% MeOH/CH₂Cl₂) to afford the title compound (0.029 g, 90%).

¹H NMR (CDCl₃-MeOD [4:2], 500 MHz) δ 8.82 (s, 1H), 8.12 (d, 1H, J=1.5 Hz), 8.09 (d, 1H, J=6.9 Hz), 7.55 (dd, 1H, J=1.7, 8.8 Hz), 7.52 (d, 1H, J=7.1 Hz), 7.41 (d, 1H, J=8.8 Hz), 7.26-7.21 (m, 2H), 6.93 (t, 1H, J=7.3 Hz), 6.85 (d, 2H, J=8.1 Hz), 4.57 (dd, 1H, J=3.9, 15.1 Hz), 4.41 (dd, 1H, J=6.7, 15.1 Hz), 4.21 (m_c, 1H), 3.93 (dd, 1H, J=4.3, 9.5 Hz), 3.86 (dd, 1H, J=7.0, 9.5 Hz). MS (ESI) m/z 414.8 [M+H]⁺ ([M+H]⁺, C₂₀H₁₈BrN₂O₃ requires 414.2).

Example 187

P7C3-S198: 8-bromo-5-(2-hydroxy-3-phenoxypropyl)-5H-pyrido[3,2-b]indole 1-oxide

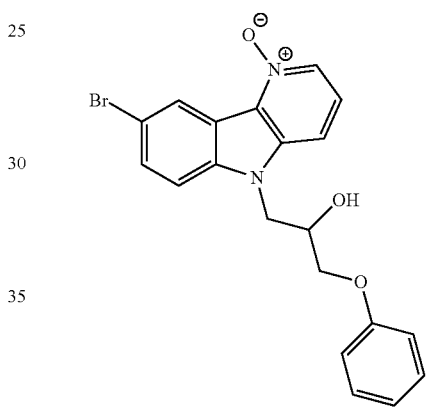

P7C3-S198 was synthesized and isolated in 53% yield analogously to P7C3-S195 except P7C3-S194 was used.

¹H NMR (CDCl₃-MeOD [4:2], 500 MHz) δ 8.68 (s, 1H), 7.99 (s, 1H), 7.57 (m_c, 1H), 7.48 (d, 1H, J=8.7 Hz), 7.35 (d, 1H, J=8.7 Hz), 7.18 (m_c, 1H), 7.14 (t, 2H, J=7.6 Hz), 6.82 (t, 1H, J=7.1 Hz), 6.76 (d, 2H, J=8.4 Hz), 4.51 (dd, 1H, J=3.7, 15.1 Hz), 4.35 (dd, 1H, J=6.5, 15.1 Hz), 4.24 (m_c, 1H), 3.86-3.74 (m, 2H).

MS (ESI) m/z 412.8 [M−H]⁻ ([M−H]⁻, C₂₀H₁₈BrN₂O₃ requires 412.2).

Example 188

P7C3-S204: (6-bromo-9H-pyrido[3,4-b]indol-3-yl)methanol

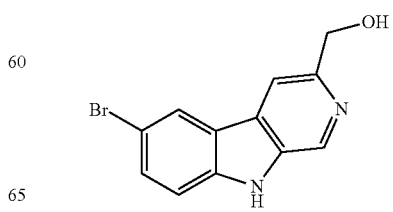

The title compound was an intermediate in the synthesis of P7C3-S190.

Example 189

P7C3-S205: ethyl 6-bromo-9H-pyrido[3,4-b]indole-3-carboxylate

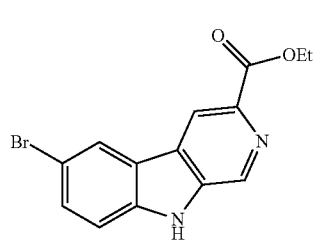 [SMILES: CCOC(=O)c1cc2c(cn1)[nH]c1ccc(Br)cc12]

The title compound was an intermediate in the synthesis of P7C3-S173.

Example 190

P7C3-S208: tert-butyl (3-(3,6-dibromo-9H-carbazol-9-yl)-2-fluoropropyl)carbamate Step 1: 1-azido-3-(3,6-dibromo-9H-carbazol-9-yl)propan-2-ol

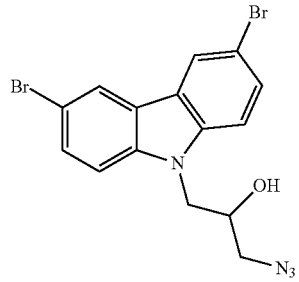 [SMILES: [N-]=[N+]=NCC(O)Cn1c2ccc(Br)cc2c2cc(Br)ccc21]

3,6-dibromo-9-(oxiran-2-ylmethyl)-9H-carbazole (500 mg, 1.3 mmol), NaN$_3$ (111 mg, 1.7 mmol), NH$_4$Cl (91 mg, 1.7 mmol), were combined in 4 ml of EtOH and 1 ml of H$_2$O and heated to 80° C. overnight. Upon completion, the EtOH was evaporated and the mixture was partitioned between EtOAc and H$_2$O. The organic layer was washed with brine and dried over Na$_2$SO$_4$ and concentrated. The material was used in the next step without further purification.

$^1$H NMR (500 MHz, CDCl$_3$) δ 8.14 (s, 1H), 7.57 (d, J=8.7 Hz, 1H), 7.34 (d, J=8.7 Hz, 1H), 4.35 (d, J=5.9 Hz, 1H), 4.25 (dd, J=9.9, 4.9 Hz, 1H), 3.49 (dt, J=12.4, 4.5 Hz, 1H), 3.38-3.30 (m, 1H), 2.15 (s, 1H). ESI m/z: 466.7 ([M+HCOO]$^-$, C$_{12}$H$_7$BrN$_2$O$_2$ requires 424.1)

Step 2: 9-(3-azido-2-fluoropropyl)-3,6-dibromo-9H-carbazole

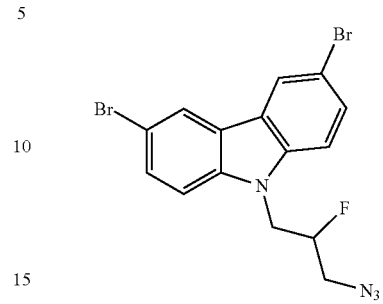

Synthesized according to representative procedure 4, except 1-azido-3-(3,6-dibromo-9H-carbazol-9-yl)propan-2-ol was used.

$^1$H NMR (500 MHz, CDCl$_3$) δ 8.15 (s, 2H), 7.59 (d, J=8.7 Hz, 2H), 7.33 (d, J=8.7 Hz, 2H), 5.08-4.90 (m, 1H), 4.55 (dt, J=9.5, 5.1 Hz, 2H), 3.62-3.52 (m, 1H), 3.39 (ddd, J=24.1, 13.7, 4.7 Hz, 1H). ESI m/z: 469.6 ([M+HCOO]$^-$, C$_{20}$H$_{11}$Br$_2$FN$_4$ requires 423.94)

Step 3: 3-(3,6-dibromo-9H-carbazol-9-yl)-2-fluoropropan-1-amine

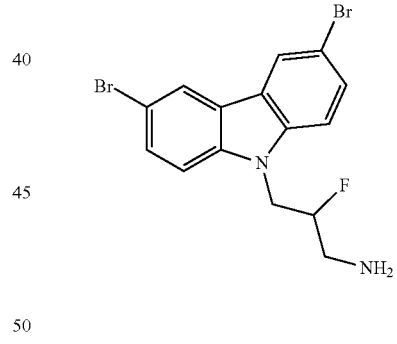

9-(3-azido-2-fluoropropyl)-3,6-dibromo-9H-carbazole (60 mg, 0.14 mmol) and triphenylphosphine (44 mg, 0.168 mmol) were combined in 0.5 mL of THF and stirred overnight at 60° C. Upon completion 1 ml of H$_2$O was added and the mixture was stirred for 1 hour. The mixture was extracted with EtOAc. The organic layer was washed with H$_2$O, brine, and dried over Na$_2$SO$_4$ and concentrated to a white foam. This material was used in the next step without further purification.

$^1$H NMR (500 MHz, MeOH-d$_4$) δ 8.29 (s, 1H), 7.60 (d, J=8.7 Hz, 1H), 7.53 (s, 1H), 5.16 (d, J=50.4 Hz, 1H), 4.73 (dd, J=23.1, 5.3 Hz, 1H), 3.43 (d, J=14.2 Hz, 1H), 3.24-3.11 (m, 1H). ESI m/z: 398.7 ([M+H]$^+$, C$_{15}$H$_{13}$Br$_2$FN$_2$ requires 398.94)

251

Step 4: P7C3-S208: tert-butyl (3-(3,6-dibromo-9H-carbazol-9-yl)-2-fluoropropyl)carbamate

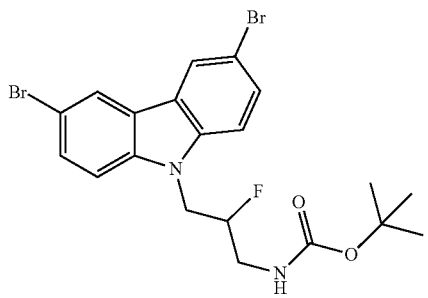 [SMILES: CC(C)(C)OC(=O)NCC(F)Cn1c2ccc(Br)cc2c2cc(Br)ccc21]

3-(3,6-dibromo-9H-carbazol-9-yl)-2-fluoropropan-1-amine (21 mg 0.0524 mmol) was dissolved in 500 ul of THF and cooled to 0° C. Boc anhydride (12.6 mg, 0.0576 mmol) was dissolved in THF and added dropwise. The reaction was stirred overnight at room temperature. Upon completion the material was concentrated to remove excess THF and partitioned between EtOAc and H$_2$O. The organic layer was washed with brine and dried over Na$_2$SO$_4$. The crude mixture was purified on SiO$_2$ (0 to 50% EtOAc/hexanes to afford the desired product in 42% yield.

$^1$H NMR (500 MHz, CDCl$_3$) δ 8.15 (s, 2H), 7.57 (d, J=8.7 Hz, 2H), 7.30 (d, J=8.7 Hz, 2H), 4.94 (d, J=57.3 Hz, 2H), 4.59-4.39 (m, 2H), 3.68-3.52 (m, 1H), 3.30 (ddd, J=21.4, 13.4, 6.2 Hz, 1H), 1.46 (s, 9H). ESI m/z: 498.8 ([M+H]$^+$, C$_{20}$H$_{21}$Br$_2$FN$_2$O$_2$ requires 499.0)

Example 191

P7C3-S213: 2-(3,6-dibromo-9H-carbazol-9-yl)acetamide

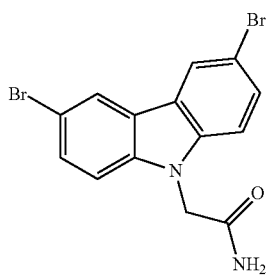 [SMILES: NC(=O)Cn1c2ccc(Br)cc2c2cc(Br)ccc21]

Ethyl 2-(3,6-dibromo-9H-carbazol-9-yl)acetate (P7C3-S164) (10 mg, 0.024 mmol) and ammonium hydroxide (100 ul) were stirred at 60° C. overnight. Upon completion the reaction was filtered and rinsed with H$_2$O to give the desired product in quantitative yield.

$^1$H NMR (500 MHz, Acetone-d$_6$) δ 8.40 (d, J=1.9 Hz, 2H), 7.61 (dd, J=8.7, 1.9 Hz, 2H), 7.54 (d, J=8.7 Hz, 2H), 7.07 (s, 1H), 6.64 (s, 1H), 5.08 (s, 2H). ESI m/z: 424.7 ([M+HCOO]$^-$, C$_{14}$H$_{10}$Br$_2$FN$_2$O requires 378.92)

252

Example 192

P7C3-S214: 2-(3,6-dibromo-9H-carbazol-9-yl)-N-methylacetamide

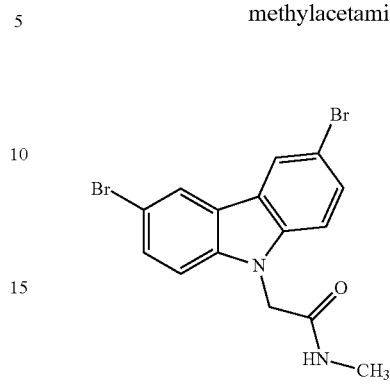

2-(3,6-dibromo-9H-carbazol-9-yl)acetic acid (P7C3-S165) (50 mg, 0.13 mmol) was suspended in 1 ml of dichloromethane. Methylamine (2.0 M in THF) (0.144 mmol) was added followed by a catalytic amount of dimethylamino pyridine. The mixture was cooled to 0° C. in an ice bath and a solution of dicyclohexyl carbodiimide in 1 ml of dichloromethane was added dropwise. The mixture was stirred overnight at room temperature. Upon completion, the DCM mixture was washed with H$_2$O, brine, dried over Na$_2$SO$_4$, and concentrated. The crude mixture was purified on SiO$_2$ (0 to 50% EtOAc/hexanes) followed by a precipitation from MeOH/H$_2$O to afford the desired product in 42% yield.

$^1$H NMR (500 MHz, CDCl$_3$) δ 8.19 (s, 2H), 7.61 (d, J=8.6 Hz, 2H), 7.23 (s, 2H), 5.37 (s, 1H), 4.89 (s, 2H), 2.72 (d, J=4.9 Hz, 3H). ESI m/z: 439.7 ([M+HCOO]$^-$, C$_{15}$H$_{12}$Br$_2$N$_2$O requires 392.93)

Example 193

P7C3-S215: 2-(3,6-dibromo-9H-carbazol-9-yl)-N,N-dimethylacetamide

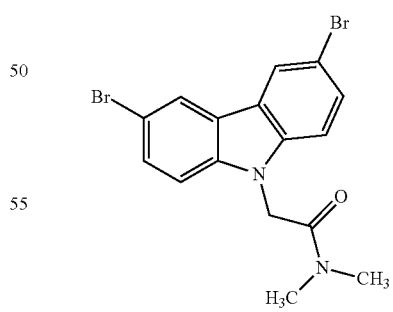

Synthesized analogously to P7C3-S214, except dimethylamine was used.

$^1$H NMR (500 MHz, CDCl$_3$) δ 8.15 (s, 2H), 7.54 (d, J=8.7 Hz, 2H), 7.19 (d, J=8.7 Hz, 2H), 5.01 (s, 2H), 3.09 (s, 3H), 2.99 (s, 3H). ESI m/z: 452.6 ([M+HCOO]$^-$, C$_{16}$H$_{14}$Br$_2$N$_2$O requires 406.95)

Example 194

P7C3-S217: 3-(3,6-dibromo-9H-carbazol-9-yl)-2-fluoropropan-1-amine hydrochloride

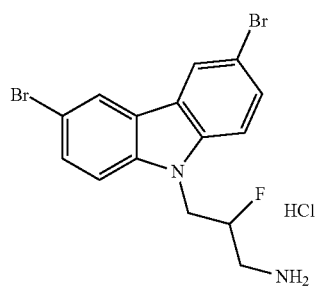 [SMILES: NCC(F)Cn1c2ccc(Br)cc2c2cc(Br)ccc21 ; Cl]

The free base of P7C3-S217 was an intermediate in the synthesis of P7C3-S208. The HCl salt was formed by adding 1M HCl to a solution of the free base in CH$_2$Cl$_2$ at 0° C. A white solid was collected by filtration and washed with cold CH$_2$Cl$_2$.

Example 195

P7C3-S218: N-(3 (3,6-dibromo-9H-carbazol-9-yl)-2-fluoropropyl)acetamide

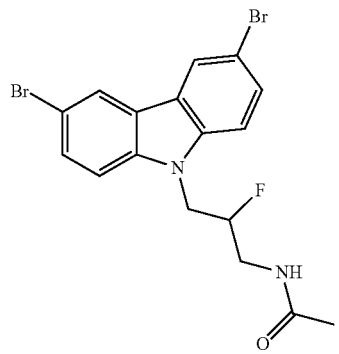 [SMILES: CC(=O)NCC(F)Cn1c2ccc(Br)cc2c2cc(Br)ccc21]

3-(3,6-dibromo-9H-carbazol-9-yl)-2-fluoropropan-1-amine hydrochloride (P7C3-S217) (25 mg, 0.057 mmol) was dissolved in dichloromethane (2 mL) with triethylamine (12 mg, 0.12 mmol). The solution was cooled to 0° C. and acetyl chloride (4.49 mg, 0.057 mmol) was added. Desired product precipitated out of solution and within 10 minutes the reaction had gone to completion. The precipitate was filtered, rinsed with H$_2$O, and dried under vacuum.

$^1$H NMR (500 MHz, CDCl$_3$) δ 8.15 (d, J=1.7 Hz, 2H), 7.57 (dd, J=8.7, 1.8 Hz, 2H), 7.30 (d, J=8.7 Hz, 2H), 5.75 (s, 1H), 4.98 (dddd, J=13.1, 9.5, 6.6, 2.6 Hz, 1H), 4.58-4.41 (m, 2H), 3.83 (dddd, J=29.0, 14.6, 6.9, 2.6 Hz, 1H), 3.36-3.23 (m, 1H), 2.03 (s, 3H). ESI m/z: 440.7 ([M+H]$^+$, C$_{17}$H$_{15}$Br$_2$FN$_2$O requires 440.95)

Example 196

P7C3-S219: N-(5-(3-((3-(3,6-dibromo-9H-carbazol-9-yl)-2-hydroxypropyl)amino)phenoxy)pentyl)-5-(2-oxohexahydro-1H-thieno[3,4-d]imidazol-4-yl)pentanamide

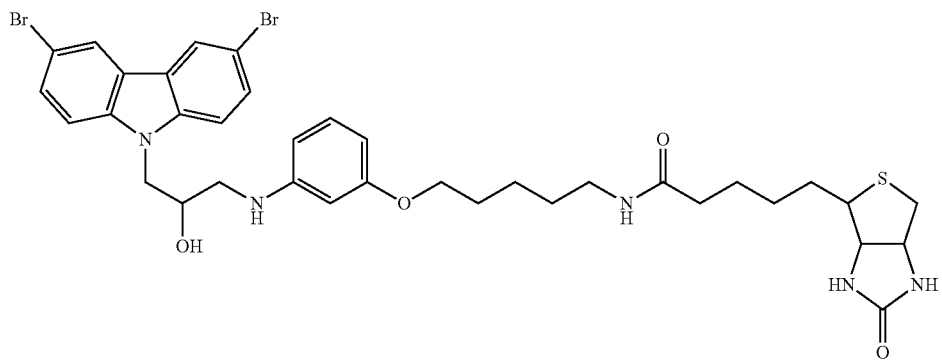 [SMILES: O=C(CCCCC1SCC2NC(=O)NC21)NCCCCCOc1cccc(NCC(O)Cn2c3ccc(Br)cc3c3cc(Br)ccc32)c1]

The title compound was synthesized analogously to P7C3-S100 using biotin N-succinimidyl ester. The mixture was chromatographed in 5-10% MeOH/CH$_2$Cl$_2$. Isolated yield=37%.

MS (ESI), m/z: calculated 799.1, found 799.7 (M+1)$^+$.

Example 197

P7C3-S220: 2-(3,6-dibromo-9H-carbazol-9-yl)propanamide

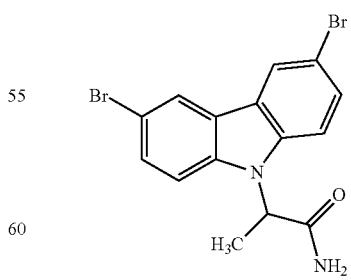

The title compound was prepared analogously to P7C3-S213.

$^1$H NMR (500 MHz, CDCl$_3$) δ 8.18 (s, 2H), 7.58 (d, J=8.7 Hz, 2H), 7.30 (d, J=8.7 Hz, 2H), 5.58 (s, 1H), 5.42 (s, 1H), 5.27 (q, J=7.1 Hz, 1H), 1.74 (d, J=7.1 Hz, 3H). ESI m/z: 394.7 ([M+H]⁺, $C_{15}H_{12}Br_2N_2O$ requires 394.93)

Example 198

P7C3-S221: 6-bromo-9H-pyrido[3,4-b]indole-3-carbonitrile

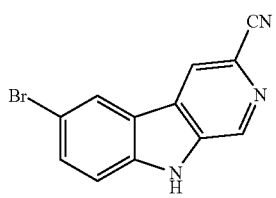 [SMILES: N#Cc1cc2c(cn1)[nH]c1ccc(Br)cc12]

The title compound was an intermediate in the synthesis of P7C3-S192.

Example 199

P7C3-S226: 6-bromo-3-methyl-9H-pyrido[3,4-b]indole

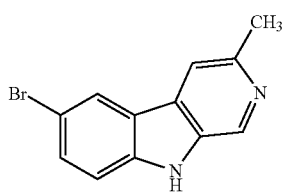

The title compound was an intermediate in the synthesis of P7C3-S190.

Example 200

P7C3-S233: 9-((1H-tetrazol-5-yl)methyl)-3,6-dibromo-9H-carbazole

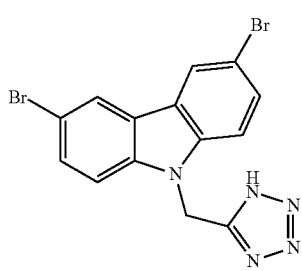 [SMILES: Brc1ccc2c(c1)c1cc(Br)ccc1n2Cc1nnn[nH]1]

Following a published procedure (J.O.C., 1993, 4139-4141), a solution of 2-(3,6-dibromo-9H-carbazol-9-yl)acetonitrile (P7C3-S235) (75 mg, 0.123 mmol) and azidotrimethylsilane (32 ul, 0.24 mmol) in toluene (500 uL) was added to dibutyltin oxide (3 mg, 0.012 mmol) and heated to reflux overnight. The reaction was cooled to room temperature, concentrated to remove toluene, and partitioned between EtOAc and 10% $NaHCO_{3(aq)}$. The aqueous layers were combined and acidified to pH 2 and extracted with EtOAc (2×).

The organic layers were combined and washed with brine, dried over $Na_2SO_4$ and concentrated. The crude material was purified on $SiO_2$ (0-50% EtOAc/hexanes.)
¹H NMR (500 MHz, Acetone-d₆) δ 8.43 (s, 2H), 7.69 (d, J=8.7 Hz, 2H), 7.64 (d, J=8.6 Hz, 2H), 6.11 (s, 2H). ESI m/z: 403.5 ([M−H]⁺, $C_{14}H_9Br_2N_5$ requires 403.92)

Example 201

P7C3-S234: methyl (2-(3,6-dibromo-9H-carbazol-9-yl)acetyl)carbamate

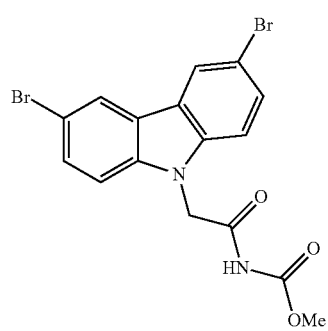 [SMILES: COC(=O)NC(=O)Cn1c2ccc(Br)cc2c2cc(Br)ccc21]

Following a published procedure (PCT Int. App: 2011054851), 2-(3,6-dibromo-9H-carbazol-9-yl)acetamide (P7C3-S213) (50 mg, 0.13 mmol) was dissolved in 1 ml of THF and cooled to 0° C. Methylchloroformate (12 uL, 0.157 mmol) was added followed slow addition of LiOᵗBu (25 mg, 0.31 mmol) in 1 ml of THF. Upon completion, the mixture was partitioned between 2 N HCl and EtOAc. Upon adding EtOAc, a precipitate formed which was filtered, rinsed with $H_2O$ and hexanes and dried under reduced pressure.
¹H NMR (500 MHz, THF-d8) δ 12.71 (s, 1H), 10.14 (s, 2H), 9.36 (d, J=8.7 Hz, 2H), 9.22 (d, J=8.7 Hz, 2H), 7.45 (s, 2H), 5.66 (s, 3H). ESI m/z: 436.6 ([M−H]⁺, $C_{16}H_{12}Br_2N_2O_3$ requires 436.92)

Example 202

P7C3-S241: N-(3-(3,6-dibromo-9H-carbazol-9-yl)-2-fluoropropyl)-1,1,1-trifluoro-N-(3-methoxyphenyl)methanesulfonamide

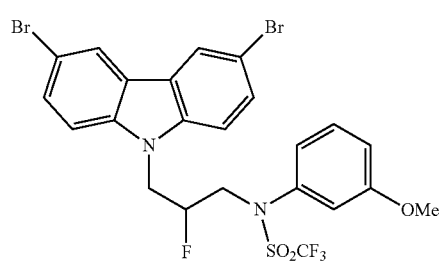

Following General Procedure 4, P7C3-S244 was fluorinated to give the title compound.
¹H NMR (400 MHz, CDCl₃) δ 8.15 (d, J=1.9 Hz, 2H), 7.56 (dd, J=8.7, 1.9 Hz, 2H), 7.32 (t, J=8.2 Hz, 1H), 7.21 (d, J=8.6 Hz, 2H), 6.99-6.90 (m, 2H), 6.86 (m, 1H), 5.08-4.86 (dm, 1H), 4.57-4.44 (m, 2H), 4.09 (m, 2H), 3.79 (s, 3H). MS (ESI), m/z: calculated 635.93, found 680.6 (M+HCOO⁻)⁻.

Example 203

P7C3-S243: N-(3-(3,6-dibromo-9H-carbazol-9-yl)-2-fluoropropyl)-6-methoxypyridin-2-amine

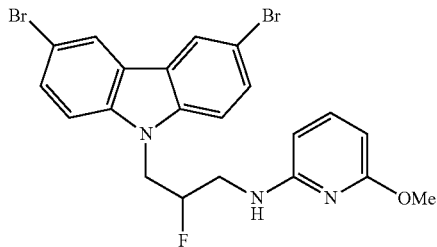 [SMILES: COc1cccc(NCC(F)Cn2c3ccc(Br)cc3c3cc(Br)ccc32)n1]

2-(Dicyclohexylphosphino)-3,6-dimethoxy-2'-4'-6'-tri-i-propyl-1,1'-biphenyl (BrettPhos, 35.6 mg, 0.066 mmol) and chloro[2-(dicyclohexylphosphino)-3,6-dimethoxy-2'-4'-6'-tri-i-propyl-1,1'-biphenyl][2-(2-aminoethyl)phenyl]palladium(II) (52.8 mg, 0.066 mmol) were charged to a vial containing the free amine of P7C3-S217 (116.8 mg, 0.29 mmol). The vial was purged with nitrogen for ten minutes before addition of 1,4-dioxane (4.75 ml) followed by the addition of lithium bis(trimethylsilyl)amide solution (1.0 M solution in THF, 610 μl). The reaction was heated at 100° C. for 5.5 hours. The mixture was cooled and centrifuged to separate out solids. The filtrate was loaded directly onto a silica gel column and purified in 80% DCM/hexanes (+0.1% TEA). The purest fractions (80-90% pure) were treated with DCM/hexanes and the solid pellet contained the purified product.

$^1$H NMR (CDCl$_3$, 400 MHz) δ 8.16 (d, J=1.9 Hz, 2H), 7.56 (d, J=1.9 Hz, 2H), 7.35-(t, J=7.8 Hz, 1H), 7.30 (d, J=8.7 Hz, 1H), 6.04 (dd, J=32.7, 8.0 Hz, 2H), 5.29-5.02 (dm, 1H), 4.65-4.46 (m, 3H), 3.87-3.74 (m, 1H), 3.70 (s, 3H), 3.66-3.49 (m, 1H). MS (ESI), m/z: calculated 504.98, found 506.7 (M+1).

Example 204

P7C3-S244: N-(3-(3,6-dibromo-9H-carbazol-9-yl)-2-hydroxypropyl)-1,1,1-trifluoro-N-(3-methoxyphenyl)methanesulfonamide Step 1: 1,1,1-trifluoro-N-(3-methoxyphenyl)methane sulfonamide

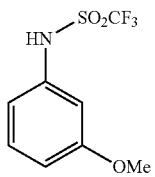

A solution of trifluoromethanesulfonic anhydride (45 ml, 26.7 mmol) in methylene chloride (250 ml) was added dropwise to an ice chilled solution of m-anisidine (25 ml, 22.3 mmol) and triethylamine (39 ml, 28.0 mmol) in methylene chloride (1.25 L). The reaction was stirred overnight at ambient temperature. Workup was performed portionwise. Each of the two portions was basified by addition of 250 ml of 2.5 N NaOH solution and 625 ml MeOH. The aqueous was extracted thrice (100 ml each) with methylene chloride. The combined aqueous phases was acidified to pH 2 with 18% HCl and again extracted with methylene chloride three times. The organic layer is dried over MgSO$_4$, filtered and condensed to give 17.69 g of brown solid in 77% yield.

$^1$H NMR (CDCl$_3$, 400 MHz) δ7.48-7.13 (m, 1H), 6.97-6.61 (m, 3H), 3.82 (s, 3H). MS (ESI), m/z: calculated 255.21, found 255.9 (M+1)$^+$.

Step 2: N-(3-(3,6-dibromo-9H-carbazol-9-yl)-2-hydroxypropyl)-1,1,1-trifluoro-N-(3-methoxyphenyl)methanesulfonamide (P7C3-S244)

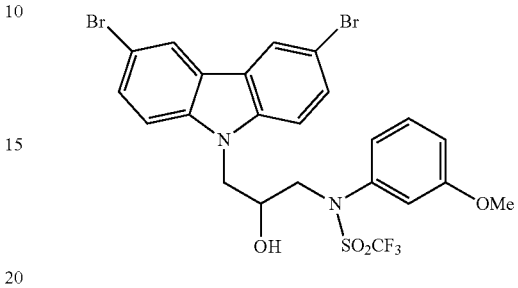

N-butyllithium (2.5 M in hexanes, 48 ml) was added dropwise to an ice-cooled solution of 1,1,1-trifluoro-N-(3-methoxyphenyl)methanesulfonamide (22.07 g, 86.5 mmol) in dry dioxane (145 ml) over a 40 minute period. The solution was then stirred at ambient temperature for 15 minutes before addition of 3,6-dibromo-9-(oxiran-2-ylmethyl)-9H-carbazole (25.05 g, 65.7 mmol) followed by heating at 90° C. for an hour. The reaction was cooled then diluted with 1.2 L ethyl acetate and washed several times with water and finally brine. The organic layer was dried over MgSO$_4$, filtered and condensed to give an orange viscous mixture. The residue was dissolved in 150 ml of 60% methylene chloride/hexanes, then concentrated to yellow foam to which a further 150 ml of 60% methylene chloride/hexanes was added and stirred overnight. The mixture was filtered and washed several times with 60% methylene chloride/hexanes until the solid was white giving 20.1 g of 99%

$^1$H NMR (CDCl$_3$, 400 MHz) δ 8.13 (d, J=1.9 Hz, 2H), 7.54 (dd, J=8.7, 1.9 Hz, 2H), 7.33 (t, J=8.1 Hz, 1H), 7.22 (d, J=8.7 Hz, 2H), 6.95 (dd, J=8.4, 2.3 Hz, 2H), 6.88 (s, 1H), 4.56-4.10 (m, 4H), 3.99 (m, 1H), 3.81 (s, 3H), 1.98 (d, J=4.2 Hz, 1H). MS (ESI), m/z: calculated 633.94, found 678.6 (M+HCOO)$^-$.

Example 205

P7C3-S255: 1-(3,6-dibromo-9H-carbazol-9-yl)-3-((4-methoxybenzyl)(3-methoxyphenyl)amino)propan-2-ol

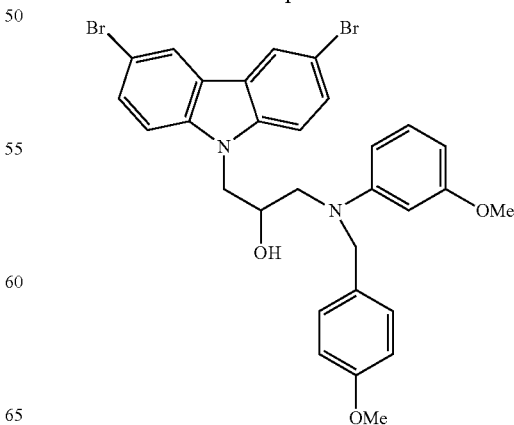

P7C3-S255 was synthesized analogously to P7C3-S244 using representative procedure 3 and 3-methoxy-N-(4-methoxybenzyl)aniline. Yield=31%

$^1$H NMR (CDCl$_3$, 400 MHz) δ 8.07 (d, J=2.0 Hz, 2H), 7.50 (dd, J=8.7, 2.0 Hz, 2H), 7.19 (d, J=8.7 Hz, 2H), 7.12-7.04 (m, 3H), 6.81 (d, J=8.6 Hz, 2H), 6.36 (ddd, J=12.7, 8.1, 2.4 Hz, 2H), 6.28 (t, J=2.4 Hz, 1H), 4.48 (d, J=2.7 Hz, 2H), 4.35-4.27 (m, 1H), 4.28-4.10 (m, 2H), 3.78 (s, 3H), 3.65 (s, 3H), 3.54-3.34 (m, 2H), 2.22 (s, 1H). MS (ESI), m/z: calculated 622.05, found 666.7 (M+HCOO)$^-$.

Example 206

P7C3-S261: N-(3-(3,6-dibromo-9H-carbazol-9-yl)-2-hydroxypropyl)-2,2,2-trifluoroacetamide

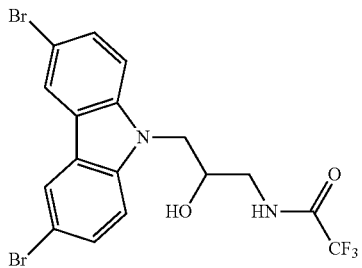 [SMILES: O=C(NCC(O)Cn1c2ccc(Br)cc2c2cc(Br)ccc21)C(F)(F)F]

TFAA (78 μL, 0.5526 mmol) was added to a solution of 1-amino-3-(3,6-dibromo-9H-carbazol-9-yl)propan-2-ol (100 mg, 0.2518 mmol) and pyridine (61 μL, 0.7536 mmol) in 1.7 mL DCM. After thirty minutes, TLC showed complete consumption of starting material. The reaction mixture was separated using NaHCO$_3$. The aqueous layer was washed with DCM. The combined organic layers were dried and concentrated to give crude material as a tan solid. Crude material was dissolved in hot CHCl$_3$ and triturated with hexanes. 50.6 mg (40.8% yield) of clean product was collected by vacuum filtration.

$^1$H NMR (500 MHz, CDCl$_3$) δ 8.16 (d, J=1.7 Hz, 2H), 7.59 (dd, J=8.7, 1.8 Hz, 2H), 7.31 (d, J=8.7 Hz, 2H), 6.71 (s, 1H), 4.41-4.28 (m, 2H), 3.79 (dd, J=13.1, 6.7 Hz, 1H), 3.49 (s, 1H), 3.46-3.39 (m, 1H). MS (ESI) m/z=492.6 ([M+H]$^+$, C17H13Br2F3N2O2 requires 491.93)

Example 207

P7C3-S263: tert-butyl (3-(3,6-dibromo-9H-carbazol-9-yl)-2-hydroxypropyl)carbamate

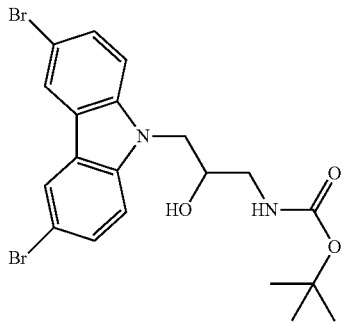 [SMILES: CC(C)(C)OC(=O)NCC(O)Cn1c2ccc(Br)cc2c2cc(Br)ccc21]

Boc anhydride (82.4 mg, 0.3777 mmol) was added to a solution of 1-amino-3-(3,6-dibromo-9H-carbazol-9-yl)propan-2-ol (100 mg, 0.2518 mmol) and triethylamine (70 μL, 0.5036 mmol) in 1.7 mL DCM. The reaction stirred overnight at room temperature. The reaction mixture was separated with brine and the aqueous layer washed twice with DCM. The combined organic layers were dried and concentrated to afford crude material as an off-white solid. This was subjected to column chromatography using DCM/MeOH to afford 4.6 mg (3.7% yield) product as a white solid.

$^1$H NMR (500 MHz, CDCl$_3$) δ 8.14 (d, J=1.9 Hz, 3H), 7.56 (dd, J=8.6, 1.9 Hz, 3H), 7.34 (d, J=8.7 Hz, 3H), 4.86 (s, 1H), 4.31 (d, J=6.2 Hz, 3H), 3.40-3.25 (m, 1H), 3.09-2.97 (m, 1H), 1.45 (s, 13H), 3.25-3.09 (m, 2H). MS (ESI) m/z=440.7 ([M-Boc]$^+$, C20H22Br2N2O3 requires 496.00

Example 208

P7C3-S271: 5-(2-hydroxy-3-phenoxypropyl)-5H-pyrimido[5,4-b]indole-2-carboxylic acid

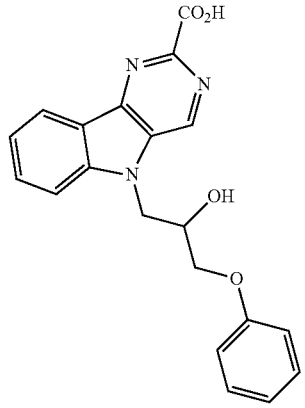 [SMILES: O=C(O)c1ncc2c(n1)c1ccccc1n2CC(O)COc1ccccc1]

Following Representative Procedure 7, the title compound was synthesized from P7C3-S262 (0.028 g, 0.117 mmol) and 2-(phenoxymethyl)oxirane (24 μL, 0.175 mmol) (0.030 g, 70%).

$^1$H NMR (CDCl$_3$-MeOD [4:2], 500 MHz) δ 9.02 (s, 1H), 8.35 (d, 1H, J=7.9 Hz), 7.49 (d, 2H, J=3.7 Hz), 7.22 (dt, 1H, J=4.0, 7.9 Hz), 7.08 (t, 2H, J=8.0 Hz), 6.77 (t, 1H, J=7.4 Hz), 6.72 (d, 2H, J=8.0 Hz), 4.59 (dd, 1H, J=4.4, 15.1 Hz), 4.45 (dd, 1H, J=6.5, 15.1 Hz), 4.25 (me, 1H), 3.81 (dd, 1H, J=4.4, 9.5 Hz), 3.76 (dd, 1H, J=6.5, 9.5 Hz). MS (ESI) m/z 363.9 [M+H]$^+$ ([M+H]$^+$, C$_{20}$H$_{18}$N$_3$O$_4$ requires 364.4).

Example 209

P7C3-S273: N-(3-(3,6-dibromo-9H-carbazol-9-yl)-2-hydroxypropyl)acetamide

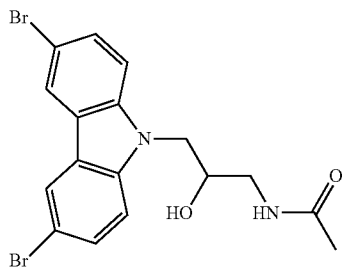 [SMILES: CC(=O)NCC(O)Cn1c2ccc(Br)cc2c2cc(Br)ccc21]

A solution of acetic anhydride (29 μL, 0.3022 mmol) in 0.7 mL DCM was added to a solution of 1-amino-3-(3,6-dibromo-9H-carbazol-9-yl)propan-2-ol (100 mg, 0.2518 mmol) and triethylamine (42 μL, 0.3022 mmol) in 1 mL DCM at 0° C. After stirring overnight, the reaction mixture was diluted with DCM, then washed with 18% HCl, brine, and NaHCO3. The organic layer was dried and concentrated to give crude material as a pink-tinted solid. Preparatory TLC using 5% MeOH/DCM as the eluent resulted in 6.5 mg (5.9% yield) product as a white solid.

¹H NMR (500 MHz, CDCl₃) δ 8.15 (d, J=2.5 Hz, 2H), 7.59-7.54 (m, 2H), 7.34 (dd, J=8.9, 4.2 Hz, 2H), 5.77 (s, 1H), 4.31 (q, J=5.5, 4.3 Hz, 2H), 4.26 (s, 2H), 3.57 (d, J=3.8 Hz, 1H), 3.46-3.26 (m, 3H), 2.01 (d, J=4.3 Hz, 3H). MS (ESI) m/z=438.7 ([M+H]⁺, C17H16Br2N2O2 requires 437.96

Example 210

P7C3-S274: ethyl (3-(3,6-dibromo-9H-carbazol-9-yl)-2-hydroxypropyl)carbamate

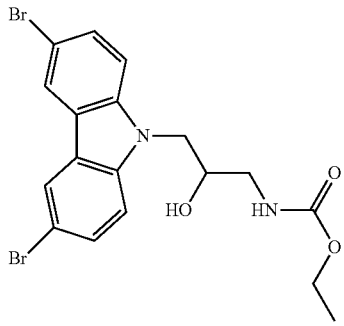 [SMILES: CCOC(=O)NCC(O)Cn1c2ccc(Br)cc2c2cc(Br)ccc21]

The title compound was prepared analogously to P7C3-S218. The crude material was chromatographed using 5% MeOH/DCM as the eluent. 24.5 mg (20.7% yield) product was obtained as a white solid.

¹H NMR (500 MHz, CDCl₃) δ 8.15 (s, 2H), 7.56 (d, J=8.6 Hz, 2H), 7.33 (dd, J=8.6, 1.6 Hz, 2H), 4.98 (s, 1H), 4.31 (d, 2H), 4.26 (s, 1H), 4.14 (q, J=7.2 Hz, 2H), 3.45-3.36 (m, 1H), 3.29-3.17 (m, 1H), 3.01 (s, 1H), 1.26 (t, J=7.9, 3.7 Hz, 3H). MS (ESI) m/z=468.7 ([M+H]⁺, C18H18Br2N2O3 requires 467.97

Example 211

P7C3-S278: 6-bromo-9-(3-(4-bromophenoxy)-2-hydroxypropyl)-9H-carbazole-3-carbonitrile Step 1: 9H-carbazole-3-carbonitrile

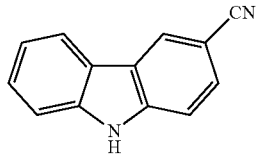 [SMILES: N#Cc1ccc2[nH]c3ccccc3c2c1]

To a solution of 3-bromo-9H-carbazole (4.00 g, 16.3 mmol, 1 equiv) in N-Methyl-2-pyrrolidinone (40 mL) was added copper(I) cyanide (1.6012 g, 17.9 mmol, 1.1 equiv). The mixture was sealed and heated at 200° C. until TLC showed no starting material. The reaction solution was cooled and 60 mL of water was added. The off-white precipitate was filtered off and washed with EtOAc (3×20 mL). This filtrate was extracted with ethyl acetate (3×20 mL). The combined organic layers were washed with water (20 mL) and brine (20 mL), and then dried over Na₂SO₄. The solvent was removed under reduced pressure to afford red-brown oil. Methanol was added to the crude oil to afford 0.8251 g off-white precipitate as pure product. The mother liquid from the methanol precipitation was concentrated and purified by chromatography (25% EtOAc/Hex) to provide 0.28 g off-white solid. The combined yield was 35.5%.

¹H NMR (CD₃OD, 400 MHz) δppm 7.26 (ddd, J=8.0, 6.9, 1.3 Hz, 1H) 7.54-7.45 (m, 2H) 7.57 (dd, J=8.4, 0.6 Hz, 1H) 7.67 (dd, J=8.5, 1.6 Hz, 1H) 8.18-8.12 (m, 1H) 8.49 (dd, J=1.5, 0.6 Hz, 1H). MS (ESI) m/z=192.9 ([M+H]⁺), C13H8N2 requires 192.07

Step 2: 9-(2-hydroxy-3-phenoxypropyl)-9H-carbazole-3-carbonitrile

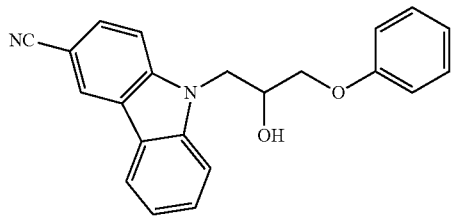 [SMILES: N#Cc1ccc2c(c1)c1ccccc1n2CC(O)COc1ccccc1]

To a solution of 3-cyano-9H-carbazole (0.4998 g, 2.6 mmol, 1 equiv) in THF (40 mL) was added "BuLi (1.6 M in hexane, 3.25 mL, 5.2 mmol, 2 equiv). The mixture was stirred at −78° C. for 2 hours. 1,2-epoxy-3-phenoxypropane (0.7809 g, 5.2 mmol, 2 equiv) was added and the mixture was stirred at 45° C. overnight. Water (50 mL) was added and the mixture was extracted by dichloromethane (3×30 mL). The combined dichloromethane layers were washed by brine (2×30 mL) and then dried over Na₂SO₄. The solvent was removed under reduced pressure, and the product was chromatographed on silica gel with dichloromethane to yield 0.7736 g white foamed solid (86%).

¹H NMR (CD₃OD, 400 MHz) δppm 3.95 (dd, J=9.8, 4.6 Hz, 1H) 4.02 (dd, J=9.8, 5.4 Hz, 1H) 4.46-4.35 (m, 1H) 4.57 (dd, J=15.0, 6.9 Hz, 1H) 4.70 (dd, J=15.2, 5.0 Hz, 1H) 7.00-6.88 (m, 3H) 7.34-7.21 (m, 3H) 7.49 (t, J=7.8 Hz, 1H) 7.65 (d, J=8.3 Hz, 2H) 7.72 (d, J=8.5 Hz, 1H) 8.17 (d, J=7.8 Hz, 1H) 8.49 (s, 1H). MS (ESI) m/z=342.9 ([M+H]⁺), 364.9 ([M+Na]⁺), C22H18N2O2 requires 342.14

Step 3: 6-bromo-9-(3-(4-bromophenoxy)-2-hydroxypropyl)-9H-carbazole-3-carbonitrile (P7C3-S278)

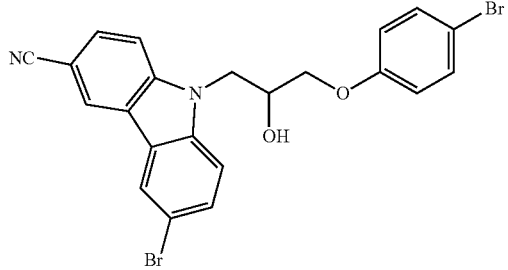 [SMILES: N#Cc1ccc2c(c1)c1cc(Br)ccc1n2CC(O)COc1ccc(Br)cc1]

To a solution of the product of Step 2 (0.7736 g, 2.26 mmol, 1 equiv) in THF (8 mL) was added N-Bromosuccinimide (0.8043 g, 4.52 mmol, 2 equiv). The mixture was stirred at room temperature for 30 minutes. THF was removed on the vacuum and the crude residue was purified by silica gel chromatography (30% ethyl acetate in hexanes) afford 1.0230 g white solid as product, yield 90.5%.

¹H NMR (CDCl₃, 400 MHz) δppm 3.88 (dd, J=9.5, 4.7 Hz, 1H) 3.99 (dd, J=9.5, 4.7 Hz, 1H) 4.69-4.38 (m, 3H)

6.81-6.70 (m, 2H) 7.44-7.35 (m, 3H) 7.54 (t, J=6.5 Hz, 1H) 7.59 (dd, J=8.7, 1.9 Hz, 1H) 7.66 (d, J=8.6 Hz, 1H) 8.20 (d, J=1.3 Hz, 1H) 8.31 (s, 1H). MS (ESI) m/z=498.7 ([M+H]+), C22H19Br2N3O2 requires 497.96

Example 212

P7C3-S279: methyl 9-(2-hydroxy-3-phenoxypropyl)-9H-pyrido[3,4-b]indole-3-carboxylate

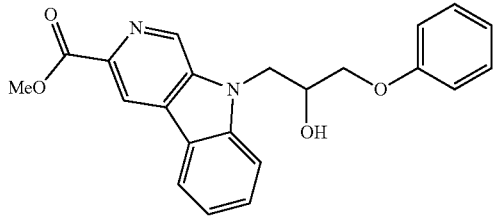 [SMILES: COC(=O)c1cc2c3ccccc3n(CC(O)COc3ccccc3)c2cn1]

To a solution of P7C3-S172 (10.9 mg, 0.03 mmol, 1 equiv) in DMF (0.5 mL) was added iodomethane (6.4 mg, 0.045 mmol, 1.5 equiv) and potassium carbonate (12.4 mg, 0.09 mmol, 3 equiv). The mixture was sealed and stirred in a 4-mL vial at room temperature for overnight. The crude reaction was diluted with 3 mL of dichloromethane and washed with brine (3×3 mL). The organic layers were dried over Na$_2$SO$_4$ and dichloromethane was removed under vacuum to yield yellow crude oil. It was further purified by silica gel chromatography using 10% of dichloromethane in methanol as elute to afford 8.6 mg white solid as product, yield 82.0%.

$^1$H NMR (CDCl$_3$, 400 MHz) δppm 3.64 (s, 3H) 4.14 (ddd, J=15.8, 9.3, 5.6 Hz, 2H) 4.58 (dd, J=14.6, 7.3 Hz, 1H) 4.68 (d, J=4.4 Hz, 1H) 4.76 (dd, J=14.6, 3.3 Hz, 1H) 6.98 (dd, J=13.9, 7.6 Hz, 3H) 7.31 (dd, J=8.5, 7.5 Hz, 2H) 7.36 (td, J=7.5, 3.4 Hz, 1H) 7.62 (d, J=3.7 Hz, 2H) 8.14 (d, J=7.8 Hz, 1H) 8.57 (s, 1H) 9.00 (s, 1H). MS (ESI) m/z=377.1 ([M+H]+), C22H20N2O4 requires 376.14

Example 213

P7C3-S282: 1-(3,6-dimethoxy-9H-carbazol-9-yl)-3-phenoxypropan-2-ol

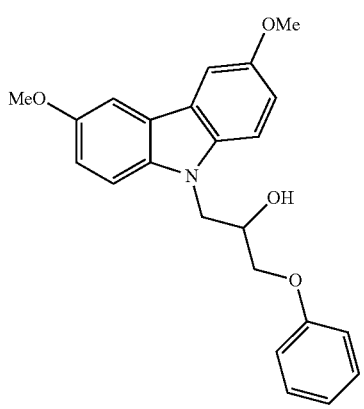 [SMILES: COc1ccc2c(c1)c1cc(OC)ccc1n2CC(O)COc1ccccc1]

Following Representative Procedure 7, the title compound was synthesized from 3,6-dimethoxy-9H-carbazole (Hsieh, B. B.; Litt, M. H. *Macromolecules*, 1986, 19, 516-520) (0.030 g, 0.0917 mmol) and 2-(phenoxymethyl)oxirane (19 μL, 0.128 mmol) in dry THF:DMF (1:1) (0.459 mL) (0.028 g, 81%).

$^1$H NMR (CDCl$_3$, 400 MHz) δ 7.51 (s, 2H), 7.35 (d, 2H, J=8.6 Hz), 7.29 (d, 2H, J=8.6 Hz), 7.05 (dd, 2H, J=2.4, 8.8 Hz), 6.98 (t, 1H, J=7.4 Hz), 6.88 (d, 2H, J=7.9 Hz), 4.52 (m$_c$, 1H), 4.46 (m$_c$, 2H), 4.00-3.85 (m, 8H). MS (ESI) m/z 378.2 [M+H]+ ([M+H]+, C23H24NO4 requires 378.4).

Example 214

P7C3-S283: 2-chloro-N-(3-(3,6-dibromo-9H-carbazol-9-yl)-2-hydroxypropyl)acetamide

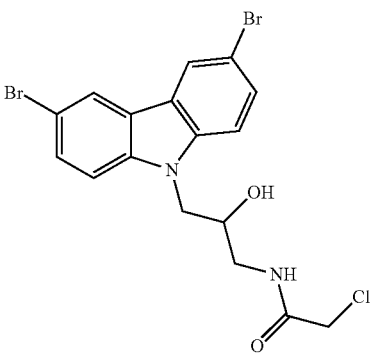 [SMILES: O=C(CCl)NCC(O)Cn1c2ccc(Br)cc2c2cc(Br)ccc21]

P7C3-S38 (0.134 g, 0.337 mmol) was dissolved in CH$_2$Cl$_2$/MeCN (9:1, 5.6 mL) and treated with Et$_3$N (70 μL, 0.50 mmol) at 0° C. Chloroacetyl chloride (29 μL, 0.370 mmol) was then added dropwise. After being stirred at room temperature for 45 min, the reaction was quenched with a solution of 1N HCl. The organic phase was separated, washed with brine, dried over Na$_2$SO$_4$, filtered and condensed. The crude mixture was purified by chromatography (SiO$_2$, 0-80% EtOAc/Hexanes) to afford the title compound (0.091 g, 60%).

$^1$H NMR (acetone-d6, 400 MHz) δ 8.36 (s, 2H), 7.74-7.51 (m, 4H), 4.65 (d, 1H, J=4.7 Hz), 4.49 (dd, 1H, J=3.4, 15.0 Hz), 4.41 (dd, 1H, J=8.3, 15.0 Hz), 4.29 (m$_c$, 1H), 4.13 (s, 2H), 3.63-3.50 (m, 1H), 3.43 (dt, 1H, J=5.7, 12.8 Hz). MS (ESI) m/z 474.6 [M+H]+ ([M+H]+, C17H16Br2ClN2O2 requires 475.5).

Example 215

P7C3-S284: 2-chloro-N-(3-(3,6-dibromo-9H-carbazol-9-yl)-2-hydroxypropyl)acetamide

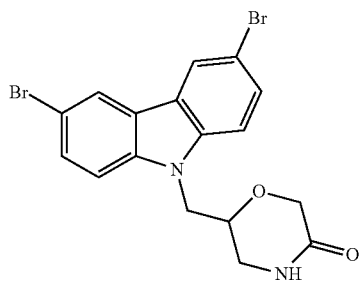 [SMILES: O=C1COC(Cn2c3ccc(Br)cc3c3cc(Br)ccc32)CN1]

Following a reported procedure (Metro, T. X.; Pardo, D. G.; Cossy, J. *J. Org. Chem.* 2008, 73, 707-710), P7C3-S283 (0.091 g, 0.192 mmol) was dissolved in iPrOH (7.7 mL) and treated with tBuOK (0.054 g, 0.48 mmol) in iPrOH (1.9 mL) at 0° C. The mixture was stirred at room temperature for 4 h. The reaction was then quenched with 1N HCl and concentrated in vacuum. The residue was diluted with water a then extracted with EtOAc. The organic layers were washed with brine, dried over $Na_2SO_4$, filtered and condensed. The crude mixture was purified by chromatography ($SiO_2$, EtOAc) to afford the title compound (0.060 g, 72%).

$^1$H NMR ($d_6$-DMSO, 400 MHz) δ 8.47 (d, 2H, J=1.9 Hz), 7.67 (d, 2H, J=8.7 Hz), 7.60 (dd, 2H, J=1.9, 8.7 Hz), 4.55 (d, 2H, J=5.5 Hz), 4.10 ($m_c$, 1H), 3.98-3.77 (m, 2H), 3.18 (t, 2H, J=11.3 Hz). MS (ESI) m/z 438.6 [M+H]$^+$ ([M+H]$^+$, $C_{17}H_{14}Br_2N_2O_2$ requires 439.1), 460.6 [M+Na]$^+$ ([M+Na]$^+$, $C_{17}H_{13}Br_2N_2NaO_2$ requires 460.1).

Example 216

P7C3-S287: 2-(3-bromo-6-methyl-9H-carbazol-9-yl)-N-(phenylsulfonyl)acetamide

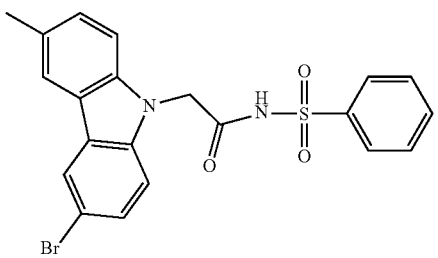 [SMILES: Cc1ccc2c(c1)c1cc(Br)ccc1n2CC(=O)NS(=O)(=O)c1ccccc1]

The title compound was prepared analogously to P7C3-S232. Column chromatography (1:4 THF:Hexanes) resulted in collection of 86.7 mg (35.5% yield) product as a white solid.

$^1$H NMR (400 MHz, Acetone-$d_6$) δ 8.23 (d, J=1.9 Hz, 1H), 7.97 (d, J=1.1 Hz, 1H), 7.95 (d, J=1.5 Hz, 1H), 7.94 (s, 1H), 7.65-7.60 (m, 1H), 7.56-7.50 (m, 2H), 7.45 (dd, J=8.7, 2.0 Hz, 1H), 7.34-7.28 (m, 1H), 7.26 (d, J=0.7 Hz, 1H), 7.24 (dd, J=8.4, 1.6 Hz, 1H), 5.12 (s, 2H), 2.47 (s, 3H). MS (ESI) m/z=457.0 ([M+H]$^+$, C21H17BrN2O3S requires 456.01.)

Example 217

P7C3-S288: 2-(3-bromo-6-methyl-9H-carbazol-9-yl)acetamide

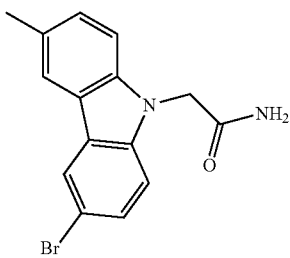 [SMILES: Cc1ccc2c(c1)c1cc(Br)ccc1n2CC(N)=O]

The title compound was prepared analogously to P7C3-S213.

$^1$H NMR (400 MHz, CDCl$_3$) δ 8.19 (d, J=1.9 Hz, 1H), 7.86 (s, 1H), 7.57 (dd, J=8.6, 1.9 Hz, 1H), 7.36 (dd, J=8.3, 1.6 Hz, 1H), 7.28 (d, J=8.4 Hz, 1H), 7.24 (s, 1H), 5.34 (d, J=31.8 Hz, 2H), 4.88 (s, 2H), 2.54 (s, 3H). MS (ESI) m/z=317.0 ([M+H]$^+$, $C_{15}H_{13}BrN_2O$ requires 316.02)

Example 218

P7C3-S294: 2-(3-bromo-6-methyl-9H-carbazol-9-yl) ethanol

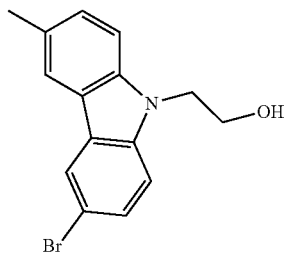 [SMILES: Cc1ccc2c(c1)c1cc(Br)ccc1n2CCO]

The title compound was prepared analogously to P7C3-S171.

$^1$H NMR (400 MHz, CDCl$_3$) δ 8.17 (d, J=1.9 Hz, 1H), 7.84 (s, 1H), 7.52 (dd, J=8.6, 2.0 Hz, 1H), 7.38-7.28 (m, 3H), 4.44 (t, J=5.4 Hz, 2H), 4.05 (q, J=5.5 Hz, 2H), 2.53 (s, 3H), 1.47 (t, J=6.0 Hz, 1H).

MS (APCI) m/z=304.0 ([M+H]$^+$, C15H14BrNO requires 303.03).

Example 219

P7C3-S295: N-(3-(3-bromo-6-methyl-9H-carbazol-9-yl)-2-fluoropropyl)-6-methoxypyridin-2-amine

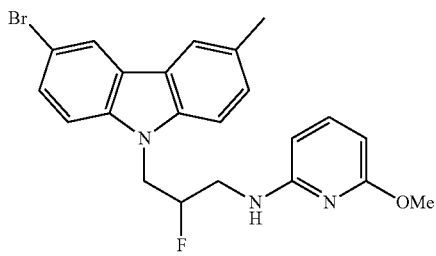 [SMILES: COc1cccc(NCC(F)Cn2c3ccc(C)cc3c3cc(Br)ccc32)n1]

A vial containing S286 (50.5 mg, 0.13 mmol), 2-iodo-6-methoxypyridine (29.6 mg, 0.13 mmol), chloro[2-(dicyclohexylphosphino)-3,6-dimethoxy-2'-4'-6'-tri-i-propyl-1,1'-biphenyl][2-(2-aminoethyl)phenyl]palladium(II) (BrettPhos palladacycle, 10.8 mg, 0.014 mmol) and 2-(dicyclohexylphosphino)-3,6-dimethoxy-2'-4'-6'-tri-i-propyl-1,1'-biphenyl (BrettPhos, 6.8 mg, 0.013 mmol) was purged with nitrogen for 20 minutes before the addition of dioxane (2.45 ml) followed by the dropwise addition of LHMDS (1.0 M in THF, 0.5 mmol). The reaction was stirred for an hour before being centrifuged. The supernatant was chromoatographed on silica gel in 10-30% THF/hexanes. Yield=25%

$^1$H NMR (400 MHz, $(CD_3)_2CO$) δ 8.27 (dd, J=1.7, 0.9 Hz, 1H), 7.98 (dt, J=1.9, 0.9 Hz, 1H), 7.53 (t, J=1.4 Hz, 1H), 7.49 (d, J=8.5 Hz, 1H), 7.35-7.26 (m, 2H), 6.92 (s, 1H), 6.14 (d, J=8.0 Hz, 1H), 5.91 (dd, J=7.8, 0.7 Hz, 1H), 5.33-5.04

(m, 1H), 4.77 (dd, J=5.5, 3.8 Hz, 1H), 4.71 (d, J=5.5 Hz, 1H), 3.86-3.76 (m, 1H), 3.74-3.64 (m, 1H), 3.60 (s, 3H), 2.49 (s, 3H). MS (ESI), m/z: calculated 441.09, found 442.0 (M+1).

Additional compounds of the presently disclosed embodiments can also be synthesized via similar schemes and methods as described above.

Pro-Neurogenic Efficacy/Neuroprotection Activity of Various Compounds:

Compounds were tested in vivo for dose-responsive neurotrophic efficacy. The results are shown in Table 1.

TABLE 1

| Test Material | ($\times 10^{-06}$) BrdU+ cells/mm$^3$ dentate gyrus | SEM: (standard error of the mean) |
|---|---|---|
| Vehicle | 14.5 | 1.08 |
| FGF-2: (fibroblast growth factor 2) | 28.4 | 2.12 |
| Example 1a ((S)-P7C3-OMe) | 29.8 | 2.0 |
| Example 1b ((R)-P7C3-OMe) | 18.3 | 0.8 |
| Example 2 | 24.4 | 1.4 |
| Example 3a | 30.9 | 3 |
| Example 3b | 29.6 | 1.3 |
| Example 3c | 16.1 | 1.74 |
| Example 3d | 27.1 | 1.34 |
| Example 4 | 23.7 | 0.6 |
| Example 5 | 21.5 | 2.18 |
| Example 6a (P7C3A20) | 38 | 2.4 |
| Example 6b | 25.5 | (one animal tested) |
| Example 7a | 18.4 | 1.8 |
| Example 7b | 23.4 | 1.31 |
| Example 8 | 23.2 | 0.8 |
| Example 9 | 16.2 | 1.7 |
| Example 10 | 27 | 1.3 |
| Example 11 | 15.1 | 0.6 |
| Example 12 | 21.7 | 2.9 |
| Example 13 | 28.5 | 2.6 |
| Example 14 | 17.8 | 1.9 |
| Example 15 | 15.1 | 0.9 |
| Example 16 | 17.1 | 0.9 |
| Example 17 | 20.8 | 0.3 |
| Example 19 | 15 | 0.5 |
| Example 20 | 23.2 | 0.48 |
| Example 21 | 27.6 | 3.4 |
| Example 22 | 27.3 | 1.8 |
| Example 23 | 21.5 | 2.2 |
| Example 25 | 16.8 | 1.3 |
| Example 26 | 15.6 | 1 |
| Example 28 | 21 | 0.6 |
| Example 29 | 17.6 | 2.3 |
| Example 30 | 13.4 | 1.2 |
| Example 31 | 14.7 | 1 |
| Example 32 | 16 | 0.4 |
| Example 33 | 14 | 0.2 |
| Example 36 | 19 | 2.54 |
| Example 39 | 23.4 | 1.1 |
| Example 40 | 14.4 | 1.5 |
| Example 41 | 16 | 1.1 |
| Example 43 | 21.3 | 2.6 |
| Example 45 (P7C3) | 30 | 1.42 |
| Example 76 (P7C3-S229) | 26.5 | 3.7 |
| Example 87 | 25.4 | 2.4 |
| Example 88a | 16.2 | 1 |
| Example 88b | 30.6 | 3.66 |
| Example 89 | 23.4 | 0.26 |
| Example 90 | 33.3 | 3.3 |
| Example 91 | 18.3 | 2.9 |
| Example 92 | 29 | 1.6 |
| Example 93 | 20.1 | 2.5 |
| Example 94 | 23.9 | 2.43 |
| Example 95 | 21.5 | 1.2 |
| Example 96 | 34.2 | 4.29 |
| Example 97a | 32.4 | 3.84 |
| Example 97b | 26.3 | 1.55 |
| Example 101 | 25.8 | 2.6 |
| Example 102 | 27.6 | 2.7 |
| Example 103 | 16.8 | 1.13 |
| Example 104 | 25.1 | 2 |
| Example 105 P7C3-S67 | 17.7 | 1.4 |
| Example 107 | 19.3 | 1.4 |
| Example 108 P7C3-S68 | 14.6 | 0.84 |
| Example 109 | 23.7 | 0.75 |
| Example 110 P7C3-S70 | 14.7 | 0.6 |
| Example 111 P7C3-S71 | 14.3 | 1.5 |
| Example 112 P7C3-S72 | 23.3 | 2.2 |
| Example 113 P7C3-S73 | 20.8 | 1.5 |
| Example 114 P7C3-S75 | 20.6 | 3.5 |
| Example 115 P7C3-S77 | 24 | 1.5 |
| Example 116 P7C3-S78 | 28.1 | 1.71 |
| Example 117 P7C3-S79 | 27.3 | 2.17 |
| Example 118 P7C3-S80 | 25.9 | 1.1 |
| Example 119 P7C3-S81 | 25.1 | 1.8 |
| Example 120 P7C3-S82 | 23.6 | 0.74 |
| Example 121 P7C3-S83 | 24.9 | 0.8 |
| Example 122 P7C3-S84 | 25.6 | 1.4 |
| Example 123 P7C3-S91 | 16.3 | 1.1 |
| Example 124 P7C3-S92 | 16.8 | 2 |
| Example 126 P7C3-S94 | 16.9 | 1.4 |
| Example 127 P7C3-S95 | 17.2 | 0.9 |
| Example 128 P7C3-S96 | 17.4 | 0.9 |
| Example 129 P7C3-S97 | 15.1 | 1.6 |
| Example 130 P7C3-S98 | 13.8 | 1.8 |
| Example 131 P7C3-S99 | 15.2 | 0.9 |
| Example 132 P7C3-S100 | 24 | 0.6 |
| Example 133 P7C3-S101 | 19.8 | 1.4 |
| Example 134 P7C3-S102 | 17.7 | 1.6 |
| Example 135 P7C3-S103 | 13.9 | 0.8 |
| Example 137 P7C3-S105 | 21.6 | 1.4 |
| Example 138 P7C3-S106 | 21.7 | 0.8 |
| Example 139 P7C3-S107 | 14.6 | 0.5 |
| Example 140 P7C3-S108 | 15.2 | 0.4 |
| Example 141 P7C4-S109 | 18.8 | 1.7 |
| Example 142 P7C3-S110 | 21 | 1.2 |
| Example 143 P7C3-S111 | 24.5 | 2.2 |

TABLE 1-continued

In Vivo Activity

| Test Material | (×10⁻⁰⁶) BrdU+ cells/mm³ dentate gyrus | SEM: (standard error of the mean) |
|---|---|---|
| Example 144a P7C3-S113 | 31.5 | 2 |
| Example 144b P7C3-S114 | 15.2 | 1.3 |
| Example 145 P7C3-S115 | 13.2 | 2.1 |
| Example 148 P7C3-S131 | 17.9 | 1.5 |
| Example 150 P7C3-S138 | 20.8 | 4 |
| Example 151 P7C3-S141 | 22.5 | 2.3 |
| Example 152 P7C3-S142 | 26.4 | 3.3 |
| Example 153 P7C3-S146 | 29 | 2.6 |
| Example 154 P7C3-S147 | 26.5 | 1.1 |
| Example 155 P7C3-S150 | 16.7 | 1.4 |
| Example 156 P7C3-S151 | 29.8 | 2 |
| Example 157 P7C3-S153 | 21.4 | 1.8 |
| Example 158a P7C3-S154 | 19.7 | 2.5 |
| Example 158b P7C3-S155 | 26.1 | 3.7 |
| Example 159 P7C3-S157 | 20.3 | 0.4 |
| Example 160 P7C3-S159 | 13.8 | 1.5 |
| Example 161 P7C3-S160 | 26.2 | 3 |
| Example 162 P7C3-S161 | 22.7 | 2.4 |
| Example 163 P7C3-S164 | 15.2 | 1.8 |
| Example 164 P7C3-S165 | 35.7 | 4.7 |
| Example 165 P7C3-S166 | 35.6 | 2.4 |
| Example 166 P7C3-S167 | 27.2 | 2.6 |
| Example 167 P7C3-S168 | 29.1 | 1.1 |
| Example 168 P7C3-S172 | 28.3 | 2.3 |
| Example 169 P7C3-S173 | 25.5 | 3 |
| Example 170 P7C3-S174 | 18.6 | 1.5 |
| Example 171 P7C3-S175 | 24.6 | 2.6 |
| Example 172 P7C3-S176 | 13.8 | 1 |
| Example 173 P7C3-S177 | 27.7 | 1.80 |
| Example 174 P7C3-S178 | 27.5 | 2.3 |
| Example 175 P7C3-S179 | 34.5 | 2.3 |
| Example 177 P7C3-S183 | 15.4 | 1 |
| Example 178 P7C3-S184 | 13.4 | 1.7 |
| Example 179 P7C3-S186 | 16.1 | 1.3 |
| Example 180 P7C3-S187 | 25.2 | 2.3 |
| Example 181 P7C3-S188 | 26.1 | 1.3 |
| Example 182 P7C3-S190 | 16.7 | 0.3 |
| Example 183 P7C3-S191 | 21.4 | 0.8 |
| Example 184 P7C3-S192 | 21 | 2.1 |
| Example 185 P7C3-S194 | 16.2 | 1.2 |
| Example 186 P7C3-S195 | 17.9 | 1.9 |
| Example 187 P7C3-S198 | 22 | 1.0 |
| Example 188 P7C3-S204 | 28.4 | 1.5 |
| Example 189 P7C3-S205 | 29.1 | 2.7 |
| Example 190 P7C3-S208 | 27 | 2.6 |
| Example 191 P7C3-S213 | 13 | 0.7 |
| Example 192 P7C3-S214 | 19.7 | 2 |
| Example 193 P7C3-S215 | 16.6 | 0.9 |
| Example 194 P7C3-S217 | 24.6 | 2.9 |
| Example 195 P7C3-S218 | 18.9 | 1.6 |
| Example 196 P7C3-S219 | 16.8 | 2.8 |
| Example 197 P7C3-S220 | 21 | 2.5 |
| Example 198 P7C3-S221 | 29.5 | 2 |
| Example 199 P7C3-S226 | 25.6 | 2 |
| Example 200 P7C3-S233 | 14.5 | 0.7 |
| Example 201 P7C3-S234 | 35.6 | 1.3 |
| Example 202 P7C3-S241 | 30.9 | 1.5 |
| Example 203 P7C3-S243 | 35.7 | 3.8 |
| Example 204 P7C3-S244 | 23.2 | 1.9 |
| Example 205 P7C3-S255 | 35.3 | 2.1 |
| Example 206 P7C3-S261 | 19.3 | 2 |
| Example 207 P7C3-S263 | 24.1 | 3.3 |
| Example 208 P7C3-S271 | 34.6 | 1.7 |
| Example 209 P7C3-S273 | 22.8 | 2.4 |
| Example 210 P7C3-S274 | 25.7 | 2 |
| Example 211 P7C3-S278 | 36.2 | 3.3 |
| Example 212 P7C3-S279 | 25 | 0.9 |

Compounds were evaluated for pro-neurogenic efficacy/neuroprotection in our standard in vivo assay at 10 μM concentration in four 12 week old adult male C57/B16 mice.

The (+) (dextrorotatory) enantiomer of 1-(3,6-Dibromo-9H-carbazol-9-yl)-3-(3-methoxyphenylamino)-propan-2-ol as described herein exhibited higher activity.

The (−) (levorotatory) enantiomer of 1-(3,6-Dibromo-9H-carbazol-9-yl)-3-(3-methoxyphenylamino)-propan-2-ol as described herein exhibited lower activity. 2

Previously, a commercial sample of P7C3-S229 was tested in the neurogenesis assay and found to be indistinguishable from vehicle when dosed intracranially as a 10 micromolar solution (MacMillan et al., *J. Am. Chem. Soc.,* 2011; (133):1428-1437). Subsequently, a separate sample was independently synthesized and tested analogously, and found to be active. While there may be many reasons for this discrepancy, without wishing to be bound by theory, it has been hypothesized that possible explanations include: 1) The identity of the commercial sample was not rigorously confirmed; it may have been a different substance. 2) The purity of the commercial sample was not rigorously confirmed; an impurity may have counteracted the pro-neurogenic activity of the commercial sample. 3) P7C3-S229 displays low solubility. Slight variation in the formulation of different samples or the physical characteristics of the sample (e.g. crystalline vs. amorphous solid) may have resulted in differences in exposure in the in vivo experiment.

It is also believed that P7C3-S295 (Example 219), based on the structure, can have high biological activity (e.g., in the pro-neurogenic efficacy/neuroprotection assay in mice models described herein). Additional experiments (in vitro and in vivo) are underway to further characterize the effect of P7C3-S295 in disease models described herein.

A. Identification of Pro-Neurogenic or Neuroprotective Compounds:

In an effort to identify compounds that might stimulate the birth of new neurons, or protect newborn neurons from cell death, a library of 1,000 compounds was screened using an in vivo assay. In the initial screen, compounds were randomly pooled into groups often and administered intracerebroventricularly at a constant rate over seven days into the left lateral ventricle of living mice via Alzet osmotic minipumps. Compounds were administered at a concentration of 10 µM for each molecule, making a total solute concentration of 100 µM. After seven days of infusion at a constant rate of 0.5 L/hour, a total of 84 µL of volume will have left the pump (0.00084 µMoles) and entered the cerebrospinal fluid. The average volume of a brain from a 12 week old male, C57/B6 mouse in our study is 500 mm$^3$. The maximal amount of drug was estimated that could potentially be present in the brain, taking the extreme and unlikely scenario of 100% absorbance of the drug into brain tissue and 0% clearance throughout the seven day infusion period. Under these conditions, at the end of one week of infusion each compound would be present at 1.7 µMolar concentration. Since the actual amount of chemical compound in the brain is likely to be only a fraction of this predicted level, it is reasonable to estimate that compounds were administered at mid to low-nanomolar concentrations.

Figure 2:
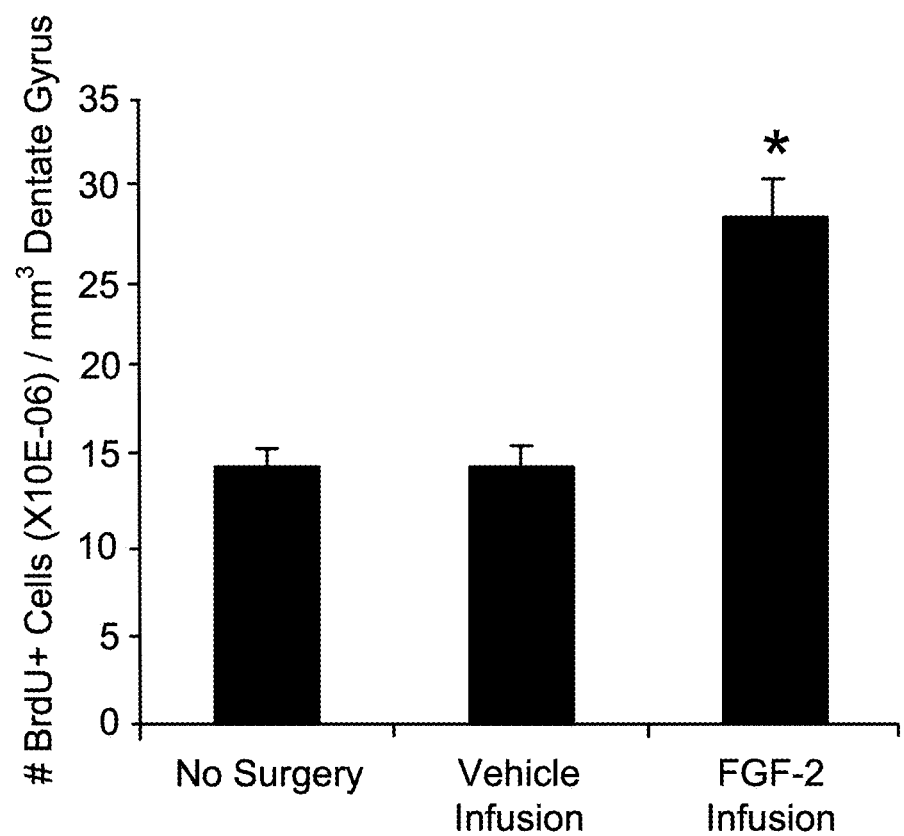
FIG. 2: Surgical placement of cannula and pumps did not affect hippocampal neurogenesis or survival of newborn neurons on the contralateral side of the brain. Mice infused with vehicle (artificial cerebrospinal fluid) over seven days by means of surgically implanted Alzet osmotic minipumps (Vehicle Infusion, n=5) displayed no difference in hippocampal neural precursor cell proliferation, as assessed by BrdU incorporation normalized for dentate gyms volume, from mice treated identically except not having undergone surgery (No Surgery, n=4). When Alzet osmotic minipumps were loaded with fibroblast growth factor 2 (FGF-2; 10 mg/mL) (n=5), however, hippocampal neural precursor cell proliferation roughly doubled with respect to both of the other two groups (*, p<0.001, Student's t test).

During compound infusion, animals were intraperitoneally (IP) injected daily with the thymidine analog, bromodeoxyuridine (BrdU), as a means of scoring the birth and survival of proliferating neural precursor cells in the hippocampus. Because both social interaction and voluntary exercise are known to stimulate hippocampal neurogenesis, mice were housed individually without access to running wheels throughout the screening period. Following the week-long period of compound administration, animals were perfused and sacrificed. Dissected brain tissue was fixed, embedded, sectioned, stained with antibodies to BrdU, and evaluated by light microcopy as a means of quantifying neurogenesis and survival of newborn neural precursor cells localized to the subgranular layer of the dentate gyms on the brain hemisphere contralateral to the side of mini-pump cannulation. Every fifth section throughout the entire rostral-caudal extent of the hippocampus was analyzed, and the total number of BrdU+ cells was normalized against the measured volume of the dentate gyms. Because both increased proliferation and survival of newborn neurons are important screening parameters, the screen was conducted over seven days in order to cast a wide net to detect molecules that might augment either process. The choice of parameters for the screen was based on pulse-chase experiments with a single injection of BrdU, under identical conditions to those used in our screen, which revealed that 40% of newborn cells in the dentate gyms die within the first five days of their birth (FIG. 1). Intracranial infusions of either fibroblast growth factor 2 (FGF-2) or artificial cerebral spinal fluid (aCSF) vehicle via the same, week-long protocol were employed as positive and negative controls. There was no difference in the number of BrdU-labeled cells in the dentate gyms between mice subjected to surgical pump implantation and infusion with vehicle, and mice having had no surgery (FIG. 2). This confirmed the validity of the in vivo approach to assess the ability of intracerebroventricularly infused compounds to enhance hippocampal neurogenesis in the contralateral hemisphere.

Figure 3:
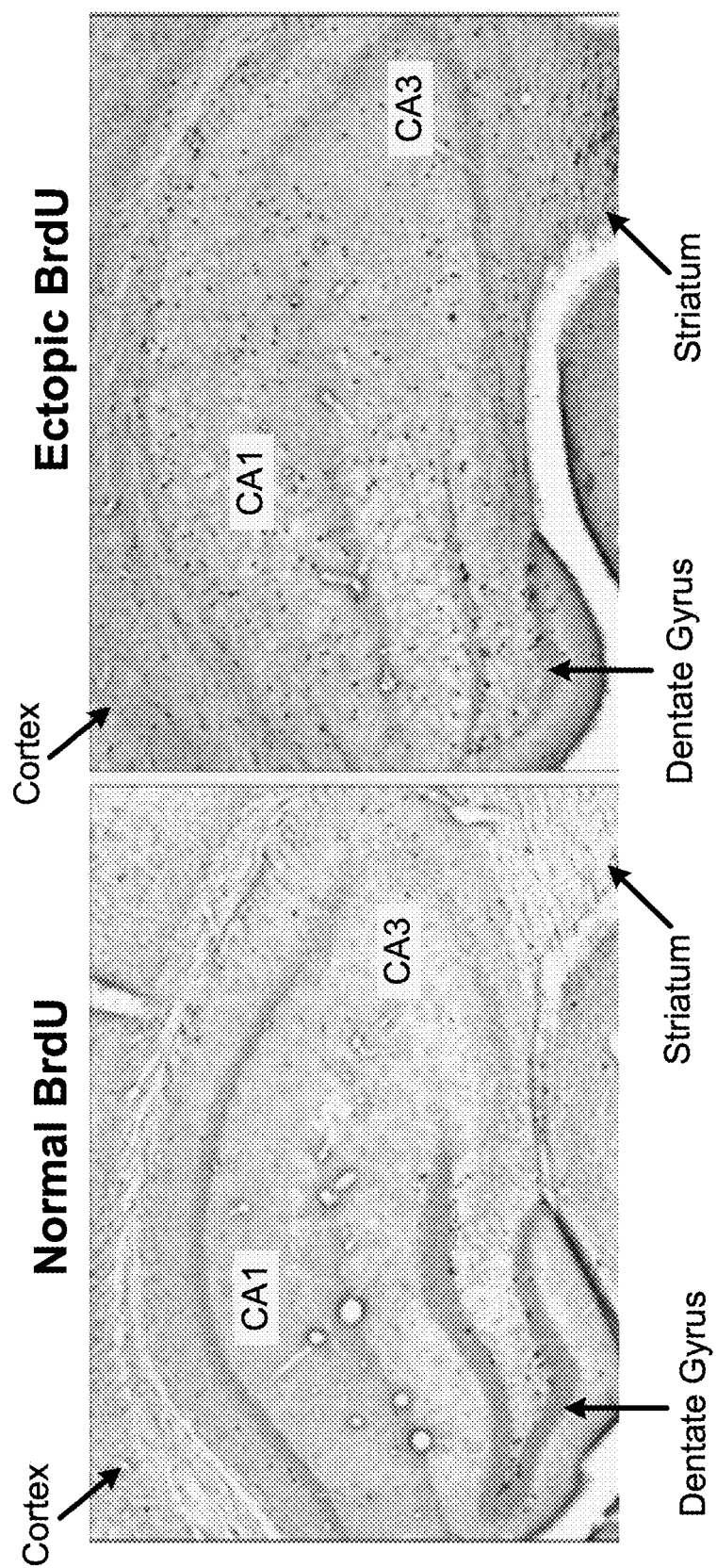
FIG. 3: Ectopic incorporation of BrdU served to eliminate molecules from further consideration. Immunohistochemical staining of BrdU in the hippocampal field should normally be restricted to the SGZ of the dentate gyrus, as shown on the left. The in vivo neurogenic screen employed was designed to detect small molecules that selectively stimulated BrdU incorporation into replicating cells of the SGZ. Infrequently, some compounds exhibited non-specific BrdU incorporation in ectopic regions, such as CA3, CA1, cortex, and striatum, as shown on the right. Any molecules that demonstrated ectopic incorporation of BrdU were eliminated from the study.

Considered to be important is that stimulation of neurogenesis triggered by any compound be localized to the exact region of the brain known to produce new neurons at an enhanced level in response to healthy activities such as wheel running, access to an enriched environment, or access to social interaction. For this reason attention was focused solely on compound pools that stimulated BrdU incorporation only in the subgranular zone of the dentate gyms. Prominent nonspecific incorporation of BrdU in ectopic regions, such as CA3, CA1, cortex, or striatum, was presumed to reflect pathological inflammation, as proliferating cells incorporate BrdU in DNA synthesis, or to indicate other forms of toxicity, as cells also incorporate BrdU during DNA repair. Any compound pools yielding ectopic BrdU incorporation were eliminated from the screen. For an example, see FIG. 3.

Figure 4:
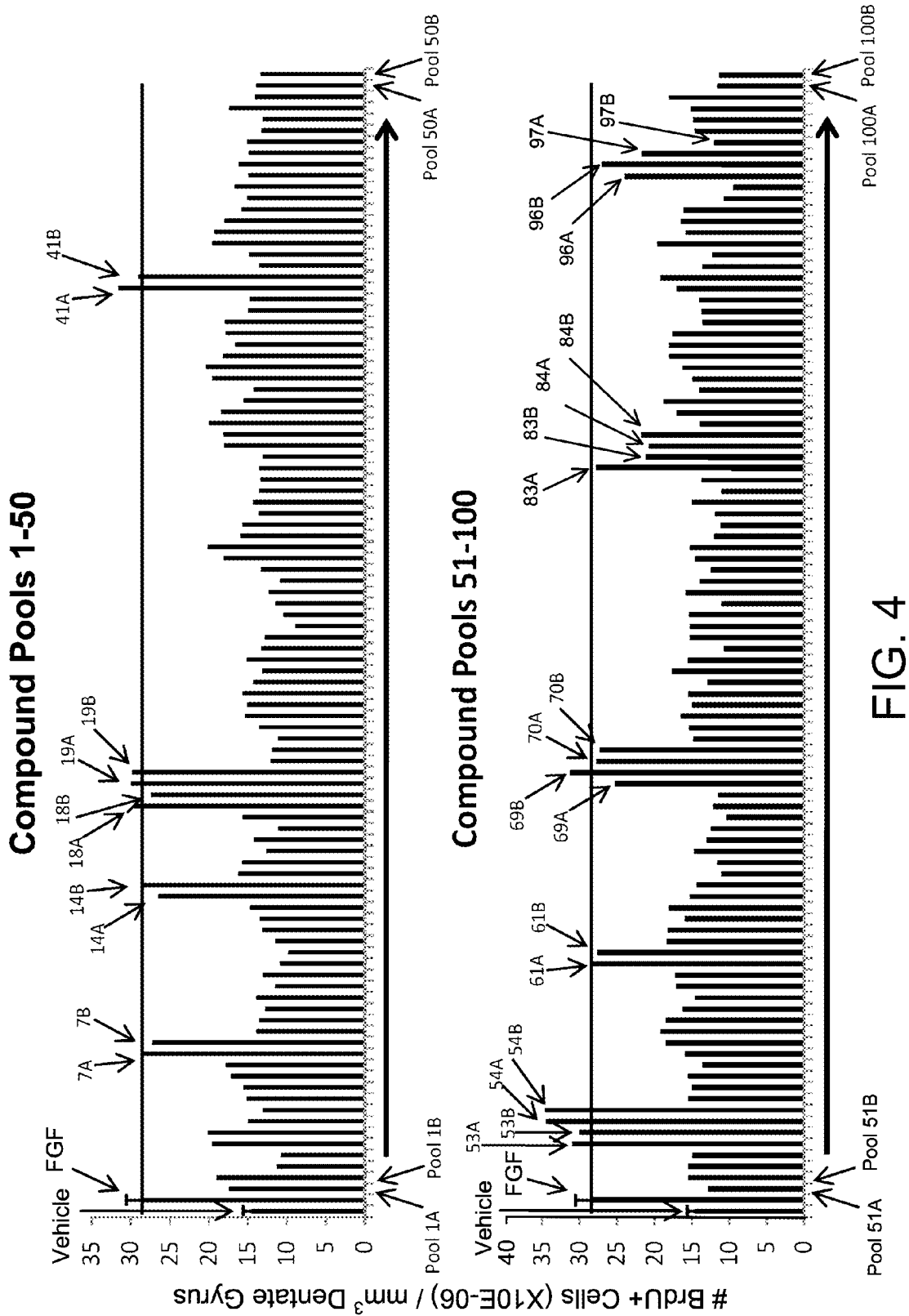
FIG. 4: Screening of 100 pools of 10 compounds identified 10 pools with pro-neurogenic efficacy. The total number of BrdU-labeled cells in the dentate gyms subgranular zone (SGZ) approximately doubled following seven day infusion with fibroblast growth factor 2 (FGF-2; 10 mg/mL) (n=5) relative to mice infused with vehicle (artificial cerebrospinal fluid (aCSF) (n=5). Each pool often compounds was tested for pro-neurogenic efficacy over a 7 day period in two independent mice at 10 µM concentration for each individual compound. Pools 7, 14, 18, 19, 41, 53, 54, 61, 69 and 70 displayed comparable stimulation of neural precursor cell proliferation as FGF-2 infusion. The majority of pools displayed no effect on hippocampal neural precursor cell proliferation.
Figure 5:
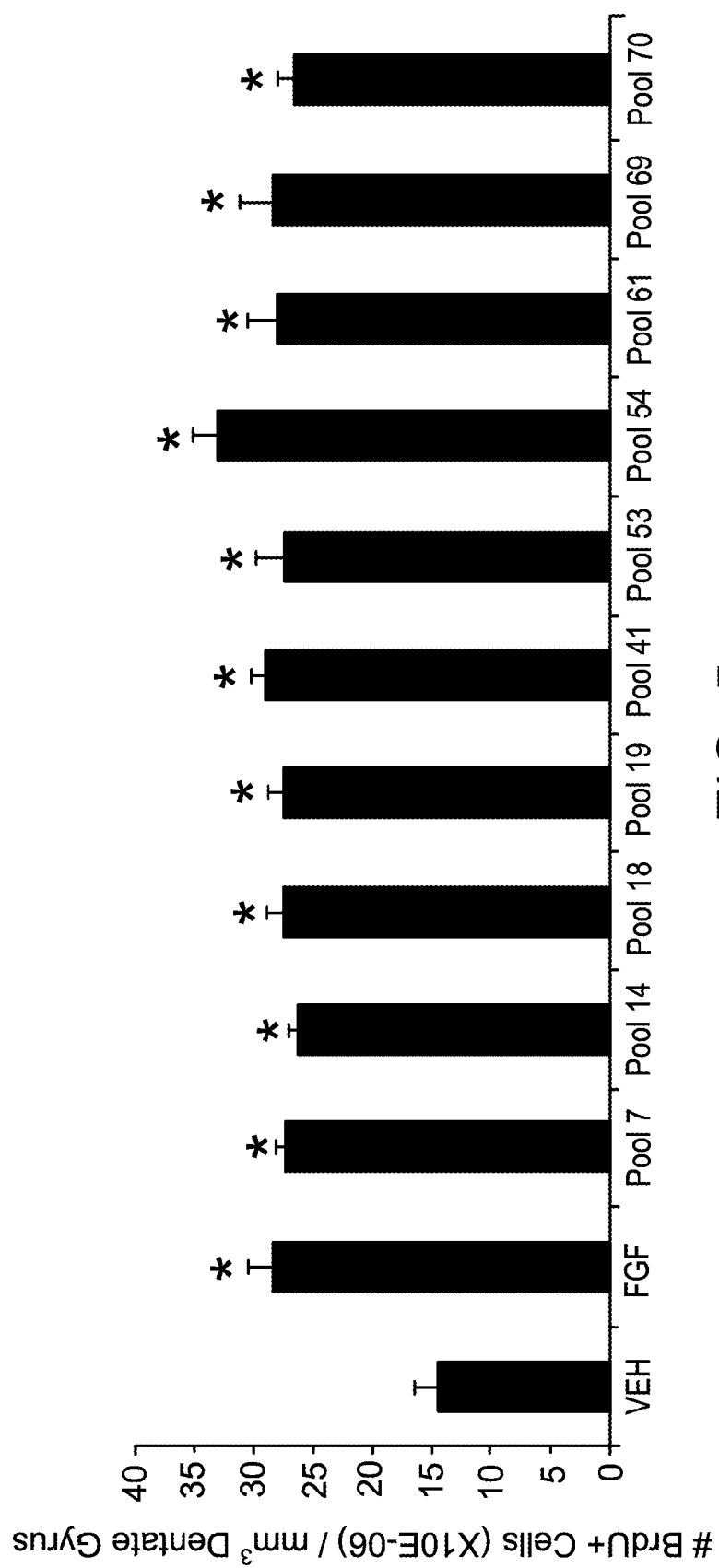
FIG. 5: Re-evaluation of positive pools verified statistical significance of enhanced BrdU-incorporation. Subsequent to their initial identification, pools 7, 14, 18, 19, 41, 53, 54, 61, 69, and 70 were re-evaluated in 2 additional mice each. Results shown are average with SEM of all 4 mice evaluated for each compound. All pools significantly (*, P<0.001, Student's t test) stimulated neural precursor cell proliferation in the hippocampal dentate gyms SGZ relative to vehicle control.
Figure 6A:
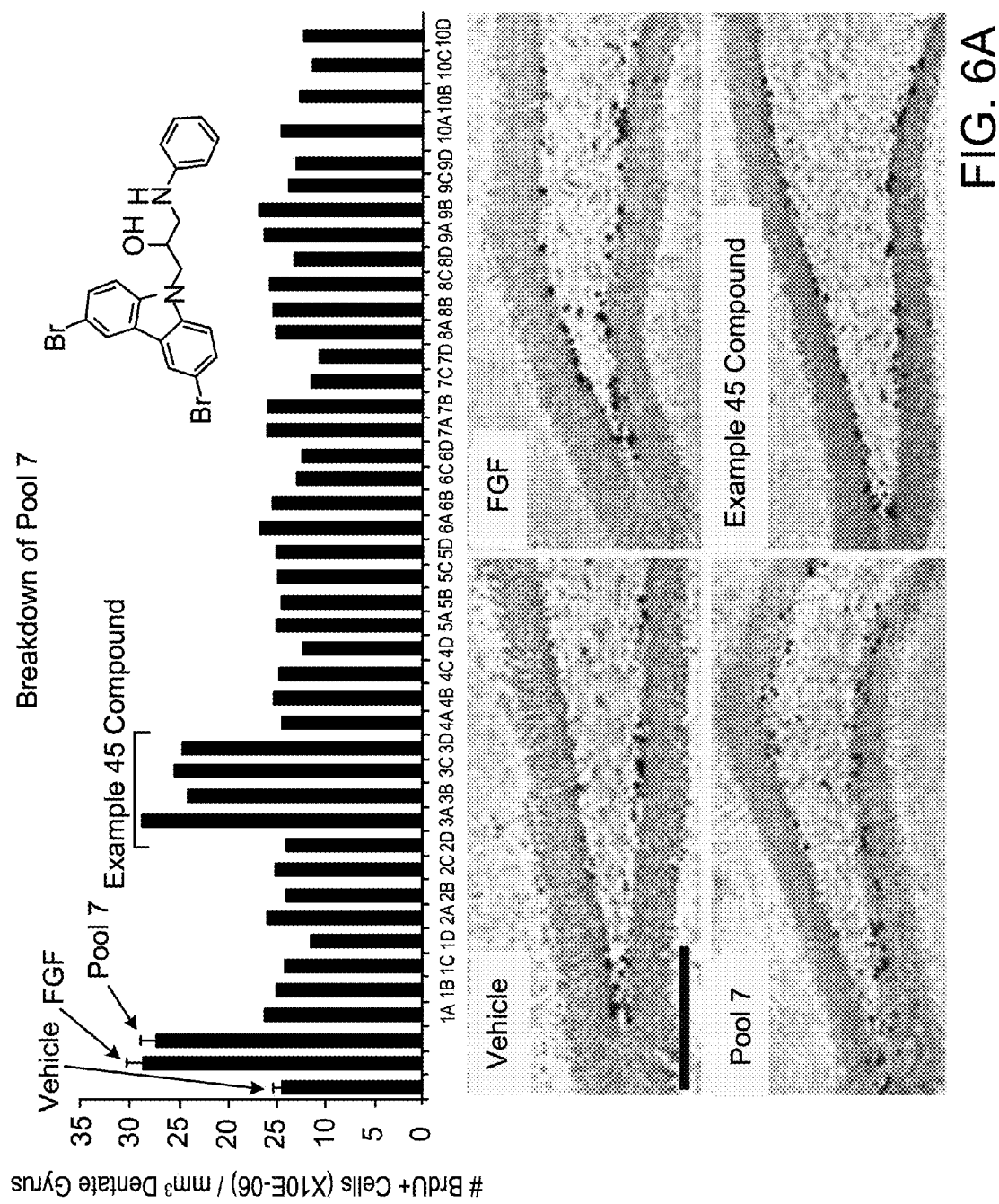
Figure 6C:
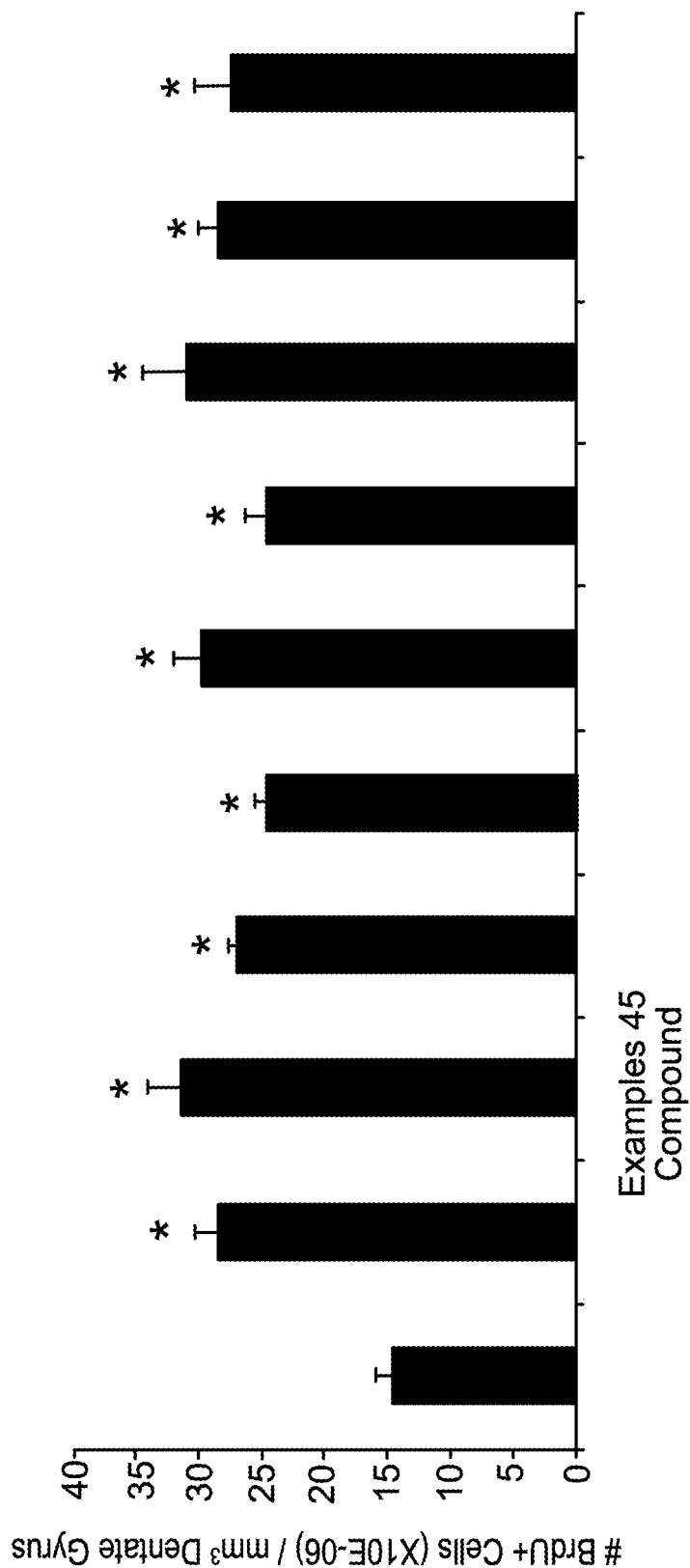

Each of the 100 pools was tested on two independent mice. As shown in FIG. 4, ten of the 100 test pools were observed to enhance dentate gyms-specific neurogenesis to an extent roughly equivalent to FGF-2. Each pool that scored positive in the initial two test animals was subsequently re-evaluated in two additional mice, and all ten pools were found to exert their pro-neurogenic effect with statistical significance (FIG. 5). In order to identify single, pro-neurogenic compounds, positive pools were broken down into their ten component molecules, each of which was infused individually at two concentrations (10 µM and 100 µM) in two mice per concentration. FIG. 6A shows the results of break-down assays on pool #7, wherein it was discovered that neurogenesis was selectively stimulated by one of the constituent chemicals of the pool (compound #3), chemicals in the pool demonstrating no effect. This molecule was designated as Example 45 Compound or P7C3. In breaking down the ten positive pools, eight pools yielded a single pro-neurogenic compound (FIG. 6B). To ensure that the pro-proliferative or neuroprotective effect on neural stem cells was not an artifact of storage conditions in the UTSWMC chemical compound library, re-supplied compounds were verified to by 99% pure by mass spectrometry, evaluated in 4 mice each at 10 µM concentration, and shown to retain either pro-proliferative or neuroprotective properties in neural stem cells (FIG. 6C).

Pharmacokinetic analysis of Example 45 Compound in plasma and whole brain tissue was undertaken after single IV, IP and oral gavage administrations. Example 45 Compound was noted to be orally bioavailable, readily able to cross the blood-brain barrier, and endowed with a plasma terminal half life of 6.7 hours after IP delivery. These favorable pharmacological properties facilitated a dose response experiment wherein daily oral administration of Example 45 Compound to adult mice was monitored for both brain levels of the chemical and pro-neurogenic efficacy (FIG. 7). Maximal, pro-neurogenic efficacy was observed at oral doses of 5 mg/kg and above, and graded reductions in efficacy were observed at doses of 2.5 and 1 mg/kg. Liquid chromatography-mass spectrometry analysis of the brain levels of Example 45 Compound in the dose ranges of 1, 2.5 and 5 mg/kg revealed corresponding compound concentrations of 213 nM (101 ng/g brain tissue), 1.13 µM (534 ng/g brain tissue) and 1.35 µM (640 ng/g brain tissue) five hours after dosing.

Figure 8:
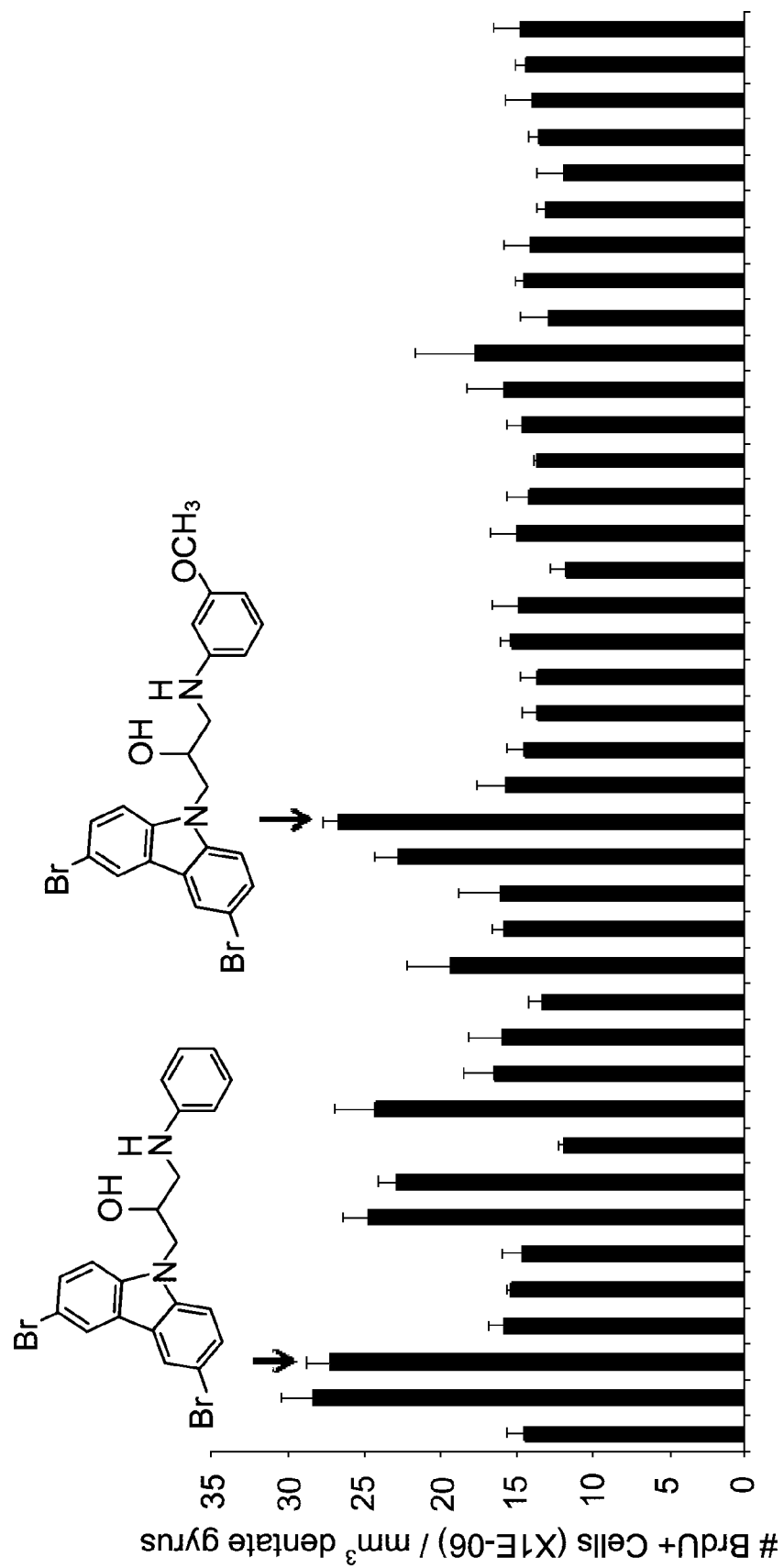
FIG. 8: Analysis of molecules related structurally to Example 45 Compound (P7C3) revealed a region of the compound that could be chemically modified without loss of in vivo activity. An in vivo SAR study was conducted using 37 chemical analogs of Example 45 Compound, each evaluated in 4 or 5 adult C57/B6 male mice. Some analogs revealed activity comparable to the parent compound, whereas others showed significantly diminished activity, or evidence of pro-neurogenic effect intermediate between vehicle and FGF controls. This exercise enabled identification of regions of the parent compound that might be amenable to chemical modification without loss of activity. As an example, Example 62 Compound retained robust activity with the aniline ring of Example 45 Compound substituted by an anisidine. This derivative compound was exploited to yield a fluorescent derivative by attaching a coumarin moiety to the N-phenyl ring.
Figure 9B:
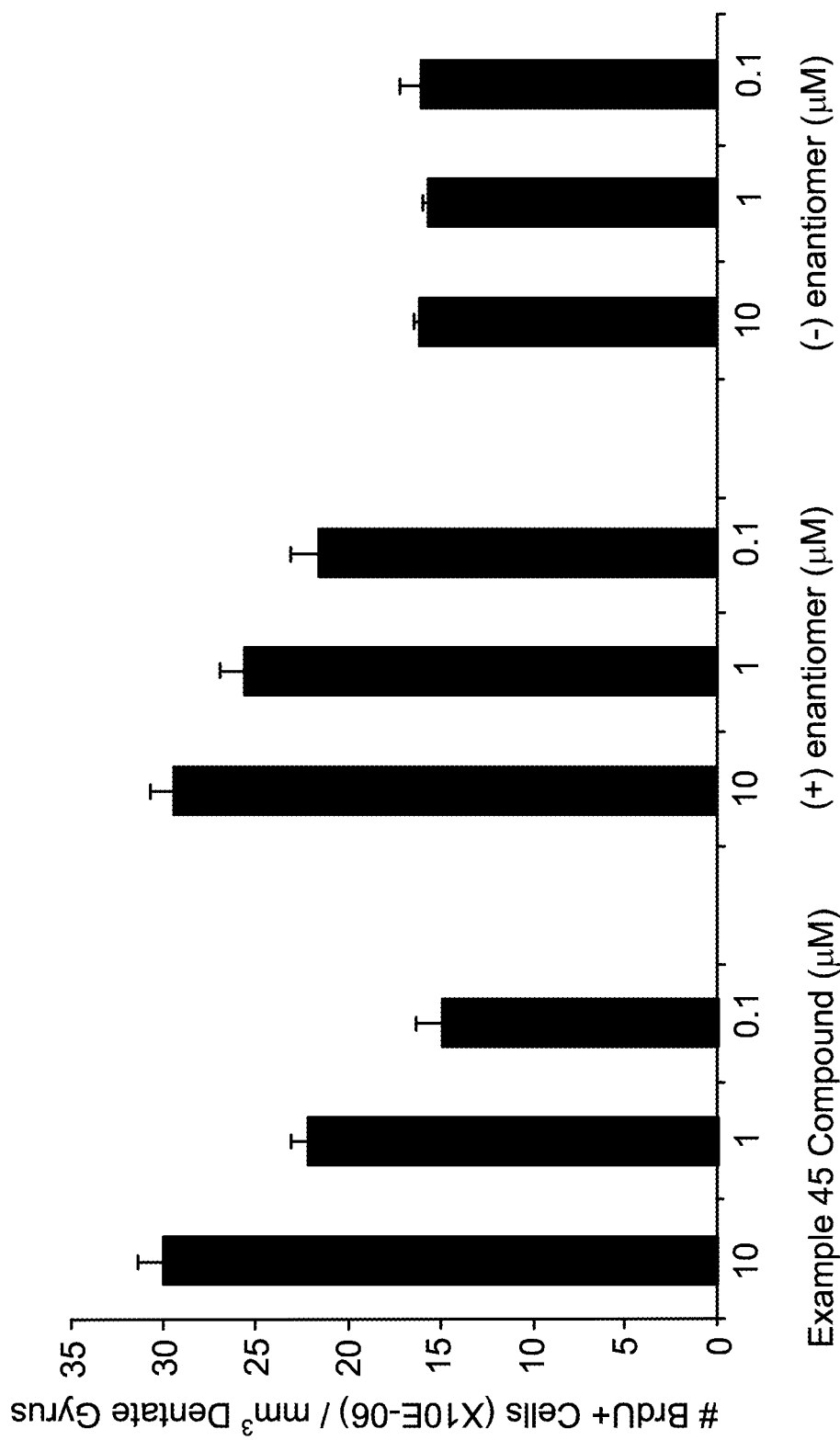

B. Enantiomer Selective Activity of Example 45 Compound Derivatives:

In order to further study Example 45 Compound, an in vivo structure activity relationship (SAR) study was conducted using 37 chemical derivatives of the compound for pro-neurogenic activity via direct administration into the brain of adult mice via Alzet minipumps. Compounds were administered for one week at 10 uM into 4 mice per compound, along with daily IP injections of BrdU. Following compound administration, animals were perfused, sacrificed and subjected to sectioning, staining and light microscopy in order to monitor hippocampal neurogenesis localized to the subgranular layer of the dentate gyms. Roughly 10% of the variant compounds retained pro-neurogenic activity indistinguishable from the parent compound. An approximately equal number of compounds yielded slightly diminished activity, yet the majority of variants were of significantly diminished activity (FIG. 8). For example, a variant of Example 45 Compound having a methoxy substitution on the aniline ring (Example 62 Compound) was re-tested for pro-neurogenic activity via direct administration into the brain of adult mice via Alzet minipumps. The compound was administered for one week at 10 µM into 4 mice which were injected daily with BrdU. Following compound administration, animals were perfused, sacrificed and subjected to sectioning, staining and light microscopy in order to monitor hippocampal neurogenesis localized to the subgranular layer of the dentate gyms. The methoxy derivative exhibited activity comparable to Example 45 Compound. Subsequently, the (+) and (−) enantiomers of Example 62 Compound were prepared (FIG. 9A). The two enantiomers were evaluated in the in vivo neurogenesis assay. The (+)-enantiomer of Example 62 Compound retained potent pro-neurogenic activity, and the (−) enantiomer displayed diminished activity (FIG. 9B). Other derivatives have also been resynthesized and retested, as described above.

Figure 10A:
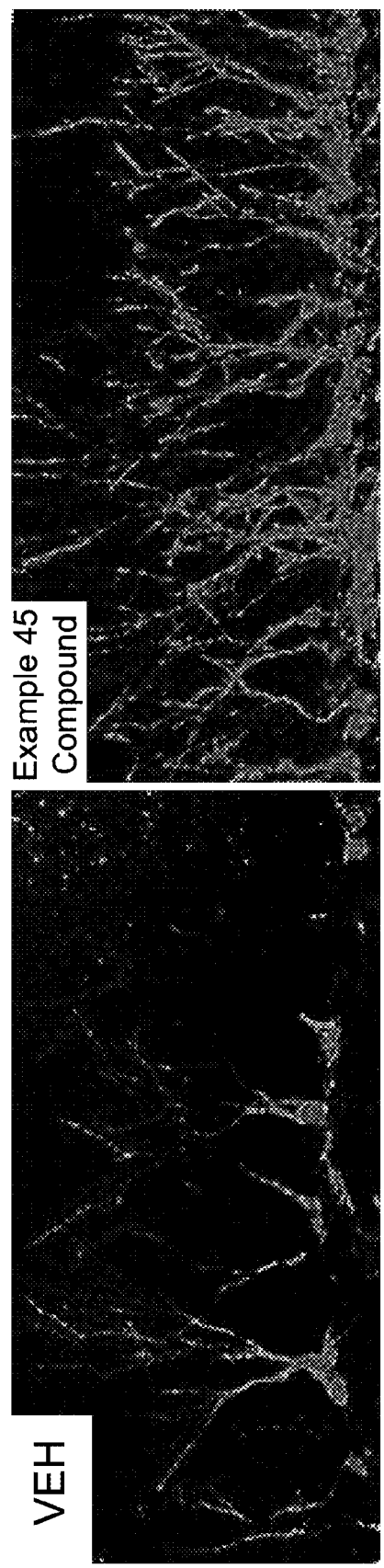

C. Example 45 Compound Enhances the Survival of Newborn Neurons:

The nature of the cells produced in the subgranular zone of the dentate gyrus was investigated when Example 45 Compound was administered as follows. Animals were exposed to oral administration of Example 45 Compound for 30 days. Brain tissue was then prepared for immunohistochemical staining with an antibody to doublecortin (DCX), a microtubule-associated protein that serves as a marker of neurogenesis in the dentate gyrus by virtue of transient expression in newly formed neurons, but not glial cells, between the timing of their birth and final maturation (Brown et al., 2003). As shown in FIG. 10A, the relative abundance of doublecortin-positive neurons increased dramatically as a function of exposure to prolonged administration of Example 45 Compound. Although this observation does not rule out the possibility that the compound might also enhance the formation of glial cells, it clearly shows that Example 45 Compound enhanced the formation of cells destined to become neurons.

Example 45 Compound-mediated neurogenesis was next investigated to see whether it was attributable to increased cell proliferation or protection of newborn cells from cell death during the time between their birth and eventual incorporation into the granular layer of the dentate gyrus. This was accomplished by comparing the ability of Example 45 Compound to enhance either short- or long-term increases in the incorporation of BrdU in the dentate gyrus (FIG. 10B). Animals exposed to orally-delivered Example 45 Compound or vehicle for 30 days were administered a single pulse of BrdU via IP injection. Short-term effects on neuron birth were monitored by sacrificing animals one hour post-BrdU injection, followed by fixation of the tissue, sectioning and immunohistochemical detection of BrdU incorporation into cells localized in the subgranular layer of the dentate gyrus. Example 45 Compound administration did not lead to an elevation in the level of BrdU-positive cells relative to vehicle in this short-term assay. At one day after BrdU administration both groups still showed no statistically significant differences in number of BrdU+ cells in the dentate gyrus. By contrast, at the 5 day time point, by which time 40% of newborn cells in our assay normally die (FIG. 1), animals that received Example 45 Compound showed a statistically significant, 25% increase in BrdU+ cells compared to the vehicle-only control group. This difference between groups progressed with time such that mice that received a daily oral dose of Example 45 Compound for 30 days starting 24 hours after the pulse treatment of BrdU exhibited a 5-fold increase in the abundance of BrdU-positive cells in the dentate gyrus relative to vehicle-only controls. Notably, in this longer-term trial, BrdU-positive cells were observed not only along the subgranular layer of the dentate gyrus where new neurons are known to be born, but also within the granular layer itself. It is hypothesized that these cells represent mature neurons that have migrated into the granular layer, completed the differentiation process, and incorporated themselves into the dentate gyrus as properly wired neurons. Observations supportive of this interpretation will be presented in a subsequent section of this document. In summary, these experiments give evidence that Example 45 Compound enhances the formation of neurons in the mature hippocampus, and that its mode of action would appear to take place at some point subsequent to their birth.

It should be appreciated by one of ordinary skill in the art that the above described cell proliferation tests can also be used to test other compounds of presently disclosed embodiments.

Figure 11:
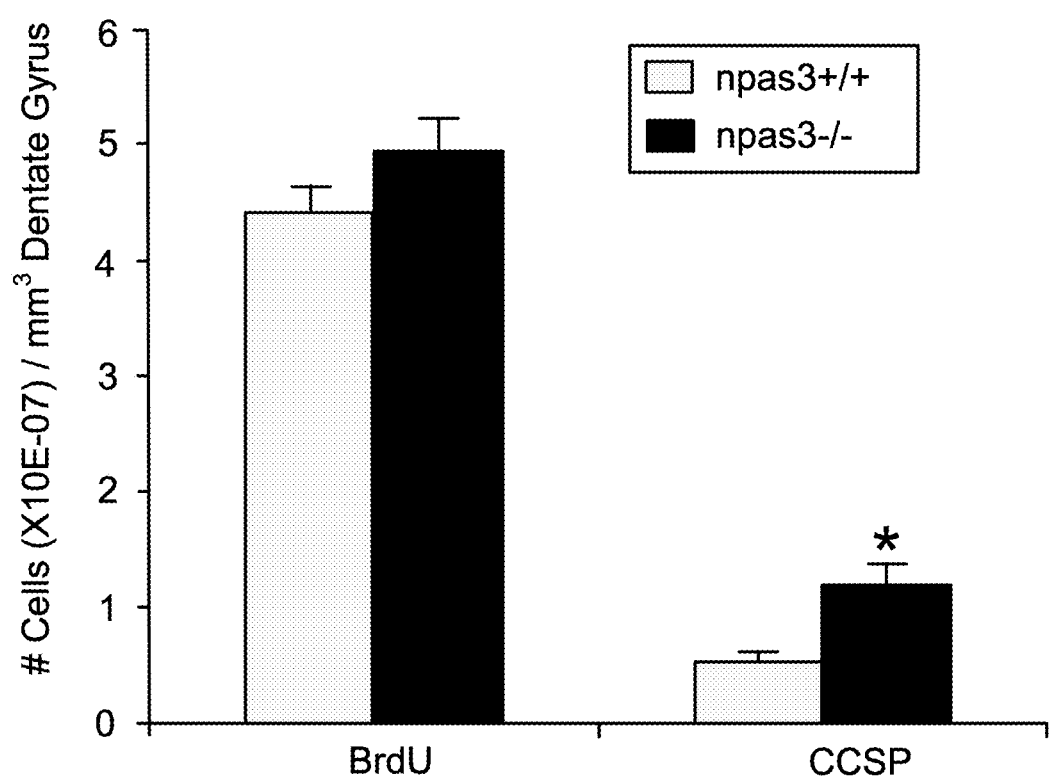
FIG. 11: Quantification of short term (1 hour pulse) BrdU incorporation and cleaved-caspase 3 (CCSP3) formation in the dentate gyrus showed that NPAS3-deficient mice have the same rate of proliferation of newborn cells in the dentate as wild type littermates (BrdU), but roughly twice the level of programmed cell death (CCSP3) (*, P<0.01, Student's t test). Three 6 week old male mice (NPAS3-deficient or wild type littermates) in each group were evaluated.

D. Example 45 Compound Normalizes Apoptosis and Ameliorates Morphological and Electrophysiological Deficits in the Dentate Gyrus of NPAS3-Deficient Mice:

Mice lacking both copies of the gene encoding neuronal PAS domain protein 3 (NPAS3) suffer a profound impairment in adult neurogenesis (Pieper et al., Proc. Natl. Acad. Sci. USA 2005, 102, 14052-14057). By evaluating BrdU incorporation in a short-term assay of neurogenesis by sacrificing animals 1 hours after BrdU pulse, it was observed that NPAS3-deficient animals have no detectable deficit in the birth of neurons in the subgranular layer of the dentate gyms (FIG. 11). This is in contrast to our earlier observations of profoundly diminished BrdU labeling in the dentate gyms of NPAS3-deficient animals when BrdU is administered for a longer period of time (12 days) (Pieper et al., Proc. Natl. Acad. Sci. USA 2005, 102, 14052-14057). Knowing that the NPAS3 transcription factor is required for proper expression of the fibroblast growth factor receptor 1 (FGFR1) in the hippocampus (Pieper et al., Proc. Natl. Acad. Sci. USA 2005, 102, 14052-14057), it is possible that impediments in growth factor signaling might impair the trophic environment critical for the survival of newborn neurons in the dentate gyms. As an initial test of this hypothesis, brain tissue prepared from NPAS3-deficient animals was compared with that of wild type littermates for the presence of cleaved caspase 3 (CCSP3)-positive cells in the subgranular layer of the dentate gyms. A statistically significant, 2-fold increase in CCSP3-positive (apoptotic) cells was observed in the dentate gyms of NPAS3-deficient animals (FIG. 11). This enhanced rate of programmed cell death is likely to account, at least in part, for the nearly complete elimination of adult neurogenesis in mice lacking the NPAS3 transcription factor (Pieper et al., Proc. Natl. Acad. Sci. USA 2005, 102, 14052-14057).

Figure 12A:
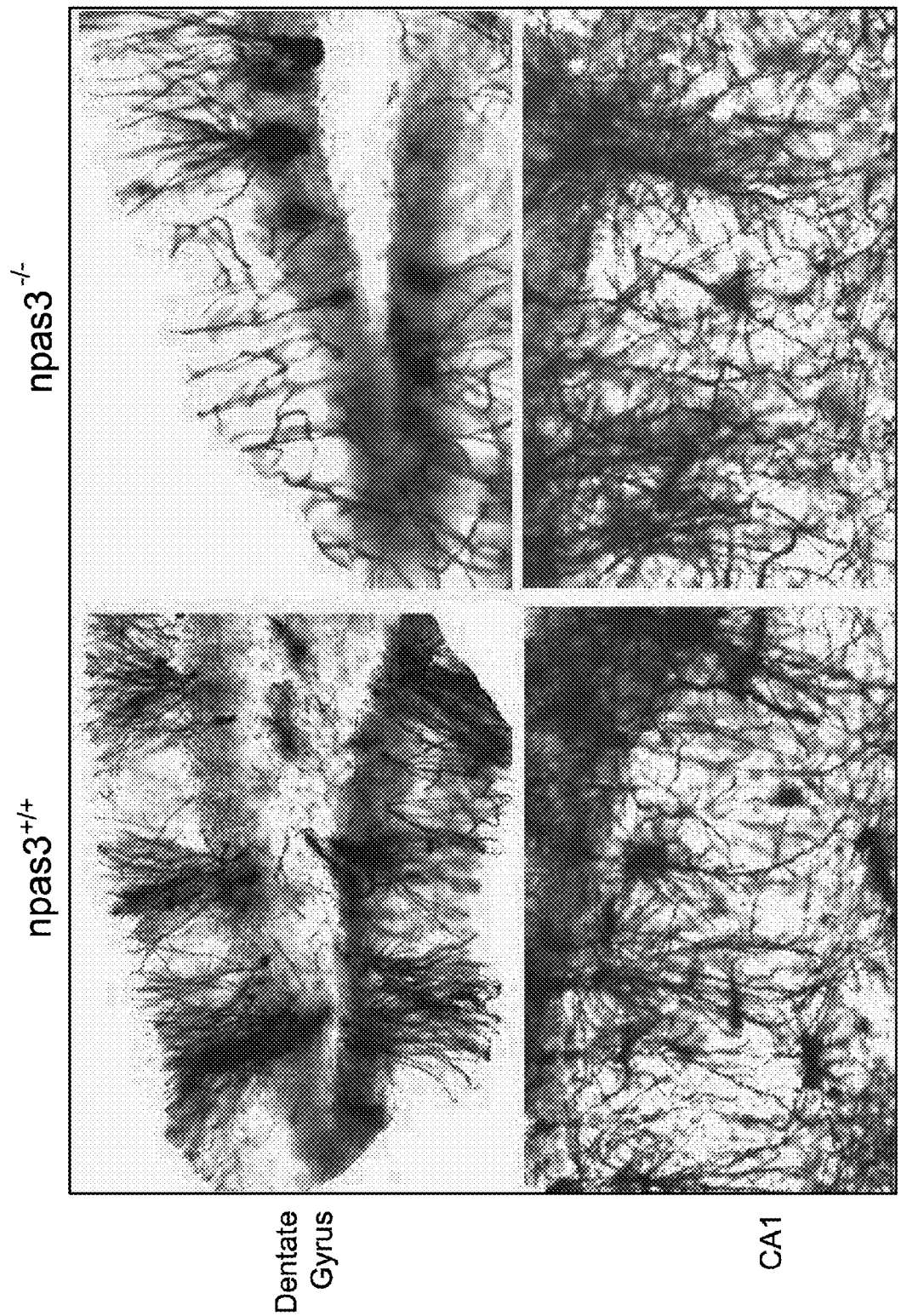
FIG. 12A and FIG. 12B: Granule cell neurons in the dentate gyrus of NPAS3-deficient mice displayed morphological deficits in dendritic branching and spine density.
Figure 12B:
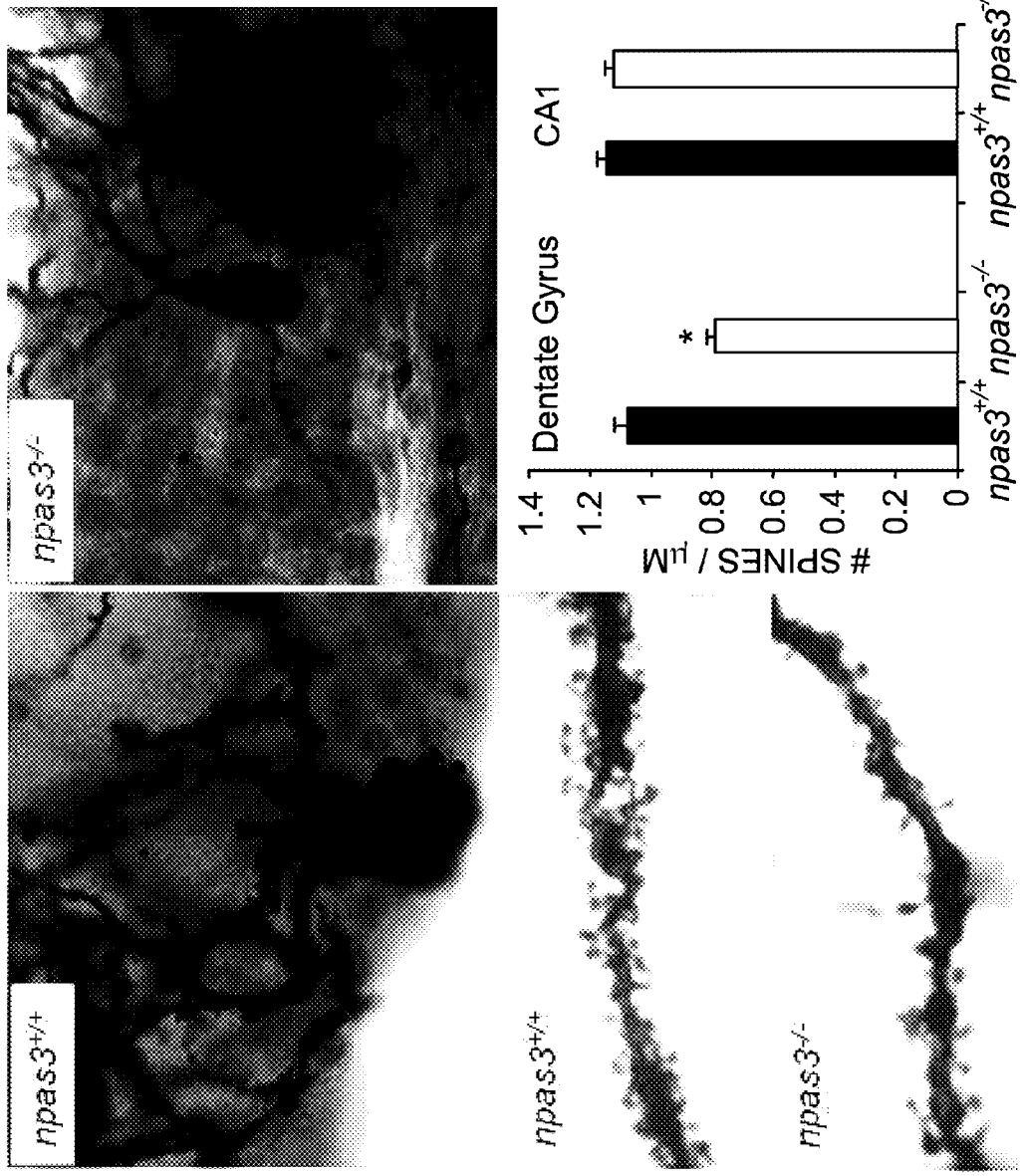
Figure 13A:
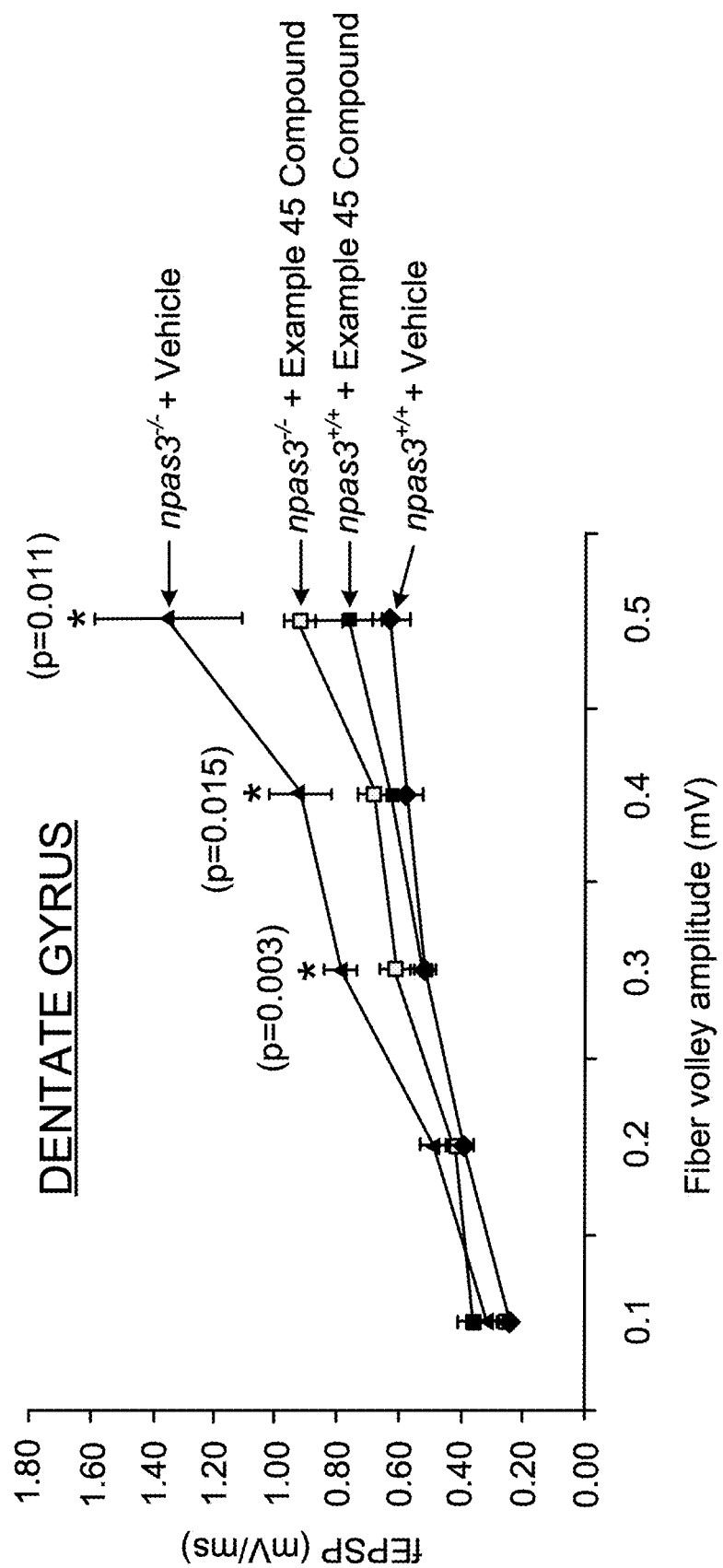
FIG. 13A and FIG. 13B: In hippocampal slice preparation from npas3$^{-/-}$ mice, synaptic transmission was increased both in the outer molecular layer of the dentate gyrus (FIG. 13A) and the CA1 region of the hippocampus (FIG. 13B) relative to hippocampal slices from wild type mice. Extended treatment with Example 45 Compound normalized synaptic responses in the dentate gyrus but not the CA1 region of npas3$^{-/-}$ mice. Extended treatment with Example 45 Compound did not affect wild-type responses. Data are presented as the mean±SEM. Each group consisted of 1 or 2 slice preparation from each of 5 mice.
Figure 13B:
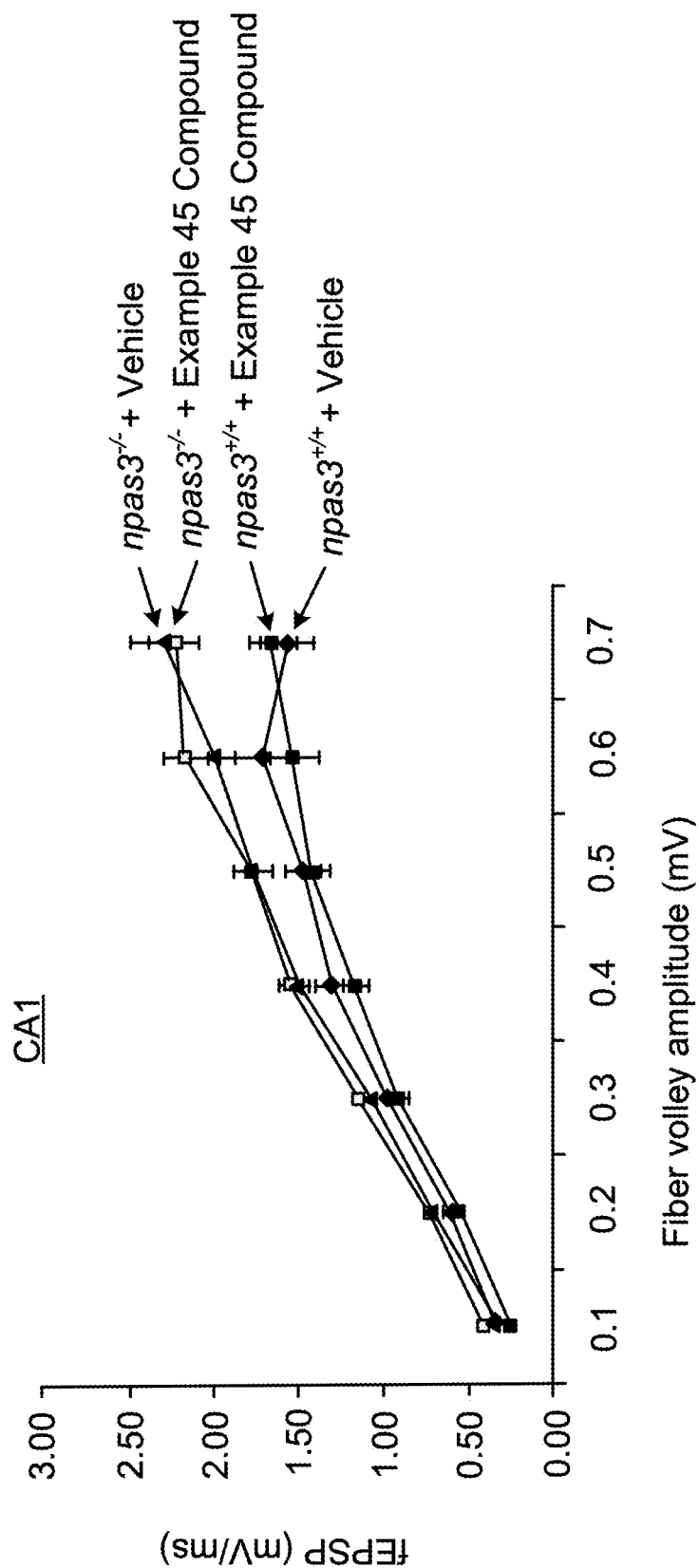

In addition to this quantitative deficit in adult neurogenesis, abnormalities have been observed in both the morphology and electrophysiology of granular neurons of the dentate gyms of NPAS3-deficient animals. Relative to wild type animals, Golgi-Cox staining revealed severe attenuation in dendritic branching and spine density of dentate gyms granular neurons of NPAS3-deficient animals (FIGS. 12A and 12B). By contrast, no genotype-dependent differences in these measures were observed in pyramidal cells of the CA1 region of the hippocampus. Equivalently specific deficits were observed by electrophysiologic recordings of NPAS3-deficient animals compared with wild type littermates (FIGS. 13A and 13B). Whole field recordings of excitatory postsynaptic potentials (fEPSP) revealed significant deficits in NPAS3-deficient animals, relative to wild type littermates. In the dentate gyms, stimulating and recording electrodes were positioned in the outer molecular layer, which is innervated by axons of the perforant pathway originating from the entorhinal cortex. In the CA1 region of the hippocampus, stimulation and recording electrodes were positioned in the stratum radiatum, which is innervated by the Schaffer collateral axons of CA3 pyramidal cells. Stimulus intensity was increased in 5 µA increments, the slope of the decreasing part of field potentials was measured, and fEPSP was quantified relative to the amplitude of the fiber volley, which represents firing of action potentials in pre-synaptic axons. This analysis revealed aberrant hyper-excitability of synaptic transmission in npas3$^{-/-}$ mice both in the outer molecular layer of the dentate gyms and in the CA1 region (FIGS. 13A and 13B).

Figure 14:
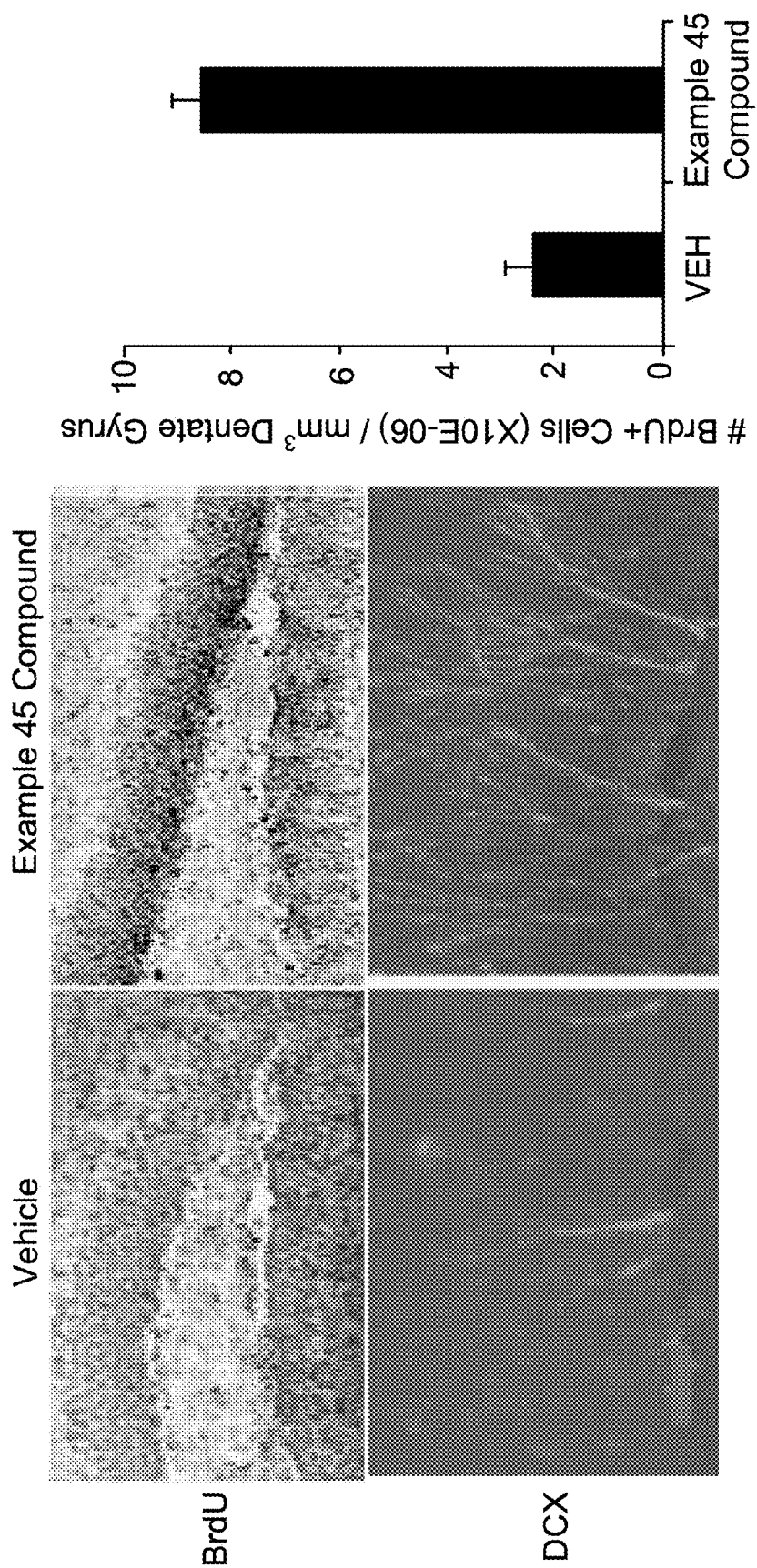
FIG. 14: Example 45 Compound has pro-neurogenic or neuroprotective efficacy in the dentate gyrus of NPAS3-deficient animals. Six 12 week old npas3$^{-/-}$ mice were orally administered vehicle or Example 45 Compound (20 mg/kg/d) for 12 days, and also injected daily with BrdU (50 mg/kg). At the end of day 12, mice were sacrificed and tissue was stained for BrdU and doublecortin (DCX). BrdU staining showed that Example 45 Compound increased the magnitude of neurogenesis in npas3$^{-/-}$ mice by roughly 4-fold, as graphically represented above (*, P<0.001, Student's t test). DCX staining shows that Example 45 Compound also promoted more extensive process formation in differentiating neurons of the adult dentate gyrus in npas3$^{-/-}$ mice.

Armed with these genotype- and region-specific deficits in both neuron morphology and electrophysiological activity, whether prolonged administration of Example 45 Compound might favorably repair either deficit in NPAS3-deficient animals was tested. Before embarking on this effort, it was first confirmed that Example 45 Compound was capable of enhancing hippocampal neurogenesis in NPAS3-deficient mice, by demonstrating that Example 45 Compound enhances both BrdU incorporation as well as expression of doublecortin in newborn neurons in the dentate gyms of npas3$^{-/-}$ mice (FIG. 14). Knowing that formation of the dentate gyms initiates in the late pre-natal mouse embryo around embryonic day 14 (Stanfield and Cowan, 1988, The development of the hippocampal region. In Cerebral Cortex, E. G. Jones and A. Peters, eds. (New York: Plenum Press), pp. 91-131), animals were exposed to Example 45 Compound for as extended a period of time as possible in order to give the compound the best possible chance for exhibiting favorable effects. Following oral gavage of pregnant female mice, 14 day embryos were recovered, dissected and processed by acetonitrile:water extraction so that Example 45 Compound levels could be measured in the embryonic brain. Daily administration of 20 mg/kg of Example 45 Compound to pregnant females yielded appreciable levels of the compound in the brain tissue of developing embryos. It was similarly observed that oral administration of the compound to lactating females led to delivery of Example 45 Compound to the brain tissue of weanling pups. In both cases, LC/MS-based quantitation of Example 45 Compound revealed levels of compound accumulation at or above the 1.35 µM limit required to support adult neurogenesis (FIG. 7). Finally, it was observed that daily IP administration of Example 45 Compound to weaned pups at 20 mg/kg was sufficient to yield brain levels of Example 45 Compound at or above the level required to enhance adult neurogenesis.

Figure 15:
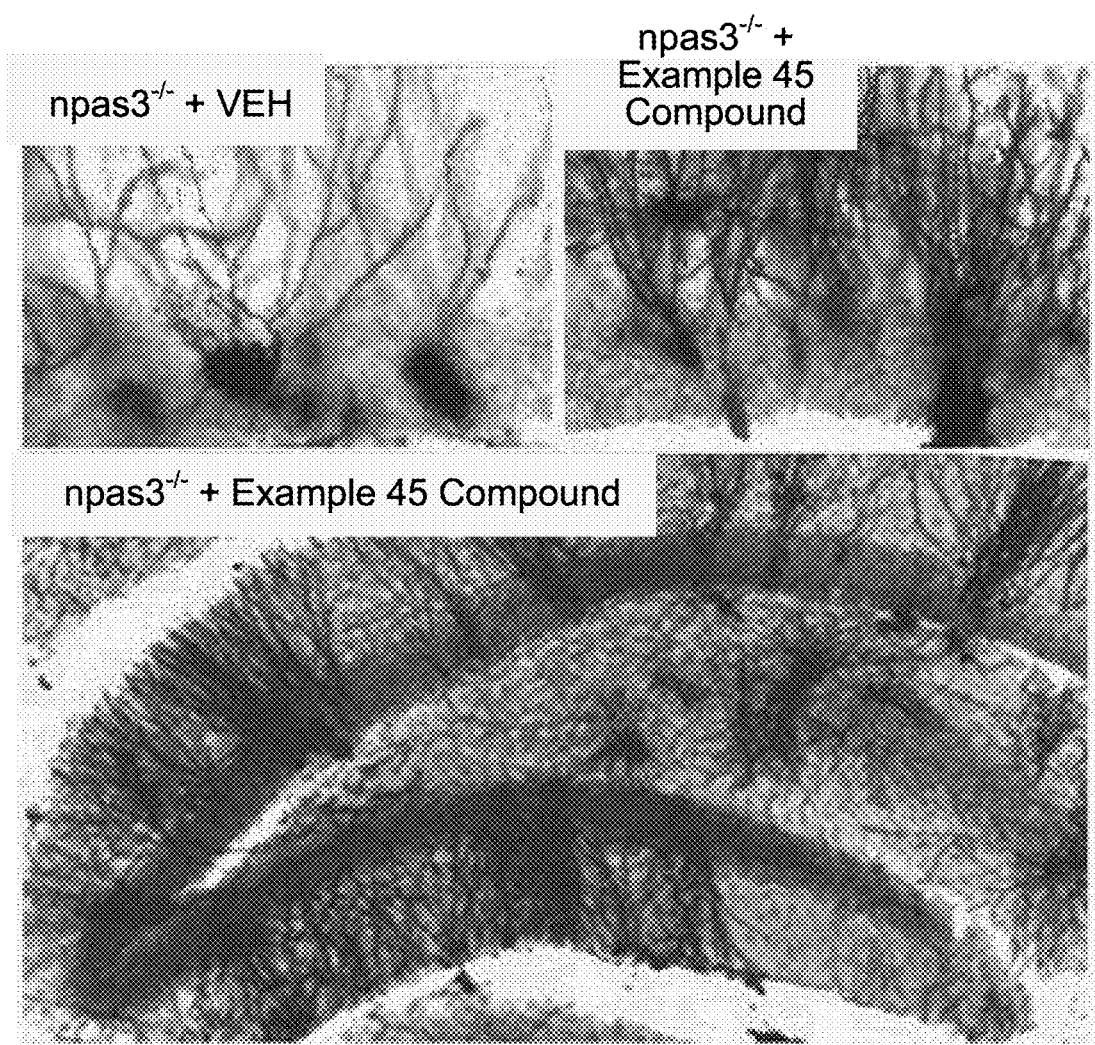
FIG. 15: Golgi-Cox staining of neurons in the dentate gyrus shows that extended daily treatment of npas3$^{-/-}$ mice with Example 45 Compound (20 mg/kg/d) enhanced dendritic arborization. Hi-power micrographs are shown on top, and a lower power micrograph illustrating the entire dentate gyrus is shown below.

Female mice heterozygous at the NPAS3 locus were mated to heterozygous males. Two weeks post-mating, females were given a daily oral gavage of either 20 mg/kg of Example 45 Compound or vehicle-only formula. Dosing was continued throughout the last trimester of pregnancy, as well as the two week post-natal period of lactation. Following weaning, pups were given a daily IP dose of either 20 mg/kg Example 45 Compound or vehicle control. At about 7 weeks of age, mice were switched to oral gavage delivery of the same dose of Example 45 Compound. When mice were 3 months of age they were sacrificed and brain tissue was dissected and subjected to either Golgi-Cox staining or electrophysiological recording. As shown in FIG. 15, prolonged exposure to Example 45 Compound robustly repaired morphological deficits in the dendritic branching of granular neurons of the dentate gyrus in NPAS3-deficient mice. Moreover, as shown in FIG. 13A, the electrophysiological deficit in the dentate gyms of NPAS3-deficient mice was also corrected following prolonged exposure of mice to Example 45 Compound. The corresponding electrophysiological deficit in CA1 region of the hippocampus, however, was not affected (FIG. 13B), underscoring the specificity of Example 45 Compound to improving functioning of the dentate gyms in this animal model.

Figure 16:
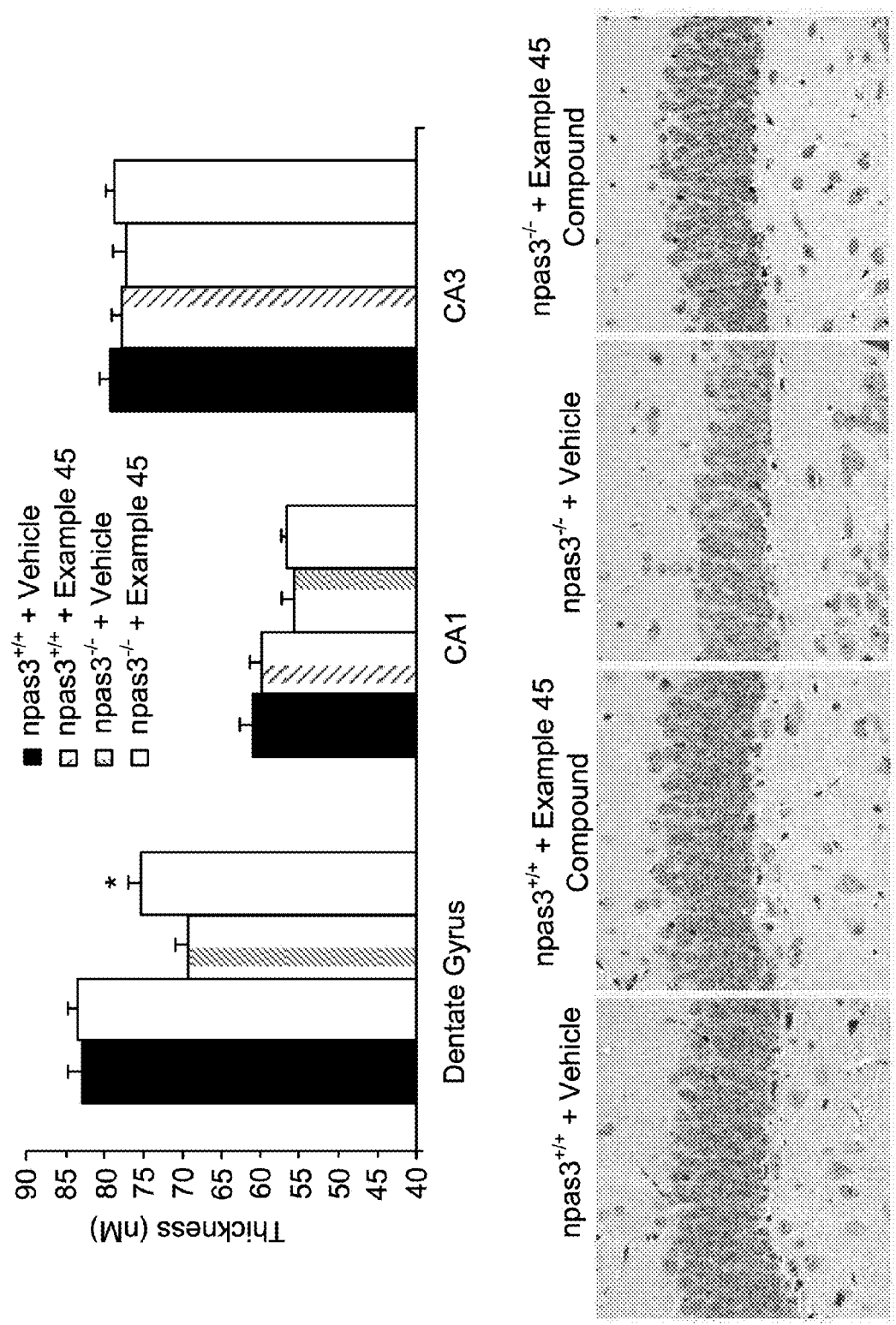
FIG. 16: Measured thickness of hippocampal subfields in npas3$^{-/-}$ and wild type littermate mice that were treated with Example 45 Compound (20 mg/kg/d) or vehicle every day from embryonic day 14 until 3 months of age demonstrated that Example 45 Compound selectively increased the thickness of the dentate gyrus granular cell layer to a level approaching wild type thickness (*, P<0.01, Student's t test), without affecting thickness of the pyramidal cell layers of CA1 or CA3 regions.

It is also notable that, relative to vehicle-only controls, administration of Example 45 Compound did not affect any aspect of the health of mothers, embryos, weanlings or young adult mice. Gross histology of brain tissue was normal in both compound- and vehicle-treated animals, and there was no evidence of neuronal cell loss or degenerative changes (cytoplasmic eosinophilia, vacuolization or nuclear pyknosis). The only morphological change, other than normalization of dendritic arborization of granular neurons of the dentate gyms, was a compound-dependent increase in the thickness of the granular layer of the dentate gyms itself (FIG. 16). The thickness of the granular layer of the dentate gyrus is roughly 40% less in NPAS3-deficient animals than wild type littermates. Prolonged administration of Example 45 Compound through late embryonic development, early post-natal development, and two months post-weaning significantly corrected this deficit without affecting the thickness of other hippocampal layers in NPAS3-deficient mice (FIG. 16).

Figure 17:
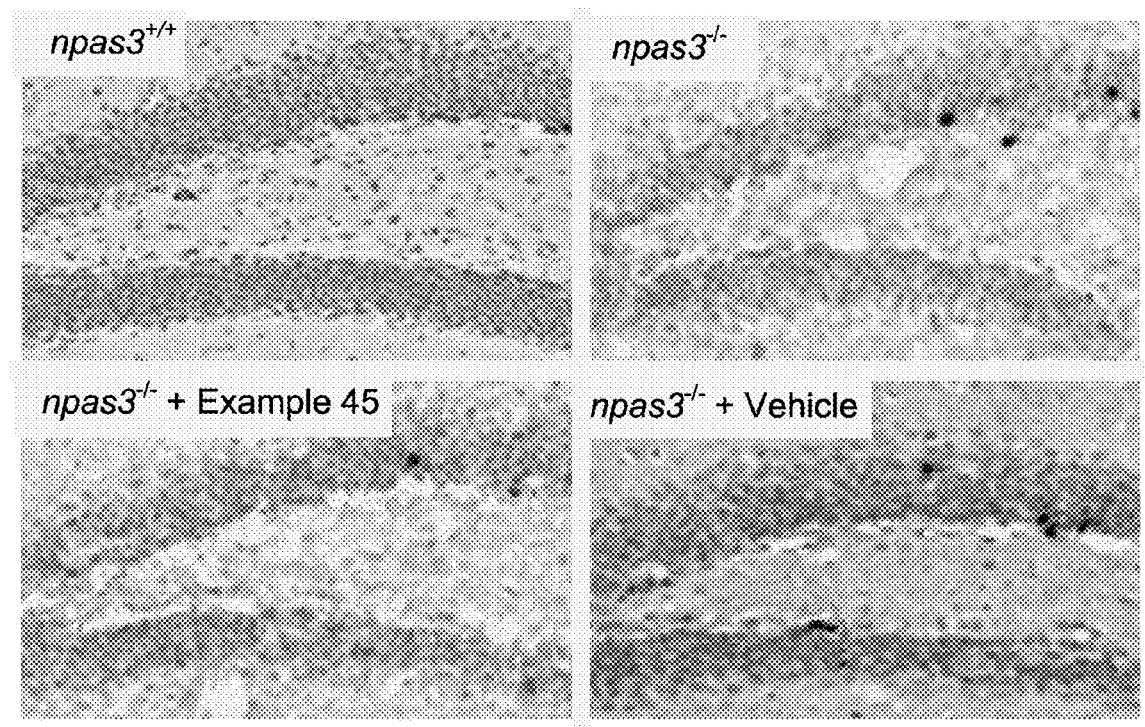
FIG. 17: Immunohistochemical detection of cleaved caspase 3 (CCSP3), a marker of apoptosis, showed elevated levels of programmed cell death in the dentate gyrus of NPAS3-deficient animals. Apoptosis in NPAS3-deficient animals was inhibited by treatment with Example 45 Compound (20 mg/kg/d, p.o., for 12 days), whereas analogous treatment with vehicle alone had no effect. Images shown are representative of 10-12 sections evaluated per animal, with 3-5 eight-week-old male NPAS3-deficient mice per group.

Recognizing that the reduced thickness of the granular layer of the dentate gyrus in NPAS3-deficient animals could be attributed to elevated levels of apoptosis of newborn hippocampal neural precursor cells, the effect of Example 45 Compound treatment on apoptosis in the hippocampus of NPAS3-deficient animals was examined through immunohistochemical staining of cleaved caspase 3 (CCSP3). As shown in FIG. 17, 12 days of treatment with orally delivered Example 45 Compound (20 mg/kg) to adult NPAS3-deficient animals significantly reduced CCSP3 staining in the dentate gyms, whereas vehicle-treatment had not effect. It is thereby proposed that Example 45 Compound facilitated repair of the granular layer of the dentate gyms in NPAS3-deficient mice by ameliorating a genotype-specific exacerbation of programmed cell death.

It should be appreciated by one of ordinary skill in the art that the above described apoptosis tests can also be used to test other compounds of presently disclosed embodiments.

Figure 18:
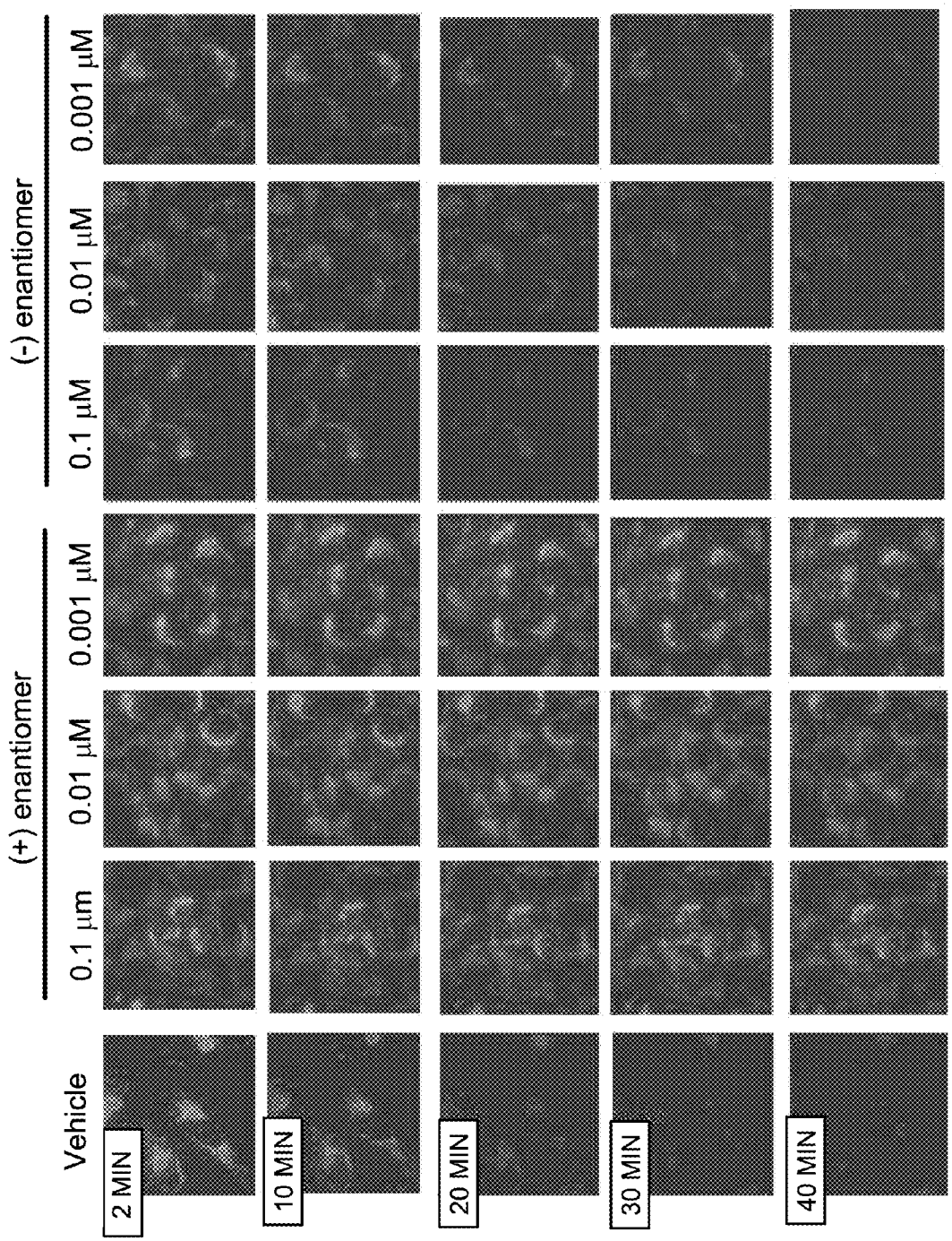
FIG. 18A and FIG. 18B: Example 45 Compound acts mechanistically in the mitochondria.

E. Example 45 Compound Protects Mitochondrial Integrity:

Extensive evidence pioneered by the laboratory of Xiaodong Wang has shown that an intrinsic pathway leading to programmed cell death emanates from mitochondria (Liu et al., Cell 1996, 86, 147-157; Yang et al., Science 1997, 275, 1129-1132). With the help of the Wang lab, assays were established to test whether Example 45 Compound might protect mitochondria from calcium-induced dissolution (Distelmaier et al., Cytometry A 2008, 73, 129-138). Tetramethylrhodamine methyl ester (TMRM) is a cell-permeant, cationic red-orange fluorescent dye that is readily sequestered by active mitochondria. When loaded with TMRM dye, vehicle-only treated cells released the dye within 15 minutes of exposure to the calcium ionophore A23187. By contrast, dye release was prevented in cells exposed to as little as 10 ng of Example 45 Compound (FIG. 18A). As with in vivo neurogenesis assay, as well as the in vitro protection from $A\beta_{(25-35)}$-mediated toxicity of cultured cortical neurons, preservation of mitochondrial membrane potential in this assay was observed only with the (+) enantiomer of Example 62 Compound (FIG. 18B).

It should be appreciated by one of ordinary skill in the art that the above described mitochondrial integrity tests can also be used to test other compounds of presently disclosed embodiments.

Figure 19:
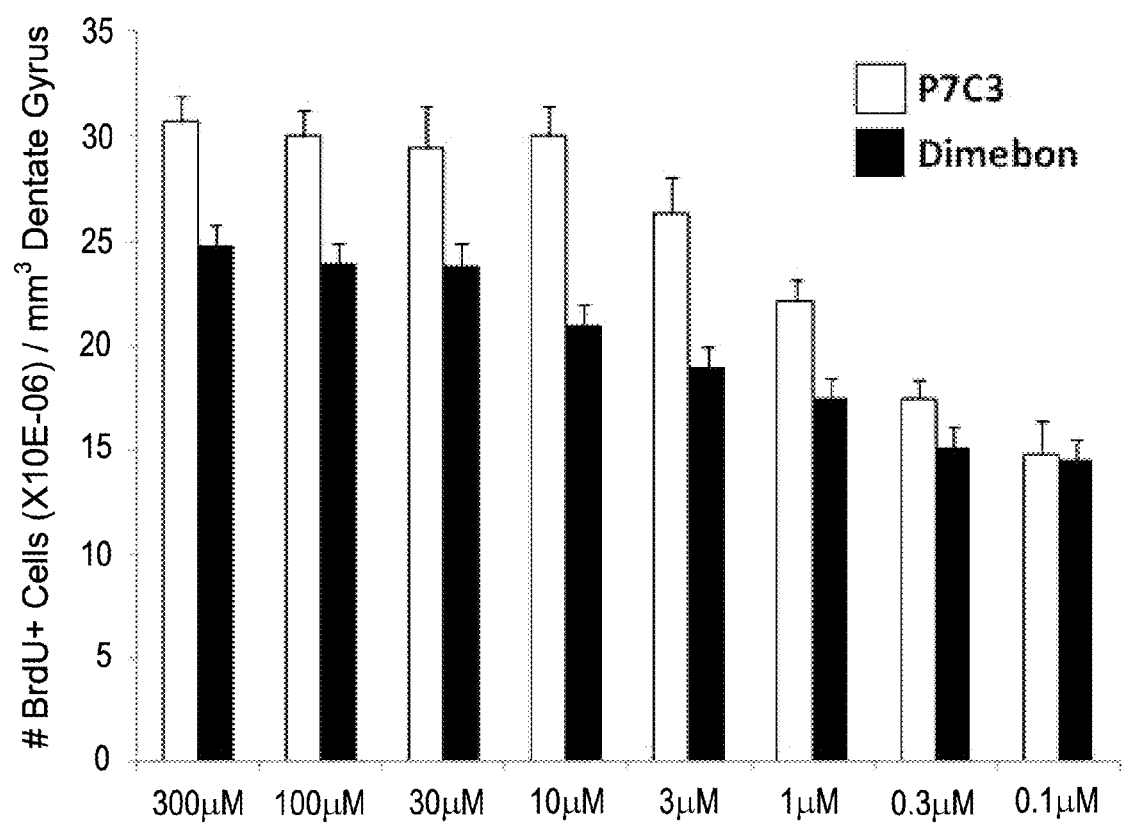
FIG. 19A, FIG. 19B and FIG. 19C: Example 45 Compound as compared to a known drug.
Figure 19:
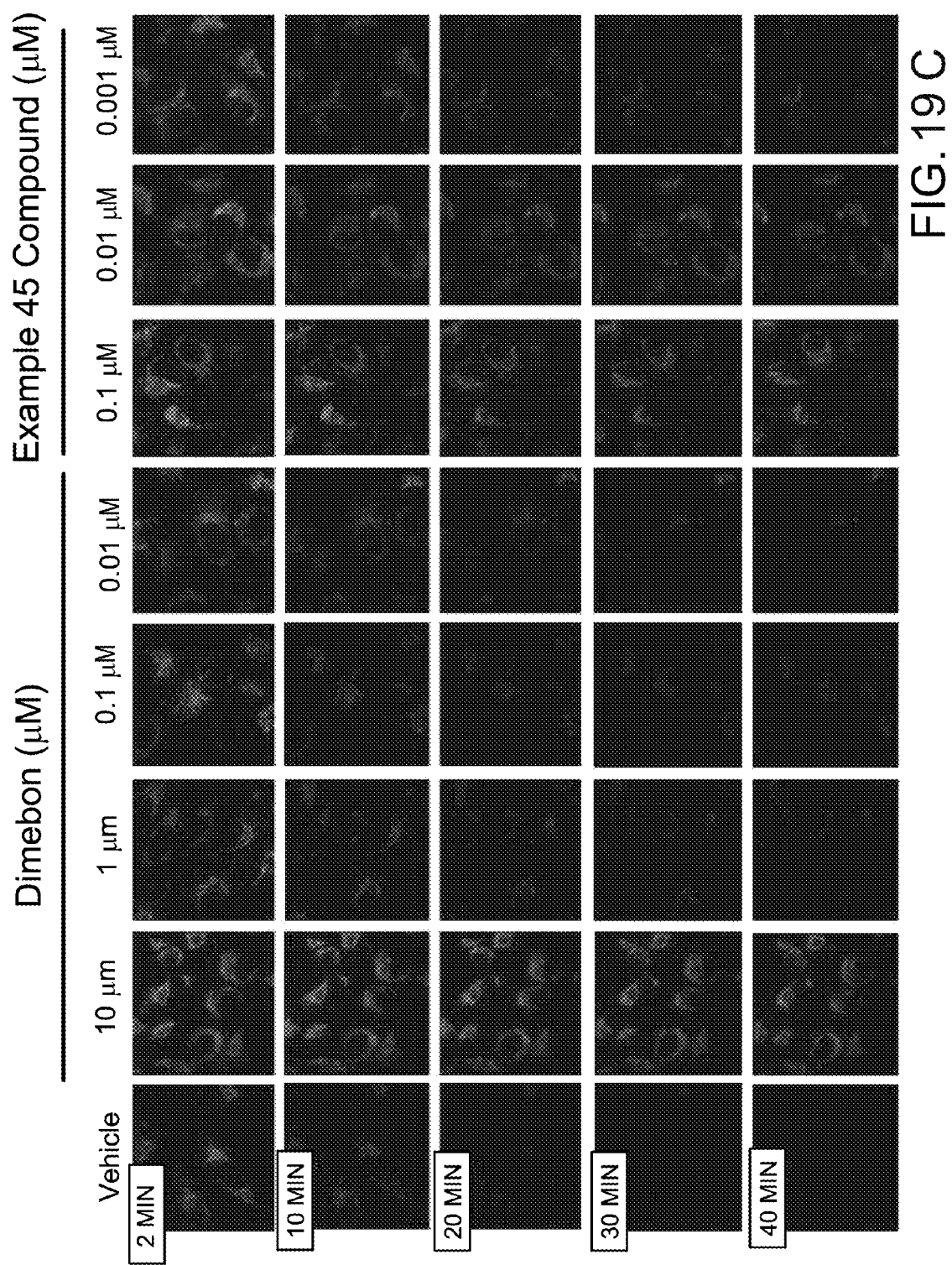

F. Comparison of Example 45 Compound and Dimebon:

A chemical compound sharing structural similarity to Example 45 Compound is 2,3,4,5-Tetrahydro-2,8-dimethyl-5-(2-(6-methyl-3-pyridyl)ethyl)-1H-pyrido(4,3-b)indole (FIG. 19A). An anti-histamine, trade named Dimebon, was anecdotally noticed over the decades to ameliorate symptoms of dementia (O'Brien, Lancet Neurol. 2008, 7, 768-769; Burns and Jacoby, Lancet 2008, 372, 179-180). More recently, an American biotechnology company designated Medivation initiated clinical trials to formally test whether Dimebon might improve the symptoms of patients suffering from Alzheimer's disease. The results of FDA-sponsored, phase 2 clinical trials in Alzheimer's disease were recently published, reporting favorable response rates (Doody et al., Lancet 2008, 372, 207-215). Example 45 Compound and Dimebon were compared in three functional assays. The in vivo test for effects on hippocampal neurogenesis revealed activity for both compounds, with Example 45 Compound exhibiting between 10- and 30-fold higher level of potency and a ceiling of efficacy roughly 40% higher than the anti-histamine drug (FIG. 19B). Dimebon has been implicated in protecting mitochondria (Bachurin et al., Ann. NY Acad. Sci. 2001, 939, 425-435; Bachurin et al., Ann. NY Acad. Sci. 2003, 993, 334-344, discussion 345-349). Therefore Dimebon was compared with Example 45 Compound in the calcium-induced mitochondrial dissolution assay. Both compounds were observed to be active, and it was again observed that the relative potency of Example 45 Compound was superior to Dimebon (FIG. 19C). Protection of mitochondrial membrane permeability was lost for Example 45 Compound between the 10 and 1 nM doses, whereas that of Dimebon was lost between 10 and 1 µM.

Example 45 Compound and Dimebon were tested for binding to the H1 histamine receptor. While Dimebon displayed high affinity for this receptor (IC50<100 nM), both enantiomers of Example 45 Compound display low H1 affinity (IC50>10 µM).

It should be appreciated by one of ordinary skill in the art that the above described binding activity tests can also be used to test other compounds of presently disclosed embodiments.

G. Effect of Example 45 Compound on Aged Rats

Next, aged Fisher rats were used as a means of performing behavioral tests capable of assessing the potential benefits of Example 45 Compound on hippocampus-dependent learning. It is well established that normal rodent aging is associated with attenuation of hippocampal neurogenesis (Kuhn et al., J. Neurosci. 1996, 16, 2027-2033; Driscoll et al., Neuroscience 2006, 139, 1173-1185). Reduced neurogenesis in aged rats is likely related to increased neuronal apoptosis in the aged rat brain (Martin et al., J. Biol. Chem. 2002, 277, 34239-34246; Kim et al., Exp. Gerontol. 2010, 45, 357-365). These changes have been hypothesized to contribute to cognitive decline as a function of terminal aging.

Figure 20A:
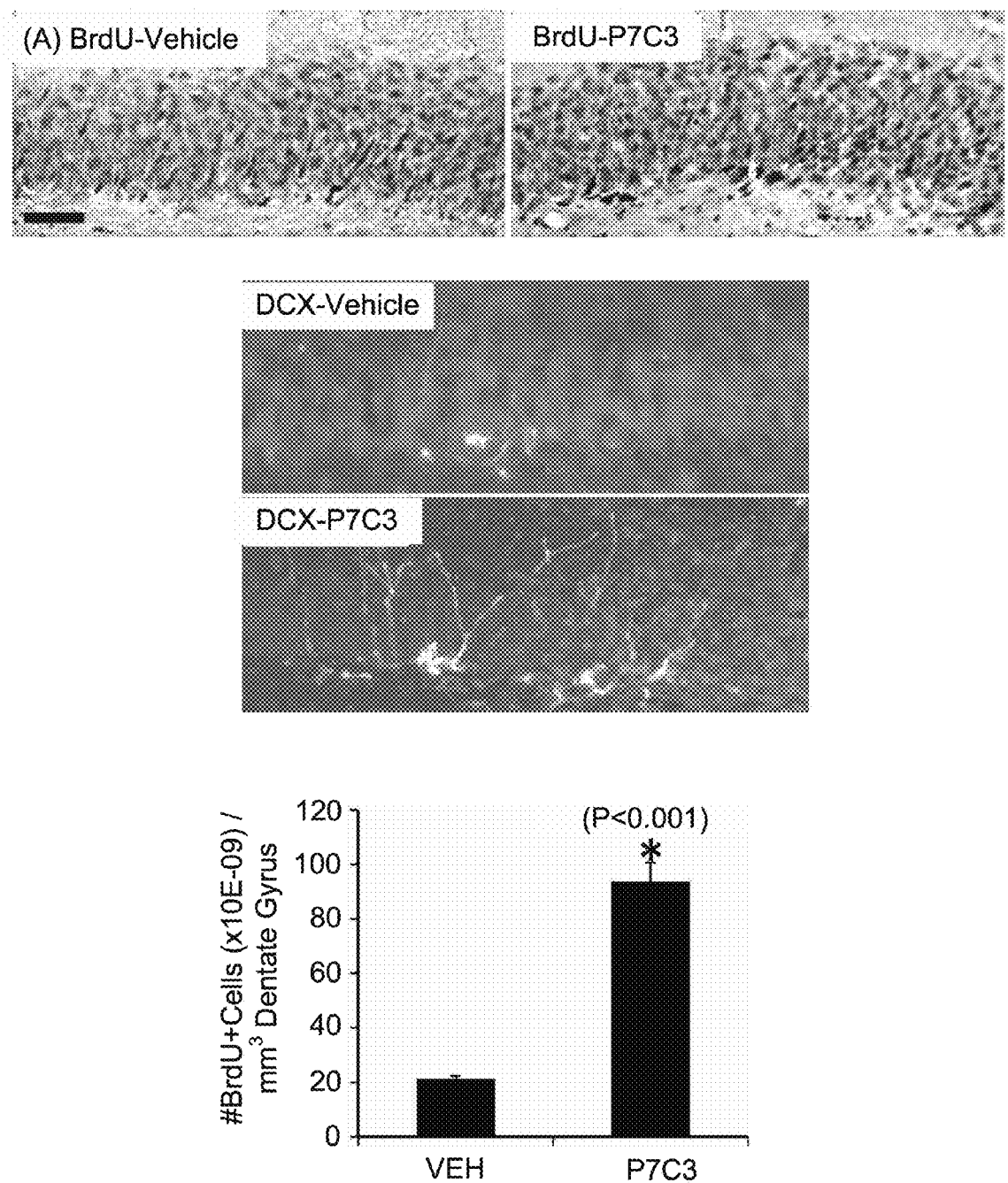

It was first evaluated whether Example 45 Compound would enhance hippocampal neurogenesis in aged rats as it does in adult mice. Rats were injected with a daily, IP dose of either 10 mg/kg of Example 45 Compound or vehicle, coinjected with a daily dose of BrdU, and then sacrificed after 7 days for immunohistochemistry. As shown in FIG. 20A, compound-treated animals revealed a 500% increase in BrdU labeling in the dentate gyms relative to vehicle-treated controls. Immunohistochemical staining with antibodies to doublecortin likewise revealed a robust, compound-specific enrichment in this marker of newborn neurons. Having observed proneurogenic efficacy of Example 45 Compound in this short term assay, it was then tested whether prolonged administration of Example 45 Compound might ameliorate age-related decline in cognition by subjecting 18-month-old rats to daily administration of either i 0 mg/kg of Example 45 Compound or vehicle only for 2 months. Animals of both groups were further subjected to weekly IP administration of BrdU (50 mg/kg) for later immunohistochemical measurements of hippocampal neurogenesis. As a control, both Example 45 Compound- and vehicle-treated groups were confirmed to display equal ability to physically participate in the task, and learn the task, as shown by decreased latency times to find the hidden platform over the 5 day training period, both before and after 2 months of treatment (FIG. 20B). Moreover, neither swim speed (FIG. 20C) nor locomotor activity (FIG. 20D) varied with age or treatment paradigm.

Figure 21A:
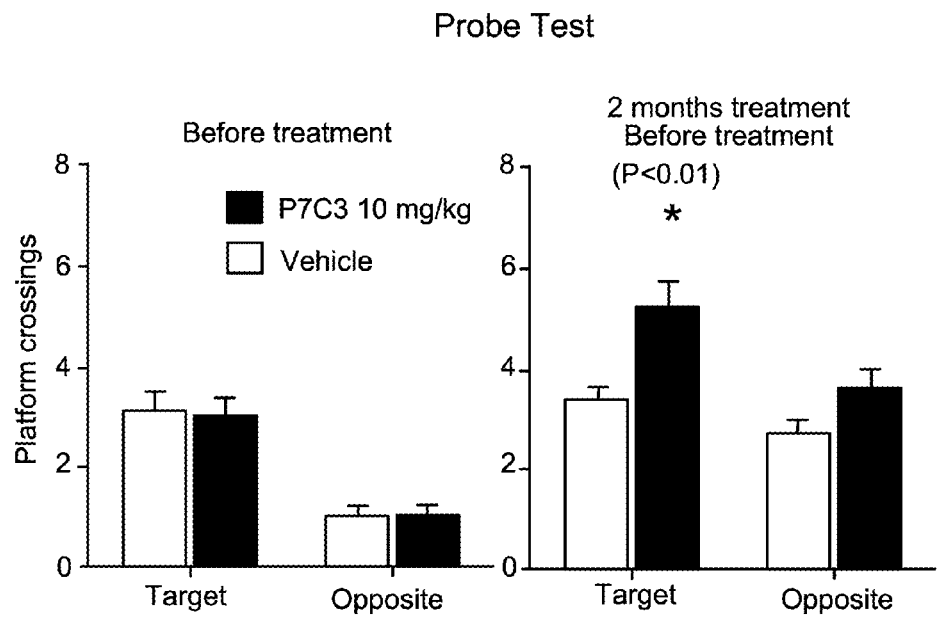
FIG. 21A, FIG. 21B, FIG. 21C and FIG. 21D: Example 45 Compound Enhances Hippocampal Neurogenesis, Ameliorates Cognitive Decline, and Prevents Weight Loss in Terminally Aged Rats (FIG. 21A) Prior to treatment, both groups (n—23 for each group) showed similar frequency of crossings through the goal platform. After 2 months of treatment, however, Example 45 Compound-treated rats displayed a statistically significant increase of crossings through the goal platform area relative to vehicle treated rats.

After 2 months of compound or vehicle administration, cognitive ability was assessed blind to treatment group by removing the goal platform. Animals of the Example 45 Compound-treated group retained a statistically significant improvement in ability to navigate to the region of the missing platform, as evidenced by performance in the probe test. As shown in FIG. 21A, when the platform was removed from the maze, rats treated with Example 45 Compound crossed the precise location previously containing the platform significantly more often than vehicle-treated rats. Furthermore, Example 45 Compound-treated rats spent a higher percentage of time in the general goal area, defined as the quadrant previously containing the platform, than vehicle-treated rats (35.5%±2.2% for Example 45 Compound treated, 28.1%±2.6% for vehicle treated, Student's t Test, p<0.02).

Figure 21B:
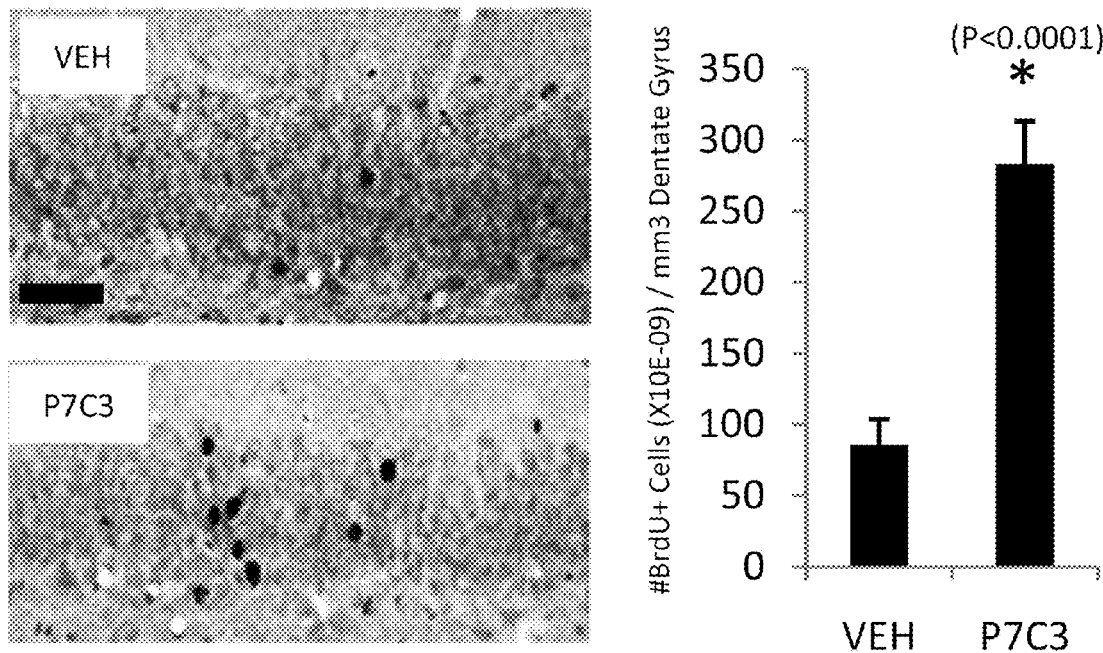
Figure 21C:
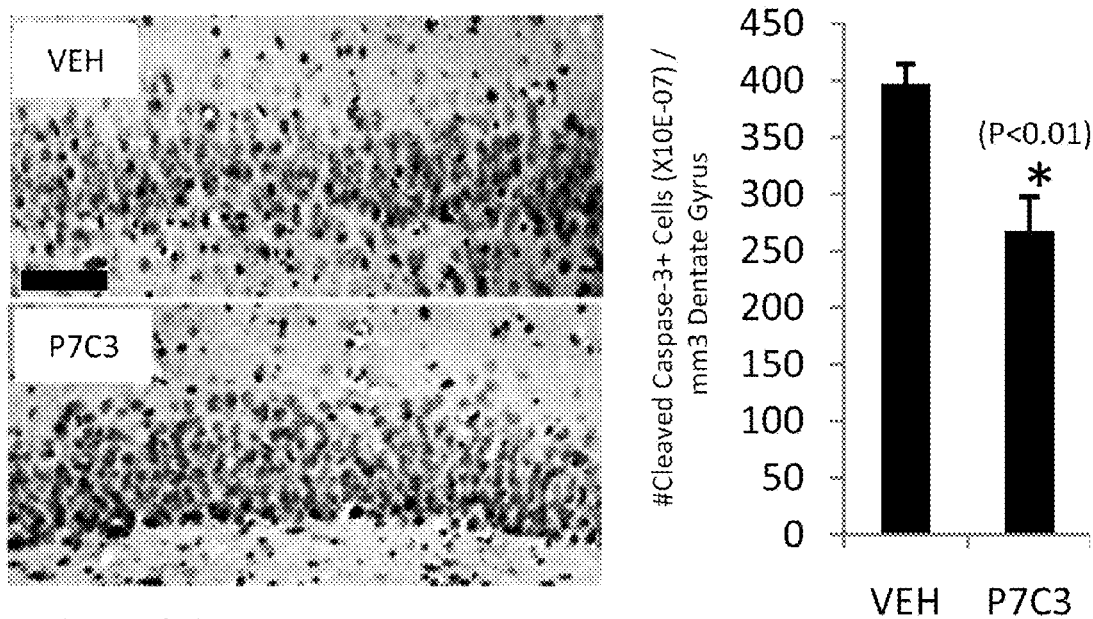
Figure 21D:
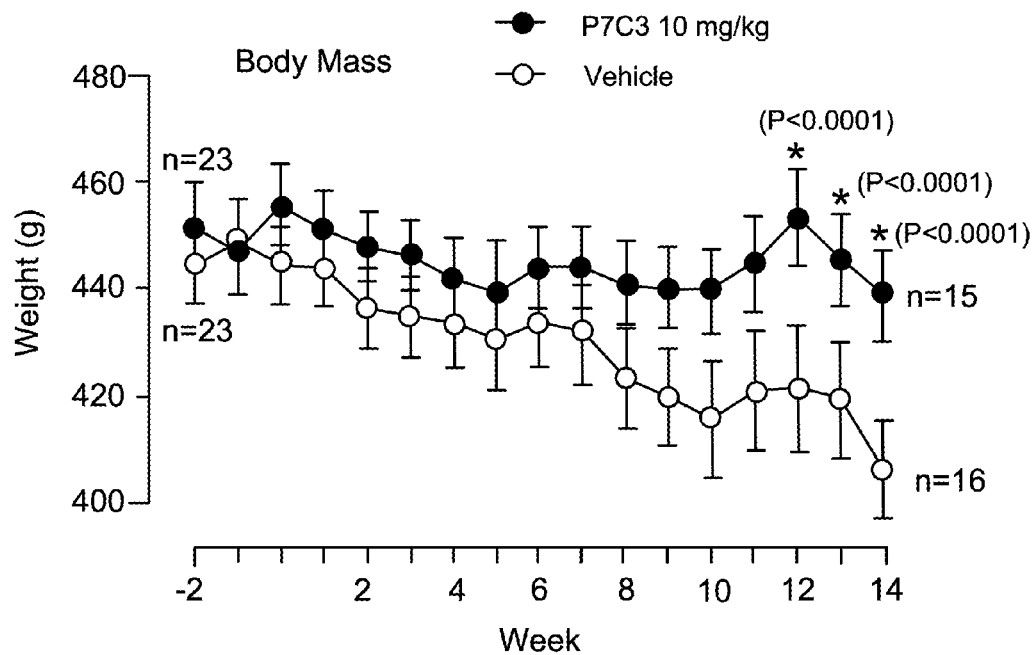

After behavioral testing, animals were sacrificed for immunohistochemical detection of BrdU and CCSP3. As shown in FIG. 21B, the dentate gyrus of rats exposed to Example 45 Compound showed a 3-fold higher level of BrdU-positive neurons than that of the vehicle group. Moreover, Example 45 Compound-treated animals showed a statistically significant reduction in the number of CCSP3-positive cells relative to vehicle controls (FIG. 21C). Unexpectedly, administration of Example 45 Compound helped rats maintain stable body weight with aging, in contrast to vehicle-treated rats, whose weight declined steadily with age (FIG. 21D). Example 45 Compound-mediated effects on body weight were independent of food intake (FIG. 20E), and treatment of aged rats with Example 45 Compound had no effect on postfasting blood glucose levels (FIG. 20E). Next it was tested whether Example 45 Compound-mediated preservation of body weight in aged rats operates via central or peripheral modes of action.

It should be appreciated by one of ordinary skill in the art that the above described in vivo tests in rats or other animal models can also be used to test other compounds of presently disclosed embodiments.

H. Example 45 Compound Augments Hypothalamic Neurogenesis

Positioned immediately below the thalamus and forming the floor and lower lateral walls of the third ventricle, the hypothalamus consists of multiple groups of cells that regulate the autonomic nervous system and also control motivational behaviors via extensive neuronal connections to the pituitary gland, thalamus, midbrain and cerebral cortex. These functions include water balance, biological rhythms, feeding and drinking drive, sexual activity, pituitary gland function and temperature regulation. Neural stem cells in the adult brain reside in the wall of the third ventricle and proliferate in response to various stimuli, and formation of new neurons in the hypothalamus has also been observed in the hypothalamic parenchyma. Administration of trophic factors such as brain-derived neurotrophic factor and ciliary neurotrophic factor enhances neurogenesis in the rodent hypothalamus. Furthermore, newborn neurons in the adult hypothalamus integrate into existing hypothalamic neural circuits and express neuronal markers such as POMC (phosphorylated signal transducer of activator of transcription), neuropeptide Y, ocytocin and vasopressin. During hypothalamic development, POMC-expressing progenitor cells differentiate into two populations of cells with antagonistic roles, expressing either POMC or neuropeptide Y, that exert opposite effects in regulating energy balance. It is thus proposed that differential regulation of postnatally-generated neurons in the hypothalamus might form the basis of developing new treatments to regulate food intake behavior. This hypothesis is supported by observations that acute ablation of new hypothalamic neurons leads to severe anorexia and weight loss.

Figure 27:
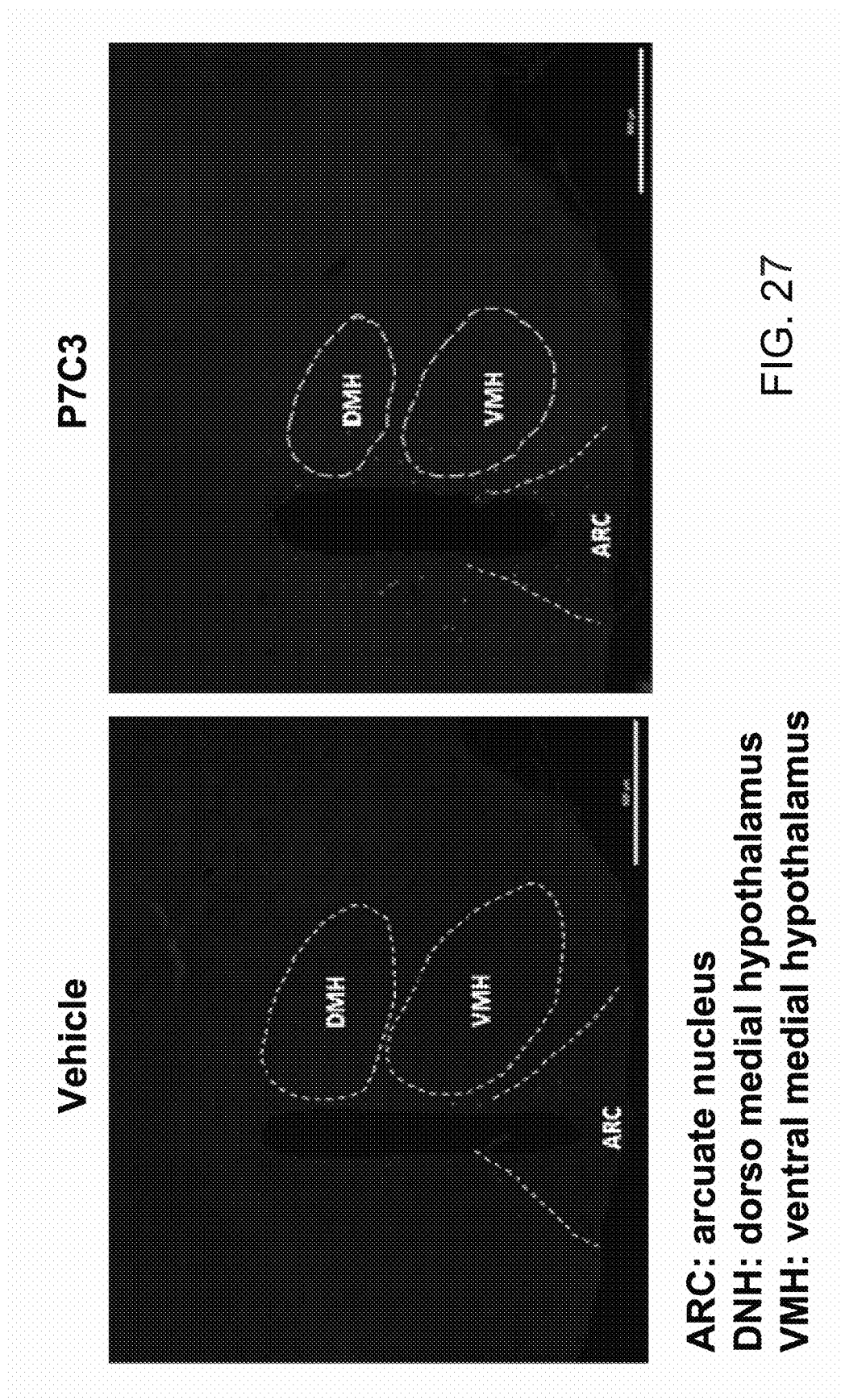
FIG. 27. Example 45 Compound (P7C3) Augments Hypothalamic Neurogenesis. Administration of P7C3 for a one month period of time augments proliferation of hypothalamic neural precursor cells (shown in red) in the arcuate nucleus (ARC), dorsomedial hypothalamus (DMH) and ventralmedial hypothalamus (VMH). Micrographs shown are representative of staining from every third section throughout the hypothalamus in 4-6 mice for each treatment group.

It was evaluated whether P7C3 might augment hypothalamic neurogenesis by administering either vehicle or P7C3 (10 mg/kg twice daily, i.p.) to nine week old male C57BL/6 mice, starting two days before implantation of 7 day Alzet osmotic minipumps (model 1007d) loaded with BrdU (1 mg/kg). Pumps were connected to a cannula that delivered BrdU at a constant rate into the left lateral ventricle for the seven day period, during which time animals continued to receive either vehicle or P7C3. Pumps were surgically removed at the conclusion of their 7 day operating period, and mice were allowed to survive for 4 more weeks, during which time they continued to receive either vehicle or P7C3. At the end of the 4 week period, mice were deeply anesthetized with intraperitoneal (i.p.) injection of mouse anesthetic cocktail and transcardially perfused with 4% paraformaldehyde (PFA) in phosphate buffered saline (pH 7.4). Brains were then dissected and post-fixed overnight at 4 degrees Celsius in 4% PFA, and cryoprotected in 30% sucrose in PBS. Fixed brains were embedded in O.C.T and cut at 20 micrometer thickness with a cryostat. Every third section was immunohistochemically stained for BrdU (Accurate, rat anti-Brdu, 1:400) per our standard procedures. Anti-rat Dylight 596 was used to visualize BrdU incorporation. As can be seen from FIG. 27, treatment with P7C3 markedly enhances hypothalamic neurogenesis in the rodent brain, with a significantly increased amount of BrdU positive staining.

It should be appreciated by one of ordinary skill in the art that the above described hypothalamic neurogenesis tests can also be used to test other compounds of presently disclosed embodiments.

Because P7C3 (and its derivatives and analogs) can enhance hypothalamic neurogenesis, compounds of the presently disclosed embodiments can be useful for regulating hypothalamic functions such as water balance, biological rhythms, feeding and drinking drive, sexual activity, pituitary gland function and temperature regulation. For example, given P7C3's role in maintaining stable body weight in aging rats, compounds of the presently disclosed embodiments can provide therapeutic benefits to patients experiencing physiological weight loss for various reasons, such as normal aging, radiation treatment, chemotherapy, anorexia, cachexia, diabetes, stress, substance abuse, dementia, stroke, cancer, infection, as well as other diseases and/or conditions.

I. Example 45 Compound Protects Mitochondria

Figure 22B:
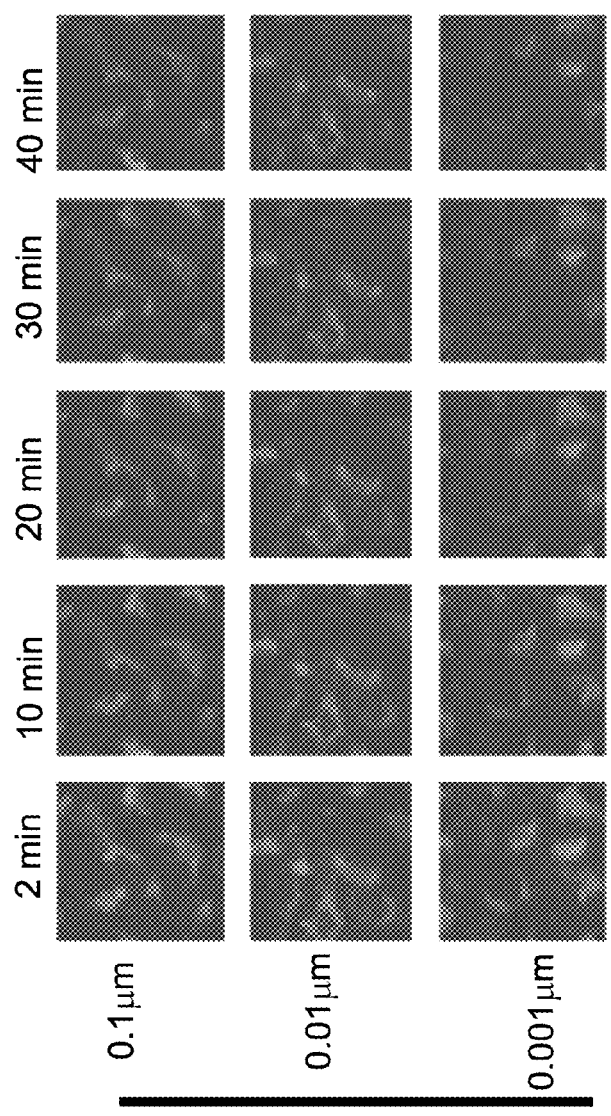
Figure 22C:
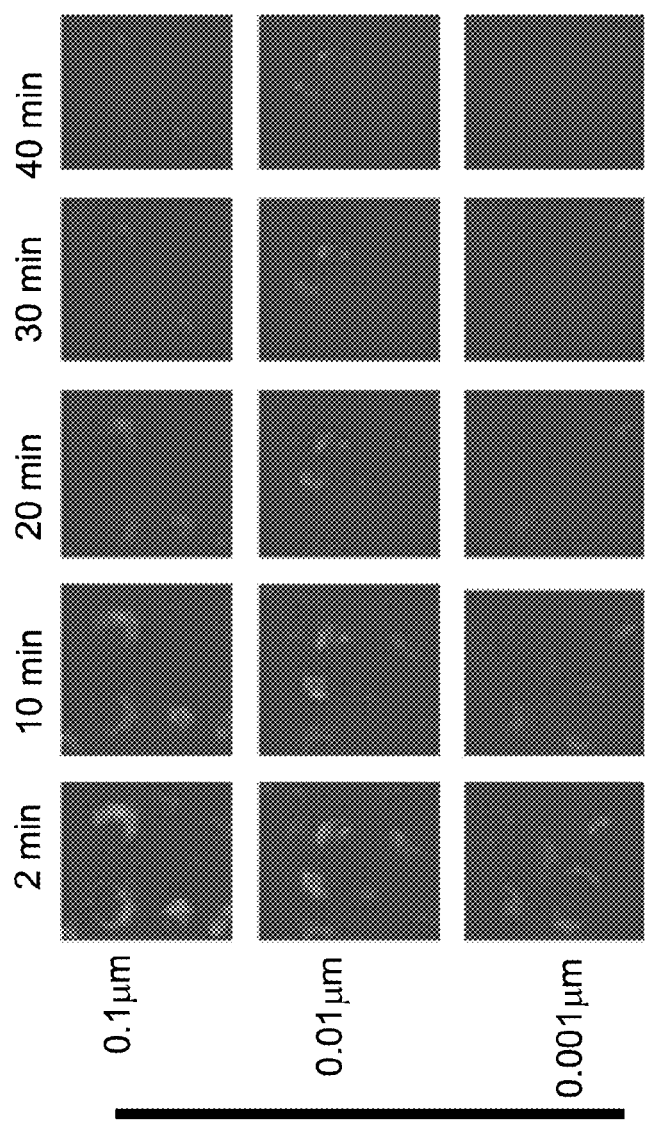
Figure 22D:
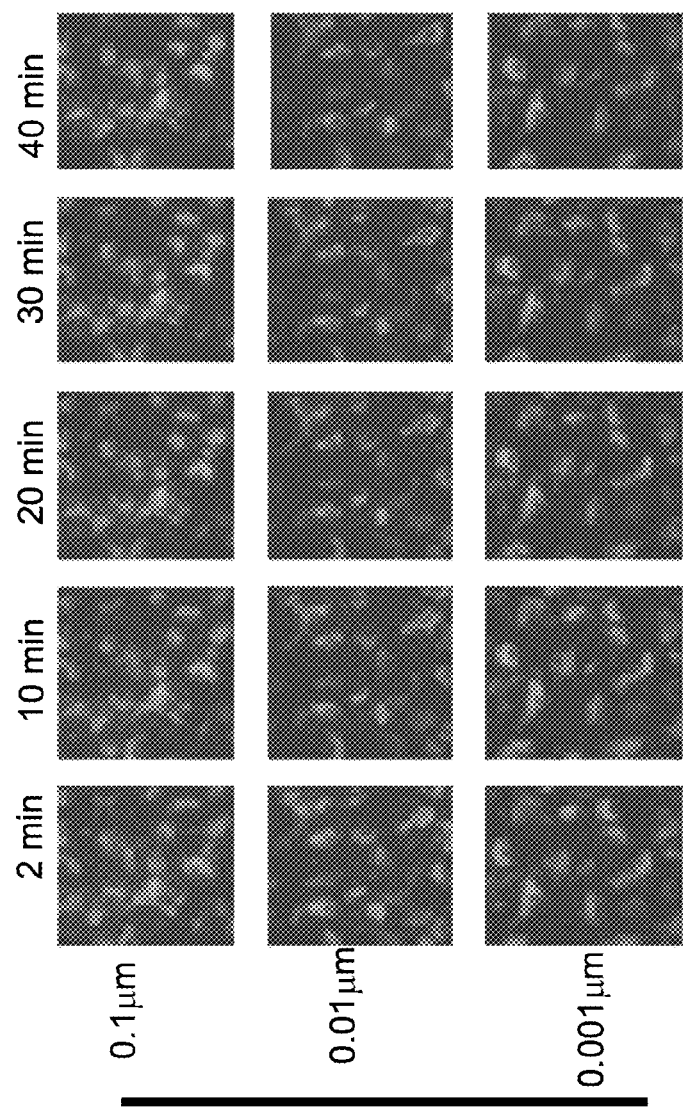
Figure 22E:
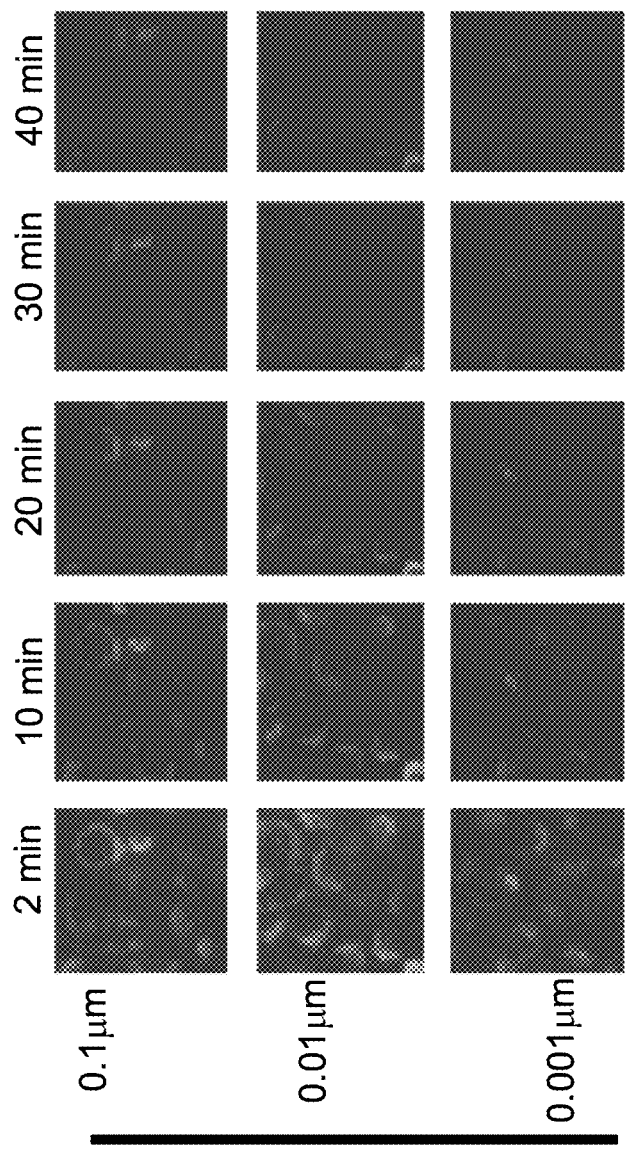

Since P7C3 ameliorates the death of newborn neurons in the dentate gyrus in living mice, it is possible that its function might relate to mitochondrial integrity. Assays were established to test whether P7C3 might protect cultured U20S cells from calcium-induced mitochondrial dissolution (Distelmaier et al., Cytometry A 2008, 73, 129-138). Tetramethylrhodamine methylester (TMRM) dye is sequestered by active mitochondria, and, when loaded with TMRM, vehicle-treated cells released the dye within 15 rain of exposure to the calcium ionophor A23187. By contrast, dye release was fully prevented in cells exposed to as little as 10 nM of P7C3 (FIG. 22A). Compounds known to be less active in vivo were also less active in this assay (not shown). Preservation of mitochondrial membrane potential in this assay was observed for the R-enantiomer of P7C3-OMe, Example 1b, (FIG. 22B), but not the S-enantiomer, Example 1a, (FIG. 22C). Finally, protection of mitochondrial membrane permeability was observed at an enhanced level for a compound variant P7C3A20 (Example 6a), which also exhibited a high level of proneurogenic activity (FIG. 22D). Derivatives that have less proneurogenic activity than P7C3 such as Example 33 (FIG. 22E) and Example 21 (FIG. 22F), displayed less protective effect in preserving mitochondrial integrity at the tested doses in cultured primary cortical neurons.

Figure 23:
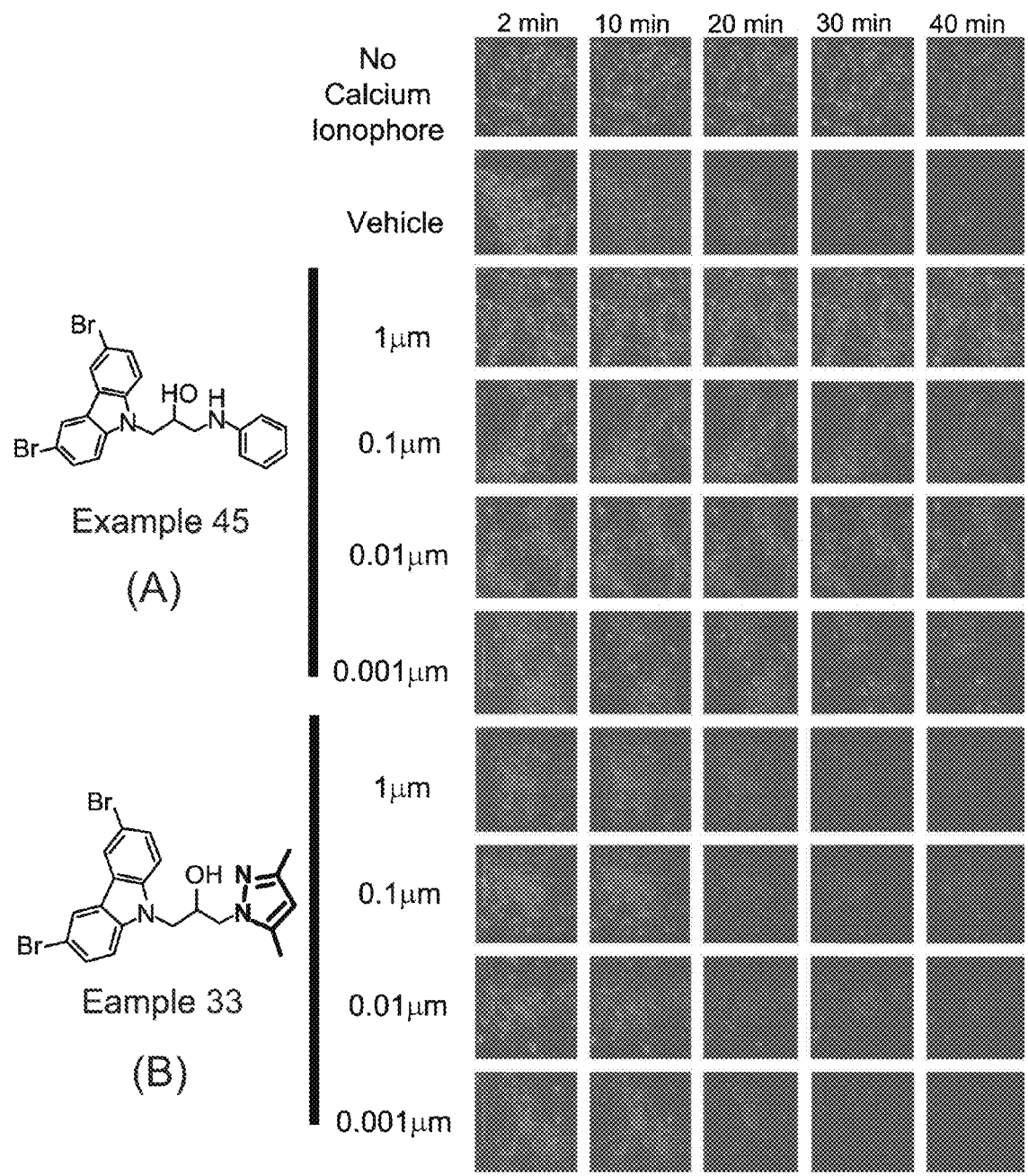
FIG. 23: Example 45 Compound Preserves Mitochondrial Membrane Potential in Cultured Primary Cortical Neurons. Cortical neurons cultures from rats on embryonic day 14 were loaded with tetramethylrhodamine methyl ester (TMRM) dye after 6 days of maturation. The top panels (no calcium ionophore) show that the dye alone did not affect the health of neurons. The remaining panels are from cells that were exposed to the calcium ionophore A23187 at time zero. With vehicle-alone, cortical neuron mitochondrial membrane potential was rapidly lost after exposure to the ionophore. Escalating doses of Example 45 Compound (A) preserved mitochondrial membrane potential following exposure to the calcium ionophore A23187 in a dose dependent manner, with full protection achieved at 1 mM. The less active compound (B) was less effective in preserving mitochondrial membrane potential at any dose tested. Results shown are representative of 10 fields analyzed in each of 2 experimental runs for all conditions.

It was also examined whether Example 45 Compound preserves mitochondrial membrane potential in cultured primary cortical neurons (FIG. 23). Cortical neurons cultures from rats on embryonic day 14 were loaded with tetramethylrhodamine methyl ester (TMRM) dye after 6 days of maturation. The top panels (no calcium ionophore)

show that the dye alone did not affect the health of neurons. The remaining panels are from cells that were exposed to the calcium ionophore A23187 at time zero. With vehicle-alone, cortical neuron mitochondrial membrane potential was rapidly lost after exposure to the ionophore. Escalating doses of Example 45 Compound preserved mitochondrial membrane potential following exposure to the calcium ionophore A23187 in a dose dependent manner, with full protection achieved at 1 mM. The less active compound (Example 33) was less effective in preserving mitochondrial membrane potential at any dose tested. Results shown are representative of 10 fields analyzed in each of 2 experimental runs for all conditions.

It should be appreciated by one of ordinary skill in the art that the above described mitochondrial tests can also be used to test other compounds of presently disclosed embodiments.

J. Example 45 Compound Normalizes Elevated Levels of Hippocampal Apoptosis in npas3$^{-/-}$ Mice Recognizing that reduced thickness of the npas3$^{-/-}$ dentate gyms granular layer could be attributed to increased apoptosis of proliferating neural precursor cells, the effect of Example 45 Compound (P7C3) treatment on apoptosis in the hippocampus of npas3$^{-/-}$ mice was examined through immunohistochemical staining of CCSP3. As shown in FIG. 17, after 12 days of orally delivered Example 45 Compound (20 mg/kg) to adult npas3−/− mice, a statistically significant reduction in CCSP3 staining was observed in the dentate gyms. It is thereby proposed that Example 45 Compound facilitates repair of the granular layer of the dentate gyms in npas3$^{-/-}$ mice by overcoming a genotype-specific enhancement in apoptosis.

It should be appreciated by one of ordinary skill in the art that the above described mice model and other animal model can also be used to test other compounds of presently disclosed embodiments.

K. Example 45 Compound (P7C3) Provides Therapeutic Benefit in Animal Model of Amyotrophic Lateral Sclerosis (ALS)

ALS, also known as Lou Gehrig's disease, is an adult-onset (typically between ages 40-70), rapidly progressive and fatal disease caused by selective degeneration of upper (cortical layer V within the primary motor cortex) and lower (spinal cord) motor neurons, the nerve cells in the central nervous system that control voluntary muscle movement. An estimated 5000 people in the United States are diagnosed with ALS every year. This disorder causes muscle weakness and atrophy throughout the body, and patients with ALS ultimately lose their ability to initiate and control all voluntary movement. The earliest parts of the body affected in ALS reflect those motor neurons that are damaged first. About 75% of patients experience onset of symptoms in their arms or legs manifested as difficulty with manual dexterity or ambulation, while about 25% experience 'bulbar onset' of ALS—difficulty speaking clearly or swallowing. A small proportion of patients have respiratory onset of ALS in the form of weakness of the intercostal muscles that support breathing. Regardless of the region of onset, muscle weakness and atrophy invariably spread to other parts of the body as the disease progresses. Most patients develop a constellation of symptoms that includes difficulty moving, dysphagia (difficulty swallowing), dysarthria (difficulty speaking or forming words) and classical manifestations of loss of upper motor neurons (muscular spasticity, hyperreflexia and overactive gag reflex) and lower motor neurons (muscular weakness, muscle atrophy, muscle cramps and fasciculations). Sensory nerves and the autonomic nervous system are usually spared, though may be involved in some patients. About 20% of ALS patients also develop fronto-temporal lobar dementia (FTLD), while 30-50% of patients develop subtle cognitive changes that can be observed with detailed neuropsychological testing. Around 15-45% of patients with ALS also experience what is called "pseudobulbar affect"—a form of emotional lability in which patients manifest intermittent bouts of uncontrollable laughter, crying or smiling. This symptom domain is thought to be related to degeneration of bulbar upper motor neurons, resulting in exaggerated motor expressions of emotion. Although disease progression varies between individuals, most patients are eventually unable to stand or walk, get in or out of bed on their own, or use their hands and arms. Difficulty chewing and swallowing further leads to progressive weight loss and increased risk of choking and aspiration pneumonia. Towards the end stages of disease, as the diaphragm and intercostal muscles weaken, most patients require ventilator support. Individuals with ALS most commonly die of respiratory failure or pneumonia within 2-5 years of diagnosis.

Ninety-five percent of ALS cases occur sporadically (SALS), with no identifiable cause or family history of the disease. The remaining 5% of cases are inherited, known as Familial ALS (FALS). Because FALS and SALS are clinically and neuropathologically similar, the pathogenesis of these forms of ALS may converge on a common pathogenic pathway. Approximately 20% of FALS and 3% of SALS cases are associated with autosomal dominant mutations in the SOD1 gene on chromosome 21, and about 150 different mutations dispersed throughout this gene have been identified in FALS. SOD1 encodes cytosolic Cu/Zn superoxide dismutase, an antioxidant enzyme that protects cells by converting superoxide (a toxic free radical generated through normal metabolic activity of mitochondria) to hydrogen peroxide. Unchecked, free radicals accumulate and damage both mitochondrial and nuclear DNA, as well as proteins within cells. In ALS linked to mutations in SOD1, cytotoxicity of motor neurons appears to result from a gain of toxic SOD1 function, rather than from loss of dismutase activity. Although the exact molecular mechanisms underlying toxicity are unclear, mutation-induced conformational changes in SOD1 are known to lead to misfolding and subsequent cytotoxic aggregation of mutant SOD1 in cell bodies and axons. Aggregate accumulation of mutant SOD1 is thought to disrupt cellular functions and precipitate neuron death by damaging mitochondria, proteasomes, protein folding chaperones, or other proteins.

Transgenic animal models of mutant SOD1 are currently used for research into the pathogenic mechanisms thought to broadly underlie ALS, such as G93A SOD1 mutant mice. Mice hemizygous for the G93A-SOD1 transgene express 18+/−2.6 copies of a form of SOD1 found in some patients with FALS (a substitution of glycine to alanine at codon 93). This was the first mutant form of SOD1 to be expressed in mice, and is the most widely used and well-characterized mouse model of ALS. Superoxide dismutase activity in these mice is left intact such that the pathogenic effect of the mutant transgene appears to be gain of function, as is thought to occur in human patients. In these mice, death of motor neurons in the ventral horn of the spinal cord and loss of myelinated axons in ventral motor roots leads to paralysis and muscle atrophy. Upper cortical motor neurons in these mice also die as the disease progresses, and protein aggregates of mutant SOD1 are found only in diseased tissues, with greater amounts being detected during motor neuron degeneration. Around 100 days of age, G93A-SOD1 mice become paralyzed in one or more limbs with paralysis due to loss of motor neurons from the spinal cord. This paralysis rapidly spreads throughout the body, culminating in 50% death when mice are 128.9+/−9.1 days old.

Figure 24A:
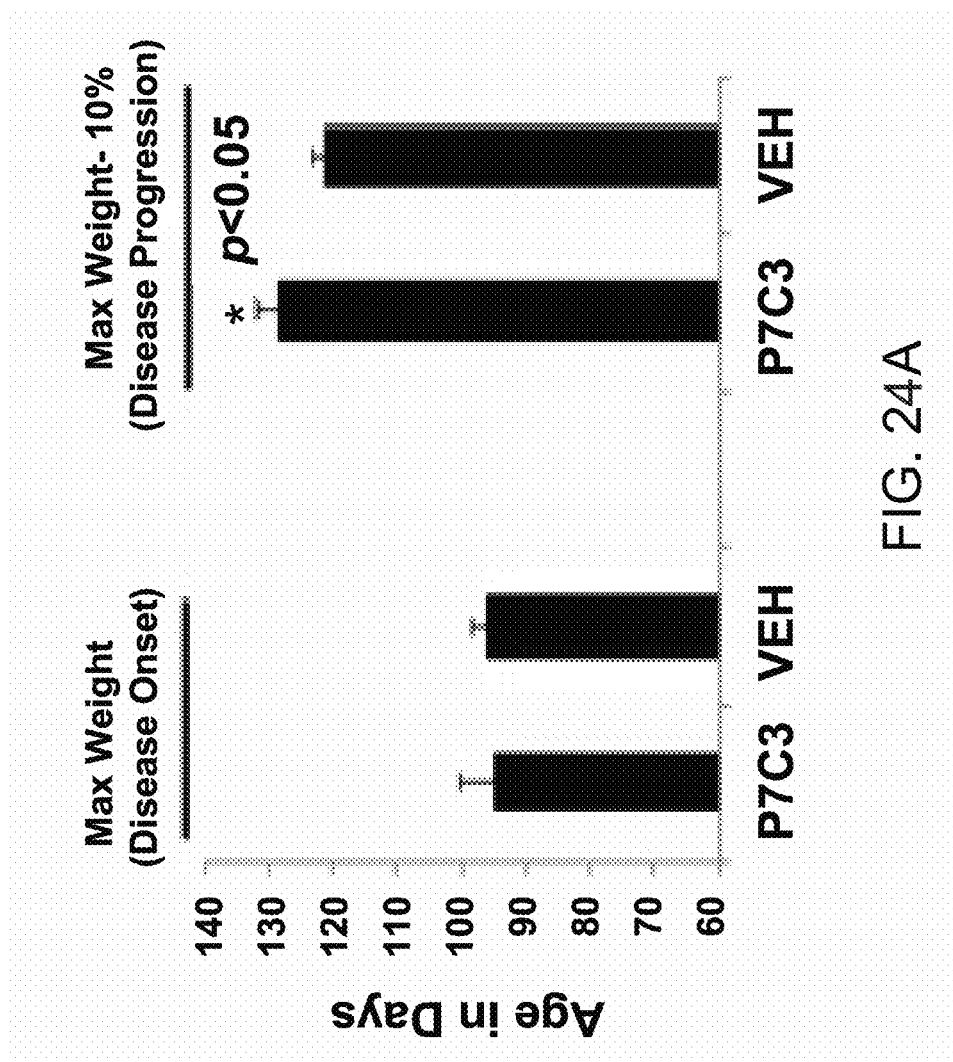
FIG. 24A, FIG. 24B, FIG. 24C and FIG. 24D. Example 45 Compound (P7C3) Provides Therapeutic Benefit in Animal Model of Amyotrophic Lateral Sclerosis (ALS). Female G93A SOD1 mice (n=30 in each group, with all mice sibling matched across treatment groups) were treated with either vehicle or P7C3 (10 mg/kg i.p. twice daily) starting at 40 days of age. P7C3-treated mice showed a significant delay in disease progression, as evidenced by the later age by which they dropped to 10% below their maximum weight (FIG. 24A). P7C3-treated mice also attain a neurological severity score of 2 at a later age than vehicle treated mice (FIG. 24B), again indicating that P7C3-treatment slows disease progression. This score is determined as follows: '0'=full extension of hind legs away from lateral midline when the test mouse is suspended by its tail, and can hold this for 2 seconds, suspended 2-3 times; '1'=collapse or partial collapse of leg extension towards lateral midline (weakness) or trembling of hind legs during tail suspension; '2'=toes curl under at least twice during walking of 12 inches, or any part of foot drags along cage bottom/table; '3'=rigid paralysis or minimal joint movement, foot not being used for forward motion; and '4'=mouse cannot right itself within 30 seconds from either side. With further disease progression, vehicle-treated mice show the expected decline in retention time on the accelerating rotarod, with retention time averaged across 4 trials (FIG. 24C, open bars). P7C3-treated mice, however, show a consistent trend towards improved performance on this task after onset of disease (FIG. 24C, filled bars), with statistically significant improvement on days 131, 138 and 145 (*, p<0.001, Student's t Test). All graphical data shown above is mean+/−SEM, with statistical analysis conducted using the Student's t Test). As another means of disease progression, walking gait was evaluated.
Figure 24B:
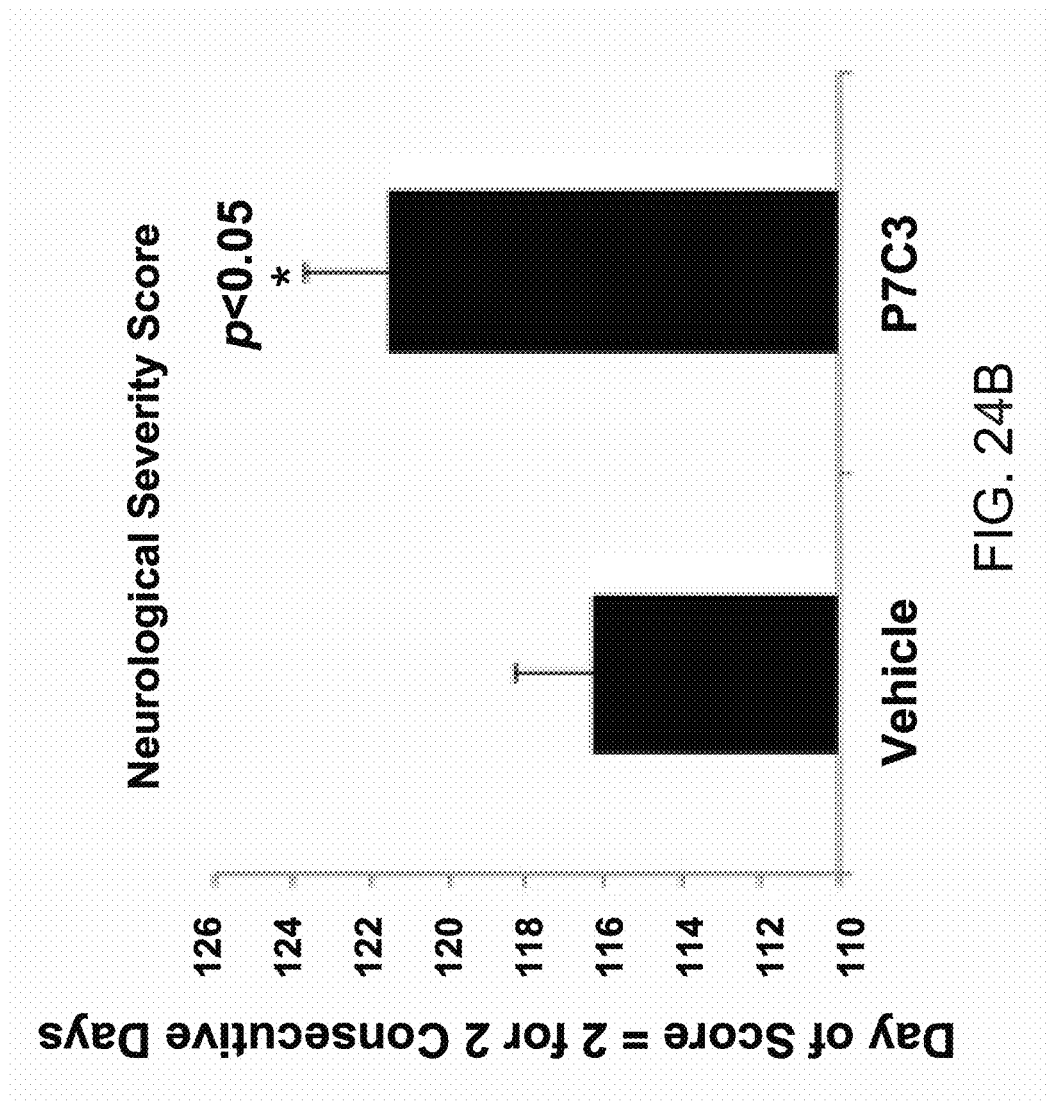
Figure 24C:
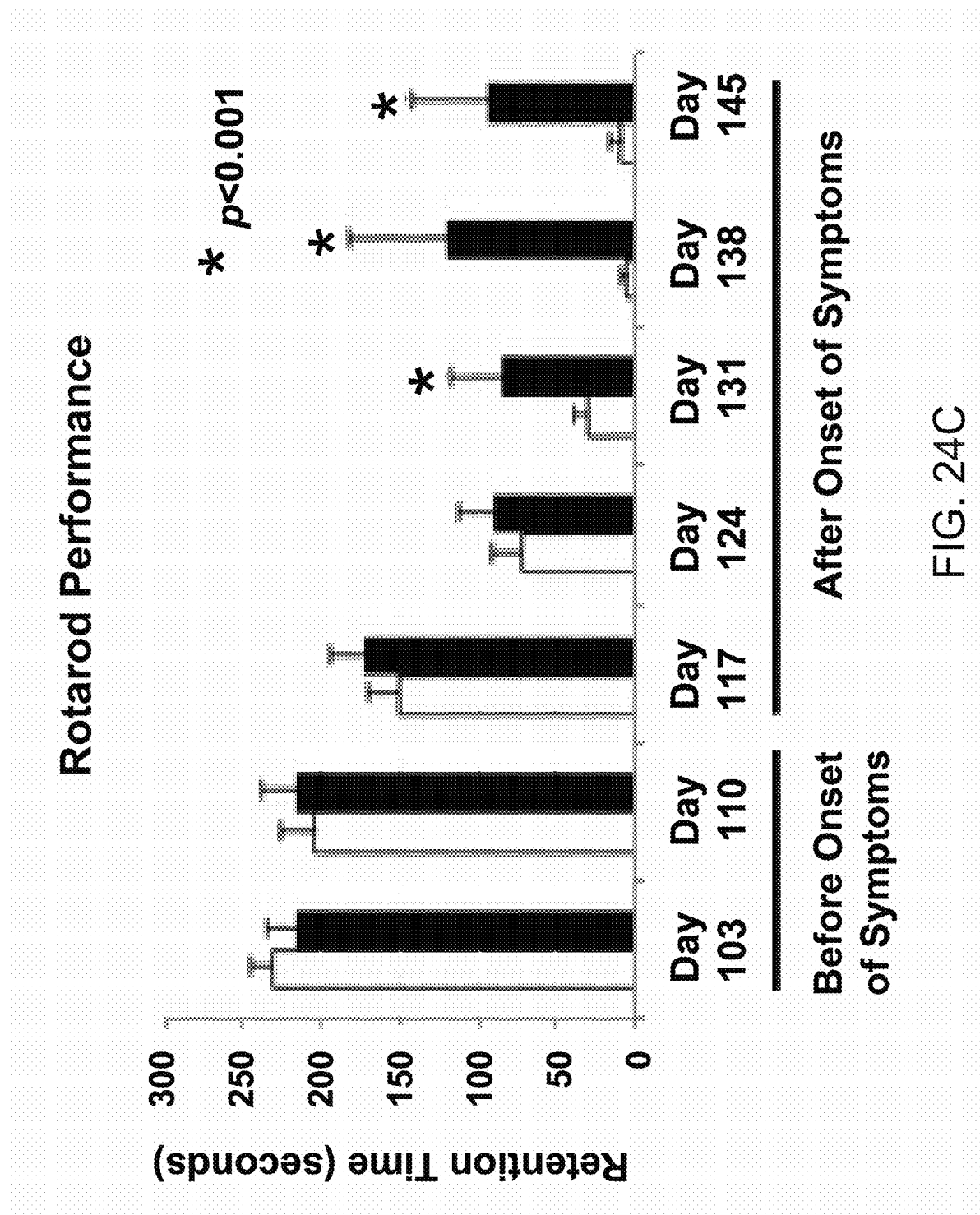
Figure 24D:
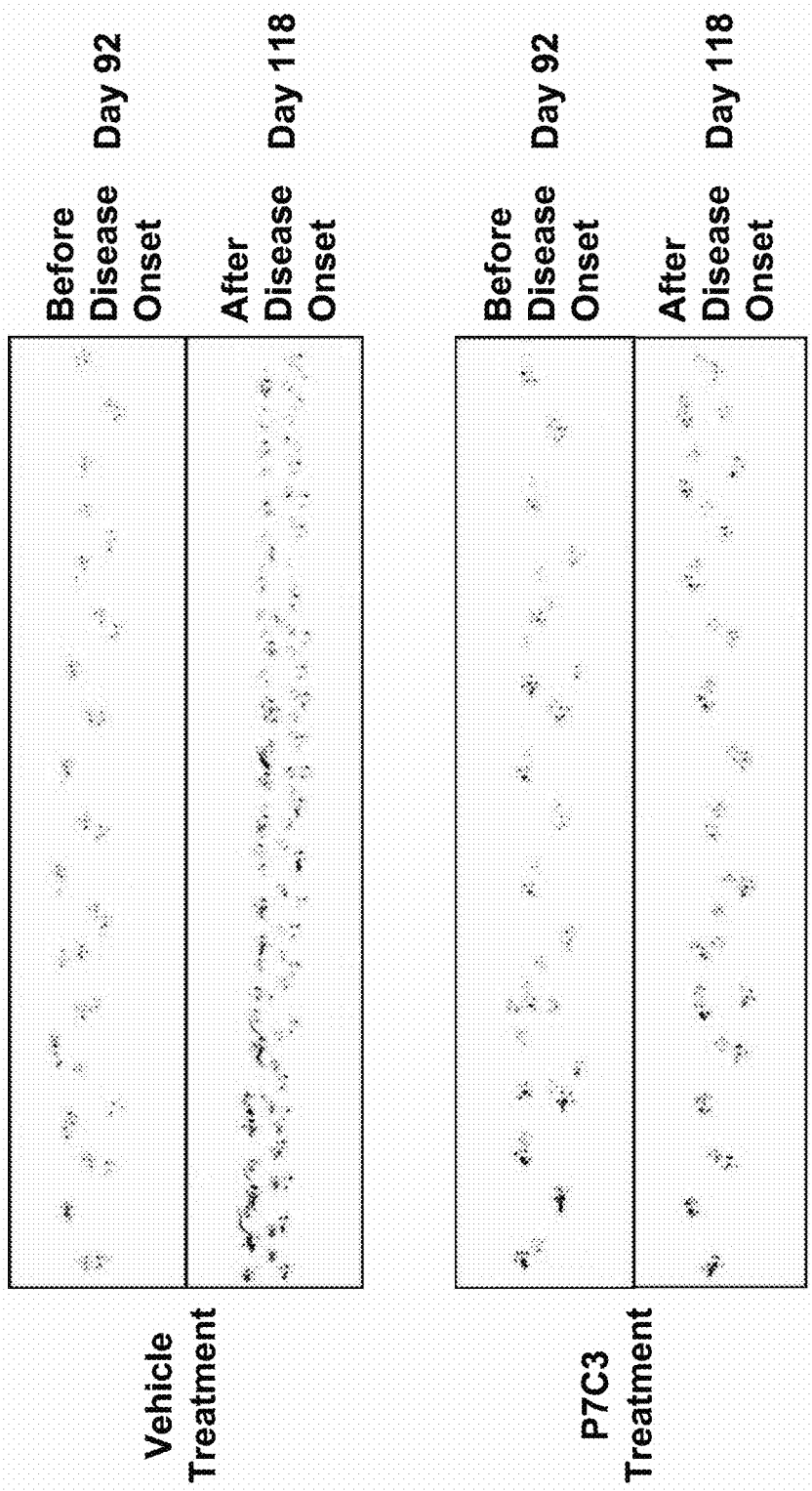

P7C3 was intraperitoneally administered to female G93A-SOD1 transgenic mice using a treatment paradigm of 10 mg/kg P7C3 i.p. twice a day, compared to vehicle, starting at 40 days of age. This treatment scheme was selected based on standard protocols for initial proof of concept screens in these mice. To control for transgene copy number, mice are sibling matched between treatment groups, as per standard protocol. After initiation of P7C3 or vehicle treatment, date of onset of illness is determined by peak weight, and initial progression of disease is defined as the day at which mice fall to 10% below their maximum weight. Mice are also assessed daily by a standard determination of neurological severity score, with a score of 2 or worse for two consecutive days serving as an additional marker of illness progression. This score is determined blind to treatment group with the scoring system described in the legend for the figure. As shown in FIG. 24A, P7C3 treatment slows disease progression in G93A-SOD1 mice in terms of delaying the time point at which mice drop to 10% below their maximum weight. Treatment with P7C3 also significantly delays the age at which G93A-SOD1 mice attain a neurological severity score of 2, another marker of disease progression, as shown in FIG. 24B. Furthermore, P7C3 treatment significantly improved performance in the accelerating rotarod task as the disease progressed in these mice, as shown in FIG. 24C, indicating a slowing of progression of motor impairment in the disease process. This protective effective of P7C3 on motor performance in G93A-SOD1 mice is also observed in the ink footprint analysis of walking gait, as shown in FIG. 24D.

It should be appreciated by one of ordinary skill in the art that the above described ALS model and other animal model can also be used to test other compounds of presently disclosed embodiments.

L. Example 6a Compound (P7C3A20) Provides Therapeutic Benefit in Animal Model of Parkinson's Disease Parkinson's disease (PD) is a progressive neurodegenerative disease characterized by the death of dopaminergic neurons in the substantia nigra, which project to the striatum to control normal movement. Though it is one of the most common nervous system disorders of the elderly, the cause of PD remains uncertain. Symptoms early in the disease are movement-related, including shaking, rigidity, slowness of movement, and difficulty with walking gait. More advanced stages of the disease are typically associated with cognitive and behavioral problems, including dementia. The early motor symptoms are partially managed by administration of drugs that enhance dopaminergic signaling. However, as the disease progresses and the dopaminergic neurons in the substantia nigra continue to die, patients reach a point at which these drugs become ineffective at treating the symptoms and additionally produce the complication of dyskinesia. Effectively preventing the death of dopaminergic neurons in the substantia nigra would therefore be an ideal treatment approach for patients with PD.

MPTP (1-methyl-4-phenyl-1,2,3,6-tetrahydropyridine) is a potent neurotoxin that selectively kills dopaminergic neurons in the substantia nigra of both mice and monkeys, causing a clinical picture resembling PD. The MPTP toxicity model can therefore be used to study the death of dopaminergic neurons with the goal of developing new treatments for PD based on neuroprotective strategies found to be effective in these neurons. To determine if P7C3A20 might be neuroprotective in the substantia nigra, the well-characterized and popular MPTP administration regimen was employed, as developed by Tatton and Kish (1997), *Neuroscience* 77: 1037-1048, and Jakson-Lewis et al. (2007), *Nature Protocols* 2: 141-151. Here, 12 week old wild type male C57BL/6 mice were treated for 3 days with P7C3A20 (10 mg/kg i.p. twice daily) or vehicle, and on the fourth day a five day regimen of 30 mg/kg/day i.p. free base MPTP was initiated. During this five day period of MPTP administration the mice continued to receive P7C3A20 or vehicle. Mice continued to receive the same dose of P7C3A20 or vehicle every day for 21 more days, at which point they were sacrificed by transcardial perfusion with 4% paraformaldehyde. Brains were post-fixed in 4% paraformaldehyde at 4 degrees Celsius overnight and then cryoprotected with 30% sucrose in phosphate-buffered saline. Fixed brains were cut at 30 microns with a sliding microtone, and every 4th section (spaced 120 microns apart) was stained with antibodies directed against tyrosine hydroxylase (TH) (Abcam, rabbit anti-TH, 1:2500). TH-positive cells were counted in the substantia nigra area. As shown in FIG. 25A and FIG. 25B, treatment with P7C3A20 significantly attenuates MPTP-mediated killing of substantia nigra dopaminergic neurons. These observations suggest that P7C3A20 and related compounds may form the basis of new neuroprotective strategies for preventing or slowing the progression of Parkinson's disease.

It should be appreciated by one of ordinary skill in the art that the above described PD model and other animal model can also be used to test other compounds of presently disclosed embodiments.

M. Example 45 Compound Provides Therapeutic Benefit in Animal Model of Huntington's Disease Huntington's disease (HD) is an autosomal dominant neurodegenerative disease characterized by the insidious and progressive development of mood disturbances, behavioral changes, involuntary choreiform movements (ceaseless and complex writhing movements of the limbs) and cognitive impairment. HD has a prevalence of about 1 in 10,000 people in the U.S., and is caused by a polyglutamine expansion of greater than 36 repeats in the N terminus of the protein huntingtin (Htt). There are currently no treatments that delay the appearance or progression of this disease. HD is pathologically characterized by a dramatic loss of neurons in the striatum and cerebral cortex, and therapeutic strategies to protect these neurons from dying might provide new treatment options for patients. The physical symptoms of HD typically have their onset between 35-44 years of age, though onset has been reported to occur at times ranging from infancy to old age. The exact way in which HD affects an individual varies and can differ even between members of the same family, but symptoms progress predictably in most cases. The earliest symptoms include a general lack of coordination and unsteady gait, and as the disease advances uncoordinated and jerky body movements become more apparent. More advanced stages are typically accompanied by an observable decline in mental abilities, associated with behavioral and psychiatric problems, such as anxiety, severe depression, blunted affect, egocentrism, aggression, and compulsive behaviors such as alcoholism, gambling or hypersexuality. Over time, physical abilities are gradually impeded until coordinated movement becomes very difficult, and mental abilities generally decline into dementia. Complications such as pneumonia, heart disease, eating difficulties leading to weight loss and malnutrition, and physical injury from falls reduce life expectancy to around twenty years after onset of symptoms. There is no cure for HD, and full-time care is required in later stages of disease.

Htt is a large cytoplasmic protein that interacts with over 100 other proteins, and appears to have multiple biological functions. The behavior of mutated Htt (mHtt) protein is not completely understood, but it is known to be toxic to neurons. Damage mainly occurs in the striatum, but in later stages other areas of the brain are also attacked, such as the cerebral cortex. As neuronal cell death progresses, symptoms associated with the functions of the affected brain areas appear. For example, planning and modulating movement are the main functions of the striatum, and difficulties with these tasks are frequent initial symptoms of HD. Disease initiation and progression are thought to involve in large part a conformational change in the mHtt protein due to the polyglutamine expansion, altered protein-protein interactions, abnormal protein aggregation in both the nucleus and cytoplasm and proteolysis, which in turn may lead to transcriptional dysregulation, excitotoxicity, mitochondrial dysfunction, and neuronal apoptosis. In addition to a role for a gain of new toxic properties of mHtt in HD pathology, there is increasing evidence that loss of wild-type Htt function also contributes to pathogenesis. For example, an essential role of Htt in mitotic spindle formation and mammalian neurogenesis has recently been identified.

One animal model of HD that can be employed for screening potential therapeutic agents is R6/2 transgenic mice. These mice express a mutant exon 1 of the human huntingtin gene, engineered to include an approximately 145-155 CAG repeat expansion. R6/2 mice phenocopy much of the neuropathology (striatal and cortical neuron cell death) and behavioral manifestations of clinical HD. They display progressive motor and cognitive impairments, ubiquitinated nuclear and cytoplasmic inclusions of mutant Htt, weight loss, decreased striatal and brain size, altered levels of neurotransmitters and their receptors, and premature death. They exhibit motor deficits as early as 5-6 weeks of age, display overt behavioral abnormalities at 8-9 weeks, and typically die between 11 and 13 weeks of age. R6/2 mice also display significantly lower levels of adult hippocampal neurogenesis relative to wild-type littermates, even before onset of symptoms.

Figure 26A:
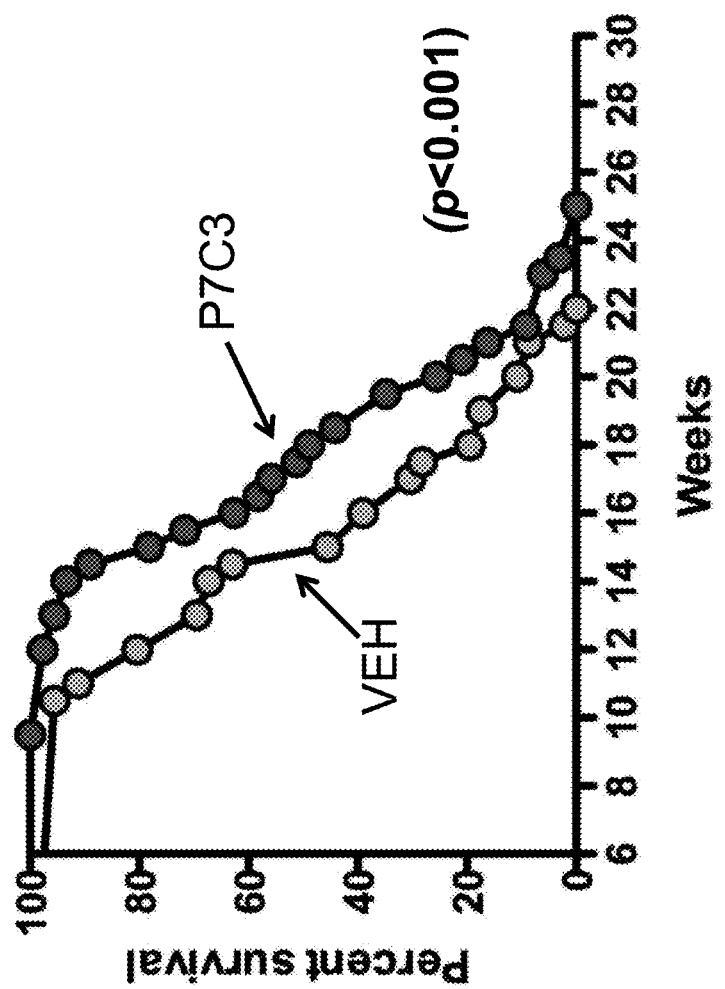
FIG. 26A and FIG. 26B. Example 45 Compound (P7C3) Provides Therapeutic Benefit in Animal Model of Huntington's Disease. 40 female R6/2 mice were included in each of VEH (vehicle) and P7C3 (10 mg/kg P7C3 i.p. twice daily) groups, and treatment was begun at 6 weeks of age.
Figure 26B:
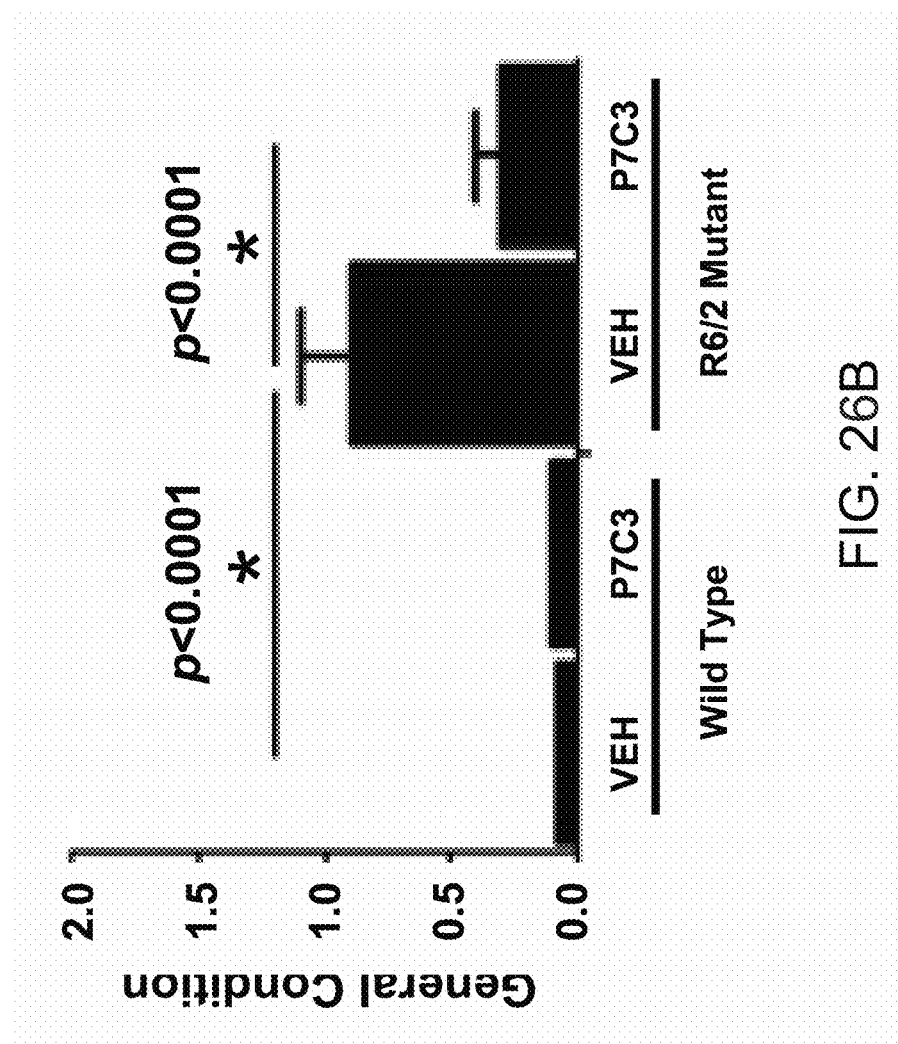

In one hypothesis, P7C3 (and its derivates) may enhance the formation of neurons in the mature hippocampus by preventing death rather than promoting proliferation of these cells. As such, P7C3 is "proneurogenic" by virtue of its neuroprotective activity. It is also possible that P7C3 (and its derivates) prevents cell death and promotes cell proliferation. It was evaluated whether P7C3 might provide therapeutic benefit in R6/2 mice. P7C3 (10 mg/kg i.p. twice daily starting at 6 weeks of age) or vehicle were administered to 40 female R6/2 mice. As shown in FIG. 26A, 50% of vehicle-treated R6/2 mice die at approximately 15 weeks of age, and treatment with P7C3 delays animal death by about three weeks. At 14 weeks of age, R6/2 mice treated with P7C3 showed improved general condition score and appearance as shown in FIG. 26B, as compared to vehicle-treated littermates. General condition score was determined by a 3 point scoring system that was conducted blind to genotype and treatment group (score of 0=fur looks groomed, normal posture (no hunch), clear eyes, alert; score of 1=fur beginning to stick up, slight hunch; score of 2=piloerection (fur sticking up), unkempt fur, hunch in back or neck area, crusty eyes). Death was monitored twice daily, and defined as either when animals were found dead, or when they were unable to right themselves after being placed on their backs with movement subsequently initiated by gentle prodding for 30 seconds. By general appearance of coat condition, grooming and spontaneous activity in the home cage, R6/2 mice treated with P7C3 also appear qualitatively better than VEH-treated R6/2 mutant mice (not shown).

It should be appreciated by one of ordinary skill in the art that the above described HD model and other animal model can also be used to test other compounds of presently disclosed embodiments.

N. Neuroprotective Efficacy of Aminopropyl Carbazoles in a Mouse Model of Parkinson's Disease Parkinson's disease (PD) is an incurable and progressive neurodegenerative disorder of predominantly idiopathic origin that is characterized by the death of dopaminergic neurons in the substantia nigra pars compacta (SNc), a region of the brain that controls motor activity by projecting dopaminergic axons to the striatum (Lees A. J., Hardy J., Revesz T (2012) Parkinson's disease. Lancet 373:2055-2066). Early symptoms in PD are primarily movement-related, including shaking, rigidity, brady- and hypo-kinesia, tremor and difficulty walking. More advanced stages of PD are associated with cognitive and behavioral problems, including dementia. Current treatment strategies for PD consist primarily of partial management of early motor symptoms with drugs that enhance dopaminergic signaling, such as L-DOPA or dopamine receptor agonists. Unfortunately, as greater numbers of dopaminergic neurons in the SNc die, these drugs fail to alleviate symptoms and additionally produce dyskinesia. There is thus a significant unmet need for new pharmacologic strategies to slow the progression of PD, such as drugs capable of blocking the death of SNc dopaminergic neurons.

We have previously reported the identification of an aminopropyl carbazole (P7C3) discovered via an unbiased, in vivo screen for small molecules capable of enhancing postnatal hippocampal neurogenesis. P7C3 displays enantiomeric-selective stabilization of mitochondrial membrane potential, and enhances neurogenesis by blocking apoptosis of newborn neurons in the dentate gyrus (Pieper A. A., et al. (2010) Discovery of a Proneurogenic, Neuroprotective Chemical. Cell 142:39-51). Prolonged oral or intraperitoneal (i.p.) administration of P7C3 to rodents safely improves hippocampal functioning. For example, administration of P7C3 to mice suffering from pathologically high levels of neuronal apoptosis in the dentate gyrus, neuronal PAS domain protein 3 (NPAS3)—deficient mice (Pieper A. A., et al. (2005) The neuronal PAS domain protein 3 transcription factor controls FGF-mediated adult hippocampal neurogenesis in mice. Proc Natl Acad Sci USA 102: 14052-14057), restored hippocampal structure and function with no obvious physiologic side effects (Pieper A. A., et al. (2010) Discovery of a Proneurogenic, Neuroprotective Chemical. Cell 142:39-51). In addition, extended administration of P7C3 to aged rats safely impeded hippocampal cell death and preserved cognitive ability as a function of terminal aging (Pieper A. A., et al. (2010) Discovery of a Proneurogenic, Neuroprotective Chemical. Cell 142:39-51).

Through an in vivo structure-activity relationship (SAR) study, we have identified analogs of P7C3 displaying either increased or decreased activity. In particular, a chemical variant known as P7C3A20 was observed to have greater potency and efficacy than P7C3. P7C3A20 differs from P7C3 by virtue of replacing the hydroxyl group at the chiral center of the linker with a fluorine, and the addition of a methoxy group to the aniline ring. This analog displays a more favorable toxicity profile than P7C3, with no hERG channel binding, histamine receptor binding or toxicity to HeLa cells. We have also found that Dimebon, an antihistaminergic drug long deployed in Russia that is claimed to have anti-apoptotic and mitochondrial protective properties, displays modest efficacy in the same biologic assays employed to discover and characterize P7C3 and P7C3A20. The chemical structure of Dimebon is related to the P7C3 class of aminopropyl carbazoles, yet its rank order of activity relative to chemical derivatives of P7C3 is very low. Here, we report that the neuroprotective activity of these agents extends beyond promoting long-term survival of newborn cells in the adult hippocampus. Specifically, we show that the most active variants of P7C3 exhibit robust protection of mature dopaminergic neurons in both mouse and worm models of neurodegeneration, and propose that substituted carbazoles may represent attractive chemical scaffolds for the optimization of therapeutic agents for the treatment of Parkinson's disease.

Results

Neuroprotective Efficacy of P7C3, P7C3A20 and Dimebon for Newborn Hippocampal Neurons.

Adult hippocampal neurogenesis in mice is an approximately month-long process, during which time the majority of newborn cells die as they transition through a "differentiation gauntlet" lasting about 1 month before surviving cells become functionally wired into the central nervous system. We have previously found that approximately 40% of these newborn cells die within the first week following their birth in the subgranular zone of the dentate gyrus. P7C3 was originally discovered through a week-long in vivo screen designed to identify small molecules that might enhance either proliferation or survival of newborn hippocampal neural precursor cells. Subsequent bromodeoxyuridine (BrdU) pulse-chase labeling studies revealed that P7C3 does not affect neural precursor proliferation, but instead augments survival of newborn cells by blocking apoptosis. P7C3A20 was found to be active at lower doses and to have a higher ceiling of efficacy (CoE) than P7C3 in this 7 day in vivo assay, whereas Dimebon was shown to be substantially less potent and efficacious than P7C3.

Figure 28:
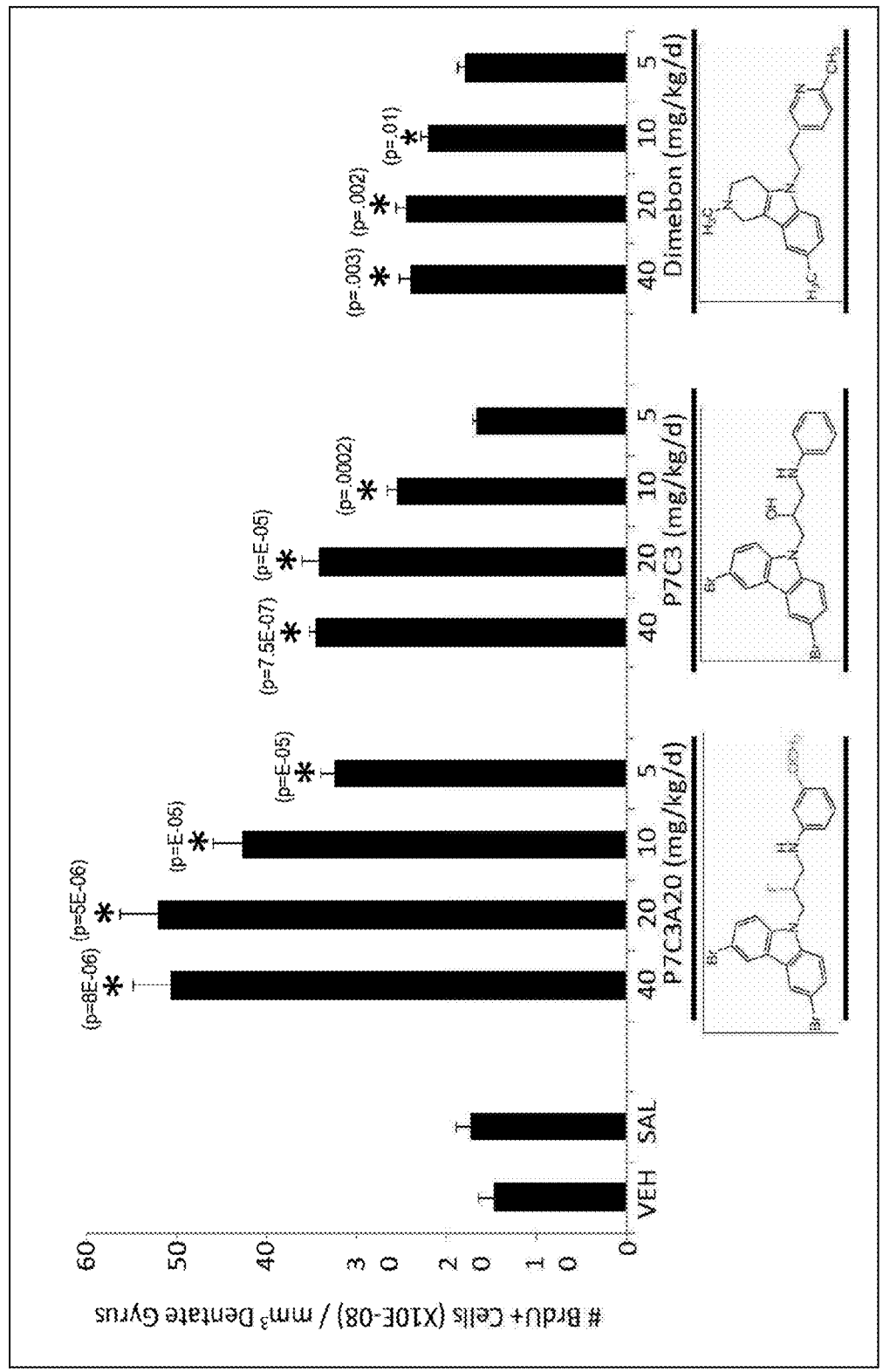
FIG. 28. Neuroprotective efficacy of P7C3, P7C3A20 and Dimebon for newborn neurons in the adult hippocampus. Test compounds were evaluated by dose response assay for their ability to block normal apoptotic cell death of newborn neural precursor cells in the adult dentate gyms. P7C3A20 exhibits the greatest potency and ceiling of efficacy, and Dimebon the least. P7C3 is intermediate in both measures. 6 animals were tested per group. Dosing is expressed as total mg/day, and compounds were administered intraperitoneally in divided doses twice daily. Data are expressed as mean+SEM. Values for P7C3 and P7C3A20 were compared to those of vehicle (VEH), and values for Dimebon were compared to those of saline (SAL).

In order to more carefully compare the neuroprotective efficacy of these compounds in abetting hippocampal neurogenesis, we conducted dose-response studies in a 30 day BrdU pulse-chase survival assay (FIG. 28). Briefly, newborn cells were labeled with a single intraperitoneal (i.p.) injection of BrdU (150 mg/kg), followed by daily treatment with the three test compounds beginning the following day. After 30 days of compound administration, mice were transcardially perfused with 4% paraformaldehyde, brains were dissected, and immunohistochemical detection of BrdU followed by standard microscopic imaging and normalization for dentate gyms volume was used to quantify the number of surviving cells. As shown in FIG. 28, P7C3A20 increased neuron survival by almost 100% at the lowest dose tested (5 mg/kg/day). By contrast, neither P7C3 nor Dimebon exhibited any effect at this dose. At the next higher dose (10 mg/kg/day), P7C3 and Dimebon showed 65% and 15% neuroprotective efficacy, respectively, whereas P7C3A20 showed neuroprotective ceiling of efficacy (CoE) of about 175%. All three compounds exhibited their maximal individual CoEs at the two highest doses tested (20 or 40 mg/kg/day), with P7C3A20's CoE being highest (≈230% increase in survival), P7C3's CoE being intermediate (∓130% increase in survival) and Dimebon's CoE being the lowest (≈30% increase in survival).

Efficacy Assays for P7C3, P7C3A20 and Dimebon for Protection from MPTP-Toxicity to Dopaminergic Neurons in Mice.

The protective efficacy of the three test compounds for newborn hippocampal neurons in the 30 day survival assay prompted us to investigate whether they might also have neuroprotective efficacy in mature neurons outside of the hippocampus. To investigate this hypothesis, we utilized the 1-methyl-4-phenyl-1,2,3,6-tetrahydropyridine (MPTP) model of neuronal cell death. MPTP is a potent toxin that selectively kills neurons in the substantia nigra of both rodents and primates, causing clinical manifestations resembling PD (Fukuda T. (2001) Neurotoxicity of MPTP. *Neuropathology* 21:323-332). MPTP is lipophilic and readily crosses into the brain, where it is metabolized by monoamine oxidase B in glial cells into the highly toxic cation 1-methyl-4-phenylpyridinium (MPP$^+$). MPP$^+$ is selectively concentrated in SNc dopaminergic neurons by virtue of its high affinity for the plasma membrane dopamine transporter, and toxicity is further potentiated by binding of MPP$^+$ to melanin in these cells, creating a depot mechanism that maintains prolonged high intracellular concentrations of MPP$^+$. MPTP toxicity is routinely used to study the death of dopaminergic neurons as a possible means of discovering new treatments for PD based on neuroprotective strategies found to be effective in this model.

Figure 29A:
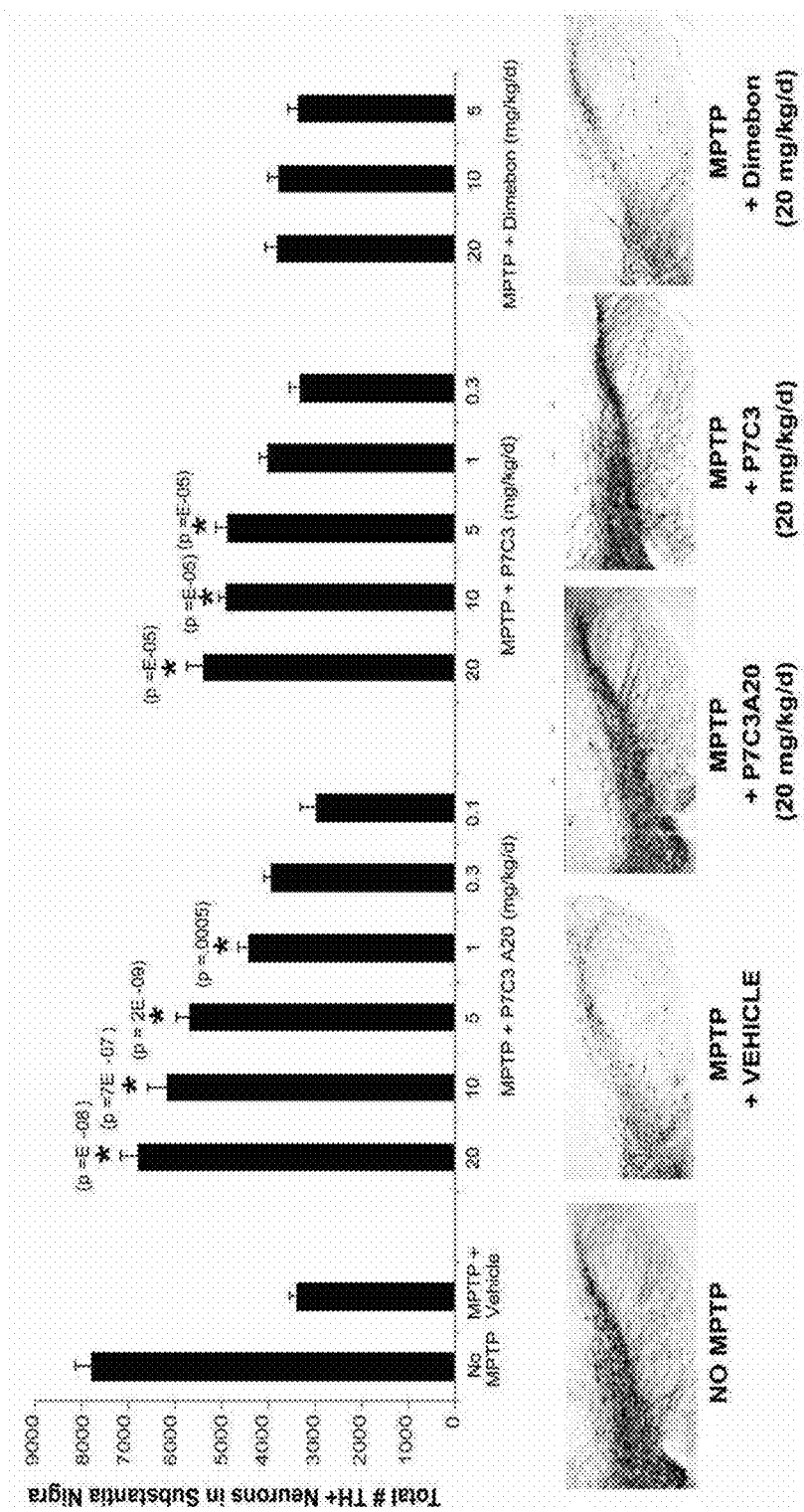
FIG. 29A and FIG. 29B. Neuroprotective efficacy of P7C3 and P7C3A20 from MPTP-toxicity to SNc dopaminergic neurons.

We compared the protective efficacy of our agents in the Tatton and Kish model of MPTP administration, which induces prolonged apoptotic death of SNc dopaminergic neurons lasting about 3 weeks after a short course of daily MPTP administration. Mice were treated daily for 5 days with 30 mg/kg/day free base MPTP. On the sixth day, 24 hours after receiving the fifth and final dose of MPTP, daily treatment with P7C3, P7C3A20, Dimebon or vehicle was initiated. This testing paradigm ensured that any observed activity of P7C3 or its analogs could be attributed to neuroprotective effects, and not to disruption of MPTP uptake or metabolism. Dose-response studies were conducted in which mice received twice daily doses of each compound (or vehicle) for the ensuing 21 days (FIG. 29A). Treatment groups consisted of 15 animals each. At the end of the 21 day treatment period, mice were sacrificed by transcardial perfusion with 4% paraformaldehyde, and fixed brains were sectioned through the striatum and SNc at 30 μM intervals. Every fourth section (spaced 120 μM apart) was stained with antibodies specific to tyrosine hydroxylase (TH) (Abcam, rabbit anti-TH, 1:2500). The TH enzyme catalyzes the conversion of the amino acid L-tyrosine to L-3,4-dihydroxyphenylalanine (L-DOPA), which serves as the precursor for dopamine. TH staining thus provides a means to immunohistochemically identify dopaminergic neurons. By counting the number of TH+ cells in the SNc, we were able to assess the neuroprotective efficacy of the three chemicals following MPTP exposure. All microscopic analysis was performed by two investigators, blind to treatment group.

As has been observed by others, MPTP administration reduced the number of TH+ neurons in the SNc by about 50% (VEH) (FIG. 29A). This neurotoxicity was blocked to varying degrees by both P7C3 and P7C3A20. P7C3 enhanced survival by about 40% over VEH at a dose of 5 mg/kg/day, and the highest dose of P7C3 (20 mg/kg/day) afforded almost 60% protection relative to vehicle. By contrast, the 20 mg/kg/day dose of P7C3A20 preserved the number of dopaminergic neurons in the SNc to about 85% of that seen in normal mice not exposed to MPTP. At every dose tested, P7C3A20 provided superior protection to P7C3. Both CoE and potency of P7C3A20 were greater than P7C3, with the onset of P7C3A20 efficacy (30% over VEH) at a dose of 1 mg/kg/day. Dimebon failed to confer any measurable degree of protection from MPTP at any dose.

Figure 29B:
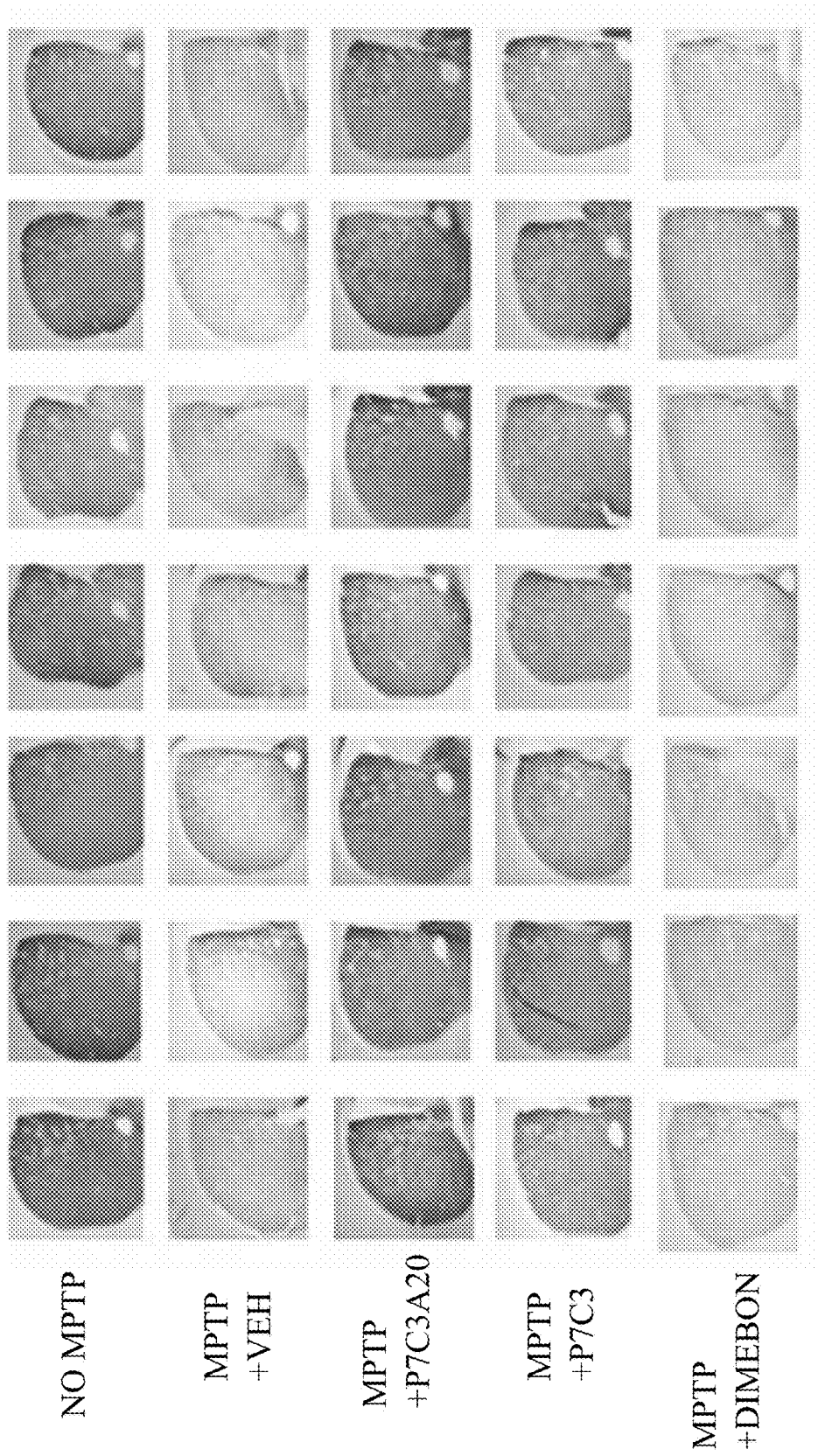

In addition to allowing quantification of dopaminergic cells in the SNc, TH staining is also routinely employed to visualize the integrity of dopaminergic axonal protections from SNc cell bodies into the striatum. FIG. 29B shows that the highest dose of P7C3A20 (20 mg/kg/day) almost completely blocked depletion of dopaminergic axons in the striatum after MPTP exposure. The highest dose of P7C3 also revealed qualitatively notable protection. By contrast, Dimebon offered no protection of dopaminergic axons in the striatum, corresponding to its lack of neuroprotective efficacy in the SNc. As shown in FIG. 30, LC/MS/MS quantification of brain and blood levels of P7C3A20 and P7C3 confirmed that the neuroprotective efficacy for each compound correlated with brain and blood levels for each chemical. Notably, P7C3A20 displayed significantly greater protective efficacy than P7C3 in spite of the fact that P7C3A20 accumulated in brain tissue at less than one-tenth the concentration of P7C3. Dimebon, which displayed no neuroprotective efficacy in the MPTP model of dopaminergic neuron cell death, showed comparable levels of brain accumulation to P7C3A20.

Efficacy Assays of P7C3, P7C3A20 and Dimebon for Protection from $MPP^+$-Toxicity to Dopaminergic Neurons in *C. elegans*.

Figure 31:
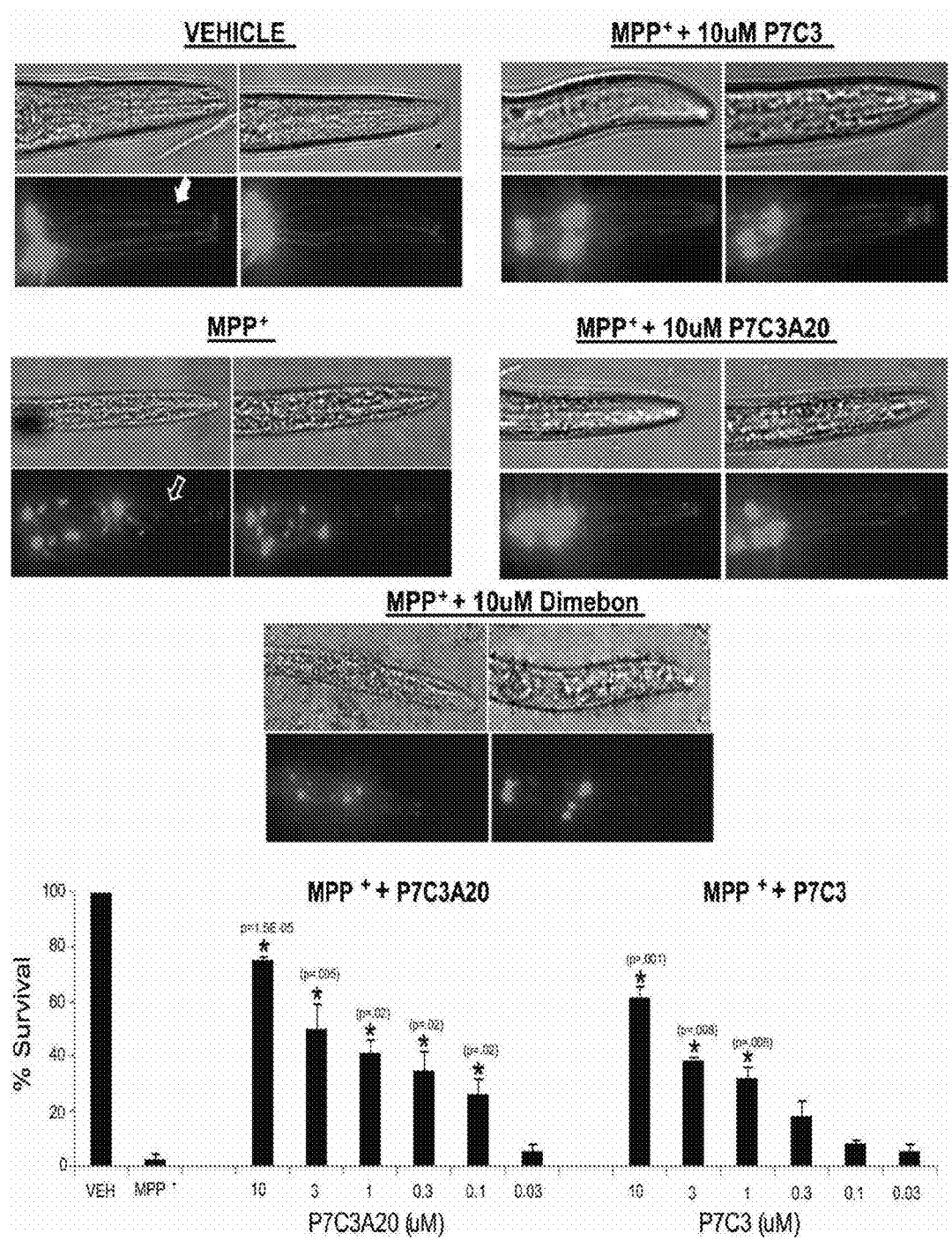
FIG. 31. Neuroprotective efficacy of P7C3 and P7C3A20 for MPP$^+$ toxicity to dopaminergic neurons in *C. elegans*. Worms were treated with 5 mM MPP$^+$ for 40 hrs, with pre-incubation for 30 minutes with different concentrations of test compounds or vehicle. VEH animals not exposed to MPP$^+$ exhibited normal GFP expression in dopaminergic neurons (filled arrow). By contrast, GFP expression was lost after 40 hrs of MPP$^+$ exposure (unfilled arrow). Both P7C3A20 and P7C3 dose-dependently protected dopaminergic neurons from MPP$^+$ toxicity, with P7C3A20 exhibiting greater potency and ceiling of efficacy. 20 worms were analyzed per group, and each group was performed in triplicate. Data are expressed as mean+SEM.

Genes, metabolic signaling pathways, neurotransmitters and receptor pharmacology are highly conserved between *C. elegans* and vertebrates, and exposure of *C. elegans* to $MPP^+$ has been reported to selectively kill dopaminergic neurons and impair mobility. To investigate the neuroprotective efficacy of P7C3A20, P7C3 and Dimebon from $MPP^+$ toxicity in *C. elegans*, we monitored dopaminergic cell death in a transgenic strain of worms in which dopaminergic neurons fluoresce green by virtue of GFP expression driven by the dopaminergic neuron-specific promoter dat-1. As shown in FIG. 31, incubation of synchronized L1 larvae for 40 hours with 5 mM $MPP^+$ elicited virtually complete destruction of all four cephalic sensilla dopaminergic dendrites. For this assessment, GFP fluorescence was observed in 20 worms per group, and was performed in triplicate. Cephalic sensilla dopaminergic dendrites were observed under 40× magnification (AMG, Evos fl microscope), and GFP signal was followed from the nerve ring to the tip of the nose, following established protocols. If any part of a dendrite was absent, as evidenced by loss of GFP signal, it was counted as degraded. All analyses were performed blind to treatment group.

Co-treatment of $MPP^+$-exposed worms with 10 µM P7C3A20 conferred 80% protection. By comparison, the neuroprotective efficacy of the same dose of P7C3 was only about 50%. Neuroprotective efficacy of both agents was diminished as the chemical dose was gradually reduced. By these measures, P7C3A20 showed greater potency than P7C3, with an onset of neuroprotective efficacy of 30% at the 0.1 µM dose. By comparison, P7C3 did not show efficacy (35%) until administered at 1.0 µM. Administration of Dimebon at the highest dose (10 µM) failed to protect dopaminergic neurons in worms from $MPP^+$-induced toxicity.

Efficacy Assays of P7C3, P7C3A20 and Dimebon for Protection from $MPP^+$-Induced Mobility Deficits in *C. elegans*.

Figure 32:
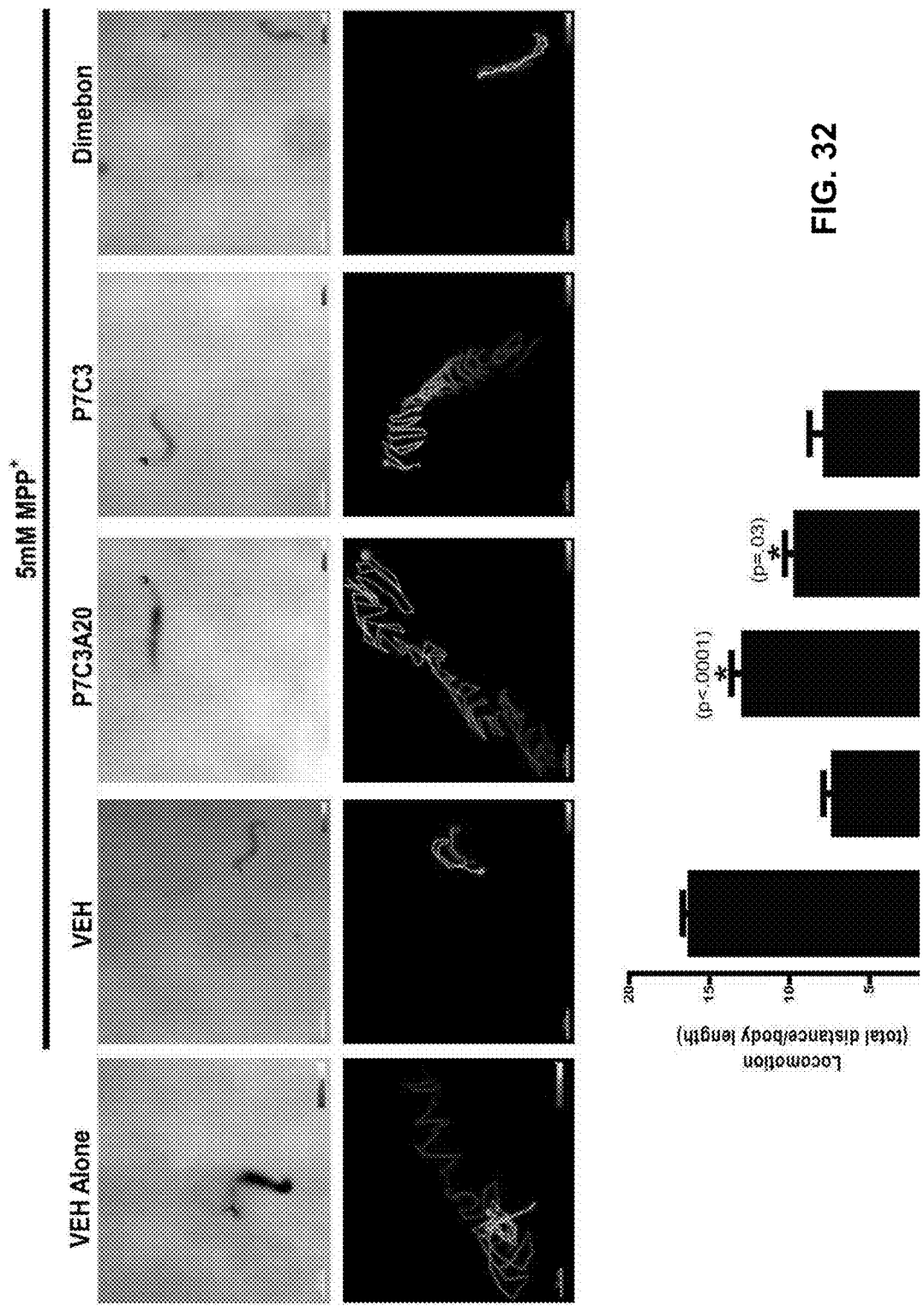
FIG. 32. Protective efficacy of P7C3 and P7C3A20 for MPP$^+$-induced mobility deficits in *C. elegans*. The top panels show worms with the head identified by a green dot. The second row of panels shows the path taken by each worm in 10 seconds, determined by tracking the green dot. Tracking is visualized as starting with blue color and progressing to white by the completion of 10 seconds. The green dot was used to determine locomotion, defined as the distance traveled by the head of the worm in 10 seconds divided by body length. Scale bars represent 70 μM. Quantitative analysis of locomotion showed that untreated VEH controls had a value of 16.2±0.49 (n=30). When worms were treated with MPP$^+$, locomotion was reduced more than 50% (7.2±0.68; n=31, p<0.0001). 10 M P7C3A20 protected mobility to almost 80% of normal (12.8±0.81; n=34, *p<0.01), and 10 μM P7C3 protected almost 60% (m.i. of 9.6±0.72; n=28, *p<0.05). 10 μM Dimebon did not offer any protection. (7.7±1.0; n=30). Experiments were performed in triplicate and data are expressed as mean+SEM.

As a behavioral measure of toxicity, worm mobility was assessed 32 hours after $MPP^+$-exposure. To quantify worm locomotion, video representations were recorded for 10 seconds at 4× magnification using a Nikon Eclipse 80i microscope. Each video segment consisted of 160 frames, and the head of each worm (10-worms per group, repeated in triplicate) was manually tracked in each frame using Imera software. The body length of each worm was also measured by Imera software. The ratio of distance traveled to body length was used to determine the movement index, defined as locomotion, as previously established (Wang J., et al. (2009) An ALS-linked mutant SOD1 produces a locomotor defect associated with aggregation and synaptic dysfunction when expressed in neurons of *Caenorhabditis elegans*. *PLoS Genetics* e10003350). As shown in FIG. 32, locomotion was reduced in *C. elegans* by 50% after 32 hours of exposure to 5 mM $MPP^+$. Co-incubation of $MPP^+$-exposed worms with 10 µM P7C3A20 conferred 80% preservation of locomotion, while 10 µM P7C3 protected to about 60% of normal levels. Dimebon offered no protective efficacy in this behavioral assay.

Correlation of Efficacy of New Analogs of P7C3 in the In Vivo Hippocampal Neurogenesis Assay with Neuroprotective Efficacy in MPTP-Mediated Dopaminergic Cell Death.

Over the past two years, we have conducted a comprehensive structure-activity relationship (SAR) study in order to improve the potency, efficacy and physical properties of the P7C3 series of molecules, as well as to eliminate real or perceived chemical liabilities. To date, we have synthesized over 300 analogs of P7C3, all of which have been evaluated by primary screening in the in vivo hippocampal neurogenesis assay. Our efforts include, but are not limited to, eliminating the bromines and aniline ring, increasing biologic activity, decreasing lipophilicity, eliminating toxicities such as hERG channel binding, increasing solubility and reducing molecular weight. Here, we show the results of evaluation of 8 of these new analogs (FIG. 33A) in both the hippocampal neurogenesis assay (4 mice for each compound) and the MPTP protection assay (10 mice for each compound) (FIG. 33B). All analyses were conducted blind to treatment group.

Figure 33A:
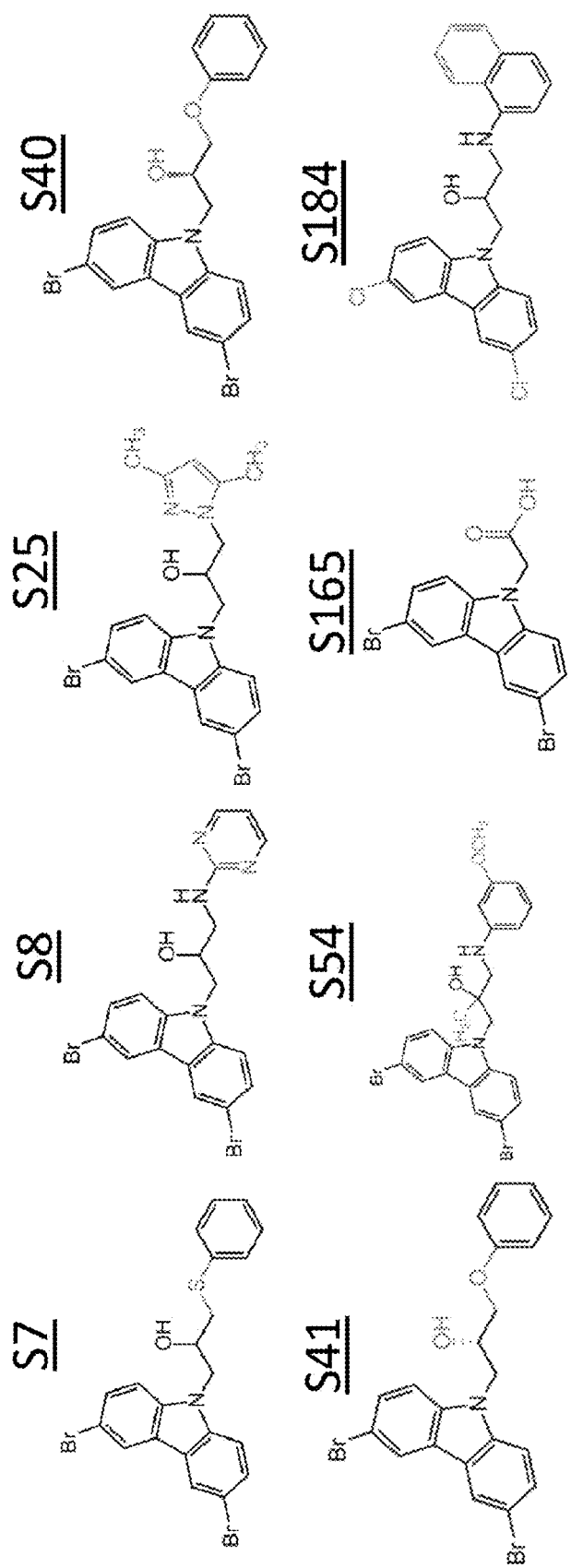
FIG. 33A and FIG. 33B. Efficacy of new P7C3 analogs in the in vivo hippocampal neurogenesis assay correlates with activity in the in vivo MPTP-neuroprotection assay.
Figure 33B:
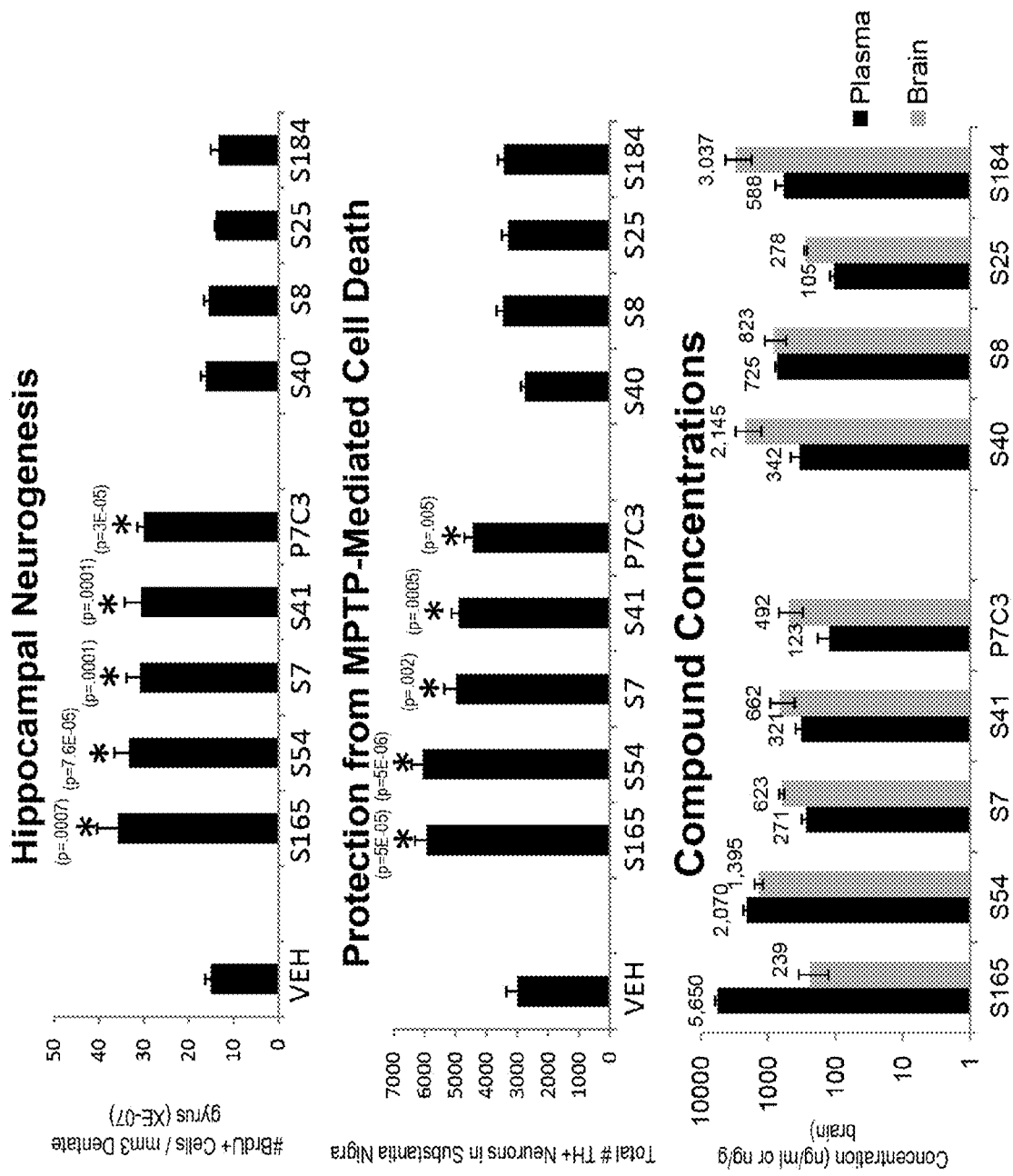

With respect to the original P7C3 scaffold, P7C3-S7 differs by replacing the aniline NH with a sulfide linker, P7C3-S8 differs by replacing the aniline phenyl ring with a pyrimidine, and P7C3-S25 differs by replacing the aniline moiety with a dimethyl pyrazole (FIG. 33A). As shown in FIG. 33B, all of the eight test molecules crossed the blood brain barrier. P7C3-S7 and P7C3-S25 were active in both the hippocampal neurogenesis assay and the MPTP protection assay. By contrast, P7C3-S8 was devoid of activity in both assays. We also compared the efficacy of members of a new enantiomeric pair in these assays. P7C3-S40 and P7C3-S41 differ from P7C3 by replacing the aniline NH with an oxygen linker (FIG. 33A). P7C3S40 and P7C3S41 are the R and S single enantiomers, respectively, and FIG. 33B shows that neuroprotective activity in both assays resides exclusively in the S enantiomer. P7C3-S54 differs from P7C3 mainly by the addition of a methyl group to the central carbon of the propyl linker, and additionally has an OMe group on the aniline ring (FIG. 33A). This analog was observed to retain neuroprotective activity in both assays. P7C3-S165 differs from P7C3 by replacing the aniline and carbinol fragments with a carboxylic acid, a change that dramatically increases polarity (FIG. 33A). Encouragingly, neuroprotection was observed in both assays (FIG. 33B).

Finally, P7C3-S184 differs from P7C3 by replacing the bromines on the carbazole with chlorines, and by replacing the aniline with a naphthyl amine (FIG. 33A). This molecule was inactive in both in vivo assays. P7C3-S184 has been reported as a (3-secretase (BACE1) inhibitor (Asso V., et al. (2008) alpha-naphthylaminopropan-2-ol derivatives as BACE1 inhibitors. *ChemMedChem* 3:1530-1534). BACE1 is an aspartate proteolytic enzyme that catalyzes the formation of Aβ peptide from amyloid precursor protein, which has been proposed as a therapeutic target for Alzheimer's disease. By analyzing BACE1 inhibition with multiple molecules in our P7C3 series, we have found no correlation between neuroprotective efficacy in our in vivo models and BACE1 inhibition (data not shown).

Discussion

The results of a target-agnostic, unbiased screen of 1,000 chemically diverse, drug-like compounds led to the identification of an aminopropyl carbazole endowed with the capacity to enhance adult neurogenesis. This compound, designated P7C3, was found to act by blocking the death of newborn neurons in the dentate gyms of adult mice. Here we have sought to answer a simple question. If P7C3 is capable of preventing the death of newborn neurons during hippocampal neurogenesis in adult mice, this compound may also prevent death of existing neurons in animal models of neurodegenerative disease. More specifically, we have administered MPTP to mice as a means of killing dopamine neurons. Fully 24 hours after removal of the toxin, mice were treated with varying doses of one of three compounds for a period of three weeks. Thereafter mice were sacrificed and assayed for evidence of neuroprotective efficacy. As a second, related animal model of neuron death, C. elegans worms were co-treated with $MPP^+$ and varying doses of P7C3, P7C3A20 and Dimebon as a means of assessing neuroprotective activity.

The three compounds chosen for extensive testing, P7C3, its structurally related analog P7C3A20, and Dimebon, were selected by virtue of the knowledge that they demonstrate distinct pro-neurogenic activities. Among dozens of chemical analogs of P7C3 evaluated in the study first reporting this category of pro-neurogenic compounds, P7C3A20 displayed the highest potency and ceiling of pro-neurogenic efficacy. In addition to the P7C3 and P7C3A20 chemicals, we included Dimebon in the present study for two reasons. First, even though P7C3 and Dimebon both contain three-ring heterocycles, Dimebon was found to display significantly diminished levels of potency and efficacy relative to P7C3 in our original study. Its pro-neurogenic activity in the hippocampus of adult mice was observed only at relatively high doses, and its ceiling of efficacy was clearly diminished relative to both P7C3 and P7C3A20. Likewise, when tested for its ability to protect mitochondrial membrane integrity following exposure of cultured cells to a calcium ionophore, Dimebon exhibited a protective potency between 100- and 1,000-fold lower than P7C3. Second, Dimebon has been the subject of extensive clinical studies in both Alzheimer's disease and Huntington's disease. Despite early indications of efficacy in a phase 2 trial for Alzheimer's disease (Doody R. S., et al. (2008) Effect of Dimebon on cognition, activities of daily living, behaviour, and global function in patients with mild-to-moderate Alzheimer's disease: a randomised, double-blind, placebo-controlled study. Lancet 372:207-215), Dimebon failed in two independent phase 3 trials. By testing the properties of these three compounds in the present study of neuroprotective efficacy, one having a very favorable efficacy profile as a pro-neurogenic chemical (P7C3A20), another having an intermediate efficacy profile (P7C3), and a third having a far more modest efficacy profile (Dimebon), we sought to determine whether this hierarchy of activities might be preserved.

Encouragingly, we observe that the A20 chemical variant of P7C3 displays significant neuroprotective efficacy in the MPTP model of dopaminergic neuron cell death in both rodents and worms. P7C3, the original compound discovered in the unbiased screen of 1,000 drug-like chemicals for pro-neurogenic activity, displayed a lower level of neuroprotective activity in the mouse and worm models of dopaminergic neuron death than P7C3A20. By contrast, Dimebon showed no protective activity in either assay. Although others have recently demonstrated that treatment of an Alzheimer's disease mouse model (TgCRND8 mice) with Dimebon improves memory and lowers accumulation of insoluble Aβ42 in the brain, Dimebon appears too weakly active to afford neuroprotection in the models of Parkinson's disease that we have utilized.

We conclude that P7C3 and P7C3A20 protect dopaminergic neurons from MPTP-induced cell death with a hierarchy of activity that is analogous to their abilities to protect newborn hippocampal neurons from cell death. If correct, this interpretation offers the possibility that the relatively straightforward assay we have employed to monitor the activities of hundreds of chemical variants of P7C3, wherein adult neurogenesis is monitored over a seven day period following direct administration of test compounds into the adult mouse brain, may represent a trusted surrogate for the refinement of drug-like chemicals having broad neuroprotective activity. Indeed, we hereby observe that an unbiased, blinded analysis of nine analogs of P7C3 confirms this correlation. Five of these molecules showed significant efficacy in our standard in vivo hippocampal neurogenesis assay, and these same five molecules also showed significant neuroprotective efficacy from MPTP-mediated neurotoxicity to dopaminergic neurons. The four analogs that were inactive in the in vivo neurogenesis likewise showed no efficacy in the in vivo MPTP neurotoxicity assay. Taken together, these results show that the relatively rapid evaluation of new molecules in the in vivo neurogenesis assay is predictive of their neuroprotective efficacy in the MPTP assay.

Ongoing SAR efforts with our P7C3 series of molecules using the in vivo neurogenesis assay appears to qualify as a rapid and accurate way to guide the refinement of this series of molecules into a neuroprotective drug for Parkinson's disease. In this context, several of the analogs shown in FIG. 33 represent potential improvements to P7C3. We have been primarily concerned with the presence of an aniline ring, as this functionality can be associated with toxicity. Encouragingly, three of the analogs (P7C3S7, -S41, and -S165) lack aniline rings and display potency equal to or greater than P7C3 in both in vivo assays. We further note that P7C3 was originally identified as a racemic mixture, and that racemic mixtures may require additional characterization for clinical development. P7C3S41 and P7C3S165 address this limitation because the former is a single enantiomer while the latter lacks stereochemistry altogether. Finally, we have sought to reduce the polarity and molecular weight of these neuroprotective compounds. P7C3S165 is significantly lighter than P7C3 (mw=383 Da, vs 474 Da for P7C3) and, by virtue of the carboxylic acid, substantially more polar. These results suggest that it should be possible to further improve the physical properties of these analogs in efforts to optimize derivatives suitable for clinical testing.

Consistent with the interpretation that the activity of P7C3 analogs in the in vivo neurogenesis assay correlates with neuroprotective efficacy in mature neurons are the results of assays of P7C3, P7C3A20 and Dimebon in a mouse model of amyotrophic lateral sclerosis. In this model, using mice expressing a high level of a human transgene encoding a mutated variant of the gene encoding human Cu,Zn superoxide dismutase, we have observed the same hierarchy of activities wherein P7C3A20 is active, P7C3 is intermediately active and Dimebon is inactive. If the more active variants of this class of compounds indeed possess neuroprotective properties, and if we can rely on the relatively rapid in vivo assay of enhanced neurogenesis in order to rank order compounds for structure-activity relationship (SAR) scoring, it should be possible to optimize variants with the goal of selecting an appropriately qualified chemical to advance for human testing. To date, no safely tolerated, neuroprotective chemical is available for the treatment of any of a wide range of neurodegenerative diseases, including Parkinson's disease, Alzheimer's disease and amyotrophic lateral sclerosis. Based upon the observations reported herein, we propose that a properly optimized variant of the P7C3 class of pro-neurogenic, neuroprotective chemicals may offer promise for the treatment of neurodegenerative disease.

Materials and Methods

Approval for the animal experiments described herein was obtained by the University of Texas Southwestern Medical Center Institutional Animal Care and Use Committee.

Statistics: All p values were obtained with the Student's t test.

Day Survival Assay of Newborn Hippocampal Neurons: Because both social activity and voluntary exercise enhance hippocampal neurogenesis, mice were individually housed without access to running wheels throughout the entire procedure, beginning one week prior to bromodeoxyuridine (BrdU, Sigma-Aldrich) labeling of newborn cells. Throughout the study, mice had ad libitum access to food and water. BrdU was injected intraperitoneally at 150 mg/kg i.p., and 24 hours later administration of test compounds or vehicle was initiated. P7C3 and P7C3A20 were dissolved in 5% dextrose (pH 7.0) with 2.5% DMSO and 10% Cremaphor EL (Sigma, C5135). Dimebon was dissolved in normal saline. Compounds were compared to their respective controls, and were tested at 2.5, 5, 10 and 20 mg/kg twice daily (i.p.) for 30 days. The injection site was alternated between right and left sides. Each group consisted of six 12-week-old adult male C57 Bl/6 mice. Animals were monitored daily for general health and weight loss. Cage changes were performed per routine scheduling. After 30 days of compound administration, mice were sacrificed by transcardial perfusion with 4% paraformaldehyde at pH 7.4, and their brains were processed for immunohistochemical detection of incorporated BrdU in the dentate gyms. Dissected brains were immersed in 4% paraformaldehyde overnight at 4 degrees Celsius, then cryoprotected in sucrose before being sectioned with a Leica SM2000R sliding microtome coronally into 40 μM thick free-floating sections. Unmasking of BrdU antigen was achieved through incubating tissue sections for two hours in 50% formamide/2×SSC at 65 degrees Celsius, followed by five minute wash in 2×SSC and subsequent incubation for thirty minutes in 2M HCl at 37 degrees Celsius. Sections were processed for immunohistochemical staining with mouse monoclonal anti-BrdU (1:100, Roche). Diaminobenzidine was used as a chromagen, and tissue was counter-stained with hematoxylin to aid in visualization of the neuroanatomy. Images were analyzed with a Nikon Eclipse 90i motorized research microscope with Plan Apo lenses coupled with Metamorph Image Acquisition software (Nikon). Quantification of all staining was done blind to treatment group. The number of BrdU+ cells in the entire dentate gyrus was quantified by counting BrdU+ cells within the dentate gyrus in every fifth section throughout the entire hippocampus and then normalizing for dentate gyms volume. P7C3-S7, -S8, -S40, -S41, -S54, -S165 and -A20 were synthesized as previously described. P7C3-S184 was synthesized as previously described by Asso et al. (2008) alpha-naphthylaminopropan-2-ol derivatives as BACE1 inhibitors. *ChemMedChem* 3:1530-1534.

Pharmacokinetic Analysis: C57BL/6 mice treated with MPTP and then dosed IP with compound for 21 days were utilized for pharmacokinetic (PK) analysis of total P7C3, P7C3A20 and Dimebon levels in plasma and brain. In a separate set of experiments designed to test the ability of new P7C3 analogs to cross the blood brain barrier, C57BL/6 mice were dosed IP a single time with compounds at 10 mg/kg. P7C3, P7C3A20 and Dimebon were formulated for administration as described above. Analogs were formulated in 5% Dextrose, pH 7.4, containing 5% DMSO and 10% Cremophor EL with the exception of P7C3-S8 which required 10% DMSO and 20% Cremophor EL dissolved in 5% Dextrose for delivery. Six hours after the final compound dose, animals were given an inhalation overdose of $CO_2$ and whole blood and brain collected. Plasma was prepared from blood and was stored along with the brain tissue at −80° C. until analysis. Brain homogenates were prepared by homogenizing the tissues in a 3-fold volume of PBS. Total brain homogenate volume was estimated as volume of PBS added plus volume of brain in mL. One hundred mL of either plasma or brain homogenate was processed by addition of a two- or four-fold excess of methanol or acetonitrile containing formic acid and an internal standard (IS), N-benzylbenzamide (Sigma-Aldrich, lot #02914LH) to precipitate plasma or tissue protein and release bound drug. The final formic acid concentration was 0.1%, and the final IS concentration was 25 ng/ml. Extraction conditions were optimized prior to PK analysis for efficient and reproducible recovery over a three log range of concentrations. The samples were vortexed 15 sec, incubated at room temp for 10' and spun 2×16,100 g in a standard refrigerated microcentrifuge. The supernatant was then analyzed by LC/MS/MS. Standard curves were prepared by addition of the appropriate compound to plasma or brain homogenate. A value of 3× above the signal obtained in the blank plasma or brain homogenate was designated the limit of detection (LOD). The limit of quantitation (LOQ) was defined as the lowest concentration at which back calculation yielded a concentration within 20% of the theoretical value and above the LOD signal. LOQ values for plasma and brain ranged from 0.5 to 500 ng/ml but were well-below the concentrations measured at 6 hours for all of the compounds. Compound levels were monitored by LC/MS/MS using an AB/Sciex (Framingham, Mass.) 3200 Qtrap mass spectrometer coupled to a Shimadzu (Columbia, Md.) Prominence LC. The compounds were detected with the mass spectrometer in MRM (multiple reaction monitoring) mode by following the precursor to fragment ion transition 474.9→337.8 for P7C3 (pos. mode; $M+H^+$), 507.0→204.1 for P7C3A20 (pos. mode; $M+H^+$), 320.3→277.3 for Dimebon (pos. mode; $M+H^+$), 381.9→80.7 for P7C3-S165 (neg. mode; $M-H^+$), 519.0→338.0 for P7C3-S54 (pos. mode; $M+H^+$), 536.0→536.0 (redundant MRM) for P7C3-S7 (neg mode; $M+HCOO^-$), 520.0→520.0 for P7C3-S41 (neg mode; $M+HCOO^-$); 520. 1→520.1 for P7C3-S40 (neg mode; $M+HCOO^-$), 477. 1→138.2 for P7C3-S8 (pos. mode; $M+H^+$), 478.0→153.2 for P7C3-S25 (pos. mode; $M+H^+$), and 435.2→248.2 for P7C3-S184 (pos. mode; $M+H^+$). The IS, N-benzylbenzamide, was monitored using a 212.1→91.1 transition (pos. mode; $M+H^+$). An Agilent (Santa Clara, Calif.) XDB C18 column (50×4.6 mm, 5 micron packing) was used for chromatography with the following conditions: Buffer A: dH20+0.1% formic acid, Buffer B: methanol+ 0.1% formic acid, 0-1. 5 min 0% B, 1.5-2.5 min gradient to 100% B, 2.5-3.5 min 100% B, 3.5 to 3.6 min gradient to 0% B, 3.6 to 4.5 min 0% B. Chromatography conditions were identical for all compounds, except the initial and final concentration of Buffer B, which was set to 0% for P7C3 and P7C3A20 and 3% for Dimebon and all of the other P7C3 analogs.

Maintenance of *C. elegans*: *C. elegans* were grown at 20 degrees Celsius on nematode growth medium (NGM) agar in 60 mm Petri plates according to standard protocols. Worms were fed the *Escherichia coli* nutrient-rich strain HB101. All experiments were performed using BZ555 [Pdat-1::GFP], obtained from the *Ceanorhabditis* Genetics Center at the University of Minnesota, USA. BZ555 is an integrated transgenic strain (chromosome IV) that expresses GFP under the control of the dopamine neuron specific promoter dat-1. To obtain first-stage synchronous larvae (L1's), gravid adults were treated with alkaline hypochlorite solution, rinsed three times in M9 buffer, suspended in 6 ml of M9 and shaken for 12-14 hrs at room temperature, according to standard protocols. Compound tests were performed in 500 µl solution of PBS, compounds, and a bacterial density of HB101 at OD600 of 2 at 20 degrees Celsius in 12-well plates (BD Falcon; Thermo Fisher Scientific Inc.).

Assessment of MPTP-Mediated Neurotoxicity to Murine SNc Neurons: 15 adult male C57Bl/6 mice were individually housed for one week and then injected daily for 5 days with 30 mg/kg/day (i.p.) free base MPTP (Sigma). On day 6, 24 hours after receiving the fifth and final dose of MPTP, daily treatment with P7C3, P7C3A20, Dimebon or vehicle was initiated. Mice were housed in disposable caging, and protective gear and precautions were implemented for handling MPTP in accordance with UT Southwestern Medical Center policy. Dose response studies were conducted in which mice received twice daily doses of each compound (or vehicle) by intraperitoneal injection for the following 21 days, after which mice were sacrificed by transcardial perfusion with 4% paraformaldehyde. Brains were dissected, fixed overnight in 4% paraformaldehyde, and cryoprotected in sucrose for freezing by standard procedures. Frozen brains were sectioned through the striatum and SNc at 30 uM intervals, and every fourth section (spaced 120 µM apart) was stained with antibodies directed against tyrosine hydroxylase (TH) (Abcam, rabbit anti-TH, 1:2500). Diaminobenzidine was used as a chromagen, and tissue was counter-stained with hematoxylin to aid in visualization of the neuroanatomy. Images were analyzed with a Nikon Eclipse 90i motorized research microscope with Plan Apo lenses coupled with Metamorph Image Acquisition software (Nikon). TH+ neurons were counted with Image J software (NIH) in every section by 2 blinded investigators and results were averaged and multiplied by the sectioning interval to determine the total number of TH+ neurons per SNc.

Assessment of $MPP^+$ Dopaminergic Neuron Toxicity in *C. elegans*: Synchronized L1 larvae were plated into each well of a 12-well plate (approximately 400 larvae per well) containing PBS, Vehicle or compounds, with or without 5 mM $MPP^+$ iodide (Sigma) freshly diluted in PBS. DMSO was used as vehicle (VEH) and the concentration in treatment groups was maintained below 1%. The assay solution (500 ml) was incubated for 40 hrs at 20 degrees Celsius. The worms were then washed in $dH_2O$ and supernatant was aspirated. To examine dopaminergic neuron toxicity, worms were anesthetized (0.1% tricaine, 0.01% tetramizole) for 5 min and then transferred to microscope slides and coverslipped. Pictures were taken at 40× magnification (AMG, Evos fl microscope). Each experiment was conducted in triplicate with 10-20 worms counted per condition. For quantification, investigators were blind to treatment condition. Quantification was done by observing all four cephalic sensilla (CEP) dendrites, per standard protocol. Briefly, GFP fluorescence was visualized from the nerve ring to the tip of the nose, and if any portion of a dendrite was absent then it was counted as being degenerated.

Locomotion Analysis of *C. elegans*: A video-based assay was used to assess the swim speed, distance traveled and length of worms. After exposure to $MPP^+$ for 32 hrs, worms were washed, resuspended in M9 buffer (500 ul) and transferred to microscope slides. A 10 second movie was recorded at 4× magnification using a Nikon Eclipse 80i microscope. Each movie consisted of 160 frames and the distance traveled by the head of each worm was manually tracked in each frame using Imera software. This software was also used to measure the length of the worm body. The ratio of movement distance to body length was used as a movement index, and defined as locomotion per standard protocols.

O. Neuroprotective Efficacy of Aminopropyl Carbazoles in a Mouse Model of Amyotrophic Lateral Sclerosis Amyotrophic lateral sclerosis (ALS), also known as Lou Gehrig's disease, is a relatively rare, adult-onset, rapidly progressive and fatal disease that involves degeneration of spinal cord motor neurons (Tandan R, Bradley W. G. (1985) Amyotrophic lateral sclerosis. Part 1. Clinical features, pathology, and ethical issues in management. *Ann Neurol* 18:271-280). This disorder causes muscle weakness and atrophy throughout the body, and patients with ALS ultimately lose all voluntary movement. The earliest parts of the body affected in ALS reflect those motor neurons that are damaged first. Regardless of the region of onset, however, muscle weakness and atrophy invariably spread to other parts of the body as the disease progresses. Although disease progression varies between individuals, most patients are eventually unable to stand or walk, get in or out of bed on their own, or use their hands and arms. Difficulty with chewing, swallowing and breathing leads to progressive weight loss and increased risk of choking and aspiration pneumonia. Towards the end stages of disease, as the diaphragm and intercostal muscles weaken, most patients require ventilator support. Individuals with ALS most commonly die of respiratory failure or pneumonia within 2-5 years of diagnosis. There are no current treatments for ALS.

Approximately 20% of inherited cases of ALS, and 3% of sporadic cases, are associated with autosomal dominant mutations in the SOD1 gene on chromosome 21, and about 150 different mutations dispersed throughout the gene have been identified thus far. SOD1 encodes cytosolic Cu/Zn superoxide dismutase, an antioxidant enzyme that protects cells by converting superoxide (a toxic free radical generated through normal metabolic activity of mitochondria) to hydrogen peroxide. Unchecked, free radicals damage both mitochondrial and nuclear DNA, as well as proteins within cells. In ALS linked to mutations in SOD1, cytotoxicity of motor neurons appears to result from a gain of toxic SOD1 function, rather than from loss of dismutase activity. Although the exact molecular mechanisms underlying toxicity are unclear, mutation-induced conformational changes in SOD1 lead to misfolding and subsequent aggregation of mutant SOD1 in cell bodies and axons. Aggregate accumulation of mutant SOD1 is thought to disrupt cellular functions and precipitate neuron death by damaging mitochondria, proteasomes, protein folding chaperones, or other proteins.

Transgenic animal models of mutant SOD1, such as G93A-SOD1 mutant mice, are currently used for research into the pathogenic mechanisms thought to broadly underlie ALS. Mice hemizygous for the G93A-SOD1 transgene express 18+/−2.6 copies of a form of SOD1 found in some patients with inherited ALS (a substitution of glycine to alanine at codon 93). This was the first mutant form of SOD1 to be expressed in mice, and is the most widely used and well-characterized mouse model of ALS. Superoxide dismutase activity in these mice is intact, and the pathogenic effect of the mutant transgene appears to be gain of function, as is thought to occur in human patients. Death of motor neurons in these mice occurs in the ventral horn of the spinal cord and is associated with paralysis and muscle atrophy. Around 100 days of age, G93A-SOD1 mice characteristically experience the onset of paralysis in one or more limbs, due to loss of spinal cord motor neurons. Paralysis spreads rapidly throughout the body, culminating in death of 50% of the mice within seven weeks of disease onset.

We have previously reported the identification of a proneurogenic, neuroprotective aminopropyl carbazole (P7C3) discovered through a target-agnostic in vivo screen of postnatal hippocampal neurogenesis (Pieper et al. (2010) Discovery of a Proneurogenic, Neuroprotective Chemical. Cell 142:39-51). Prolonged administration of P7C3 to mice suffering from pathologically high levels of neuronal apoptosis in the dentate gyrus safely restored hippocampal structure and function with no observable physiologic side effects. Furthermore, extended administration of P7C3 to aged rats impeded hippocampal cell death and preserved cognitive ability as a function of terminal aging.

We have synthesized and characterized a variant of P7C3, known as P7C3A20, which has greater potency and proneurogenic efficacy than the parent compound. P7C3A20 differs structurally by replacement of the hydroxyl group at the chiral center of the linker with a fluorine, and the addition of a methoxy group to the aniline ring. P7C3A20 also displays a more favorable toxicity profile than P7C3, with no hERG channel binding, histamine receptor binding or toxicity to HeLa cells. We have also found that Dimebon, an antihistaminergic drug that is chemically related to P7C3 and reported to have anti-apoptotic and mitochondrial protective properties, displays modest efficacy in the same biologic assays employed to discover and characterize P7C3 and P7C3A20. However, it does so with substantially less potency and ceiling of efficacy (CoE).

Armed with three related chemicals, one having very high pro-neurogenic activity (P7C3A20), one having intermediate activity (P7C3), and one having only modest activity (Dimebon), we initiated efficacy studies in two animal models of neurodegenerative disease. We report above evidence of significant neuroprotective activity of P7C3A20 in a rodent model of Parkinson's disease (PD). P7C3 exhibited intermediate activity in the PD animal model, and Dimebon showed no evidence of efficacy. The correlative activities of chemicals tested in the neurogenesis and PD assays were extended to eight additional analogs of P7C3. In every case, derivatives of P7C3 that were active in the neurogenesis assay were also active in the animal model of PD, and inactive variants were inactive in both assays.

Here, we have employed the same approach to score the activities of P7C3A20, P7C3 and Dimebon in a model of neuron death outside of the brain. To address this question, we utilized G93A-SOD1 mutant mice, a model of amyotrophic lateral sclerosis (ALS) characterized by spinal motor neuron death associated with decreased motor functioning. As was observed for the rodent model of PD, we hereby report robust activity of P7C3A20 in the G93A-SOD1 mouse model of ALS, intermediate activity for P7C3, and no activity for Dimebon.

Results

Efficacy of Early Administration of P7C3 to G93A-SOD1 Mutant Mice Before Disease Onset.

As an initial test of efficacy in this disease model, we intraperitoneally administered P7C3 to female G93A-SOD1 transgenic mice using a treatment paradigm of 20 mg/kg/day P7C3, with vehicle administered to siblings, starting at 40 days of age. This treatment scheme was selected based on standard protocols for initial proof of concept screens in G93A-SOD1 mutant mice. To control for transgene copy number, mice were sibling matched between treatment groups, as per standard protocol, and quantitative PCR was performed to ensure that the copy number was maintained within the normal range. After initiation of P7C3 or vehicle treatment, date of onset of illness was determined by peak weight, and initial progression of disease was defined as the day at which mice fell to 10% below their maximum weight. Mice were also assessed daily by a standard measure of neurological severity score ranging from 0-4, with a higher number reflecting greater neurologic impairment. In addition to weight loss, a score of 2 or greater for two consecutive days was also employed as an indication of disease progression.

P7C3 treatment slowed disease progression in G93A-SOD1 mice, as indicated by delaying the time point at which mice dropped to 10% below their maximum weight. Treatment with P7C3 also delayed the age at which G93A-SOD1 mice advanced to a neurological severity score of 2. Furthermore, P7C3 treatment improved performance in the accelerating rotarod task as a function of disease progression, indicating a slowing of progression of motor impairment. This effect of slowing disease progression did not translate into increased survival of the animals, which is consistent with other interventions that have ameliorated disease symptoms in rodent models of ALS without improving survival.

Comparison of the Efficacy of Administration of P7C3A20, P7C3 and Dimebon at Disease Onset for Blocking Spinal Motor Neuron Cell Death in G93A-SOD1 Mutant Mice.

Based on the promising results of early (day 40) administration of P7C3 to G93A-SOD1 mutant mice, we next sought to determine whether P7C3A20, P7C3 or Dimebon could protect ventral horn spinal motor neurons when administered at the expected time of disease onset (day 80). We initiated administration of either P7C3, P7C3A20 or Dimebon, each at a dose of 20 mg/kg/day, and analyzed motor neuron cell survival by staining lumbar spinal sections for choline acetyltransferase (ChAT). ChAT, the enzyme that synthesizes the neurotransmitter acetylcholine, serves as a marker for spinal cord motor neurons. All sections were counted blind to treatment group in order to quantify motor neuron survival, and five mice for each treatment group were analyzed at 90, 100, 110 and 120 days. Each treatment group was compared to its own sibling-matched group that received the corresponding vehicle.

Figure 34B:
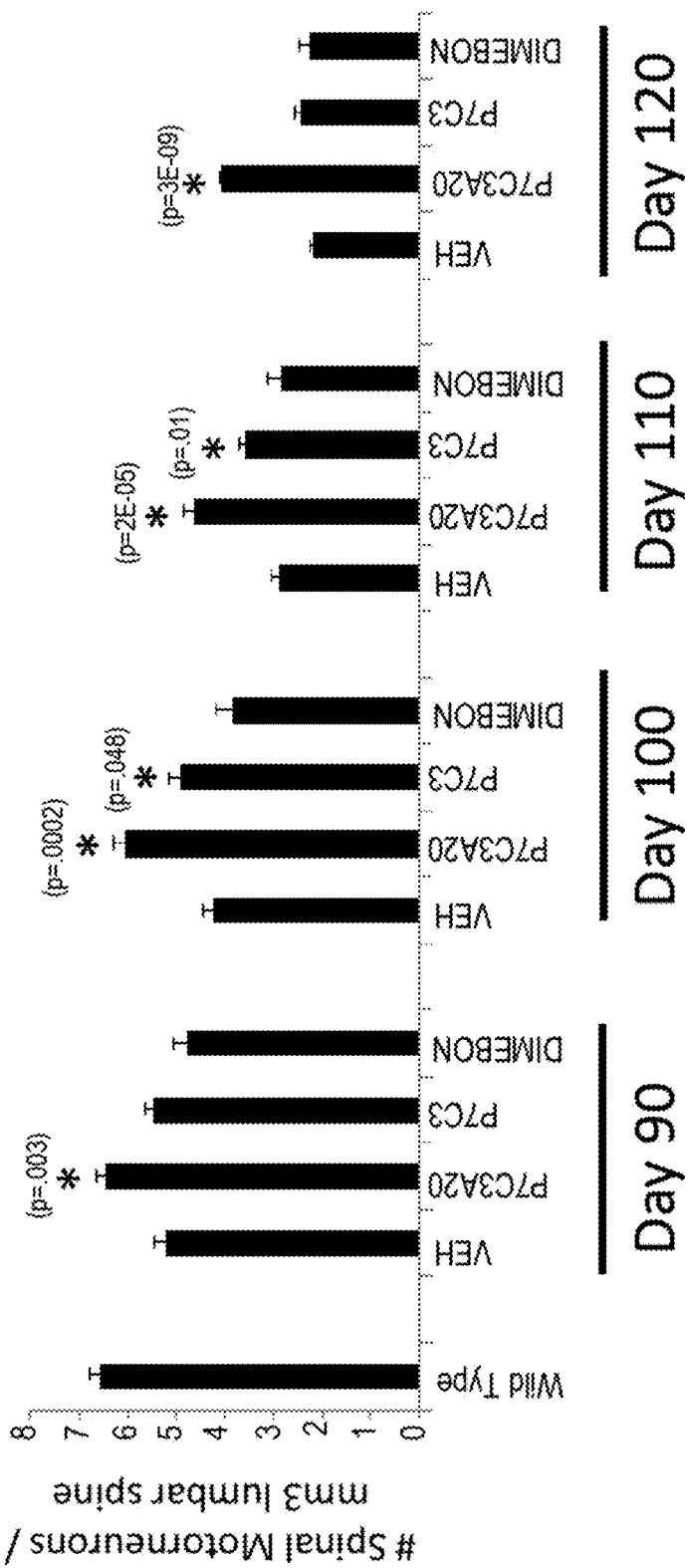

As shown in FIG. 34, the wild type bar represents the average number of spinal motor neurons in 110 day old, vehicle-treated, wild-type littermate mice. Because survival of motor neurons did not differ between the various vehicle treatment groups within any given time point, the results were combined for ease of presentation. For animals expressing the G93A-SOD1 transgene, the number of spinal cord motor neurons steadily declined between days 90 and 120 (FIG. 34). At every time point, treatment with P7C3A20 provided significant protection from spinal motor neuron cell death (FIG. 34). Treatment with Dimebon revealed a rate of motor neuron loss indistinguishable from vehicle treatment groups. P7C3, by contrast, provided intermediate protection on days 100 (p=0.048) and 110 (p=0.01). By the time mice reached 120 days of age, however, the P7C3-treated group showed the same degree of motor neuron cell loss as vehicle and Dimebon-treated groups. Representative immunohistological staining of spinal cord sections is shown in FIG. 34 from each of the five mice examined on day 110. Taken together, these results demonstrate that daily administration of P7C3A20 starting at disease onset effectively blocks spinal motor neuron cell death in G93A-SOD1 mutant mice. P7C3 was active by these measures, but to a lesser extent than P7C3A20, whereas Dimebon was completely devoid of neuroprotective activity.

Comparison of the Efficacy of Administration of P7C3A20, P7C3 and Dimebon at Disease Onset for Preserving Rotarod Performance in G93A-SOD1 Mutant Mice.

Having observed evidence of compound-mediated protection of spinal cord motor neurons, we next sought to determine whether motor performance might also be protected in these mice. Motor performance was monitored by the accelerating rotarod task standardly employed for evaluation of rodent models of ALS. We again initiated administration of P7C3, P7C3A20 or Dimebon on day 80, at 20 mg/kg/day, starting with no less than 20 mice per treatment group. Each animal in each group had its own sibling-matched vehicle control, and testing was conducted blind to treatment group. Rotarod training was initiated on day 50 for 2 days, and repeated weekly testing was conducted every 7 days thereafter. Each mouse was subjected to four trials of 600 seconds each, with a 20 minute recovery break between each trial. The latency time to fall was averaged across all 4 trials.

Figure 35:
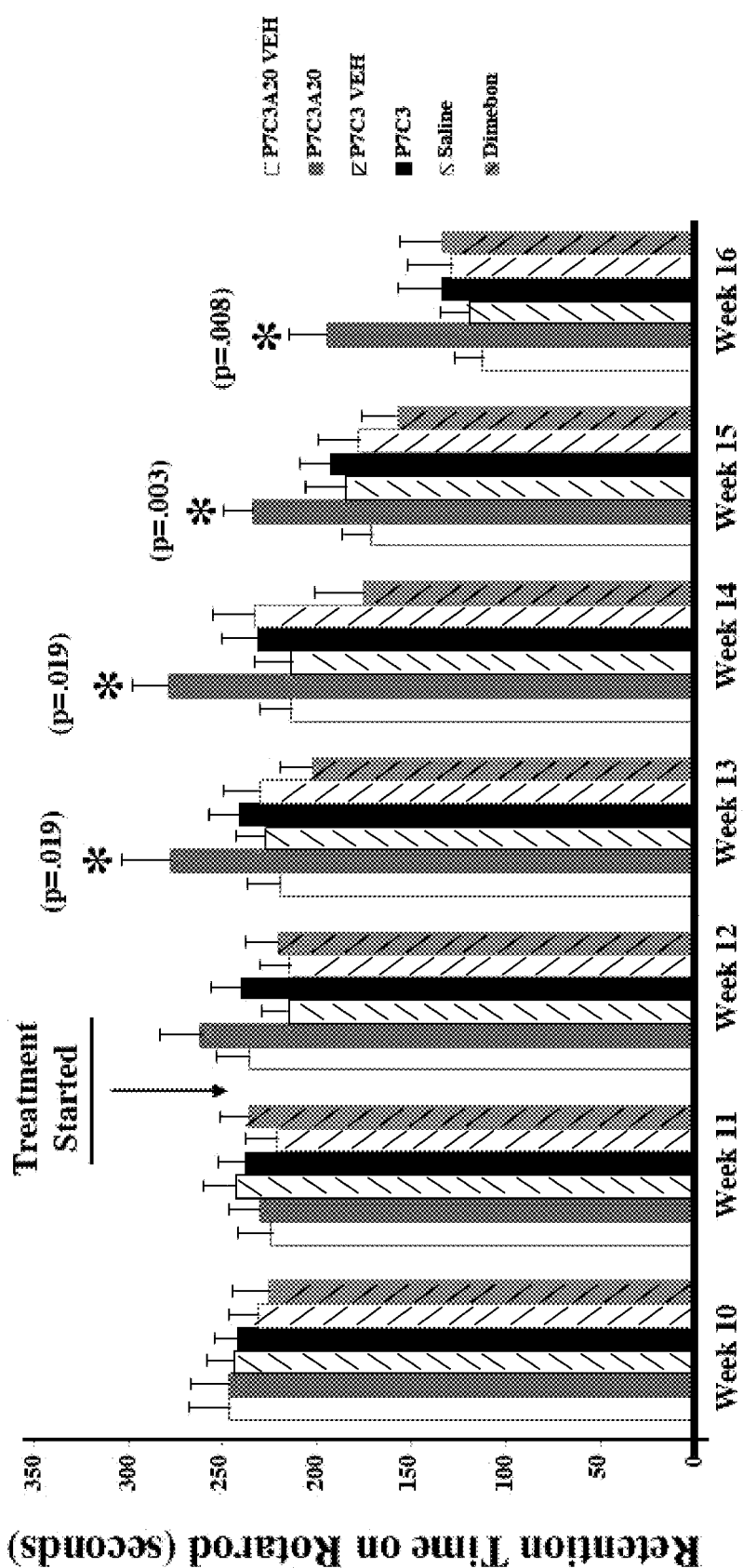
FIG. 35. P7C3A20 preserves performance in the accelerating rotarod test when administered at the time of disease onset to G93A-SOD1 mutant mice. Treatment of G93A-SOD1 mutant mice with 20 mg/kg/d of P7C3A20, P7C3 or Dimebon, or the appropriate vehicle, was initiated on day 80, with 20 mice per group. All compounds were administered at 20 mg/kg/day i.p. in divided doses. Each compound-treated mouse had a sex-matched sibling that received vehicle. Only sibling pairs were analyzed at each time point. By week 16, there were 13 compound-vehicle pairs remaining in each group. All vehicle treated mice showed the expected decline in retention time on the accelerating rotarod over time, and P7C3 and Dimebon groups showed no difference in retention time compared to their vehicle groups. Mice treated with P7C3A20 showed significantly higher retention time on the rotarod at weeks 13, 14, 15 and 16. All testing and analysis was performed blind to treatment group.

As shown in FIG. 35, performance in all treatment groups was equal at weeks 10 and 11. Treatment with the test compounds was initiated midway between weeks 11 and 12, on day 80, and at week 12 there were no significant differences between groups. By week 13, however, P7C3A20-treated mice showed significantly better performance (p=0.019) than the corresponding vehicle treatment group. In subsequent weeks, both P7C3 and Dimebon, as well as all vehicle groups, continued to decline at a steady pace in performance in this task, with P7C3A20-treated mice performing significantly better at each time point. Rotarod data were not collected beyond week 16 because too few animals survived to this time point for valid comparison across groups.

As noted with early initiation of administration (day 40) of P7C3, this intervention improved rotarod performance but did not extend survival of the mice. Also, despite improvement in rotarod performance in P7C3A20-treated mice when daily treatment was initiated on day 80, we did not observe any delay in other measures of disease progression (neurological score or weight loss). This observation may reflect the increased challenge for efficacy associated with administering compounds at the time of disease onset. Taken together, our results show that administration at the time of disease onset of the most potent member of the P7C3 series of neuroprotective drugs, P7C3A20, significantly improves performance of G93A-SOD1 mice in the accelerating rotarod test. Both P7C3 and Dimebon were insufficiently active to preserve motor function in the accelerating rotarod task at 20 mg/kg/day when administration was initiated at the time of disease onset.

Comparison of the Efficacy of Administration of P7C3A20, P7C3 and Dimebon at Disease Onset for Preserving Walking Gait in G93A-SOD1 Mutant Mice.

Figure 36A:
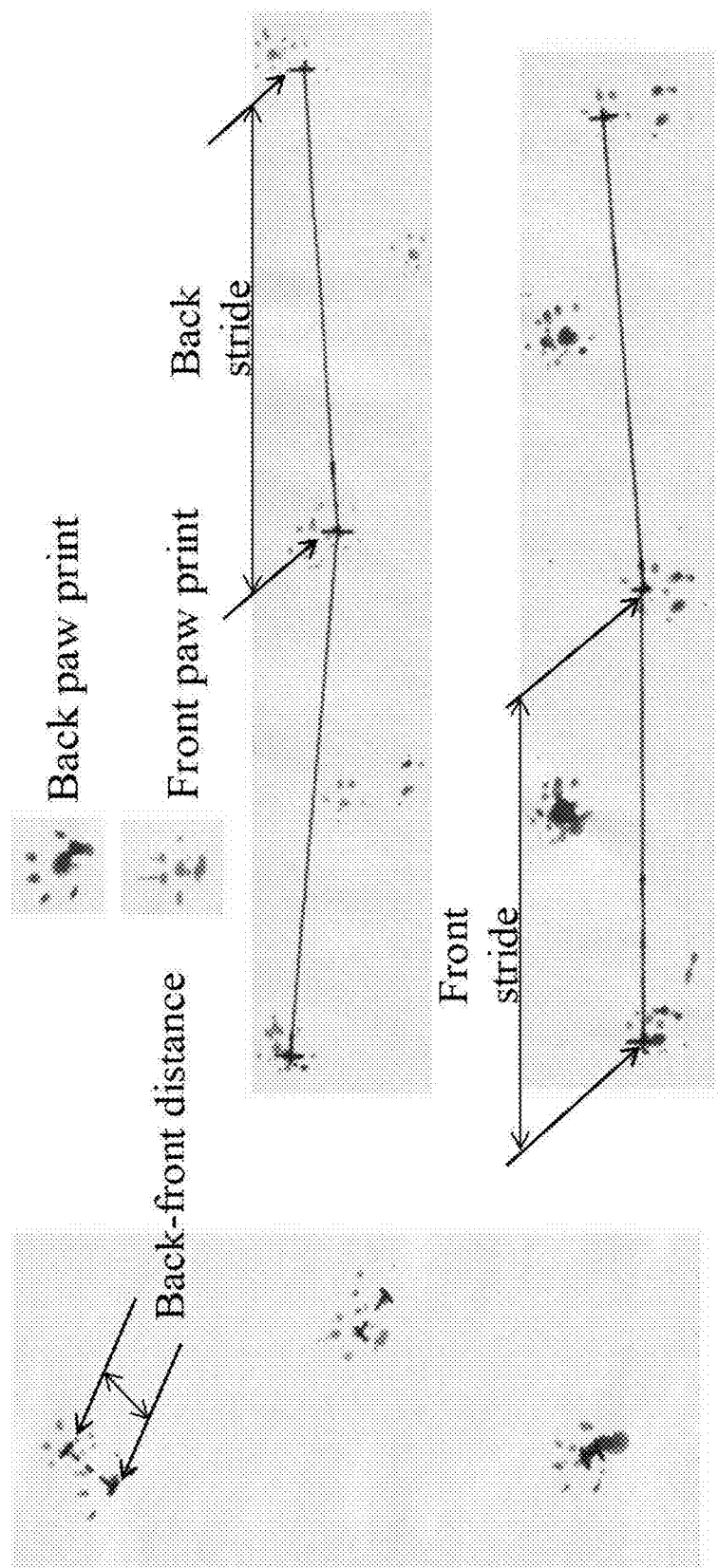
FIG. 36A and FIG. 36B. P7C3A20 preserves walking gait when administered at the time of disease onset to G93A-SOD1 mutant mice.

Analysis of walking gait offers a second means of assessing motor limb strength and coordination in rodent models of ALS. We conducted this analysis in the same mice used for the accelerating rotarod task, at three time points: 90, 118 and 132 days. Briefly, the front paws of each test mouse were dipped in orange tempera paint, and the back paws in blue tempera paint. Mice were then directed into a bisected PVC-tube placed on top of artists easel paper, such that the mouse was prompted to walk through the tunnel for a distance of 30 inches, leaving a trail of pawprints on the paper. Key parameters of the pawprints were then manually measured, as described in Methods. These parameters included front and back stride length, front and back width, and front-to-back paw distance (FIG. 36A).

Figure 36B:
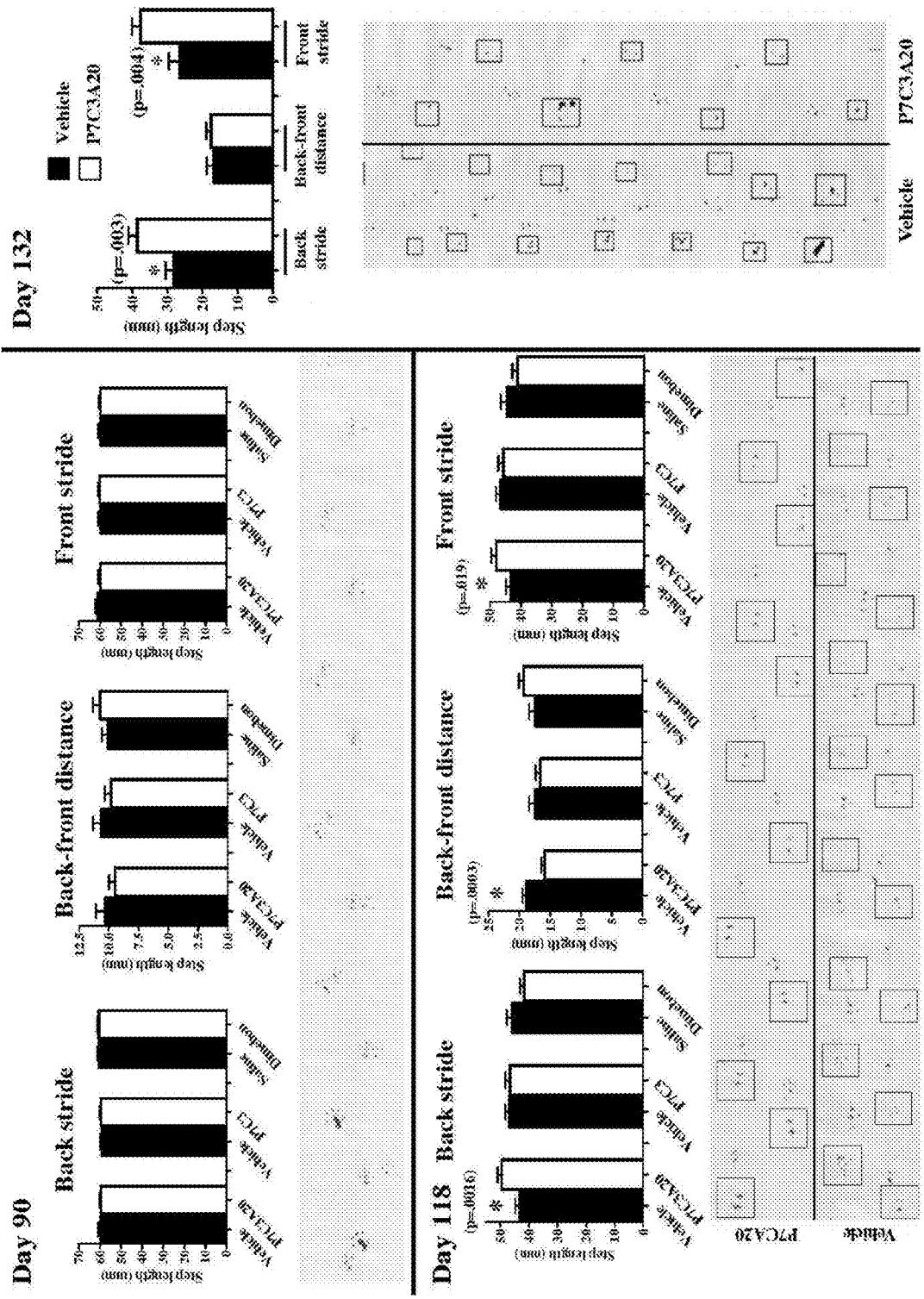

Twenty total measurements (10 on each side) for each parameter were recorded per mouse, and 20 mice per group were evaluated at the 90 and 118 day time points. All measurements were conducted blind to treatment group. Front and back widths showed no difference as a function of treatment group or disease progression until day 132, at which point P7C3A20 treatment was observed to preserve back width. Three of the measured parameters (back stride, back-front distance and front stride) showed significant improvement as a function of treatment with P7C3A20 earlier in the disease process, whereas none of these parameters in the walking gait analysis at 20 mg/kg/day were significantly improved by treatment with P7C3 or Dimebon (FIG. 36B).

Back stride is defined as the distance between each successive back paw print on a single side, and one of the first features of disease in G93ASOD1 mutant mice is the onset of hind limb muscle weakness. As the disease progresses, mice are unable to move their hind limbs as much with each step, and back stride distance decreases. This was evident on day 118, in which P7C3, Dimebon and all vehicle treatment groups showed reduced back stride length (FIG. 36B). Back stride measure was significantly (p=0.0016) preserved to a near-normal level in P7C3A20-treated mice (FIG. 36B). Front stride is analogously defined as the distance between each successive front paw print on a single side, and as the disease progresses this measure also shortens as a consequence of the reduced hind limb stride that prevents the mouse from moving as great a distance with each step. Compromised front stride length thus confirms the deficit associated with back stride length, and we observed that on day 118 this measure was indeed reduced in P7C3, Dimebon and all vehicle treatment groups, yet preserved to almost normal levels in P7C3A20-treated mice (FIG. 36B).

On day 132, there were insufficient numbers of mice in the P7C3-VEH and Dimebon-VEH groups that could participate in the task, due to complete paralysis of one or more limbs in the majority of the original test group. In the A20-VEH group, however, there were still ten P7C3A20 mice that were able to walk across the paper. Here, we observed that improvements in back stride and front stride were preserved, but there was no longer a difference in back-front distance. Back-front distance is defined as the distance between a back pawprint and the front pawprint on the same side. Early on, as the disease progresses in this animal model of ALS, the back-front distance steadily increases because the front limbs are able to extend normally, but the hindlimbs are not strong enough to formulate proper steps that should result in the back paw landing on top of the front paw print. It is evident in FIG. 36B that as assayed on day 118, treatment with P7C3A20 attenuated this increase in back-front distance. On day 132, however, the differences between VEH and P7CA20 treated mice in back-front distance were lost. At this stage, the disease was sufficiently advanced that this measure reflects the additional complication of front limb weakness, such that the mice were unable to extend their front limbs normally. As a result, the back-front distance declined, and there were no differences between P7C3A20 and its sibling-matched vehicle group. Taken together, our results of gait analysis demonstrate that treatment with P7C3A20 at the time of disease onset helps preserve walking gait in the G93A-SOD1 mouse model of ALS.

Analysis of Plasma, Brain and Spinal Cord Levels of P7C3, P7C3A20 and Dimebon.

Figure 37:
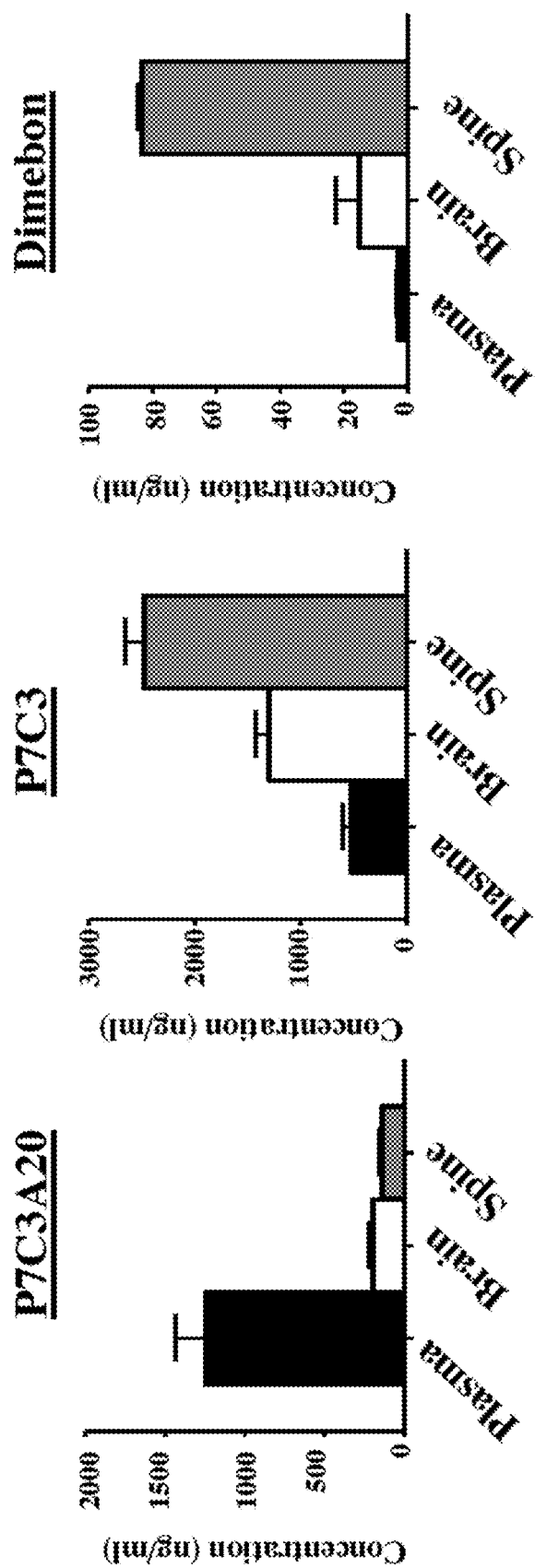
FIG. 37. Plasma, brain and spinal cord levels of P7C3A20, P7C3 and Dimebon. Five mice for each compound group were treated for 21 days with 20 mg/kg/day of the compound, starting on day 85. Blood, brain and spinal cord were harvested six hours after the last injection and compound levels were measured by LC/MS/MS. Concentrations are presented as mean±SEM.

LC/MS/MS quantification of brain and blood levels of P7C3, P7C3A20 and Dimebon confirmed that all three compounds were able to enter both the brain and spinal cord (FIG. 37). Notably, P7C3A20 displayed significantly greater protective efficacy compared to the other two compounds, despite the fact that P7C3A20 accumulated in spinal cord tissue at less than one-twentieth the concentration of P7C3. Dimebon, which displayed no protective efficacy in G93A-SOD1 mice, showed comparable levels of spinal cord accumulation to P7C3A20. These results parallel findings observed in evaluation of the neuroprotective efficacy of these same three compounds in MPTP-treated mice.

Discussion

The results of an unbiased screen of 1,000 chemically diverse, drug-like compounds led to the identification of an aminopropyl carbazole endowed with the capacity to enhance adult neurogenesis. This compound, designated P7C3, was found to act by blocking the death of newborn neurons in the dentate gyms of adult mice. We have also found that P7C3, P73A20 and other active analogs protect dopamingergic neurons of the substantia nigra from MPTP-induced neurotoxicity. Here we have sought to determine whether this class of pro-neurogenic compounds might also block nerve cell death outside of the brain.

We selected P7C3, P7C3A20 and Dimebon for testing because they display distinct levels of pro-neurogenic, neuroprotective activity when assayed for protection from apoptotic cell death of either newborn hippocampal neurons or following MPTP-toxicity to mature dopaminergic neurons. P7C3A20 displays the highest potency and ceiling of efficacy amongst these three molecules. We evaluated Dimebon because of extensive studies in human clinical trials, and its relative similarity in chemical structure to P7C3. When tested for its ability to protect mitochondrial membrane integrity following exposure of cultured cells to a calcium ionophore, Dimebon exhibited a protective potency between 100- and 1,000-fold lower than P7C3. Similarly modest activity was observed when Dimebon was assayed in our standard model of hippocampal neurogenesis. The reduced potency and efficacy of Dimebon has been further revealed in its inability to protect dopaminergic neurons in the substantia nigra from MPTP-toxicity. Finally, Dimebon has been extensively studied in human clinical trials of both Alzheimer's disease and Huntington's disease. Although early indications in a phase 2 trial suggested that Dimebon might be efficacious for Alzheimer's disease, the drug failed in two independent phase 3 trials. By testing the properties of these three related compounds in the present study of protective efficacy in an animal model of ALS, we sought to determine whether the hierarchy of activities amongst these three molecules might be preserved.

Encouragingly, we observe that P7C3A20 significantly blocks death of spinal motor neurons in the G93A-SOD1 mouse model of ALS. Importantly this protective effect is observed when administration of the compound is initiated at the time of disease onset, and it correlates with preservation of muscle strength and coordination as assessed through the accelerating rotarod test and analysis of walking gait. P7C3 offered intermediate protection from cell death when administered at the time of disease onset. Administration of P7C3 for a prolonged period of time by initiating treatment much earlier (day 40) did preserve motor function as assayed by the accelerating rotarod task. Dimebon offered no protection in any of these measures. Although efficacy of Dimebon in an animal model of Alzheimer's disease (TGCRND8) mice has recently been reported, this drug appears too weakly active to afford any protection in the G93A-SOD1 mutant mouse model of ALS.

We conclude that P7C3A20 and P7C3 display a hierarchy of activities analogous to their abilities to protect newborn hippocampal neurons from cell death, to block MPTP-mediated killing of mature dopaminergic neurons in the substantia nigra, and to protect spinal motor neurons from dying in G93A-SOD1 mutant mice. These collective observations give evidence that the relatively straightforward assay of monitoring adult hippocampal neurogenesis over a seven day period following direct administration of new analogs of P7C3 into the adult mouse brain may represent a trusted surrogate for the refinement of drug-like chemicals having neuroprotective activity. Over the past two years we have conducted a comprehensive structure-activity relationship (SAR) study in order to improve the chemical scaffold of the P7C3 series of molecules. To date, we have synthesized over 250 analogs of P7C3, all of which have been evaluated in the in vivo hippocampal neurogenesis assay. Our goal in these efforts to foster the discovery of a neuroprotective drug is to maximize neuroprotective efficacy and alleviate real or perceived vulnerabilities in the chemical structures. These efforts include, but are not limited to, eliminating the carbazole bromines, eliminating the aniline ring, increasing biologic activity, decreasing lipophilicity, eliminating any toxicities including hERG channel binding, increasing solubility and reducing molecular weight. By use of the in vivo hippocampal neurogenesis assay, these ongoing SAR efforts with P7C3 analogs may offer an effective way to guide optimization of this series of molecules towards a neuroprotective drug candidate.

No safely tolerated, neuroprotective chemical is available for the treatment of any form of neurodegenerative disease, including Parkinson's disease, Alzheimer's disease and amyotrophic lateral sclerosis. Based upon the observations reported herein, we propose that a properly optimized variant of the P7C3 class of pro-neurogenic, neuroprotective chemicals may represent a viable candidate for the treatment of neurodegenerative disease.

Materials and Methods

Approval for the animal experiments described herein was obtained by the University of Texas Southwestern Medical Center Institutional Animal Care and Use Committee.

Statistics: All p values were obtained with the Student's t test, by comparing treatment groups to their individual sibling-matched vehicle treatment groups.

Analysis of motor neuron survival in the spinal cord: After transcardial perfusion with 4% paraformaldehyde (PFA), lumbar spinal cord was dissected and post-fixed overnight in 4% PFA, cryoprotected in 30% sucrose at 4 degrees Celsius, and then embedded in OCT and sectioned on a Thermo-Fisher cryostat (HM550) at 30 μM thickness. Every seventh section was immunohistochemically stained with goat anti-choline acetyltransferase (ChAT) (Millipore). Briefly, sections were incubated in 1% $H_2O_2$ for 45 minutes at room temperature, rinsed in tris-buffered saline (TBS), treated with 0.1% Triton-TBS and then blocked for 60 minutes in 3% BSA, 5% donkey serum, 0.3% triton-100 in TBS. Sections were then incubated in goat anti-ChAT (1:100) in the same blocking solution overnight at 4 degrees Celsius. The next day, sections were rinsed in TBS and incubated with donkey anti-goat biotin (1:200, Jackson Immune). Signal was amplified with an ABC kit from Vector Labs, and diaminobenzidine was used as a chromagen. Immunostained tissue was then photographed at 4× using a Nikon Eclipse 90i motorized microscope, and the number of ChAT-positive neurons was counted in a blinded manner by two investigators, followed by normalization for ventral horn volume.

Rotarod: Beginning on day 50, mice were trained on the accelerating rotarod using Colombia Instruments Rotamex-5. Training consisted of mice being placed on a rotarod moving at 5 rpm for 300 seconds. Mice were trained to stay on the rotarod for the entire 300 seconds. If a mouse fell, it was placed back on the rotarod and the 300 second trial was started again. Training took place on two consecutive days. On day 52, mice ran their first full rotarod test, as described in Current Protocols for Neuroscience. The rotarod began at 4 rpm and accelerated to 40 rpm over 600 seconds, increasing by 1.25 rpm every 20 seconds. The time to fall was automatically recorded. Each run was separated by 20 minutes to allow the mice to rest, and each mouse participated in 4 runs. Mice were run every seven days until the time at which they were unable to stay on the rotarod for more than 10 seconds for 3 trials.

Pawprint Analysis: Five measurements were taken: front and back stride, front and back width, and front to back distance, as described in Current Protocols for Neuroscience. 20 total measures were taken for each measurement. Front and back stride were collected as a straight line from paw print to the following paw print. Front to back distance was collected as a straight line from back paw print to corresponding front paw print. Correspondence was based on closest front footprint. Width from paw print was measured by drawing a line at a 90 degree angle from the line connecting the stride previous and the paw being analyzed. The distance was recorded as length of line from paw to the stride line opposite the paw print. Mice attaining a score of three were eliminated from analysis as measurements could not be taken for a foot not being used in forward motion.

Pawprints were recorded at 90, 118 and 132 days of age. A 6 inch by 42 inch PVC pipe cut in half lengthwise was placed on top of a piece of easel paper (27"×30¼"). Each mouse had paws covered in non-toxic tempera paint (orange front, blue back) and was placed at one end of the pipe. The mouse ran quickly to the other end of the pipe when released, and the procedure was repeated until 10 clear back and front prints were made for each side while the subject was running. Pawprints were scanned using a hand scanner, and then visualized for measurement in Nikon Metamorph software. Measurements were based on established guidelines.

Neurological Scoring: Neurological score was performed every day starting with compound treatment at 80 days, and was determined as follows: '0'=full extension of hind legs away from lateral midline when the test mouse was suspended by its tail, and could hold this for 2 seconds, suspended 2-3 times; '1'=collapse or partial collapse of leg extension towards lateral midline (weakness) or trembling of hind legs during tail suspension; '2'=toes curl under at least twice during walking of 12 inches, or any part of foot drags along cage bottom/table; '3'=rigid paralysis or minimal joint movement, foot not being used for forward motion; and '4'=mouse cannot right itself within 30 seconds from either side. Upon reaching a score of 2, animals were given a fresh Petri dish with wet food in the dish daily. When mice achieved a score of 4 for two consecutive days they were euthanized.

Weight Data: Mice were weighed daily starting on the day of initiation of compound administration in order to assess disease progression and readjust compound dosage. A digital balance with a step of 0.01 g was used, and mice were placed in a small plastic container on the scale when weighed. Weight was taken between 11 am and 1 pm every day.

Quantitative PCR: Quantitative PCR done in accordance with guidelines established by Jackson Laboratory protocol for SOD1-G93A mice.

Synthesis and Preparation of P7C3A20: Preparation of compound as described above.

Pharmacokinetic Analysis of P7C3, P7C3A20 and Dimebon: Analysis of compound as described above.

P. The Example 45 Class of Neuroprotective Compounds Reduces Depressive-Like Behavior in Mice Major depression remains insufficiently treated in our society. To facilitate the development of more efficacious antidepressant agents, the neurobiology underlying the antidepressant actions of the gut hormone ghrelin have been investigated. In mice, endogenous ghrelin elevation protects against development of severe depressive-like behavior following chronic social defeat stress (CSDS) and also produces an antidepressant-like response to caloric restriction. It is now shown that ghrelin receptor (Ghsr)-null mice suffer from marked impairments in hippocampal neurogenesis after CSDS and after caloric restriction. Notably, the neuroprotective compound P7C3 wields an antidepressant-like effect in Ghsr-null mice, and the more potent analog P7C3-A20 additionally demonstrates antidepressant efficacy in wild-type mice. Thus, augmenting hippocampal neurogenesis with the P7C3 class of neuroprotective compounds may represent a new strategy for treating depression.

The orexigenic gut hormone ghrelin induces feeding by activating growth hormone secretagogue receptors (Ghsr; ghrelin receptor) in the hypothalamus, caudal brainstem and elsewhere in the central nervous system. Within the hippocampus and ventral tegmental area, Ghsr mediates ghrelin's enhancement of reward-related behaviors, cue-potentiated feeding, hippocampal spine synaptic density, and memory retention. Ghrelin additionally confers neuroprotective efficacy in models of kainic acid hippocampal toxicity, spinal cord motor neuron excitotoxicity, dopaminergic neuron toxicity, and oxygen glucose deprivation in hypothalamic and cortical neurons. Notably, ghrelin also exerts antidepressant efficacy in people and various rodent models. Ghsr-polymorphism has been associated with major depression in humans, and administration of ghrelin improves mood in some patients with major depression. In mice, raising ghrelin levels either directly through acute injection or indirectly via caloric restriction elicits an antidepressant response in the forced swim test (FST), a common screening tool used in rodents to identify new candidate antidepressant drugs. Additionally, sustained elevations of plasma ghrelin occur in mice exposed to CSDS, which is a model of prolonged psychosocial stress that features aspects of major depression and posttraumatic stress disorder, and Ghsr-null mice exhibit more severe depressive-like behavior after CSDS than wild-type littermates. Psychosocial stress also leads to increased plasma ghrelin in humans. Thus, stress-associated activation of ghrelin signaling pathways may serve a protective function against depression.

The mechanism by which ghrelin confers antidepressant efficacy has previously eluded the field, although clues in the literature point to involvement of the hippocampus. Several studies have correlated changes in hippocampal neurogenesis and cell survival in the dentate gyrus (DG) with regulation of depressive-like behavior. Furthermore, antidepressant drugs and environmental factors that elevate mood such as exercise, environmental enrichment, and social interaction increase hippocampal neurogenesis. By contrast, negative regulators of neurogenesis and cell survival such as chronic stress, old age, drugs of abuse and social isolation are associated with depressed mood. Additionally, ablation of neurogenesis decreases the efficacy of some antidepressant drugs in rodent models. It also has been reported that ghrelin potently stimulates hippocampal neurogenesis within the DG. In considering this evidence linking neurogenesis with depressive-like behavior as well as the role of ghrelin in hippocampal neurogenesis and distribution of Ghsr expression in the hippocampus, it is hypothesized that the antidepressant efficacy of ghrelin might be related to its proneurogenic effect. If so, both Ghsr-null mice and even wild-type mice with intact ghrelin signaling may be protected from stress-induced depression by therapeutic strategies that augment hippocampal neurogenesis.

Reported here are the results of experiments that utilized the P7C3-series of neuroprotective compounds and Ghsr-null mice to test the hypotheses. More specifically, the aim was to directly attribute the exaggerated impairment in hippocampal neurogenesis as a cause of the marked depressive-like behavior in Ghsr-null mice. Demonstrating whether the depressive-like behavior so easily induced in Ghsr-null mice by chronic stress due to their lack of responsiveness to the proneurogenic effects of stress-induced ghrelin could be minimized by administration of P7C3 class of compounds with known neuroprotective efficacy would prove this cause-and-effect linkage. Indeed, the P7C3 class of compounds were shown to block the impairments in hippocampal neurogenesis induced by stress and Ghsr deficiency. Regarding the behavioral effects of the P7C3 class, an even more far-reaching efficacy than had initially been expected was observed. Notably, not only did P7C3 wield an antidepressant-like effect in the highly sensitive Ghsr-null mice, but also the more potent P7C3-A20 analog additionally demonstrated antidepressant efficacy in wild-type littermates. These observations prompted direct comparisons regarding proneurogenic efficacy between the P7C3-class of compounds and several marketed antidepressant agents. The P7C3-class of compounds was shown to elevate the magnitude of hippocampal neurogenesis with significantly greater efficacy than a wide spectrum of currently available antidepressant drugs representing the major classes currently prescribed to patients. More specifically, in addition to P7C3 and P7C3-A20, only four out of fourteen marketed antidepressant medications that we tested significantly increased hippocampal neurogenesis. In particular, the norepinephrine-dopamine reuptake inhibitor bupropion, the monoamine oxidase inhibitor phenelzine, and the tricyclic antidepressants clomipramine and desipramine increased hippocampal neurogenesis by about 49%, 52%, 75% and 102% over vehicle, respectively. Of those, only clomipramine and desipramine were statistically as effective at P7C3, and none was statistically as effective as the highly active P7C3-A20 molecule. The remaining antidepressant medications tested, including the selective serotonin reuptake inhibitors paroxetine, citalopram, fluoxetine and sertraline, the serotonin-norepinephrine reuptake inhibitor venlafaxine, the noradrenergic and specific serotonergic antidepressant mirtazapine, the monoamine oxidase inhibitor tranylcypromine, and the tricyclic antidepressants nortriptyline and imipramine, did not affect the magnitude of neurogenesis in the assay utilized.

As a general conclusion, the observations made herein regarding ghrelin's antidepressant-like effects, ghrelin receptor expression and action in the hippocampus, and exacerbations in both depressive-like behavior and hippocampal neurogenesis impairment in Ghsr-null mice suggested that the P7C3 class of neuroprotective compounds, similar to the naturally-occurring proneurogenic hormone ghrelin, might indeed have antidepressant actions that might be most obvious in the highly sensitive Ghsr-null mouse model. Indeed, it is demonstrated herein that the P7C3 class of neuroprotective compounds reduced depressive-like behavior in mice by augmenting ghrelin-induced hippocampal neurogenesis. Furthermore, the direct comparison between the proneurogenic efficacies of the P7C3-class of compounds and several marketed antidepressant agents led to another unexpected discovery: if augmentation of hippocampal neurogenesis is crucial for the manifestation of antidepressant efficacy of both endogenous substances such as ghrelin and exogenous compounds, as the current studies confirm, then the P7C3 class could potentially surpass the efficacy of currently prescribed antidepressant drugs.

Experiments and Results

Chronic Stress Severely Reduces DG Neurogenesis in Ghsr-Null Mice

Figure 38:
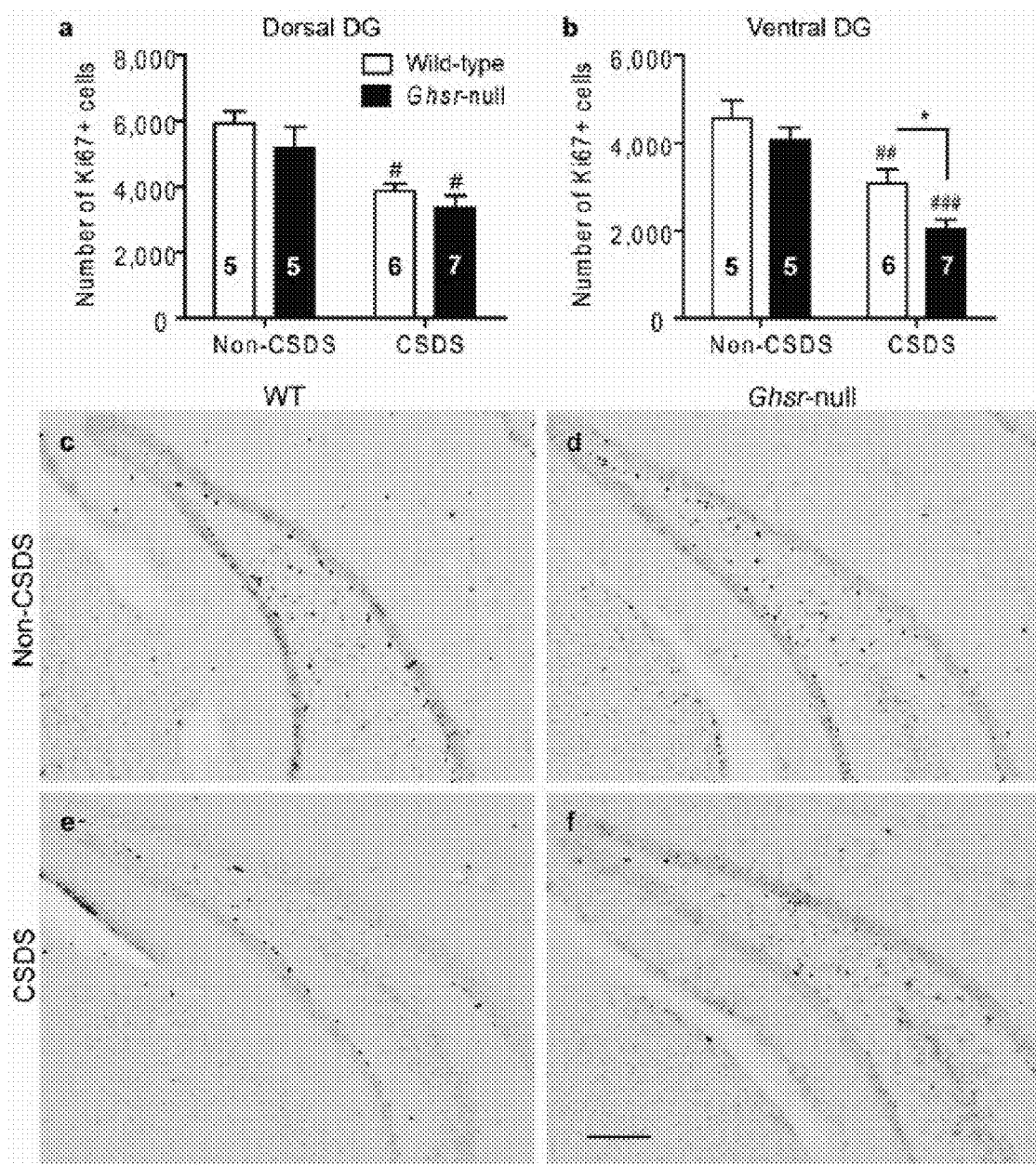
FIG. 38. Effect of CSDS on cellular proliferation in the DG of Ghsr-null and wild-type littermates. (a, b) Ki67-immunoreactive cell counts in the SGZ of the dorsal (a) and ventral (b) DG of CSDS-exposed or non-CSDS-exposed control mice. Group sizes (n) indicated within bars. (c-f) Representative photomicrograph images of Ki67-immuno-labeled brain sections in the ventral DG of CSDS-exposed and non-CSDS-exposed wild-type and Ghsr-null mice. Legend in (a) pertains to (b). Scale bar in (f; 300 µm) pertains to (c-f)). *$P<0.05$, comparing genotypes. #$P<0.05$, ##$P<0.01$, ###$P<0.001$, comparing treatment.
Figure 44:
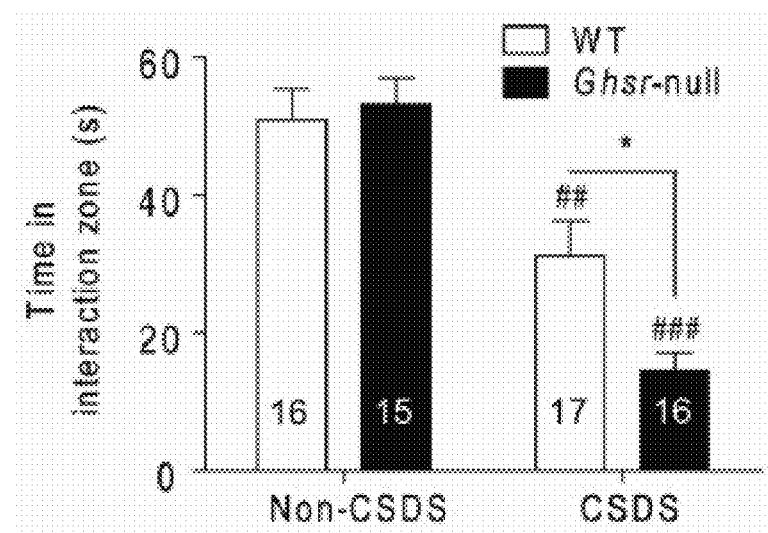
FIG. 44. Depressive-like behavior in Ghsr-null and wild-type littermates. Time spent in the social interaction zone when the target is present in CSDS-exposed and non-CSDS-exposed Ghsr-null and wild-type littermates. *P<0.05, comparing genotypes. ##P<0.01, ###P<0.001, as compared to non-CSDS controls.

The CSDS model of chronic psychosocial stress exposes male mice to repeated bouts of social subordination by an older and larger aggressor mouse for 5 min per day over 10 days. At the conclusion of this exposure, the stressed mouse typically shows significantly reduced social interaction (SI) with a novel mouse, mimicking stress-induced social avoidance and depression in humans. When male Ghsr-null mice were exposed to CSDS, they spent significantly less time interacting with a novel mouse, compared to wild-type littermates (FIG. 44), consistent with previous reports. To determine whether this more severe depression phenotype correlated with effects on hippocampal neurogenesis, brain tissue was harvested from both CSDS-exposed and non-CSDS-exposed mice and performed immunohistochemistry for Ki67, a marker of proliferating cells, in the DG subgranular zone (SGZ) where newborn neural precursor cells proliferate. The ventral (posterior ⅓) and dorsal (anterior ⅔) regions of the DG were separately analyzed due to evidence that the ventral DG specifically regulates mood while the dorsal DG is more involved in learning and memory. Whereas both wild-type and Ghsr-null mice displayed an equally significant reduction in the number of Ki67+ cells after CSDS in the dorsal DG (FIG. 38, panel a), CSDS exposure elicited a significantly greater reduction in Ki67+ cells in the ventral DG of Ghsr-null mice than in wild-type littermates (FIG. 38, panels b-f).

Figure 39:
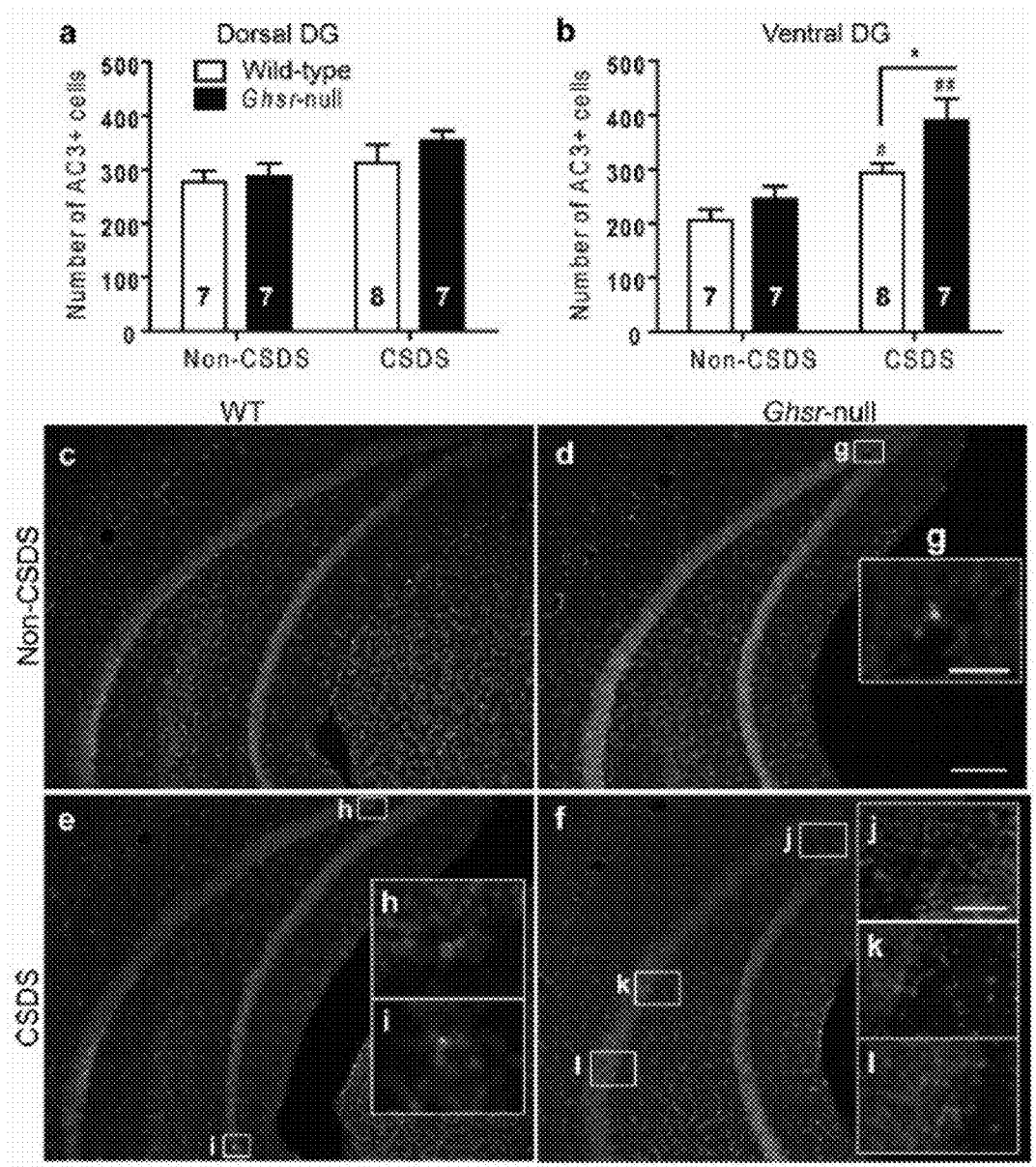
FIG. 39. Effect of CSDS on apoptosis in the DG of Ghsr-null and wild-type littermates. (a, b). AC3-immunoreactive cell counts in the SGZ of the dorsal (a) and ventral (b) DG of CSDS-exposed or non-CSDS-exposed mice. Group sizes indicated. (c-f) Representative photomicrograph images of the ventral DG from each study group. (g-l) Magnified images of AC3-immunoreactive cells. Legend in (a) pertains to (b). Scale bar in (f; 300 µm) pertains to (c-f), in (g; 50 µm) pertains to (g-i), in (j; 75 µm) pertains to (j-l). *$P<0.05$, comparing genotypes. #$P<0.05$, ##$P<0.01$, comparing treatment.

Because the vast majority of newborn hippocampal neural precursor cells in mice die by apoptosis, and pharmacologically inhibiting apoptosis has been demonstrated to augment hippocampal neurogenesis, it was tested whether apoptosis of newborn neural precursor cells might also be affected by CSDS. Therefore, adjacent tissue sections were immunohistochemically stained for activated caspase 3 (AC3), a marker of apoptotic cells. While CSDS had no effect on AC3+ cell numbers in the dorsal DG (FIG. 39, panel a), the ventral DG of all animals displayed a significant elevation after CSDS. This selective increase in AC3+ cells in the ventral DG was even more pronounced in Ghsr-null mice (FIG. 39, panels b-l).

Figure 45:
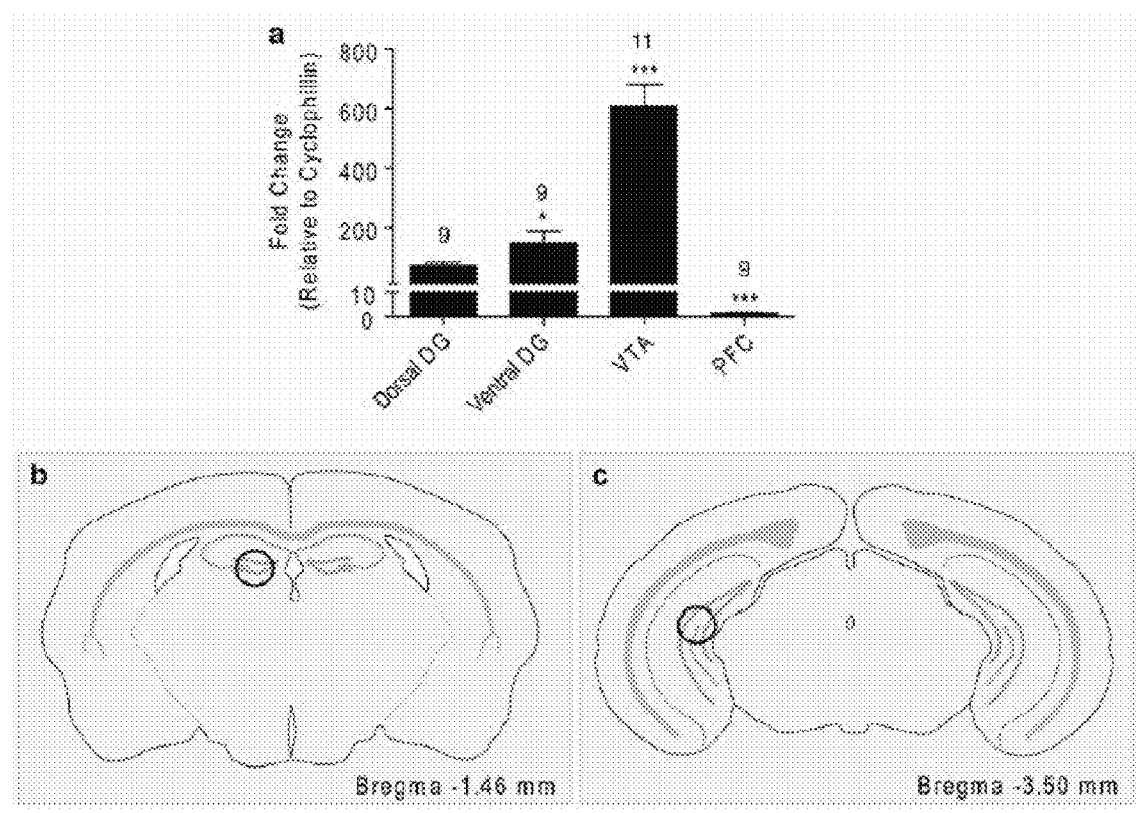
FIG. 45. Relative Ghsr mRNA expression across brain regions in wild-type mice. (a) Relative Ghsr mRNA expression in the dorsal DG, ventral DG, ventral tegmental area (VTA), and prefrontal cortex (PFC). (b, c) Image traces of coronal sections representing dorsal (b) and ventral (c) regions where punches were collected for qPCR analysis. Group sizes indicated above bars. *P<0.05, *** P<0.001, as compared to the dorsal DG.

Taken together, these results demonstrate that proliferation of newborn hippocampal neurons throughout the dentate gyrus is decreased in both wild-type and Ghsr-null littermates after CSDS, with an added effect of elevated cell death localized to the ventral DG. This net reduction in ventral DG neurogenesis is significantly more pronounced in Ghsr-null mice, and thus parallels the exacerbated depression-like behavior observed after CSDS in Ghsr-null mice as compared to wild-type littermates. Localization of this ghrelin effect to the ventral DG may be related to higher baseline Ghsr expression within the ventral DG relative to the dorsal DG, as demonstrated by quantitative RT-PCR of hippocampal tissue punches taken from unstressed, wild-type mice (FIG. 45), and to the previously-described role for the ventral DG in regulating mood.

Figure 40:
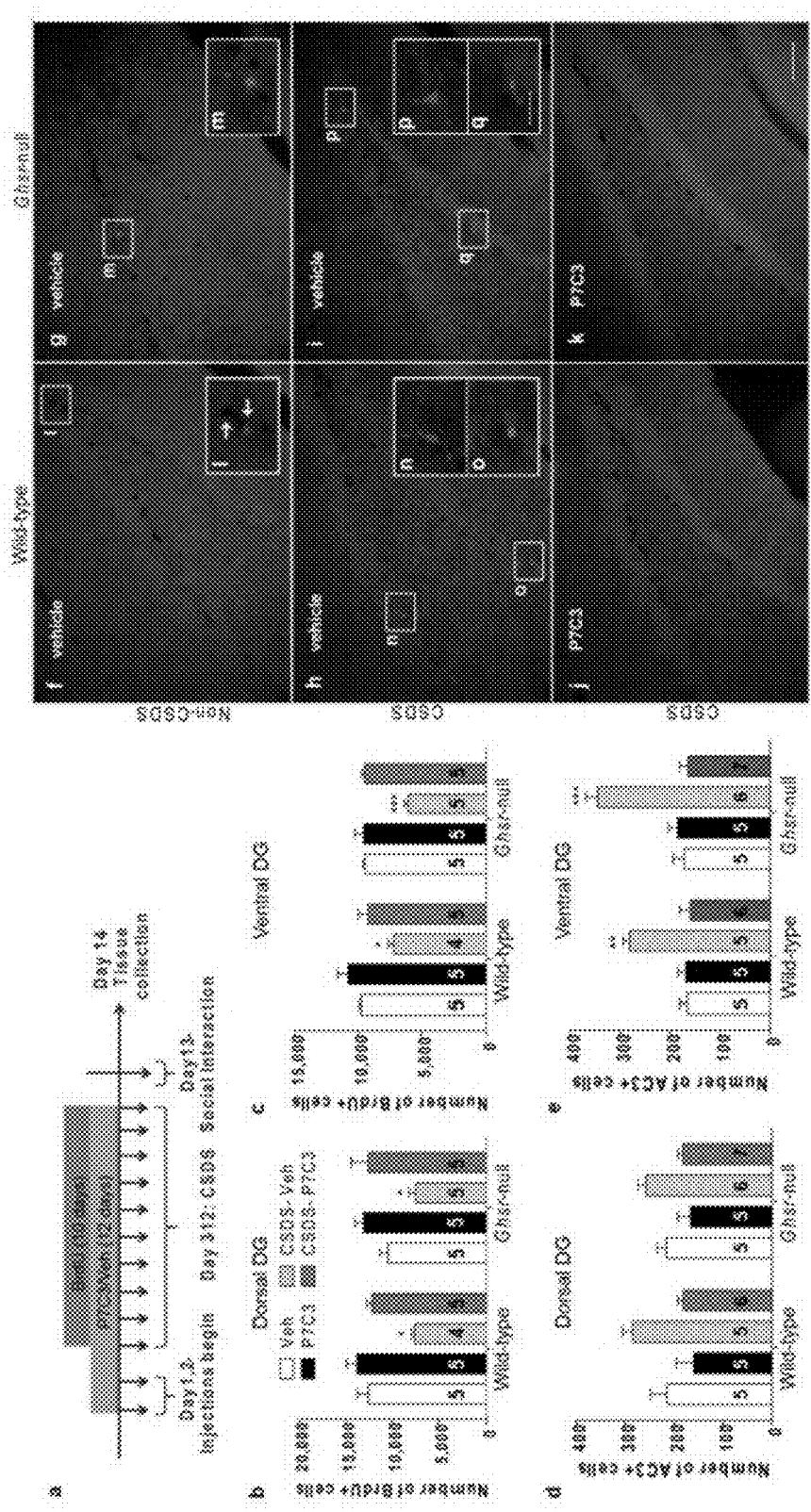
FIG. 40. Effects of P7C3 on DG cellular proliferation and apoptosis following CSDS. (a) Protocol schematic. (b-e) BrdU-immunoreactive and AC3-immunoreactive cell counts in the dorsal and ventral DG of CSDS-exposed and non-CSDS-exposed mice treated with P7C3 vs. vehicle. Group sizes indicated. (f-k) Representative photomicrograph images of double-immunolabeled (BrdU and AC3) ventral DG sections. (l-q) Magnified images of immunoreactive cells (AC3, leftward-facing arrow; BrdU, rightward-facing arrow). Scale bar in (k; 100 µm) pertains to (f-k), in (q; 25 µm) pertains to (l-q). *$P<0.05$, $P<0.01$, *$P<0.001$, as compared to respective non-CSDS-exposed, vehicle-treated control group.
Figure 46:
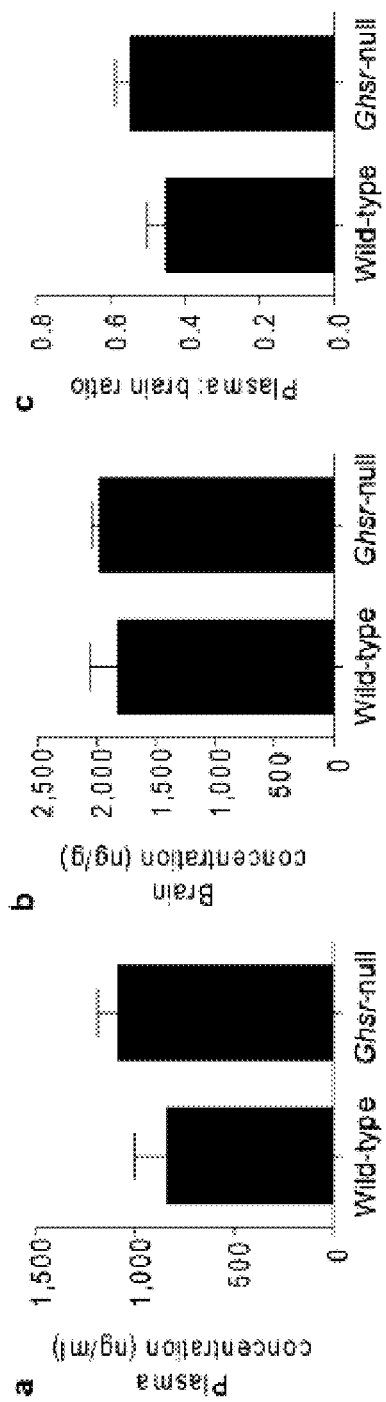
FIG. 46. P7C3 brain penetration. (a, b) P7C3 levels measured in the plasma (a) or brain (b) of Ghsr-null mice and wild-type littermates 6 hrs after final P7C3 injection. (c) Plasma to brain ratio of P7C3 levels in Ghsr-null mice and wild-type littermates. (N=3/group)

P7C3 Compounds Augment DG Neurogenesis and Reduce Depression in Chronic Stress-Exposed Mice It was next investigated whether protecting neural precursor cells from CSDS-associated apoptosis might help protect against the depressive-like phenotype. To test this idea, P7C3 was utilized, a neuroprotective aminopropyl carbazole that elevates hippocampal neurogenesis by blocking apoptosis without affecting the proliferation rate of hippocampal neural precursor cells in the dentate gyrus. A twice-daily schedule of intraperitoneal P7C3 injections (20 mg/kg/d in divided doses) was initiated two days prior to CSDS and continued throughout the 10 day procedure for both wild-type and Ghsr-null littermates. Throughout the 10 days of CSDS, the thymidine analog bromodeoxyuridine (BrdU; 50 mg/kg i.p.) was administered daily to label newborn cells (FIG. 40, panel a). Liquid chromatography-tandem mass spectrometry analysis of plasma and brain P7C3 concentrations revealed that similar compound levels were achieved in wild-type and Ghsr-null mice (FIG. 46).

Similar to the above Ki67 results, immunohistochemical examination of brain tissue from these mice revealed that CSDS reduced the number of BrdU+ cells in both vehicle-treated wild-type and Ghsr-null mice throughout the DG, with a more significant reduction in the ventral DG of Ghsr-null mice ( FIG. 40, panels b-c, f-i, l-q). In both wild type and Ghsr-null mice, P7C3 administration during CSDS preserved normal levels of neurogenesis throughout both dorsal and ventral regions of the DG ( FIG. 40, panels b-c, f-k). In parallel, vehicle-treated mice displayed an elevation of AC3+ cells only in the ventral DG after CSDS, an outcome associated with a more significant increase in Ghsr-null mice (FIG. 40, panels d-e) and blocked by P7C3 administration (FIG. 40, panels e-k). Thus, P7C3 blocked CSDS-associated reductions in both cellular proliferation and survival in the DG, with greater statistical significance in the ventral DG of Ghsr-null mice.

Of note, P7C3 administration did not significantly augment BrdU or AC3 immunoreactivity in the DG of non-stressed control animals, a finding that differs from the original discovery of P7C3 (FIG. 40, panels a-d). This may be attributed to changes in experimental technique. In particular, the original screen by which P7C3 was discovered utilized singly-housed 12-week-old adult male mice completely deprived of environmental enrichment. This design was employed to maintain basal neurogenesis at a consistently low level for purposes of the discovery screen. By contrast, the current group of non-stressed control animals consisted of younger (8-weeks-of-age) mice that were group housed (in the same cage with a member of the same strain across a perforated divider) under conditions of normal environmental enrichment, all of which elevate baseline hippocampal neurogenesis.

Figure 41:
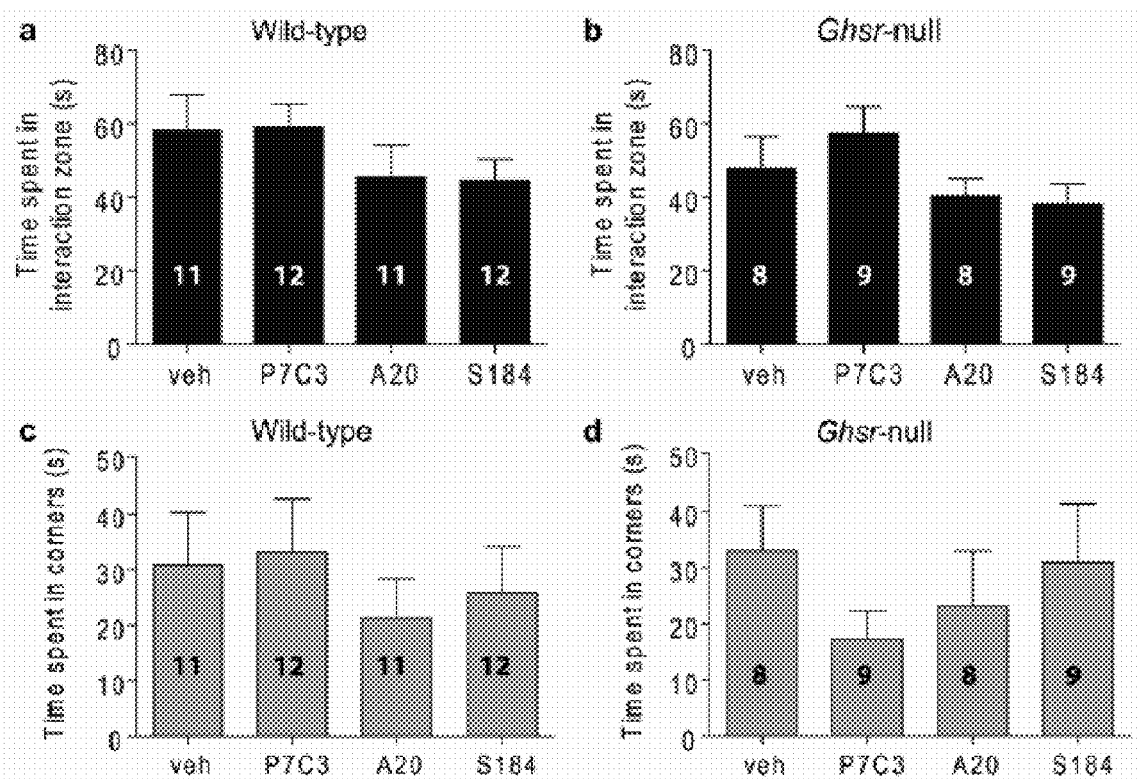
FIG. 41. Effects of P7C3 on CSDS-induced depressive-like behavior, as measured by the social interaction test. (a, b) Times spent in the interaction zone with target present for wild-type (a) and Ghsr-null (b) mice. (c, d) Times spent in the corners by wild-type (c) and Ghsr-null (d) mice. Group sizes indicated. *$P<0.05$, **$P<0.01$, as compared to respective vehicle-treated control group.
Figure 47:
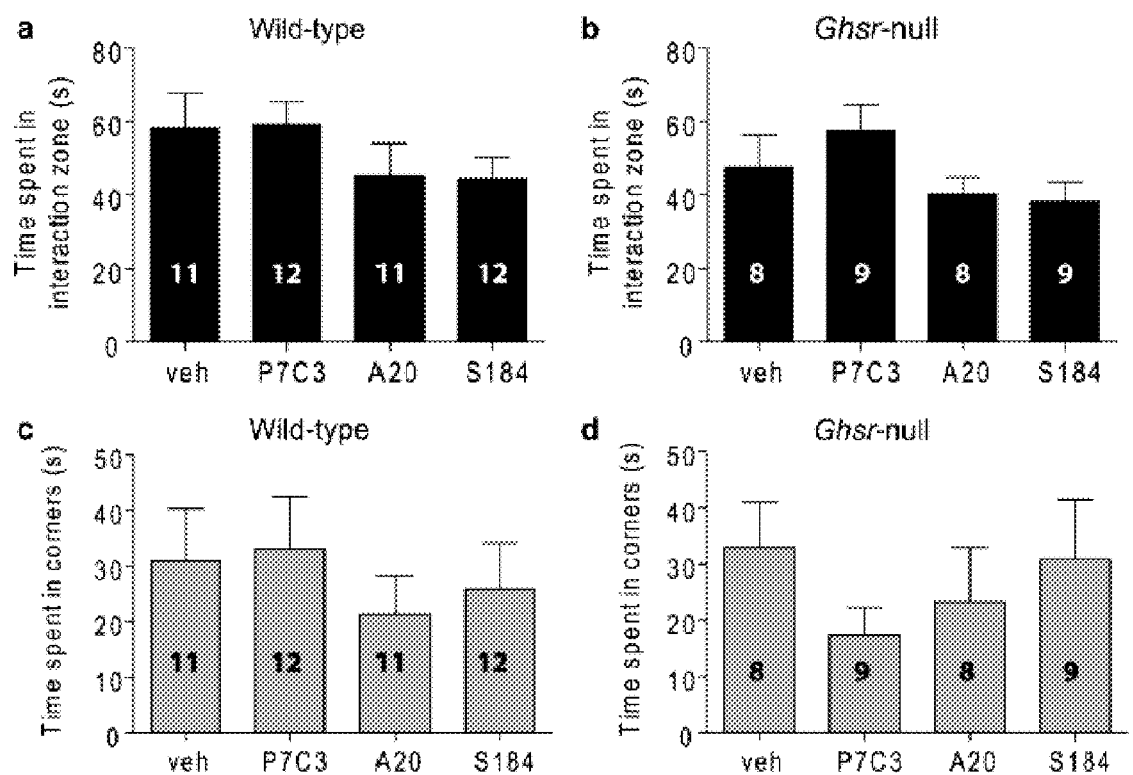
FIG. 47. Effect of P7C3 compounds on depressive-like behavior in non-CSDS exposed mice. (a, b) Time spent in the social interaction zone when target is present for wild-type (a) and Ghsr-null (b) mice. (c, d) Time spent in the corners when the target is present for wild-type (c) and Ghsr-null (d) mice. Group sizes as indicated.

Next, P7C3 and two chemical analogs were employed to investigate whether P7C3-mediated preservation of ventral DG neurogenesis during CSDS might correlate with an antidepressant-like behavioral effect. The analog P7C3-A20 (Example 45) substitutes a fluoride at the hydroxyl position in the linker region of the molecule, conferring greater neuroprotective efficacy than P7C3, as demonstrated recently in animal models of Parkinson's disease and amyotrophic lateral sclerosis. Conversely, the analog P7C3-S184 (Example 178) replaces bromines on the carbazole moiety with chlorines and the aniline moiety with a naphthyl amine, leaving the analog completely devoid of neuroprotective activity. In CSDS-exposed wild-type mice, P7C3 treatment had no significant effect on depression-like behavior (FIG. 41, panels a, c). However in Ghsr-null mice, both P7C3 and P7C3-A20 showed antidepressant efficacy, reflected by increased time spent in the interaction zone and reduced time spent in the corners of the testing chamber (FIG. 41, panels b, d). The more highly active analog P7C3-A20 also significantly reduced the amount of time spent in the corners for wild-type mice after CSDS (FIG. 41, panel c). The inactive analog P7C3-S184 had no effect on stress-induced depressive-like behavior in either genotype (FIG. 41, panels a-d). Neither P7C3 nor the two tested analogs influenced social interaction test performance in non-CSDS-exposed control mice (FIG. 47). Thus, P7C3 displayed antidepressant efficacy in stressed Ghsr-null mice, while the more highly active analog P7C3-A20 exhibited antidepressant efficacy both in stressed Ghsr-null mice and in their more resilient, stressed wild-type littermates.

Figure 42:
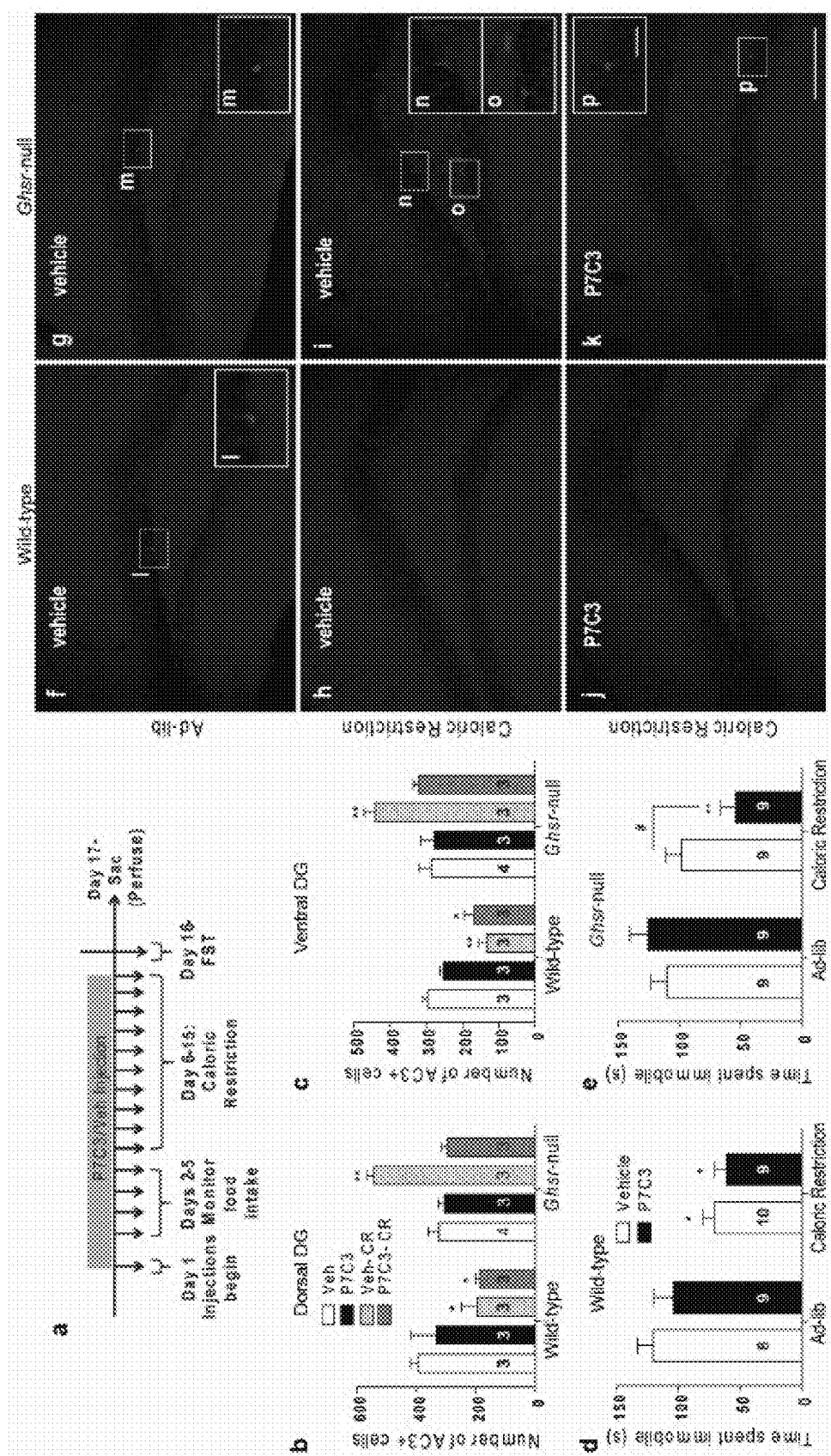
FIG. 42. Effects of P7C3 on caloric restriction-induced DG cell survival and antidepressant-like behavior, as measured by FST. (a) Protocol schematic. (b, c) AC3-immunoreactive cell counts in the DG of calorie-restricted and ad libitum-fed mice treated with P7C3 vs. vehicle. (d, e) FST immobility time. Group sizes indicated. (f-k) Representative photomicrograph images of AC3-immunolabeled ventral DG sections. (l-p) Magnified images of AC3-immunoreactive cells. Scale bar in (k; 150 μm) pertains to (f-k), in (p; 25 μm) pertains to (l-p). *P<0.05, **P<0.01, as compared to respective ad libitum-fed, vehicle-treated control group. #P<0.05, comparing compound treatment.

P7C3 Restores the Antidepressant Response to Caloric Restriction in Ghsr-Null Mice Prolonged caloric restriction in wild-type mice elicits an antidepressant-like response in the FST (decreased immobility), whereas this effect is not observed in Ghsr-null mice. To investigate whether this might be related to differences in apoptosis in the DG, similar to that observed above following CSDS, Ghsr-null and wild-type littermates were exposed to ad libitum food access vs. 60% caloric restriction for 10 days. Five days prior to this exposure and throughout the 10-day feeding period, mice received either P7C3 or vehicle. On Day 16, FST performance was assessed, followed by sacrifice of the animals for quantification of AC3+ cells in the DG (FIG. 42, panel a). Surprisingly, the number of AC3+ cells after caloric restriction was reduced throughout the DG in wild-type mice, yet was increased in Ghsr-null mice ( FIG. 42, panels b-c, f-p). In caloric-restricted wild-type mice, P7C3 did not further reduce the number of AC3+ cells (FIG. 42, panels b-c), whereas in Ghsr-null mice, P7C3 blocked the increase in apoptosis observed after caloric restriction (FIG. 42, panels b-c).

With respect to behavior, caloric restriction significantly decreased immobility in the FST in vehicle-treated wild-type mice, but not in vehicle-treated Ghsr-null mice, as previously demonstrated with non-injected, caloric-restricted mice (FIG. 42, panels d-e). While P7C3 administration had no further effect on reducing immobility in caloric-restricted wild-type mice, it did significantly decrease immobility in caloric-restricted Ghsr-null mice. Thus, the anti-apoptotic efficacy of P7C3 within the DG of Ghsr-null mice restores the antidepressant-like effect of caloric restriction to that observed in wild-type mice ( FIG. 42, panels d-e).

Comparison of P7C3 Class to Approved Antidepressants

Figure 43:
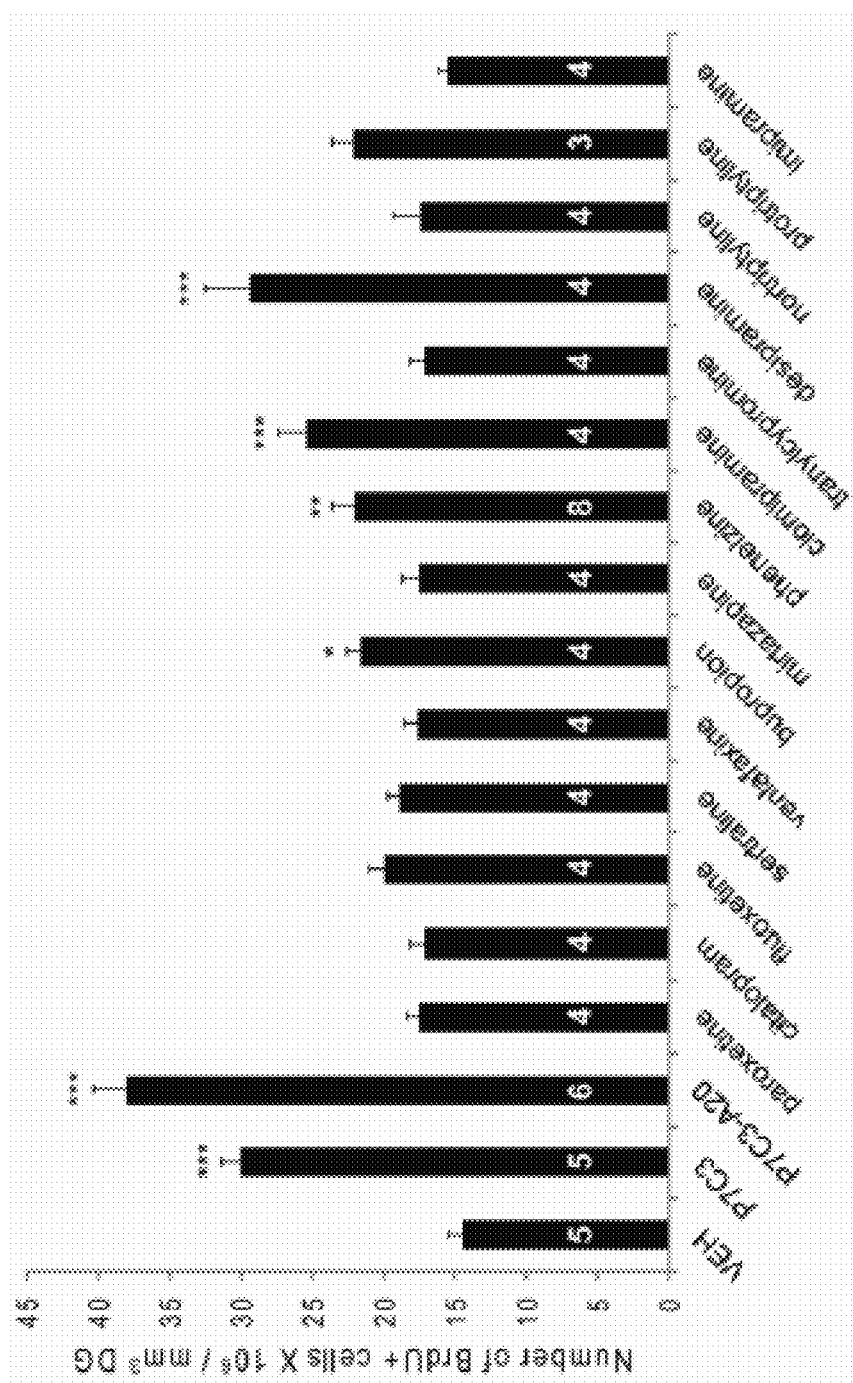
FIG. 43. Effect of P7C3 compounds and antidepressants on DG proliferation. BrdU-immunoreactive DG cell counts in wild-type mice receiving infusions of P7C3 compounds or antidepressants. Group sizes indicated. *P<0.05, P<0.01, *P<0.001, as compared to vehicle-treated group.

The neuroprotective efficacies of both P7C3 and P7C3-A20 were next compared to currently marketed antidepressant medications, using screening conditions identical to those by which P7C3 was originally discovered. This experiment was based on the antidepressant actions of P7C3 and P7C3-A20 characterized here, and the dependence on hippocampal neurogenesis for behavioral efficacy of some marketed antidepressant medications in mice. Continuous and direct intracerebroventricular infusion of P7C3 or P7C3-A20 over a one week period of time into the left lateral ventricle markedly augmented hippocampal neurogenesis by about 100% or 160%, respectively, as reflected by increased BrdU labeling in the DG (FIG. 43). By contrast, only four out of fourteen antidepressant medications tested significantly increased DG BrdU labeling over that observed with vehicle. In particular, the norepinephrine-dopamine reuptake inhibitor bupropion, the monoamine oxidase inhibitor phenelzine, and the tricyclic antidepressants clomipramine and desipramine increased DG neurogenesis by about 49%, 52%, 75% and 102% over vehicle, respectively. Of those, only clomipramine and desipramine were statistically as effective at P7C3 in inducing BrdU incorporation, and none was statistically as effective as the highly active P7C3-A20 molecule. The remaining antidepressant medications tested, including the selective serotonin reuptake inhibitors paroxetine, citalopram, fluoxetine and sertraline, the serotonin-norepinephrine reuptake inhibitor venlafaxine, the noradrenergic and specific serotonergic antidepressant mirtazapine, the monoamine oxidase inhibitor tranylcypromine, and the tricyclic antidepressants nortriptyline and imipramine, did not affect the magnitude of neurogenesis in this one week assay. Thus, the proneurogenic efficacy of the new P7C3-class of compounds is superior to that noted for a wide spectrum of antidepressant drugs representing the major classes currently prescribed to patients. If indeed, as the current studies confirm, augmentation of hippocampal neurogenesis is crucial for the manifestation of antidepressant efficacy of both endogenous substances such as ghrelin and exogenous compounds administered to patients, then the rapidity and magnitude of proneurogenic efficacy offered by highly active members of the P7C3 class suggest that this chemical scaffold may serve as a basis for developing new antidepressants with superior efficacy to those currently available to patients suffering from depressive illness.

Discussion:

Despite the multitude of antidepressant drugs currently offered to patients, major depression remains a significant cause of morbidity and mortality in our society. Thus, there is a great need to further understand the mechanisms underlying depression in order to develop new treatments. To that end, impaired hippocampal neurogenesis has been identified as a general contributing factor to the depression associated with chronic psychosocial stress in the mouse models. Furthermore, effects seen in Ghsr-null mice suggest that hippocampal neuroprotection is a primary mechanism by which stress-induced elevations in ghrelin protect against what would otherwise be worsened stress-associated depression. These new insights led us to test the antidepressant efficacy of the P7C3 class of neuroprotective compounds in the animal models of depression.

Here, it was demonstrated for the first time that the P7C3 class of neuroprotective agents elevates hippocampal neurogenesis more acutely and with greater magnitude than a wide variety of existing antidepressant medications representative of the major classes currently prescribed to patients. Indeed, the exacerbated depression-like behavior and decrease in neurogenesis observed in CSDS-exposed Ghsr-null mice was blocked by P7C3. Notably, even baseline depression-like behavior observed in CSDS-exposed wild-type mice was minimized by P7C3-A20, a well-characterized more highly active analog of P7C3. Absence of a behavioral response to P7C3-S184, a P7C3 analog that lacks neuroprotective efficacy, further supports specificity of the neuroprotective properties of P7C3 and P7C3-A20 in conferring antidepressant efficacy. Furthermore, the inability of Ghsr-null mice to mount an antidepressant response to caloric restriction was also linked to acquired deficits in hippocampal neurogenesis, and both this and behavior were restored to normal through treatment of Ghsr-null animals with P7C3. It is thus proposed that the P7C3 class of neuroprotective compounds provides a basis for developing a new class of antidepressant medications.

The results here further suggest that individuals with depression associated with insufficient ghrelin responses might be effectively treated by strongly neuroprotective agents, as embodied by the P7C3 class. For instance, individuals who have undergone Roux-en-Y gastric bypass weight loss surgery have a higher rate of suicide than the general population. As most studies have demonstrated either decreased or unchanged plasma ghrelin levels following Roux-en-Y gastric bypass, neuroprotection by the P7C3 class of compounds may substitute for that lacking due to the atypical ghrelin response. The role of impaired hippocampal neurogenesis also needs to be investigated as a contributory factor to other forms of depression besides those associated with chronic psychosocial stress or defective ghrelin signaling in order to further determine the extent of applicability of specifically augmenting hippocampal neurogenesis to treat depression. It is believed that the chemical scaffold represented by P7C3 and P7C3-A20 will provide a basis for optimizing and advancing a new class of pharmacologic agents for treatment of depression.

Supplementary Materials:

Animal and Housing

Male Ghsr-null and wild-type littermates on a pure C57/BL/6J genetic background were generated as described previously (J. C. Chuang et al., Ghrelin mediates stress-induced food-reward behavior in mice. *J Clin Invest* 121, 2684 (2011); J. M. Zigman, et al., Expression of ghrelin receptor mRNA in the rat and the mouse brain. *J Comp Neurol* 494, 528 (2006)). Mice were housed in a 12-hour-light/dark cycle with ad libitum access to water and regular chow (Teklad Global Diet 16% Protein Diet [2016]; Harlan Teklad, Madison, Wis.) unless otherwise stated. All procedures were performed according to protocols approved by The University of Texas Southwestern Medical Center Institutional Animal Care and Use of Committee guidelines.

P7C3 Compounds

P7C3 was from Asinex (Moscow, Russia) and P7C3-A20 was prepared as described (A. A. Pieper et al., Discovery of a proneurogenic, neuroprotective chemical. *Cell* 142, 39 (2010)).

Behavioral Testing

Figure 48:
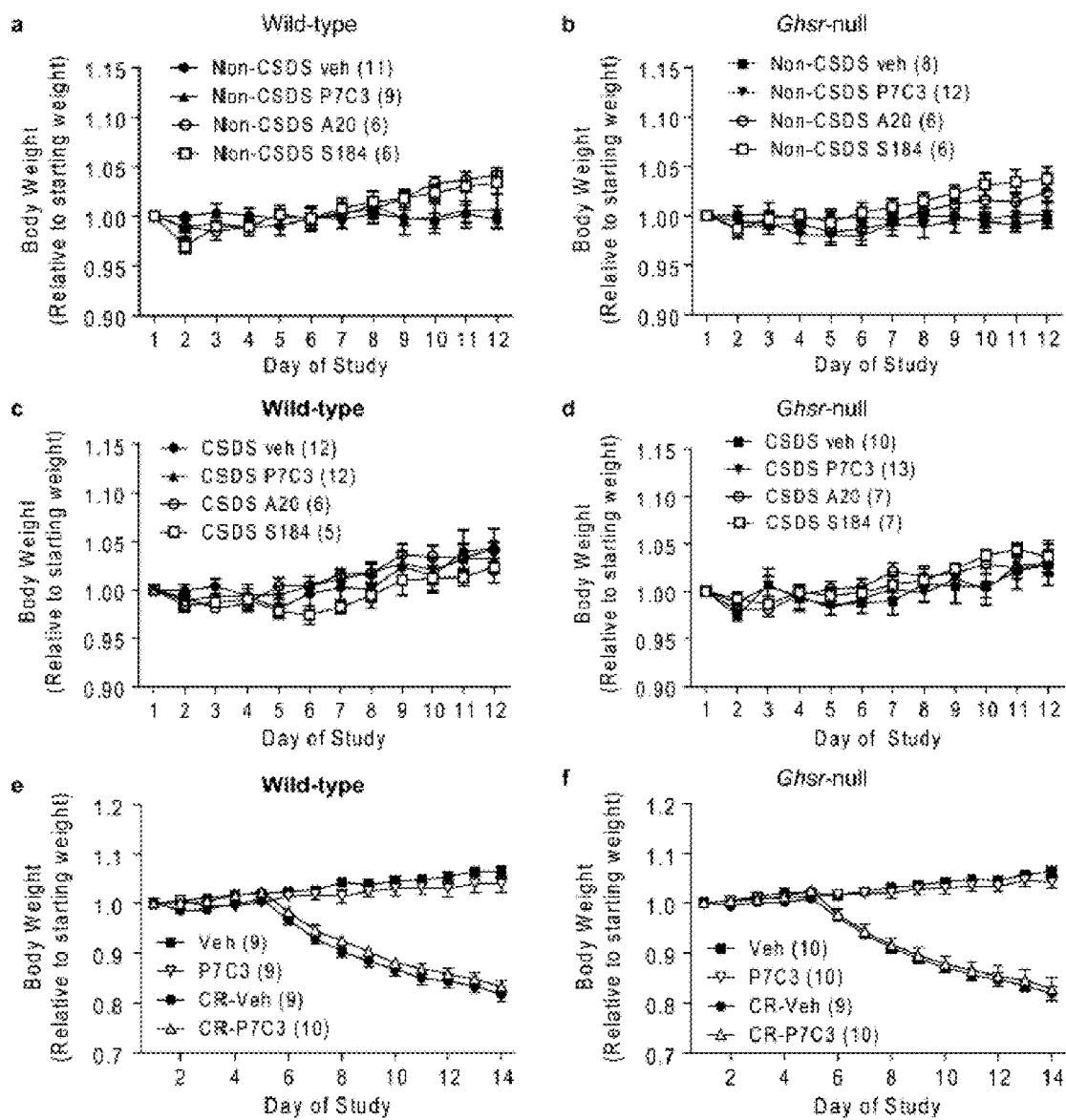
FIG. 48. Effect of P7C3 compounds on body weight. (a-d) Relative body weights for non-CSDS-exposed wild-type (a) and Ghsr-null (b) mice as well as CSDS-exposed wild-type (c) and Ghsr-null (d) mice. (e, f) Relative body weights for calorie-restricted (CR) or ad libitum-fed wild-type (e) or Ghsr-null (f) mice. Group sizes are indicated within parentheses.

Behavioral tests were performed as described previously (J. C. Chuang et al., Ghrelin mediates stress-induced food-reward behavior in mice. *J Clin Invest* 121, 2684 (2011); M. Lutter et al., The orexigenic hormone ghrelin defends against depressive symptoms of chronic stress. *Nat Neurosci* 11, 752 (2008)). Injections of P7C3 compounds were administered at 9 a.m. and 5 p.m. daily and BrdU was administered at 9 a.m., as per the schedule in the main text and FIGS. 40*a* and 42a. All mice were weighed each morning to calculate doses. Body weights were unaffected by administration of the compounds (FIG. 48).

Chronic Social Defeat Stress (CSDS)

CSDS was performed similar to methods used previously in the lab (J. C. Chuang et al., Ghrelin mediates stress-induced food-reward behavior in mice. *J Clin Invest* 121, 2684 (2011)). Test mice were housed individually in large cages paired with a CD1 aggressor mouse, separated by a plastic divider with holes so as to allow sensory contact. For 5 min a day, the plastic divider was removed, exposing test mice to the CD1 mouse. After 5 min of exposure to the CD1 mouse, test mice were again separated and paired with a new CD1 mouse for the remainder of the 24 hours. This process was repeated for 10 days. Following the 5 min sensory contact on the $10^{th}$ day, mice were separated and singly housed prior to social interaction test. Control mice were housed in equivalent cages with members of the same strain and handled daily. The social interaction test consists of placing mice in an arena with a small cage at one end. The movements of test mice were tracked for 2.5 min in the absence of another mouse, followed by 2.5 min in the presence of a novel CD1 mouse, or the "target". Ethovision 3.0 software (Noldus, Leesburg, Va.) measured the duration spent in the interaction zone or in the corners. As done previously, data is presented as time spent in the interaction zone when the target is present or time spent in the corners when the target is present (J. C. Chuang et al., Ghrelin mediates stress-induced food-reward behavior in mice. *J Clin Invest* 121, 2684 (2011)).

Caloric Restriction Study

The 60% calorie restriction protocol was performed as previously (M. Lutter et al., The orexigenic hormone ghrelin defends against depressive symptoms of chronic stress. *Nat Neurosci* 11, 752 (2008)). Mice received twice-daily injections of either P7C3 (20 mg/kg/d in divided doses) or vehicle 5 days prior to and during 10 days of calorie restriction or ad-lib feeding, replicating the injection protocol used for the CSDS studies. On Day 16, the forced swim test was performed for each mouse as done previously.

Immunohistochemistry and Stereology

Immunohistochemistry and quantification were performed as described previously (J. C. Chuang et al., Ghrelin mediates stress-induced food-reward behavior in mice. *J Clin Invest* 121, 2684 (2011); J. E. Malberg et al., Chronic antidepressant treatment increases neurogenesis in adult rat hippocampus. *J Neurosci* 20, 9104 (2000); A. A. Pieper et al., Discovery of a proneurogenic, neuroprotective chemical. *Cell* 142, 39 (2010)). Mice first were anesthetized and perfused transcardially with formalin (or paraformaldehyde for FIG. 43). Brains were extracted, coronally sectioned into 8 equal series at 25 µm thickness (or 5 equal series at 40 µm thickness for FIG. 43) using a sliding microtome, and then mounted onto Superfrost slides (Fisher Scientific, Richardson, Tex.), using previously described methods (J. C. Chuang et al., Ghrelin mediates stress-induced food-reward behavior in mice. *J Clin Invest* 121, 2684 (2011); J. M. Zigman et al., Expression of ghrelin receptor mRNA in the rat and the mouse brain. *J Comp Neurol* 494, 528 (2006)). Standard procedures for immunolabeling of slides were employed consisting of antigen retrieval, 1 hr in blocking solution, overnight incubation in primary antibody solution, and 1 hr in appropriate secondary antibody solution. Primary antibodies included mouse-anti-BrdU (1:100, Roche Diagnostic, Mannheim, Germany), rabbit-anti-AC3 (1:450, Cell Signaling, Beverly, Mass.), and Rabbit-anti-Ki67 (1:1000, Vector Labs, Burlingame, Calif.). Counting of labeled cells was done manually at a magnification of 40× on a Zeiss Axioskop 2 microscope (Carl Zeiss Inc., Thornwood, N.Y.). For each brain, labeled cells were counted in all hippocampal sections from one of the 8 series (or one of the 5 series for FIG. 43). Final quantification of the whole DG of each mouse was obtained by adding labeled cell counts from all sections and multiplying by the number of series. Dorsal DG or ventral DG cell counts were obtained by adding labeled cell counts for either the first ⅔ of sections or last ⅓ of sections, respectively, and multiplying by the number of series. Photomicrograph images were taken using Axiovision software. Image editing software Adobe Photoshop CS2 (San Jose, Calif.) was used to adjust brightness and contrast of photomicrographs and prepare figures.

Quantitative RT-PCR

Mice were euthanized by live decapitation, and brains were processed with a brain matrix and a 15-guage blunt needle to excise 1-mm thick tissue punches from various sites. RNA was extracted from tissues, processed and reverse-transcribed, and the resulting cDNA was used as template for quantitative PCR, as previously described (A. K. Walker et al., Disruption of cue-potentiated feeding in mice with blocked ghrelin signaling. *Physiol Behav* 108, 34 (2012); J. C. Chuang et al., Ghrelin mediates stress-induced food-reward behavior in mice. *J Clin Invest* 121, 2684 (2011)). Quantitative PCR was performed using iTaq SYBER Green Supermix with Rox (BioRad, Hercules, Calif.) and previously validated Ghsr and cyclophilin primer sets in an Applied Biosystems 7900HT Sequence Detection System (Applied Biosystems, Foster City, Calif.), as described (Id.). Relative mRNA levels were determined with cyclophilin used as the housekeeping gene and calculated with the comparative threshold cycle ($\Delta\Delta Ct$) method (J. C. Chuang et al., Ghrelin mediates stress-induced food-reward behavior in mice. *J Clin Invest* 121, 2684 (2011)).

P7C3 Brain Penetration Study

Mice were injected with either P7C3 (10 mg/kg) or vehicle twice every day at 9 am and 5 pm for a total of 19 days. Pharmacokinetic analysis was performed as done previously (A. A. Pieper et al., Discovery of a proneurogenic, neuroprotective chemical. *Cell* 142, 39 (2010)). Six hours after the last injection of either P7C3 or 0.9% saline (for vehicle treated mice), mice were deeply anesthetized with chloral hydrate (500 mg/kg, i.p.) for blood and brain collection. Blood was collected transcardially using an EDTA-coated syringe, and blood was dispensed into EDTA-coated vials on ice. Whole brain was then removed, weighed, and snap-frozen in liquid nitrogen. Blood was spun down to separate plasma, which was kept at −80° C. until analysis was performed. Brain tissue was homogenized in a 3-fold volume of PBS to prepare lysates. Liquid chromatography and mass spectrometry were used to determine levels of P7C3.

Comparison of P7C3 Compounds and Antidepressant Drugs

Proneurogenic efficacies in the DG of P7C3 and P7C3A20 were compared to those of vehicle (artificial cerebrospinal fluid) and several marketed antidepressant compounds (Sigma-Aldrich, St. Louis, Mo.) according to established methods. In brief, mice were housed individually in cages without running wheels or any form of environmental enrichment, in order to create an environment predicted to have as low of a baseline level of hippocampal neurogenesis as possible. Compounds (10 µM, i.c.v.) were administered for 7 days via subcutaneously implanted Alzet osmotic minipumps connected to a cannula directed into the left lateral ventricle, with implantation day designated as day 0. Starting on day 1, mice also received daily injections of BrdU (50 mg/kg, i.p.) at 9 am daily, for 6 days. Twenty four hours after the sixth BrdU injection, mice were transcardially perfused as described above.

Statistical Analyses

Two-way ANOVAs with Bonferonni post-hoc tests were performed when analyzing the effect of genotype and stress or genotype and injection/stress treatment on social interaction or cell counts for Ki67, AC3, and BrdU. One-way ANOVA with Dunnett's post-hoc test was performed when assessing the effect P7C3 analogs on social interaction, the effect of anti-depressants on BrdU cell number, or the effect of brain region on gene expression. If unequal variance was indicated by Bartlett's test, log transformation was performed prior to statistical analysis. Two-tailed unpaired t-tests were performed when analyzing P7C3 brain penetration data. Significant p-value was defined as $p<0.05$. GraphPad Prism 5.0 was used for all statistical analysis. Data are presented as mean±s.e.m.

Other Embodiments

Additional embodiments include:
methods for promoting postnatal mammalian neurotrophism in a patient determined to be in need thereof, comprising administering to the patient an effective amount of a neurotrophic carbazole compound of formula 1:

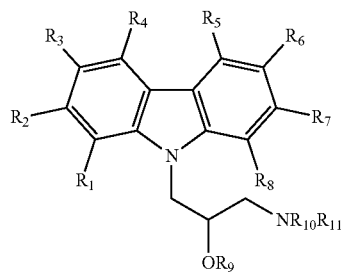

wherein:
$R_1$-$R_8$ are each independently selected hydrogen, heteroatom, heteroatom functional group, and optionally-substituted, optionally heteroatom lower (C1-C6) alkyl;
$R_9$ is hydrogen or optionally-substituted, optionally heteroatom lower (C1-C6) alkyl; and
$R_{10}$ and $R_{11}$ are each independently selected hydrogen, optionally-substituted, optionally heteroatom C1-C6 alkyl, optionally-substituted, optionally heteroatom C2-C6 alkenyl, optionally-substituted, optionally heteroatom C2-C6 alkynyl, and optionally-substituted, optionally heteroatom C6-C14 aryl, including tautomers, stereoisomers and pharmaceutically-acceptable salts thereof.

Unless otherwise noted, all structures depicted herein encompass interconvertable tautomers as if each were separately depicted.

The presently disclosed embodiments encompass all alternative combinations of particular embodiments:
wherein $R_1$-$R_8$ are each independently selected hydrogen and halide;
wherein $R_1$, $R_2$, $R_4$, $R_5$, $R_7$ and $R_8$ are hydrogen, and $R_3$ and $R_6$ are halide, such as Cl, Br, I and F;
wherein $R_9$ is hydrogen;
wherein $R_{10}$ is hydrogen and $R_{11}$ is optionally-substituted, optionally heteroatom C6-C14 aryl;
wherein $R_{10}$ and $R_{11}$ are joined to form a 5-7 membered, optionally substituted heterocyclic ring;
wherein $R_{10}$ and $R_{11}$ are joined to form an optionally substituted pyrrolidine or a piperidine;
wherein $R_{10}$ is hydrogen and $R_{11}$ is substituted phenyl, such as halide- or C1-C6 alkoxy-phenyl, including para-, meta-, or ortho positions;
wherein $R_{10}$ is hydrogen and $R_{11}$ is napthyl;
wherein the compound has a formula of Table 1 (herein) or Table 2 (herein);
wherein the compound has formula 2:

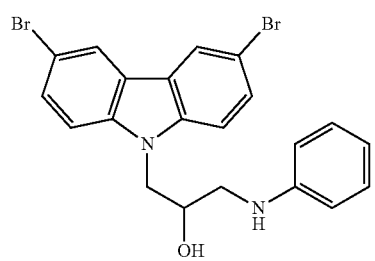 [SMILES: OC(CNc1ccccc1)Cn1c2ccc(Br)cc2c2cc(Br)ccc21]

wherein (a) at least one of $R_1$-$R_8$ is heteroatom, optionally-substituted, or optionally heteroatom lower (C1-C6) alkyl, and at least one of $R_1$-$R_4$ or at least one of $R_5$-$R_8$ is different; or (b) $R_9$ is optionally-substituted, optionally heteroatom lower (C1-C6) alkyl;
further comprising the step of detecting a resultant neurotrophism, particularly neurogenesis; and/or
further comprising the antecedent step of determining that the patient has aberrant neurotrophism, particularly aberrant neurogenesis, particularly aberrant hippocampal and/or hypothalamic neurogenesis, or a disease or disorder associated therewith, particularly by detecting and/or diagnosing the same.

The presently disclosed embodiments also provide novel pharmaceutical, particularly novel neurogenic, compositions in unit dosage comprising a disclosed neurotrophic carbazole not previously known or suggested to provide pharmacological, particularly neurogenic, activity, or a pharmaceutically-acceptable salt thereof, and a pharmaceutically acceptable excipient.

The presently disclosed embodiments also provide disclosed novel neurotrophic carbazoles and pharmaceutically-acceptable salts thereof.

The term "heteroatom" as used herein generally means any atom other than carbon, hydrogen or oxygen. Preferred heteroatoms include oxygen (O), phosphorus (P), sulfur (S), nitrogen (N), silicon (S), arsenic (As), selenium (Se), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the presently disclosed embodiments. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: –OR', =O, =NR', =N—OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR'—SO$_2$NR''', —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R''' each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the presently disclosed embodiments. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R''', —OC(O)R', —C(O)R', —CO$_2$R', —CONR'R", —OC(O)NR'R", —NR"C(O)R', —NR"CO$_2$R', —NR'—SO$_2$NR"R''', —S(O)R', —SO2R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R''', —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R''', —NR'—SO$_2$NR"R''', —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alko-xy and perfluoro(C1-C4)alkyl, in a number ranging from zero to the total number of open valences on the aromatic ring system; and where R', R" and R''' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Typically, an aryl or heteroaryl group will have from zero to three substituents, with those groups having two or fewer substituents being preferred in the presently disclosed embodiments. In one embodiment, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, where R' and R$^{11}$ are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4)alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl.

The invention claimed is:

1. A method for treating a depressive disorder comprising: administering to a subject in need thereof an effective amount of a compound, or a pharmaceutically acceptable salt thereof, having formula (III); wherein the depressive disorder is selected from the group consisting of dysthymia, atypical depression, melancholic depression, postpartum depression, seasonal affective disorder, recurrent brief depression, minor depressive disorder, substance-induced mood disorder, mood disorder due to a general medical condition, anxiety, and depression not otherwise specified:

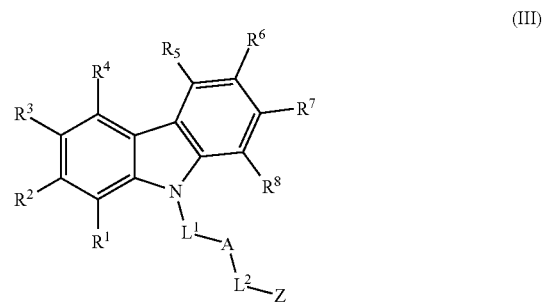

(III)

wherein:
each of $R^1$, $R^2$, $R^3$, $R^4$, $R^5$, $R^6$, $R^7$, and $R^8$ is independently selected from hydrogen, halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyano, —$NH_2$, —$NH(C_1$-$C_6$ alkyl), —$N(C_1$-$C_6$ alkyl)$_2$, —$NHC(O)(C_1$-$C_6$ alkyl), and nitro;
each of $L^1$ and $L^2$ is $CH_2$;
A is $CR^{41}R^{42}$, wherein one of $R^{41}$ and $R^{42}$ is halo or $OR^9$, and the other of $R^{41}$ and $R^{42}$ is hydrogen, halo, $OR^9$ or $C_1$-$C_3$ alkyl; wherein $R^9$ is $C_1$-$C_3$ alkyl that is optionally substituted with hydroxyl or $C_1$-$C_3$ alkoxy;
Z is —$NR^{10}R^{11}$ or —$OR^{12}$ or —$S(O)_nR^{13}$, wherein n is 0, 1, or 2;
each of $R^{10}$ and $R^{11}$ is independently selected from:
  (a) hydrogen;
  (b) $C_6$-$C_{10}$ aryl that is optionally substituted with from 1-4 $R^b$;
  (c) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
  (d) $C_1$-$C_6$ alkyl or $C_1$-$C_6$ haloalkyl, each of which is optionally substituted with from 1-3$R^d$;
  (e) —$C(O)(C_1$-$C_6$ alkyl), —$C(O)(C_1$-$C_6$ haloalkyl), or —$C(O)O(C_1$-$C_6$ alkyl); and
  (f) $C_2$-$C_6$ alkenyl or $C_2$-$C_6$ alkynyl;
wherein one of $R^{10}$ and $R^{11}$ is (b) or (c);
each of $R^{12}$ and $R^{13}$ is:
  (i) $C_6$-$C_{10}$ aryl that is optionally substituted with from 1-4 $R^b$; or
  (ii) heteroaryl containing from 5-14 ring atoms, wherein from 1-6 of the ring atoms is independently selected from N, NH, N($C_1$-$C_3$ alkyl), O, and S; and wherein said heteroaryl is optionally substituted with from 1-4 $R^b$;
$R^b$ at each occurrence is independently selected from the substituents delineated in (aa) through (dd) below:
  (aa) $C_1$-$C_6$ alkoxy; $C_1$-$C_6$ haloalkoxy; $C_1$-$C_6$ thioalkoxy; $C_1$-$C_6$ thiohaloalkoxy; —O—$(CH_2)_{1-3}$—[O$(CH_2)_{1-3}]_{1-3}$—H; $C_1$-$C_6$ alkyl, $C_1$-$C_6$ haloalkyl, —$NH(C_1$-$C_6$ alkyl), —$N(C_1$-$C_6$ alkyl)$_2$, —$NHC(O)(C_1$-$C_6$ alkyl); wherein the alkyl portion of each is optionally substituted with from 1-3 independently selected $R^e$;
  (bb) halo; hydroxyl; cyano; nitro; —$NH_2$; azido; sulfhydryl; $C_2$-$C_6$ alkenyl; $C_2$-$C_6$ alkynyl; —$C(O)H$; —$C(O)(C_1$-$C_6$ alkyl); —$C(O)(C_1$-$C_6$ haloalkyl); $C(O)OH$; —$C(O)O(C_1$-$C_6$ alkyl); —$C(O)NH_2$; —$C(O)NH(C_1$-$C_6$ alkyl); —$C(O)N(C_1$-$C_6$ alkyl)$_2$; —$SO_2(C_1$-$C_6$ alkyl); —$SO_2NH_2$; —$SO_2NH(C_1$-$C_6$ alkyl); —$SO_2N(C_1$-$C_6$ alkyl)$_2$;
  (cc) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and
  (dd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; nitro; —$NH_2$; —$NH(C_1$-$C_6$ alkyl), —$N(C_1$-$C_6$ alkyl)$_2$, —$NHC(O)(C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl; and $R^e$ at each occurrence is, independently selected from hydroxy, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —$NH(C_1$-$C_6$ alkyl); N($C_1$-$C_6$ alkyl)$_2$;—$NHC(O)(C_1$-$C_6$ alkyl); cyano; —$C(O)H$; —$C(O)(C_1$-$C_6$ alkyl); —$C(O)(C_1$-$C_6$ haloalkyl); $C(O)OH$; —$C(O)O(C_1$-$C_6$ alkyl); —$C(O)NH_2$; —$C(O)NH(C_1$-$C_6$ alkyl); $C(O)N(C_1$-$C_6$ alkyl)$_2$; —$SO_2(C_1$-$C_6$alkyl); —$SO_2NH_2$; $SO_2NH(C_1$-$C_6$ alkyl); —$SO_2N(C_1$-$C_6$ alkyl)$_2$; and $L^3$-($C_1$-$C_6$ alkylene)-Cy, where in$L^3$ is a —O—, —NH—, —$NCH_3$—, —$C(O)$—, —$C(O)NH$—, —$C(O)NCH_3$—, —NHC(O)—, or —$NCH_3C(O)$—, and Cy is a saturated, partially unsaturated or aromatic carbocyclic or heterocyclic ring system.

2. The method of claim 1, wherein the carbon attached to $R^{41}$ and $R^{42}$ is substituted with four different substituents, and is (R) or (S) configured.

3. The method of claim 2, wherein the compound or salt is (+) (dextrorotatory) or (−) (levorotatory).

4. The method of claim 1, wherein the effective amount of the compound or salt reduces neuron cell death.

5. The method of claim 1, wherein the compound is selected from:

N-(3-(3,6-dibromo-9H-carbazol-9-yl)-2-fluoropropyl)-3-methoxyaniline;

N-(3-(3,6-dibromo-9H-carbazol-9-yl)-2-methoxypropyl)-3-methoxyaniline;

N-(3-(3,6-dibromo-9H-carbazol-9-yl)-2-fluoropropyl)-3-methoxy-N-methylaniline;

N-(3-(3,6-dibromo-9H-carbazol-9-yl)-2,2-difluoropropyl)-3-methoxyaniline;

3,6-dibromo-9-(2-fluoro-3-phenoxypropyl)-9H-carbazole;

3,6-dibromo-9-(2-fluoro-3-(phenylsulfonyl)propyl)-9H-carbazole;

N-(3-(3,6-dibromo-9H-carbazol-9-yl)-2-fluoropropyl) aniline;

3,6-dibromo-9-(2,2-difluoro-3-phenoxypropyl)-9H-carbazole;

N-(3-(3,6-dibromo-9H-carbazol-9-yl)-2-fluoropropyl)-4-methoxyaniline;

N-(2-bromo-3-(3,6-dibromo-9H-carbazol-9-yl)propyl)-N-(4-methoxyphenyl)-4-nitrobenzenesulfonamide;

Ethyl 2-(4-(3-(3,6-dibromo-9H-carbazol-9-yl)-2-fluoropropylamino)phenoxy)acetate;

N-(3-(3,6-dibromo-9H-carbazol-9-yl)-2-fluoropropyl)-4-(2-(2-methoxyethoxy)ethoxy)aniline and N-(3-(3,6-dibromo-9H-carbazol-9-yl)-2-fluoropropyl)-6-methoxypyridin-2-amine.

6. A method for treating a depressive disorder comprising: administering to a subject in need thereof an effective amount of a compound, or a pharmaceutically acceptable salt thereof, having the following formula); wherein the depressive disorder is selected from the group consisting of dysthymia, atypical depression, melancholic depression, postpartum depression, seasonal affective disorder, recurrent brief depression, minor depressive disorder, substance-induced mood disorder, mood disorder due to a general medical condition, anxiety, and depression not otherwise specified:

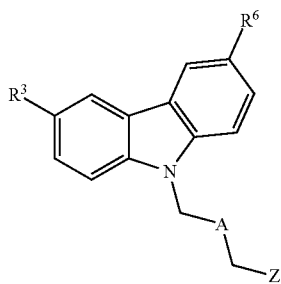

wherein:

R³ and R⁶ are each independently selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyano, —NH₂, —NH($C_1$-$C_6$ alkyl), —N($C_1$-$C_6$ alkyl)₂, —NHC(O)($C_1$-$C_6$ alkyl), and nitro;

A is $CR^{A1}R^{A2}$, wherein $R^{A1}$ is selected from hydrogen, halo, $C_1$-$C_3$ alkyl, and $OR^9$, and $R^{A2}$ is selected from halo, $C_1$-$C_3$ alkyl, and $OR^9$;

Z is selected from —NHR¹⁰; —N(CH₃)R¹¹; —OR¹²; and —S(O)ₙR¹³, wherein n is 0, 1, or 2;

R⁹ is hydrogen or $C_1$-$C_3$ alkyl that is optionally substituted with hydroxyl or $C_1$-$C_3$ alkoxy;

R¹⁰, R¹¹, R¹² and R¹³ are each independently selected from:
(a) $C_6$-$C_{10}$ aryl that is optionally substituted with 1 to 4 $R^b$; or
(b) heteroaryl containing from 6-14 ring atoms, wherein from 1-6 of the ring atoms are independently selected from N, NH, N($C_1$-$C_3$ alkyl), O, and S; and wherein said heteroaryl is optionally substituted with from 1 to 4 $R^b$;

$R^b$ at each occurrence is independently selected from the substituents delineated in (aa) through (dd) below:
(aa) $C_1$-$C_6$ alkoxy; $C_1$-$C_6$ haloalkoxy; $C_1$-$C_6$ thioalkoxy; $C_1$-$C_6$ thiohaloalkoxy; —O—(CH₂)₁₋₃—[O(CH₂)₁₋₃]₁₋₃—H; $C_1$-$C_6$ alkyl, $C_1$-$C_6$ haloalkyl, —NH($C_1$-$C_6$ alkyl), —N($C_1$-$C_6$ alkyl)₂, —NHC(O)($C_1$-$C_6$ alkyl);
(bb) halo; hydroxyl; cyano; nitro; —NH₂; azido; sulfhydryl; $C_2$-$C_6$ alkenyl; $C_2$-$C_6$ alkynyl; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH₂; —C(O)NH($C_1$-$C_6$ alkyl); C(O)N($C_1$-$C_6$ alkyl)₂; —SO₂($C_1$-$C_6$ alkyl); —SO₂NH₂; —SO₂NH($C_1$-$C_6$ alkyl); —SO₂N($C_1$-$C_6$ alkyl)₂;
(cc) $C_3$-$C_6$ cycloalkyl or heterocyclyl containing from 5 to 6 ring atoms, wherein from 1 to 2 of the ring atoms of the heterocyclyl is independently selected from N, NH, N($C_1$-$C_6$ alkyl), NC(O)($C_1$-$C_6$ alkyl), O, and S; and
(dd) phenyl or heteroaryl containing from 5 to 6 ring atoms, wherein from 1 to 2 of the ring atoms of the heteroaryl is independently selected from N, NH, N($C_1$-$C_3$ alkyl), O, and S; wherein each of said phenyl and heteroaryl is optionally substituted with from 1 to 3 substituents independently selected from halo; hydroxyl; cyano; nitro; —NH₂; —NH($C_1$-$C_6$ alkyl), —N($C_1$-$C_6$ alkyl)₂, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_{1\text{-}6}$ haloalkyl;

wherein when R³ and R⁶ are both halo, one of $R^{A1}$ and $R^{A2}$ is OH and the other is hydrogen, Z is —NHR¹⁰, and R¹⁰ is $C_6$-$C_{10}$ aryl that is optionally substituted with 1 to 4 $R^b$, then R¹⁰ is unsubstituted phenyl or phenyl substituted with 1 $R^b$.

7. The method of claim 6, wherein the carbon attached to $R^{A1}$ and $R^{A2}$ is substituted with four different substituents, and is (R) or (S) configured.

8. The method of claim 7, wherein the compound or salt is (+) (dextrorotatory) or (−) (levorotatory).

9. The method of claim 6, wherein the effective amount of the compound or salt reduces neuron cell death.

10. The method of claim 6, wherein the compound is selected from:
1-(3,6-dibromo-9H-carbazol-9-yl)-3-(phenylthio)propan-2-ol;
N-(3-(3,6-dibromo-9H-carbazol-9-yl)-2-fluoropropyl)-3-methoxyaniline;
N-(3-(3,6-dibromo-9H-carbazol-9-yl)-2-methoxypropyl)-3-methoxyaniline;
1-(3,6-Dimethyl-9H-carbazol-9-yl)-3-(3-methoxyphenylamino)propan-2-ol;
1-(3-Bromo-6-methyl-9H-carbazol-9-yl)-3-(3-methoxyphenylamino)-propan-2-ol;
1-(3,6-Dichloro-9H-carbazol-9-yl)-3-(3-methoxyphenylamino)propan-2-ol;
1-(3,6-Dibromo-9H-pyrido[3,4-b]indol-9-yl)-3-(phenylamino)propan-2-ol;
1-(3-Azidophenylamino)-3-(3,6-dibromo-9H-carbazol-9-yl)propan-2-ol;
1,3-Bis(3,6-dibromo-9H-carbazol-9-yl)propan-2-ol;
1-(9H-Carbazol-9-yl)-3-(3,6-dibromo-9H-carbazol-9-yl)propan-2-ol;
1-(3,6-dibromo-9H-carbazol-9-yl)-3-(pyridin-2-ylamino)propan-2-ol;
1-(3,6-dibromo-9H-carbazol-9-yl)-3-((3-methoxyphenyl)(methyl)-amino)propan-2-ol;
1-(3,6-dibromo-9H-carbazol-9-yl)-3-(pyrimidin-2-ylamino)propan-2-ol;
N-(3-(3,6-dibromo-9H-carbazol-9-yl)-2-fluoropropyl)-3-methoxy-N-methylaniline;
1-(3,6-dibromo-9H-carbazol-9-yl)-3-(3-ethoxyphenylamino)propan-2-ol;
1-(3,6-dibromo-9H-carbazol-9-yl)-3-(phenylsulfinyl)propan-2-ol;
1-(3,6-dibromo-9H-carbazol-9-yl)-3-(phenylsulfonyl)propan-2-ol;
1-(3-bromo-9H-carbazol-9-yl)-3-(3-methoxyphenylamino)propan-2-ol;
1-(3,6-dibromo-9H-carbazol-9-yl)-3-phenoxypropan-2-ol;
1-(3,6-dibromo-9H-carbazol-9-yl)-3-(pyridin-3-ylamino)propan-2-ol;
1-(3,6-dibromo-9H-carbazol-9-yl)-3-(pyridin-4-ylamino)propan-2-ol;
N-(3-(3,6-dibromo-9H-carbazol-9-yl)-2,2-difluoropropyl)-3-methoxyaniline;
1-(3,6-dibromo-9H-carbazol-9-yl)-3-phenoxypropan-2-ol;
(S)-1-(3,6-dibromo-9H-carbazol-9-yl)-3-phenoxypropan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;

1-(4-azidophenylamino)-3-(3,6-dibromo-9H-carbazol-9-yl)propan-2-ol;
1-(3-azido-6-bromo-9H-carbazol-9-yl)-3-(3-methoxyphenylamino)propan-2-ol;
1-(3,6-dibromo-9H-carbazol-9-yl)-3-(4-methoxyphenoxy) propan-2-ol;
1-(3,6-dichloro-9H-carbazol-9-yl)-3-(phenylsulfonyl)propan-2-ol;
3,6-dibromo-9-(2-fluoro-3-(phenylsulfonyl)propyl)-9H-carbazole;
(S)-1-(3,6-dibromo-9H-carbazol-9-yl)-3-(phenylsulfonyl) propan-2-ol;
(R)-1-(3,6-dibromo-9H-carbazol-9-yl)-3-(phenylsulfonyl) propan-2-ol;
1-(3,6-dicyclopropyl-9H-carbazol-9-yl)-3-(phenylamino)propan-2-ol;
1-(3,6-diiodo-9H-carbazol-9-yl)-3-(phenylamino)propan-2-ol;
1-(3,6-diethynyl-9H-carbazol-9-yl)-3-(3-methoxyphenylamino) propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline;
3,6-dibromo-9-(2,2-difluoro-3-phenoxypropyl)-9H-carbazole;
N-(3-(3,6-dibromo-9H-carbazol-9-yl)-2-fluoropropyl)-4-methoxyaniline;
N-(2-bromo-3-(3,6-dibromo-9H-carbazol-9-yl)propyl)-N-(4-methoxyphenyl)-4-nitrobenzenesulfonamide;
Ethyl 2-(4-(3-(3,6-dibromo-9H-carbazol-9-yl)-2-fluoropropylamino)phenoxy)acetate;
N-(3-(3,6-dibromo-9H-carbazol-9-yl)-2-fluoropropyl)-4-(2-(2-methoxyethoxy)ethoxy)aniline and
N-(3-(3,6-dibromo-9H-carbazol-9-yl)-2-fluoropropyl)-6-methoxypyridin-2-amine.

11. The method of claim 6, wherein the compound is selected from:
1-(3,6-dibromo-9H-carbazol-9-yl)-3-(phenylthio)propan-2-ol;
1-(3,6-dibromo-9H-carbazol-9-yl)-3-phenoxypropan-2-ol;
1-(3,6-dibromo-9H-carbazol-9-yl)-3-(phenylsulfinyl)propan-2-ol;
1-(3,6-dibromo-9H-carbazol-9-yl)-3-(phenylsulfonyl) propan-2-ol;
N-(3-(3,6-dibromo-9H-carbazol-9-yl)-2-fluoropropyl)-3-methoxyaniline;
N-(3-(3,6-dibromo-9H-carbazol-9-yl)-2-fluoropropyl)-3-methoxy-N-methylaniline;
N-(3-(3,6-dibromo-9H-carbazol-9-yl)-2-methoxypropyl)-3-methoxyaniline;
1-(3-bromo-6-methyl-9H-carbazol-9-yl)-3-(3-methoxyphenylamino)-propan-2-ol;
1-(3,6-dibromo-9H-carbazol-9-yl)-3-(pyridin-2-ylamino) propan-2-ol;
(R)-1-(3,6-dibromo-9H-carbazol-9-yl)-3-phenoxypropan-2-ol;
3,6-dibromo-9-(2-fluoro-3-phenoxypropyl)-9H-carbazole;
1-(3,6-dibromo-9H-carbazol-9-yl)-3-(3-methoxyphenylamino)-2-methylpropan-2-ol;
1-(4-azidophenylamino)-3-(3,6-dibromo-9H-carbazol-9-yl)propan-2-ol;
3,6-dibromo-9-(2-fluoro-3-(phenylsulfonyl)propyl)-9H-carbazole;
(S)-1-(3,6-dibromo-9H-carbazol-9-yl)-3-(phenylsulfonyl) propan-2-ol;
(R)-1-(3,6-dibromo-9H-carbazol-9-yl)-3-(phenylsulfonyl) propan-2-ol;
9-(2-hydroxy-3-(3-methoxyphenylamino)propyl)-9H-carbazole-3,6-dicarbonitrile;
N-(3-(3,6-dibromo-9H-carbazol-9-yl)-2-fluoropropyl)aniline;
N-(3-(3,6-dibromo-9H-carbazol-9-yl)-2-fluoropropyl)-4-methoxyaniline; and
N-(3-(3,6-dibromo-9H-carbazol-9-yl)-2-fluoropropyl)-6-methoxypyridin-2-amine.

12. The method of claim 6, wherein the compound is selected from:
N-(3-(3,6-dibromo-9H-carbazol-9-yl)-2-fluoropropyl)-6-methoxypyridin-2-amine;
N-(3-(3,6-dibromo-9H-carbazol-9-yl)-2-fluoropropyl)-3-methoxyaniline;
N-(3-(3,6-dibromo-9H-carbazol-9-yl)-2-fluoropropyl)-3-methoxy-N-methylaniline;
3,6-dibromo-9-(2-fluoro-3-phenoxypropyl)-9H-carbazole;
3,6-dibromo-9-(2-fluoro-3-(phenylsulfonyl)propyl)-9H-carbazole;
N-(3-(3,6-dibromo-9H-carbazol-9-yl)-2-fluoropropyl)aniline; and
N-(3-(3,6-dibromo-9H-carbazol-9-yl)-2-fluoropropyl)-4-methoxyaniline.

13. The method of claim 6, wherein the compound is N-(3-(3,6-dibromo-9H-carbazol-9-yl)-2-fluoropropyl)-3-methoxyaniline or N-(3-(3,6-dibromo-9H-carbazol-9-yl)-2-fluoropropyl)-6-methoxypyridin-2-amine.

14. A method for treating a depressive disorder comprising: administering to a subject in need thereof an effective amount of a compound, or a pharmaceutically acceptable salt thereof, having the following formula); wherein the depressive disorder is selected from the group consisting of dysthymia, atypical depression, melancholic depression, postpartum depression, seasonal affective disorder, recurrent brief depression, minor depressive disorder, substance-induced mood disorder, mood disorder due to a general medical condition, anxiety, and depression not otherwise specified:

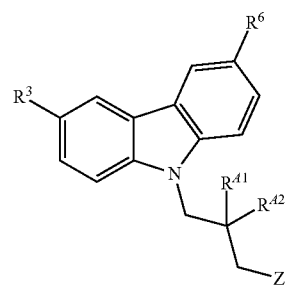

wherein
$R^3$ and $R^6$ are each independently selected from halo, hydroxyl, sulfhydryl, $C_1$-$C_6$ alkoxy, $C_1$-$C_6$ thioalkoxy, $C_1$-$C_6$ haloalkoxy, $C_1$-$C_6$ thiohaloalkoxy, $C_1$-$C_6$ alkyl, $C_1$-$C_6$ haloalkyl, $C_2$-$C_6$ alkynyl, cyano, —NH$_2$, —NH($C_1$-$C_6$ alkyl), —N($C_1$-$C_6$ alkyl)$_2$, —NHC(O)($C_1$-$C_6$ alkyl), and nitro;
$R^{41}$ and $R^{42}$ are each independently selected from hydrogen, halo, CH$_3$, and OR$^9$, wherein one of $R^{41}$ and $R^{42}$ is halo or OR$^9$;

Z is selected from —NHR$^{10}$; —N(CH$_3$)R$^{11}$; —OR$^{12}$; and —S(O)$_n$R$^{13}$, wherein n is 0, 1, or 2;

R$^9$ is hydrogen or C$_1$-C$_3$ alkyl that is optionally substituted with hydroxyl or C$_1$-C$_3$ alkoxy;

R$^{10}$, R$^{11}$, R$^{12}$ and R$^{13}$ are each independently selected from:
(a) C$_6$-C$_{10}$ aryl that is optionally substituted with 1 to 4 R$^b$; or
(b) heteroaryl containing from 6-14 ring atoms, wherein from 1-6 of the ring atoms are independently selected from N, NH, N(C$_1$-C$_3$ alkyl), O, and S; and wherein said heteroaryl is optionally substituted with from 1 to 4 R$^b$;

R$^b$ at each occurrence is independently selected from the substituents delineated in (aa) through (dd) below:
(aa) C$_1$-C$_6$ alkoxy; C$_1$-C$_6$ haloalkoxy; C$_1$-C$_6$ thioalkoxy; C$_1$-C$_6$ thiohaloalkoxy; —O—(CH$_2$)$_{1-3}$—[O(CH$_2$)$_{1-3}$]$_{1-3}$—H; C$_1$-C$_6$ alkyl, C$_1$-C$_6$ haloalkyl, —NH(C$_1$-C$_6$ alkyl), —N(C$_1$-C$_6$ alkyl)$_2$, —NHC(O)(C$_1$-C$_6$ alkyl);
(bb) halo; hydroxyl; cyano; nitro; —NH$_2$; azido; sulfhydryl; C$_2$-C$_6$ alkenyl; C$_2$-C$_6$ alkynyl; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$;
(cc) C$_3$-C$_6$ cycloalkyl or heterocyclyl containing from 5 to 6 ring atoms, wherein from 1 to 2 of the ring atoms of the heterocyclyl is independently selected from N, NH, N(C$_1$-C$_6$ alkyl), NC(O)(C$_1$-C$_6$ alkyl), O, and S; and
(dd) phenyl or heteroaryl containing from 5 to 6 ring atoms, wherein from 1 to 2 of the ring atoms of the heteroaryl is independently selected from N, NH, N(C$_1$-C$_3$ alkyl), O, and S; wherein each of said phenyl and heteroaryl is optionally substituted with from 1 to 3 substituents independently selected from halo; hydroxyl; cyano; nitro; —NH$_2$; —NH(C$_1$-C$_6$ alkyl), —N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl;

wherein when R$^3$ and R$^6$ are both halo, one of R$^{41}$ and R$^{42}$ is OH and the other is hydrogen, Z is —NHR$^{10}$, and R$^{10}$ is defined according to (a), then R$^{10}$ is unsubstituted phenyl or phenyl substituted with 1 R$^b$.

15. The method of claim 14, wherein the carbon attached to R$^{41}$ and R$^{42}$ is substituted with four different substituents, and is (R) or (S) configured.

16. The method of claim 14, wherein the compound is N-(3-(3,6-dibromo-9H-carbazol-9-yl)-2-fluoropropyl)-3-methoxyaniline or N-(3-(3,6-dibromo-9H-carbazol-9-yl)-2-fluoropropyl)-6-methoxypyridin-2-amine.

17. The method of claim 14, wherein the effective amount of the compound or salt reduces neuron cell death.

18. A method for treating a depressive disorder comprising: administering to a subject in need thereof an effective amount of a compound, or a pharmaceutically acceptable salt thereof, having the following formula); wherein the depressive disorder is selected from the group consisting of dysthymia, atypical depression, melancholic depression, postpartum depression, seasonal affective disorder, recurrent brief depression, minor depressive disorder, substance-induced mood disorder, mood disorder due to a general medical condition, anxiety, and depression not otherwise specified:

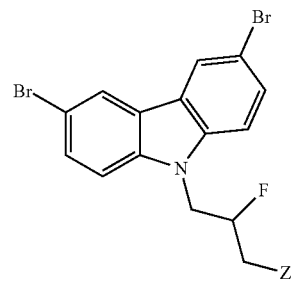

wherein:
Z is selected from —NHR$^{10}$; —N(CH$_3$)R$^{11}$; —OR$^{12}$; and —S(O)$_n$R$^{13}$, wherein n is 0, 1, or 2;

R$^{10}$, R$^{11}$, R$^{12}$ and R$^{13}$ are each independently selected from:
(a) C$_6$-C$_{10}$ aryl that is optionally substituted with 1 to 4 R$^b$; or
(b) heteroaryl containing from 6-14 ring atoms, wherein from 1-6 of the ring atoms are independently selected from N, NH, N(C$_1$-C$_3$ alkyl), O, and S; and wherein said heteroaryl is optionally substituted with from 1 to 4 R$^b$;

R$^b$ at each occurrence is independently selected from the substituents delineated in (aa) through (dd) below:
(aa) C$_1$-C$_6$ alkoxy; C$_1$-C$_6$ haloalkoxy; C$_1$-C$_6$ thioalkoxy; C$_1$-C$_6$ thiohaloalkoxy; —O—(CH$_2$)$_{1-3}$—[O(CH$_2$)$_{1-3}$]$_{1-3}$—H; C$_1$-C$_6$ alkyl, C$_1$-C$_6$ haloalkyl, —NH(C$_1$-C$_6$ alkyl), —N(C$_1$-C$_6$ alkyl)$_2$, —NHC(O)(C$_1$-C$_6$ alkyl);
(bb) halo; hydroxyl; cyano; nitro; —NH$_2$; azido; sulfhydryl; C$_2$-C$_6$ alkenyl; C$_2$-C$_6$ alkynyl; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$;
(cc) C$_3$-C$_6$ cycloalkyl or heterocyclyl containing from 5 to 6 ring atoms, wherein from 1 to 2 of the ring atoms of the heterocyclyl is independently selected from N, NH, N(C$_1$-C$_6$ alkyl), NC(O)(C$_1$-C$_6$ alkyl), O, and S; and
(dd) phenyl or heteroaryl containing from 5 to 6 ring atoms, wherein from 1 to 2 of the ring atoms of the heteroaryl is independently selected from N, NH, N(C$_1$-C$_3$ alkyl), O, and S; wherein each of said phenyl and heteroaryl is optionally substituted with from 1 to 3 substituents independently selected from halo; hydroxyl; cyano; nitro; —NH$_2$; —NH(C$_1$-C$_6$ alkyl), —N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl.

19. The method of claim 18, wherein the carbon attached to fluoro is (R) or (S) configured.

20. The method of claim 19, wherein the compound or salt is (+) (dextrorotatory) or (−) (levororotatory).

21. The method of claim 18, wherein the effective amount of the compound or salt reduces neuron cell death.

22. The method of claim 18, wherein the compound is N-(3-(3,6-dibromo-9H-carbazol-9-yl)-2-fluoropropyl)-3-methoxyaniline or N-(3-(3,6-dibromo-9H-carbazol-9-yl)-2-fluoropropyl)-6-methoxypyridin-2-amine.

23. The method of claim 1, wherein the compound augments ghrelin-induced hippocampal neurogenesis.

24. The method of claim 1, wherein the depressive disorder is associated with insufficient ghrelin response.

25. The method of claim 24, wherein said insufficient ghrelin response results in impaired or reduced hippocampal neurogenesis.

\* \* \* \* \*

UNITED STATES PATENT AND TRADEMARK OFFICE
CERTIFICATE OF CORRECTION

PATENT NO. : 9,616,048 B2
APPLICATION NO. : 14/886332
DATED : April 11, 2017
INVENTOR(S) : Steven L. McKnight et al.

Page 1 of 1

It is certified that error appears in the above-identified patent and that said Letters Patent is hereby corrected as shown below:

In the Specification

In Column 1, Lines 27-31 below the STATEMENT REGARDING FEDERALLY SPONSORED RESEARCH, delete:
"This invention was made with government support under Grant Numbers 5DP1OD00027605, 5R37MH05938809, 1R01MH087986, 1R01MH085298 and 1R01DA024680, which were awarded by the National Institute of Health; the Government has certain rights in the invention."
And add:
--This invention was made with government support under grant numbers OD000276, MH059388, and MH087986 awarded by the National Institutes of Health. The government has certain rights in the invention.--

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*